US011918612B2

(12) United States Patent
Henn et al.

(10) Patent No.: US 11,918,612 B2
(45) Date of Patent: Mar. 5, 2024

(54) SYNERGISTIC BACTERIAL COMPOSITIONS AND METHODS OF PRODUCTION AND USE THEREOF

(71) Applicant: Seres Therapeutics, Inc., Cambridge, MA (US)

(72) Inventors: Matthew R. Henn, Somerville, MA (US); Kevin Daniel Litcofsky, Boston, MA (US); Anthony Mario D'Onofrio, Northborough, MA (US); Toshiro K. Ohsumi, Cambridge, MA (US); Mary-Jane Lombardo McKenzie, Arlington, MA (US); Geoffrey Von Maltzahn, Boston, MA (US); David N. Cook, Brooklyn, NY (US); David Arthur Berry, Brookline, MA (US); Noubar B. Afeyan, Lexington, MA (US); John Grant Aunins, Doylestown, PA (US)

(73) Assignee: Seres Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/588,122

(22) Filed: Jan. 28, 2022

(65) Prior Publication Data

US 2022/0257674 A1 Aug. 18, 2022

Related U.S. Application Data

(62) Division of application No. 16/230,807, filed on Dec. 21, 2018, now Pat. No. 11,266,699, which is a division of application No. 15/039,007, filed as application No. PCT/US2014/067491 on Nov. 25, 2014, now Pat. No. 10,258,655.

(60) Provisional application No. 61/908,702, filed on Nov. 25, 2013, provisional application No. 61/908,698, filed on Nov. 25, 2013, provisional application No. 62/004,187, filed on May 28, 2014.

(51) Int. Cl.

| | |
|---|---|
| ***A61K 39/295*** | (2006.01) |
| ***A23L 33/135*** | (2016.01) |
| ***A61K 35/74*** | (2015.01) |
| ***A61K 35/742*** | (2015.01) |
| ***A61K 45/06*** | (2006.01) |
| ***C12N 1/20*** | (2006.01) |
| *A61K 35/00* | (2006.01) |

(52) U.S. Cl.

CPC .......... *A61K 35/742* (2013.01); *A23L 33/135* (2016.08); *A61K 35/74* (2013.01); *A61K 45/06* (2013.01); *C12N 1/20* (2013.01); *A61K 2035/11* (2013.01); *A61K 2035/115* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 3,009,861 | A | 11/1961 | Gordon et al. |
| 3,009,864 | A | 11/1961 | Webb et al. |
| 3,228,838 | A | 1/1966 | Rinfret et al. |
| 3,608,030 | A | 9/1971 | Tint et al. |
| 4,077,227 | A | 3/1978 | Larson et al. |
| 4,205,132 | A | 5/1980 | Sandine et al. |
| 4,655,047 | A | 4/1987 | Temple et al. |
| 4,689,226 | A | 8/1987 | Nurmi et al. |
| 4,839,281 | A | 6/1989 | Gorbach et al. |
| 5,196,205 | A | 3/1993 | Borody et al. |
| 5,425,951 | A | 6/1995 | Goodrich et al. |
| 5,436,002 | A | 7/1995 | Payne et al. |
| 5,443,826 | A | 8/1995 | Borody et al. |
| 5,599,795 | A | 2/1997 | McCann et al. |
| 5,648,206 | A | 7/1997 | Goodrich et al. |
| 5,951,977 | A | 9/1999 | Nisbet et al. |
| 5,965,128 | A | 10/1999 | Doyle et al. |
| 6,589,771 | B1 | 7/2003 | Marshall et al. |
| 6,645,530 | B1 | 11/2003 | Borody et al. |
| 7,326,551 | B2 | 2/2008 | Maupin-Furlow et al. |
| 7,427,398 | B2 | 9/2008 | Baillon et al. |
| 7,628,982 | B2 | 12/2009 | Klaviniskis et al. |
| 7,632,520 | B2 | 12/2009 | Khandelwal et al. |
| 7,708,988 | B2 | 5/2010 | Farmer et al. |
| 7,731,976 | B2 | 6/2010 | Cobb et al. |
| 7,763,420 | B2 | 7/2010 | Stritzker et al. |
| 7,981,411 | B2 | 7/2011 | Nadeau et al. |
| 7,998,473 | B2 | 8/2011 | Boileau et al. |
| 8,021,654 | B2 | 9/2011 | Rehberger et al. |
| 8,034,601 | B2 | 10/2011 | Boileau et al. |
| 8,039,006 | B2 | 10/2011 | Prato et al. |
| 8,147,482 | B2 | 4/2012 | Shimizu et al. |

(Continued)

FOREIGN PATENT DOCUMENTS

| | | |
|---|---|---|
| CN | 102131928 A | 7/2011 |
| CN | 102940652 A | 2/2013 |

(Continued)

OTHER PUBLICATIONS

Potentials of Probiotics in Pig Nutrition, AllAboutFeed News, Jan. 31, 2007, 6 pages.

(Continued)

*Primary Examiner* — Jennifer E Graser

(74) *Attorney, Agent, or Firm* — Sterne, Kessler, Goldstein & Fox P.L.L.C.

(57) ABSTRACT

Provided are therapeutic compositions containing microbial populations for prevention, treatment and reduction of symptoms associated with a dysbiosis of a mammalian subject such as a human.

19 Claims, 7 Drawing Sheets

Specification includes a Sequence Listing.

(56) References Cited

U.S. PATENT DOCUMENTS

| | | | |
|---|---|---|---|
| 8,187,590 | B2 | 5/2012 | Farmer et al. |
| 8,236,508 | B2 | 8/2012 | Mutharasan et al. |
| 8,388,996 | B2 | 3/2013 | Gehling et al. |
| 8,460,648 | B2 | 6/2013 | Borody et al. |
| 8,906,668 | B2 | 12/2014 | Henn et al. |
| 8,968,721 | B2 | 3/2015 | Harel |
| 9,011,834 | B1 | 4/2015 | McKenzie et al. |
| 9,028,841 | B2 | 5/2015 | Henn et al. |
| 9,180,147 | B2 | 11/2015 | McKenzie et al. |
| 9,408,872 | B2 | 8/2016 | Borody et al. |
| 9,446,080 | B2 | 9/2016 | McKenzie et al. |
| 9,610,307 | B2 | 4/2017 | Berry et al. |
| 9,808,519 | B2 | 11/2017 | Honda et al. |
| 10,258,655 | B2 | 4/2019 | Henn et al. |
| 2001/0036453 | A1 | 11/2001 | Reid et al. |
| 2004/0028689 | A1 | 2/2004 | Borody et al. |
| 2004/0170617 | A1 | 9/2004 | Finegold et al. |
| 2005/0048515 | A1 | 3/2005 | Garner et al. |
| 2005/0180962 | A1 | 8/2005 | Raz et al. |
| 2006/0046246 | A1 | 3/2006 | Zeng et al. |
| 2006/0067924 | A1 | 3/2006 | Lee et al. |
| 2006/0188523 | A1 | 8/2006 | Pei et al. |
| 2006/0233830 | A1 | 10/2006 | Wong et al. |
| 2007/0141139 | A1 | 6/2007 | Vandenberg et al. |
| 2008/0213752 | A1 | 9/2008 | Stave et al. |
| 2009/0197249 | A1 | 8/2009 | Gillevet et al. |
| 2010/0074872 | A1 | 3/2010 | Blaser et al. |
| 2010/0215745 | A1 | 8/2010 | Lazzari et al. |
| 2011/0081320 | A1 | 4/2011 | Westall et al. |
| 2011/0113863 | A1 | 5/2011 | Fuhrmann et al. |
| 2011/0189132 | A1 | 8/2011 | Garner et al. |
| 2011/0280840 | A1 | 11/2011 | Blaser et al. |
| 2011/0280847 | A1 | 11/2011 | Sorg et al. |
| 2012/0020950 | A1 | 1/2012 | Davis et al. |
| 2012/0021429 | A1 | 1/2012 | Rublee et al. |
| 2012/0021921 | A1 | 1/2012 | Scott et al. |
| 2012/0058094 | A1 | 3/2012 | Blaser et al. |
| 2012/0064592 | A1 | 3/2012 | O'Mullan et al. |
| 2012/0128633 | A1 | 5/2012 | Veiga et al. |
| 2012/0128634 | A1 | 5/2012 | Veiga et al. |
| 2012/0148629 | A1 | 6/2012 | Holvoet et al. |
| 2012/0149584 | A1 | 6/2012 | Olle et al. |
| 2012/0165215 | A1 | 6/2012 | Andersen et al. |
| 2012/0177650 | A1 | 7/2012 | Borody et al. |
| 2012/0207726 | A1 | 8/2012 | Lipkin et al. |
| 2012/0238468 | A1 | 9/2012 | Tuk et al. |
| 2012/0264637 | A1 | 10/2012 | Wiener-Kronish et al. |
| 2012/0276149 | A1 | 11/2012 | Littman et al. |
| 2012/0276201 | A1 | 11/2012 | Trachtman et al. |
| 2012/0315249 | A1 | 12/2012 | Olmstead et al. |
| 2013/0017999 | A1 | 1/2013 | Fremont et al. |
| 2013/0022575 | A1 | 1/2013 | Cassity et al. |
| 2013/0045274 | A1 | 2/2013 | Hlavka et al. |
| 2013/0045874 | A1 | 2/2013 | Ehrlich et al. |
| 2013/0065862 | A1 | 3/2013 | Johnson |
| 2013/0115232 | A1 | 5/2013 | Ferrara et al. |
| 2013/0121968 | A1 | 5/2013 | Quay et al. |
| 2013/0149339 | A1 | 6/2013 | Honda et al. |
| 2013/0149375 | A1 | 6/2013 | Geall |
| 2013/0195820 | A1 | 8/2013 | Wacklin et al. |
| 2013/0266539 | A1 | 10/2013 | Borody et al. |
| 2014/0045744 | A1 | 2/2014 | Gordon et al. |
| 2014/0135398 | A1 | 5/2014 | Matar et al. |
| 2014/0147417 | A1 | 5/2014 | Sadowsky et al. |
| 2014/0147425 | A1 | 5/2014 | Henn et al. |
| 2014/0199281 | A1 | 7/2014 | Henn et al. |
| 2014/0328803 | A1 | 11/2014 | McKenzie et al. |
| 2014/0341921 | A1 | 11/2014 | Honda et al. |
| 2014/0342438 | A1 | 11/2014 | Allen-Vercoe et al. |
| 2015/0011415 | A1 | 1/2015 | Levin et al. |
| 2015/0093360 | A1 | 4/2015 | McKenzie et al. |
| 2015/0190435 | A1 | 7/2015 | Henn et al. |
| 2016/0271188 | A1 | 9/2016 | Berry et al. |
| 2017/0165302 | A1 | 6/2017 | Henn et al. |

FOREIGN PATENT DOCUMENTS

| | | | |
|---|---|---|---|
| DE | 102006062250 | A1 | 6/2008 |
| EA | 006847 | B1 | 8/2004 |
| EP | 0033584 | A3 | 4/1982 |
| EP | 0446069 | A1 | 9/1991 |
| EP | 0456418 | A2 | 11/1991 |
| EP | 0433299 | A4 | 4/1992 |
| EP | 0479820 | B1 | 9/1994 |
| EP | 1107772 | B1 | 4/2006 |
| EP | 1631312 | B1 | 9/2008 |
| EP | 2337569 | A2 | 6/2011 |
| EP | 2338989 | A1 | 6/2011 |
| EP | 2519108 | A1 | 11/2012 |
| EP | 2626076 | A1 | 8/2013 |
| EP | 2684469 | A1 | 1/2014 |
| EP | 2750682 | B1 | 5/2016 |
| JP | H0656679 | A | 3/1994 |
| JP | 2007332083 | A | 12/2007 |
| JP | 2010539179 | A | 12/2010 |
| JP | 5019563 | B2 | 9/2012 |
| RU | 2035186 | C1 | 5/1995 |
| RU | 2439145 | C2 | 1/2012 |
| WO | WO-9001335 | A1 | 2/1990 |
| WO | WO-9408598 | A1 | 4/1994 |
| WO | WO-9708598 | A1 | 3/1997 |
| WO | WO-9709886 | A1 | 3/1997 |
| WO | WO-9826787 | A1 | 6/1998 |
| WO | WO-0010582 | A2 | 3/2000 |
| WO | WO-0193904 | A1 | 12/2001 |
| WO | WO-0207741 | A1 | 1/2002 |
| WO | WO-0243649 | A2 | 6/2002 |
| WO | WO-2005017095 | A2 | 2/2005 |
| WO | WO-2005110445 | A2 | 11/2005 |
| WO | WO-2006012586 | A2 | 2/2006 |
| WO | WO-2007036230 | A1 | 4/2007 |
| WO | WO-2007136553 | A2 | 11/2007 |
| WO | WO-2008076696 | A2 | 6/2008 |
| WO | WO-2008077614 | A2 | 7/2008 |
| WO | WO-2008083157 | A2 | 7/2008 |
| WO | WO-2010030997 | A1 | 3/2010 |
| WO | WO-2010062369 | A2 | 6/2010 |
| WO | WO-2010124387 | A1 | 11/2010 |
| WO | WO-2010151842 | A2 | 12/2010 |
| WO | WO-2011005756 | A1 | 1/2011 |
| WO | WO-2011022542 | A2 | 2/2011 |
| WO | WO-2011022660 | A1 | 2/2011 |
| WO | WO-2011033310 | A1 | 3/2011 |
| WO | WO-2011043654 | A1 | 4/2011 |
| WO | WO-2011046616 | A2 | 4/2011 |
| WO | WO-2011060123 | A1 | 5/2011 |
| WO | WO-2011094027 | A1 | 8/2011 |
| WO | WO-2011103123 | A2 | 8/2011 |
| WO | WO-2011107481 | A2 | 9/2011 |
| WO | WO-2011107482 | A2 | 9/2011 |
| WO | WO-2011113801 | A1 | 9/2011 |
| WO | WO-2011152566 | A2 | 12/2011 |
| WO | WO-2012009712 | A2 | 1/2012 |
| WO | WO-2012016287 | A2 | 2/2012 |
| WO | WO-2012033814 | A2 | 3/2012 |
| WO | WO-2012045150 | A1 | 4/2012 |
| WO | WO-2012064981 | A2 | 5/2012 |
| WO | WO-2012108830 | A1 | 8/2012 |
| WO | WO-2012116289 | A2 | 8/2012 |
| WO | WO-2012122478 | A1 | 9/2012 |
| WO | WO-2012122522 | A2 | 9/2012 |
| WO | WO-2012142605 | A1 | 10/2012 |
| WO | WO-2012148991 | A1 | 11/2012 |
| WO | WO-2012159023 | A2 | 11/2012 |
| WO | WO-2013016636 | A1 | 1/2013 |
| WO | WO-2013019896 | A1 | 2/2013 |
| WO | WO-2013032328 | A1 | 3/2013 |
| WO | WO-2013037067 | A1 | 3/2013 |
| WO | WO-2013037068 | A1 | 3/2013 |
| WO | WO-2013050792 | A1 | 4/2013 |
| WO | WO-2013053836 | A1 | 4/2013 |
| WO | WO-2013080561 | A1 | 6/2013 |
| WO | WO-2013166031 | A1 | 11/2013 |
| WO | WO-2013171515 | A1 | 11/2013 |

(56) References Cited

FOREIGN PATENT DOCUMENTS

| | | | |
|---|---|---|---|
| WO | WO-2013176774 | A1 | 11/2013 |
| WO | WO-2013177596 | A2 | 11/2013 |
| WO | WO-2014082050 | A1 | 5/2014 |
| WO | WO-2014121298 | A2 | 8/2014 |
| WO | WO-2014121301 | A1 | 8/2014 |
| WO | WO-2014121302 | A2 | 8/2014 |
| WO | WO-2014121304 | A1 | 8/2014 |
| WO | WO-2014145958 | A2 | 9/2014 |
| WO | WO-2014153194 | A2 | 9/2014 |
| WO | WO-2014177667 | A1 | 11/2014 |
| WO | WO-2015018307 | A1 | 2/2015 |
| WO | WO-2015077794 | A1 | 5/2015 |
| WO | WO-2015095241 | A2 | 6/2015 |
| WO | WO-2017091783 | A2 | 6/2017 |
| WO | WO-2017160711 | A1 | 9/2017 |
| WO | WO-2019089643 | A1 | 5/2019 |

OTHER PUBLICATIONS

Aas, J., Gessert, C.E., and Bakken, J.S. (2003). Recurrent Clostridium difficile colitis: case series involving 18 patients treated with donor stool administered via a nasogastric tube. Clinical Infectious Diseases 36(5), 580-585.

Abrams, R.S., "Open-Label, Uncontrolled Trial of Bowel Sterilization and Repopulation with Normal Bowel Flora for Treatment of Inflammatory Bowel Disease," Current Therapeutic Research, Dec. 1997, pp. 1001-1012, vol. 58, No. 12.

Accoceberry, I et al., "One-Step Purification of Enterocytozoon Bieneusi Spores from Human Stools by Immunoaffinity Expanded-Bed Adsorption, " Journal of Clinical Microbiology, May 2001, pp. 1974-1951, vol. 39, No. 5.

Achtman, M., and Wagner, M. (2008). Microbial diversity and the genetic nature of microbial species. Nat. Rev. Microbiol. 6(6), 431-440.

Allen-Vercoe, E., Reid, G., Viner, N., Gloor, G.B., Hota, S., Kim, P., Lee, C., O'Doherty, K., Vanner, S.J., Weese, J.S., et al. (2012). A Canadian Working Group report on fecal microbial therapy: microbial ecosystems therapeutics. Can. J. Gastroenterol. 26(7), 457-462.

Allen-Vercoe, E., Strauss, J., and Chadee, K. (2011). Fusobacterium nucleatum: an emerging gut pathogen? Gut Microbes 2(5), 294-298.

Anderson, K.F., Lonsway, D.R., Rasheed, J.K., Biddle, J., Jensen, B., McDougal, L.K., Carey, R.B., Thompson, A., Stocker, S., Limbago, B., et al. (2007). Evaluation of Methods to Identify the Klebsiella pneumoniae Carbapenemase in Enterobacteriaceae. J. Clin. Microbiol. 45(8), 2723-2725.

Arumugam, M., Raes, J., Pelletier, E., Paslier, D.L., Yamada, T., Mende, D.R., Fernandes, G.R., Tap, J., Bruls, T., Batto, J.-M., et al. (2011). Enterotypes of the human gut microbiome. Nature 473(7346), 174-180.

Atarashi, K., Tanoue, T., Oshima, K., Suda, W., Nagano, Y., Nishikawa, H., Fukuda, S., Saito, T., Narushima, S., Hase, K., et al. (2013). Treg induction by a rationally selected mixture of Clostridia strains from the human microbiota. Nature 500(7461), 232-236.

Atarashi, K., Tanoue, T., Shima, T., Imaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331(6015), 337-341.

Australian First Examination Report, Australian Application No. 2013347805, dated Apr. 13, 2017, 3 pages.

Australian First Examination Report, Australian Application No. 2014212004, dated Sep. 21, 2017, 6 pages.

Australian First Examination Report, Australian Application No. 2014232370, dated Oct. 19, 2017, 4 pages.

Backhed, F. et al., (2004). The gut microbiota as an environmental factor that regulates fat storage, PNAS, Nov. 2, 2014, pp. 15718-15723, vol. 101, No. 44.

Bader, J., Albin, A., and Stahl, U. (2012). Spore-forming bacteria and their utilisation as probiotics. Benef Microbes 3(1), 67-75.

Bakken, J.S. (2009). Fecal bacteriotherapy for recurrent Clostridium difficile infection. Anaerobe 15(6), 285-289.

Bakken, J.S., Borody, T., Brandt, L.J., Brill, J.V., Demarco, D.C., Franzos, M.A., Kelly, C., Khoruts, A., Louie, T., Martinelli, L.P., et al. (2011). Treating Clostridium difficile infection with fecal microbiota transplantation. Clin. Gastroenterol. Hepatol. 9(12), 1044-1049.

Barreau, M., Pagnier, I., and La Scola, B. (2013). Improving the identification of anaerobes in the clinical microbiology laboratory through MALDI-TOF mass spectrometry. Anaerobe 22, 123-125.

Bauer, T.M. et al., "Derivation and Validation of Guidelines for Stool Cultures for Enteropathogenic Bacteria Other Than Clostridium difficile in Hospitalized Adults," The Journal of the American Medical Association, Jan. 17, 2001, pp. 313-319, vol. 285.

Ben-Amor, K., Heilig, H., Smidt, H., Vaughan, E.E., Abee, T., and De Vos, W.M. (2005). Genetic diversity of viable, injured, and dead fecal bacteria assessed by fluorescence-activated cell sorting and 16S rRNA gene analysis. Applied and Environmental Microbiology 71(8), 4679-4689.

Berstd, A. et al., "Fecal Fat Determination with a Modified Titration Method," Scandinavian Journal of Gastroenterology, 2010, pp. 603-607, vol. 45.

Bhatia, A. et al., "Proionibacterium Acnes and Chronic Diseases," The Infectious Etiology of Chronic Diseases: Defining the Relationship, Enhancing the Research, and Mitigating the Effects: Workshop Summary., Knobler, S.L. et al. (eds.), 2004, pp. 74-80, may be downloaded at<URL:http://www.nap.edu/catalog/11026.html>.

Bidawid, S., Farber, J.M., Sattar, S.A., and Hayward, S. (2000). Heat inactivation of hepatitis A virus in dairy foods. J. Food Prot. 63(4), 522-528.

Bloedt, K., Riecker, M., Poppert, S., and Wellinghausen, N. (2009). Evaluation of new selective culture media and a rapid fluorescence in situ hybridization assay for identification of Clostridium difficile from stool samples. J Med Microbiol 58(7), 874-877.

Bokulich, N.A., Subramanian, S., Faith, J.J., Gevers, D., Gordon, J.I., Knight, R., Mills, D.A., and Caporaso, J.G. (2013). Quality-filtering vastly improves diversity estimates from Illumina amplicon sequencing. Nat Methods 10(1), 57-59.

Bolivar, I. et al., "Bacterial Diversity in Oral Samples of Children in Niger with Acute Noma, Acute Necrotizing Gingivitis and Healthy Controls," PLOS Neglected Tropical Diseases, Mar. 2012, pp. 1-11, vol. 6, No. 3, E1556; Uncultured *Catonella* sp. partial 16S rRNA Gene, Clone 402A04(oral): Nucleotide: NCBI: GenBank: AM420133.1, last accessed Mar. 12, 2014, pp. 12-13.

Borody, T.J. et al. (2011). Fecal microbiota transplantation (FMT) in multiple sclerosis. Poster abstract at American College of Gastroenterology Annual Scientific Meeting and Postgraduate Course Oct. 28, 2011.

Borody, T.J., and Khoruts, A. (2012). Fecal microbiota transplantation and emerging applications. Nat Rev Gastroenterol Hepatol 9(2), 88-96.

Borriello, S.P. (1990). The influence of the normal flora on Clostridium difficile colonisation of the gut. Ann. Med. 22(1), 61-67.

Borriello, S.P., and Barclay, F.E. (1985). Protection of hamsters against Clostridium difficile ileocaecitis by prior colonisation with non-pathogenic strains. J Med Microbiol 19(3), 339-350.

Borriello, S.P., and Barclay, F.E. (1986). An in-vitro model of colonisation resistance to Clostridium difficile infection. Journal of Medical Microbiology 21(4), 299-309.

Borriello, S.P., and Honour, P. (1981). Simplified procedure for the routine isolation of Clostridium difficile from faeces. J Clin Pathol 34(10), 1124-1127.

Boyles, W.A., and Lincoln, R.E. (1958). Separation and concentration of bacterial spores and vegetative cells by foam flotation. Appl Microbiol 6(5), 327-334.

Brandt, L.J. (2012). Fecal Transplantation for the Treatment of Clostridium difficile Infection. Gastroenterol Hepatol (N Y) 8(3), 191-194.

Brandt, L.J., Aroniadis, O.C., Mellow, M., Kanatzar, A., Kelly, C., Park, T., Stollman, N., Rohlke, F., and Surawicz, C. (2012). Long-Term Follow-Up of Colonoscopic Fecal Microbiota Transplant for Recurrent Clostridium difficile Infection. The American Journal of Gastroenterology 107(7), 1079-1087.

(56) References Cited

OTHER PUBLICATIONS

Bräuniger, S., Peters, J., Borchers, U., and Kao, M. (2000). Further studies on thermal resistance of bovine parvovirus against moist and dry heat. International Journal of Hygiene and Environmental Health 203(1), 71-75.

Broda, D.M., De Lacy, K.M., and Bell, R.G. (1998). Efficacy of heat and ethanol spore treatments for the isolation of psychrotrophic *Clostridium* spp. associated with the spoilage of chilled vacuum-packed meats. International Journal of Food Microbiology 39(1-2), 61-68.

Brosius, J. et al., "Complete Nucleotide Sequence of a 16S Ribosomal RNA Gene from *Eschericia coli*," Proc. Natl. Acad. Sci., Oct. 1978, pp. 4801-4805, vol. 75, No. 10.

Bueche, M., Wunderlin, T., Roussel-Delif, L., Junier, T., Sauvain, L., Jeanneret, N., and Junier, P. (2013). Quantification of Endospore-Forming Firmicutes by Quantitative PCR with the Functional Gene spo0A. Applied and Environmental Microbiology 79(17), 5302-5312.

Buffie, C.G., and Pamer, E.G. (2013). Microbiota-mediated colonization resistance against intestinal pathogens. Nature Reviews Immunology 13(11), 790-801.

Burke, C.J., Hsu, T.A., and Volkin, D.B. (1999). Formulation, stability, and delivery of live attenuated vaccines for human use. Crit Rev Ther Drug Carrier Syst 16(1), 1-83.

Cani, P.D., Possemiers, S., Wiele, T.V. De, Guiot, Y., Everard, A., Rottier, O., Geurts, L., Naslain, D., Neyrinck, A., Lambert, D.M., et al. (2009). Changes in gut microbiota control inflammation in obese mice through a mechanism involving GLP-2-driven improvement of gut permeability. Gut 58(8), 1091-1103.

Carvalho, A.S., Silva, J., Ho, P., Teixeira, P., Malcata, F.X., and Gibbs, P. (2008). Effects of Various Sugars Added to Growth and Drying Media upon Thermotolerance and Survival throughout Storage of Freeze-Dried *Lactobacillus delbrueckii* ssp. *bulgaricus*. Biotechnology Progress 20(1), 248-254.

Champagne, C.P., Mondou, F., Raymond, Y., and Roy, D. (1996). Effect of polymers and storage temperature on the stability of freeze-dried lactic acid bacteria. Food Research International 29(5-6), 555-562.

Chang, J.Y., Antonopoulos, D.A., Kalra, A., Tonelli, A., Khalife, W.T., Schmidt, T.M., and Young, V.B. (2008). Decreased diversity of the fecal Microbiome in recurrent Clostridium difficile-associated diarrhea. J. Infect. Dis. 197(3), 435-438.

Chapman, C.M.C., Gibson, G.R., and Rowland, I. (2012). In vitro evaluation of single- and multi-strain probiotics: Inter-species inhibition between probiotic strains, and inhibition of pathogens. Anaerobe 18(4), 405-413.

Chen, X., Katchar, K., Goldsmith, J.D., Nanthakumar, N., Cheknis, A., Gerding, D.N., and Kelly, C.P. (2008). A Mouse Model of Clostridium difficile-Associated Disease. Gastroenterology 135(6), 1984-1992.

Chinese First Office Action, Chinese Application No. 201480019395.8, dated Jul. 17, 2017, 29 pages.

Chiu, C-H. et al., "Rapid Identification of Salmonella Serovars in Feces by Specific Detection of Virulence Genes, invA and spvC, by an Enrichment Broth Culture-Multiplex PCR Combination Assay," Journal of Clinical Microbiology, Oct. 1996, pp. 2619-2622, vol. 34, No. 10.

Chow, J., Tang, H., and Mazmanian, S.K. (2011). Pathobionts of the Gastrointestinal Microbiota and Inflammatory Disease. Curr Opin Immunol 23(4), 473-480.

Claesson, M.J., Wang, Q., O'Sullivan, O., Greene-Diniz, R., Cole, J.R., Ross, R.P., and O'Toole, P.W. (2010). Comparison of two next-generation sequencing technologies for resolving highly complex microbiota composition using tandem variable 16S rRNA gene regions. Nucleic Acids Res 38(22), e200.

Clemente, J.C., Ursell, L.K., Parfrey, L.W., and Knight, R. (2012). The impact of the gut microbiota on human health: an integrative view. Cell 148(6), 1258-1270.

Coleman, W.H., "Mechanism of Killing Spores of Bacillus Cereus and Bacillus Megaterium by Wet Heat," The Society for Applied Microbiology, Letters in Applied Microbiology, 2010. pp. 507-514, vol. 50.

David, L.A., Maurice, C.F., Carmody, R.N., Gootenberg, D.B., Button, J.E., Wolfe, B.E., Ling, A. V., Devlin, A.S., Varma, Y., Fischbach, M.A., et al. (2013). Diet rapidly and reproducibly alters the human gut microbiome. Nature advance online publication.

De Angelis, M., Piccolo, M., Vannini, L., Siragusa, S., De Giacomo, A., Serrazzanetti, D.I., Cristofori, F., Guerzoni, M.E., Gobbetti, M., and Francavilla, R. (2013). Fecal Microbiota and Metabolome of Children with Autism and Pervasive Developmental Disorder Not Otherwise Specified. PLoS One 8(10), e76993.

De Vos, W.M. (2013). Fame and future of faecal transplantations-developing next-generation therapies with synthetic microbiomes: Fame and future of faecal transplantations. Microbial Biotechnology 6(4), 316-325.

Defined Fecal Microbiota Transplantation for Clostridium Difficile Diarrhea. <http://clinicaltrials.gov/ct2/show/NCT01868373> Accessed Mar. 26, 2014.

Dendukuri, N., "Probiotic Therapy for the Prevention and Treatment of Clostridium Difficile—Associated Diarrhea: A Systematic Review," Canadian Medical Association Journal, Jul. 19, 2005, pp. 167-170, vol. 173, No. 2.

Derrien, M. (2004). *Akkermansia muciniphila* gen. nov., sp. nov., a human intestinal mucin-degrading bacterium. International Journal of Systematic and Evolutionary Microbiology 54(5), 1469-1476.

Dethlefsen, L., Huse, S., Sogin, M.L., and Relman, D.A. (2008). The Pervasive Effects of an Antibiotic on the Human Gut Microbiota, as Revealed by Deep 16S rRNA Sequencing. PLoS Biology 6(11), e280.

Detmer, A., and Glenting, J. (2006). Live bacterial vaccines-a review and identification of potential hazards. Microb Cell Fact 5, 23.

Dezfulian, M. et al., "Selective Medium for Isolation of Clostridium botulinum from Human Feces," Journal of Clinical Microbiology, Mar. 1981, pp. 526-531, vol. 13, No. 3.

Dharmani, P., De Simone, C., and Chadee, K. (2013). The Probiotic Mixture VSL#3 Accelerates Gastric Ulcer Healing by Stimulating Vascular Endothelial Growth Factor. PLoS One 8(3), e58671.

Dietrich, G., Collioud, A., and Rothen, S.A. (2008). Developing and Manufacturing Attenuated Live Bacterial Vaccines. <http://www.biopharminternational.com/biopharm/Vaccine+Manufacturing+Articles/Developing-and-Manufacturing-Attenuated-Live-Bacte/ArticleStandard/Article/detail/557306> Accessed Mar. 25, 2014.

Dowell, V.R. et al., "Coproexamination for Botulinal Toxin and Clostridium botulinum," JAMA, Oct. 24, 1977, pp. 1829-1832, vol. 238, No. 7.

Dragon, D.C., and Rennie, R.P. (2001). Evaluation of spore extraction and purification methods for selective recovery of viable Bacillus anthracis spores. Lett. Appl. Microbiol. 33(2), 100-105.

D'Souza, D.H., and Su, X. (2010). Efficacy of chemical treatments against murine norovirus, feline calicivirus, and MS2 bacteriophage. Foodborne Pathogens and Disease 7(3), 319-326.

Duc, L. (2003). Germination of the spore in the gastrointestinal tract provides a novel route for heterologous antigen delivery. Vaccine 21(27-30), 4215-4224.

Duc, L.H., Hong, H.A., Fairweather, N., Ricca, E., and Cutting, S.M. (2003). Bacterial Spores as Vaccine Vehicles. Infection and Immunity 71(5), 2810-2818.

Dumas, M.E. et al., (2006). Metabolic profiling reveals a contribution of gut microbiota to fatty liver phenotype in insulin-resistant mice, PNAS, Aug. 15, 2006, pp. 12511-12516, vol. 103, No. 33.

Dutta, S.K., Girotra, M., Garg, S., Dutta, A., Von Rosenvinge, E.C., Maddox, C., Song, Y., Bartlett, J.G., Vinayek, R., and Fricke, W.F. (2014). Efficacy of Combined Jejunal and Colonic Fecal Microbiota Transplantation for Recurrent Clostridium difficile Infection. Clinical Gastroenterology and Hepatology.

Edwards, A.D., and Slater, N.K.H. (2008). Formulation of a live bacterial vaccine for stable room temperature storage results in loss of acid, bile and bile salt resistance. Vaccine 26(45), 5675-5678.

(56) References Cited

OTHER PUBLICATIONS

Eiseman, B., Silen, W., Bascom, G.S., and Kauvar, A.J. (1958). Fecal enema as an adjunct in the treatment of pseudomembranous enterocolitis. Surgery 44(5), 854-859.
Elving, J., Emmoth, E., Albihn, A., Vinneras, B., and Ottoson, J. (2012). Composting for Avian Influenza Virus Elimination. Applied and Environmental Microbiology 78(9), 3280-3285.
Emanuelsson, F., Claesson, B.E.B., Ljungstrom, L., Tvede, M., and Ung, K.-A. (2014). Faecal microbiota transplantation and bacteriotherapy for recurrent Clostridium difficile infection: A retrospective evaluation of 31 patients. Scandinavian Journal of Infectious Diseases 46(2), 89-97.
Endt, K., Stecher, B., Chaffron, S., Slack, E., Tchitchek, N., Benecke, A., Van Maele, L., Sirard, J.-C., Mueller, A.J., Heikenwalder, M., et al. (2010). The Microbiota Mediates Pathogen Clearance from the Gut Lumen after Non-Typhoidal Salmonella Diarrhea. PLoS Pathog 6(9), e1001097.
European Examination Report, European Application No. 14745749.3, dated Oct. 31, 2017, 3 pages.
European Examination Report, European Application No. 14745792.3, dated Dec. 21, 2017, 6 pages.
European Examination Report, European Application No. 14746341.8, dated Jun. 13, 2017, 11 pages.
European Examination Report, European Application No. 14746455.6, dated Oct. 31, 2017, 6 pages.
European Examination Report, European Application No. 14763266.5, dated Nov. 13, 2017, 4 pages.
European Examination Report, European Application No. 14768281.9, dated Dec. 18, 2017, 4 pages.
European Examination Report, European Application No. 14821918.1, dated Jan. 29, 2018, 4 pages.
European Extended Search Report, European Application No. 13856249.1, dated Jan. 26, 2017, 19 pages.
European Extended Search Report, European Application No. 14745749.3, dated Jan. 23, 2017, 13 pages.
European Extended Search Report, European Application No. 14745792.3, dated Dec. 23, 2016, 17 pages.
European Extended Search Report, European Application No. 14746341.8, dated Sep. 28, 2016, 10 pages.
European Extended Search Report, European Application No. 14746455.6, dated Nov. 24, 2016, 10 pages.
European Extended Search Report, European Application No. 14763266.5, dated Aug. 16, 2016, 7 pages.
European Extended Search Report, European Application No. 14768281.9, dated Jul. 18, 2016, 10 pages.
European Extended Search Report, European Application No. 14870947.0, dated Oct. 17, 2017, 11 pages.
European Partial Supplementary Report, European Application No. 14745749.3, dated Oct. 14, 2016, 6 pages.
European Partial Supplementary Report, European Application No. 14745792.3, dated Sep. 20, 2016, 11 pages.
European Partial Supplementary Search Report, European Application No. 14870947.0, dated Jul. 11, 2017, 14 pages.
Everard, A., Belzer, C., Geurts, L., Ouwerkerk, J.P., Druart, C., Bindels, L.B., Guiot, Y., Derrien, M., Muccioli, G.G., Delzenne, N.M., et al. (2013). Cross-talk between Akkermansia muciniphila and intestinal epithelium controls diet-induced obesity. Proceedings of the National Academy of Sciences 110(22), 9066-9071.
Fairhead, H., Setlow, B., Waites, W.M., and Setlow, P. (1994). Small, acid-soluble proteins bound to DNA protect Bacillus subtilis spores from being killed by freeze-drying. Applied and Environmental Microbiology 60(7), 2647-2649.
Faith, J.J., Ahern, P.P., Ridaura, V.K., Cheng, J., and Gordon, J.I. (2014). Identifying Gut Microbe-Host Phenotype Relationships Using Combinatorial Communities in Gnotobiotic Mice. Sci Transl Med 6(220), 220ra11-220ra11.
Fakhry, S., Sorrentini, I., Ricca, E., De Felice, M., and Baccigalupi, L. (2008). Characterization of spore forming Bacilli isolated from the human gastrointestinal tract. Journal of Applied Microbiology 105(6), 2178-2186.
Faust, et al., "Microbial Co-occurrence Relationships in the Human Microbiome," PLoS Computational Biology, Jul. 2012, e1002606, 17 pages, vol. 8, No. 7.
Fell Jr., N.F., Pellegrino, P.M., and Gillespie, J.B. (2001). Mitigating phosphate interference in bacterial endospore detection by Tb dipicolinate photoluminescence. Analytica Chimica Acta 426(1), 43-50.
Fichtel, J., Köster, J., Rullkötter, J., and Sass, H. (2007). Spore dipicolinic acid contents used for estimating the number of endospores in sediments. FEMS Microbiology Ecology 61(3), 522-532.
Fischbach, M.A., Bluestone, J.A., and Lim, W.A. (2013). Cell-Based Therapeutics: The Next Pillar of Medicine. Sci Transl Med 5(179), 179ps7.
Fonseca, F., Béal, C., and Corrieu, G. (2001). Operating Conditions That Affect the Resistance of Lactic Acid Bacteria to Freezing and Frozen Storage. Cryobiology 43(3), 189-198.
Franz, C.M.A.P., Huch, M., Abriouel, H., Holzapfel, W., and Gálvez, A. (2011). Enterococci as probiotics and their implications in food safety. International Journal of Food Microbiology 151(2), 125-140.
Friedman-Moraco, R.J., Mehta, A.K., Lyon, G.M., and Kraft, C.S. (2014). Fecal Microbiota Transplantation for Refractory Clostridium difficile Colitis in Solid Organ Transplant Recipients: Fecal Microbiota Transplantation in Solid Organ Transplant Recipients. American Journal of Transplantation 14(2), 477-480.
Fuentes, S., Van Nood, E., Tims, S., Heikamp-De Jong, I., Ter Braak, C.J., Keller, J.J., Zoetendal, E.G., and De Vos, W.M. (2014). Reset of a critically disturbed microbial ecosystem: faecal transplant in recurrent Clostridium difficile infection. The ISME Journal.
GenBank HQ819637, "Uncultured Organism Clone ELU0180-T56-S-NIPCRAMgANa_000311 Small Subunit Ribosomal RNA Gene, Partial Sequence," Jul. 30, 2012, 1 page, [Online] [Retrieved on Aug. 21, 2014] Retrieved from the Internet<URL:http://www.ncbi.nlm.nih.gov/nuccore/HQ819637>.
Gevers, D., Kugathasan, S., Denson, L.A., Vazquez-Baeza, Y., Van Treuren, W., Ren, B., Schwager, E., Knights, D., Song, S.J., Yassour, M., et al. (2014). The Treatment-Naive Microbiome in New-Onset Crohn's Disease. Cell Host & Microbe 15(3), 382-392.
Gilligan, P.H. (2013). Identification of Pathogens by Classical Clinical Tests. In the Prokaryotes, E. Rosenberg, E.F. DeLong, S. Lory, E. Stackebrandt, and F. Thompson, eds. (Springer Berlin Heidelberg), pp. 57-89.
Goodman, A.L., Kallstrom, G., Faith, J.J., Reyes, A., Moore, A., Dantas, G., and Gordon, J.I. (2011). From the Cover: Extensive personal human gut microbiota culture collections characterized and manipulated in gnotobiotic mice. Proceedings of the National Academy of Sciences 108(15), 6252-6257.
Goodman, N.S., Gottfried, R.J., and Rogoff, M.H. (1967). Biphasic system for separation of spores and crystals of Bacillus thuringiensis. Journal of Bacteriology 94(2), 485.
Gough, E. et al., "Systematic Review of Intestinal Microbiota Transplantation (Fecal Bacteriotherapy) for Recurrent Clostridium Dfficile Infection," Clin. Infect. Dis., Nov. 15, 2011, pp. 994-1002, vol. 53, No. 10.
Gould, G.W., and Sale, A.J. (1970). Initiation of germination of bacterial spores by hydrostatic pressure. J. Gen. Microbiol. 60(3), 335-346.
Grabow, W.O., Clay, C.G., Dhaliwal, W., Vrey, M.A., and Müller, E.E. (1999). Elimination of viruses, phages, bacteria and Cryptosporidium by a new generation Aquaguard point-of-use water treatment unit. Zentralbl Hyg Umweltmed 202(5), 399-410.
Greenway, F., Wang, S., and Heiman, M. (2014). A novel cobiotic containing a prebiotic and an antioxidant augments the glucose control and gastrointestinal tolerability of metformin: a case report. Beneficial Microbes 5(1), 29-32.
Grehan, M.J., Borody, T.J., Leis, S.M., Campbell, J., Mitchell, H., and Wettstein, A. (2010). Durable alteration of the colonic microbiota by the administration of donor fecal flora. J. Clin. Gastroenterol. 44(8), 551-561.
Grimoud, J. et al., "In Vitro Screening of Probiotic Lactic Acid Bacteria and Prebiotic Glucooligosaccharides to Select Effective Synbiotics," Anaerobe, Clinical Microbiology, Oct. 2010, pp. 493-500, vol. 16, No. 5.

(56) References Cited

OTHER PUBLICATIONS

Gupta, R.K. et al., "Differentiation Between Heat Resistance and Octyl Alcohol Resistance of the Cells of Bacillus Cereus T.," Biochemical and Biophysical Research Communications, 1970, pp. 23-30, vol. 38, No. 1.
Halmann, M. et al., "Stages in Germination of Spores of Bacillus Lichenformis," J. Bacteriol., 1962, pp. 1187-1193, vol. 84.
Hamilton, M.J., Weingarden, A.R., Sadowsky, M.J., and Khoruts, A. (2012). Standardized frozen preparation for transplantation of fecal microbiota for recurrent Clostridium difficile infection. Am. J. Gastroenterol. 107(5), 761-767.
Hamilton, M.J., Weingarden, A.R., Unno, T., Khoruts, A., and Sadowsky, M.J. (2013). High-throughput DNA sequence analysis reveals stable engraftment of gut microbiota following transplantation of previously frozen fecal bacteria. Gut Microbes 4(2), 125-135.
Harmsen, H. J. M., Gibson, G. R., Elfferich, P., Raangs, G. C., Wildeboer-Veloo, A. C. M., Argaiz, A., Roberfroid, M. B., and Welling, G. W. (2000). Comparison of viable cell counts and fluorescence in situ hybridization using specific rRNA-based probes for the quantification of human fecal bacteria. FEMS Microbiology Letters 183(1), 125-129.
Harrison, F., "Bacterial Cooperation in the Wild and in the Clinic: Are Pathogen Social Behaviours Relevant Outside the Laboratory?" Bioessays, Dec. 27, 2012, pp. 108-112, vol. 35, No. 2.
Hasan, J.A., Japal, K.M., Christensen, E.R., and Samalot-Freire, L.C. (2011). In vitro production of Clostridium difficile spores for use in the efficacy evaluation of disinfectants: a precollaborative investigation. J AOAC Int 94(1), 259-272.
Hayashi, Y. et al., "Western Blot (Immunoblot) Assay of Small Round-Structured Virus Associated with an Acute Gastroenteritis Outbreak in Tokyo," Journal of Clinical Microbiology, Aug. 1989, pp. 1728-1733, vol. 27.
Hell, M., Bernhofer, C., Stalzer, P., Kern, J.M., and Claassen, E. (2013). Probiotics in Clostridium difficile infection: reviewing the need for a multistrain probiotic. Beneficial Microbes 4(1), 39-51.
Hemmerling, A., Harrison, W., Schroeder, A., Park, J., Korn, A., Shiboski, S., Foster-Rosales, A., and Cohen, C.R. (2010). Phase 2a Study Assessing Colonization Efficiency, Safety, and Acceptability of Lactobacillus crispatus CTV-05 in Women With Bacterial Vaginosis: Sexually Transmitted Diseases 37(12), 745-750.
Herron, P.R., and Wellington, E.M.H. (1990). New Method for Extraction of Streptomycete Spores from Soil and Application to the Study of Lysogeny in Sterile Amended and Nonsterile Soil. Appl Environ Microbiol 56(5), 1406-1412.
Hewitt, J., Rivera-Aban, M., and Greening, G.E. (2009). Evaluation of murine norovirus as a surrogate for human norovirus and hepatitis A virus in heat inactivation studies. Journal of Applied Microbiology 107(1), 65-71.
Hickson, M. et al., "Probiotics in the Prevention of Antibiotic-Associated Diarrhoea and Clostridium Difficile Infection," Therapeutic Advances in Gastroenterology, 2011, pp. 185-197, vol. 4, No. 3.
Hindle, A.A., and Hall, E.A.H. (1999). Dipicolinic acid (DPA) assay revisited and appraised for spore detection. The Analyst 124(11), 1599-1604.
Hirsch, E.B., and Tam, V.H. (2010). Detection and treatment options for Klebsiella pneumoniae carbapenemases (KPCs): an emerging cause of multidrug-resistant infection. J. Antimicrob. Chemother. 65(6), 1119-1125.
Hofsten, B.V. (1966). Partition of *Escherichia coli* in an aqueous polymer two-phase system. Experimental Cell Research 41(1), 117-123.
Holmes, E., Kinross, J., Gibson, G.R., Burcelin, R., Jia, W., Pettersson, S., and Nicholson, J.K. (2012). Therapeutic Modulation of Microbiota-Host Metabolic Interactions. Science Translational Medicine 4(137), 137rv6-137rv6.
Hoppe, B., Groothoff, J.W., Hulton, S.-A., Cochat, P., Niaudet, P., Kemper, M.J., Deschênes, G., Unwin, R., and Milliner, D. (2011). Efficacy and safety of Oxalobacter formigenes to reduce urinary oxalate in primary hyperoxaluria. Nephrol. Dial. Transplant. 26(11), 3609-3615.
Hoyles, L., Honda, H., Logan, N.A., Halket, G., La Ragione, R.M., and McCartney, A.L. (2012). Recognition of greater diversity of *Bacillus* species and related bacteria in human faeces. Res. Microbiol. 163(1), 3-13.
Hurst, C.J., and Gerba, C.P. (1989). Fate of viruses during wastewater sludge treatment processes. Critical Reviews in Environmental Control 18(4), 317-343.
Iizuka, M. et al., "Elemental Diet Modulates the Growth of Clostridium difficile in the Gut Flora," Aliment Pharmacol. Ther., Jul. 2004, pp. 151-157, vol. 20, Suppl. 1.
Israel Office Action, Israel Application No. 238973, dated Apr. 20, 2017, 4 pages (with concise explanation of relevance).
Itoh, K., and Mitsuoka, T. (1985). Characterization of clostridia isolated from faeces of limited flora mice and their effect on caecal size when associated with germ-free mice. Laboratory Animals 19(2), 111-118.
Itoh, K., Lee, W.K., Kawamura, H., Mitsuoka, T., and Magaribuchi, T. (1987). Intestinal bacteria antagonistic to Clostridium difficile in mice. Lab Anim 21(1), 20-25.
Itoh, K., Urano, T., and Mitsuoka, T. (1986). Colonization resistance against Pseudomonas aeruginosa in gnotobiotic mice. Lab Anim 20(3), 197-201.
Jalanka-Tuovinen, J., Salojarvi, J., Salonen, A., Immonen, O., Garsed, K., Kelly, F.M., Zaitoun, A., Palva, A., Spiller, R.C., and De Vos, W.M. (2013). Faecal microbiota composition and host-microbe cross-talk following gastroenteritis and in postinfectious irritable bowel syndrome. Gut 0, 1-9.
Janda, J.M. et al., "16S rRNA Gene Sequencing for Bacterial Identification in the Diagnostic Laboratory: Pluses, Perils and Pitfalls," Journal of Clinical Microbiology, Sep. 2007, pp. 2761-2764, vol. 45, No. 9.
Japanese First Office Action, Japanese Application No. P2015-544179, dated Sep. 19, 2017, 8 pages.
Japanese Office Action, Japanese Application No. 2015-556240, dated Oct. 3, 2017, 8 pages.
Japanese Office Action, Japanese Application No. 2015-556241, dated Sep. 26, 2017, 12 pages.
Japanese Office Action, Japanese Application No. P2016-502561, dated Feb. 6, 2018, 10 pages.
Jeffs, L.B., and Khachatourians, G.G. (1997). Estimation of spore hydrophobicity for members of the genera Beauveria, Metarhizium, and Tolypocladium by salt-mediated aggregation and sedimentation. Canadian Journal of Microbiology 43(1), 23-28.
Jensen, N.S., and Canale-Parola, E. (1986). *Bacteroides pectinophilus* sp. nov. and *Bacteroides galacturonicus* sp. nov.: two pectinolytic bacteria from the human intestinal tract. Appl. Environ. Microbiol. 52(4), 880-887.
Johnson, S. et al., "Is Primary Prevention of Clostridium Difficile Infection Possible with Specific Probiotics?" International Journal of Infectious Diseases, Nov. 2012, pp. e786-e792, vol. 16, No. 11.
Johnston, R. et al., "Method to Facilitate the Isolation of Clostridium botulinum Type E," J. Bacteriol., 1964, pp. 1521-1522, vol. 88.
Jones, M.L., Martoni, C.J., and Prakash, S. (2012a). Cholesterol lowering and inhibition of sterol absorption by Lactobacillus reuteri NCIMB 30242: a randomized controlled trial. Eur J Clin Nutr 66(11), 1234-1241.
Jones, M.L., Martoni, C.J., Parent, M., and Prakash, S. (2012b). Cholesterol-lowering efficacy of a microencapsulated bile salt hydrolase-active Lactobacillus reuteri NCIMB 30242 yoghurt formulation in hypercholesterolaemic adults. British Journal of Nutrition 107(10), 1505-1513.
Joosten, H. et al., "Salmonelle Detection in Probiotic Products," International Journal of Food Microbiology, Jul. 2006, pp. 104-107, vol. 110, No. 1.
Jordan, F. et al., "Network Ecology: Topological Constraints on Ecosystem Dynamics," Physics of Life Reviews, Dec. 2004, pp. 139-172, vol. 1, Issue 3 (Abstract Only).

(56) References Cited

OTHER PUBLICATIONS

Jorgensen, J.H., and Ferraro, M.J. (2009). Antimicrobial Susceptibility Testing: A Review of General Principles and Contemporary Practices. Clin Infect Dis., Medical Microbiology, 49(11), 1749-1755.
Jorup-Rönström, C., Håkanson, A., Sandell, S., Edvinsson, O., Midtvedt, T., Persson, A.-K., and Norin, E. (2012). Fecal transplant against relapsing Clostridium difficile-associated diarrhea in 32 patients. Scand. J. Gastroenterol. 47(5), 548-552.
Jousimies-Somer, H., Summanen, P., Citron, D.M., Baron, E.J., Wexler, H.M., and Finegold, S.M. (2002). Wadsworth-KLT Anaerobic Bacteriology Manual, 6th edition (California: Star), pp. 55-74, 81-132, 165-185.
Kailasapathy, K. (2002). Microencapsulation of probiotic bacteria: technology and potential applications. Curr Issues Intest Microbiol 3(2), 39-48.
Kamiya, S., Yamakawa, K., Ogura, H., and Nakamura, S. (1989). Recovery of spores of Clostridium difficile altered by heat or alkali. J Med Microbiol 28(3), 217-221.
Kanamoto, T. et al., "Genetic Heterogeneities and Phenotypic Characteristics of Strains of the Genus *Abiotrophia* and Proposal of *Abiotrophia para-adiacens* sp. nov.," Journal of Clinical Microbiology, Feb. 2000, pp. 492-498, vol. 38, No. 2; *Abiotropia para-adjacens* gene for 16S rRNA, partial sequence, strain: Nucleotide: NCBI: GenBank: AB022027.1, last accessed Mar. 12, 2014, p. 8.
Kanehisa Laboratories. KEGG: Kyoto encyclopedia of genes and genomes <http://www.genome.jp/kegg/> Accessed Mar. 27, 2014.
Karasawa, T. et al., "A Defined Growth Medium for Clostridium difficile," Microbiology, Feb. 1995, pp. 371-375, vol. 151, No. 2.
Kazamias, M. et al., "Enhanced Fermentation of Mannitol and Release of Cytotoxin by Clostridium difficile in Alkaline Culture Media," Applied and Environmental Microbiology, Jun. 1995, pp. 2425-2427, vol. 61, No. 6.
Kelly, D., Campbell, J.I., King, T.P., Grant, G., Jansson, E.A., Coutts, A.G.P., Pettersson, S., and Conway, S. (2003). Commensal anaerobic gut bacteria attenuate inflammation by regulating nuclear-cytoplasmic shuttling of PPAR-γ and RelA. Nature Immunology 5(1), 104-112.
Khoruts, A. (2013). How Does Fecal Microbiota Transplantation Treat Clostridium difficile Infection? <https://www.genome.gov/Multimedia/Slides/HumanMicrobiomeScience2013/39_Khoruts.pdf> Accessed Mar. 21, 2014.
Khoruts, A., and Sadowsky, M.J. (2011). Therapeutic transplantation of the distal gut microbiota. Mucosal Immunol 4(1), 4-7.
Khoruts, A., Dicksved, J., Jansson, J.K., and Sadowsky, M.J. (2010). Changes in the composition of the human fecal microbiome after bacteriotherapy for recurrent Clostridium difficile-associated diarrhea. J. Clin. Gastroenterol. 44(5), 354-360.
Kim, B., Kim, N.J., Kim, M., Kim, Y.S., Woo, J., and Ryu, J. (2003). Bacteraemia Due to Tribe Proteeae: A Review of 132 Cases During a Decade (1991-2000). Scandinavian Journal of Infectious Diseases 35(2), 98-103.
Kim, J.Y. et al., "Effect of Oral Probiotics (Bifidobacterium lactis AD011 and Lactobacillus acidophilus AD031) Administration on Ovalbumin-Induced Food Allergy Mouse Model," J. Microbiol. Biotechnol., 2008, pp. 1393-1400, vol. 18, No. 8.
Klayraung, S., Viernstein, H., and Okonogi, S. (2009). Development of tablets containing probiotics: Effects of formulation and processing parameters on bacterial viability. International Journal of Pharmaceutics 370(1-2), 54-60.
Kollmann, M. et al., Design Principles of a Bacterial Signalling Network, Nature, Nov. 24, 2005, pp. 504-507, vol. 438, No. 7067.
Kong, Q., He, G.-Q., Jia, J.-L., Zhu, Q.-L., and Ruan, H. (2011). Oral Administration of Clostridium butyricum for Modulating Gastrointestinal Microflora in Mice. Curr Microbiol 62(2), 512-517.
Konstantinidis, K.T., Ramette, A., and Tiedje, J.M. (2006). The bacterial species definition in the genomic era. Philos Trans R Soc Lond B Biol Sci 361(1475), 1929-1940.
Koonin, E.V. (2002). Chapter 22 The clusters of orthologous groups (COGS) database: Phylogenetic classification of proteins from complete genomes. <http://www.ncbi.nlm.nih.gov/books/NBK21090/pdf/ch22.pdf> Accessed Mar. 27, 2014.
Koransky, J.R. et al., "Use of Ethanol for Selective Isolation of Sporeforming Microorganisms," Applied and Environmental Microbiology, Apr. 1978, pp. 762-765, vol. 35.
Koransky, J.R., Allen, S.D., and Dowell, V.R., Jr (1978). Use of ethanol for selective isolation of sporeforming microorganisms. Appl. Environ. Microbiol. 35(4), 762-765.
Kort, R., O'Brien, A.C., Stokkum, I.H.M. Van, Oomes, S.J.C.M., Crielaard, W., Hellingwerf, K.J., and Brul, S. (2005). Assessment of Heat Resistance of Bacterial Spores from Food Product Isolates by Fluorescence Monitoring of Dipicolinic Acid Release. Appl. Environ. Microbiol. 71(7), 3556-3564.
Kucerova, Z., Moura, H., Leitch, G.J., Sriram, R., Bern, C., Kawai, V., Vargas, D., Gilman, R.H., Ticona, E., and Vivar, A. (2004). Purification of Enterocytozoon bieneusi spores from stool specimens by gradient and cell sorting techniques. Journal of Clinical Microbiology 42(7), 3256-3261.
Kumar, M. et al., "Cholesterol-Lowering Probiotics as Potential Biotherapeutics for Metabolic Diseases," Experimental Diabetes Research, 2012, Article ID 902917, 14 pages, vol. 2012.
Kump, P.K., Gröchenig, H.-P., Lackner, S., Trajanoski, S., Reicht, G., Hoffmann, K.M., Deutschmann, A., Wenzl, H.H., Petritsch, W., Krejs, G.J., et al. (2013). Alteration of intestinal dysbiosis by fecal microbiota transplantation does not induce remission in patients with chronic active ulcerative colitis. Inflamm. Bowel Dis. 19(10), 2155-2165.
Kunde, S., Pham, A., Bonczyk, S., Crumb, T., Duba, M., Conrad, H., Jr, Cloney, D., and Kugathasan, S. (2013). Safety, tolerability, and clinical response after fecal transplantation in children and young adults with ulcerative colitis. J. Pediatr. Gastroenterol. Nutr. 56(6), 597-601.
Landy, J., Al-Hassi, H.O., Mclaughlin, S.D., Walker, A.W., Ciclitira, P.J., Nicholls, R.J., Clark, S.K., and Hart, A.L. (2011). Review article: faecal transplantation therapy for gastrointestinal disease. Alimentary Pharmacology & Therapeutics 34(4), 409-415.
Lawley, T.D., Clare, S., Walker, A. W., Stares, M.D., Connor, T.R., Raisen, C., Goulding, D., Rad, R., Schreiber, F., Brandt, C., et al. (2012). Targeted Restoration of the Intestinal Microbiota with a Simple, Defined Bacteriotherapy Resolves Relapsing Clostridium difficile Disease in Mice. PLoS Pathog 8(10), e1002995.
Lawson, P.A., Song, Y., Liu, C., Molitoris, D.R., Vaisanen, M.-L., Collins, M.D., and Finegold, S.M. (2004). *Anaerotruncus colihominis* gen. nov., sp. nov., from human faeces. Int J Syst Evol Microbiol 54(2), 413-417.
Lee, I.-K., and Liu, J.-W. (2006). Clinical characteristics and risk factors for mortality in Morganella morganii bacteremia. J Microbiol Immunol Infect 39(4), 328-334.
Lee, J.S., Cha, D.S., and Park, H.J. (2004). Survival of Freeze-Dried Lactobacillus bulgaricus KFRI 673 in Chitosan-Coated Calcium Alginate Microparticles. J. Agric. Food Chem. 52(24), 7300-7305.
Lee, M., Hesek, D., Shah, I.M., Oliver, A.G., Dworkin, J., and Mobashery, S. (2010). Synthetic peptidoglycan motifs for germination of bacterial spores. Chembiochem 11(18), 2525-2529.
Lehar, J. (2007). Chemical combination effects predict connectivity in biological systems, Molecular Systems Biology, pp. 1-14, vol. 3, Article No. 80.
Lemon, K.P., Armitage, G.C., Relman, D.A., and Fischbach, M.A. (2012). Microbiota-Targeted Therapies: An Ecological Perspective. Science Translational Medicine 4(137), 137rv5-137rv5.
Leslie, S.B., Israeli, E., Lighthart, B., Crowe, J.H., and Crowe, L.M. (1995). Trehalose and sucrose protect both membranes and proteins in intact bacteria during drying. Applied and Environmental Microbiology 61(10), 3592-3597.
Li, A-D. et al., "Clinical Features and Bacterial Culture on Stools of Patients with Acute Diarrhea," Chinese Journal of Health Laboratory Technology, Mar. 10, 2012, pp. 559-561, vol. 2, No. 6.
Liggins, M., Ramirez, N., Magnuson, N., and Abel-Santos, E. (2011). Progesterone analogs influence germination of Clostridium sordellii and Clostridium difficile spores in vitro. J. Bacteriol. 193(11), 2776-2783.

(56) References Cited

OTHER PUBLICATIONS

Lindsay, J.A., Beaman, T.C., and Gerhardt, P. (1985). Protoplast water content of bacterial spores determined by buoyant density sedimentation. J. Bacteriol. 163(2), 735-737.
Liu, K., Linder, C.R., and Warnow, T. (2011). RAxML and FastTree: Comparing Two Methods for Large-Scale Maximum Likelihood Phylogeny Estimation. PLoS One 6(11), e27731.
Livingston, S.J., Kominos, S.D., and Yee, R.B. (1978). New medium for selection and presumptive identification of the Bacteroides fragilis group. J. Clin. Microbiol. 7(5), 448-453.
Lodish, H. et al., "Viruses: Structure, Function, and Uses," Molecular Cell Biology, 4th Edition, 2000, pp. 1-12.
Logan, N.A., "Bacillus and Relatives in Foodborne Illness," Journal of Applied Microbiology, Mar. 20, 2012, pp. 417-429, vol. 112, No. 3.
Lopetuso, L.R., Scaldaferri, F., Petito, V., and Gasbarrini, A. (2013). Commensal Clostridia: leading players in the maintenance of gut homeostasis. Gut Pathogens 5(1), 23.
Lozupone, C., Faust, K., Raes, J., Faith, J.J., Frank, D.N., Zaneveld, J., Gordon, J.I., and Knight, R. (2012). Identifying genomic and metabolic features that can underlie early successional and opportunistic lifestyles of human gut symbionts. Genome Res 22(10), 1974-1984.
Malik, K.A. (1988). A new freeze-drying method for the preservation of nitrogen-fixing and other fragile bacteria. Journal of Microbiological Methods 8(5), 259-271.
Manichanh, C. (2006). Reduced diversity of faecal microbiota in Crohn's disease revealed by a metagenomic approach. Gut 55(2), 205-211.
Matsuda, K. et al., "Sensitive Quantitative Detection of Commensal Bacteria by rRNA-Targeted Reverse Transcription-PCR," Applied and Environmental Microbiology, Jan. 2007, pp. 32-39, vol. 73, No. 1.
Mbithi, J.N., Springthorpe, V.S., and Sattar, S.A. (1990). Chemical disinfection of hepatitis A virus on environmental surfaces. Applied and Environmental Microbiology 56(11), 3601-3604.
McFarland, L.V. et al., "Pharmaceutical Probiotics for the Treatment of Anaerobic and Other Infections," Anaerobe, Jan. 1997, pp. 73-78, vol. 3, No. 2-3.
McFarland, L.V., "Use of Probiotics to Correct Dysbiosis of Normal Microbiota Following Disease or Disruptive Events: A Systematic Review," BMJ Open, 2014, pp. 1-18, vol. 4.
McGuire, G., Denham, M.C., and Balding, D.J. (2001). Models of Sequence Evolution for DNA Sequences Containing Gaps. Mol Biol Evol 18(4), 481-490.
McNulty, N.P., Yatsunenko, T., Hsiao, A., Faith, J.J., Muegge, B.D., Goodman, A.L., Henrissat, B., Oozeer, R., Cools-Portier, S., Gobert, G., et al. (2011). The impact of a consortium of fermented milk strains on the gut microbiome of gnotobiotic mice and monozygotic twins. Sci Transl Med 3(106), 106ra106.
Mevissen-Verhage, E.A., Marcelis, J.H., Vos, M.N. De, Amerongen, W.C.H., and Verhoef, J. (1987). *Bifidobacterium, Bacteroides*, and *Clostridium* spp. in fecal samples from breast-fed and bottle-fed infants with and without iron supplement. J. Clin. Microbiol. 25(2), 285-289.
Miller, R.S., and Hoskins, L.C. (1981). Mucin degradation in human colon ecosystems. Fecal population densities of mucin-degrading bacteria estimated by a "most probable number" method. Gastroenterology 81(4), 759-765.
Mireau, I. et al., "Industrial-Scale Production and Purification of a Heterologous Protein in Lactococcus Lactis Using the Nisin-Controlled Gene Expression System NICE: The Case of Lysostaphin," Microbial Cell Factories, May 27, 2005, pp. 1-9, vol. 4, No. 15.
Miyamoto-Shinohara, Y., Sukenobe, J., Imaizumi, T., Nakahara, T., and Others (2008). Survival of freeze-dried bacteria. The Journal of General and Applied Microbiology 54(1), 9.
Momose, Y. et al., "165 rRNA Gene Sequence-Based Analysis of Clostridia Related to Conversion of Germfree Mice to the Normal State, " Journal of Applied Microbiology, 2009, pp. 2088-2097, vol. 107.
Morgan, C.A., Herman, N., White, P.A., and Vesey, G. (2006). Preservation of micro-organisms by drying; A review. Journal of Microbiological Methods 66(2), 183-193.
Murri, M., Leiva, I., Gomez-Zumaquero, J.M., Tinahones, F.J., Cardona, F., Soriguer, F., and Queipo-Ortuño, M.I. (2013). Gut microbiota in children with type 1 diabetes differs from that in healthy children: a case-control study. BMC Med 11(1), 1-12.
Myllyluoma, E. et al., "Effects of Multispecies Probiotic Combination on Helicobacter pylori Infection in Vitro," Clinical and Vaccine Immunology, Sep. 2008, pp. 1472-1482, vol. 15, No. 9.
Naaber P et al "Inhibition of Clostridium difficile strains by intestinal *Lactobacillus* species" Journal of Medical Microbiology, 2004, pp. 551-554, vol. 53.
New Zealand Examination Report, New Zealand Application No. 713298, dated Sep. 26, 2017, 5 pages.
New Zealand First Examination Report, New Zealand Application No. 709392, dated Oct. 5, 2015, 7 pages.
New Zealand First Examination Report, New Zealand Application No. 711771, dated Nov. 23, 2015, 6 pages.
New Zealand First Examination Report, New Zealand Application No. 711773, dated Nov. 24, 2015, 6 pages.
New Zealand First Examination Report, New Zealand Application No. 713298, dated Feb. 28, 2017, 6 pages.
New Zealand Fourth Examination Report, New Zealand Application No. 713298, dated Mar. 15, 2018, 2 pages.
New Zealand Second Examination Report, New Zealand Application No. 709392, dated Jun. 9, 2016, 7 pages.
New Zealand Third Examination Report, New Zealand Application No. 711771, dated Nov. 4, 2016, 4 pages.
New Zealand Third Examination Report, New Zealand Application No. 713298, dated Feb. 15, 2018, 6 pages.
Nicholson, W.L., and Law, J.F. (1999). Method for purification of bacterial endospores from soils: UV resistance of natural Sonoran desert soil populations of< i>*Bacillus*</i> spp. with reference to< /i> B. subtilis</i> strain 168. Journal of Microbiological Methods 35(1), 13-21.
NIH human microbiome project. <http://www.hmpdacc.org/> Accessed Mar. 27, 2014.
Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).
Nitert, M.D., Barrett, H.L., Foxcroft, K., Tremellen, A., Wilkinson, S., Lingwood, B., Tobin, J.M., McSweeney, C., O'Rourke, P., McIntyre, H.D., et al. (2013). Spring: an RCT study of probiotics in the prevention of gestational diabetes mellitus in overweight and obese women. BMC Pregnancy and Childbirth 13(1), 50.
Noack, J., Kleessen, B., Proll, J., Dongowski, G., and Blaut, M. (1998). Dietary guar gum and pectin stimulate intestinal microbial polyamine synthesis in rats. J. Nutr. 128(8), 1385-1391.
Nyangale, et al., "Gut Microbial Activity, Implications for Health and Disease: the Potential Role of Metabolite Analysis," J. Proteome Res., 2012, pp. 5573-5585. vol. 11, No. 12.
O'Hara, C.M., Brenner, F.W., and Miller, J.M. (2000). Classification, identification, and clinical significance of Proteus, Providencia, and Morganella. Clin. Microbiol. Rev. 13(4), 534-546.
Okada, Y., Setoyama, H., Matsumoto, S., Imaoka, A., Nanno, M., Kawaguchi, M., and Umesaki, Y. (1994). Effects of fecal microorganisms and their chloroform-resistant variants derived from mice, rats, and humans on immunological and physiological characteristics of the intestines of ex-germfree mice. Infect. Immun. 62(12), 5442-5446.
Olle, B. (2013). Medicines from microbiota. Nat. Biotechnol. 31(4), 309-315.
Openbiome. Quality metrics. <http://static.squarespace.com/static/50e0c29ae4b0a05702af7e6a/t/52e19689e4b0b28f802c9b4e/1390517129976/OpenBiome%20Quality%20Metrics.pdf> Accessed Mar. 21, 2014.
Owens, C., Broussard, E., and Surawicz, C. (2013). Fecal microbiota transplantation and donor standardization. Trends in Microbiology 21(9), 443-445.
Paine, R.T. (1969). A note on trophic complexity and community stability. American Naturalist 103(929), 91-93.

(56) References Cited

OTHER PUBLICATIONS

Palmfeldt, J., and Hahn-Hägerdal, B. (2000). Influence of culture pH on survival of< i> Lactobacillus reuteri</i> subjected to freeze-drying. International Journal of Food Microbiology 55(1), 235-238.
Pamer, E.G. (2014). Fecal microbiota transplantation: effectiveness, complexities, and lingering concerns. Mucosal Immunology 7(2), 210-214.
Papadimitriou, K. et al., "Discovering Probiotic Microorganisms: In Vitro, In Vivo, Genetic and Omics Approaches," Frontiers in Microbiology, Feb. 17, 2015, pp. 1-28, vol. 6, Article 58.
Paredes-Sabja, D., Udompijitkul, P., and Sarker, M.R. (2009). Inorganic phosphate and sodium ions are cogerminants for spores of Clostridium perfringens type A food poisoning-related isolates. Appl. Environ. Microbiol. 75(19), 6299-6305.
Path Vaccine and Pharmaceutical Technologies Group. Summary of stability data for investigational formulations of vaccines. <http://www.path.org/publications/files/TS_vaccine_stability_table_invest.pdf> Accessed Mar. 21, 2014.
PCT International Search Report and Written Opinion, PCT Application No. PCT/US13/71758, dated May 5, 2014, 45 pages.
PCT International Search Report and Written Opinion, PCT Application No. PCT/US14/14738, dated Jul. 30, 2014, 32 pages.
PCT International Search Report and Written Opinion, PCT Application No. PCT/US14/14744, dated May 21, 2014, 36 pages.
PCT International Search Report and Written Opinion, PCT Application No. PCT/US14/14745, dated Jul. 30, 2014, 31 pages.
PCT International Search Report and Written Opinion, PCT Application No. PCT/US14/14747, dated Jun. 13, 2014, 27 pages.
PCT International Search Report and Written Opinion, PCT Application No. PCT/US14/70684, dated Jun. 10, 2015, 24 pages.
PCT International Search Report and Written Opinion, PCT Application No. PCT/US2014/029539, dated Oct. 10, 2014, 17 pages.
PCT International Search Report and Written Opinion, PCT Application No. PCT/US2014/030817, dated Dec. 5, 2014, 16 pages.
PCT International Search Report and Written Opinon, PCT Application No. PCT/US2014/067491, dated Apr. 2, 2015, 14 pages.
PCT Invitation to Pay Additional Fees, PCT Application No. PCT/US13/71758, dated Feb. 25, 2014, 4 pages.
PCT Invitation to Pay Additional Fees, PCT Application No. PCT/US14/14745, dated May 16, 2014, 2 pages.
PCT Invitation to Pay Additional Fees, PCT Application No. PCT/US14/29539, dated Jul. 31, 2014, 3 pages.
PCT Invitation to Pay Additional Fees, PCT Application No. PCT/US14/70684, dated Mar. 24, 2015, 2 pages.
PCT Invitation to Pay Additional Fees, PCT Application No. PCT/US2014/014738, dated May 16, 2014, 2 pages.
PCT Invitation to Pay Additional Fees, PCT Application No. PCT/US2014/030817, dated Sep. 8, 2014, 5 pages.
Peck, M.W et al., "Development and Application of a New Method for Specific and Sensitive Enumeration of Spores of Nonproteolytic Clostridium Botulinum Types B, E and F in Foods and Food Materials," Applied and Environmental Microbiology, Oct. 2010, pp. 6607-6614, vol. 76, No. 19.
Pehkonen, K.S., Roos, Y.H., Miao, S., Ross, R.P., and Stanton, C. (2008). State transitions and physicochemical aspects of cryoprotection and stabilization in freeze-drying of Lactobacillus rhamnosus GG (LGG). Journal of Applied Microbiology 104(6), 1732-1743.
Peighambardoust, S.H., Golshan Tafti, A., and Hesari, J. (2011). Application of spray drying for preservation of lactic acid starter cultures: a review. Trends in Food Science & Technology 22(5), 215-224.
Pellegrino, P.M., Fell Jr., N.F., and Gillespie, J.B. (2002). Enhanced spore detection using dipicolinate extraction techniques. Analytica Chimica Acta 455(2), 167-177.
Perez, F., Pultz, M.J., Endimiani, A., Bonomo, R.A., and Donskey, C.J. (2011). Effect of antibiotic treatment on establishment and elimination of intestinal colonization by KPC-producing Klebsiella pneumoniae in mice. Antimicrob. Agents Chemother. 55(6), 2585-2589.
Perez, J., Springthorpe, V.S., and Sattar, S.A. (2011). Clospore: a liquid medium for producing high titers of semi-purified spores of Clostridium difficile. J AOAC Int 94(2), 618-626.
Peterson, D.A. et al., "Metagenomic Approaches for Defining the Pathogenesis of Inflammatory Bowel Diseases," Cell Host Microbe, Jun. 2008, pp. 417-427, vol. 3, No. 6.
Petrof E. et al. Stool Substitute Transplant Therapy for the Eradication of C. diff infection. Microbiome 1(1)1-12, Jan. 2013.
Petrof, E.O et al., "Stool Substitute Transplant Therapy for the Eradication of Clostridium difficile Infection: RePOOPulating" The Gut Microbiome, Jan. 9, 2013, pp. 1-12, vol. 1, No. 3.
Petrof, E.O., Claud, E.C., Gloor, G.B., and Allen-Vercoe, E. (2013a). Microbial ecosystems therapeutics: a new paradigm in medicine? Beneficial Microbes 4(1), 53-65.
Petrof, E.O., Gloor, G.B., Vanner, S.J., Weese, S.J., Carter, D., Daigneault, M.C., Brown, E.M., Schroeter, K., and Allen-Vercoe, E. (2013b). Stool substitute transplant therapy for the eradication of Clostridium difficile infection: "RePOOPulating" the gut, Microbiome, Jan. 9, 2013, p. 3, vol. 1, No. 1.
Pharmacy, 2011, pp. 79-86, vol. 62, No. 3. [With English Main Sub-Points].
Picot, A., and Lacroix, C. (2004). Encapsulation of bifidobacteria in whey protein-based microcapsules and survival in simulated gastrointestinal conditions and in yoghurt. International Dairy Journal 14(6), 505-515.
Pillai, A. et al., "Probiotics for Treatment of Clostridium Difficile-Associated Colitis in Adults (Review)," Cochrane Database of Systematic Reviews, The Cochrane Collaboration, John Wiley & Sons, Ltd., 2010, 18 pages.
Pinn, D. et al. (2013). Follow-up Study of Fecal Microbiota Transplantation (FMT) for the Treatment of Refractory Irritable Bowel Syndrome (IBS). Abstract ACG 2013.
Plassart et al.(Anaerobe 19 (2013) 77-78).
Postgate, J.R., and Hunter, J.R. (1961). On the Survival of Frozen Bacteria. J Gen Microbiol 26(3), 367-378.
Prilassnig, M. et al., "Are Probiotics Detectable in Human Feces After Oral Uptake by Healthy Volunteers?" The Middle European Journal of Medicine, Aug. 2007, pp. 456-462, vol. 119, Nos. 15-16.
Prioult, G. et al., "Effect of Probiotic Bacteria on Induction and Maintenance of Oral Tolerance to β-Lactoglobulin in Gnotobiotic Mice," Clinical and Diagnostic Laboratory Immunology, Sep. 2003, pp. 787-792, vol. 10, No. 5.
Pultz, N.J., Hoyen, C.K., and Donskey, C.J. (2004). Inhibition of methicillin-resistant *Staphylococcus aureus* by an in vitro continuous-flow culture containing human stool microflora. FEMS Microbiology Letters 241(2), 201-205.
Queenan, A.M., and Bush, K. (2007). Carbapenemases: the Versatile β-Lactamases. Clin. Microbiol. Rev. 20(3), 440-458.
Quigley, E.M.M et al., "Small Intestinal Bacterial Overgrowth: Roles of Antibiotics, Prebiotics and Probiotics," Gastroenterology, Feb. 2006, pp. 78-90, vol. 130.
Raibaud, P., Ducluzeau, R., Dubos, F., Hudault, S., Bewa, H., and Muller, M.C. (1980). Implantation of bacteria from the digestive tract of man and various animals into gnotobiotic mice. Am J Clin Nutr 33(11), 2440-2447.
Ramirez, N., and Abel-Santos, E. (2010). Requirements for germination of Clostridium sordellii spores in vitro. J. Bacteriol. 192(2), 418-425.
Rao, A.V., Shiwnarain, N., and Maharaj, I. (1989). Survival of Microencapsulated Bifidobacterium pseudolongum in Simulated Gastric and Intestinal Juices. Canadian Institute of Food Science and Technology Journal 22(4), 345-349.
Reeves, A.E., Koenigsknecht, M.J., Bergin, I.L., and Young, V.B. (2012). Suppression of Clostridium difficile in the Gastrointestinal Tracts of Germfree Mice Inoculated with a Murine Isolate from the Family Lachnospiraceae. Infection and Immunity 80(11), 3786-3794.
Rehman, A. et al., "Effect of Probiotics and Antibiotics on the Intestinal Homeostasis in a Computer Controlled Model of the Large Intestine," BMC Microbiology, 2012, 10 pages, vol. 12, No. 47.

(56) References Cited

OTHER PUBLICATIONS

Rexroad, J., Wiethoff, C.M., Jones, L.S., and Middaugh, C.R. (2002). Lyophilization and the thermostability of vaccines. Cell Preservation Technology 1(2), 91-104.
Ridaura, V.K., Faith, J.J., Rey, F.E., Cheng, J., Duncan, A.E., Kau, A.L., Griffin, N.W., Lombard, V., Henrissat, B., Bain, J.R., et al. (2013). Gut Microbiota from Twins Discordant for Obesity Modulate Metabolism in Mice. Science 341(6150), 1241214-1241214.
Robinson, I.M. et al., "Emendation of Acetivibrio and Description of Acetivibrio ethanolgignens, a New Species from the Colons of Pigs with Dysentery," International Journal of Systematic Bacteriology, Jul. 1981, pp. 333-338, vol. 31, No. 3.
Rode, L.J., and Foster, J.W. (1961). Germination of bacterial spores with alkyl primary amines1. J Bacteriol 81(5), 768-779.
Roffe, C. (1996). Biotherapy for antibiotic-associated and other diarrhoeas. J. Infect. 32(1), 1-10.
Rohlke, F., Surawicz, C.M., and Stollman, N. (2010). Fecal flora reconstitution for recurrent Clostridium difficile infection: results and methodology. J. Clin. Gastroenterol. 44(8), 567-570.
Rosen, D.L., Sharpless, C., and McGown, L.B. (1997). Bacterial Spore Detection and Determination by Use of Terbium Dipicolinate Photoluminescence. Anal. Chem. 69(6), 1082-1085.
Russell, A.D., "The Destruction of Bacterial Spores," 1982, pp. 191-193.
Russian First Office Action, Russian Patent Application No. 2015124366, dated Dec. 13, 2016, 12 pages.
Russian Office Action, Russian Application No. 2015137399, dated Mar. 22, 2016, 8 pages.
Russian Second Office Action, Russian Application No. 2015124366, dated Feb. 12, 2018, 10 pages.
Russian Second Office Action, Russian Patent Application No. 2015137399, dated Mar. 14, 2017, 8 pages.
Sack, D.A., Shimko, J., Sack, R.B., Gomes, J.G., Macleod, K., O'Sullivan, D., and Spriggs, D. (1997). Comparison of alternative buffers for use with a new live oral cholera vaccine, Peru-15, in outpatient volunteers. Infect. Immun. 65(6), 2107-2111.
Sacks, L.E., and Alderton, G. (1961). Behavior of bacterial spores in aqueous polymer two-phase systems. J. Bacteriol. 82, 331-341.
Sahlström, L., Bagge, E., Emmoth, E., Holmqvist, A., Danielsson-Tham, M.-L., and Albihn, A. (2008). A laboratory study of survival of selected microorganisms after heat treatment of biowaste used in biogas plants. Bioresour. Technol. 99(16), 7859-7865.
Santivarangkna, C., Kulozik, U., and Foerst, P. (2007). Alternative Drying Processes for the Industrial Preservation of Lactic Acid Starter Cultures. Biotechnology Progress 23(2), 302-315.
Sattar, S.A., Jason, T., Bidawid, S., and Farber, J. (2000). Foodborne spread of hepatitis A: recent studies on virus survival, transfer and inactivation. The Canadian Journal of Infectious Diseases 11(3), 159.
Savaiano, D.A., Ritter, A.J., Klaenhammer, T., Walker, M.R., Carlson, H.L.F., and Ruckle, J. (2012). A Novel High Purity Short-Chain Galacto-Oligosaccharide (RP-G28) Improves Lactose Digestion and Symptoms of Lactose Intolerance. Gastroenterology 142(5), S-182.
Savaiano, D.A., Ritter, A.J., Klaenhammer, T.R., Walker, W.A., James, G.M., Longcore, A.T., Chandler, J.R., and Foyt, H.L. (2013). Improving lactose digestion and symptoms of lactose intolerance with a novel galacto-oligosaccharide (RP-G28): a randomized, double-blind clinical trial. Nutrition Journal 12(1), 160.
Seale, R.B., Flint, S.H., McQuillan, A.J., and Bremer, P.J. (2008). Recovery of Spores from Thermophilic Dairy Bacilli and Effects of Their Surface Characteristics on Attachment to Different Surfaces. Appl Environ Microbiol 74(3), 731-737.
Seo, M., Inoue, I., Tanaka, M., Matsuda, N., Nakano, T., Awata, T., Katayama, S., Alpers, D.H., and Komoda, T. (2013). Clostridium butyricum Miyairi 588 improves high-fat diet-induced non-alcoholic fatty liver disease in rats. Dig. Dis. Sci. 58(12), 3534-3544.
Setlow, B. et al., "Mechanisms of Killing Spores of Bacillus Subtilis by Acid, Alkali and Ethanol," Journal of Applied Microbiology, 2002, pp. 362-375, vol. 92.
Setlow, B., Cowan, A. E., and Setlow, P. (2003). Germination of spores of Bacillus subtilis with dodecylamine. Journal of Applied Microbiology 95(3), 637-648.
Setlow, B., Yu, J., Li, Y.-Q., and Setlow, P. (2013). Analysis of the germination kinetics of individual Bacillus subtilis spores treated with hydrogen peroxide or sodium hypochlorite. Letters in Applied Microbiology 57(4), 259-265.
Shafaat, H.S., and Ponce, A. (2006). Applications of a Rapid Endospore Viability Assay for Monitoring UV Inactivation and Characterizing Arctic Ice Cores. Appl. Environ Microbiol 72(10), 6808-6814.
Shah, I.M., Laaberki, M.-H., Popham, D.L., and Dworkin, J. (2008). A eukaryotic-like Ser/Thr kinase signals bacteria to exit dormancy in response to peptidoglycan fragments. Cell 135(3), 486-496.
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, N.P., "Symposium: Probiotic Bacteria: Probiotic Bacteria: Selective Enumeration and Survival in Dairy Foods," Oct. 7, 1999, 14 pages.
Shah, S. (2012). Clostridium difficile in inflammatory Bowel Disease: a dangerous mix (Clostridium difficile Symposium, Miriam Hospital, Providence, RI).
Shahinas, D., Silverman, M., Sittler, T., Chiu, C., Kim, P., Allen-Vercoe, E., Weese, S., Wong, A., Low, D.E., and Pillai, D.R. (2012). Toward an Understanding of Changes in Diversity Associated with Fecal Microbiome Transplantation Based on 16S rRNA Gene Deep Sequencing. mBio 3(5), e00338-12-e00338-12.
Sharpe, E.S., Nickerson, K.W., Bulla Jr, L.A., and Aronson, J.N. (1975). Separation of spores and parasporal crystals of Bacillus thuringiensis in gradients of certain x-ray contrasting agents. Applied Microbiology 30(6), 1052.
Sheu, T.-Y., Marshall, R.T., and Heymann, H. (1993). Improving Survival of Culture Bacteria in Frozen Desserts by Microentrapment. Journal of Dairy Science 76(7), 1902-1907.
Siaterlis, A., Deepika, G., and Charalampopoulos, D. (2009). Effect of culture medium and cryoprotectants on the growth and survival of probiotic lactobacilli during freeze drying. Letters in Applied Microbiology 48(3), 295-301.
Sigma-Tau. VSL#3. <http://www.vsl3.com/> Accessed Mar. 21, 2014.
Skaar, E., "The Battle for Iron Between Bacterial Pathogens and Their Vertebrate Hosts," PLoS Pathog., Aug. 12, 2010, pp. 1-4, vol. 6, No. 8.
Sleator, R.D. et al., "Designer Probiotics: A Potential Therapeutic for Clostridium difficile?" Journal of Medical Microbiology, Jun. 2008, pp. 793-794, vol. 57, No. 6.
Snitkin, E.S., Zelazny, A.M., Thomas, P.J., Stock, F., Henderson, D.K., Palmore, T.N., and Segre, J.A. (2012). Tracking a Hospital Outbreak of Carbapenem-Resistant Klebsiella pneumoniae with Whole-Genome Sequencing. Sci Transl Med 4(148), 148ra116-148ra116.
Solanki, H.K., Pawar, D.D., Shah, D.A., Prajapati, V.D., Jani, G.K., Mulla, A.M., and Thakar, P.M. (2013). Development of Microencapsulation Delivery System for Long-Term Preservation of Probiotics as Biotherapeutics Agent. BioMed Research International 2013, 1-21.
SOP No. MB-28-00. <http://www.epa.gov/pesticides/methods/MB-28-00.pdf> Accessed Mar. 27, 2014.
Sorg, J.A., and Sonenshein, A.L. (2008). Bile Salts and Glycine as Cogerminants for Clostridium difficile Spores. J Bacteriol 190(7), 2505-2512.
Sow, H., Desbiens, M., Morales-Rayas, R., Ngazoa, S.E., and Jean, J. (2011). Heat Inactivation of Hepatitis A Virus and a Norovirus Surrogate in Soft-Shell Clams (*Mya arenaria*). Foodborne Pathogens and Disease 8(3), 387-393.

(56) References Cited

OTHER PUBLICATIONS

Stams, A.J.M., Van Dijk, J.B., Dijkema, C., and Plugge, C.M. (1993). Growth of Syntrophic Propionate-Oxidizing Bacteria with Fumarate in the Absence of Methanogenic Bacteria. Appl Environ Microbiol 59(4), 1114-1119.
Stefka, A.T. et al., "Commensal Bacteria Protect Against Food Allergen Sensitization," PNAS, Sep. 9, 2014, pp. 13145-13150, vol. 111, No. 36.
Stevens, K.A., and Jaykus, L.-A. (2004). Bacterial Separation and Concentration from Complex Sample Matrices: A Review. Critical Reviews in Microbiology 30(1), 7-24.
Su, W.J., Waechter, M.J., Bourlioux, P., Dolegeal, M., Fourniat, J., and Mahuzier, G. (1987). Role of volatile fatty acids in colonization resistance to Clostridium difficile in gnotobiotic mice. Infect. Immun. 55(7), 1686-1691.
Talwalkar, A., and Kailasapathy, K. (2003). Effect of microencapsulation on oxygen toxicity in probiotic bacteria. Australian Journal of Dairy Technology 58(1), 36-39.
Tamir, H., and Gilvarg, C. (1966). Density Gradient Centrifugation for the Separation of Sporulating Forms of Bacteria. J. Biol. Chem. 241(5), 1085-1090.
Tanaka, M. et al., "Increased Fasting Plasma Ghrelin Levels in Patients with Bulimia Nervosa," European Journal of Endocrinology, Jun. 2002, pp. 1-3, vol. 146.
Taur, Y., and Pamer, E.G. (2014). Harnessing Microbiota to Kill a Pathogen: Fixing the microbiota to treat Clostridium difficile infections. Nature Medicine 20(3), 246-247.
Taur, Y., Xavier, J.B., Lipuma, L., Ubeda, C., Goldberg, J., Gobourne, A., Lee, Y.J., Dubin, K.A., Socci, N.D., Viale, A., et al. (2012). Intestinal Domination and the Risk of Bacteremia in Patients Undergoing Allogeneic Hematopoietic Stem Cell Transplantation. Clin Infect Dis 55(7), 905-914.
The Human Microbiome Project Consortium (2012). Structure, function and diversity of the healthy human microbiome. Nature 486(7402), 207-214.
Tisa, L.S., Koshikawa, T., and Gerhardt, P. (1982). Wet and dry bacterial spore densities determined by buoyant sedimentation. Applied and Environmental Microbiology 43(6), 1307-1310.
Tvede, M., and Rask-Madsen, J. (1989). Bacteriotherapy for chronic relapsing Clostridium difficile diarrhoea in six patients. Lancet 1(8648), 1156-1160.
Ubeda, C., Bucci, V., Caballero, S., Djukovic, A., Toussaint, N.C., Equinda, M., Lipuma, L., Ling, L., Gobourne, A., No, D., et al. (2013). Intestinal Microbiota Containing *Barnesiella* Species Cures Vancomycin-Resistant Enterococcus faecium Colonization. Infect. Immun. 81(3), 965-973.
Ubeda, C., Taur, Y., Jenq, R.R., Equinda, M.J., Son, T., Samstein, M., Viale, A., Socci, N.D., Van Den Brink, M.R.M., Kamboj, M., et al. (2010). Vancomycin-resistant Enterococcus domination of intestinal microbiota is enabled by antibiotic treatment in mice and precedes bloodstream invasion in humans. Journal of Clinical Investigation 120(12), 4332-4341.
United States Office Action, U.S. Appl. No. 14/091,201, dated Mar. 25, 2014, 19 pages.
United States Office Action, U.S. Appl. No. 14/197,044, dated Aug. 13, 2014, 5 pages.
United States Office Action, U.S. Appl. No. 14/221,190, dated Jul. 22, 2014, 19 pages.
United States Office Action, U.S. Appl. No. 14/313,828, dated Aug. 13, 2014, 5 pages.
United States Office Action, U.S. Appl. No. 14/313,828, dated Dec. 10, 2014, 7 papges.
United States Office Action, U.S. Appl. No. 14/313,828, dated May 15, 2015, 11 pages.
United States Office Action, U.S. Appl. No. 14/592,481, dated Dec. 22, 2015, 21 pages.
United States Office Action, U.S. Appl. No. 14/765,810, dated Jan. 23, 2017, 20 pages.
United States Office Action, U.S. Appl. No. 14/765,810, dated Jan. 25, 2018, 11 pages.
United States Office Action, U.S. Appl. No. 14/765,810, dated Jan. 8, 2018, 8 pages.
United States Office Action, U.S. Appl. No. 14/765,812, dated Aug. 25, 2016, 10 pages.
United States Office Action, U.S. Appl. No. 14/765,812, dated Dec. 7, 2017, 10 pages.
United States Office Action, U.S. Appl. No. 14/776,676, dated Mar. 23, 2017, 9 pages.
United States Office Action, U.S. Appl. No. 14/777,252, dated Aug. 29, 2017, 16 pages.
United States Office Action, U.S. Appl. No. 14/777,252, dated May 11, 2017, 9 pages.
United States Office Action, U.S. Appl. No. 14/777,252, dated Nov. 3, 2016, 16 pages.
United States Office Action, U.S. Appl. No. 14/884,655, dated Aug. 17, 2016, 9 pages.
United States Office Action, U.S. Appl. No. 14/884,655, dated May 5, 2016, 10 pages.
United States Office Action, U.S. Appl. No. 15/068,438, dated Apr. 28, 2016, 9 pages.
United States Office Action, U.S. Appl. No. 15/104,873, dated Oct. 17, 2017, 7 pages.
Van Der Woude, M.W., and Baumler, A.J. (2004). Phase and Antigenic Variation in Bacteria. Clin Microbiol Rev 17(3), 581-611.
Van Immerseel, F. et al., "Butyric Acid-Producing Anaerobic Bacteria as a Novel Probiotic Treatment Approach for Inflammatory Bowel Disease," Journal of Medical Microbiology, JMM Editorial, 2010, pp. 141-143.
Van Kregten, E., Westerdaal, N.A., and Willers, J.M. (1984). New, simple medium for selective recovery of Klebsiella pneumoniae and Klebsiella oxytoca from human feces. J Clin Microbiol 20(5), 936-941.
Van Nood, E., Vrieze, A., Nieuwdorp, M., Fuentes, S., Zoetendal, E.G., De Vos, W.M., Visser, C.E., Kuijper, E.J., Bartelsman, J.F.W. M., Tijssen, J.G.P., et al. (2013). Duodenal Infusion of Donor Feces for Recurrent Clostridium difficile. New England Journal of Medicine 368(5), 407-415.
Vandenplas, Y., Veereman, G., Van Der Werff Ten Bosch, J., Goossens, A., Pierard, D., Samsom, J.N., and Escher, J.C. (2014). Fecal Microbial Transplantation in a One-Year-Old Girl with Early Onset Colitis-Caution Advised: Journal of Pediatric Gastroenterology and Nutrition 1.
Vidal, M., Forestier, C., Charbonnel, N., Henard, S., Rabaud, C., and Lesens, O. (2010). Probiotics and Intestinal Colonization by Vancomycin-Resistant Enterococci in Mice and Humans. J Clin Microbiol 48(7), 2595-2598.
Villano, S.A., Seiberling, M., Tatarowicz, W., Monnot-Chase, E., and Gerding, D.N. (2012). Evaluation of an Oral Suspension of VP20621, Spores of Nontoxigenic Clostridium difficile Strain M3, in Healthy Subjects. Antimicrobial Agents and Chemotherapy 56(10), 5224-5229.
Wagman, J., and Weneck, E.J. (1963). Preservation of bacteria by circulating-gas freeze drying. Applied Microbiology 11(3), 244-248.
Waites, W.M., and Wyatt, L.R. (1971). Germination of spores of Clostridium bifermentans by certain amino acids, lactate and pyruvate in the presence of sodium or potassium ions. J. Gen. Microbiol. 67(2), 215-222.
Waites, W.M., and Wyatt, L.R. (1974). The effect of pH, germinants and temperature on the germination of spores of Clostridium bifermentans. J. Gen. Microbiol. 80(1), 253-258.
Walker, A.W., and Lawley, T.D. (2012). Therapeutic modulation of intestinal dysbiosis. Pharmacological Research 69(1), 75-86.
Wang, M. et al., "Comparison of Bacterial Diversity Along the Human Intestinal Tract by Direct Cloning and Sequencing of 16S rRNA Genes," FEMS Microbiology Ecology, 2005, pp. 219-231, vol. 54.
Wang, S., and Curtiss III, R. (2014). Development of *Streptococcus pneumoniae* Vaccines Using Live Vectors. Vaccines 2(1), 49-88.
Weingarden, A.R., Chen, C., Bobr, A., Yao, D., Lu, Y., Nelson, V.M., Sadowsky, M.J., and Khoruts, A. (2013). Microbiota transplantation

(56) References Cited

OTHER PUBLICATIONS restores normal fecal bile acid composition in recurrent Clostridium difficile infection. AJP: Gastrointestinal and Liver Physiology 306(4), G310-G319.

Wiencek, K.M. et al., "Hydrophobicity of Bacillus and Clostridium Spores," Applied and Environmental Microbiology, Sep. 1990, pp. 2600-2605, vol. 56, No. 9.

Wilson, K. et al., "Role of Competition for Nutrients in Suppression of Clostridium difficile by the Colonic Microflora," Infection and Immunity, Oct. 1988, pp. 2610-2614, vol. 56, No. 10.

Wilson, K.H., and Sheagren, J.N. (1983). Antagonism of toxigenic Clostridium difficile by nontoxigenic C. difficile. Journal of Infectious Diseases 147(4), 733.

Wilson, K.H., Silva, J., and Fekety, F.R. (1981). Suppression of Clostridium difficile by Normal Hamster Cecal Flora and Prevention of Antibiotic-Associated Cecitis. Infect Immun 34(2), 626-628.

Woo, T.D.H., Oka, K., Takahashi, M., Hojo, F., Osaki, T., Hanawa, T., Kurata, S., Yonezawa, H., and Kamiya, S. (2011). Inhibition of the cytotoxic effect of Clostridium difficile in vitro by Clostridium butyricum Miyairi 588 strain. J. Med. Microbiol. 60(Pt 11), 1617-1625.

Wróbel, B. (2008). Statistical measures of uncertainty for branches in phylogenetic trees inferred from molecular sequences by using model-based methods. J. Appl. Genet. 49(1), 49-67.

Wroblewski, D., Hannett, G.E., Bopp, D.J., Dumyati, G.K., Halse, T.A., Dumas, N.B., and Musser, K.A. (2009). Rapid Molecular Characterization of Clostridium difficile and Assessment of Populations of C. difficile in Stool Specimens. Journal of Clinical Microbiology 47(7), 2142-2148.

Yamakawa, K. et al., "Enhancement of Clostridium difficile Toxin Production in Biotin-Limited Conditions," J. Med. Microbiol., Feb. 1996, pp. 111-114, vol. 44, No. 2.

Yamamura, H., Hayakawa, M., and Iimura, Y. (2003). Application of sucrose-gradient centrifugation for selective isolation of *Nocardia* spp. from soil. Journal of Applied Microbiology 95(4), 677-685.

Yang, W.W. (2010). Fast Viability Assessment of Clostridium Spores Survival in Extreme Environments. PhD thesis California Institute of Technology.

Yang, W.-W., and Ponce, A. (2009). Rapid endospore viability assay of Clostridium sporogenes spores. International Journal of Food Microbiology 133(3), 213-216.

Yang, W.-W., and Ponce, A. (2011). Validation of a Clostridium Endospore Viability Assay and Analysis of Greenland Ices and Atacama Desert Soils. Appl. Environ. Microbiol. 77(7), 2352-2358.

Yang, W.-W., Crow-Willard, E.N., and Ponce, A. (2009). Production and characterization of pure Clostridium spore suspensions. J. Appl. Microbiol. 106(1), 27-33.

Yi, X., and Setlow, P. (2010). Studies of the Commitment Step in the Germination of Spores of *Bacillus* Species. J. Bacteriol. 192(13), 3424-3433.

Yuguchi Hiroya et al., "Hakkonyuu/nyuusankin inryou to chounaikinsou "Fermented Milk/Lactic Acid Bacteria Beverages and Intestinal Bacterial Flora,"" New Food Industry, UDA, Moritaka, New Food Industry K.K., 1987, pp. 71-88, vol. 29, No. 7. [With English Subtitle Translations].

Yung, P.T., and Ponce, A. (2008). Fast Sterility Assessment by Germinable-Endospore Biodosimetry. Appl. Environ. Microbiol. 74(24), 7669-7674.

Yunoki, M., Tsujikawa, M., Urayama, T., Sasaki, Y., Morita, M., Tanaka, H., Hattori, S., Takechi, K., and Ikuta, K. (2003). Heat sensitivity of human parvovirus B19. Vox Sanguinis 84(3), 164-169.

Zeng, Y., Fan, H., Chiueh, G., Pham, B., Martin, R., Lechuga-Ballesteros, D., Truong, V.L., Joshi, S.B., and Middaugh, C.R. (2009). Towards development of stable formulations of a live attenuated bacterial vaccine: a preformulation study facilitated by a biophysical approach. Hum Vaccin 5(5), 322-331.

Zhao, J., Krishna, V., Moudgil, B., and Koopman, B. (2008). Evaluation of endospore purification methods applied to Bacillus cereus. Separation and Purification Technology 61(3), 341-347.

Office action dated Nov. 1, 2017, in U.S. Appl. No. 15/039,007, inventor Henn; Matthew, R., et al., filed May 24, 2016, 12 pages.

Office action dated Jun. 12, 2018, in U.S. Appl. No. 15/039,007, inventor Henn; Matthew, R., et al., filed May 24, 2016, 9 pages.

14th International Congress of Immunology, Kobe, Japan, International Immunology, Aug. 2010, 3 pages, vol. 22, Issue Suppl 1 Pt 3.

Abt, M.C., et al., "Commensal Bacteria Calibrate the Activation Threshold of Innate Antiviral Immunity," Immunity, 37(1):158-170, Cell Press, United States, ( Jul. 2012 ).

Anonymous, "Ecobiotic Drugs," Seres Therapeutics, Oct. 22, 2015,http://web.archive.org/web/20151 022091731 /http://web.archive.org/web/20151ecobiotic-drugs, retrieved Mar. 7, 2017 (3 pages).

Anonymous, "Microbiome Therapeutics Platform," Seres Therapeutics, Retrieved on [Oct. 23, 2015], Retrieved from (http://web.archive.org/web/20 151023063153/), Retrieved from (http://www.serestherapeutics.com/ou rscience/ microbiome-therapeutics-platform), Retrieved on [Mar. 7, 2017], 3 pages.

Anonymous, "Product Pipeline," Seres Therapeutics, Oct. 22, 2015], Retrived from (<http:web.="" arch="" ive.org="" web="" 20="" 151="" 022091722="" http:="" http://www.serestherapeutics.com/pipeline/products)</http:>, Retrieved on [Mar. 7, 2017], (3 pages).

Arpaia, N., et al., "Metabolites Produced by Commensal Bacteria Promote Peripheral Regulatory T-cell Generation," Nature 504(7480):451-455, Nature Publishing Group, England (Dec. 2013).

Bajaj, J.S., et al., "Colonic Mucosal Microbiome Differs From Stool Microbiome in Cirrhosis and Hepatic Encephalopathy and is Linked to Cognition and Inflammation.," American Journal of Physiology. Gastrointestinal and Liver Physiology, 303(6):75-85, American Physiological Society, United States, (Sep. 2012).

Barrasa, J.I., et al., "Bile Acids in the Colon, From Healthy to Cytotoxic Molecules.," Toxicology in Vitro : an International Journal Published in Association With Bibra, 27(2):964-977, Pergamon Press , England, (Mar. 2013).

Bartlett, J.G., et al., "Antibiotic-associated Pseudomembranous Colitis Due to Toxin-Producing Clostridia," The New England journal of medicine, 298(10):531-534, Massachusetts Medical Society, United States , (Mar. 1978 ).

Begley et al., "Bile Salt Hydrolase Activity in Probiotics," Appl. Environ Microbial. 72(3): I729-173 8 (2006).

Bergey's Manual of Determinative Bacteriology, Ninth Edition, John G. Holt et al., Williams & Wilkins, 1994, pp. 527, 531, 577, 579 (6 pages total).

Borody, T,J., et al., "Treatment of Ulcerative Colitis Using Fecal Bacteriotherapy," Journal of Clinical Gastroenterology 37(1):42-47, Wolters Kluwer Health, Inc, United States (Jul. 2003).

Brandl et al., "Vancomycin-resistant enterococci exploit anti biotic-induced innate immune deficit,". Nature 455(7214):804-807 (2008).

Britton, R.A., et al., "Role of the Intestinal Microbiota in Resistance to Colonization by Clostridium Difficile," Gastroenterology 146(6):1547-1553, W.B. Saunders, United States (May 2014).

Browne, H,P., et al., "Culturing of 'unculturable' Human Microbiota Reveals Novel Taxa and Extensive Sporulation," Nature 533(7604):543-546, Nature Publishing Group, England (May 2016).

Buffie, C. G., et al. , "Precision Microbiome Reconstitution Restores Bile Acid Mediated Resistance to Clostridium Difficile, " Nature 517(7533):205-208, Nature Publishing Group, England (Jan. 2015).

Carlier, J.P., et al., "Proposal to Unify Clostridium Orbiscindens Winter et al. 1991 and Eubacterium Plautii (Séguin 1928) Hofstad and Aasjord 1982, With Description of *Flavonifractor plautii* Gen. Nov., Comb. Nov., and Reassignment of *Bacteroides capillosus* to *Pseudoflavonifractor capillosus* Gen. Nov., Comb. Nov.," International Journal of Systematic and Evolutionary Microbiology 60(Pt 3):585-590, Microbiology Society, England (Mar. 2010).

Chen, X., et al., "Overview of Clostridium Difficile Infection: Implications for China," Gastroenterology Report, 1(3):153-158, Oxford University Press and Science Digestive, England, (Nov. 2013).

Clifford, R.J.,et al., "Detection of Bacterial 16s Rrna and Identification of Four Clinically Important Bacteria by Real-time Pcr.," Plos One, 7(11):48558, Public Library of Science, United States, (2012).

Collins, M,D., et al., "The Phylogeny of the Genus *Clostridium*: Proposal of Five New Genera and Eleven New Species Combina-

(56) References Cited

OTHER PUBLICATIONS tions," International Journal of Systematic Bacteriology 44(4):812-826, Society for General Microbiology, England (Oct. 1994).
Dabard J., et al., "Ruminococcin A, a New lantibiotic Produced by a Ruminococcus Gnavus Strain Isolated from Human Feces," Applied and Environmental Microbiology, 67(9):4111-4118, American Society for Microbiology, United States (Sep. 2001).
De Aguiar Vallim, T.Q., et al., "Pleiotropic Roles of Bile Acids in Metabolism," Cell Metabolism, 17(5):657-669, Cell Press, United States, (May 2013).
Derrien, M.,et al., "Modulation of Mucosal Immune Response, Tolerance, and Proliferation in Mice Colonized by the Mucin-degrader Akkermansia Muciniphila.," Frontiers in Microbiology, 2:166, Frontiers Research Foundation, Switzerland., (Aug. 2011).
Derrien, M.,et al., "Mucin-bacterial Interactions in the Human Oral Cavity and Digestive Tract.," Gut Microbes, 1(4):254-268, PA : Taylor & Francis, United States, (Jul. 2010).
Dewhirst, F.E., et al., "Phylogeny of the Defined Murine Microbiota: Altered Schaedler Flora," Applied and Environmental Microbiology 65(8):3287-3292, American Society for Microbiology, United States (Aug. 1999).
Duan, J., et al., "Microbial Colonization Drives Expansion of Il-1 Receptor 1-expressing and Il-17-producing Gamma/delta T Cells," Cell host & microbe, 7(2):140-150, Cell Press, United States, (Feb. 2010).
Eeckhaut, V., et al., "The Anaerobic Butyrate-producing Strain Butyricicoccus Pullicaecorum Decreases Colonic Inflammation and Ulceration in a Tnbs-induced Colitis Rat Model," 5th Probiotics, Prebiotics and New Foods Congress, 2009,1 page.
Elhage, R. et al., "Emerging Trends in "Smart Probiotics": Functional Consideration for the Development of Novel Health and Industrial Applications," Frontiers in Microbiology, Sep. 2017, pp. 1-11, vol. 8, Article 1889.
Evidence of Effects of Probiotics Against Antimicrobial-Related Diarrhea, Pharmacy, Paper, 12 pages, (2011).
Farache, J., et al., "Luminal Bacteria Recruit Cd103+ Dendritic Cells Into the Intestinal Epithelium to Sample Bacterial Antigens for Presentation," Immunity, 38(3):581-595, Cell Press, United States, (Mar. 2013).
Ferreira, R.B., et al., "The Intestinal Microbiota Plays a Role in *Salmonella*-induced Colitis Independent of Pathogen Colonization," Plos One, 6(5):e20338, Public Library of Science, United States, (May 2011).
Fitzpatrick, L.R., "Probiotics for the treatment of Clostridium difficile associated disease", World Journal of Gastrointestinal Pathophysiology, 4(3): 47-52, Baishideng Publishing Group, United States (Aug. 2013).
Foditsch, C., et al., "Isolation and Characterization of Faecalibacterium prausnitzii from Calves and Piglets," PLOS One, 9(12):e116465, Public Library of Science, United States (Dec. 31, 2014).
Frank, D.N., et al., "Molecular-phylogenetic Characterization of Microbial Community Imbalances in Human Inflammatory Bowel Diseases," Proceedings of the National Academy of Sciences of the United States of America 104(34):13780-13785, National Academy of Sciences, United States (Aug. 2007).
Furusawa, Y., et al., "Commensal Microbe-derived Butyrate Induces the Differentiation of Colonic Regulatory T Cells ," Nature 504(7480):446-450, Nature Publishing Group, England (Dec. 2013).
Gaboriau-Routhiau, V., et al., "The Key Role of Segmented Filamentous Bacteria in the Coordinated Maturation of Gut Helper T Cell Responses," Immunity 31(4):677-689, Cell Press, United States (Oct. 2009).
Geuking, M.B., et al., "Intestinal Bacterial Colonization Induces Mutualistic Regulatory T Cell Responses," Immunity 34(5):794-806, Cell Press, United States (May 2011).
Giel, J.L., et al., "Metabolism of Bile Salts in Mice Influences Spore Germination in Clostridium Difficile," Plos One, 5(1):e8740, Public Library of Science, United States, (Jan. 2010).
Hayashi, H., et al., "Phylogenetic Analysis of the Human Gut Microbiota Using 16s Rdna Clone Libraries and Strictly Anaerobic Culture-based Methods," Microbiology and Immunology 46(8):535-548, Wiley-Blackwell, Australia (2002).
Heeg, D et al., "Spores of Clostridium difficile Clinical Isolates Display a Diverse Germination Response to Bile Salts," PLoS One 7(2):e32381 (2012).
Hill, D.A., et al., "Commensal bacteria-derived signals regulate basophil hematopoiesis and allergic inflammation, " Nat Med., 18(4):538-546 (2012).
Holdeman, L,V., et al., "Human Fecal Flora: Variation in Bacterial Composition Within Individuals and a Possible Effect of Emotional Stress," Applied and Environmental Microbiology 31(3):359-375, American Society for Microbiology, United States (Mar. 1976).
Honda, K., et al., "Regulations of T cell reponses by intestinal commensal bacteria," Journal of Intestinal Microbiology 25(2):103-104, (Apr. 2011).
Ivanov, I.I., et al., "Induction of intestinal Th 17 cells by segmented filamentous bacteria," Cell, 139(3):485-498 (2009).
Ivanov, I.I., et al., "Specific Microbiota Direct the Differentiation of Il-17-Producing T-Helper Cells in the Mucosa of the Small Intestine," Cell Host Microbe 4(4):337-349, Cell Press, United States (Oct. 2008) including supplemental data.
Jawetz, et al., "Chapter 11: Spore-Forming Gram-Positive Bacilli: *Bacillus* and *Clostridium* Species," Jawetz, Melnick&Adelberg's Medical Microbiology, 26e:1-15 (Mar. 7, 2017).
Zhou, D., et al., "Total Fecal Microbiota Transplantation Alleviates Highfat Diet-Induced Steatohepatitis in Mice via Beneficial Regulation of Gut Microbiota," Scientific Reports 7(1):11 pages, Nature Publishing Group, England (May 2017).
Jenq et al., "Intestinal Blautia Is Associated with Reduced Death from Graft-versus-Host Disease," Biology ofBlood and Marrow Transplantation 21:1373-1383 (2015).
Jenq et al., "Regulation of intestinal inflammation by microbiota following allogeneic bone marrow transplantation," J Exp. Med. 209(5):903-911 (2012).
Kakihana, K., et al., "Fecal Microbiota Transplantation for Patients with Steroid-Resistant Acute Graft-Versus-Host Disease of the Gut," Blood 128(16):2083-2088, American Society of Hematology, United States (Oct. 2016).
Kang, D.J., et al., "Clostridium scindens baiCD and baiH genes encode stereo-specific 7a/7~-hydroxy-3-oxo-114-cholenoic acid oxidoreductases," Biochim Biophys Acta 1781(1-2): 16-25 (2008).
Kelly, D., et al., "Commensal Gut Bacteria: Mechanisms of Immune Modulation ," Trends in Immunology 26(6):326-333, Elsevier Science Ltd, England (Jun. 2005).
Kitahara, M., et al., "Assignment of *Eubacterium* sp. VPI 12708 and Related Strains with High Bile Acid 7alpha-dehydroxylating Activity to Clostridium Scindens and Proposal of *Clostridium hylemonae* sp. nov., Isolated from Human Faeces," International Journal of Systematic and Evolutionary Microbiology 50(3):971-978, Microbiology Society, England (May 2000).
Lawson, P.A., "Anaerotruncus," Bergey's Manual of Systematics of Archaea and Bacteria, Bergey's Manual Trust, 2009, pp. 1-4.
Liu, C., et al., "Reclassification of *Clostridium coccoides, Ruminococcus hansenii, Ruminococcus hydrogenotrophicus, Ruminococcus luti, Ruminococcus* Productus and *Ruminococcus schinkii* as *Blautia coccoides* Gen. Nov., Comb. Nov., *Blautia hansenii* Comb. Nov., *Blautia hydrogenotrophica* Comb. Nov., *Blautia luti* Comb. Nov., *Blautia producta* Comb. Nov., *Blautia schinkii* Comb. Nov. And Description of *Blautia wexlerae* Sp. Nov., Isolated From Human Faeces," International Journal of Systematic and Evolutionary Microbiology 58(Pt 8):1896-1902, Microbiology Society, England (Aug. 2008).
Louis, P and Flint, H.J., "Diversity, Metabolism and Microbial Ecology of Butyrate-producing Bacteria From the Human Large Intestine," FEMS Microbiology Letters 294(1):1-8, Oxford University Press, England (May 2009).
Maslowski, K.M. et al., "Diet, Gut Microbiota and Immune Responses," Nature Immunology, Jan. 2011, pp. 5-9, vol. 12, No. 1.
Maynard et al., "Reciprocal interactions of the intestinal microbiota and immune system," Nature 489:231-241 (2012).

(56) References Cited

OTHER PUBLICATIONS

Morris, G.N., et al., "*Clostridium scindens* sp. nov., A Human Intestinal Bacterium with Desmolytic Activity on Corticoids," International Journal of Systematic and Evolutionary Microbiology 35(4):478-481, (Oct. 1985).
Narushima, S., et al., "Characterization of the 17 Strains of Regulatory T Cell-Inducing Human-Derived Clostridia," Gut Microbes 5(3):333-339, Taylor & Francis, United States (May-Jun. 2014).
Park et al., "*Blautia faecis* sp. nov., isolated from human faeces," Int J Syst Evol Microbial. 63:599-603 (2013).
Qiu, X., et al., "Faecalibacterium prausnitzii Upregulates Regulatory T Cells and Anti- Inflammatory Cytokines In Treating TNBS-Induced Colitis," Crohn's and Colitis 7(11):e558-e568, Elsevier Science, England (Dec. 2013 ).
Rakoff-Nahoum, S., et al., "Recognition of Commensal Microflora by Toll-like Receptors is Required for Intestinal Homeostasis," Cell, 118(2):229-241, Cell Press, United States, (Jul. 2004).
Rasti et al., "Inhibition of Clostridium scindens and Clostridium hiranonis growth by Bifidobacterium pseudocatenulatum G4 in simulated colonic pH," Journal of Food Agriculture and Environment 11 (2): 127-131, WFL Publisher Ltd, Poland (2013).
Reeves, A.E.,et al., "The Interplay Between Microbiome Dynamics and Pathogen Dynamics in a Murine Model of Clostridium Difficile Infection.," Gut Microbes, 2(3):145-158, Philadelphia, PA : Taylor & Francis, (May 2011).
Ridlon, J.M., et al., "Clostridium Scindens: a Human Gut Microbe With a High Potential to Convert Glucocorticoids Into Androgens.," Journal of Lipid Research, 54(9):2437-2449, American Society for Biochemistry and Molecular Biology, United States, (Sep. 2013).
Rossen, N.G., et al., "Findings From a Randomized Controlled Trial of Fecal Transplantation for Patients With Ulcerative Colitis.," Gastroenterology, 149(1):110-118, W.B. Saunders, United States (Jul. 2015).
Rossi, O., et al., "Faecalibacterium Prausnitzii A2-165 has a High Capacity to Induce IL-10 in Human and Murine Dendritic Cells and Modulates T Cell Responses," Scientific Reports 6:12 pages, (Jan. 2015).
Salzman et al., "Analysis of 16S libraries of mouse gastrointestinal microflora reveals a large new group of mouse intestinal bacteria," Microbiology 148:3651-3660 (2002).
Sartor, R.B., "Therapeutic Correction of Bacterial Dysbiosis Discovered by Molecular Techniques," Proceedings of the National Academy of Sciences of the United States of America 105(43):16413-16414, National Academy of Sciences, United states (Oct. 2008).
Sokol, H., et al., "Faecalibacterium Prausnitzii Is an Anti-Inflammatory Commensal Bacterium Identified By Gut Microbiota Analysis of Crohn Disease Patients," Proceedings of the National Academy of Sciences 105(43):16731-16736, National Academy of Sciences, United States (Oct. 2008).
Sokol, H., et al., "Low Counts of Faecalibacterium Prausnitzii in Colitis Microbiota," Inflammatory Bowel Diseases 15(8):1183-1189, Lippincott Williams & Wilkins, nited States (Aug. 2009).
Stackebrandt, E., et al., "Taxonomic Note: A Place for DNA-DNA Reassociation and 16s IRNA Sequence Analysis in the Present Species Definition in Bacteriology ," International Journal of Systematic Bacteriology 44 (4):846-849, (Oct. 1994).
Takaishi, H., et al., "Imbalance in Intestinal Microflora Constitution Could Be Involved In the Pathogenesis of Inflammatory Bowel Disease," International Journal of Medical Microbiology 298(5-6):463-572, Urban & Fischer Verlag, Germany (Jul. 2008 ).
Thompson-Chagoyan, O.C., et al., "Aetiology of Inflammatory Bowel Disease (IBD): Role of Intestinal Microbiota and Gut-associated Lymphoid Tissue Immune Response," Clinical Nutrition, 24(3):339-352, Elsevier,England (Feb. 2005).
Wells, C.L. et al., Chapter 18: Clostridia: Sporeforming Anaerobic Bacilli, Medical Microbiology, 4th Edition, 1996, pp. 1-20.
Abubucker, S., et al., "Metabolic Reconstruction for Metagenomic Data and Its Application to the Human Microbiome.," Plos Computational Biology, 8(6):1002358, Public Library of Science, United States, (2012).
Ahern et al., "The interleukin-23 axis m intestinal inflammation," Immunological Reviews 226:147-159 (2008).
Ahmad, T., et al., "Biomarkers of Myocardial Stress and Fibrosis as Predictors of Mode of Death in Patients With Chronic Heart Failure.," Jacc. Heart Failure, 2(3):260-268, Elsevier,United States, (Jun. 2014).
Altschul, S.F., et al., "Basic Local Alignment Search Tool," Journal of Molecular Biology 215(3):403-410, Elsevier, England (Oct. 1990).
Altschul, S.F., et al., "Gapped BLAST and PSI-BLAST: A New Generation of Protein Database Search Programs," Nucleic Acids Research 25(17):3389-3402, Oxford University Press, England (Sep. 1997).
Andoh, A., et al., "Terminal Restriction Fragment Polymorphism Analyses of Fecal Microbiota in Five Siblings Including Two with Ulcerative Colitis," Gastroenterology 2(5):343-345, Springer Japan (Oct. 2009).
Application as Filed WO 2011/152566, Filed Jun. 3, 2011, 151 pages.
ASBMT RFI 2016—Disease Classifications Corresponding to CIBMTR Classifications. 2016.
Atarashi, K. et al., Supporting Online Material for "Induction of Colonic Regulatory T Cells by Indigenous *Clostridium* Species," Science Express, Dec. 23, 2010, 26 pages.
Atta, "Gene therapy for liver regeneration: Experimental studies and prospects for clinical trials," World J Gastroenterol., 16(32):4019-4030 (20I0).
Autoimmune Disease List, There Are More Than 100 Autoimmune Diseases, American Autoimmune Related Diseases Association, AARDA, Inc., 2014, 4 pages.
Babel, N.et al., "Analysis ofT Cell Receptor Repertoire by Newly Established CDR3 High-Throughput Sequencing Allows for Monitoring/Tracing of Antigen-Specific T Cells in Peripheral Blood and Tissue," pp. 063-40, 141h ICI Abstract Book, 141h International Congress of Immunology, 2010, 3 pages.
Bacigalupo, A.,et al., "Defining the Intensity of Conditioning Regimens: Working Definitions.," Biology of Blood and Marrow Transplantation : Journal of the American Society for Blood and Marrow Transplantation, 15(12): 1628-1633, Carden Jennings Publishing, United States, (Dec. 2009).
Barrell, C.,et al., "Reduced-intensity Conditioning Allogeneic Stem Cell Transplantation in Pediatric Patients and Subsequent Supportive Care.," Oncology Nursing Forum, 39(6):451-458, Oncology Nursing Society, United States, (Nov. 2012).
Basler, M., et al., "Tit-for-tat: Type Vi Secretion System Counterattack During Bacterial Cell-cell Interactions," Cell, 152(4):884-894, Cell Press, United States, (Feb. 2013 ).
Basler, M., et al., "Type Vi Secretion Requires a Dynamic Contractile Phage Tail-like Structure," Nature, 483(7388):182-186, Nature Publishing Group, England, (Feb. 2012 ).
Beelen et al., "Influence of Intestinal Bacterial Decontamination Using Metronidazole and Ciprofloxacin or Ciprofloxacin Alone on the Development of Acute Graft-Versus-Host Disease After Marrow Transplantation in Patients with Hematologic Malignancies: Final Results and Long-Term Follow-Up of an Open-Label Prospective Randomized Trial," Blood 93(10):3267-3275 (1999).
Belkaid, Y, and Rouse, B,T., "Natural Regulatory T Cells in Infectious Disease," Nature Immunology 6(4):353-360, Nature America Inc, United States (Apr. 2005).
Bernstein, H., et al., "Bile Acids as Carcinogens in Human Gastrointestinal Cancers.," Mutation research, 589(1):47-65, Elsevier, Netherlands, (Jan. 2005).
Bolger, A.M.,et al., "Trimmomatic: a Flexible Trimmer for Illumina Sequence Data.," Bioinformatics (Oxford, England), 30(15):2114-2120, Oxford University Press,England, (Aug. 2014).
Buffie, C.G., et al., "Profound Alterations of Intestinal Microbiota Following a Single Dose of Clindamycin Results in Sustained Susceptibility to Clostridium Difficile-induced Colitis," Infection and Immunity, 80(1):62-73, American Society For Microbiology, United States, (Jan. 2012 ).
Caballero, S. et al. "Distinct but Spatially Overlapping Intestinal Niches for Vancomycin-Resistant Enterococcus faecium and

(56) References Cited

OTHER PUBLICATIONS

Carbapenem-Resistant Klebsiella Pneumoniae" PLOS Pathogens 11(9):e1005132, Public Library of Science, United States (2015).
Caporaso, J.G., et al., "QIIMEAllows Analysis of High-throughput Community Sequencing Data," Nature Methods, 7(5):335-336, Nature Publishing Group, United States, (May 2010 ).
Caporaso, J.G., et al., "Ultra-High-Throughput Microbial Community Analysis on the Illumina Hiseq and Miseq Platforms," The Isme Journal, 6(8):1621-1624, Nature Publishing Group, England, (Aug. 2012).
Casula, G. and Cutting, S.M., "Bacillus Probiotics: Spore Germination in the Gastrointestinal Tract," Applied and Environmental Microbiology 68(5):2344-2352, American Society for Microbiology, United States (May 2002).
Cato, E.P., et al., "Clostridium Oroticum Comb. Nov. Amended Description," International Journal of Systematic and Evolutionary Microbiology 17(1):9-13, (Jan. 1968).
Certified translation of second priority document, PCT/JP2010/071746, 79 pages, Dec. 27, 2017.
Chen, W.,et al., "Human Intestinal Lumen and Mucosa-associated Microbiota in Patients With Colorectal Cancer.," Plos One, 7(6):39743, Public Library of Science, United States, (2012).
Chinese First Office Action, Chinese Application No. 201380071190X, Jul. 4, 2018, 11 pages (with a concise explanation of relevance).
Zilberberg, M.D.,et al., "Increase in Adult Clostridium Difficile-related Hospitalizations and Case-fatality Rate, United States, 2000-2005.," Emerging Infectious Diseases, 14(6):929-931, National Center for Infectious Diseases, Centers for Disease Control and Prevention (CDC), United States., (Jun. 2008).
Chromek, M.,et al., "The Antimicrobial Peptide Cathelicidin Protects Mice From *Escherichia coli* O157:h7-mediated Disease.," Plos One, 7(10):46476, Public Library of Science,United States, (2012).
Chung, H., et al., "Gut Immune Maturation Depends on Colonization With a Host-specific Microbiota," Cell 149(7):1578-1593, Cell Press, United States (Jun. 2012).
Cline, M.J., "Perspectives for Gene Therapy: Inserting New Genetic Information Into Mammalian Cells by Physical Techniques and Viral Vectors," Pharmacology & Therapeutics 29(1):69-92, Pergamon Press, England (1985).
Cohen, Statistical Power Analysis for the Behavioral Sciences, Second Edition (Routledge, Hillsdale, NJ, 1988).
Cooke et al., "LPS antagonism reduces graft-versus-host disease and preserves graftversus-leukemia activity after experimental bone marrow transplantation," J. Clin. Invest. 107:1581-1589 (2001).
Cooke, K.R.,et al., "An Experimental Model of Idiopathic Pneumonia Syndrome After Bone Marrow Transplantation: I. The Roles of Minor H Antigens and Endotoxin.," Blood, 88(8):3230-3239, American Society of Hematology, United States, (Oct. 1996).
Copelan, E.,et al., "A Scheme for Defining Cause of Death and Its Application in the T Cell Depletion Trial.," Biology of Blood and Marrow Transplantation : Journal of the American Society for Blood and Marrow Transplantation, 13(12):1469-1476, Carden Jennings Publishing,United States, (Dec. 2017).
Cotten, M., et al., "Receptor-mediated Transport of DNA Into Eukaryotic Cells," Methods in Enzymology 217:618-644, Academic Press, United States (1993).
Cover Page of Science, Jan. 21, 2011, 1 page.
Cruz, M. C., et al., "Immunosuppressive and Nonimmunosuppressive Cyclosporine AnalogsAre Toxic to the Opportunistic Fungal Pathogen Cryptococcus neoformans via Cyclophilin-Dependent Inhibition of Calcineurin," Antimicrob. Agents Chemother. 44(1): 143-149, American Society for Microbiology (2000).
Cunliffe, R.N. and Scott, B.B., "Review Article: Monitoring for Drug Side-effects in Inflammatory Bowel Disease," Alimentary Pharmacology & Therapeutics 16(4):647-662, Wiley-Blackwell, England (Apr. 2002).
Current Uses and Outcomes of Hematopoietic Stem Cell Transplantation 2012 CIBMTR Summary Slides, 2012.
Das et al., "Blockade ofinterleukin-23 signaling results in targeted protection ofthe colon and allows for separation of graft-versus-host and graft-versus-leukemia responses," Blood 115(25):5249-5258 (2010).
Das, R.,et al., "Interleukin-23 Secretion by Donor Antigen-presenting Cells is Critical for Organ-specific Pathology in Graft-versus-host Disease.," Blood, 113(10):2352-2362, American Society of Hematology,United States, (Mar. 2009).
Day 3: 14th International Congress of Immunology, Aug. 22-27, 2010, Japan, 3 page.
Delay, M.L.,et al., "Hla-b27 Misfolding and the Unfolded Protein Response Augment Interleukin-23 Production and Are Associated With Th17 Activation in Transgenic Rats. ," Arthritis and Rheumatism, 60(9):2633-2643, Hoboken, N.J. : Wiley-Blackwell,United States, (Sep. 2009).
Desantis, T.Z.,et al., "Greengenes, a Chimera-Checked 16S RRNA Gene Database and Workbench Compatible With ARB.," Applied and Environmental Microbiology, 72(7):5069-5072, American Society for Microbiology,United States, (Jul. 2006).
Dethlefsen, L., et al., "Incomplete Recovery and Individualized Responses of the Human Distal Gut Microbiota to Repeated Antibiotic Perturbation," Proceedings of the National Academy of Sciences of the United States of America, 108 Suppl 1:4554-4561, National Academy of Sciences, United States, (Mar. 2011).
Diehl, G.E., et al., "Microbiota Restricts Trafficking of Bacteria to Mesenteric Lymph Nodes by Cx(3)crl(Hi) Cells," Nature, 494(7435):116-120, Nature Publishing Group, England, (Feb. 2013).
Duc, L.H., et al., "Characterization of Bacillus Probiotics Available for Human Use," Applied and Environmental Microbiology 70(4):2161-2171, American Society for Microbiology, United States (Apr. 2004).
Duncker, S.C.,et al., "The D-alanine Content of Lipoteichoic Acid is Crucial for Lactobacillus Plantarum-mediated Protection From Visceral Pain Perception in a Rat Colorectal Distension Model.," Neurogastroenterology and Motility : the Official Journal of the European Gastrointestinal Motility Society, 20(7):843-850, Blackwell Scientific Publications, c1994, England, (Jul. 2008).
E. Meyers and W. Miller (CABIOS, 4: 11-17 (1989)).
Edgar, R.C., et al., "Uchime Improves Sensitivity and Speed of Chimera Detection," Bioinformatics, 27(16):2194-2200, Oxford University Press, England, (Aug. 2011).
El-Houssieny, R., et al., "Recovery and Detection of Microbial Contaminants in Some Non-Sterile Pharmaceutical Products," Archives of Clinical Microbiology, 4(6):1-14, Ain Shams University, Egypt (2013).
Eriguchi et al., "Graft versus-host disease disrupts intestinal microbial ecology by inhibiting Paneth cell production of a-defensins," Blood 120(1):223-231 (2012).
European Examination Report for EP Application No. EP 11728077.6, dated Sep. 18, 2015, 4 pages.
European Examination Report for EP Application No. EP 13856249.1, dated May 23, 2018, 6 pages.
European Examination Report for EP Application No. EP 14746341.8, dated Apr. 18, 2018, 7 pages.
European Summons to Attend Oral Proceedings Pursuant to Rule 115(1) EPC for EP Application No. EP 14768281.9, mailed on Jul. 11, 2018, 10 pages.
Evelien Wynendaele et al., "Crosstalk between the microbiome and cancer cells by quorum sensing peptides", Elsevier Peptides 65 (2015) 40-48.
Ezaki, T., et al., "16s Ribosomal Dna Sequences of Anaerobic Cocci and Proposal of Ruminococcus Hansenii Comb. Nov. And Ruminococcus Productus Comb. Nov," International Journal of Systematic Bacteriology 44(1):130-136, Society for General Microbiology, England (Jan. 1994).
Final Office Action dated Nov. 1, 2019, in U.S. Appl. No. 16/054,864, Gregory Mckenzie et al., filed Aug. 3, 2018, 10 pages.
Final Office Action dated Apr. 14, 2020, in U.S. Appl. No. 16/223,008, Henn, M.R et al., filed Dec. 17, 2018, 11 pages.
Final Office action dated Dec. 11, 2019, in U.S. Appl. No. 14/765,812, Afey An; N et al., filed Aug. 4, 2015, 10 pages.
Final Office action dated Jan. 18, 2019, in U.S. Appl. No. 14/765,814, Cook; D. et al., filed Aug. 4, 2015, 14 pages.

(56) References Cited

OTHER PUBLICATIONS

Final Office Action dated Jul. 29, 2020, in U.S. Appl. No. 15/778,095, Button, J. et al., filed May 22, 2018, 40 pages.
Final Office Action dated Jun. 22, 2018, in U.S. Appl. No. 14/776,676, 15 pages.
Final Office Action dated May 5, 2020, in dated U.S. Appl. No. 14/765,814, Cook, D. et al., filed Aug. 4, 2015, 16 pages.
Freifeld et al., "Clinical Practice Guideline for the Use of Antimicrobial Agents in Neutropenic Patients with Cancer: 2010 Update by the Infectious Diseases Society of America," Clinical Infectious Diseases 52(4):e56-e93 (2011).
Gallo, R.L and Hooper, L.V, "Epithelial Antimicrobial Defence of the Skin and Intestine," Nature Reviews Immunology , 12(7):503-516, Nature Publishing Group, England, (Jun. 2012).
Ganesh et al., "Commensal Akkermansia muciniphila Exacerbates Gut Inflammation in *Salmonella typhimurium*-Infected Gnotobiotic Mice, " PLoS One 8(9):e74963 (2013).
GenBank: AccessionNo. NR 118589.1, accessed on Jun. 20, 2020.
Gennaro, A.R., Editor "Remington's Pharmaceutical Sciences", 18th Edition, Mack Publishing Co., 5 pages, 1990 (Table of Contents).
Goldberg et al., "T Cell-Depleted Stem Cell Transplantation for Adults with High-Risk Acute Lymphoblastic Leukemia: Long-Term Survival for Patients in First Complete Remission with a Decreased Risk of Graft-versus-Host Disease," Biol. Blood Marrow Transplant 19:208-213 (2013).
Goldspiel, B.R., et al., "Human Gene Therapy," Clinical Pharmacy 12(7):488-505, American Society Of Hospital Pharmacists, United States (1993).
Grangette et al., "Enhanced antiinflammatory capacity of a Lactobacillus plantarum mutant synthesizing modified teichoic acids," PNAS 102(29): 10321-10326 (2005).
Gut definition. Merriam Webster Dictionary. https://www.merriamwebster. com/dictionary/gut, retrieved Mar. 9, 2020.
Hahn et al., "Risk factors for Acute Graft-Versus-Host Disease after Human Leukocyte Antigen-Identical Sibling Transplants for Adults With Leukemia," J Clin. Oncol. 26(35):5728-5734 (2008).
Hall, B.G., et al., "Building Phylogenetic Trees From Molecular Data With Mega," Molecular biology and Evolution, 30(5):1229-1235, Oxford University Press, United States, (May 2013).
Hand, T.W., et al., "Acute Gastrointestinal Infection Induces Long-lived Microbiota-specific T Cell Responses," Science, 337(6101):1553-1556, American Association for the Advancement of Science, United States, (Sep. 2012).
Hansen, A.K. et al., "Handbook of Laboratory Animal Bacteriology," Second Edition, CRC Press, 2015, p. 158 (3 total pages).
Hata, D.J. et al., "Blood Group B Degrading Activity of Ruminococcus Gnavus Alpha-Galactosidase," Artif. Cells Blood Substit. lmmobil. Biotechnol., May 2004, pp. 263-274, vol. 32, No. 2.
Hazenberg, M.P., et al., "Conversion of Germ-free Mice to the Normal State by Clostridia," Zeitschrift für Versuchstierkunde 18(4):185-190, Gustav Fischer Verlag, Germany (1976).
Hiemenz, "Management of Infections Complicating Allogeneic Hematopoietic Stem Cell Transplantation," Semin Hematol 46:289-312 (2009).
Holler et al., "Metagenomic Analysis of the Stool Microbiome in Patients Receiving Allogeneic Stem Cell Transplantation: Loss of Diversity Is Associated with Use of Systemic Antibiotics and More Pronounced m Gastrointestinal Graft-versus-Host Disease," Biol. Blood Marrow Transplant. 20:640-645 (2014).
Hong et al., "1H NMR-based Metabonomic Assessment of Probiotic Effects in a Colitis Mouse Model," Arch Pharm Res 33(7): 1091-1101 (2010).
Hong, H.A., et al., "The Use of Bacterial Spore Formers as Probiotics," FEMS Microbiology Reviews 29(4):813-835, Oxford University Press, England (Sep. 2005).
Hue et al., "Interleukin-23 drives innate and T cell-mediated intestinal inflammation," JEM 203(11):2473-2483 (2006).
Human Microbiome Project Consortium, "Structure, Function and Diversity of the Healthy Human Microbiome, " Nature, 486(7402):207-214, Nature Publishing Group, England (Jun. 2012).
Huse, S.M., et al., "Exploring Microbial Diversity and Taxonomy Using SSU rRNA Hypervariable Tag Sequencing," PLoS Genetics 4(11):e1000255, Public Library of Science, United States (Nov. 2008).
Hylemon, P.B., et al., "Bile acids as regulatory molecules, " Journal of Lipid Research 50(8):1509-1520, Lipid Research, Inc., United States (Aug. 2009).
ICI Wrap-up Report Immunology in the 21st Century: Defeating Infection, Autoimmunity, Allergy and Cancer, 14th International Congress of Immunology, Aug. 22-27, 2010, Japan, 1 page.
International Search Report and Patentability for Application No. PCT/US2016/063697, dated May 29, 2018, Button et al., "Designed Bacterial Compositions," filed Nov. 23, 2016, 27 pages.
International Search Report and Written Opinion for Application No. PCT/US2016/041538, dated Sep. 23, 2016, Cook., et al., "Methods of Treating Colitis," filed Jul. 8, 2016, 12 Pages.
International Search Report and Written Opinion for International Application No. PCT/US2016/063697, European Patent Office, H V Rijswijk, dated May 19, 2017, 24 pages.
International Search Report and Written Opinion for International Application No. PCT/US2019/025010, European Patent Office, Netherlands, dated Jul. 11, 2019.
International Search Report dated Apr. 14, 2016 in International Application No. PCT/US2015/062734.
International Search Report for International Application No. PCT/US2015/31627, ISA/US, Commissioner for Patents, Alexandria, Virginia, dated Sep. 8, 2015.
International Statistical Classification of Diseases and Related Health Problems 1 O'h Review, Chapter 1: Certain Infectious and Parasitic Diseases (AOO-B99), 2016, 2 pages.
Jacobs et al., "1H NMR metabolite profiling of feces as a tool to assess the impact of nutrition on the human microbiome," NMR in Biomedicine 21:615-626 (2008).
Jaffe et al., "Prevention of Peritransplantation Viridans Streptococcal Bacteremia with Early Vancomycin Administration: A Single-Center Observational Cohort Study," Clin Infect Dis. 39:1625-1632 (2004).
Jagasia et al., "Risk factors for acute GVHD and survival after hematopoietic cell transplantation," Blood 119(1):296-307 (2012).
Jakubowski et al., "T Cell-Depleted Unrelated Donor Stem Cell Transplantation Provides Favorable Disease-Free Survival for Adults with Hematologic Malignancies," Biol. Blood Marrow Transplant 17:1335-1342 (2011).
Janeway, C.A. et al., "Autoimmune Responses are Directed Against Self Antigens," Immunobiology: The Immune System in Health and Disease, 51th Edition, Garland Science, 2001, pp. 1-14.
Janeway, C.A. et al., lmmuno Biology, 61th Edition, Garland Science Publishing, 2005, p. 414.
Japanese Office Action, Japanese Application No. 2015-556240, Jun. 5, 2018, 5 pages.
Jarry, A., et al., "Mucosal IL-10 and TGF-Beta Play Crucial Roles in Preventing LPS-driven, IFN-gamma-mediated Epithelial Damage in Human Colon Explants," The Journal of Clinical Investigation, 118(3):1132-1142, American Society for Clinical Investigation, United States (Mar. 2008).
Johansson et al., "The two mucus layers of colon are organized by the MUC2 mucin, whereas the outer layer is a legislator of host-microbial interactions," PNAS 108(Suppl. 1):4659-4665 (2011).
Jones et al., "Mortality and Gross Pathology of Secondary Disease in Germfree Mouse Radiation Chimeras," Radiat Res. 45(3):577-588 (1971).
Jousimies-Somer, General Considerations, Preliminary Identification Methods, Advanced Identification Methods, Chapter 4, 2002, pp. 55-185.
Kabeerdoss, J., et al., "Clostridium Leptum Group Bacteria Abundance and Diversity in the Fecal Microbiota of Patients With Inflammatory Bowel Disease: A Case-control Study in India," BMC Gastroenterology 13:20, BioMed Central, England (Jan. 2013).

(56) References Cited

OTHER PUBLICATIONS

Kamboj et al., "Clostridium difficile Infection after Allogeneic Hematopoietic Stem Cell Transplant: Strain Diversity and Outcomes Associated with NAP1/027," Biol. Blood Marrow Transplant 20:1626-1633 (2014).
Kamboj et al., "The Changing Epidemiology of Vancomycin-Resistant Enterococcus (VRE) Bacteremia m Allogeneic Hematopoietic Stem Cell Transplant (HSCT) Recipients," Biol Blood Marrow Transplant 16:1576-1581 (2010).
Keynan, Y., et al., "The Role of Regulatory T Cells in Chronic and Acute Viral Infections," Clinical Infectious Diseases 46(7):1046-1052, Oxford University Press, United states (Apr. 2008).
Kim, S.W.,et al., "Treatment of Refractory or Recurrent Clostridium Difficile Infection," The Korean Journal of Gastroenterology = Taehan Sohwagi Hakhoe Chi, 60(2):71-78, Korean Society of Gastroenterology, [2003],Korea (South), (Aug. 2012).
Kinnebrew, M.A., et al., "Early Clostridium Difficile Infection During Allogeneic Hematopoietic Stem Cell Transplantation," Plos One, 9(3):e90158, Public Library of Science, United States, (Mar. 2014).
Koeth, R.A., et al., "Intestinal Microbiota Metabolism of L-carnitine, a Nutrient in Red Meat, Promotes Atherosclerosis," Nature Medicine, 19(5):576-585, Nature Publishing Company, United States, (May 2013).
Kriegler, M., Gene Transfer and Expression, A Laboratory Manual, Stockton Press, NY (1990).
Krishna, S.G., et al., "Risk Factors, Preemptive Therapy, and Antiperistaltic Agents for Clostridium Difficile Infection in Cancer Patients," Transplant Infectious Disease, 15(5):493-501, Munksgaard, Denmark, (Oct. 2013 ).
Krogius-Kurikka, L., et al., "Sequence Analysis of Percent G+C Fraction Libraries of Human Faecal Bacterial Dna Reveals a High Number of Actinobacteria," BMC Microbiology 9:68, BioMed Central, England (Apr. 2009).
Kron et al., "Adenovirus Vectors and Subviral Particles for Protein and Peptide Delivery," Curr Gene Ther 12:362-373 (2012).
Kyne, L., et al., "Health Care Costs and Mortality Associated With Nosocomial Diarrhea Due to Clostridium Difficile," Clinical Infectious Diseases, 34(3):346-353, Oxford University Press, United States, (Feb. 2002 ).
Lackie, J.M. and Dow, J.A.T., "The Dictionary of Cell and Molecular Biology, " 3rd Edition, Academic Press, United States (1999).
Langille, M.G., et al., "Predictive Functional Profiling of Microbial Communities Using 16s Rrna Marker Gene Sequences," Nature biotechnology, 31(9):814-821, Nature America Publishing, United States, (Sep. 2013).
Langrish et al., "IL-12 and IL-23: master regulators of innate and adaptive immunity," Immunological Reviews 202:96-105 (2004).
LaRocco et al., "Infection in the Bone Marrow Transplant Recipient and Role of the Microbiology Laboratory in Clinical Transplantation," Clinical Microbiology Reviews 1 0(2):277-297 (1997).
Lathrop, S.K., et al., "Peripheral Education of the Immune System by Colonic Commensal Microbiota," Nature, 478(7368):250-254, Nature Publishing Group, England, (Sep. 2011 ).
Lau, S.K.P., et al., "Bacteraemia Caused By Anaerotruncus Colihominis and Emended Description of the Species," Clinical Pathology 59(7):748-752, BMJ Pub. Group, England (Jul. 2006).
Lindner et al., "Diversification of memory B cells drives the continuous adaptation of secretory antibodies to gut microbiota," Nature Immunology 16(8):880-890 (2015).
Loeffler, J.P., et al., "Gene Transfer Into Primary and Established Mammalian Cell Lines With Lipopolyamine-coated DNA," Methods in Enzymology 217:599-618, Academic Press, United States (1993).
Louie, T.J., et al., "Tolevamer, a Novel Nonantibiotic Polymer, Compared With Vancomycin in the Treatment of Mild to Moderately Severe Clostridium Difficile-associated Diarrhea," Clinical Infectious Diseases, 43(4):411-420, Oxford University Press, United States, (Aug. 2006).
Lozupone, C and Knight, R., "UniFrac: a New Phylogenetic Method for Comparing Microbial Communities," Applied and Environmental Microbiology 71(12):8228-8235, American Society for Microbiology, United States (Dec. 2005).
Lozupone et al., "UniFrac—An online tool for comparing microbial community diversity in a phylogenetic context," BMC Bioinformatics 7:371 (2006).
Machine Translation of PCT Specification, PCT Application No. PCT/JP2010/071746, Filed Dec. 3, 2010, 79 pages.
MacMillan et al., "What predicts high risk acute graft-versus-host disease (GVHD) at onset?: identification of those at highest risk by a novel acute GVHD risk score," Br. J. Haematol 157:732-741 (2012).
MacPherson, A.J and Uhr, T., "Induction of Protective Iga by Intestinal Dendritic Cells Carrying Commensal Bacteria," Science, 303(5664):1662-1665, American Association for the Advancement of Science, United States, (Mar. 2004).
Magurran, "Measuring Biological Diversity," Malden, MA: Blackwell Publishing; 2004.
Maizels, R.M. and Smith, K.A., "Regulatory T Cells in Infection," Advances in Immunology 112:73-136, Academic Press, United states (2011).
Malard et al., "Impact of Cyclosporine-A Concentration on the Incidence of Severe Acute Graft-Versus-Host Disease after Allogeneic Stem Cell Transplantation," Biol. Blood Marrow Transplant 16:28-34 (2010).
Manafi, M. Handbook of Culture Media for Food and Water Microbiology, 3rd Edition, Janet E.L. Corry et al., 2012, pp. 223-260.
Manges, A.R., et al., "Comparative Metagenomic Study of Alterations to the Intestinal Microbiota and Risk of Nosocomial Clostridum Difficile-associated Disease," The Journal of Infectious Diseases, 202(12):1877-1884, Oxford University Press, United States, (Dec. 2010).
Manichanh, C. et al., "Reshaping the Gut Microbiome with Bacterial Transplantation and Antibiotic Intake," Genome Research, 2010, pp. 1411-1419, vol. 20.
Marcus et al., "Deoxycholic acid and the pathogenesis of gall stones," Gut, 29, 522-533, BMJ Publishing Group, England (1988).
Marsh, J.W., et al., "Association of Relapse of Clostridium Difficile Disease With Bi/napl/027," Journal of Clinical Microbiology, 50(12):4078-4082, American Society for Microbiology, United States, (Dec. 2012).
Martin et al., "Increasingly Frequent Diagnosis of Acute Gastrointestinal Graft-versus-Host Disease after Allogeneic Hematopoietic Cell Transplantation," Biol. Blood Marrow Transplant. 10:320-327 (2004).
Martinet., et al., "Irreversible Coupling of immunoglobulin Fragments to Preformed Vesicles", J. Biol. Chern., 1982, vol. 257, No. 1, pp. 286-288.
Martinez-Montiel, M.P., et al., "Pharmacologic Therapy for Inflammatory Bowel Disease Refractory to Steroids," Clinical and Experimental Gastroenterology 8:257-269, Dove Medical Press, New Zealand (Aug. 2015).
McAuliffe et al., "Genetic Analysis of Two Bile Salt Hydrolase Activities in Lactobacillus acidophilus NCFM," Appl. Environ Microbial., 71(8):4925-4929 (2005).
Mexican Office Action, Mexican Application No. MX/a/2015/006491, dated Jun. 25, 2018, 8 pages, (with concise explanation of relevance).
Mexican Office Action, Mexican Application No. MX/a/2015/009991, dated Jul. 16, 2018, (with concise explanation of relevance).
Meyers, "Infection in Bone Marrow Transplant Recipients," The American Journal of Medicine 81(Suppl. 1A):27-38 (1986).
M'Koma, A.E., "Inflammatory Bowel Disease: an Expanding Global Health Problem," Clinical Medicine Insights. Gastroenterology 6:33-47, SAGE Publications, United States (Aug. 2013).
Morgan, R.A. and Anderson, W.F., "Human Gene Therapy," Annual Review of Biochemistry 62:191-217, Annual Reviews, United States (1993).

(56) References Cited

OTHER PUBLICATIONS

Mulligan, R.C., "The Basic Science of Gene Therapy," Science 260(5110):926-932, American Association for the Advancement of Science, United States (1993).
Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).
Nitzan, O., et al., "Role of Antibiotics for Treatment of Inflammatory Bowel Disease, " World Journal of Gastroenterology, 22(3):1078-1087, Baishideng Publishing Group, United States (Jan. 2016).
Non Final Office Action dated Apr. 7, 2020, in U.S. Appl. No. 16/054,864, Gregory McKenzie et al., filed Aug. 3, 2018, 15 pages.
Non Final Office Action dated Mar. 15, 2019, in U.S. Appl. No. 16/054,864, Gregory McKenzie et al., filed Aug. 3, 2018, 9 pages.
Non Final Office Action dated Apr. 17, 2018, in U.S. Appl. No. 14/765,814, 14 pages.
Non Final Office Action dated Jun. 15, 2018, in U.S. Appl. No. 15/359,439, 13 pages.
Non final Office action dated Mar. 21, 2019, in U.S. Appl. No. 14/765,812, Afey An; N. et al., filed Aug. 4, 2015, 10 pages.
Non final Office action dated Nov. 14, 2019, in U.S. Appl. No. 14/765,814, Cook; D. et al., filed Aug. 4, 2015, 17 pages.
Non Final Office Action dated Oct. 22, 2019, in U.S. Appl. No. 15/742,732, Cook, D. et al., filed Jan. 8, 2018, 10 pages.
Non-Final Office Action dated Oct. 29, 2019, in U.S. Appl. No. 15/990,539, Henn,M.R. et al., filed May 25, 2018, 25 pages.
Non-Final Office Action dated Dec. 9, 2019, in U.S. Appl. No. 16/223,008, Matthew R. Henn et al., filed Dec. 17, 2018, 17 pages.
Non-Final Office action dated Dec. 31, 2019, in U.S. Appl. No. 16/051,747, Maltzahn, G.V. et al., filed Aug. 1, 2018, 46 pages.
Non-Final Office Action dated Mar. 10, 2020, in U.S. Appl. No. 15/778,095, Button, J. et al., filed May 22, 2018, 28 pages.
Non-Final Office Action dated Mar. 23, 2020, in U.S. Appl. No. 15/990,539, Henn,M.R. et al., filed May 25, 2018, 10 pages.
Non-Patent Literature Submitted with Notice of Opposition to a European Patent, dated Jul. 18, 2017, European Patent No. EP2575835: Other Evidence, E102635, 1 page.
Office Action dated Aug. 19, 2016, in U.S. Appl. No. 14/592,481, Henn, M.R., et al., filed Jan. 8, 2015.
Office action dated Dec. 21, 2018, in U.S. Appl. No. 15/986,369, Pamer; E. et al., filed May 22, 2018, 15 pages.
Office Action dated Feb. 25, 2014, in European Patent Application No. 11728077.6 filed Jun. 3, 2011.
Office Action dated Feb. 26, 2019, in U.S. Appl. No. 15/312,610, Pamer, E. et al., filed Nov. 18, 2016, 22 pages.
Office action dated Jan. 13, 2020, in U.S. Appl. No. 15/986,369, Pamer; E. et al., filed May 22, 2018, 10 pages.
Office Action dated Jul. 10, 2018, in U.S. Appl. No. 15/312,610, Pamer,E. et al., filed Nov. 18, 2016, 16 pages.
Office Action dated Mar. 28, 2019, in U.S. Appl. No. 15/603,916, VanDenBrink; M. et al., filed May 24, 2017, 24 pages.
Office Action dated May 14, 2019, in U.S. Appl. No. 15/603,916, VanDenBrink; M. et al., filed May 24, 2017, 25 pages.
Office Action dated Nov. 13, 2019, in U.S. Appl. No. 15/603,916, VanDenBrink; M. et al., filed May 24, 2017, 21 pages.
Office action dated Oct. 22, 2019, in U.S. Appl. No. 15/1742,732, Cook; D. et al., filed Jan. 8, 2018, 10 pages.
Office Action dated Sep. 18, 2015, in European Patent Application No. 11728077.6 filed Jun. 3, 2011.
Office action dated Sep. 20, 2019, in U.S. Appl. No. 15/986,369, Pamer; E. et al., filed May 22, 2018, 10 pages.
O'Garra, A., et al., "IL-10-producing and Naturally Occurring CD4+ Tregs: Limiting Collateral Damage," The Journal of Clinical Investigation 114(10):1372-1378, American Society for Clinical Investigation, United states (Nov. 2004).
Olszak, T., et al., "Microbial Exposure During Early Life Has Persistent Effects on Natural Killer T Cell Function," Science (New York, N.Y.), 336(6080):489-493, American Association for the Advancement of Science , United States, (Apr. 2012).
Ott, S.J., et al., "Quantification of Intestinal Bacterial Populations by Real-time Pcr With a Universal Primer Set and Minor Groove Binder Probes: a Global Approach to the Enteric Flora," Journal of Clinical Microbiology, 42(6):2566-2572, American Society for Microbiology, United States, (Jun. 2004).
Out, C., et al., "Bile Acid Sequestrants: More Than Simple Resins," Current opinion in lipidology, 23(1):43-55, Lippincott Williams & Wilkins, England, (Feb. 2012).
Parham et al., "A Receptor for the Heterodimeric Cytokine IL-23 is Composed of IL-12R~1 and a Novel Cytokine Receptor Subunit, IL-23R1," J Immunol 168:5699-5708—2002.
Partial Supplementary European Search Report dated Jan. 4, 2018 in Application No. 15796000.6.
Passweg et al., "Influence of protective isolation on outcome of allogeneic bone marrow transplantation for leukemia," Bone Marrow Transplantation 21:1231-1238 (1998).
Pei-Show Juo., The Concise Dictionary of Biomedicine and Molecular Biology, 2nd Edition, CRC Press, United States (2002).
Pelaseyed et al., "The mucus and mucins of the goblet cells and enterocytes provide the first defense line of the gastrointestinal tract and interact with the immune system," Immunological Reviews 260:8-20 (2014).
Petersen, F. B., et al., "Infectious Complications m Patients Undergoing Marrow Transplantation: A Prospective Randomized Study of the Additional Effect of Decontamination and Laminar Airflow Isolation among Patients Receiving Prophylactic Systemic Antibiotics," Scand J. Infect Dis. 19(5):559-567 (1987).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Ponce et al., "Graft-versus-Host Disease after Double-Unit Cord Blood Transplantation Has Unique Features and an Association with Engrafting Unit-To-Recipient HLA Match, " Biol. Blood Marrow Transplant 19:904-911 (2013).
Porada et al., "Treatment of Hemophilia A in Utero and Postnatally using Sheep as a Model for Cell and Gene Delivery," J. Genet Syndr Gene Ther., 25:Suppl. 1, 26 pages 2012).
Priority Document JP 2010-129134 for PCT Application No. PCT/JP2011/063302, Filed Jun. 4, 2010, 42 pages.
Priority Document PCT/JP2010/071746 for PCT Application No. PCT/JP2011/063302, Filed Dec. 3, 2010, 107 pages.
Rea, M.C., et al., "Effect of Broad- and Narrow-spectrum Antimicrobials on Clostridium Difficile and Microbial Diversity in a Model of the Distal Colon," Proceedings of the National Academy of Sciences of the United States of America, 108 Suppl 1:4639-4644, National Academy of Sciences, United States, ( Mar. 2011 ).
Rea, M.C., et al., "Thuricin Cd, a Posttranslationally Modified Bacteriocin With a Narrow Spectrum of Activity Against Clostridium Difficile," Proceedings of the National Academy of Sciences of the United States of America, 107(20):9352-9357, National Academy of Sciences, (May 2010).
Response dated Jan. 28, 2015 in Examination, European Application No. 11728077.6, 3 pages.
Response to Official Communication dated Sep. 18, 2018, European Application No. 11728077.6, filed Nov. 18, 2015 , 2 pages.
Rheinwald, J.G., "Chapter 15 Serial Cultivation of Normal Human Epidermal Keratinocytes," Methods in Cell Biology 21A:229-254, Academic Press, United States (1980).
Ridlon, J.M and Hylemon, P.B., "Identification and Characterization of Two Bile Acid Coenzyme a Transferases From Clostridium Scindens, a Bile Acid 7α-dehydroxylating Intestinal Bacterium.," Journal of Lipid Research, 53(1):66-76, American Society for Biochemistry and Molecular Biology, United States, (Jan. 2012).
Ridlon, J.M., "Enzymology and Molecular Biology of Bile Acid 7alpha- And 7beta-Dehydroxylation By The Intestinal Bacteria Clostridium Scindens And Clostridium Hylemonae," VCU Theses and Dissertations, Paper 736 (2008).
Ridlon,J.M,.et al., "Bile Salt Biotransformations by Human Intestinal Bacteria.," Journal of Lipid Research, 47(2):241-259, American Society for Biochemistry and Molecular Biology, (Feb. 2006).
Roberts, B., "Generation and Development of Defined Microbial Drug Products," Vedanta Biosciences, 17 pages (2016).

(56) References Cited

OTHER PUBLICATIONS

Rosero, J.A., et al., "Reclassification of Eubacterium Rectale (Hauduroy et al. 1937) Prévot 1938 in a New Genus *Agathobacter* Gen. Nov. As *Agathobacter* Rectalis Comb. Nov., and Description of *Agathobacter ruminis* Sp. Nov., Isolated From the Rumen Contents of Sheep and Cows," International Journal of Systematic and Evolutionary Microbiology, 66(2):768-773, Microbiology Society, England (Feb. 2016).
Rowlings, P. A., et al., "IBMTR Severity Index for grading acute graft-versus-host disease: retrospective comparison with Glucksberg grade," Br J Haematol. 97:855-864 (1997).
Rubin, E. and Farber, J.L., "Pathology," Second Edition, Philadelphia, J. B. Lippincott Company (1994).
Rupnik, M.,et al., "Clostridium Difficile Infection: New Developments in Epidemiology and Pathogenesis.," Nature Reviews. Microbiology, 7(7):526-536, Nature Pub. Group, c2003-,England, (Jul. 2009).
Russell et al., "Early Outcomes After Allogeneic Stem Cell Transplantation for Leukemia and Myelodysplasia Without Protective Isolation: A 1 0-year Experience," Biol. Blood Marrow Transplant 6(2): 109-114 (2000).
Russian Office Action, Russian Application No. 201537399, dated Aug. 15, 2016, 8 pages.
Sakamoto et al., "Eubacterium limosum strain JCM 6421 16S ribosomal RNA gene, partial sequence" NCBI Reference Sequence, 2 pages, Nov. 23, 2016.
Sanchez, A.M. and Yang, Y., "The Role of Natural Regulatory T Cells in Infection," Immunologic Research 49(1-3):124-134, Humana Press, United states (Apr. 2011 ).
Schloss, P.D., et al., "Introducing Mothur: Open-source, Platform-independent, Community-supported Software for Describing and Comparing Microbial Communities," Applied and Environmental Microbiology 75(23):7537-7541, American Society for Microbiology, United States (Dec. 2009).
Schloss, P.D., et al., "Reducing the Effects of Pcr Amplification and Sequencing Artifacts on 16s Rrna-based Studies," PLoS One 6(12):e27310, Public Library of Science, United States (Dec. 2011).
Schwab et al., "Neutrophil granulocytes recruited upon translocation of intestinal bacteria enhance graft-versus-host disease via tissue damage," Nature Medicine 20(6):648-654—2014.
Segata et al., "Metagenomic biomarker discovery and explanation," Genome Biol. 12:R60—2011.
Seguy et al., "Enteral Feeding and Early Outcomes of Patients Undergoing Allogeneic Stem Cell Transplantation following Myeloablative Conditioning," Transplantation 82:835-839 (2006).
Seki, H., et al., "Prevention of Antibiotic-Associated Diarrhea in Children by Clostridium Butyricum Miyairi," Pediatrics International, 45(1):86-90, Blackwell Science Asia, Australia (Feb. 2003).
Sequence Listing, PCT Application No. PCT/JP2011/063302, 43 pages, Dec. 8, 2011.
Sghir, A., et al., "Quantification of Bacterial Groups Within Human Fecal Flora by Oligonucleotide Probe Hybridization," Applied and Environmental Microbiology 66(5):2263-2266, American Society for Microbiology, United States (May 2000).
Shannon, "The Mathematical Theory of Communication," M.D. Computing 14( 4): 3 06-317 (1997).
Sheneman, L.,et al., "Clearcut: a Fast Implementation of Relaxed Neighbor Joining.," Bioinformatics (Oxford, England), 22(22):2823-2824, Oxford University Press, c1998,England, (Nov. 2006).
Sheptulin, A.A., "Refractory and Relapsing Forms of Clostridium difficile-Associated Colitis," www.gastro-j.ru, 2011, pp. 50-53 (with English abstract).
Shono et al., "A Small-Molecule c-Rel Inhibitor Reduces Alloactivation of T Cells without Compromising Antitumor Activity," Cancer Discovery 4(5):578-591 (2014).
Smith, P.M., et al., "The Microbial Metabolites, Short-Chain Fatty Acids, Regulate Colonic Treg Cell Homeostasis," Science 341(6145):569-573, American Association for the Advancement of Science, United States (Aug. 2013 ).
Solomkin et al., "Diagnosis and Management of Complicated Intra-abdominal Infection in Adults and Children: Guidelines by the Surgical Infection Society and the Infectious Diseases Society of America," Clin Infect Dis. 50:133-164 (2010).
Song, Y., et al., "Clostridium boltei partial 16S rRNA gene, strain 16351" Database NCBI Nucleotide [online] accession No. AJ508452, Apr. 18, 2003, [retrieved on Dec. 22, 2020], retrieved from the internet:< url: https://www.ncbi.nlm.nih.gov/nuccore/AJ508452, 2 pages.
Sorg et al., "Bile Salts and Glycine as Cogerminants for Clostridium difficile Spores," J. Bacteriology 190(7):2505-2512 (2008).
Sorg, J.A and Sonenshein, A.L., "Chenodeoxycholate is an Inhibitor of Clostridium Difficile Spore Germination.," Journal of Bacteriology, 191(3):1115-1117, American Society for Microbiology, United States, (Feb. 2009).
Stein, R.R.,et al., "Ecological Modeling From Time-series Inference: Insight Into Dynamics and Stability of Intestinal Microbiota.," Plos Computational Biology, 9(12):1003388, Public Library of Science, [2005], United States , (Sep. 2013).
Stemple, D.L. and Anderson, D.J., "Isolation of a Stem Cell for Neurons and Glia From the Mammalian Neural Crest," Cell 71(6):973-985, Cell Press, United States (Dec. 1992).
Storb et al., "Graft-Versus-Host Disease and Survival in Patients with Aplastic Anemia Treated by Marrow Grafts from HLA-Identical Siblings. Beneficial Effect of a Protective Environment," N Engl J Med. 308:302-307 (1983).
Sudarsanam, P., et al., "[Clostridium] Bolteae ATCC BAA-613 C_bolteae-3.0.1_Cont299, Whole Genome Shotgun Sequence," Database NCBI Nucleotide [online] accession No. ABCC02000039, Jan. 14, 2008, [retrieved on Dec. 22, 2020], retrieved from the internet:< url :< a=""href="https://www.ncbi.nlm.nih.gov/nuccore/ABCC02000039.1/">https://www.ncbi.nlm.nih.gov/nuccore/ABCC02000039.1/, 99 pages.
Supplementary Partial European Search Report dated Jun. 14, 2018 in Application No. EP 15862844.
Surawicz, C.M and Alexander, J., "Treatment of Refractory and Recurrent Clostridium Difficile Infection," Nature Reviews Gastroenterology & Hepatology, 8(6):330-339, Nature Publishing Group, England (Jun. 2011).
Swidsinski et al., "Spatial Organization and Composition of the Mucosal Flora in Patients with Inflammatory Bowel Disease," Journal of Clinical Microbiology 43(7):3380-3389—2005.
Taur et al., "The effects of intestinal tract bacterial diversity on mortality following allogeneic hematopoietic stem cell transplantation," Blood 124(7): 1174-1182 (2014).
Technical Data, HiMedia Laboratories Pvt. Ltd., M581 BP, 2011, pp. 1-2.
The Oxford Dictionary of Biochemistry and Molecular Biology, Revised Edition, Oxford University Press, England, 2 pages. (2000).
Theriot, C.M. et al., "Antibiotic-induced Shifts in the Mouse Gut Microbiome and Metabolome Increase Susceptibility to Clostridium Difficile Infection," Nature Communications, 5:3114, Nature Publishing Group, England (Jan. 2014).
Thomas, C., et al., "Targeting Bile-acid Signalling for Metabolic Diseases," Nature Reviews. Drug Discovery 7(8):678-693, Nature Pub. Group, England (Aug. 2008).
Tolstoshev, P., "Gene Therapy, Concepts, Current Trials and Future Directions," Annual Review of Pharmacology and Toxicology 33:573-596, Annual Reviews, United States (1993).
Trends in Biotechnology, TIBTECH 11(5): 155-215 (1993) (Table of Contents).
Turnbaugh, P.J.,et al., "A Core Gut Microbiome in Obese and Lean Twins.," Nature, 457(7228):480-484, Nature Publishing Group, England, (Jan. 2009).
Vigorito et al., "Evaluation of NIH consensus criteria for classification of late acute and chronic GVHD," Blood 114(3):702-708 (2009).
Vogt et al. "Chemical communication in the gut: Effects of microbiota-generated metabolites on gastrointestinal bacterial pathogens," Anaerobe 34:106-115, Elsevier, Netherlands (2015).
Vossen et al., "Complete Suppression of the Gut Microbiome Prevents Acute Graft-Versus Host Disease following Allogeneic Bone Marrow Transplantation, " PLoS One 9(9):el05706 (2014).
Wachsman, J.T., et al., "Characterization of an Orotic Acid Fermenting Bacterium, *Zymobacterium Oroticum*, Nov. Gen., Nov.

(56) References Cited

OTHER PUBLICATIONS

Spec," Bacteriology 68(4):400-404, American Society for Microbiology, United States (Oct. 1954).
Wang, Q., et al., "Naive Bayesian Classifier for Rapid Assignment of Rrna Sequences Into the New Bacterial Taxonomy," Applied and Environmental Microbiology 73(16):5261-5267, American Society for Microbiology, United States (Aug. 2007).
Warren, Y.A., et al., "*Clostridium aldenense* Sp. Nov. and *Clostridium citroniae* Sp. Nov. Isolated from human clinical Infections," Journal of Clinical Microbiology 44(7):2416-2422, American Society for Microbiology, United States (Jul. 2006 ).
Weber et al., "Low urinary indoxyl sulfate levels early after transplantation reflect a disrupted microbiome and are associated with poor outcome," Blood 126(14): 1723-1728—2015.
Wells, J.E and Hylemon, P.B., "Identification and Characterization of a Bile Acid 7alpha-dehydroxylation Operon in *Clostridium* Sp. Strain to-931, a Highly Active 7alpha-dehydroxylating Strain Isolated From Human Feces.," Applied and Environmental Microbiology, 66(3):1107-1113, American Society for Microbiology,United States, (Mar. 2000).
Wells, J.E.,et al., "Development and Application of a Polymerase Chain Reaction Assay for the Detection and Enumeration of Bile Acid 7alpha-dehydroxylating Bacteria in Human Feces.," Clinica chimica acta; international journal of clinical chemistry, 331(1-2):127-134, Elsevier, Netherlands, (May 2003).
Wilson, K.H and Freter, R, "Interaction of Clostridium Difficile and *Escherichia coli* With Microfloras in Continuous-flow Cultures and Gnotobiotic Mice," Infection and Immunity, 54(2):354-358, American Society For Microbiology, United States (Nov. 1986).
Wingender, G.,et al., "Intestinal Microbes Affect Phenotypes and Functions of Invariant Natural Killer T Cells in Mice," Gastroenterology, 143(2):418-428, PA : W.B. Saunders,United States, (Aug. 2012).
Wood et al., "Kraken: ultrafast metagenomic sequence classification usmg exact alignments," Genome Biology 15:R46 (2014).
Wortman, J. R., et al., "Design and evaluation of SER-262: A fermentation-derived microbiometherapeutic for the prevention of recurrence in patients with primary clostridium difficile infection," Seres Therapeutics, Cambridge, MA, Jun. 1, 2016, Retrieved from (http://serestherapeutics.com/sites/default/files/wortman_asm_poster_final_poster_ser_262.pdf), Retrieved on [Mar. 6, 2017], 1 page.
Wu, G.Y. and Wu, C.H., "Delivery Systems for Gene Therapy," Biotherapy 3(1):87-95, Kluwer Academic Publishers, Netherlands (1991).
Yen et al., "IL-23 is essential for T cell-mediated colitis and promotes inflammation via IL-17 and IL-6," The J oumal of Clinical Investigation 116( 5): 1310-1316 (2006).
Yi, Y., et al., "Current Advances in Retroviral Gene Therapy," Current Gene Therapy 11(3):218-228, Bentham Science Publishers, Netherlands (2011).
Yutin, N. and Galperin, M.Y., "A Genomic Update on Clostridial Phylogeny: Gram-negative Spore Formers and Other Misplaced Clostridia," Environmental Microbiology 15(10):2631-2641, Blackwell Science, England (Oct. 2013).
Zar, F.A., "A Comparison of Vancomycin and Metronidazole for the Treatment of Clostridium Difficile-associated Diarrhea, Stratified by Disease Severity.," Clinical Infectious Diseases : an Official Publication of the Infectious Diseases Society of America, 45(3):302-307, Oxford University Press, United States, (Aug. 2007).
Ze, X., et al., "*Ruminococcus bromii* Is a Keystone Species for the Degradation of Resistant Starch in the Human Colon, "The ISME Journal, 6(8):1535-1543, Nature Publishing Group, England (Aug. 2012).
Zhao, Y.,et al., "Rapsearch2: a Fast and Memory-efficient Protein Similarity Search Tool for Next-generation Sequencing Data.," Bioinformatics (Oxford, England), 28(1):125-126, Oxford University Press, England, (Jan. 2012).
Zhu, C., et al., "Bile Acids in Regulation of Inflammation and Immunity: Friend or Foe?," Clinical and Experimental Rheumatology 34(4 Suppl 98):25-31, Clinical And Experimental Rheumatology S.A.S, Italy (Jul.-Aug. 2016).
Crost, E.H., et al., "Production of an antibacterial substance in the digestive tract involved in colonization-resistance against Clostridium perfringens," Anaerobe 16(6):597-603, Elsevier, Netherlands (Dec. 2010).
Kutschera, M., et al., "Isolation of catechin-converting human intestinal bacteria," J Appl Microbiol 111(1):165-175, Wiley-Blackwell, United States (Jul. 2011).
Office Action dated May 3, 2021, in U.S. Appl. No. 16/230,807, Henn, M., et al., filed Dec. 21, 2018, 17 pages.
Notice of Allowance, dated Aug. 31, 2021, in U.S. Appl. No. 16/230,807, Henn, M., et al., filed Dec. 21, 2018, 7 pages.
Office Action dated Nov. 1, 2017, in U.S. Appl. No. 15/039,007, Henn, M., et al., filed May 24, 2016.
Office Action dated Jun. 12, 2018, in U.S. Appl. No. 15/039,007, Henn, M., et al., filed May 24, 2016.
Notice of Allowance, dated Sep. 26, 2018, in U.S. Appl. No. 15/039,007, Henn, M., et al., filed May 24, 2016.

1 AAATTGAAGAGTTTGATCATGGCTCAGATTGAACGCTGGCGGCAGGCCTA
51 ACACATGCAAGTCGAACGGTAACAGGAAGAAGCTTGCTCTTTGCTGACGA
101 GTGGCGGACGGGTGAGTAATGTCTGGGAAACTGCCTGATGGAGGGGGATA
151 ACTACTGGAAACGGTAGCTAATACCGCATAACGTCGCAAGACCAAAGAGG
201 GGGACCTTCGGGCCTCTTGCCATCGGATGTGCCCAGATGGGATTAGCTAG
251 TAGGTGGGGTAACGGCTCACCTAGGCGACGATCCCTAGCTGGTCTGAGAG
301 GATGACCAGCCACACTGGAACTGAGACACGGTCCAGACTCCTACGGGAGG
351 CAGCAGTGGGGAATATTGCACAATGGGCGCAAGCCTGATGCAGCCATGCC
401 GCGTGTATGAAGAAGGCCTTCGGGTTGTAAAGTACTTTCAGCGGGGAGGA
451 AGGGAGTAAAGTTAATACCTTTGCTCATTGACGTTACCCGCAGAAGAAGC
501 ACCGGCTAACTCGTGCCCAGGCATGCGCAGGAATACGGAGGTGCAAGCGT
551 TAATCGGAATTACTGGGCGTAAAGCGCACGCAGGCGGTTTGTTAAGTCAG
601 ATGTGAAATCCCCGGGCTCAACCTGGGAACTGCATCTGATACTGGCAAGC
651 TTGAGTCTCGTAGAGGGGGGTAGAATTCCAGGTGTAGCGGTGAAATGCGT
701 AGAGATCTGGAGGAATACCGGTGGCGAAGGCGGCCCCCTGGACGAAGACT
751 CACGCTCAGGTGCGAAAGCGTGGGGAGCAAACAGGATTAGATACCCTGGT
801 AGTCCACGCCGTAAACGATGTCGACTTGGAGGTTGTGCCCTTGAGGCGTG
851 GCTTCCGGAGCTAACGCGTTAAGTCGACCGCCTGGGGAGTACGGCCGCAA
901 GGTTAAAACTCAAATGAATTGACGGGGGCCCGCACAAGCGGTGGAGCATG
951 TGGTTTAATTCGATGCAACGCGAAGAACCTTACCTGGTCTTGACATCCAC
1001 GGAAGTTTTCAGAGATGAGAATGTGCCTTCGGGAACCGTGAGACAGGTGC
1051 TGCATGGCTGTCGTCAGCTCGTGTTGTGAAATGTTGGGTTAAGTCCCGCA
1101 ACGAGCGCAACCCTTATCCTTTGTTGCCAGCGGTCCGGCCGGGAACTCAA
1151 AGGAGACTGCCAGTGATAAACTGGAGGAAGGTGGGGATGACGTCAAGTCA
1201 TCATGGCCCTTACGACCAGGGCTACACACGTGCTACAATGGCGCATACAA
1251 AGAGAAGCGACCTCGCGAGAGCAAGCGGACCTCATAAAGTGCGTCGTAGT
1301 CCGGATTGGAGTCTGCAACTCGACTCCATGAAGTCGGAATCGCTAGTAAT
1351 CGTGGATCAGAATGCCACGGTGAATACGTTCCCGGGCCTTGTACACACCG
1401 CCCGMCACACCATGGGAGTGGGTTGCAAAAGAAGTAGGTAGCTTAACCTT
1451 CGGGAGGGCGCTTACCACTTTGTGATTCATGACTGGGGTGAAGTCGTAAC
1501 AAGGTAACCGTAGGGGAACCTGCGGTTGGATCACCTCCTTA

FIG. 3

SYNERGISTIC BACTERIAL COMPOSITIONS AND METHODS OF PRODUCTION AND USE THEREOF

CROSS REFERENCE TO RELATED APPLICATIONS

This application is a divisional application of U.S. patent application Ser. No. 16/230,807, filed Dec. 21, 2018 (currently allowed), which is a divisional application of U.S. patent application Ser. No. 15/039,007, filed May 24, 2016 (now U.S. Pat. No. 10,258,655, issued on Apr. 16, 2019), which is the National Stage of International Application No. PCT/US2014/067491, filed Nov. 25, 2014, which claims the benefit of U.S. Provisional Patent Application No. 61/908,698, filed Nov. 25, 2013; U.S. Provisional Patent Application No. 61/908,702, filed Nov. 25, 2013; and U.S. Provisional Patent Application No. 62/004,187, filed May 28, 2014, the entire disclosures of which are hereby incorporated by reference in their entirety for all purposes.

REFERENCE TO A SEQUENCE LISTING SUBMITTED ELECTRONICALLY

The content of the electronically submitted sequence listing in ASCII text file (Name: 4268_0390006_Seqlisting_ST25.txt; Size: 4,152,838 bytes; and Date of Creation: Jan. 28, 2022) filed with the application is herein incorporated by reference in its entirety.

BACKGROUND

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population by about 3 years of age. Interactions between microbial strains in these populations and between microbes and the host, e.g., the host immune system, shape the community structure, with availability of and competition for resources affecting the distribution of microbes. Such resources may be food, location and the availability of space to grow or a physical structure to which the microbe may attach. For example, host diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections of the gut. For example, subjects become more susceptible to pathogenic infections when the normal intestinal microbiota has been disturbed due to use of broad-spectrum antibiotics. Some of these diseases and disorders are chronic conditions that significantly decrease a subject's quality of life and ultimately some can be fatal.

Fecal transplantation has been shown to sometimes be an effective treatment for subjects suffering from severe or refractory GI infections and other disorders by repopulating the gut with a diverse array of microbes that control key pathogens by creating an ecological environment inimical to their proliferation and survival. Such approaches have demonstrated potential to decrease host susceptibility to infection. Fecal transplantation, however, is generally used only for recurrent cases because it has the potential to transmit infectious or allergenic agents between hosts, involves the transmission of potentially hundreds of unknown strains from donor to subject, and is difficult to perform on a mass scale. Additionally, fecal transplantation is inherently non-standardized and different desired and/or undesired material may be transmitted in any given donation. Thus, there is a need for defined compositions that can be used to decrease susceptibility to infection and/or that facilitate restoration of a healthy gut microbiota.

In addition, practitioners have a need for safe and reproducible treatments for disorders currently treated on an experimental basis using fecal transplantation. Summary of the invention To meet the need for safe, reproducible treatments for disorders that can be modulated by the induction of a healthy GI microbiome and to treat diseases associated with the GI microbiome, Applicants have designed bacterial compositions of isolated bacterial strains with a plurality of functional properties, in particular that are useful for treating dysbiosis (e.g., restoring a GI microbiome to a state of health), and for treating disorders associated with infection or imbalance of microbial species found in the gut that are based on Applicants discoveries related to those bacterial strains and analysis and insights into properties related to those strains and combinations of those strains, leading to the inventions disclosed herein.

In a first aspect, provided are compositions comprising an effective amount of a bacterial composition comprising at least a first type of isolated *bacterium* capable of forming a spore, a second type of isolated *bacterium* capable of forming a spore and optionally a third type of isolated *bacterium* capable of forming a spore, wherein the first type, the second type and the optional third type are not identical, and wherein at least two of the first type, the second type and the optional third type are capable of synergistically decreasing and/or inhibiting the growth and/or colonization of at least one type of pathogenic bacteria. In some embodiments, the bacterial composition comprises at least about 2, 3, 4, 5, 6, 7, 8, 9, 10, 11, 12, 13, 14, 15, 16, 17, 18, 19 or 20 types of isolated bacteria capable of forming spores. In other embodiments, the bacterial composition comprises at least about 2, 3, 4, 5, 6, 7, 8, 9, 10, 11, 12, 13, 14, 15, 16, 17, 18, 19 or 20 types of isolated bacteria not containing at least one sporulation-associated gene. In further embodiments, the bacterial composition comprises at least about 2, 3, 4, 5, 6, 7, 8, 9, 10, 11, 12, 13, 14, 15, 16, 17, 18, 19 or 20 types of isolated bacteria in spore form. In further embodiments, the bacterial composition comprises at least about 2, 3, 4, 5, 6, 7, 8, 9, 10, 11, 12, 13, 14, 15, 16, 17, 18, 19 or 20 types of isolated bacteria in vegetative form. In further embodiments, the bacterial composition comprises at least about 2, 3, 4, 5, 6, 7, 8, 9, 10, 11, 12, 13, 14, 15, 16, 17, 18, 19 or 20 types of isolated bacteria in spore form, and wherein the bacterial composition further comprises at least about 2, 3, 4, 5, 6, 7, 8, 9, 10, 11, 12, 13, 14, 15, 16, 17, 18, 19 or 20 types of isolated bacteria in vegetative form. In further embodiments, the bacterial composition comprises at least about 5 types of isolated bacteria and at least about 20% of the isolated bacteria are capable of forming spores or are in spore form. In further embodiments, the bacterial composition comprises at least about 5 types of isolated bacteria and at least 2 of the isolated bacteria are capable of forming spores or are in spore form. In further embodiments, the first type, second type and optional third type are present in the composition in approximately equal concentrations. In further embodiments, the first type and the third type are present in the composition in approximately equal concentrations. In further embodiments, the second type and the third type are present in the composition in approximately equal concentrations. In further embodiments, the first type is present in the composition in at least about 150% the concentration of the second type and/or the third type. In further embodiments, the first type, second type and optional third type are individually present in the composition in at least about 150% the concentration of the third type. In further embodiments, the composition consists essentially of between two and about twenty types of isolated bacteria, wherein at least two types of the isolated bacteria are independently capable of spore formation. In further embodiments, at least two types of the isolated bacteria are in spore form. In further embodiments, the first, second and third types are independently selected from Table 1. In further embodiments, the first, second and third types comprise an operational taxonomic unit (OTU) distinction. In further embodiments, the OTU distinction comprises 16S rRDNA sequence similarity below about 95% identity. In further embodiments, the first, second and third types independently comprise bacteria that comprise 16S rDNA sequence at least 95% identical to 16S rDNA sequence present in a *bacterium* selected from Table 1.

In another aspect, provided are compositions comprising an effective amount of a bacterial composition comprising a first type of isolated *bacterium*; a second type of isolated *bacterium*; and a third type of isolated *bacterium*, wherein at least one of the first, second and third types are capable of forming a spore, wherein the first, second and third types are not identical, and wherein a combination of at least two of the first, second and third types are inhibitory to at least one type of pathogenic bacteria. In some embodiments, a combination of the first, second and third types is capable of being inhibitory to the pathogenic *bacterium*. In other embodiments, a combination of the first, second and third types is capable of being cytotoxic or cytostatic to the pathogenic *bacterium*. In further embodiments, a combination of the first, second and third types is capable of being cytotoxic or cytostatic to the pathogenic *bacterium*. In further embodiments, a combination of the first, second and third types is capable of inhibiting proliferation of the pathogenic bacterial present at a concentration at least equal to the concentration of the combination of the first, second and third types. In further embodiments, the pathogenic *bacterium* is selected from the group consisting of *Yersinia, Vibrio, Treponema, Streptococcus, Staphylococcus, Shigella, Salmonella, Rickettsia, Pseudomonas, Neisseria, Mycoplasma, Mycobacterium, Listeria, Leptospira, Legionella, Helicobacter, Haemophilus, Francisella, Escherichia, Enterococcus, Klebsiella, Corynebacterium, Clostridium, Chlamydia, Chlamydophila., Campylobacter, Brucella, Borrelia*, and *Bordetella*, in further embodiments, the first, second and third types synergistically interact. In further embodiments, at least one of the first, second and third types are capable of independently forming a spore. In further embodiments, at least two of the first, second and third types are capable of independently forming a spore. In further embodiments, the first, second and third types are capable of independently forming a spore.

In further embodiments, wherein the first, second and third types are capable of functionally populating the gastrointestinal tract of a human subject to whom the composition is administered. In further embodiments, the functional populating of the gastrointestinal tract comprises preventing a dysbiosis of the gastrointestinal tract. In further embodiments, the functional populating of the gastrointestinal tract comprises treating a dysbiosis of the gastrointestinal tract. In further embodiments, the functional populating of the gastrointestinal tract comprises reducing the severity of a dysbiosis of the gastrointestinal tract. In further embodiments, the functional populating of the gastrointestinal tract comprises reducing one or more symptoms of a dysbiosis of the gastrointestinal tract. In further embodiments, the functional populating of the gastrointestinal tract comprises preventing colonization of the gastrointestinal tract by a pathogenic *bacterium*. In further embodiments, the functional populating of the gastrointestinal tract comprises reducing colonization of the gastrointestinal tract by a pathogenic *bacterium*. In further embodiments, the functional populating of the gastrointestinal tract comprises reducing the number of one or more types of pathogenic bacteria in the gastrointestinal tract. In further embodiments, the functional populating of the gastrointestinal tract comprises increasing the number of one or more non-pathogenic bacteria in the gastrointestinal tract. Also provided are single dose units comprising the bacterial compositions provided herein, for example, dose units comprising at least $1\times10^7$, $1\times10^8$, $1\times10^9$, $1\times10^{10}$, $1\times10^{11}$, or $1\times10^{12}$ colony forming units (CFUs) of viable bacteria. Also provided are pharmaceutical formulations comprising an effective amount of the compositions provided herein, and further comprising an effective amount of an anti-bacterial agent, a pharmaceutical formulation comprising an effective amount of the bacterial composition, and further comprising an effective amount of an anti-fungal agent, a pharmaceutical formulation comprising an effective amount of the bacterial composition, and further comprising an effective amount of an anti-viral agent, and a pharmaceutical formulation comprising an effective amount of the bacterial composition, and further comprising an effective amount of an anti-parasitic agent.

In another aspect, provided are methods comprising administering to a human subject in need thereof an effective amount of the bacterial compositions, and further comprising administering to the human subject an effective amount of an anti-biotic agent. In some embodiments, the bacterial composition and the anti-biotic agent are administered simultaneously. In other embodiments, the bacterial composition is administered prior to administration of the anti-biotic agent. In further embodiments, provided are methods in which the number of pathogenic bacteria present in the gastrointestinal tract of the human subject is not detectably increased or is detectably decreased over a period of time. In other embodiments, the human subject is diagnosed as having a dysbiosis of the gastrointestinal tract. In other embodiments, the human subject is diagnosed as infected with a pathogenic *bacterium* selected from the group consisting of *Yersinia, Vibrio, Treponema, Streptococcus, Staphylococcus, Shigella, Salmonella, Rickettsia, Pseudomonas, Neisseria, Mycoplasma, Mycobacterium, Listeria, Leptospira, Legionella, Helicobacter, Haemophilus, Francisella, Escherichia, Enterococcus, Klebsiella, Corynebacterium, Clostridium, Chlamydia, Chlamydophila,*

*Campylobacter, Brucella, Borrelia*, and *Bordetella*. In other embodiments, the anti-bacterial agent is administered to the human subject prior to administration of the bacteria composition. In other embodiments, the number of pathogenic bacteria present in or excreted from the gastrointestinal tract of the human subject is detectably reduced within two weeks of administration of the bacterial composition.

In another aspect, provided are methods of functionally populating the gastrointestinal tract of a human subject, comprising administering to the subject an effective amount of the bacterial composition of the present invention, under conditions such that the first, second and third types functionally populate the gastrointestinal tract of the human subject. In some embodiments, the bacterial composition is orally administered, rectally administered, or the combination of orally and rectally administered. In other embodiments, the bacterial composition is topically or nasally administered or inhaled.

Also provided are methods of preparing a comestible product, comprising combining with a comestible carrier the bacterial compositions of the present invention, wherein the comestible product is substantially free of non-comestible materials.

In one aspect, provided are compositions comprising an effective amount of a bacterial composition comprising at least a first type of isolated *bacterium* capable of forming a spore and a second type of isolated *bacterium* capable of forming a spore, wherein the first type, second type and optional third type are not identical, and wherein at least one of the first type, second type and optional third type are capable of decreasing and/or inhibiting the growth and/or colonization of at least one type of pathogenic bacteria. In an embodiment, the bacterial composition comprises at least about 3, 4, 5, 6, 7, 8, 9 or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprise at least about 5 types of isolated bacteria and at least 2 of the isolated bacteria are capable of forming spores. In an embodiment, the bacterial composition comprises i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the first type, the second type and the optional third type are present in the composition in approximately equal concentrations or activity levels. I n an embodiment, the first type, the second type and the optional third type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially i) between two and about twenty types of isolated bacteria, wherein at least two types of isolated bacteria are independently capable of spore formation; ii) between two and about twenty types of isolated bacteria, wherein at least two types of isolated bacteria not known to be capable of spore formation, or iii) any combination of i) and ii). In an embodiment, the first type of isolated *bacterium* and the second type of isolated *bacterium* are selected from Table 1. In an embodiment, the first type of isolated *bacterium*, the second type of isolated *bacterium* and the optional third type of isolated *bacterium* comprise an operational taxonomic unit (OTU) distinction. In an embodiment, the OTU distinction comprises 16S rDNA sequence similarity below about 95% identity. In an embodiment, the first type of isolated *bacterium* and the second type of isolated *bacterium* independently comprise bacteria that comprise 16S rDNA sequence at least 95% identical to 16S rDNA sequence present in a *bacterium* selected from Table 1. In an embodiment, a combination of the first type, second type and optional third type are: i) cytotoxic, ii) cytostatic, iii) capable of decreasing the growth of the pathogenic *bacterium*, iv) capable of inhibiting the growth of the pathogenic *bacterium*, v) capable of decreasing the colonization of the pathogenic *bacterium*, vi) capable of inhibiting the colonization of the pathogenic *bacterium*, or vii) any combination of i)-vi). In an embodiment, the combination is capable of inhibiting proliferation of the pathogenic bacteria present at a concentration at least equal to the concentration of the combination of the first type, the second type and the optional third type. In an embodiment, the combination is capable of inhibiting proliferation of the pathogenic bacterial present at a concentration at least about twice the concentration of the combination of the first type, the second type and the optional third type. In an embodiment, the combination is capable of inhibiting proliferation of the pathogenic bacterial present at a concentration at least about ten times the concentration of the combination of the first type, the second type and the optional third type. In an embodiment, the combination is capable of proliferating in the presence of the pathogenic bacteria. In an embodiment, the pathogenic *bacterium* is selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, carbapenem-resistant Enterobacteriaceae (CRE), extended spectrum beta-lactam resistant Enterococci (ESBL), and vancomycin-resistant Enterococci (VRE). In an embodiment, the first type, the second type and the optional third type synergistically interact. In an embodiment, the first type, the second type and the optional third type synergistically interact to inhibit the pathogenic *bacterium*. In an embodiment, the composition comprises a combination of bacteria described in any row of Table 4a or Table 4b, or a combination of bacteria described in any row of Table 4a that has a ++++ or a +++ designation, or a combination of bacteria described in any row of Table 4a that has a $75^{th}$ percentile designation.

In another aspect, provided are compositions comprising an effective amount of a bacterial composition comprising at least a first type of isolated *bacterium*, a second type of isolated *bacterium* and an optional third type of isolated *bacterium*, wherein only one of the first type, the second type and the optional third type is capable of forming a spore, and wherein at least one of the first type, the second type and the optional third type is capable of decreasing the growth and/or colonization of at least one type of pathogenic bacteria.

In another aspect, provided are compositions comprising an effective amount of a bacterial composition comprising at least a first type of isolated *bacterium*, a second type of isolated *bacterium* and an optional third type of isolated *bacterium*, wherein the first type, the second type and the optional third type are not spores or known to be capable of forming a spore, and wherein at least one of the first type, the second type and the optional third type are capable of decreasing the growth and/or colonization of at least one type of pathogenic bacteria.

In an embodiment, at least one of the first type, second type and optional third type are capable of reducing the growth rate of at least one type of pathogenic bacteria. In an embodiment, at least one of the first type, second type and optional third type are cytotoxic to at least one type of pathogenic bacteria. In an embodiment, at least one of the first type, second type and optional third type are cytostatic to at least one type of pathogenic bacteria. In an embodiment, the first type, second type and optional third type are selected from Table 1. In an embodiment, the first type, second type and optional third type comprise different species. In an embodiment, the first type, second type and optional third type comprise different genera. In an embodiment, the first type, second type and optional third type comprise different families. In an embodiment, the first type, second type and optional third type comprise different orders. In an embodiment, the first type, second type and optional third type comprise a combination of bacteria described in any row of Table 4a or Table 4b, a combination of bacteria described in any row of Table 4a that has a ++++ or a +++ designation, or any or of Table 4a that has a $75^{th}$ percentile designation.

In another aspect, provided are compositions comprising an effective amount of a bacterial composition comprising at least a first type of isolated *bacterium* and a second type of isolated *bacterium*, wherein: i) the first type, second type and optional third type are independently capable of forming a spore; ii) only one of the first type, second type and optional third type is capable of forming a spore or iii) neither the first type nor the second type is capable of forming a spore, wherein the first type, second type and optional third type are not identical, wherein the first type, second type and optional third type are capable of functionally populating the gastrointestinal tract of a human subject to whom the composition is administered. In an embodiment, the first type, second type and optional third type comprise a combination of bacteria described in any row of Table 4a or Table 4b, a combination of bacteria described in any row of Table 4a that has a ++++ or a +++ designation, or any or of Table 4a that has a $75^{th}$ percentile designation. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing growth and/or colonization of the gastrointestinal tract by a pathogenic *bacterium*. In an embodiment, the functional populating of the gastrointestinal tract comprises reducing growth and/or colonization of the gastrointestinal tract by a pathogenic *bacterium*. In an embodiment, the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises 0, 1, 2, 3 or greater than 3 types of isolated bacteria capable of forming spores. In an embodiment, the bacterial composition comprises at least about 5 types of isolated bacteria capable of forming spores. In an embodiment, the bacterial composition comprises at least about 7 types of isolated bacteria capable of forming spores. In an embodiment, the first type, second type and optional third type are present in the composition in not substantially equal concentrations. In an embodiment, the first type, second type and optional third type are present in the composition in approximately equal concentrations. In an embodiment, the first type is present in the composition in at least about 150% the concentration of the second type. In an embodiment, the second type is present in the composition in at least about 150% the concentration of the first type. In an embodiment, the composition consists essentially of between two and about ten types of isolated bacteria, wherein at least one type of isolated bacteria are independently capable of spore formation. In an embodiment, the first type of isolated *bacterium* and the second type of isolated *bacterium* are selected from Table 1. In an embodiment, the first type of isolated *bacterium*, the second type of isolated *bacterium* and the optional third type of isolated *bacterium* comprise an operational taxonomic unit (OTU) distinction. In an embodiment, the OTU distinction comprises 16S rDNA sequence similarity below about 95% identity. In an embodiment, the first type of isolated *bacterium* and the second type of isolated *bacterium* independently comprise bacteria that comprise 16S rDNA sequence at least 95% identical to 16S rDNA sequence present in a *bacterium* selected from Table 1. In an embodiment, a combination of the first type, second type and optional third type are cytotoxic or cytostatic to the pathogenic *bacterium*. In an embodiment, the combination is capable of inhibiting proliferation of the pathogenic bacteria present at a concentration at least equal to the concentration of the combination of the first type, second type and optional third type. In an embodiment, the combination is capable of inhibiting proliferation of the pathogenic bacterial present at a concentration at least about twice the concentration of the combination of the first type, second type and optional third type. In an embodiment, the combination is capable of inhibiting proliferation of the pathogenic bacteria present at a concentration at least about ten times the concentration of the combination of the first type, second type and optional third type. In an embodiment, the pathogenic *bacterium* is selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the first type, second type and optional third type synergistically interact to be cytotoxic to the pathogenic *bacterium*. In an embodiment, wherein the first type, second type and optional third type synergistically interact to be cytostatic to the pathogenic *bacterium*.

In another aspect, provided are single dose units comprising the compositions of the present invention. In an embodiment, the dose unit comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of either spores or vegetative bacterial cells. In an embodiment, the dose unit comprises a pharmaceutically acceptable excipient, an enteric coating or a combination thereof. In an embodiment, the dose unit further comprises a drug selected from corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof, wherein the drug is present in an amount effective to modulate the amount and/or activity of at least one pathogen. In an embodiment, the dose unit is formulated for oral administration, rectal administration, or the combination of oral and rectal administration, or is formulated for topical, nasal or inhalation administration. In an embodiment, the dose unit comprises a of bacteria described in any row of Table 4a or Table 4b, a combination of bacteria described in any row of Table 4a that has a ++++ or a +++ designation, or any or of Table 4a that has a $75^{th}$ percentile designation.

In another aspect, provided are kits comprising in one or more containers: a first purified population of a first type of bacterial spores substantially free of viable vegetal bacterial cells; a second purified population of a second type of bacterial spores substantially free of viable vegetal bacterial cells; and optionally a third purified population of a third type of bacterial spores substantially free of viable vegetal bacterial cells, wherein the first type, second type and optional third type of bacterial spores are not identical, and wherein the first type, second type and optional third type of bacterial spores, when co-localized in a target region of a gastrointestinal tract of a human subject in need thereof, are capable of functionally populating the gastrointestinal tract. In an embodiment, the first purified population and the second purified population are present in a single container. In an embodiment, the first purified population, the second purified population and the optional third purified population present in two or optionally three containers. In an embodiment, the first purified population and the second purified population are lyophilized or substantially dehydrated. In an embodiment, the kit further comprises in one or more containers an effective amount of an anti-bacterial agent, an effective amount of an anti-viral agent, an effective amount of an anti-fungal agent, an effective amount of an anti-parasitic agent, or a combination thereof in one or more containers. In an embodiment, the kit further comprises a pharmaceutically acceptable excipient or diluent. In an embodiment, the first purified population, the second purified population and the optional third purified population comprise a combination of bacteria described in any row of Table 4a or Table 4b, a combination of bacgeria described in any row of Table 4a that has a ++++ or a +++ designation, or any or of Table 4a that has a $75^{th}$ percentile designation.

Also provided are pharmaceutical formulations comprising an effective amount of the compositions of the invention, and further comprising an effective amount of an anti-bacterial agent, an effective amount of an anti-fungal agent, an effective amount of an anti-viral agent, an effective amount of an anti-parasitic agent.

Also provided are comestible products comprising a first purified population of a first type of bacterial spores, a second purified population of a second type of bacterial spores and optionally a third purified population of a third type of bacterial spores, wherein the first type, second type and optional third type of bacterial spores are not identical, wherein the comestible product is substantially free of viable vegetal bacterial cells, and wherein the first type, second type and optional third type of bacterial spores, when administered to a human subject in need thereof are capable of functionally populating the gastrointestinal tract of the human subject. In an embodiment, the comestible product comprises a food or food additive, a beverage or beverage additive, or a medical food. In an embodiment, the comestible product comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable spores. In an embodiment, the comestible product comprises a first type of bacterial spores and a second type of bacterial spores selected from Table 1, or where the first type of bacterial spores and the second type of bacterial spores independently comprise bacterial spores that comprise 16S rDNA sequence at least 95% identical to 16S rDNA sequence present in a *bacterium* selected from Table 1. In an embodiment, the first purified population, the second purified population and the optional third purified population comprise a combination of bacteria described in any row of Table 4a or Table 4b, a combination of bacteria described in any row of Table 4a that has a ++++ or a +++ designation, or any row of Table 4a that has a $75^{th}$ percentile designation.

Also provided are methods comprising administering to a human subject in need thereof an effective amount of a bacterial composition comprising at least a first type of isolated *bacterium*, a second type of isolated *bacterium* and optionally a third type of isolated *bacterium*, wherein: the first type, second type and optional third type are independently capable of forming a spore; only one of the first type, second type and optional third type is capable of forming a spore; or none of the first type, the second type and optional third type is capable of forming a spore, wherein the first type, second type and optional third type are not identical, and wherein at least one of the first type, second type and optional third type exert an inhibitory-effect on a pathogenic *bacterium* present in the gastrointestinal tract of the human subject, such that the number of pathogenic bacteria present in the gastrointestinal tract is not detectably increased or is detectably decreased over a period of time. In an embodiment, the composition comprise a combination of bacteria described in any row of Table 4a or Table 4b, a combination of bacteria described in any row of Table 4a that has a ++++ or a +++ designation, or any or of Table 4a that has a $75^{th}$ percentile designation. In an embodiment, the human subject is diagnosed as having a dysbiosis of the gastrointestinal tract. In an embodiment, the human subject is diagnosed as infected with a pathogenic *bacterium* selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the bacterial composition is administered simultaneously with i) an antibiotic, ii) a prebiotic, or iii) a combination of i) and ii). In an embodiment, the bacterial composition is administered prior to administration of i) an antibiotic, ii) a prebiotic, or iii) a combination of i) and ii). In an embodiment, the bacterial composition is administered subsequent to administration of i) an antibiotic, ii) a prebiotic, or iii) a combination of i) and ii). In an embodiment, the number of pathogenic *bacterium* present in or excreted from the gastrointestinal tract of the human subject is detectably reduced within one month, within two weeks, or within one week of administration of the bacterial composition. In an embodiment, the number of pathogenic *bacterium* present in or excreted from the gastrointestinal tract of the human subject is detectably reduced within three days, two days or one day of administration of the bacterial composition. In an embodiment, the human subject is detectably free of the pathogenic *bacterium* within one month, two weeks, one week, three days or one day of administration of the bacterial composition. In an embodiment, the bacterial composition comprises at least about 3, 4, 5, 6, 7, 8, 9, or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises: i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the bacterial composition comprises at least about 5 types of isolated bacteria and at least 1 of the isolated bacteria are capable of forming spores. In an embodiment, the bacterial composition comprises at least about 5 types of isolated bacteria and at least 1 of the isolated bacteria is not capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type, second type and optional third type are present in the composition in approximately equal concentrations. In an embodiment, the first type, second type and optional third type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein at least two types of isolated bacteria are independently capable of spore formation. In an embodiment, the composition consists essentially of between two and about ten types of isolated bacteria, wherein at least two types of isolated bacteria are not capable of spore formation. In an embodiment, the first type of isolated *bacterium* and the second type of isolated *bacterium* are selected from Table 1. In an embodiment, the first type of isolated *bacterium*, the second type of isolated *bacterium* and the optional third type of isolated *bacterium* comprise an operational taxonomic unit (OTU) distinction. In an embodiment, the OTU distinction comprises 16S rDNA sequence similarity below about 95% identity. In an embodiment, the first type of isolated *bacterium* and the second type of isolated *bacterium* independently comprise bacteria that comprise 16S rDNA sequence at least 95% identical to 16S rDNA sequence present in a *bacterium* selected from Table 1. In an embodiment, a combination of the first type, second type and optional third type are cytotoxic or cytostatic to the pathogenic *bacterium*. In an embodiment, the combination is capable of inhibiting proliferation of the pathogenic bacterial present at a concentration at least equal to the concentration of the combination of the first type, second type and optional third type. In an embodiment, the combination is capable of inhibiting proliferation of the pathogenic bacterial present at a concentration at least about twice the concentration of the combination of the first type, second type and optional third type. In an embodiment, the combination is capable of inhibiting proliferation of the pathogenic bacterial present at a concentration at least about ten times the concentration of the combination of the first type, second type and optional third type. In an embodiment, the pathogenic *bacterium* is selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the first type, second type and optional third type synergistically interact to be cytotoxic to the pathogenic *bacterium*. In an embodiment, the first type, second type and optional third type synergistically interact to be cytostatic to the pathogenic *bacterium*.

Also provided are methods of functionally populating the gastrointestinal tract of a human subject, comprising administering to the subject an effective amount of a bacterial composition comprising at least a first type of isolated *bacterium*, a second type of isolated *bacterium*, and optionally a third type of isolated *bacterium* wherein i) the first type, second type and optional third type are independently capable of forming a spore; ii) only one of the first type, second type and optional third type is capable of forming a spore or iii) none of the first type, the second type and the optional third type is capable of forming a spore, wherein the first type, second type and optional third type are not identical, under conditions such that the first type, second type and optional third type functionally populate the gastrointestinal tract of the human subject. In an embodiment, the composition comprises a combination of bacteria described in any row of Table 4a or Table 4b, a combination of bacteria described in any row of Table 4a that has a ++++ or a +++ designation, or any row of Table 4a that has a $75^{th}$ percentile designation. In an embodiment, the bacterial composition is orally administered, rectally administered, or the combination of orally and rectally administered. In an embodiment, the bacterial composition is topically or nasally administered or inhaled. In an embodiment, the first type of isolated bacteria and the second type of isolated bacteria are selected from Table 1. In an embodiment, the bacterial composition consists essentially of spores, wherein the spores comprise spores of the first type of isolated bacteria, spores of the second type of isolated bacteria and spores of the optional third type of isolated bacteria. In an embodiment, the first type of isolated bacteria and the second type of isolated bacteria independently comprise bacterial spores that comprise 16S rDNA sequence at least 95% identical to 16S rDNA sequence present in a *bacterium* selected from Table 1. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing colonization of the gastrointestinal tract by a pathogenic *bacterium*. In an embodiment, the functional populating of the gastrointestinal tract comprises reducing colonization of the gastrointestinal tract and/or growth by a pathogenic *bacterium*. In an embodiment, wherein the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises at least about 3, 5, 7 or 9 types of isolated bacteria capable of forming spores. In an embodiment, the bacterial composition comprises at least about 5 types of isolated bacteria and at least 20% of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type, second type and optional third type are present in the composition in approximately equal concentrations. In an embodiment, the first type, second type and optional third type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein i) at least one type of isolated bacteria is capable of spore formation, ii) at least one type of isolated bacteria is not capable of spore formation, or iii) a combination of i) and ii). In an embodiment, a combination of the first type, second type and optional third type are inhibitory to the pathogenic *bacterium*. In an embodiment, the combination reduces the growth rate of the pathogenic *bacterium*. In an embodiment, the combination is cytostatic or cytotoxic to the pathogenic *bacterium*. In an embodiment, the combination is capable of inhibiting growth of the pathogenic bacterial present at a concentration at least equal to the concentration of the combination of the first type, second type and optional third type. In an embodiment, the combination is capable of inhibiting growth of the pathogenic bacterial present at a concentration at least about twice the concentration of the combination of the first type, second type and optional third type. In an embodiment, the combination is capable of inhibiting proliferation of the pathogenic bacterial present at a concentration at least about ten times the concentration of the combination of the first type, second type and optional third type. In an embodiment, the pathogenic *bacterium* is selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the first type, second type and optional third type synergistically interact to reduce or inhibit the growth of the pathogenic *bacterium*. In an embodiment, the first type, second type and optional third type synergistically interact to reduce or inhibit the colonization of the pathogenic *bacterium*. In an embodiment, the method comprises administering to the human subject a single dose unit comprising at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable bacteria. In an embodiment, the dose unit comprises a bacterial population substantially in the form of spores. In an embodiment, the dose unit comprises a pharmaceutically acceptable excipient and/or an enteric coating. In an embodiment, the unit dose is formulated for oral administration, rectal administration, or the combination of oral and rectal administration. In an embodiment, the unit dose is formulated for topical or nasal administration or for inhalation.

In another aspect, provided are methods of reducing the number of pathogenic bacteria present in the gastrointestinal tract of a human subject, comprising administering to the subject an effective amount of a pharmaceutical formulation comprising an effective amount of the composition of the present disclosure, and further comprising an effective amount of an anti-microbial agent, under conditions such that the number of pathogenic bacteria present in the gastrointestinal tract of the human subject is reduced within about one month of administration of the pharmaceutical formulation. In an embodiment, the number of pathogenic bacteria present in the gastrointestinal tract of the human subject is reduced within about two weeks of administration of the pharmaceutical formulation. In an embodiment, the number of pathogenic bacteria present in the gastrointestinal tract of the human subject is reduced within about one week of administration of the pharmaceutical formulation. In an embodiment, the number of pathogenic bacteria present in the gastrointestinal tract of the human subject is reduced within about three days of administration of the pharmaceutical formulation. In an embodiment, the number of pathogenic bacteria present in the gastrointestinal tract of the human subject is reduced within about one day of administration of the pharmaceutical formulation. In an embodiment, the anti-microbial agent comprises anti-bacterial agent. In an embodiment, the anti-microbial agent comprises anti-fungal agent. In an embodiment, the anti-microbial agent comprises anti-viral agent. In an embodiment, the anti-microbial agent comprises anti-parasitic agent.

In another aspect, provided are methods of preparing a comestible product, comprising combining with a comestible carrier a first purified population comprising at least a first type of isolated *bacterium*, a second purified population comprising at least a second type of isolated *bacterium* and optionally a third purified population comprising at least a third type of isolated *bacterium*, wherein: i) the first type, second type and optional third type are independently capable of forming a spore; ii) only one of the first type, second type and optional third type is capable of forming a spore or iii) none of the first type, the second type and the optional third type is capable of forming a spore, wherein the first type, second type and optional third type of bacteria are not identical, wherein the comestible product is substantially free of non-comestible materials. In an embodiment, at least one of the first purified population, the second purified population and the optional third purified population consist essentially of viable spores. In an embodiment, the first purified population, the second purified population and the optional third purified population consist essentially of viable spores. In an embodiment, the comestible product is substantially free of viable vegetal bacterial cells. In an embodiment, the viable spores, when the comestible product is consumed by a human subject in need thereof, are capable of functionally populating the gastrointestinal tract of the human subject. In an embodiment, the comestible product comprises a food or food additive. In an embodiment, the comestible product comprises a beverage or beverage additive. In an embodiment, the comestible product comprises a medical food. In an embodiment, the comestible product comprises at least 1×10, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable spores. In an embodiment, the first purified population, the second purified population and the optional third purified population comprise a combination of bacteria described in any row of Table 4a or Table 4b, or any row of Table 4a that has a ++++ designation or a +++ designation, or any row of Table 4a that has a $75^{th}$ percentile designation. In an embodiment, spores are of a *bacterium* selected from Table 1. In an embodiment, the first purified population and the second purified population independently comprise bacterial spores that comprise 16S rDNA sequence at least 95% identical to 16S rDNA sequence present in a *bacterium* selected from Table 1.

Also provided are methods of reducing the abundance of a pathogen in the gastrointestinal tract of a subject comprising administering a composition of in a therapeutically effective amount and allowing the bacterial composition to compete with the pathogen in the gastrointestinal tract of a subject.

Further provided are methods of treating diarrhea comprising administering a bacterial composition in a therapeutically effective amount and allowing the bacterial composition to reduce the diarrheal effect of a pathogen in the gastrointestinal tract of a subject. In an embodiment, the pathogen is *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the pathogen is *Clostridium difficile, Salmonella* spp., pathogenic *Escherichia coli*, or vancomycin-resistant *Enterococcus* spp. In an embodiment, the pathogen is *Clostridium difficile*. In an embodiment, the composition is administered orally. In an embodiment the composition comprises a combination of bacteria described in any row of Table 4a, or Table 4b, or any row of Table 4a that has a ++++ designation or a +++ designation, or any row of Table 4a that has a $75^{th}$ percentile designation.

In some aspects, the invention relates to a composition comprising a network ecology selected from Table 10. In some embodiments, the network ecology comprises network clades provided in Table 10. In other embodiments, the network ecology comprises network OTUs provided in Table 10. In some cases the composition comprises *Blautia producta, Clostridium disporicum, Clostridium innocuum, Clostridium mayombei, Clostridium orbiscindens, Clostridium symbiosum*, and Lachnospiraceae *bacterium* 5_1_57FAA. In some embodiments, the composition the composition is effective for treating at least one sign or symptom of a dysbiosis, for example, the is effective for reducing at least one sign or symptom of infection or dysbiosis associated with *C. difficile, Klebsiella pneumonii, Morganella morganii*, or vancomycin-resistant Enterococci (IRE).

In another aspect, the invention relates to a composition comprising a bacterial heterotrimer selected from a heterotrimer identified in Table 4a, Table 4b, or Table 12, such that the heterotrimer can e.g., inhibit growth of a pathobiont in a CivSim assay.

In some aspects, the invention relates to a composition comprising a bacterial heterotrimer selected from a heterotrimer identified in Table 14, Table 15, Table 16, Table 17, Table 17, Table 18, Table 19, Table 20, or Table 21, such that the organisms of the heterotrimer can augment and/or engraft in a human gastrointestinal tract. In some embodiments, the engraftment and/or augmentation can occur after administration of the composition to a human having a dysbiosis. In some embodiments, the dysbiosis is associated with the presence of *C. difficile* in the gastrointestinal tract of the human.

Additional objects and advantages will be set forth in part in the description which follows, and in part will be obvious from the description, or may be learned by practice of the embodiments. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to further explain the embodiments.

BRIEF DESCRIPTION OF TABLES

Table 1 is a list of Operational Taxonomic Units (OTU) with taxonomic assignments made to genus, species, and phylogenetic clade. Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a pathogen or pathobiont (see Definitions for description of "Pathobiont"). NIAID (National Institute of Allergy and infectious Disease) Priority Pathogens are denoted as 'Category-A', 'Category-B', or 'Category-C', and opportunistic pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository.

Table 2 provides phylogenetic clades and their members determined using 16S full-length and V4 sequencing.

Table 3 is a list of human diseases, disorders and conditions for which the provided bacterial compositions are useful.

Table 4a. Provides representative combinations of the present invention tested in vitro.

Table 4b. Provides representative combinations of the present invention tested in vitro Table 5 provides data from testing of representative ternary OTU combinations of the present invention in a CivSim assay and in vivo.

Table 6 provides data on the ability of a 15 member bacterial composition to inhibit VRE in vitro.

Table 7 provides data on the ability of a 15 member bacterial composition to inhibit *K. pneumoniae* in vitro.

Table 8 provides data on the ability of a 15 member bacterial composition to inhibit *M. morganii* in vitro.

Table 9 provides data demonstrating the efficacy of combinations of the present invention against *C. difficile* infection in a preventive murine model.

Table 10. Provides exemplary combinations of the present invention that were tested against *C. difficile* infection in a preventive murine model.

Table 11. Provides bacterial OTUs associated with a bacterial composition used to treat patients with *C. difficile* associated diarrheal disease, and to OTUs comprising the OTUs undergo engraftment and ecological augmentation to establish a more diverse microbial ecology in patients post-treatment. OTUs that comprise an augmented ecology are not present in the patient prior to treatment and/or exist at extremely low frequencies such that they do not comprise a significant fraction of the total microbial carriage and are not detectable by genomic and/or microbiological assay methods. OTUs that are members of the engrafting and augmented ecologies were identified by characterizing the OTUs that increase in their relative abundance post treatment and that respectively are: (i) present in the ethanol-treated spore preparation and absent in the patient pretreatment, or (ii) absent in the ethanol-treated spore preparation, but increase in their relative abundance through time post treatment with the preparation due to the formation of favorable growth conditions by the treatment. Notably, augmenting OTUs can grow from low frequency reservoirs in the subject, or be introduced from exogenous sources such as diet. OTUs that comprise a "core" composition in the treatment bacterial composition are denoted.

Table 12 provides bacterial compositions that exhibited inhibition against *C. difficile* as measured by a mean log inhibition greater than the 99% confidence interval (C.I.) of the null hypothesis (see Example 6, ++++) and that are identified in at least one spore ecology treatment or in a human subject microbiome after treatment with a composition.

Table 13 provides exemplary of 4-mer to 10-mer bacterial compositions that were comprised in a bacterial therapy administered to subjects with *C. difficile*-associated diarrheal disease.

Table 14 provides exemplary ternary OTUs that either engrafted or augmented in at least one patient (of 29 that responded to treatment) after treatment with a spore ecology composition. Each ternary combination was either in all doses or the organisms of the ternary combination were present together in all subjects at some post-treatment time.

Table 15 provides exemplary OTUs that engrafted in at least one subject. The ternary combinations were found in 95% of the doses of administered spore ecology compositions.

Table 16 provides exemplary OTUs that augmented in at least one patient post treatment with a spore ecology composition. The ternary combinations were found together in at least 75% of the subjects at some post-treatment timepoint.

Table 17 provides exemplary OTU combinations that were present in at least 75% of the doses of administered spore ecology compositions. All administered doses containing the listed ternary combinations had the OTU Clostridiales sp. SM4/1 as either augmenting or engrafting in the subjects given doses containing the ternary composition.

Table 18 provides exemplary ternary OTU combinations that were present in at least 75% of the doses of administered spore ecology compositions. All administered doses containing the listed ternary combinations had the OTU Clostridiales sp. SSC/2 as either augmenting or engrafting in the subjects given a composition containing the ternary combination.

Table 19 provides exemplary ternary combinations of OTUs that were present in at least 75% of the doses of administered spore ecology compositions. All administered doses containing the listed ternary combinations had the OTU *Clostridium* sp. NML 04A032 as either augmenting or engrafting in the subjects given a composition containing the ternary combination.

Table 20 provides exemplary ternary combinations of OTUs that were present in at least 75% of the doses of administered spore ecology compositions. All administered doses containing the listed ternary combinations had the OTUs *Clostridium* sp. NML 04A032, *Ruminococcus lactaris*, and *Ruminococcus torques* as either augmenting or engrafting in the subjects given a composition containing the ternary combination.

Table 21 provides exemplary ternary combinations of OTUs that are present in at least 75% of the doses of administered spore ecology compositions. All administered doses containing the listed ternary combinations had the OTUs *Eubacterium rectale, Faecalibacterium prausnitzii*, Oscillibacter sp. G2, *Ruminococcus lactaris*, and *Ruminococcus torques* as either augmenting or engrafting in the subjects given a composition containing the ternary combination.

Table 22 provides alternate names of organisms found in OTUs of the embodiments of the present invention.

BRIEF DESCRIPTION OF FIGURES

FIG. 3 highlights in bold the nucleotide sequences for each hypervariable region in the exemplary reference *E. coli* 16S sequence (SEQ ID NO: 2047) described by Brosius et al., supra.

DEFINITIONS

Figure 1:
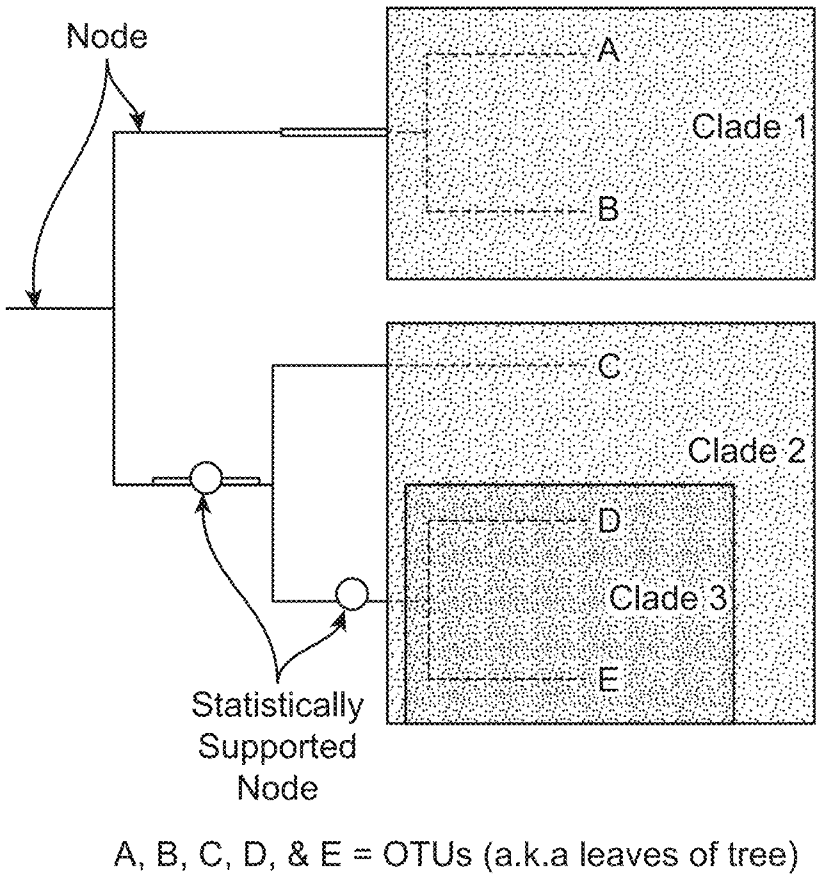
FIG. 1 shows an exemplary phylogenetic tree and the relationship of OTUs and Clades B, C, D, and E represent OTUs, also known as leaves in the tree. Clade 1 comprises OTUs A and B, Clade 2 comprises OTUs C, D and E, and Clade 3 is a subset of Clade 2 comprising OTUs D and E. Nodes in a tree that define clades in the tree can be either statistically supported or not statistically supported. OTUs within a clade are more similar to each other than to OTUs in another clade; the robustness the clade assignment is denoted by the degree of statistical support for a node upstream of the OTUs in the clade.

As used herein, the term "antioxidant" refers to, without limitation, any one or more of various substances such as beta-carotene (a vitamin A precursor), vitamin C, vitamin E, and selenium that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowoltberry, lignan, lutein, lycopene, polyphenols, selenium, vitamin A, vitamin C, vitamin E, zeaxanthin, or combinations thereof.

"Backbone Network Ecology" or simply "Backbone Network" or "Backbone" are compositions of microbes that form a foundational composition that can be built upon or subtracted from to optimize a Network Ecology or Functional Network Ecology to have specific biological characteristics or to comprise desired functional properties, respectively. Microbiome therapeutics can be comprised of these "Backbone Networks Ecologies" in their entirety, or the "Backbone Networks" can be modified by the addition or subtraction of "R-Groups" to give the network ecology desired characteristics and properties. "R-Groups" as used herein, can be defined in multiple terms including, but not limited to: individual OTUs, individual or multiple OTUs derived from a specific phylogenetic clade or a desired phenotype such as the ability to form spores, or functional bacterial compositions that comprise. "Backbone Networks" can comprise a computationally derived Network Ecology in its entirety or can be subsets of the computed network that represent key nodes in the network that contributed to efficacy such as but not limited to a composition of Keystone OTUs. The number of organisms in the human gastrointestinal tract, as well as the diversity between healthy individuals, is indicative of the functional redundancy of a healthy gut microbiome ecology. See The Human Microbiome Consortia. 2012. Structure, function and diversity of the healthy human microbiome. Nature 486: 207-214. This redundancy makes it highly likely that non-obvious subsets of OTUs or functional pathways (i.e., "Backbone Networks") are critical to maintaining states of health and or catalyzing a shift from a dysbiotic state to one of health. One way of exploiting this redundancy is through the substitution of OTUs that share a given clade (see below) or of adding members of a clade not found in the Backbone Network.

"Bacterial Composition" refers to a consortium of microbes comprising two or more OTUs. Backbone Network Ecologies, Functional Network Ecologies, Network Classes, and Core Ecologies are all types of bacterial compositions. A "Bacterial Composition" can also refer to a composition of enzymes that are derived from a microbe or multiple microbes. As used herein, Bacterial Composition includes a therapeutic microbial composition, a prophylactic microbial composition, a Spore Population, a Purified Spore Population, or ethanol treated spore population.

"Clade" refers to the OTUs or members of a phylogenetic tree that are downstream of a statistically valid node in a phylogenetic tree (FIG. 1). The clade comprises a set of terminal leaves in the phylogenetic tree (i.e., tips of the tree) that are a distinct monophyletic evolutionary unit and that share some extent of sequence similarity. Clades are hierarchical. In one embodiment, the node in a phylogenetic tree that is selected to define a clade is dependent on the level of resolution suitable for the underlying data used to compute the tree topology. Exemplary clades are delineated in Table 1 and Table 2. As used herein, clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are (i) within a specified number of bootstrap supported nodes from one another, and (ii) within 5% genetic identity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play or are predicted to play similar functional roles in a microbial ecology such as that found in the human gut. In some embodiments, one OTU from a clade can be substituted in a composition by a different OTU from the same clade.

The "Colonization" of a host organism includes the non-transitory residence of a *bacterium* or other microscopic organism. As used herein, "reducing colonization" of a host subject's gastrointestinal tract (or any other microbiotal niche) by a pathogenic or non-pathogenic *bacterium* includes a reduction in the residence time of the *bacterium* the gastrointestinal tract as well as a reduction in the number (or concentration) of the *bacterium* in the gastrointestinal tract or adhered to the luminal surface of the gastrointestinal tract. The reduction in colonization can be permanent or occur during a transient period of time. Reductions of adherent pathogens can be demonstrated directly, e.g., by determining pathogenic burden in a biopsy sample, or reductions may be measured indirectly, e.g., by measuring the pathogenic burden in the stool of a mammalian host.

A "Combination" of two or more bacteria includes the physical co-existence of the two bacteria, either in the same material or product or in physically connected products, as well as the temporal co-administration or co-localization of the two bacteria.

The term "consisting essentially of" as used herein conforms to the definition as provided in the Manual of Patent Examination and Procedure (MPEP; March 2014). The basic and novel characteristics of inventions claimed herein include the ability to catalyze changes in a microbiome ecology of a mammalian subject, e.g., a human, from dysbiotic to a more normative state, and to promote engraftment and augmentation of microbiome component as set out in the specification, e.g., see Tables 14-21. A more normative state can include, in a non-limiting example, a decrease in a sign or symptom of a disease or disorder associated with a dysbiosis.

"Cytotoxic" activity of *bacterium* includes the ability to kill a bacterial cell, such as a pathogenic bacterial cell. A "cytostatic" activity or *bacterium* includes the ability to inhibit, partially or fully, growth, metabolism, and/or proliferation of a bacterial cell, such as a pathogenic bacterial cell. Cytotoxic activity may also apply to other cell types such as but not limited to Eukaryotic cells.

"Dimer" refers to a combination of bacteria that is comprised of two OTUs. The descriptions "homodimer" and "heterodimer" refer to combinations where the two OTUs are the same or different, respectively.

"Dysbiosis" refers to a state of the microbiota or microbiome of the gut or other body area, including mucosal or skin surfaces in which the normal diversity and/or function of the ecological network is disrupted. Any disruption from a preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a subject, or the shift to an ecological network that no longer provides a beneficial function to the host and therefore no longer promotes health.

"Ecological Niche" or simply "Niche" refers to the ecological space in which an organism or group of organisms occupies. Niche describes how an organism or population or organisms responds to the distribution of resources, physical parameters (e.g., host tissue space) and competitors (e.g., by growing when resources are abundant, and when predators, parasites and pathogens are scarce) and how it in turn alters those same factors (e.g., limiting access to resources by other organisms, acting as a food source for predators and a consumer of prey).

"Germinant" is a material or composition or physical-chemical process capable of inducing vegetative growth of a *bacterium* that is in a dormant spore form, or group of bacteria in the spore form, either directly or indirectly in a host organism and/or in vitro.

"Inhibition" of a pathogen or non-pathogen encompasses the inhibition of any desired function or activity of the bacterial compositions of the present invention. Demonstrations of inhibition, such as decrease in the growth of a pathogenic *bacterium* or reduction in the level of colonization of a pathogenic *bacterium* are provided herein and otherwise recognized by one of ordinary skill in the art. Inhibition of a pathogenic or non-pathogenic *bacterium*'s "growth" may include inhibiting the increase in size of the pathogenic or non-pathogenic *bacterium* and/or inhibiting the proliferation (or multiplication) of the pathogenic or non-pathogenic *bacterium*. Inhibition of colonization of a pathogenic or non-pathogenic *bacterium* may be demonstrated by measuring the amount or burden of a pathogen before and after a treatment. An "inhibition" or the act of "inhibiting" includes the total cessation and partial reduction of one or more activities of a pathogen, such as growth, proliferation, colonization, and function. Inhibition of function includes, for example, the inhibition of expression of pathogenic gene products such as a toxin or invasive pilus induced by the bacterial composition.

"Isolated" encompasses a *bacterium* or other entity or substance that has been (1) separated from at least some of the components with which it was associated when initially produced (whether in nature or in an experimental setting), and/or (2) produced, prepared, purified, and/or manufactured by the hand of man. Isolated bacteria include those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. In some embodiments, isolated bacteria are separated from 10%, 20%, 30%, 40%, 50%, 60%, 70%, 80%, 90%, or more of the other components with which they were initially associated. In some embodiments, isolated bacteria are more than 80%, 85%, 90%, 91%, 92%, 93%, 94%, 95%, 96%, 97%, 98%, 99%, or more than 99% pure. As used herein, a substance is "pure" if it is substantially free of other components. The terms "purify," "purifying" and "purified" refer to a *bacterium* or other material that has been separated from at least some of the components with which it was associated either when initially produced or generated (e.g., whether in nature or in an experimental setting), or during any time after its initial production. A *bacterium* or a bacterial population may be considered purified if it is isolated at or after production, such as from a material or environment containing the *bacterium* or bacterial population, or by passage through culture, and a purified *bacterium* or bacterial population may contain other materials up to about 10%, about 20%, about 30%, about 40%, about 50%, about 60%, about 70%, about 80%, about 90%, or above about 90% and still be considered "isolated." In other embodiments, a purified *bacterium* or bacterial population may contain other materials up to 10%, 20%, 30%, 40%, 50%, 60%, 70%, 80%, 90%, or 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In some embodiments, purified bacteria and bacterial populations are more than 80%, 85%, 90%, 91%, 92%, 93%, 94%, 95%, 96%, 97%, 98%, 99%, or more than 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

"Keystone OTU" or "Keystone Function" refers to one or more OTUs or Functional Pathways (e.g., KEGG or COG pathways) that are common to many network ecologies or functional network ecologies and are members of networks that occur in many subjects (i.e., are pervasive). Due to the ubiquitous nature of Keystone OTUs and their associated Functions Pathways, they are central to the function of network ecologies in healthy subjects and are often missing or at reduced levels in subjects with disease. Keystone OTUs and their associated functions may exist in low, moderate, or high abundance in subjects. "Non-Keystone OTU" or "non-Keystone Function" refers to an OTU or Function that is observed in a Network Ecology or a Functional Network Ecology and is not a keystone OTU or Function.

"Microbiota" refers to the community of microorganisms that occur (sustainably or transiently) in and on an animal subject, typically a mammal such as a human, including eukaryotes, archaea, bacteria, and viruses (including bacterial viruses, i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

"Microbial Carriage" or simply "Carriage" refers to the population of microbes inhabiting a niche within or on humans. Carriage is often defined in terms of relative abundance. For example, OTU1 comprises 60% of the total microbial carriage, meaning that OTU1 has a relative abundance of 60% compared to the other OTUs in the sample from which the measurement was made. Carriage is most often based on genomic sequencing data where the relative abundance or carriage of a single OTU or group of OTUs is defined by the number of sequencing reads that are assigned to that OTU/s relative to the total number of sequencing reads for the sample. Alternatively, Carriage may be measured using microbiological assays.

"Microbial Augmentation" or simply "augmentation" refers to the establishment or significant increase of a population of microbes that are (i) absent or undetectable (as determined by the use of standard genomic and microbiological techniques) from the administered therapeutic microbial composition, (ii) absent, undetectable, or present at low frequencies in the host niche (for example: gastrointestinal tract, skin, anterior-nares, or vagina) before the delivery of the microbial composition, and (iii) are found after the administration of the microbial composition or significantly increased, for example, 2-fold, 5-fold, $1\times10^2$ $1\times10$, $1\times10^4$, $1\times10^5$, $1\times10^6$, $1\times10^7$, or greater than $1\times10^8$, in cases where they were present at low frequencies. The microbes that comprise an augmented ecology can be derived from exogenous sources such as food and the environment, or grow out from micro-niches within the host where they reside at low frequency. The administration of a bacterial microbial composition induces an environmental shift in the target niche that promotes favorable conditions for the growth of these commensal microbes. In the absence of treatment with a bacterial composition, the host can be constantly exposed to these microbes; however, sustained growth and the positive health effects associated with the stable population of increased levels of the microbes comprising the augmented ecology are not observed.

"Microbial Engraftment" or simply "engraftment" refers to the establishment of OTUs present in the bacterial composition in a target niche that are absent in the treated host prior to treatment. The microbes that comprise the engrafted ecology are found in the therapeutic microbial composition and establish as constituents of the host microbial ecology upon treatment. Engrafted OTUs can establish for a transient period of time, or demonstrate long-term stability in the microbial ecology that populates the host post treatment with a bacterial composition. The engrafted ecology can induce an environmental shift in the target niche that promotes favorable conditions for the growth of commensal microbes capable of catalyzing a shift from a dysbiotic ecology to one representative of a health state.

As used herein, the team "Minerals" is understood to include boron, calcium, chromium, copper, iodine, iron, magnesium, manganese, molybdenum, nickel, phosphorus, potassium, selenium, silicon, tin, vanadium, zinc, or combinations thereof.

"Network Ecology" refers to a consortium of clades or OTUs that co-occur in some number of subjects. As used herein, a "network" is defined mathematically by a graph delineating how specific nodes (i.e., clades or OTUs) and edges (connections between specific clades or OTUs) relate to one another to define the structural ecology of a consortium of clades or OTUs. Any given Network Ecology will possess inherent phylogenetic diversity and functional properties. A Network Ecology can also be defined in terms of its functional capabilities where for example the nodes would be comprised of elements such as, but not limited to, enzymes, clusters of orthologous groups (COGS; http://www.ncbi.nlm.nih.gov/books/NBK21090/), or KEGG Orthology Pathways (www.genome.jp/kegg/); these networks are referred to as a "Functional Network Ecology". Functional Network Ecologies can be reduced to practice by defining the group of OTUs that together comprise the functions defined by the Functional Network Ecology.

"Network Class" and "Network Class Ecology" refer to a group of network ecologies that in general are computationally determined to comprise ecologies with similar phylogenetic and/or functional characteristics. A Network Class therefore contains important biological features, defined either phylogenetically or functionally, of a group (i.e., a cluster) of related network ecologies. One representation of a Network Class Ecology is a designed consortium of microbes, typically non-pathogenic bacteria, that represents core features of a set of phylogenetically or functionally related network ecologies seen in many different subjects. In some occurrences, a Network Class, while designed as described herein, exists as a Network Ecology observed in one or more subjects. Network Class ecologies are useful for reversing or reducing a dysbiosis in subjects where the underlying, related Network Ecology has been disrupted.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

"Operational taxonomic units" and "OTU" (or plural, "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU. See e.g., Claesson et al., 2010. Comparison of two next-generation sequencing technologies for resolving highly complex microbiota composition using tandem variable 16S rRNA gene regions. Nucleic Acids Res 38: e200. Konstantinidis et al., 2006. The bacterial species definition in the genomic era. Philos Trans R. Soc Loud B Biol Sci. 361: 1929-1940. In embodiments involving the complete genome, MLSTs, specific genes, other than 16S, or sets of genes OTUs that share ≥95% average nucleotide identity are considered the same OTU. See e.g., Achtman and Wagner. 2008. Microbial diversity and the genetic nature of microbial species. Nat. Rev. Microbiol. 6: 431-440; Konstantinidis et al., 2006, supra. The bacterial species definition in the genomic era. Philos Trans R Soc Lond B Biol Sci 361: 1929-1940. OTUs can be defined by comparing sequences between organisms. Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Such characterization employs, e.g., WGS data or a whole genome sequence. As used herein, a "type" of *bacterium* refers to an OTU that can be at the level of a strain, species, clade, or family.

Table 1 below shows a List of Operational Taxonomic Units (OTU) with taxonomic assignments made to genus, species, and phylogenetic clade. Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a Pathogen or Pathobiont (see Definitions for description of "pathobiont"). NIAID Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository.

"Pathobionts" or "opportunistic pathogens" refers to specific bacterial species found in healthy hosts that may trigger immune-mediated pathology and/or disease in response to certain genetic or environmental factors (Chow et al., 2011. Curr Op Immunol. Pathobionts of the intestinal microbiota and inflammatory disease. 23: 473-80). A pathobiont is an opportunistic microbe that is mechanistically distinct from an acquired infectious organism. The term "pathogen" as used herein includes both acquired infectious organisms and pathobionts.

"Pathogen," "pathobiont" and "pathogenic" in reference to a *bacterium* or any other organism or entity that includes any such organism or entity that is capable of causing or affecting a disease, disorder or condition of a host organism containing the organism or entity, including but not limited to pre-diabetes, type 1 diabetes or type 2 diabetes.

"Phenotype" refers to a set of observable characteristics of an individual entity. As example an individual subject may have a phenotype of "health" or "disease". Phenotypes describe the state of an entity and all entities within a phenotype share the same set of characteristics that describe the phenotype. The phenotype of an individual results in part, or in whole, from the interaction of the entity's genome and/or microbiome with the environment, especially including diet.

"Phylogenetic Diversity" is a biological characteristic that refers to the biodiversity present in a given Network Ecology or Network Class Ecology based on the OTUs that comprise the network. Phylogenetic diversity is a relative term, meaning that a Network Ecology or Network Class that is comparatively more phylogenetically diverse than another network contains a greater number of unique species, genera, and taxonomic families. Uniqueness of a species, genera, or taxonomic family is generally defined using a phylogenetic tree that represents the genetic diversity all species, genera, or taxonomic families relative to one another. In another embodiment phylogenetic diversity may be measured using the total branch length or average branch length of a phylogenetic tree. Phylogenetic Diversity may be optimized in a bacterial composition by including a wide range of biodiversity.

"Phylogenetic tree" refers to a graphical representation of the evolutionary relationships of one genetic sequence to another that is generated using a defined set of phylogenetic reconstruction algorithms (e.g., parsimony, maximum likelihood, or Bayesian). Nodes in the tree represent distinct ancestral sequences and the confidence of any node is provided by a bootstrap or Bayesian posterior probability, which measures branch uncertainty.

"Prediabetes" refers a condition in which blood glucose levels are higher than normal, but not high enough to be classified as diabetes. Individuals with pre-diabetes are at increased risk of developing type 2 diabetes within a decade. According to CDC, prediabetes can be diagnosed by fasting glucose levels between 100-125 mg/dL, 2 hour post-glucose load plasma glucose in oral glucose tolerance test (OGTT) between 140 and 199 mg/dL, or hemoglobin A1c test between 5.7%-6.4%.

"rDNA," "rRNA," "16S-rDNA," "16S-rRNA," "16S," "16S sequencing," "16S-NGS," "18S," "18S-rRNA," "18S-rDNA," "18S sequencing," and "18S-NGS" refer to the nucleic acids that encode for the RNA subunits of the ribosome. rDNA refers to the gene that encodes the rRNA that comprises the RNA subunits. There are two RNA subunits in the ribosome termed the small subunit (SSU) and large subunit (LSU); the RNA genetic sequences (rRNA) of these subunits is related to the gene that encodes them (rDNA) by the genetic code. rDNA genes and their complementary RNA sequences are widely used for determination of the evolutionary relationships amount organisms as they are variable, yet sufficiently conserved to allow cross organism molecular comparisons. Typically 16S rDNA sequence (approximately 1542 nucleotides in length) of the 30S SSU is used for molecular-based taxonomic assignments of prokaryotes and the 18S rDNA sequence (approximately 1869 nucleotides in length) of 40S SSU is used for eukaryotes. 16S sequences are used for phylogenetic reconstruction as they are in general highly conserved, but contain specific hypervariable regions that harbor sufficient nucleotide diversity to differentiate genera and species of most bacteria.

"Residual habitat products" refers to material derived from the habitat for microbiota within or on a human or animal. For example, microbiota live in stool in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses, i.e., phage), fungal, mycoplasmal contaminants. In another embodiment, it means that fewer than 1x10−2%, 1x10−3%, 1x10−4%, 1x10−5%, 1x10−6%, 1x10−7%, 1x10−8 of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of 10-8 or 10-9), such as through multiple 10-fold serial dilutions. This can further be confirmed by showing that multiple isolated colonies have similar cell shapes and Gram staining behavior. Other methods for confirming adequate purity include genetic analysis (e.g., PCR, DNA sequencing), serology and antigen analysis, enzymatic and metabolic analysis, and methods using instrumentation such as flow cytometry with reagents that distinguish desired constituents from contaminants.

"Synergy" refers to an effect produced by a combination, e.g., of two microbes (for example, microbes or two different species or two different clades) that is greater than the expected additive effectives of the combination components. In certain embodiments, "synergy" between two or more microbes can result in the inhibition of a pathogens ability to grow. For example, ternary combinations synergistically inhibit *C. difficile* if their mean log inhibition is greater than the sum of the log inhibition of homotrimers of each constituent *bacterium* divided by three to account for the three-fold higher dose of each strain or for binary combinations, the log inhibition of a homodimer of each constituent *bacterium* divided by two. In another example, synergy can be calculated by defining the OTU compositions that demonstrate greater inhibition than that represented by the sum of the log inhibition of each *bacterium* tested separately. In other embodiments, synergy can be defined as a property of compositions that exhibit inhibition greater than the maximum log inhibition among those of each constituent *bacterium*'s homodimer or homotrimer measured independently. As used herein, "synergy" or "synergistic interactions" refers to the interaction or cooperation of two or more microbes to produce a combined effect greater than the sum of their separate effects.

"Spore" or a population of "spores" includes bacteria (or other single-celled organisms) that are generally viable, more resistant to environmental influences such as heat and bacteriocidal agents than vegetative forms of the same bacteria, and typically capable of germination and outgrowth. Spores are characterized by the absence of active metabolism until they respond to specific environmental signals, causing them to germinate. "Spore-formers" or bacteria "capable of forming spores" are those bacteria containing the genes and other necessary abilities to produce spores under suitable environmental conditions.

"Spore population" refers to a plurality of spores present in a composition. Synonymous terms used herein include spore composition, spore preparation, ethanol-treated spore fraction and spore ecology. A spore population may be purified from a fecal donation, e.g., via ethanol or heat treatment, or a density gradient separation or any combination of methods described herein to increase the purity, potency and/or concentration of spores in a sample. Alternatively, a spore population may be derived through culture methods starting from isolated spore former species or spore former OTUs or from a mixture of such species, either in vegetative or spore form.

In one embodiment, the spore preparation comprises spore forming species wherein residual non-spore forming species have been inactivated by chemical or physical treatments including ethanol, detergent, heat, sonication, and the like; or wherein the non-spore forming species have been removed from the spore preparation by various separations steps including density gradients, centrifugation, filtration and/or chromatography; or wherein inactivation and separation methods are combined to make the spore preparation. In yet another embodiment, the spore preparation comprises spore forming species that are enriched over viable non-spore formers or vegetative forms of spore formers. In this embodiment, spores are enriched by 2-fold, 5-fold, 10-fold, 50-fold, 100-fold, 1000-fold, 10,000-fold or greater than 10,000-fold compared to all vegetative forms of bacteria. In yet another embodiment, the spores in the spore preparation undergo partial germination during processing and formulation such that the final composition comprises spores and vegetative bacteria derived from spore forming species.

"Sporulation induction agent" is a material or physical-chemical process that is capable of inducing sporulation in a *bacterium*, either directly or indirectly, in a host organism and/or in vitro.

To "increase production of bacterial spores" includes an activity or a sporulation induction agent. "Production" includes conversion of vegetative bacterial cells into spores and augmentation of the rate of such conversion, as well as decreasing the germination of bacteria in spore form, decreasing the rate of spore decay in vivo, or ex vivo, or to increasing the total output of spores (e.g., via an increase in volumetric output of fecal material).

"Subject" refers to any animal subject including humans, laboratory animals (e.g., non-human primates, rats, mice), livestock (e.g., cows, sheep, goats, pigs, turkeys, and chickens), and household pets (e.g., dogs, cats, and rodents). The subject may be suffering from a dysbiosis, that contributes to or causes a condition classified as diabetes or pre-diabetes, including but not limited to mechanisms such as metabolic endotoxemia, altered metabolism of primary bile acids, immune system activation, or an imbalance or reduced production of short chain fatty acids including butyrate, propionate, acetate, and branched chain fatty acids.

"Trimer" refers to a combination of bacteria that is comprised of three OTUs. The descriptions "homotrimer" and "heterotrimer" refer to combinations where all three OTUs are the same or different, respectively. A "semi-heterotrimer" refers to combinations where two constituents are the same with a third that is different As used herein the term "vitamin" is understood to include any of various fat-soluble or water-soluble organic substances (non-limiting examples include vitamin A, vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid), and Vitamin B12 (various cobalamins; commonly cyanocobalamin in vitamin supplements), vitamin C, vitamin D, vitamin E, vitamin K, K1 and K2 (i.e., MK-4, MK-7), folic acid and biotin) essential in minute amounts for normal growth and activity of the body and obtained naturally from plant and animal foods or synthetically made, pro-vitamins, derivatives, analogs.

"V1-V9 regions" or "16S V1-V9 regions" refers to the first through ninth hypervariable regions of the 16S rDNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature (Brosius et al., 1978. Complete nucleotide sequence of a 16S ribosomal RNA gene from *Escherichia coli*, PNAS USA 75(144801-48051 In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rDNA by comparing the candidate sequence in question to a reference sequence and identifying the hypervariable regions based on similarity to the reference hypervariable regions, or alternatively, one can employ Whole Genome Shotgun (WGS) sequence characterization of microbes or a microbial community.

DETAILED DESCRIPTION

Applicants have discovered combinations of bacteria that, when present, are associated with improvement in the microbiome of a subject, e.g., a subject having a dysbiosis such as a dysbiosis associated with *C. difficile*. In addition, combinations of microorganisms have been identified that are associated with the engraftment and/or augmentation of organisms associated with a healthy microbiome. Applicants have also identified combinations of microorganisms that can be useful for treating antibiotic-resistant or other pathogenic bacterial conditions. In some embodiments the microbial content of such a composition comprises the organisms, in other embodiments, the microbial content of the composition consists essentially of the organisms, and in other embodiments, the microbial content of the composition consists of the organisms. In all cases, the composition may include non-microbial components. In some cases, the composition comprises at least two organisms (e.g., three organisms) or more, as are described herein.

Emergence of Antibiotic Resistance in Bacteria

Antibiotic resistance is an emerging public health issue (Carlet et al., 2011. Society's failure to protect a precious resource: antibiotics. Lancet 378: 369-371). Numerous genera of bacteria harbor species that are developing resistance to antibiotics. These include but are not limited to vancomycin resistant *Enterococcus* (VRE) and carbapenem resistant *Klebsiella* (CRKp). *Klebsiella pneumoniae* and *Escherichia coli* strains are becoming resistant to carbapenems and require the use of old antibiotics characterized by high toxicity, such as colistin (Canton et al. 2012. Rapid evolution and spread of carbapenemases among Enterobacteriaceae in Europe. Clin Microbiol Infect 18: 413-431). Additional multiply drug resistant strains of multiple species, including *Pseudomonas aeruginosa, Enterobacter* spp., and *Acinetobacter* spp. are observed clinically including isolates that are highly resistant to ceftazidime, carbapenems, and quinolones (European Centre for Disease Prevention and Control: EARSS net database. http://ecdc.europa.eu.). The Centers for Disease Control and Prevention in 2013 released a Threat Report (http://www.cdc.gov/drugresistance/threat-report-2013/) citing numerous bacterial infection threats that included *Clostridium difficile*, carbapenem-resistant Enterobacteriaceae (CRE), multidrug-resistant *Acinetobacter*, drug-resistant *Campylobacter*, extended spectrum β-lactamase producing Enterobacteriaceae (ESBLs), vancomycin-resistant *Enterococcus* (VRE), multidrug-resistant *Pseudomonas aeruginosa*, drug-resistant non-typhoidal *Salmonella*, drug-resistant *Salmonella typhi*, drug-resistant *Shigella*, methicillin-resistant *Staphylococcus aureus* (MRSA), drug-resistant *Streptococcus pneumoniae*, vancomycin-resistant *Staphylococcus aureus* (VRSA), erythromycin-resistant Group A *Streptococcus*, and clindamycin-resistant Group B *Streptococcus*. The increasing failure of antibiotics due the rise of resistant microbes demands new therapeutics to treat bacterial infections. Administration of a microbiome therapeutic bacterial composition offers potential for such therapies.

Applicants have discovered that subjects suffering from recurrent *C. difficile* associated diarrhea (CDAD) often harbor antibiotic resistant Gram-negative bacteria, in particular Enterobacteriaceae and that treatment with a bacterial composition effectively treats CDAD and reduces the antibiotic resistant Gram-negative bacteria. The gastrointestinal tract is implicated as a reservoir for many of these organisms including VRE, MRSA, *Pseudomonas aeruginosa, Acinetobacter* and the yeast *Candida* (Donskey, Clinical Infectious Diseases 2004 39:214, The Role of the Intestinal Tract as a Reservoir and Source for Transmission of Nosocomial Pathogens), and thus as a source of nosocomial infections. Antibiotic treatment and other decontamination procedures are among the tools in use to reduce colonization of these organisms in susceptible subjects including those who are immunosuppressed. Bacterial-based therapeutics would provide a new tool for decolonization, with a key benefit of not promoting antibiotic resistance as antibiotic therapies do.

Bacterial Compositions

Provided are bacteria and combinations of bacteria of the human gut microbiota with the capacity to meaningfully provide functions of a healthy microbiota or catalyze an augmentation to the resident microbiome when administered to mammalian hosts. In particular, provided are synergistic combinations that treat, prevent, delay or reduce the symptoms of diseases, disorders and conditions associated with a dysbiosis. Representative diseases, disorders and conditions potentially associated with a dysbiosis, which are suitable for treatment with the compositions and methods as described herein, are provided in Table 3. Without being limited to a specific mechanism, it is thought that such compositions inhibit the growth, proliferation, and/or colonization of one or a plurality of pathogenic bacteria in the dysbiotic microbiotal niche, so that a healthy, diverse and protective microbiota colonizes and populates the intestinal lumen to establish or reestablish ecological control over pathogens or potential pathogens (e.g., some bacteria are pathogenic bacteria only when present in a dysbiotic environment). Inhibition of pathogens includes those pathogens such as *C. difficile, Salmonella* spp., enteropathogenic *E. coli*, multi-drug resistant bacteria such as *Klebsiella*, and *E. coli*, carbapenem-resistant Enterobacteriaceae (CRE), extended spectrum beta-lactam resistant Enterococci (ESBL), and vancomycin-resistant Enterococci (VRE).

The bacterial compositions provided herein are produced and the efficacy thereof in inhibiting pathogenic bacteria is demonstrated as provided in further detail herein.

In particular, in order to characterize those antagonistic relationships between gut commensals that are relevant to the dynamics of the mammalian gut habitat, provided is an in vitro microplate-based screening system that demonstrates the efficacy of those bacterial compositions, including the ability to inhibit (or antagonize) the growth of a bacterial pathogen or pathobiont, typically a gastrointestinal microorganism. These methods provide novel combinations of gut microbiota species and OTUs that are able to restore or enhance ecological control over important gut pathogens or pathobionts in vivo.

Bacterial compositions may comprise two types of bacteria (termed "binary combinations" or "binary pairs") or greater than two types of bacteria. Bacterial compositions that comprise three types of bacteria are termed "ternary combinations". For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29, 30, 31, 32, 33, 34, 35, 36, 37, 38, 39, or at least 40, at least 50 or greater than 50 types of bacteria, as defined by species or operational taxonomic unit (OTU), or otherwise as provided herein. In one embodiment, the composition comprises at least two types of bacteria chosen from Table 1.

In another embodiment, the number of types of bacteria present in a bacterial composition is at or below a known value. For example, in such embodiments the bacterial composition comprises 50 or fewer types of bacteria, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of bacteria, 8 or fewer types of bacteria, 7 or fewer types of bacteria, 6 or fewer types of bacteria, 5 or fewer types of bacteria, 4 or fewer types of bacteria, or 3 or fewer types of bacteria. In another embodiment, a bacterial composition comprises from 2 to no more than 40, from 2 to no more than 30, from 2 to no more than 20, from 2 to no more than 15, from 2 to no more than 10, or from 2 to no more than 5 types of bacteria.

In some embodiments, bacterial compositions are provided with the ability to exclude pathogenic bacteria. Exemplary bacterial compositions are demonstrated to reduce the growth rate of one pathogen, *C. difficile*, as provided in the Examples, wherein the ability of the bacterial compositions is demonstrated by assessing the antagonism activity of a combination of OTUs or strains towards a given pathogen using in vitro assays.

In some embodiments, bacterial compositions with the capacity to durably exclude *C. difficile*, are developed using a methodology for estimating an Ecological Control Factor (ECF) for constituents within the human microbiota. The ECF is determined by assessing the antagonistic activity of a given commensal strain or combination of strains towards a given pathogen using an in vitro assay, resulting in observed levels of ecological control at various concentrations of the added commensal strains. The ECF for a commensal strain or combination of strains is somewhat analogous to the longstanding minimal inhibitory concentration (MIC) assessment that is employed in the assessment of antibiotics. The ECF allows for the assessment and ranking of relative potencies of commensal strains and combinations of strains for their ability to antagonize gastrointestinal pathogens. The ECF of a commensal strain or combination of strains may be calculated by assessing the concentration of that composition that is able to mediate a given percentage of inhibition (e.g., at least 10%, 20%, 50%, 70%, 75%, 80%, 85%, 90%, 95%, or 100%) of a target pathogen in the in vitro assay. Provided herein are combinations of strains or OTUs within the human microbiota that are able to significantly reduce the rate of gastrointestinal pathogen replication within the in vitro assay. These compositions are capable of providing a safe and effective means by which to affect the growth, replication, and disease severity of such bacterial pathogens.

Bacterial compositions may be prepared comprising at least two types of isolated bacteria, wherein a first type and a second type are independently chosen from the species or OTUs listed in Table 1. Certain embodiments of bacterial compositions with at least two types of isolated bacteria containing binary pairs are reflected in Table 4a. Additionally, a bacterial composition may be prepared comprising at least two types of isolated bacteria, wherein a first OTU and a second OTU are independently characterized by, i.e., at least 95%, 96%, 97%, 98%, 99% or including 100% sequence identity to, sequences listed in Table 1. Generally, the first bacteria and the second bacteria are not the same OTU. The sequences provided in the sequencing listing file for OTUs in Table 1 are full 16S sequences. Therefore, in one embodiment, the first and/or second OTUs may be characterized by the full 16S sequences of OTUs listed in Table 1. In another embodiment, the first and/or second OTUs may be characterized by one or more of the variable regions of the 16S sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Bacterial Compositions Described by Species

In some embodiments, compositions are defined by species included in the composition. Methods of identifying species are known in the art.

Bacterial Compositions Described by Operational Taxonomic Units (OTUs)

OTUs may be defined either by full 16S sequencing of the rDNA gene, by sequencing of a specific hypervariable region of this gene (i.e., V1, V2, V3, V4, V5, V6, V7, V8, or V9), or by sequencing of any combination of hypervariable regions from this gene (e.g., V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes. Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Bacterial Compositions Exclusive of Certain Bacterial Species or Strains

In one embodiment, the bacterial composition does not comprise at least one of *Enterococcus faecalis* (previously known as, *Streptococcus faecalis*), *Clostridium innocuum, Clostridium ramosum, Bacteroides ovatus, Bacteroides vulgatus, Bacteroides thetaoiotaomicron, Escherichia coli* (1109 and 1108-1), *Clostridum bifermentans*, and *Blautia producta* (previously known as *Peptostreptococcus productus*).

In another embodiment, the bacterial composition does not comprise at least one of *Acidaminococcus intestinalis, Bacteroides ovatus*, two species of *Bifidobacterium adolescentis*, two species of *Bifidobacterium longum, Collinsella aerofaciens*, two species of *Dorea longicatena, Escherichia coli, Eubacterium eligens, Eubacterium limosum*, four species of *Eubacterium rectale, Eubacterium ventriosumi, Faecalibacterium prausnitzii, Lactobacillus casei, Lactobacillus paracasei, Paracateroides distasonis, Raoultella* sp., one species of *Roseburia* (chosen from *Roseburia faecalis* or *Roseburia faecis*), *Roseburia intestinalis*, two species of *Ruminococcus torques*, and *Streptococcus mitis.*

In another embodiment, the bacterial composition does not comprise at least one of *Barnesiella intestinihominis; Lactobacillus reuteri*; a species characterized as one of *Enterococcus hirae, Enterococus faecium*, or *Enterococcus durans*; a species characterized as one of *Anaerostipes caccae* or *Clostridium indolis*; a species characterized as one of *Staphylococcus warneri* or *Staphylococcus pasteuri*; and *Adlercreutzia equolfaciens.*

In another embodiment, the bacterial composition does not comprise at least one of *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis. Clostridium innocuum, Clostridium irregulare, Clostridium limosum. Clostridium malenominatum, Clostridium novyi, Clostridium oroticum, Clostridium paraputrificum, Clostridium perfringens, Clostridium piiforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum.*

In another embodiment, the bacterial composition does not comprise at least one of *Clostridium innocuum, Clostridum bifermentans, Clostridium butyricum, Bacteroides fragilis, Bacteroides thetaiotaomicron, Bacteroides uniformis*, three strains of *Escherichia coli*, and *Lactobacillus* sp.

In another embodiment, the bacterial composition does not comprise at least one of *Clostridium bifermentans, Clostridium innocuum, Clostridium butyricum*, three strains of *Escherichia coli*, three strains of *Bacteroides*, and *Blautia producta* (previously known as *Peptostreptococcus productus*).

In another embodiment, the bacterial composition does not comprise at least one of *Bacteroides* sp., *Escherichia coli*, and non-pathogenic Clostridia, including *Clostridium innocuum, Clostridium bifermentans* and *Clostridium ramosum.*

In another embodiment, the bacterial composition does not comprise at least one of more than one *Bacteroides* species, *Escherichia coli* and non-pathogenic Clostridia, such as *Clostridium butyricum, Clostridium bifermentans* and *Clostridium innocuum.*

In another embodiment, the bacterial composition does not comprise at least one of *Bacteroides caccae, Bacteroides capillosus, Bacteroides coagulans, Bacteroides distasonis, Bacteroides eggerthii, Bacteroides forsythus. Bacteroides fragilis, Bacteroides fragilis-ryhm, Bacteroides gracilis, Bacteroides levii, Bacteroides macacae, Bacteroides merdae, Bacteroides ovatus, Bacteroides pneumosintes, Bacteroides putredinis, Bacteroides pyogenes, Bacteroides splanchnicus, Bacteroides stercoris, Bacteroides tectum, Bacteroides thetaiotaomicron, Bacteroides uniformis, Bacteroides ureolyticus*, and *Bacteroides vulgatus.*

In another embodiment, the bacterial composition does not comprise at least one of *Bacteroides*, Eubacteria, Fusobacteria, Propionibacteria, Lactobacilli, anaerobic cocci, *Ruminococcus, Escherichia coli, Gemmiger, Desulfomonas*, and *Peptostreptococcus.*

In another embodiment, the bacterial composition does not comprise at least one of *Bacteroides fragilis* ss. *Vulgatus, Eubacterium aerofaciens, Bacteroides fragilis* ss. *Thetaiotaomicron, Blautia producta* (previously known as *Peptostreptococcus productus* II), *Bacteroides fragilis* ss. *Distasonis, Fusobacterium prausnitzii, Coprococcus eutactus, Eubacterium aerofaciens* III, *Blautia producta* (previously known as *Peptostreptococcus productus* I), *Ruminococcus bromii, Bifidobacterium adolescentis, Gemmiger formicilis, Bifidobacterium longum, Eubacterium siraeum, Ruminococcus torques, Eubacterium rectale* III-H, *Eubacterium rectale* IV, *Eubacterium eligens, Bacteroides eggerthii, Clostridium leptum, Bacteroides fragilis* ss. A, *Eubacterium biforme, Bifidobacterium infantis, Eubacterium rectale* III-F, *Coprococcus comes, Bacteroides capillosus, Ruminococcus albus, Eubacterium formicigenerans, Eubacterium hallii, Eubacterium ventriosum* I, *Fusobacterium russii, Ruminococcus obeum, Eubacterium rectale* II, *Clostridium ramosum* I, *Lactobacillus* leichmanii, *Ruminococcus cailidus, Butyrivibrio crossotus, Acidaminococcus fermentans, Eubacterium ventriosum, Bacteroides fragilis* ss. *fragilis, Bacteroides* AR, *Coprococcus catus, Eubacterium hadrum, Eubacterium cylindroides, Eubacterium ruminantium, Eubacterium* CH-1, *Staphylococcus epidermidis, Peptostreptococcus* BL, *Eubacterium limosum, Bacteroides praeacutus. Bacteroides* L. *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Eubacterium* AG, -AK, -AL, -AL-1, -AN; *Bacteroides fragilis* ss. *ovatus*, -ss. d, -ss. f *Bacteroides* L-1, L-5; *Fusobacterium nucleatum, Fusobacterium mortiferum, Escherichia coli, Streptococcus morbiliorum, Peptococcus magnus, Peptococcus* G, AU-2*; Streptococcus intermedius, Ruminococcus lactaris, Ruminococcus* CO *Gemmiger* X, *Coprococcus* BH, —CC; *Eubacterium tenue, Eubacterium ramulus, Eubacterium* AE, -AG-H, -AG-M, -AJ, -BN-1; *Bacteroides clostridiiformis* ss. *clostridliformis, Bacteroides coagulans, Bacteroides orails, Bacteroides ruminicola* ss. *brevis*, -ss. *ruminicola, Bacteroides splanchnicus, Desuifomonas pigra, Bacteroides* L-4, -N-i; *Fusobacterium* H, *Lactobacillus* G, and *Succinivibrio* A.

In another embodiment, the bacterial composition does not comprise at least one of *Bifidobacterium bifidum* W23, *Bifidobacterium lactis* W18, *Bifidobacterium longum* W51, *Enterococcus faecium* W54, *Lactobacillus plantarum* W62, *Lactobacillus rhamnosus* W71, *Lactobacillus acidophilus* W37, *Lactobacillus acidophilus* W55, *Lactobacillus paracasei* W20, and *Lactobacillus salivarius* W24.

In another embodiment, the bacterial composition does not comprise at least one of *Anaerotruncus colihominis* DSM 17241, *Blautia producta* JCM 1471, Clostridiales *bacterium* 1 7 47FAA, *Clostridium asparagiforme* DSM 15981, *Clostridium bacterium* JC13, *Clostridium bolteae* ATCC BAA 613, *Clostridium hathewayi* DSM 13479, *Clostridium indolis* CM971, *Clostridium ramosum* DSM 1402, *Clostridium saccharogumia* SDG Mt85 3Db, *Clostridium scindens* VP 12708, *Clostridium* sp 7 3 54FAA, *Eubacterium contortum* DSM 3982, Lachnospiraceae *bacterium* 3 1 57FAA CT1, Lachnospiraceae *bacterium* 7 1 58FAA, and *Ruminococcus* sp ID8.

In another embodiment, the bacterial composition does not comprise at least one of *Anaerotruncus colihominis* DSM 17241. *Blautia producta* JCM 1471, Clostridiales *bacterium* 1 7 47FAA, *Clostridium asparagiforme* DSM 15981, *Clostridium bacterium* JC13, *Clostridium bolteae* A ICC BAA 613, *Clostridium hathewayi* DSM 13479, *Clostridium indolis* CM971, *Clostridium ramosum* DSM 1402, *Clostridium saccharogumia* SDG Mt85 3Db, *Clostridium scindens* VP 12708, *Clostridium* sp 7 3 54FAA, *Eubacterium contortum* DSM 3982, Lachnospiraceae *bacterium* 3 1 57FAA CT1, Lachnospiraceae *bacterium* 7 1 58FAA, Oscillospiraceae *bacterium* NML 061048, and *Ruminococcus* sp ID8.

In another embodiment, the bacterial composition does not comprise at least one of *Clostridium ramosum* DSM 1402, *Clostridium saccharogumia* SDG Mt85 3Db, and Lachnospiraceae *bacterium* 7 1 58FAA.

In another embodiment, the bacterial composition does not comprise at least one of *Clostridium hathewayi* DSM 13479, *Clostridium saccharogumia* SDG Mt85 3Db, *Clostridium* sp 7 3 54FAA, and Lachnospiraceae *bacterium* 3 1 57FAA CT1.

In another embodiment, the bacterial composition does not comprise at least one of *Anaerotruncus colihominis* DSM 17241, *Blautia producta* JCM 1471, *Clostridium bacterium* JC13, *Clostridium scindens* VP 12708, and *Ruminococcus* sp ID8.

In another embodiment, the bacterial composition does not comprise at least one of Clostridiales *bacterium* 1 7 47FAA, *Clostridium asparagiforme* DSM 15981, *Clostridium bolteae* ATCC BAA 613, *Clostridium indolis* CM971, and Lachnospiraceae *bacterium* 71 58FAA.

Inhibition of Bacterial Pathogens

The bacterial compositions offer a protective or therapeutic effect against infection by one or more GI pathogens of interest, some of which are listed in Table 3.

In some embodiments, the pathogenic *bacterium* is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Kiebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, extended spectrum beta-lactam resistant Enterococci (ESBL), carbapenem-resistant Enterobacteriaceae (CRE), and vancomycin-resistant Enterococci (VRE).

In some embodiments, these pathogens include, but are not limited to, *Aeromonas hydrophila, Campylobacter fetus,*

*Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* 0157:H7, *Fusarium* spp., *Helicobacter pylori, Klebsiella pneumonia, Klebsiella oxytoca, Lysteria monocytogenes, Morganella* spp., *Plesiomonas shigelloides, Proteus* spp., *Providencia* spp., *Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnicus*, and *Yersinia enterocolitica.*

In one embodiment, the pathogen of interest is at least one pathogen chosen from *Clostridium difficile, Salmonella* spp., pathogenic *Escherichia coli*, vancomycin-resistant *Enterococcus* spp., and extended spectrum beta-lactam resistant Enterococci (ESBL).

In Vitro Assays Substantiating Protective Effect of Bacterial Compositions

In one embodiment, provided is an in vitro assay utilizing competition between the bacterial compositions or subsets thereof and *C. difficile*. Exemplary embodiments of the assay are provided herein and in the Examples.

In another embodiment, provided is an in vitro assay utilizing 10% (wt/vol) Sterile-Filtered Stool (SFS). Provided is an in vitro assay to test for the protective effect of the bacterial compositions and to screen in vitro for combinations of microbes that inhibit the growth of a pathogen. The assay can operate in automated high-throughput or manual modes. Under either system, human or animal stool may be re-suspended in an anaerobic buffer solution, such as pre-reduced PBS or other suitable buffer, the particulate removed by centrifugation, and filter sterilized. This 10% sterile-filtered stool material serves as the base media for the in vitro assay. To test a bacterial composition, an investigator may add it to the sterile-filtered stool material for a first incubation period and then may inoculate the incubated microbial solution with the pathogen of interest for a second incubation period. The resulting titer of the pathogen may be quantified by any number of methods such as those described below, and the change in the amount of pathogen is compared to standard controls including the pathogen cultivated in the absence of the bacterial composition. The assay is conducted using at least one control. Stool from a healthy subject may be used as a positive control. As a negative control, antibiotic-treated stool or heat-treated stool may be used. Various bacterial compositions may be tested in this material and the bacterial compositions optionally compared to the positive and/or negative controls. The ability to inhibit the growth of the pathogen may be measured by plating the incubated material on *C. difficile* selective media and counting colonies. After competition between the bacterial composition and *C. difficile*, each well of the in vitro assay plate is serially diluted ten-fold six times, and plated on selective media, such as but not limited to cycloserine cefoxitin mannitol agar (CCMA) or cycloserine cefoxitin fructose agar (CCFA), and incubated. Colonies of *C. difficile* are then counted to calculate the concentration of viable cells in each well at the end of the competition. Colonies of *C. difficile* are confirmed by their characteristic diffuse colony edge morphology as well as fluorescence under UV light.

In another embodiment, the in vitro assay utilizes Antibiotic-Treated Stool. In an alternative embodiment, and instead of using 10% sterile-filtered stool, human or animal stool may be resuspended in an anaerobic buffer solution, such as pre-reduced PBS or other suitable buffer. The resuspended stool is treated with an antibiotic, such as clindamycin, or a cocktail of several antibiotics in order to reduce the ability of stool from a healthy subject to inhibit the growth of *C. difficile*; this material is termed the antibiotic-treated matrix. While not being bound by any mechanism, it is believed that beneficial bacteria in healthy subjects protects them from infection by competing out *C. difficile*. Treating stool with antibiotics kills or reduces the population of those beneficial bacteria, allowing *C. difficile* to grow in this assay matrix. Antibiotics in addition to clindamycin that inhibit the normal flora include ceftriaxone and piperacillin-tazobactam and may be substituted for the clindamycin. The antibiotic-treated matrix is centrifuged, the supernatant removed, and the pelleted material resuspended in filter-sterilized, diluted stool in order to remove any residual antibiotic. This washed antibiotic-treated matrix may be used in the in vitro assay described above in lieu of the 10% sterile-filtered stool.

Also provided is an In Vitro Assay utilizing competition between the bacterial compositions or subsets thereof and Vancomycin-resistant *Enterococcus faecium*. Exemplary embodiments of this Assay are provided herein and in the Examples.

Also provided is an in vitro assay utilizing competition between the bacterial compositions or subsets thereof and *Morganella morganii*. Exemplary embodiments of this Assay are provided herein and in the Examples.

Also provided is an in vitro assay utilizing competition between the bacterial compositions or subsets thereof and *Klebsiella pneumoniae*. Exemplary embodiments of this Assay are provided herein and in the Examples.

Alternatively, the ability to inhibit the growth of the pathogen may be measured by quantitative PCR (qPCR). Standard techniques may be followed to generate a standard curve for the pathogen of interest. Genomic DNA may be extracted from samples using commercially available kits, such as the Mo Bio Powersoil®-htp 96 Well Soil DNA Isolation Kit (Mo Bio Laboratories, Carlsbad, CA), the Mo Bio Powersoil® DNA Isolation Kit (Mo Bio Laboratories, Carlsbad, CA), or the QIAamp DNA Stool Mini Kit (QIAGEN, Valencia, CA) according to the manufacturer's instructions. The qPCR may be conducted using HotMasterMix (5PRIME, Gaithersburg, MD) and primers specific for the pathogen of interest, and may be conducted on a MicroAmp® Fast Optical 96-well Reaction Plate with Barcode (0.1 mL) (Life Technologies, Grand Island, NY) and performed on a BioRad C1000™ Thermal Cycler equipped with a CFX96™ Real-Time System (BioRad, Hercules, CA), with fluorescent readings of the FAM and ROX channels. The Cq value for each well on the FAM channel is determined by the CFX Manager™ software version 2.1. The $\log_{10}$ (cfu/ml) of each experimental sample is calculated by inputting a given sample's Cq value into linear regression model generated from the standard curve comparing the Cq values of the standard curve wells to the known $\log_{10}$ (cfu/ml) of those samples. The skilled artisan may employ alternative qPCR modes.

In Vivo Assay Establishing Protective Effect of Bacterial Compositions

Provided is an in vivo mouse model to test for the protective effect of the bacterial compositions against *C.*

*difficile*. In this model (based on Chen, et al., A mouse model of *Clostridium difficile* associated disease, Gastroenterology 135(6):1984-1992 (2008)), mice are made susceptible to *C. difficile* by a 7 day treatment (days −12 to −5 of experiment) with 5 to 7 antibiotics (including kanamycin, colistin, gentamycin, metronidazole and vancomycin and optionally including ampicillin and ciprofloxacin) delivered via their drinking water, followed by a single dose with Clindamycin on day −3, then challenged three days later on day 0 with 104 spores of *C. difficile* via oral gavage (i.e., oro-gastric lavage). Bacterial compositions may be given either before (prophylactic treatment) or after (therapeutic treatment) *C. difficile* gavage. Further, bacterial compositions may be given after (optional) vancomycin treatment (see below) to assess their ability to prevent recurrence and thus suppress the pathogen in vivo. The outcomes assessed each day from day −1 to day 6 (or beyond, for prevention of recurrence) are weight, clinical signs, mortality and shedding of *C. difficile* in the stool. Weight loss, clinical signs of disease, and *C. difficile* shedding are typically observed without treatment. Vancomycin provided by oral gavage on days −1 to 4 protects against these outcomes and serves as a positive control. Clinical signs are subjective, and scored each day by the same experienced observer. Animals that lose greater than or equal to 25% of their body weight are euthanized and counted as infection-related mortalities. Stool are gathered from mouse cages (5 mice per cage) each day, and the shedding of *C. difficile* spores is detected in the stool using a selective plating assay as described for the in vitro assay above, or via qPCR for the toxin gene as described herein. The effects of test materials including 10% suspension of human stool (as a positive control), bacterial compositions, or PBS (as a negative vehicle control), are determined by introducing the test article in a 0.2 mL volume into the mice via oral gavage on day −1, one day prior to *C. difficile* challenge, on day 1, 2 and 3 as treatment or post-vancomycin treatment on days 5, 6, 7 and 8. Vancomycin, as discussed above, is given on days 1 to 4 as another positive control. Alternative dosing schedules and routes of administration (e.g., rectal) may be employed, including multiple doses of test article, and 103 to $10^{10}$ of a given organism or composition may be delivered.

Methods for Preparing a Bacterial Composition for Administration to a Subject Methods for producing bacterial compositions may include three main processing steps, combined with one or more mixing steps. The steps are: organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g., R. M. Atlas, Handbook of Microbiological Media (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions (e.g., gut microbiota), an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition may be purified by additional means such as density gradient centrifugation preserved using the techniques described above. Bacterial composition banking may be done by culturing and preserving the strains individually, or by mixing the strains together to create a combined bank. As an example of cryopreservation, a bacterial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production may be conducted using similar culture steps to banking, including medium composition and culture conditions. It may be conducted at larger scales of operation, especially for clinical development or commercial production. At larger scales, there may be several subcultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

Formulations

Provided are formulations for administration to humans and other subjects in need thereof. Generally the bacterial compositions are combined with additional active and/or inactive materials to produce a final product, which may be in single dosage unit or in a multi-dose format.

In some embodiments the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments the composition comprises at least one lipid. As used herein a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments the excipient is a buffering agent. Non-limiting examples of suitable buffering agents include sodium citrate, magnesium carbonate, magnesium bicarbonate, calcium carbonate, and calcium bicarbonate.

In some embodiments the excipient comprises a preservative. Non-limiting examples of suitable preservatives include antioxidants, such as alpha-tocopherol and ascorbate, and antimicrobials, such as parabens, chlorobutanol, and phenol.

In some embodiments the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; *eucalyptus*; vanilla; citrus oil such as lemon oil, orange oil, grape and grapefruit oil; and fruit essences including apple, peach, pear, strawberry, raspberry, cherry, plum, pineapple, and apricot.

In some embodiments the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The bacterial compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments the core material comprises at least one of a solid, a liquid, and an emulsion. In some embodiments the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In some embodiments the coating material comprises at least one of a fat and an oil. In some embodiments the at least one of a fat and an oil is high temperature melting. In some embodiments the at least one of a fat and an oil is hydrogenated or partially hydrogenated. In some embodiments the at least one of a fat and an oil is derived from a plant. In some embodiments the at least one of a fat and an oil comprises at least one of glycerides, free fatty acids, and fatty acid esters. In some embodiments the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments the food product is a solid foodstuff. Suitable examples of a solid foodstuff include without limitation a food bar, a snack bar, a cookie, a brownie, a muffin, a cracker, an ice cream bar, a frozen yogurt bar, and the like.

In some embodiments, the compositions disclosed herein are incorporated into a therapeutic food. In some embodiments, the therapeutic food is a ready-to-use food that optionally contains some or all essential macronutrients and micronutrients. In some embodiments, the compositions disclosed herein are incorporated into a supplementary food that is designed to be blended into an existing meal. In some embodiments, the supplemental food contains some or all essential macronutrients and micronutrients. In some embodiments, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment an enteric-coated capsule or tablet or with a buffering or protective composition may be used.

In one embodiment, the number of bacteria of each type may be present in the same amount or in different amounts. For example, in a bacterial composition with two types of bacteria, the bacteria may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three types of bacteria, the ratio of type of bacteria may be chosen pairwise from ratios for bacterial compositions with two types of bacteria. For example, in a bacterial composition comprising bacteria A, B, and C, at least one of the ratio between bacteria A and B, the ratio between bacteria B and C, and the ratio between bacteria A and C may be chosen, independently, from the pairwise combinations above.

Methods of Treating a Subject

In some embodiments the proteins and compositions disclosed herein are administered to a subject or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a subject, when a parent commands a minor user (such as a child) to consume a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The bacterial compositions offer a protective and/or therapeutic effect against infection by one or more GI pathogens of interest and thus may be administered after an acute case of infection has been resolved in order to prevent relapse, during an acute case of infection as a complement to antibiotic therapy if the bacterial composition is not sensitive to the same antibiotics as the GI pathogen, or to prevent infection or reduce transmission from disease carriers. These pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (LT and/or ST), *Escherichia coli* 0157:H7, *Helicobacter pylori, Klebsiella pneumonia, Lysteria monocytogenes, Plesiomonas shigelloides, Salmonella* spp., *Salmonella typhi, Shigella* spp., *Staphylococcus, Staphylococcus aureus*, vancomycin-resistant *Enterococcus* spp., *Vibrio* spp., *Vibrio cholerae, Vibrio parahaemolyticus, Vibrio vulnificus*, and *Yersinia enterocolitica*.

In one embodiment, the pathogen may be *Clostridium difficile, Salmonella* spp., pathogenic *Escherichia coli*, carbapenem-resistant Enterobacteriaceae (CRE), extended spectrum beta-lactam resistant Enterococci (ESBL) and vancomycin-resistant Enterococci (VRE). In yet another embodiment, the pathogen may be *Clostridium difficile*.

The present bacterial compositions may be useful in a variety of clinical situations. For example, the bacterial compositions may be administered alone, as a complementary treatment to antibiotics (e.g., when a subject is suffering from an acute infection, to reduce the risk of recurrence after an acute infection has subsided or, or when a subject will be in close proximity to others with or at risk of serious gastrointestinal infections (physicians, nurses, hospital workers, family members of those who are ill or hospitalized).

The present bacterial compositions may be administered to animals, including humans, laboratory animals (e.g., primates, rats, mice), livestock (e.g., cows, sheep, goats, pigs, turkeys, chickens), and household pets (e.g., dogs, cats, rodents).

In the present method, the bacterial composition is administered enterically, in other words by a route of access to the gastrointestinal tract. This includes oral administration, rectal administration (including enema, suppository, or colonoscopy), by an oral or nasal tube (nasogastric, nasojejunal, oral gastric, or oral jejunal), as detailed more fully herein.

It has been reported that a GI dysbiosis is associated with diabetes (Qin et al., 2012. Nature 490:55). In some embodiments, a composition provided herein can be used to alter the microbiota of a subject having or susceptible diabetes. Typically, such a composition provides at least one, two, or three OTUs identified in the art as associated with an improvement in insulin sensitivity or other sign or symptom associated with diabetes, e.g., Type 2 or Type 1 diabetes. In some embodiments, the composition is associated with an increase in engraftment and/or augmentation of at least one, two, or three OTUs associated with an improvement in at least one sign or symptom of diabetes.

Pretreatment Protocols

Prior to administration of the bacterial composition, the subject may optionally have a pretreatment protocol to prepare the gastrointestinal tract to receive the bacterial composition. In certain embodiments, the pretreatment protocol is advisable, such as when a subject has an acute infection with a highly resilient pathogen. In other embodiments, the pretreatment protocol is entirely optional, such as when the pathogen causing the infection is not resilient, or the subject has had an acute infection that has been successfully treated but where the physician is concerned that the infection may recur. In these instances, the pretreatment protocol may enhance the ability of the bacterial composition to affect the subject's microbiome.

As one way of preparing the subject for administration of the microbial ecosystem, at least one antibiotic may be administered to alter the bacteria in the subject. As another way of preparing the subject for administration of the microbial ecosystem, a standard colon-cleansing preparation may be administered to the subject to substantially empty the contents of the colon, such as used to prepare a subject for a colonoscopy. By "substantially emptying the contents of the colon," this application means removing at least 75%, at least 80%, at least 90%, at least 95%, or about 100% of the contents of the ordinary volume of colon contents. Antibiotic treatment may precede the colon-cleansing protocol.

If a subject has received an antibiotic for treatment of an infection, or if a subject has received an antibiotic as part of a specific pretreatment protocol, in one embodiment the antibiotic should be stopped in sufficient time to allow the antibiotic to be substantially reduced in concentration in the gut before the bacterial composition is administered. In one embodiment, the antibiotic may be discontinued 1, 2, or 3 days before the administration of the bacterial composition. In one embodiment, the antibiotic may be discontinued 3, 4, 5, 6, or 7 antibiotic half-lives before administration of the bacterial composition. In another embodiment, the antibiotic may be chosen so the constituents in the bacterial composition have an MIC50 that is higher than the concentration of the antibiotic in the gut.

MIC50 of a bacterial composition or the elements in the composition may be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic may be chosen so that the infection is sensitive to the antibiotic, but the constituents in the bacterial composition are not sensitive to the antibiotic.

Routes of Administration

The bacterial compositions of the invention are suitable for administration to mammals and non-mammalian animals in need thereof. In certain embodiments, the mammalian subject is a human subject who has one or more symptoms of a dysbiosis.

When the mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is diarrhea caused by *C. difficile* including recurrent *C. difficile* infection, ulcerative colitis, colitis, Crohn's disease, or irritable bowel disease. Beneficially, the therapeutic composition is administered only once prior to improvement of the disease, disorder or condition. In some embodiments the therapeutic composition is administered at intervals greater than two days, such as once every three, four, five or six days, or every week or less frequently than every week. Or the preparation may be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In embodiments, the bacterial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The bacterial composition may be administered to at least one region of the gastrointestinal tract, including the mouth, esophagus, stomach, small intestine, large intestine, and rectum. In some embodiments it is administered to all regions of the gastrointestinal tract. The bacterial compositions may be administered orally in the form of medicaments such as powders, capsules, tablets, gels or liquids. The bacterial compositions may also be administered in gel or liquid form by the oral route or through a nasogastric tube, or by the rectal route in a gel or liquid form, by enema or instillation through a colonoscope or by a suppository.

If the composition is administered colonoscopically and, optionally, if the bacterial composition is administered by other rectal routes (such as an enema or suppository) or even if the subject has an oral administration, the subject may have a colon-cleansing preparation. The colon-cleansing preparation can facilitate proper use of the colonoscope or other administration devices, but even when it does not serve a mechanical purpose it can also maximize the proportion of the bacterial composition relative to the other organisms previously residing in the gastrointestinal tract of the subject. Any ordinarily acceptable colon-cleansing preparation may be used such as those typically provided when a subject undergoes a colonoscopy.

Dosages and Schedule for Administration

In some embodiments the bacteria and bacterial compositions are provided in a dosage form. In some embodiments the dosage form is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In some embodiments the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In some embodiments the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, from $10^5$ and $10^{12}$ microorganisms total may be administered to the subject in a given dosage form. In one mode, an effective amount may be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment may receive higher doses than those who are receiving chronic administration (such as hospital workers or those admitted into long-term care facilities).

Any of the preparations described herein may be administered once on a single occasion or on multiple occasions, such as once a day for several days or more than once a day on the day of administration (including twice daily, three times daily, or up to five times daily). Or the preparation may be administered intermittently according to a set schedule, e.g., once weekly, once monthly, or when the subject relapses from the primary illness. In another embodiment, the preparation may be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

Subject Selection

Particular bacterial compositions may be selected for individual subjects or for subjects with particular profiles. For example, 16S sequencing may be performed for a given subject to identify the bacteria present in his or her microbiota. The sequencing may either profile the subject's entire microbiome using 16S sequencing (to the family, genera, or species level), a portion of the subject's microbiome using 16S sequencing, or it may be used to detect the presence or absence of specific candidate bacteria that are biomarkers for health or a particular disease state, such as markers of multi-drug resistant organisms or specific genera of concern such as *Escherichia*. Based on the biomarker data, a particular composition may be selected for administration to a subject to supplement or complement a subject's microbiota in order to restore health or treat or prevent disease. In another embodiment, subjects may be screened to determine the composition of their microbiota to determine the likelihood of successful treatment.

Combination Therapy

The bacterial compositions may be administered with other agents in a combination therapy mode, including anti-microbial agents and prebiotics. Administration may be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

A prebiotic is a selectively fermented ingredient that allows specific changes, both in the composition and/or activity in the gastrointestinal microbiota that confers benefits upon host well being and health. Prebiotics may include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Methods for Characterization of Bacterial Compositions

In certain embodiments, provided are methods for testing certain characteristics of bacterial compositions. For example, the sensitivity of bacterial compositions to certain environmental variables is determined, e.g., in order to select for particular desirable characteristics in a given composition, formulation and/or use. For example, the constituents in the bacterial composition may be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

pH Sensitivity Testing. If a bacterial composition will be administered other than to the colon or rectum (i.e., through, for example, but not limited to, an oral route), optionally testing for pH resistance enhances the selection of bacterial compositions that will survive at the highest yield possible through the varying pH environments of the distinct regions of the GI tract. Understanding how the bacterial compositions react to the pH of the GI tract also assists in formulation, so that the number of bacteria in a dosage form can be increased if beneficial and/or so that the composition may be administered in an enteric-coated capsule or tablet or with a buffering or protective composition. As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This may be tested by exposing the bacterial composition to varying pH ranges for the expected gut transit times through those pH ranges. Therefore, as a nonlimiting example only, 18-hour cultures of bacterial compositions may be grown in standard media, such as gut microbiota medium ("GMM", see Goodman et al., Extensive personal human gut microbiota culture collections characterized and manipulated in gnotobiotic mice, PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile Acid Sensitivity Testing. Additionally, in some embodiments, testing for bile-acid resistance enhances the selection of bacterial compositions that will survive exposures to bile acid during transit through the GI tract. Bile acids are secreted into the small intestine and can, like pH, affect the survival of bacterial compositions. This may be tested by exposing the bacterial compositions to bile acids for the expected gut exposure time to bile acids. For example, bile acid solutions may be prepared at desired concentrations using 0.05 mM Tris at pH 9 as the solvent. After the bile acid is dissolved, the pH of the solution may be adjusted to 7.2 with 10% HCl. Bacterial compositions may be cultured in 2.2 ml of a bile acid composition mimicking the concentration and type of bile acids in the subject, 1.0 ml of 10% sterile-filtered stool media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria may be determined by culturing the bacteria and counting colonies on appropriate selective or non-selective media.

Antibiotic Sensitivity Testing. As a further optional sensitivity test, bacterial compositions may be tested for sensitivity to antibiotics. In one embodiment, bacterial compositions may be chosen so that the bacterial constituents are sensitive to antibiotics such that if necessary they can be eliminated or substantially reduced from the subject's gastrointestinal tract by at least one antibiotic targeting the bacterial composition.

Adherence to Gastrointestinal Cells. The bacterial compositions may optionally be tested for the ability to adhere to gastrointestinal cells. A method for testing adherence to gastrointestinal cells is described in U.S. Pat. No. 4,839,281.

The specification is most thoroughly understood in light of the teachings of the references cited within the specification. The embodiments within the specification provide an illustration of embodiments and should not be construed to limit the scope. The skilled artisan readily recognizes that many other embodiments are encompassed. All publications and patents cited in this disclosure are incorporated by reference in their entirety. To the extent the material incorporated by reference contradicts or is inconsistent with this specification, the specification will supersede any such material. The citation of any references herein is not an admission that such references are prior art.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Examples of the techniques and protocols described herein with regard to therapeutic compositions can be found in, e.g., Remington's Pharmaceutical Sciences, 16th edition, Osol, A. (ed), 1980.

Example 1. Construction of Binary Pairs in a High-Throughput 96-Well Format/Plate Preparation Pairs of bacteria were used to identify binary pairs useful for inhibition of *C. difficile*. To prepare plates for the high-throughput screening assay of binary pairs, vials of −80° C. glycerol stock bacterial banks were thawed and diluted to 1e8 CFU/mL. Each bacterial strain was then diluted 10× (to a final concentration of 1e7 CFU/mL of each strain) into 200 uL of PBS+15% glycerol in the wells of a 96-well plate. Plates were then frozen at −80° C. When needed, plates were removed from −80° C. and thawed at room temperature under anaerobic conditions for testing in a CivSim assay with *C. difficile.*

Example 2. Construction of Ternary Combinations in a High-Throughput 96-Well Format Triplet combinations of bacteria were used to identify ternary combinations useful for inhibition of *C. difficile*. To prepare plates for high-throughput screening of ternary combinations, vials of −80° C. glycerol bacterial stock banks were thawed and diluted to 1e8 CFU/mL. Each bacterial strain was then diluted 10× (to a final concentration of 1e7 CFU/mL of each strain) into 200 uL of PBS+15% glycerol in the wells of a 96-well plate. Plates were then frozen at −80° C. When needed for the assay, plates were removed from −80° C. and thawed at room temperature under anaerobic conditions when testing in a CivSim assay with *Clostridium difficile.*

Example 3. Construction of a CivSim Assay to Screen for Bacterial Compositions Inhibitory to the Growth of *Clostridium difficile*

A competition assay (CivSim assay) was used to identify compositions that can inhibit the growth of *C. difficile*. Briefly, an overnight culture of *C. difficile* was grown under anaerobic conditions in SweetB-FosIn for the growth of *C. difficile*. In some cases, other suitable media can be used. SweetB-FosIn is a version of BHI (Remel R452472) supplemented with several components as follows: Components per liter: 37 g BHI powder (Remel R452472), supplemented with 5 g yeast extract UF (Difco 210929), 1 g cysteine-HCl (Spectrum C1473), 1 g cellobiose (Sigma C7252), 1 g maltose (Spectrum MA155), 1.5 ml hemin solution, 1 g soluble starch (Sigma-Aldrich S9765), 1 g fructooligosaccharides/inulin (Jarrow Formulas 103025) and 50 mL 1 M MOPS/KOH pH 7. To prepare the hemin solution, hemin (Sigma 51280) was dissolved in 0.1 M NaOH to make a 10 mg/mL stock.

After 24 hours of growth the culture was diluted 100,000 fold into a complex medium SweetB-FosIn. In some embodiments a medium is selected for use in which all desired organisms can grow, i.e., which is suitable for the growth of a wide variety of anaerobic, and, in some cases facultative anaerobic bacterial species. The diluted *C. difficile* mixture was then aliquoted to wells of a 96-well plate (180 uL to each well). 20 uL of a bacterial composition was then added to each well at a final concentration of 1e6 CFU/mL of each or two or three species. Alternatively the assay can be tested with binary pairs at different initial concentrations (1e9 CFU/mL, 1e8 CFU/mL, 1e7 CFU/mL, 1e5 CFU/mL, 1e4 CFU/mL, 1e3 CFU/mL, 1e2 CFU/mL). Control wells only inoculated with *C. difficile* were included for a comparison to the growth of *C. difficile* without inhibition. Additional wells were used for controls that either inhibit or do not inhibit the growth of *C. difficile*. One example of a positive control that inhibits growth was a combination of *Blautia producta, Clostridium bifermentans* and *Escherichia coli*. One example of a control that shows reduced inhibition of *C. difficile* growth as a combination of *Bacteroides thetaiotaomicron, Bacteroides ovatus* and *Bacteroides vulgatus*. Plates were wrapped with parafilm and incubated for 24 hours at 37° C. under anaerobic conditions. After 24 hours, the wells containing *C. difficile* alone were serially diluted and plated to determine titer. The 96-well plate was then frozen at −80 C before quantifying *C. difficile* by qPCR assay (see Example 6). Experimental combinations that inhibit *C. difficile* in this assay are useful in compositions for prevention or treatment of *C. difficile* infection.

Example 4. Construction of a CivSim Assay to Screen for Bacterial Compositions that Produce Diffusible Products Inhibitory to the Growth of *Clostridium difficile* Using a Filter Insert To identify bacterial compositions that can produce diffusible products that inhibit *C. difficile* a modified CivSim assay was designed. In this experiment, the CivSim assay described above was modified by using a 0.22 uM filter insert (Millipore™ MultiScreen™ 96-Well Assay Plates—Item MAGVS2210) in 96-well format to physically separate *C. difficile* from the bacterial compositions. The *C. difficile* was aliquoted into the 96-well plate while the bacterial compositions were aliquoted into media on the filter overlay. The nutrient/growth medium is in contact on both sides of the 0.22 uM filter, allowing exchange of nutrients, small molecules and many macromolecules (e.g., bacteriocins, cell-surface proteins, or polysaccharides) by diffusion. In this embodiment, after a 24 hour incubation, the filter insert containing the bacterial compositions was removed. The plate containing *C. difficile* was then transferred to a 96-well plate reader suitable for measuring optical density (OD) at 600 nm. The growth of *C. difficile* in the presence of different bacterial compositions was compared based on the OD measurement. The results of these experiments demonstrated that compositions that can inhibit *C. difficile* when grown in shared medium under conditions that do not permit contact between the bacteria in the composition and *C. difficile* can be identified. Such compositions are candidates for producing diffusible products that are effective for treating *C. difficile* infection and can serve as part of a process for isolating such diffusible products, e.g., for use in treating infection.

Example 5. Construction of a CivSim Assay to Screen for Bacterial Compositions Inhibitory to the Growth of *Clostridium difficile* Using *Clostridium difficile* Selective Media for Quantification The CivSim assay described above can be modified to determine final *C. difficile* titer by serially diluting and plating to *C. difficile* selective media (Bloedt et al. 2009) such as CCFA (cycloserine cefoxitin fructose agar, Anaerobe Systems), CDSA (*Clostridium difficile* selective agar, which is cycloserine cefoxitin mannitol agar, Becton Dickinson).

Example 6. Quantification of *C. difficile* Using Quantitative PCR (qPCR)

A. Standard Curve Preparation

To quantitate *C. difficile*, a standard curve was generated from a well on each assay plate in, e.g., a CivSim assay, containing only pathogenic *C. difficile* grown in SweetB+FosIn media as provided herein and quantified by selective spot plating. Serial dilutions of the culture were performed in sterile phosphate-buffered saline. Genomic DNA was extracted from the standard curve samples along with the other wells.

B. Genomic DNA Extraction

Genomic DNA was extracted from 5 μl of each sample using a dilution, freeze/thaw, and heat lysis protocol. 5 μL of thawed samples were added to 45 μL of UltraPure water (Life Technologies, Carlsbad, CA) and mixed by pipetting. The plates with diluted samples were frozen at −20° C. until use for qPCR which included a heated lysis step prior to amplification. Alternatively the genomic DNA could be isolated using the Mo Bio Powersoil®-htp 96 Well Soil DNA Isolation Kit (Mo Bio Laboratories, Carlsbad, CA), Mo Bio Powersoil® DNA Isolation Kit (Mo Bio Laboratories, Carlsbad, CA), or the QIAamp DNA Stool Mini Kit (QIAGEN, Valencia, CA) according to the manufacturer's instructions.

C. qPCR Composition and Conditions

The qPCR reaction mixture contained 1× SsoAdvanced Universal Probes Supermix, 900 nM of Wr-tcdB-F primer (AGCAGTTGAATATAGTGGTTTAGTTAGAGTTG (SEQ ID NO: 2033), IDT, Coralville, IA), 900 nM of Wr-tcdB-R primer (CATGCTTTTTTAGTTTCTGGATTGAA (SEQ ID NO: 2034), IDT, Coralville, IA), 250 nM of Wr-tcdB-P probe (6FAM-CATCCAGTCTCAATTGTATATGTTTCTCCA (SEQ ID NO: 2035)-MGB, Life Technologies, Grand Island, NY), and Molecular Biology Grade Water (Mo Bio Laboratories, Carlsbad, CA) to 18 µl (Primers adapted from: Wroblewski, D. et al., Rapid Molecular Characterization of *Clostridium difficile* and Assessment of Populations of *C. difficile* in Stool Specimens, Journal of Clinical Microbiology 47:2142-2148 (2009)). This reaction mixture was aliquoted to wells of a Hard-shell Low-Profile Thin Wall 96-well Skirted PCR Plate (BioRad, Hercules, CA). To this reaction mixture, 2 µl of diluted, frozen, and thawed samples were added and the plate sealed with a Microseal 'B' Adhesive Seal (BioRad, Hercules, CA). The qPCR was performed on a BioRad C1000™ Thermal Cycler equipped with a CFX96™ Real-Time System (BioRad, Hercules, CA). The thermocycling conditions were 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

D. Data Analysis

The Cq value for each well on the FAM channel was determined by the CFX Manager™ 3.0 software. The $\log_{10}$ (cfu/mL) of *C. difficile* each experimental sample was calculated by inputting a given sample's Cq value into a linear regression model generated from the standard curve comparing the Cq values of the standard curve wells to the known $\log_{10}$ (cfu/mL) of those samples. The log inhibition was calculated for each sample by subtracting the $\log_{10}$ (cfu/mL) of *C. difficile* in the sample from the $\log_{10}$ (cfu/mL) of *C. difficile* in the sample on each assay plate used for the generation of the standard curve that has no additional bacteria added. The mean log inhibition was calculated for all replicates for each composition.

A histogram of the range and standard deviation of each composition was plotted. Ranges or standard deviations of the log inhibitions that were distinct from the overall distribution were examined as possible outliers. If the removal of a single log inhibition datum from one of the binary pairs that were identified in the histograms would bring the range or standard deviation in line with those from the majority of the samples, that datum was removed as an outlier, and the mean log inhibition was recalculated.

The pooled variance of all samples evaluated in the assay was estimated as the average of the sample variances weighted by the sample's degrees of freedom. The pooled standard error was then calculated as the square root of the pooled variance divided by the square root of the number of samples. Confidence intervals for the null hypothesis were determined by multiplying the pooled standard error to the z score corresponding to a given percentage threshold. Mean log inhibitions outside the confidence interval were considered to be inhibitory if positive or stimulatory if negative with the percent confidence corresponding to the interval used. Samples with mean log inhibition greater than the 99% confidence interval (C.I) of the null hypothesis are reported as ++++, those with a 95%<C.I.<99% as +++, those with a 90%<C.I.<95% as ++, those with a 80%<C.I.<90% as + while samples with mean log inhibition less than the 99% confidence interval (C.I) of the null hypothesis are reported as ----, those with a 95%<C.I.<99% as ---, those with a 90%<C.I.<95% as --, those with a 80%<C.I.<90% as -.

Example 7. Inhibition of *C. difficile* Growth by Bacterial Compositions

Using methods described herein, binary pairs were identified that can inhibit *C. difficile* (see Table 4). 622 of 989 combinations showed inhibition with a confidence interval >80%; 545 of 989 with a C.I.>90%; 507 of 989 with a C.I.>95%; 430 of 989 with a C.I. of >99%. Non-limiting but exemplary binary pairs include those with mean log reduction greater than 0.366, e.g., *Allistipes shahii* paired with *Blautia producta, Clostridium hathaweyi*, or *Collinsella aerofaciens*, or *Clostridium mayombei* paired with *C. innocuum, C. tertium, Collinsella aerofaciens*, or any of the other 424 combinations shown in Table 4. Equally important, the CivSim assay describes binary pairs that do not effectively inhibit *C. difficile.* 188 of 989 combinations promote growth with >80% confidence; 52 of 989 show a lack of inhibition with >90% confidence; 22 of 989 show a lack of inhibition with >95% confidence; 3 of 989, including *B. producta* combined with *Coprococcus catus*, Alistipes shahii combined with *Dorea formicigenerans*, and *Eubacterium rectale* combined with *Roseburia intestinalis*, show a lack of inhibition with >99% confidence. 249 of 989 combinations are neutral in the assay, meaning they neither promote nor inhibit *C. difficile* growth to the limit of measurement.

Ternary combinations with mean log inhibition greater than the 99% confidence interval (C.I) of the null hypothesis are reported as ++++, those with a 95%<C.I.<99% as +++, those with a 90%<C.I.<95% as ++, those with a 80%<C.I.<90% as + while samples with mean log inhibition less than the 99% confidence interval (C.I) of the null hypothesis are reported as ----, those with a 95%<C.I.<99% as --, those with a 90%<C.I.<95% as --, those with a 80%<C.I.<90% as -.

The CivSim assay results demonstrate that many ternary combinations can inhibit *C. difficile* (Table 4). 516 of 632 ternary combinations show inhibition with a confidence interval >80%; 507 of 632 with a C.I.>90%; 496 of 632 with a C.I.>95%; 469 of 632 with a C.I. of >99%. Non-limiting but exemplary ternary combinations include those with a score of ++++, such as *Colinsella aerofaciens, Coprococcus comes*, and *Blautia producta*. The CivSim assay also describes ternary combinations that do not effectively inhibit *C. difficile.* 76 of 632 combinations promote growth with >80% confidence; 67 of 632 promote growth with >90% confidence; 61 of 632, promote growth with >95% confidence; and 49 of 632 combinations such as, but not limited to, *Clostridium orbiscendens, Coprococcus comes*, and *Faecalibacterium prausnitzii* promote growth with >99% confidence. 40 of 632 combinations are neutral in the assay, meaning they neither promote nor inhibit *C. difficile* growth to the limit of confidence.

Of the ternary combinations that inhibit *C. difficile* with >99% confidence, those that strongly inhibit *C. difficile* can be identified by comparing their mean log inhibition to the distribution of all results for all ternary combinations tested. Those above the 75th percentile can be considered to strongly inhibit *C. difficile*. Alternatively, those above the 50th, 60th, 70th, 80th, 90th, 95th, or 99th percentile can be considered to strongly inhibit *C. difficile*. Non-limiting but exemplary ternary combinations above the 75th percentile include *Blautia producta, Clostridium tertium*, and *Rumi-*

*nococcus* gnavus and *Eubacterium rectale, Clostridium mayombei*, and *Ruminococcus bromii.*

In addition to the demonstration that many binary and ternary combinations inhibit *C. difficile*, the CivSim demonstrates that many of these combinations synergistically inhibit *C. difficile*. Exemplary ternary combinations that demonstrate synergy in the inhibition of *C. difficile* growth include, but are not limited to, *Blautia producta, Clostridium innocuum, Clostridium orbiscendens* and *Colinsella aerofaciens, Blautia producta*, and *Eubacterium rectale*. Additional useful combinations are provided throughout, e.g., in Tables 4a, 4b, and 14-21.

Two higher-order bacterial compositions were tested in the CivSim assay for inhibition of *C. difficile*. N1962 (a.k.a. S030 and N1952), a 15 member composition, inhibited *C. difficile* by an average of 2.73 log 10 CFU/mL with a standard deviation of 0.58 log 10 CFU/mL while N1984 (a.k.a. S075), a 9 member composition, inhibited *C. difficile* by an average of 1.42 log 10 CFU/mL with a standard deviation of 0.45 log 10 CFU/mL.

These data collectively demonstrate that the CivSim assay can be used to identify compositions containing multiple species that are effective at inhibiting growth, that promote growth, or do not have an effect on growth of an organism, e.g., a pathogenic organism such as *C. difficile.*

Example 8. In Vivo Validation of Ternary Combinations' Efficacy in a Murine Model of *Clostridium difficile* Infection To test the therapeutic potential of a bacterial composition such as but not limited to a spore population, a prophylactic mouse model of *C. difficile* infection was used (model based on Chen et al. 2008. A mouse model of *Clostridium difficile*-associated disease. Gastroenterology 135: 1984-1992). Briefly, two cages of five mice each were tested for each arm of the experiment. All mice received an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and vancomycin (0.056 mg/ml) in their drinking water on days −14 through −5 and a dose of 10 mg/kg clindamycin by oral gavage on day −3. On day −1, test compositions were spun for 5 minutes at 12,100 rcf, their supernatants' removed, and the remaining pellets were resuspended in sterile PBS, prereduced if bacterial composition was not in spore form, and delivered via oral gavage. On day 0 the mice were challenged by administration of approximately 4.5 log 10 cfu of *C. difficile* (ATCC 43255) or sterile PBS (for the naive arm) via oral gavage. Mortality, weight and clinical scoring of *C. difficile* symptoms based upon a 0-4 scale by combining scores for appearance (0-2 points based on normal, hunched, piloerection, or lethargic), and clinical signs (0-2 points based on normal, wet tail, cold-to-the-touch, or isolation from other animals), with a score of 4 in the case of death, were assessed every day from day −2 through day 6. Mean minimum weight relative to day −1 and mean maximum clinical score as well as average cumulative mortality were calculated. Reduced mortality, increased mean minimum weight relative to day −1, and reduced mean maximum clinical score with death assigned to a score of 4 relative to the vehicle control were used to assess the ability of the test composition to inhibit infection by *C. difficile.*

Ternary combinations were tested in the murine model described above at 1e9 CFU/mL per strain. The results are shown in Table 5. The data demonstrate that the CivSim assay results are highly predictive of the ability of a combination to inhibit weight loss in *C. difficile* infection. Weight loss in this model is generally considered to be indicative of disease.

In one embodiment, compositions to screen for efficacy in vivo can be selected by ranking the compositions based on a functional metric such as but not limited to in vitro growth inhibition scores; compositions that are ranked ≥ the 75th percentile can be considered to strongly inhibit growth and be selected for in vivo validation of the functional phenotype. In other embodiments, compositions above the 50th, 60th, 70th, 80th, 90th, 95th, or 99th percentile can be considered to be the optimal candidates. In another embodiment, combinations with mean log inhibition greater than the 99% confidence interval (C.I) of the null hypothesis are selected. In other embodiments, compositions greater than the 95%, 90%, 85%, or 80% confidence interval (C.I.) are selected. In another embodiment, compositions demonstrated to have synergistic inhibition are selected (see Example 7) for testing in an in vivo model such as that described above.

Compositions selected to screen for efficacy in in vivo models can also be selected using a combination of growth inhibition metrics. In a non-limiting example: (i) compositions are selected based on their log inhibition being greater than the 99% confidence interval (C.I.) of the null hypothesis, (ii) the selected subset of compositions is further selected to represent those that are ranked ≥ the 75th percentile in the distribution of all inhibition scores, (iii) the subset of (ii) is then further selected based on compositions that demonstrate synergistic inhibition. In some embodiments, different confidence intervals (C.I.) and percentiles are used to create the composition subsets, e.g., see Table 4b.

Of the twelve exemplary ternary combinations selected, all were demonstrated to inhibit *C. difficile* in the CivSim assay (see Example 6) with >99% confidence. Ten of the twelve compositions demonstrated a protective effect when compared to a vehicle control with respect to the Mean Minimum Relative Weight. All twelve compositions outperformed vehicle with respect to Mean Maximum Clinical Score while eleven of twelve compositions surpassed the vehicle control by Cumulative Mortality. A non-limiting, but exemplary ternary combination, *Collinsella aerofaciens, Clostridium buytricum*, and *Ruminococcus* gnavus, was protective against symptoms of *C. difficile* infection, producing a Mean Minimum Relative Weight of 0.96, a Mean Maximum Clinical Score of 0.2, and Cumulative Mortality of 0% compared to the vehicle control of 0.82, 2.6, and 30%, respectively. These results demonstrate that the in vitro CivSim assay can be used to identify compositions that are protective in an in vivo murine model. This is surprising given the inherent dynamic nature of in vivo biological systems and the inherent simplification of the in vitro assays; it would not be expected that there is a direct correlation of in vitro in in vivo measures of inhibition and efficacy. This is in part because of the complexity of the in vivo system into which a composition is administered for treatment in which it might have been expected that confounding factors would obscure or affect the ability of a composition deemed effective in vitro to be effective in vivo.

Example 9. Construction of a CivSim Assay to Screen for Bacterial Compositions Inhibitory to the Growth of Vancomycin-Resistant *Enterococcus* (VRE) Using Vancomycin-Resistant *Enterococcus* Selective Medium for Quantification and Composition Screening To determine the ability of a composition to compete with a pathogenic *bacterium*, e.g., vancomycin-resistant *Entero-*

*coccus*, a competition assay was developed. In these experiments, an overnight culture of a vancomycin-resistant strain of *Enterococcus faecium* was grown anaerobically in SweetB-FosIn for 24 hours. A glycerol stock of a bacterial composition was thawed from −80° C. and diluted to 1e6 CFU/mL per strain in SweetB-FosIn in the appropriate wells of a 96-well plate. The plate was incubated anaerobically at 37° C. for 1 hour to allow the previously frozen bacteria to revive. After the 1 hour initial incubation, VRE was inoculated into appropriate wells at target concentrations of 1e2 or 1e3 CFU/mL. Wells were also inoculated with VRE alone, without a bacterial composition. The plate was incubated anaerobically at 37° C. for 24 hours. Aliquots were removed at 15 hours and 24 hours and the VRE titers determined. At each time-point, well contents were serially diluted and plated to agar plates selective for VRE (Enterococcosel Agar+8 ug/mL vancomycin hydrochloride) (Enterococcosel Agar from BBL 212205, vancomycin hydrochloride from Sigma 94747). The selective plates were incubated aerobically at 37° C. for 24 hours before counting colonies to determine final titer of VRE in each well of the CivSim plate. Log Inhibition of VRE was determined by subtracting the final titer of a competition well from the final titer of a well containing VRE alone. Multiple ratios of the starting concentrations of VRE and bacterial compositions were tested to optimize for conditions resulting in the greatest signal. A competition time of 15 hours, a starting concentration of VRE at 1e2 CFU/mL and a starting concentration of N1962 (a.k.a. S030 and N1952) at 1e6 CFU/mL showed the greatest inhibition of growth compared to control.

Using the conditions described above, one 15-member and 44 heterotrimeric bacterial compositions were tested in the assay, the results of which are provided in Tables 4 and 6. Of the 44 heterotrimeric compositions tested, 43 inhibited VRE with >80% confidence, 41 inhibited VRE with >95% confidence, and 39 inhibited VRE with >99% confidence. One ternary composition tested did not demonstrate inhibition or induction with >80% confidence.

Of the ternary combinations that inhibit VRE with >99% confidence, those that strongly inhibit VRE can be identified by comparing their mean log inhibition to the distribution of all results for all ternary combinations tested. Those above the 75th percentile can be considered to strongly inhibit VRE. Alternatively, those above the 50th, 60th, 70th, 80th, 90th, 95th, or 99th percentile can be considered to strongly inhibit VRE. Non-limiting but exemplary ternary combinations that inhibit VRE with >99% confidence and above the 75th percentile include *Blautia producta, Clostridium innocuum*, and *Ruminococcus* gnavus and *Blautia producta, Clostridium butyricum*, and *Clostridium hylemonae.*

The 15-member composition, N1962 (a.k.a. S030 and N1952), inhibited VRE by at least 0.7 log 10 CFU/mL across all of the conditions tested and demonstrating inhibition of 5.7 log 10 CFU/mL in the optimal conditions.

These data demonstrate methods of identifying compositions useful for prophylaxis and treatment of VRE infection.

Example 10. Construction of a CivSim Assay to Screen for Bacterial Compositions Inhibitory to the Growth of *Klebsiella pneumoniae* Using *Klebsiella* Selective Medium for Quantification To determine the ability of a composition to compete with a pathogenic *bacterium*, e.g., *Klebsiella pneumoniae*, a competition assay was developed. In these experiments, an overnight culture of a vancomycin-resistant strain of *Klebsiella pneumoniae* was grown anaerobically in SweetB-FosIn for 24 hours. A glycerol stock of a bacterial composition (N1962) was thawed from −80° C. and diluted to 1e6 CFU/mL per strain in SweetB-FosIn in the appropriate wells of a 96-well plate. The plate was incubated anaerobically at 37° C. for 1 hour to allow the previously frozen bacteria to revive. After the 1 hour initial incubation, *K. pneumoniae* was inoculated into appropriate wells at target concentrations of 1e2 or 1e3 CFU/mL. Wells were also inoculated with *K. pneumoniae* alone, without a bacterial composition. The plate was incubated anaerobically at 37° C. for 24 hours. Aliquots were removed at 15 hours and 24 hours to titer for the final concentration of *K. pneumoniae* at the end of competition. At each time-point, wells were serially diluted and plated to agar plates selective for *K. pneumoniae* (MacConkey Lactose Agar, Teknova M0149). The selective plates were incubated aerobically at 37° C. for 24 hours before counting colonies to determine final titer of *K. pneumoniae* in each well of the CivSim plate. Log Inhibition of *K. pneumoniae* was determined by subtracting the final titer of a competition well from the final titer of a well containing *K. pneumoniae* alone. Multiple ratios of the starting concentrations of *K. pneumoniae* and bacterial compositions were tested to optimize for conditions giving the greatest signal. The results of the assay are provided in Table 7. A competition time of 15 hours, a starting concentration of *K. pneumoniae* at 1e2 CFU/mL and a starting concentration of N1962 (a.k.a. S030 and N1952) at 1e6 CFU/mL showed the greatest inhibition of growth compared to control. N1962 (a.k.a. S030 and N1952) inhibited *K. pneumoniae* by 0.1-4.2 log 10 CFU/mL across the conditions tested.

Example 11. Construction of a CivSim Assay to Screen for Bacterial Compositions Inhibitory to the Growth of *Morganella morganii* Using *Morganella* Selective Media for Quantification To determine the ability of a composition to compete with a pathogenic *bacterium*, e.g., *Morganella morganii*, a competition assay was developed. In this experiment, an overnight culture of a vancomycin-resistant strain of *Morganella morganii* was grown anaerobically in SweetB-FosIn for 24 hours. A glycerol stock of a bacterial composition, N1962, was thawed from −80° C. and diluted to 1e6 CFU/mL per strain in SweetB-FosIn in the appropriate wells of a 96-well plate. The plate was incubated anaerobically at 37° C. for 1 hour to allow the previously frozen bacteria to revive. After the 1 hour initial incubation, *M. morganii* was inoculated into appropriate wells at target concentrations of 1e2 or 1e3 CFU/mL. Wells were also inoculated with *M. morganii* alone, without a bacterial composition. The plate was incubated anaerobically at 37° C. for 24 hours. Aliquots were removed at 15 hours and 24 hours to titer for the final concentration of *M. morganii* at the end of competition. At each time-point, wells were serially diluted and plated to agar plates selective for *M. morganii* (MacConkey Lactose Agar, Teknova M0149). The selective plates were incubated aerobically at 37° C. for 24 hours before counting colonies to determine final titer of *M. morganii* in each well of the CivSim plate. Log Inhibition of *M. morganii* was determined by subtracting the final titer of a competition well from the final titer of a well containing *M. morganii* alone. Multiple ratios of the starting concentrations of *M. morganii* and bacterial compositions were tested to optimize for conditions providing the greatest signal. A competition time of 15 hours, a starting concentration of *M. morganii* at 1e2 CFU/ mL and a starting concentration of N1962 (a.k.a. S030 and N1952) at 1e6 CFU/mL showed the greatest inhibition of growth compared to control.

A 15-member bacterial composition, N1962 (a.k.a. S030 and N1952), was tested in the assay, the results of which are provided in Table 8. N1962 (a.k.a. S030 and N1952) inhibited *M. morganii* by 1.4 to 5.8 log 10 CFU/mL across the conditions tested.

Example 12. Sequence-Based Genomic Characterization of Operational Taxonomic Units (OTU) and Functional Genes Method for Determining 16S rDNA Gene Sequence As described above, OTUs are defined either by full 16S sequencing of the rDNA gene, by sequencing of a specific hypervariable region of this gene (i.e., V1, V2, V3, V4, V5, V6, V7, V8, or V9), or by sequencing of any combination of hypervariable regions from this gene (e.g., V1-3 or V3-5). The bacterial 16S rDNA gene is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes. rDNA gene sequencing methods are applicable to both the analysis of non-enriched samples, but also for identification of microbes after enrichment steps that either enrich the microbes of interest from a microbial composition or a microbial sample and/or the nucleic acids that harbor the appropriate rDNA gene sequences as described below. For example, enrichment treatments prior to 16S rDNA gene characterization will increase the sensitivity of 16S as well as other molecular-based characterization nucleic acid purified from the microbes.

Using techniques known in the art, to determine the full 16S sequence or the sequence of any hypervariable region of the 16S rDNA sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Method for Determining 18S rDNA and ITS Gene Sequence

Methods to assign and identify fungal OTUs by genetic means can be accomplished by analyzing 18S sequences and the internal transcribed spacer (ITS). The rRNA of fungi that forms the core of the ribosome is transcribed as a single gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al. Nuclear ribosomal internal transcribed spacer (ITS) region as a universal DNA barcode marker for Fungi. PNAS USA 109:6241-6246. 2012). 18S rDNA is typically used for phylogenetic reconstruction however the ITS can serve this function as it is generally highly conserved but contains hypervariable regions that harbor sufficient nucleotide diversity to differentiate genera and species of most fungus.

Using techniques known in the art, to determine the full 18S and ITS sequences or a smaller hypervariable section of these sequences, genomic DNA is extracted from a microbial sample, the rDNA amplified using polymerase chain reaction (PCR), the PCR products cleaned, and nucleotide sequences delineated to determine the genetic composition rDNA gene or subdomain of the gene. The sequencing method used may be, but is not limited to, Sanger sequencing or using a next-generation sequencing method, such as an Illumina (sequencing by synthesis) method using barcoded primers allowing for multiplex reactions.

Method for Determining Other Marker Gene Sequences

In addition to the 16S and 18S rDNA gene, an OTU can be defined by sequencing a selected set of genes or portions of genes that are known marker genes for a given species or taxonomic group of OTUs. These genes may alternatively be assayed using a PCR-based screening strategy. For example, various strains of pathogenic *Escherichia coli* can be distinguished using DNAs from the genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv). The optimal genes to utilize for taxonomic assignment of OTUs by use of marker genes will be familiar to one with ordinary skill in the art of sequence based taxonomic identification.

Genomic DNA Extraction

Genomic DNA can be extracted from pure or enriched microbial cultures using a hot alkaline lysis method. For example, 1 μl of microbial culture is added to 9 μl of Lysis Buffer (25 mM NaOH, 0.2 mM EDTA) and the mixture is incubated at 95° C. for 30 minutes. Subsequently, the samples are cooled to 4° C. and neutralized by the addition of 10 μl of Neutralization Buffer (40 mM Tris-HCl) and then diluted 10-fold in Elution Buffer (10 mM Tris-HCl). Alternatively, genomic DNA is extracted from pure or enriched microbial cultures using commercially available kits such as the Mo Bio Ultraclean® Microbial DNA Isolation Kit (Mo Bio Laboratories, Carlsbad, CA) or by methods known to those skilled in the art. For fungal samples, DNA extraction can be performed by methods described previously (e.g., see US20120135127) for producing lysates from fungal fruiting bodies by mechanical grinding methods.

Amplification of 16S Sequences for Downstream Sanger Sequencing

To amplify bacterial 16S rDNA (e.g., in FIG. 2 and FIG. 3), 2 μl of extracted gDNA is added to a 20 μl final volume PCR reaction. For full-length 16 sequencing the PCR reaction also contains 1× HotMaster®Mix (5PRIME, Gaithersburg, MD), 250 nM of **27*f*** (AGRGTTTGATCMTGGCTCAG (SEQ ID NO: 2036), IDT, Coralville, IA), and 250 nM of 1492r (TACGGYTACCTTGTTAYGACTT (SEQ ID NO: 2037), IDT, Coralville, IA), with PCR Water (Mo Bio Laboratories, Carlsbad, CA) for the balance of the volume.

Figure 2:
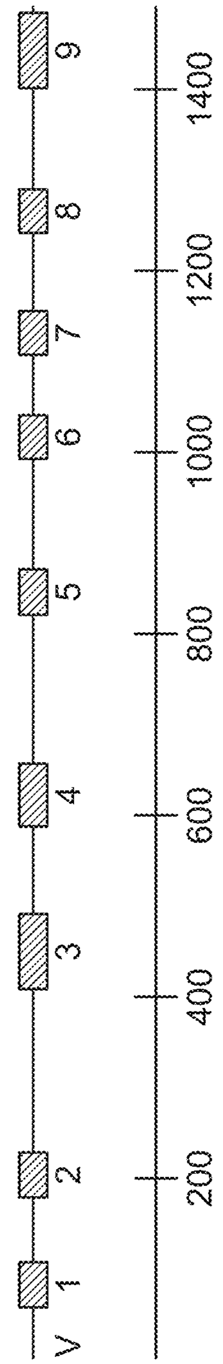
FIG. 2 provides a schematic of 16S rDNA gene and denotes the coordinates of hypervariable regions 1-9 (V1-V9), according to an embodiment of the invention. Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al., Complete nucleotide sequence of a 16S ribosomal RNA gene (16S rRNA) from *Escherichia coli*, PNAS 75(10):4801-4805 (1978).
Figure 4:
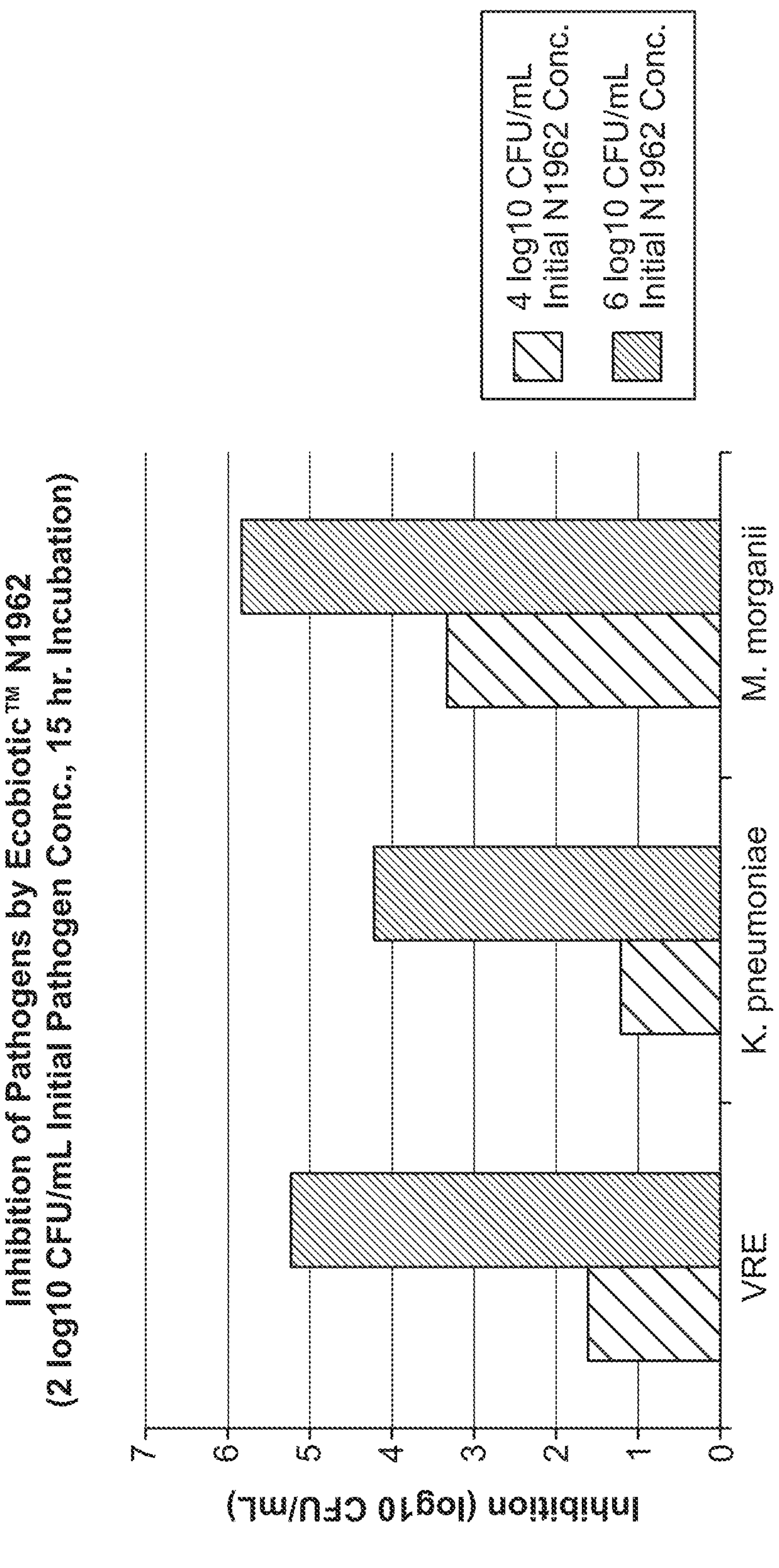
FIG. 4 provides representative combinations of the present invention tested in vitro and their respective inhibition of pathogen growth.

FIG. 2 shows the hypervariable regions mapped onto a 16s sequence and the sequence regions corresponding to these sequences on a sequence map. A schematic is shown of a 16S rDNA gene and the figure denotes the coordinates of hypervariable regions 1-9 (V1-V9), according to an embodiment of the invention. Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al. (Complete nucleotide sequence of a 16S ribosomal RNA gene (16S rRNA) from *Escherichia coli*, PNAS USA 75(10):4801-4805. 1978).

Alternatively, other universal bacterial primers or thermostable polymerases known to those skilled in the art are used. For example, primers are available to those skilled in the art for the sequencing of the "V1-V9 regions" of the 16S rDNA (e.g., FIG. 2). These regions refer to the first through ninth hypervariable regions of the 16S rDNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. See Brosius et al., 1978, supra. In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rDNA (e.g., FIG. 2) by comparing the candidate sequence in question to the reference sequence (as in FIG. 3) and identifying the hypervariable regions based on similarity to the reference hypervariable regions. FIG. 3 highlights in bold the nucleotide sequences for each hypervariable region in the exemplary reference *E. coli* 16S sequence described by Brosius et al., supra.

The PCR is typically performed on commercially available thermocyclers such as a BioRad MyCycler™ Thermal Cycler (BioRad, Hercules, CA). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

To remove nucleotides and oligonucleotides from the PCR products, 2 μl of HT ExoSap-IT® (Affymetrix, Santa Clara, CA) is added to 5 μl of PCR product followed by a 15 minute incubation at 37° C. and then a 15 minute inactivation at 80° C.

Amplification of 16S Sequences for Downstream Characterization By Massively Parallel Sequencing Technologies Amplification performed for downstream sequencing by short read technologies such as Illumina require amplification using primers known to those skilled in the art that additionally include a sequence-based barcoded tag. For example, to amplify the 16s hypervariable region V4 region of bacterial 16S rDNA, 2 μl of extracted gDNA is added to a 20 μl final volume PCR reaction. The PCR reaction also contains 1× HotMasterMix (5PRIME, Gaithersburg, MD), 200 nM of V4_515f_adapt (AATGATACGGCGACCACCGAGATCTACACTATGGTAATTGTGTGCCAGCMGCCGCGGT AA (SEQ ID NO: 2038), IDT, Coralville, IA), and 200 nM of barcoded 806rbc (CAAGCAGAAGACGGCATACGAGAT_12bpGolayBarcode_AGTCAGTCAGCCGGACTACHV GGGTWTCTAAT (SEQ ID NO: 2039), IDT, Coralville, IA), with PCR Water (Mo Bio Laboratories, Carlsbad, CA) for the balance of the volume. In the preceding primer sequences non-ACTG nucleotide designations refer to conventional degenerate codes as are used in the art. These primers incorporate barcoded adapters for Illumina sequencing by synthesis. Optionally, identical replicate, triplicate, or quadruplicate reactions may be performed. Alternatively other universal bacterial primers or thermostable polymerases known to those skilled in the art are used to obtain different amplification and sequencing error rates as well as results on alternative sequencing technologies.

The PCR amplification is performed on commercially available thermocyclers such as a BioRad MyCycler™ Thermal Cycler (BioRad, Hercules, CA). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~1.5 kb product. PCR cleanup is performed as described above.

Sanger Sequencing of Target Amplicons from Pure Homogeneous Samples

To detect nucleic acids for each sample, two sequencing reactions are performed to generate a forward and reverse sequencing read. For full-length 16s sequencing primers 27f and 1492r are used. 40 ng of ExoSap-IT-cleaned PCR products are mixed with 25 pmol of sequencing primer and Mo Bio Molecular Biology Grade Water (Mo Bio Laboratories, Carlsbad, CA) to 15 μl total volume. This reaction is submitted to a commercial sequencing organization such as Genewiz (South Plainfield, NJ) for Sanger sequencing.

Amplification of 18S and ITS regions for Downstream Sequencing

To amplify the 18S or ITS regions, 2 μL fungal DNA were amplified in a final volume of 30 μL with 15 μL AmpliTaq Gold 360 Mastermix, PCR primers, and water. The forward and reverse primers for PCR of the ITS region are 5'-TCCTCCGCTTATTGATATGC-3' (SEQ ID NO: 2040) and 5'-GGAAGTAAAAGTCGTAACAAGG-3' (SEQ ID NO: 2041) and are added at 0.2 uM concentration each. The forward and reverse primers for the 18s region are 5'-GTAGTCATATGCTTGTCTC-3' (SEQ ID NO: 2042) and 5'-CTTCCGTCAATTCCTTTAAG-3' (SEQ ID NO: 2043) and are added at 0.4 uM concentration each. PCR is performed with the following protocol: 95° C. for 10 minutes, 35 cycles of 95° C. for 15 seconds, 52° C. for 30 seconds, 72° C. for 1.5 seconds; and finally 72° C. for 7 minutes followed by storage at 4° C. All forward primers contained the M13F-20 sequencing primer, and reverse primers included the M13R-27 sequencing primer. PCR products (3 μL) were enzymatically cleaned before cycle sequencing with 1 μL ExoSap-IT and 1 μL Tris EDTA and incubated at 37° C. for 20 minutes followed by 80° C. for 15 minutes. Cycle sequencing reactions contained 5 μL cleaned PCR product, 2 μL BigDye® Terminator v3.1 Ready Reaction Mix, 1 μL 5× Sequencing Buffer, 1.6 pmol of appropriate sequencing primers designed by one skilled in the art, and water in a final volume of 10 μL. The standard cycle sequencing protocol is 27 cycles of 10 seconds at 96° C., 5 seconds at 50° C., 4 minutes at 60° C., and hold at 4° C. Sequencing cleaning is performed with the BigDye XTerminator Purification Kit as recommended by the manufacturer for 10 μL volumes. The genetic sequence of the resulting 18S and ITS sequences is performed using methods familiar to one with ordinary skill in the art using either Sanger sequencing technology or next-generation sequencing technologies such as but not limited to Illumina.

Preparation of Extracted Nucleic Acids for Metagenomic Characterization by Massively Parallel Sequencing Technologies Extracted nucleic acids (DNA or RNA) are purified and prepared by downstream sequencing using standard methods familiar to one with ordinary skill in the art and as described by the sequencing technology's manufactures instructions for library preparation. In short, RNA or DNA are purified using standard purification kits such as but not limited to Qiagen's RNeasy® Kit or Promega's Genomic DNA purification kit. For RNA, the RNA is converted to cDNA prior to sequence library construction. Following purification of nucleic acids, RNA is converted to cDNA using reverse transcription technology such as but not limited to Nugen Ovation® RNA-Seq System or Illumina Truseq as per the manufacturer's instructions. Extracted DNA or transcribed cDNA are sheared using physical (e.g., Hydroshear), acoustic (e.g., Covaris), or molecular (e.g., Nextera) technologies and then size selected as per the sequencing technologies manufacturer's recommendations. Following size selection, nucleic acids are prepared for sequencing as per the manufacturer's instructions for sample indexing and sequencing adapter ligation using methods familiar to one with ordinary skill in the art of genomic sequencing.

Massively Parallel Sequencing of Target Amplicons from Heterogeneous Samples

DNA Quantification & Library Construction

The cleaned PCR amplification products are quantified using the Quant-iT™ PicoGreen® dsDNA Assay Kit (Life Technologies, Grand Island, NY) according to the manufacturer's instructions. Following quantification, the barcoded cleaned PCR products are combined such that each distinct PCR product is at an equimolar ratio to create a prepared Illumina library.

Nucleic Acid Detection

The prepared library is sequenced on Illumina HiSeq or MiSeq sequencers (Illumina, San Diego, CA) with cluster generation, template hybridization, isothermal amplification, linearization, blocking and denaturation and hybridization of the sequencing primers performed according to the manufacturer's instructions. 16SV4SeqFw (TATGGTAATTGTGTGCCAGCMGCCGCGGTAA (SEQ ID NO: 2044)), 16SV4SeqRev (AGTCAGTCAGCCGGACTACHVGGGTWTCTAAT (SEQ ID NO: 2045)), and 16SV4Index (ATTAGAWACCCBDGTAGTCCGGCTGACTGACT (SEQ ID NO: 2046)) (IDT, Coralville, IA) are used for sequencing. Other sequencing technologies can be used such as but not limited to 454, Pacific Biosciences, Helicos, Ion Torrent, and Nanopore using protocols that are standard to someone skilled in the art of genomic sequencing.

Example 13. Sequence Read Annotation

Primary Read Annotation

Nucleic acid sequences are analyzed and annotated to define taxonomic assignments using sequence similarity and phylogenetic placement methods or a combination of the two strategies. A similar approach can be used to annotate protein names, protein function, transcription factor names, and any other classification schema for nucleic acid sequences. Sequence similarity based methods include those familiar to individuals skilled in the art including, but not limited to BLAST, BLASTx, tBLASTn, tBLASTx, RDP-classifier, DNAclust, and various implementations of these algorithms such as Qiime or Mothur. These methods rely on mapping a sequence read to a reference database and selecting the match with the best score and e-value. Common databases include, but are not limited to the Human Microbiome Project, NCBI non-redundant database, Greengenes, RDP, and Silva for taxonomic assignments. For functional assignments reads are mapped to various functional databases such as but not limited to COG, KEGG, BioCyc, and MetaCyc. Further functional annotations can be derived from 16S taxonomic annotations using programs such as PICRUST (M. Langille, et al. 2013. Nature Biotechnology 31, 814-821). Phylogenetic methods can be used in combination with sequence similarity methods to improve the calling accuracy of an annotation or taxonomic assignment. Tree topologies and nodal structure are used to refine the resolution of the analysis. In this approach we analyze nucleic acid sequences using one of numerous sequence similarity approaches and leverage phylogenetic methods that are known to those skilled in the art, including but not limited to maximum likelihood phylogenetic reconstruction (see e.g., Liu et al., 2011. RAxML and FastTree: Comparing Two Methods for Large-Scale Maximum Likelihood Phylogeny Estimation. PLoS ONE 6: e27731; McGuire et al., 2001. Models of sequence evolution for DNA sequences containing gaps. Mol. Biol. Evol 18: 481-490; Wróbel B. 2008. Statistical measures of uncertainty for branches in phylogenetic trees inferred from molecular sequences by using model-based methods. J. Appl. Genet. 49: 49-67). Sequence reads (e.g., 16S, 18S, or ITS) are placed into a reference phylogeny comprised of appropriate reference sequences. Annotations are made based on the placement of the read in the phylogenetic tree. The certainty or significance of the OTU annotation is defined based on the OTU's sequence similarity to a reference nucleic acid sequence and the proximity of the OTU sequence relative to one or more reference sequences in the phylogeny. As an example, the specificity of a taxonomic assignment is defined with confidence at the level of Family, Genus, Species, or Strain with the confidence determined based on the position of bootstrap supported branches in the reference phylogenetic tree relative to the placement of the OTU sequence being interrogated. Nucleic acid sequences can be assigned functional annotations using the methods described above.

Clade Assignments

Clade assignments were generally made using full-length sequences of 16S rDNA and of V4. The ability of 16S-V4 OTU identification to assign an OTU as a specific species depends in part on the resolving power of the 16S-V4 region of the 16S gene for a particular species or group of species. Both the density of available reference 16S sequences for different regions of the tree as well as the inherent variability in the 16S gene between different species will determine the definitiveness of a taxonomic annotation. Given the topological nature of a phylogenetic tree and the fact that tree represents hierarchical relationships of OTUs to one another based on their sequence similarity and an underlying evolutionary model, taxonomic annotations of a read can be rolled up to a higher level using a cade-based assignment procedure. Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) share a defined percent similarity (for 16S molecular data typically set to 95%-97% sequence similarity). OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, are likely to play similar functional roles in a microbial ecology such as that found in the human gut. Compositions substituting one species with another from the same clade are likely to have conserved ecological function and therefore are useful in the present invention. Notably in addition to 16S-V4 sequences, clade-based analysis can be used to analyze 18S, ITS, and other genetic sequences.

Notably, 16S sequences of isolates of a given OTU are phylogenetically placed within their respective clades, sometimes in conflict with the microbiological-based assignment of species and genus that may have preceded 16S-based assignment. Discrepancies between taxonomic assignments based on microbiological characteristics versus genetic sequencing are known to exist from the literature.

For a given network ecology or functional network ecology one can define a set of OTUs from the network's representative clades. As example, if a network was comprised of clade_100 and clade_102 it can be said to be comprised of at least one OTU from the group consisting of *Corynebacterium coyleae, Corynebacterium mucifaciens*, and *Corynebacterium ureicelerivorans*, and at least one OTU from the group consisting of *Corynebacterium appendicis, Corynebacterium genitalium, Corynebacterium glaucum, Corynebacterium imitans, Corynebacterium riegelii, Corynebacterium* sp. L_2012475, *Corynebacterium* sp. NML 93_0481, *Corynebacterium sundsvallense*, and *Corynebacterium tuscaniae* (see Table 1). Conversely as example, if a network was said to consist of *Corynebacterium coyleae* and/or *Corynebacterium mucifaciens* and/or *Corynebacterium ureicelerivorans*, and also consisted of *Corynebacterium appendicis* and/or *Corynebacterium genitalium* and/or *Corynebacterium glaucum* and/or *Corynebacterium imitans* and/or *Corynebacterium riegelii* and/or *Corynebacterium* sp. L_2012475 and/or *Corynebacterium* sp. NML 93_0481 and/or *Corynebacterium sundsvallense* and/or *Corynebacterium tuscaniae* it can be said to be comprised of clade_100 and clade_102.

The applicants made clade assignments to all OTUs disclosed herein using the above described method and these assignments are reported in Table 1. Results of the network analysis provides, in some embodiments, e.g., of compositions, substitution of clade_172 by clade_172i. In another embodiment, the network analysis provides substitution of clade_198 by clade_198i. In another embodiment, the network analysis permits substitution of clade_260 by clade_260c, clade_260g or clade_260h. In another embodiment, the network analysis permits substitution of clade_262 by clade_262i. In another embodiment, the network analysis permits substitution of clade_309 by clade_309c, clade_309e, clade_309g, clade_309h or clade_309i. In another embodiment, the network analysis permits substitution of clade_313 by clade_313f. In another embodiment, the network analysis permits substitution of clade_325 by clade_325f. In another embodiment, the network analysis permits substitution of clade_335 by clade_335i. In another embodiment, the network analysis permits substitution of clade_351 by clade_351e. In another embodiment, the network analysis permits substitution of clade_354 by clade_354e. In another embodiment, the network analysis permits substitution of clade_360 by clade_360c, clade_360g, clade_360h, or clade_360i. In another embodiment, the network analysis permits substitution of clade_378 by clade_378e. In another embodiment, the network analysis permits substitution of clade_38 by clade_38e or clade_38i. In another embodiment, the network analysis permits substitution of clade_408 by clade_408b, clade_408d, clade_408f, clade_408g or clade_408h. In another embodiment, the network analysis permits substitution of clade_420 by clade_420f. In another embodiment, the network analysis permits substitution of clade_444 by clade_444i. In another embodiment, the network analysis permits substitution of clade_478 by clade_478i. In another embodiment, the network analysis permits substitution of clade_479 by clade_479c, by clade_479g or by clade_479h. In another embodiment, the network analysis permits substitution of clade_481 by clade_481a, clade_481b, clade_481e, clade_481g, clade_481h or by clade_481i. In another embodiment, the network analysis substitution of clade_497 by clade_497e or by clade_497f. In another embodiment, the network analysis permits substitution of clade_512 by clade_512i. In another embodiment, the network analysis permits the network analysis permits substitutions of clade_516 by clade_516c, by clade_516g or by clade_516h. In another embodiment, the network analysis permits the network analysis permits substitutions of clade_522 by clade_522i. In another embodiment, the network analysis permits the network analysis permits substitutions of clade_553 by clade_553i. In another embodiment, the network analysis permits the network analysis permits substitutions of clade_566 by clade_566f. In another embodiment, the network analysis permits the network analysis permits substitutions of clade_572 by clade_572i. In another embodiment, the network analysis permits the network analysis permits substitutions of clade_65 by clade_65e. In another embodiment, the network analysis permits the network analysis permits substitutions of clade_92 by clade_92e or by clade_92i. In another embodiment, the network analysis permits the network analysis permits substitutions of clade_96 by clade_96g or by clade_96h. In another embodiment, the network analysis permits the network analysis permits substitutions of clade_98 by clade_98i. These permitted clade substitutions are described in Table 2.

Metagenomic Read Annotation

Metagenomic or whole genome shotgun sequence data is annotated as described above, with the additional step that sequences are either clustered or assembled prior to annotation. Following sequence characterization as described above, sequence reads are demultiplexed using the indexing (i.e. barcodes). Following demultiplexing sequence reads are either: (i) clustered using a rapid clustering algorithm such as but not limited to UCLUST (http://drive5.com/usearch/manual/uclust_algo.html) or hash methods such VICUNA (Xiao Yang, Patrick Charlebois, Sante Gnerre, Matthew G Coole, Niall J. Lennon, Joshua Z. Levin, James Qu, Elizabeth M. Ryan, Michael C. Zody, and Matthew R. Henn. 2012. De novo assembly of highly diverse viral populations. BMC Genomics 13:475). Following clustering a representative read for each cluster is identified based and analyzed as described above in "Primary Read Annotation". The result of the primary annotation is then applied to all reads in a given cluster. (ii) A second strategy for metagenomic sequence analysis is genome assembly followed by annotation of genomic assemblies using a platform such as but not limited to MetAMOS (Treangen et al. 2013 Genome Biology 14: R2), HUMAaN (Abubucker et al. 2012. Metabolic Reconstruction for Metagenomic Data and Its Application to the Human Microbiome ed. J. A. Eisen. PLoS Computational Biology 8: e1002358) and other methods familiar to one of skill in the art.

Example 14. OTU Identification Using Microbial Culturing Techniques

The identity of the bacterial species that grow up from a complex fraction can be determined in multiple ways. For example, individual colonies can be picked into liquid media in a 96 well format, grown up and saved as 15% glycerol stocks at −80° C. Aliquots of the cultures can be placed into cell lysis buffer and colony PCR methods can be used to amplify and sequence the 16S rDNA gene (Example 1). Alternatively, colonies may be streaked to purity in several passages on solid media. Well-separated colonies are streaked onto the fresh plates of the same kind and incubated for 48-72 hours at 37° C. The process is repeated multiple times to ensure purity. Pure cultures can be analyzed by phenotypic- or sequence-based methods, including 16S rDNA amplification and sequencing as described in Example 1. Sequence characterization of pure isolates or mixed communities e.g., plate scrapes and spore fractions can also include whole genome shotgun sequencing. The latter is valuable to determine the presence of genes associated with sporulation, antibiotic resistance, pathogenicity, and virulence. Colonies can also be scraped from plates en masse and sequenced using a massively parallel sequencing method as described in Example 1 such that individual 16S signatures can be identified in a complex mixture. Optionally, the sample can be sequenced prior to germination (if appropriate DNA isolation procedures are used to lyse and release the DNA from spores) in order to compare the diversity of germinable species with the total number of species in a spore sample. As an alternative or complementary approach to 16S analysis, MALDI-TOF-mass spec can also be used for species identification (Barreau et al., 2013. Improving the identification of anaerobes in the clinical microbiology laboratory through MALDI-TOF mass spectrometry. Anaerobe 22: 123-125).

Example 15. Microbiological Strain Identification Approaches

Pure bacterial isolates can be identified using microbiological methods as described in Wadsworth-KTL Anaerobic Microbiology Manual (Jouseimies-Somer et al., 2002. Wadsworth-KTL Anaerobic Bacteriology Manual), and The Manual of Clinical Microbiology (ASM Press, 10th Edition). These methods rely on phenotypes of strains and include Gram-staining to confirm Gram positive or negative staining behavior of the cell envelope, observance of colony morphologies on solid media, motility, cell morphology observed microscopically at 60× or 100× magnification including the presence of bacterial endospores and flagella. Biochemical tests that discriminate between genera and species are performed using appropriate selective and differential agars and/or commercially available kits for identification of Gram-negative and Gram-positive bacteria and yeast, for example, RapID tests (Remel) or API tests (bioMerieux). Similar identification tests can also be performed using instrumentation such as the Vitek 2 system (bioMerieux). Phenotypic tests that discriminate between genera and species and strains (for example the ability to use various carbon and nitrogen sources) can also be performed using growth and metabolic activity detection methods, for example the Biolog Microbial identification microplates. The profile of short chain fatty acid production during fermentation of particular carbon sources can also be used as a way to discriminate between species (Wadsworth-KTL Anaerobic Microbiology Manual, Jousimies-Somer, et al 2002). MALDI-TOF-mass spectrometry can also be used for species identification (as reviewed in Anaerobe 22:123).

Example 16. Construction of an In Vitro Assay to Screen for Combinations of Microbes Inhibitory to the Growth of Pathogenic *E. coli*

A modification of the in vitro assay described herein is used to screen for combinations of bacteria inhibitory to the growth of *E. coli*. In general, the assay is modified by using a medium suitable for growth of the pathogen inoculum. For example, suitable media include Reinforced Clostridial Media (RCM), Brain Heart Infusion Broth (BHI) or Luria Bertani Broth (LB) (also known as Lysogeny Broth). *E. coli* is quantified by using alternative selective media specific for *E. coli* or using qPCR probes specific for the pathogen. For example, aerobic growth on MacConkey lactose medium selects for enteric Gram-negative bacteria, including *E. coli*. qPCR is conducted using probes specific for the shiga toxin of pathogenic *E. coli*.

In general, the method can be used to test compositions in vitro for their ability to inhibit growth of any pathogen that can be cultured.

Example 17. Construction of an In Vitro Assay to Screen for Combinations of Microbes Inhibitory to the Growth of Vancomycin-Resistant *Enterococcus* (VRE)

The in vitro assay can be used to screen for combinations of bacteria inhibitory to the growth of vancomycin-resistant *Enterococcus* spp. (VRE) by modifying the media used for growth of the pathogen inoculum. Several choices of media can be used for growth of the pathogen such as Reinforced Clostridial Media (RCM), Brain Heart Infusion Broth (BHI) or Luria Bertani Broth (LB). VRE is quantified by using alternative selective media specific for VRE or using qPCR probes specific for the pathogen. For example, m-*Enterococcus* agar containing sodium azide is selective for *Enterococcus* spp. and a small number of other species. Probes known in the art that are specific to the van genes conferring vancomycin resistance are used in the qPCR or such probes can be designed using methods known in the art.

Example 18. In Vitro Assay Screening Bacterial Compositions for Inhibition of *Salmonella*

The in vitro assay described herein is used to screen for combinations of bacteria inhibitory to the growth of *Salmonella* spp. by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). *Salmonella* spp. are quantified by using alternative selective media specific for *Salmonella* spp. or using qPCR probes specific for the pathogen. For example, MacConkey agar is used to select for *Salmonella* spp. and the invA gene is targeted with qPCR probes; this gene encodes an invasion protein carried by many pathogenic *Salmonella* spp. and is used in invading eukaryotic cells.

Example 19. In Vivo Validation of the Efficacy of Network Ecology Bacterial Compositions for Prevention of *Clostridium difficile* Infection in a Murine Model To test the therapeutic potential of the bacterial composition, a prophylactic mouse model of *C. difficile* infection was used (model based on Chen et al., 2008. A mouse model of *Clostridium difficile*-associated disease. Gastroenterology 135: 1984-1992). Two cages of five mice each were tested for each arm of the experiment. All mice received an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and vancomycin (0.056 mg/ml) in their drinking water on days −14 through −5 and a dose of 10 mg/kg clindamycin by oral gavage on day −3. On day −1, test articles were spun for 5 minutes at 12,100 rcf, their supernatants' removed, and the remaining pellets were resuspended in sterile PBS, prereduced if bacterial composition was not in spore form, and delivered via oral gavage. On day 0 they were challenged by administration of approximately 4.5 log 10 cfu of *C. difficile* (ATCC 43255) or sterile PBS (for the naive arm) via oral gavage. Optionally a positive control group received vancomycin from day −1 through day 3 in addition to the antibiotic protocol and *C. difficile* challenge specified above. Stool were collected from the cages for analysis of bacterial carriage. Mortality, weight and clinical scoring of *C. difficile* symptoms based upon a 0-4 scale by combining scores for appearance (0-2 points based on normal, hunched, piloerection, or lethargic), and clinical signs (0-2 points based on normal, wet tail, cold-to-the-touch, or isolation from other animals) are assessed every day from day −2 through day 6. Mean minimum weight relative to day −1 and mean maximum clinical score where a death was assigned a clinical score of 4 as well as average cumulative mortality are calculated. Reduced mortality, increased mean minimum weight relative to day −1, and reduced mean maximum clinical score with death assigned to a score of 4 relative to the vehicle control are used to assess the success of the test article.

Table 9 and Table 10 report results for 14 experiments in the prophylactic mouse model of *C. difficile* infection where treatment was with a bacterial composition. In the 14 experiments, 157 of the arms tested network ecologies, with 86 distinct networks ecologies tested (Table 10). Indicia of efficacy of a composition (test article) in these experiments is a low cumulative mortality for the test composition relative to the vehicle control, a mean minimum relative weight of at least 0.85 (e.g., at least 0.90, at least 0.95, or at least 0.97), and a mean maximum clinical score less than 1, e.g., 0.9, 0.8, 0.7, 0.5, 0.2, or 0. Of the 157 arms of the experiment, 136 of the arms and 73 of the networks performed better than the respective experiment's vehicle control arm by at least one of the following metrics: cumulative mortality, mean minimum relative weight, and mean maximum clinical score. Examples of efficacious networks include but are not limited to networks N1979 as tested in SP-361 which had 0% cumulative mortality, 0.97 mean minimum relative weight, and 0 mean maximum clinical score or N2007 which had 10% cumulative mortality, 0.91 mean minimum relative weight, and 0.9 mean maximum clinical score with both networks compared to the vehicle control in SP-361 which had 30% cumulative mortality, 0.88 mean minimum relative weight, and 2.4 mean maximum clinical score. In SP-376, N1962 had no cumulative mortality, mean maximum clinical scores of 0 at both target doses tested with mean minimum relative weights of 0.98 and 0.95 for target doses of 1e8 and 1e7 CFU/OTU/mouse respectively. These results confirm that bacterial compositions comprised of binary and ternary and combinations thereof are efficacious as demonstrated using the mouse model.

Figure 5:
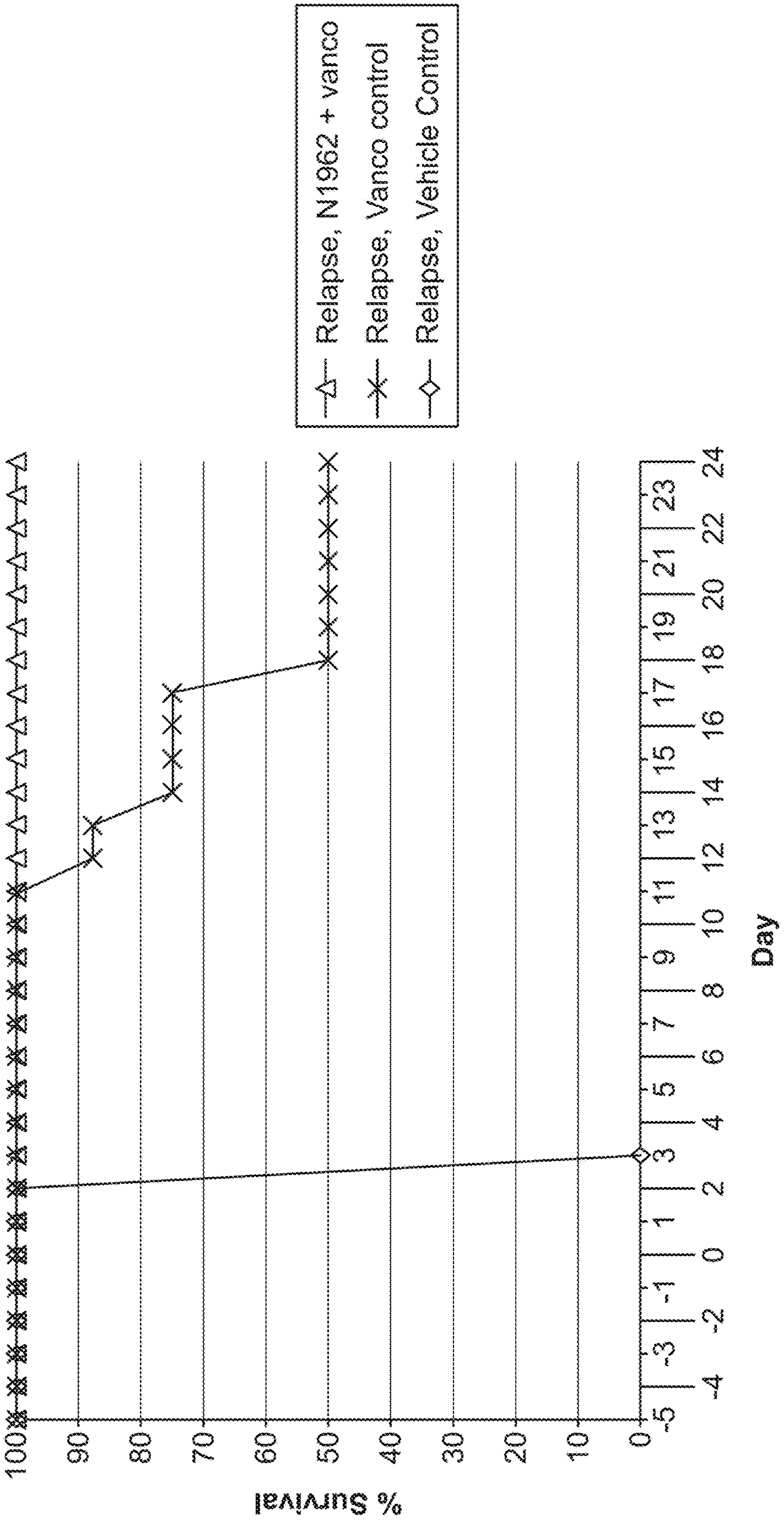
FIG. 5 shows an in vivo hamster *Clostridium difficile* relapse prevention model to validate efficacy of network ecology bacterial composition, according to an embodiment of the invention.

Example 20. In Vivo Validation of Network Ecology Bacterial Composition Efficacy in Prophylactic and Relapse Prevention Hamster Model Previous studies with hamsters using toxigenic and non-toxigenic strains of *C. difficile* demonstrated the utility of the hamster model in examining relapse post antibiotic treatment and the effects of prophylaxis treatments with cecal flora in *C. difficile* infection (Wilson et al., 1981. Infect Immun 34:626-628), Wilson et al., 1983. J Infect Dis 147:733, Borriello et al., 1985. J Med Microbiol 19:339-350) and more broadly in gastrointestinal infectious disease. Accordingly, to demonstrate prophylactic use of bacterial compositions comprising specific operational taxonomic units to ameliorate *C. difficile* infection, the following hamster model was used. Clindamycin (10 mg/kg s.c.) was administered to animals on day −5, the test composition or control was administered on day −3, and *C. difficile* challenge occurred on day 0. In the positive control arm, vancomycin was then administered on days 1-5 (and vehicle control was delivered on day −3). Stool were collected on days −5, −4, −1, 1, 3, 5, 7, 9 and fecal samples were assessed for pathogen carriage and reduction by microbiological methods. 16S sequencing approaches or other methods could also be utilized by one skilled in the art. Mortality was assessed multiple times per day through 21 days post *C. difficile* challenge. The percentage survival curves showed that a bacterial composition (N1962) comprised of OTUs that were shown to be inhibitory against *C. difficile* in an in vitro inhibition assay (see above examples) better protected the hamsters compared to the vancomycin control, and vehicle control (FIG. 5).

These data demonstrate the efficacy of a composition in vivo, as well as the utility of using an in vitro inhibition method as described herein to predict compositions that have activity in vivo.

Example 21. Method of Preparing a Bacterial Composition for Administration to a Subject Two or more strains that comprise the bacterial composition are independently cultured and mixed together before administration. Both strains are independently be grown at 37° C., pH 7, in a GMM or other animal-products-free medium, pre-reduced with 1 g/L cysteine HCl. After each strain reaches a sufficient biomass, it is preserved for banking by adding 15% glycerol and then frozen at −80° C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

A bacterial composition can be derived by selectively fractionating the desired bacterial OTUs from a raw material such as but not limited to stool. As an example, a 10% w/v suspension of human stool material in PBS was prepared that was filtered, centrifuged at low speed, and then the supernatant containing spores was mixed with absolute ethanol in a 1:1 ratio and vortexed to mix. The suspension was incubated at room temperature for 1 hour. After incubation the suspension was centrifuged at high speed to concentrate spores into a pellet containing a purified spore-containing preparation. The supernatant was discarded and the pellet resuspended in an equal mass of glycerol, and the purified spore preparation was placed into capsules and stored at −80° C.; this preparation is referred to as an ethanol-treated spore population.

Example 22. Method of Treating a Subject with Recurrent *C. difficile* Infection with a Bacterial Composition In one example, a subject has suffered from recurrent bouts of *C. difficile*. In the most recent acute phase of the illness, the subject is treated with an antibiotic sufficient to ameliorate the symptoms of the illness. To prevent another relapse of *C. difficile* infection, a bacterial composition described herein is administered to the subject. For example, the subject is administered one of the present bacterial compositions at a dose in the range of $1e10^7$ to $1e10^{12}$ in, e.g., a lyophilized form, in one or more gelatin capsules (e.g., 2, 3, 4, 5, 10, 15 or more capsules) containing 10 mg of lyophilized bacteria and stabilizing components. The capsule is administered by mouth and the subject resumes a normal diet after 4, 8, 12, or 24 hours. In another embodiment, the subject may take the capsule by mouth before, during, or immediately after a meal. In a further embodiment, the subject takes the dose daily for a specified period of time.

Stool is collected from the subject before and after treatment. In one embodiment stool is collected at 1 day, 3 days, 1 week, and 1 month after administration. The presence of *C. difficile* is found in the stool before administration of the bacterial composition, but stool collections after administration show a reduction in the level of *C. difficile* in the stool (for example, at least 50% less, 60%, 70%, 80%, 90%, or 95%) to no detectable levels of *C. difficile*, as measured by qPCR and if appropriate, compared to a healthy reference subject microbiome, as described above. Typically, the quantitation is performed using material extracted from the same amounts of starting material, e.g., stool. ELISA for toxin protein or traditional microbiological identification techniques may also be used. Effective treatment is defined as a reduction in the amount of *C. difficile* present after treatment.

In some cases, effective treatment, i.e., a positive response to treatment with a composition disclosed herein is defined as absence of diarrhea, which itself is defined as 3 or more loose or watery stools per day for at least 2 consecutive days or 8 or more loose or watery stools in 48 hours, or persisting diarrhea (due to other causes) with repeating (three times) negative stool tests for toxins of *C. difficile.*

Treatment failure is defined as persisting diarrhea with a positive *C. difficile* toxin stool test or no reduction in levels of *C. difficile*, as measured by qPCR sequencing. ELISA or traditional microbiological identification techniques may also be used.

In some cases, effective treatment is determined by the lack of recurrence of signs or symptoms of *C. difficile* infection within, e.g., 2 weeks, 3 weeks, 4 weeks, 5 weeks, 10 weeks, 12 weeks, 16 weeks, 20 weeks, or 24 weeks after the treatment.

Example 23. Treatment of Subjects with *Clostridium difficile* Associated Diarrheal Disease with a Bacterial Composition Microbial Population Engraftment, Augmentation, and Reduction of Pathogen Carriage in Patients Treated with Spore Compositions Complementary genomic and microbiological methods were used to characterize the composition of the microbiota of 15 subjects with recurrent *C. difficile* associated disease (CDAD) that were treated with a bacterial composition. The microbiome of these subjects was characterized pretreatment and initially up to 4 weeks post-treatment and further to 24 weeks. An additional 15 subjects were treated and data for those subjects was collected to at least 8 weeks post-treatment and up to 24 weeks post-treatment. The bacterial compositions used for treatment were comprised of spore forming bacteria and constitute a microbial spore ecology derived from healthy human stool. Methods for preparing such compositions can be found in PCT/US2014/014715.

Figure 6:
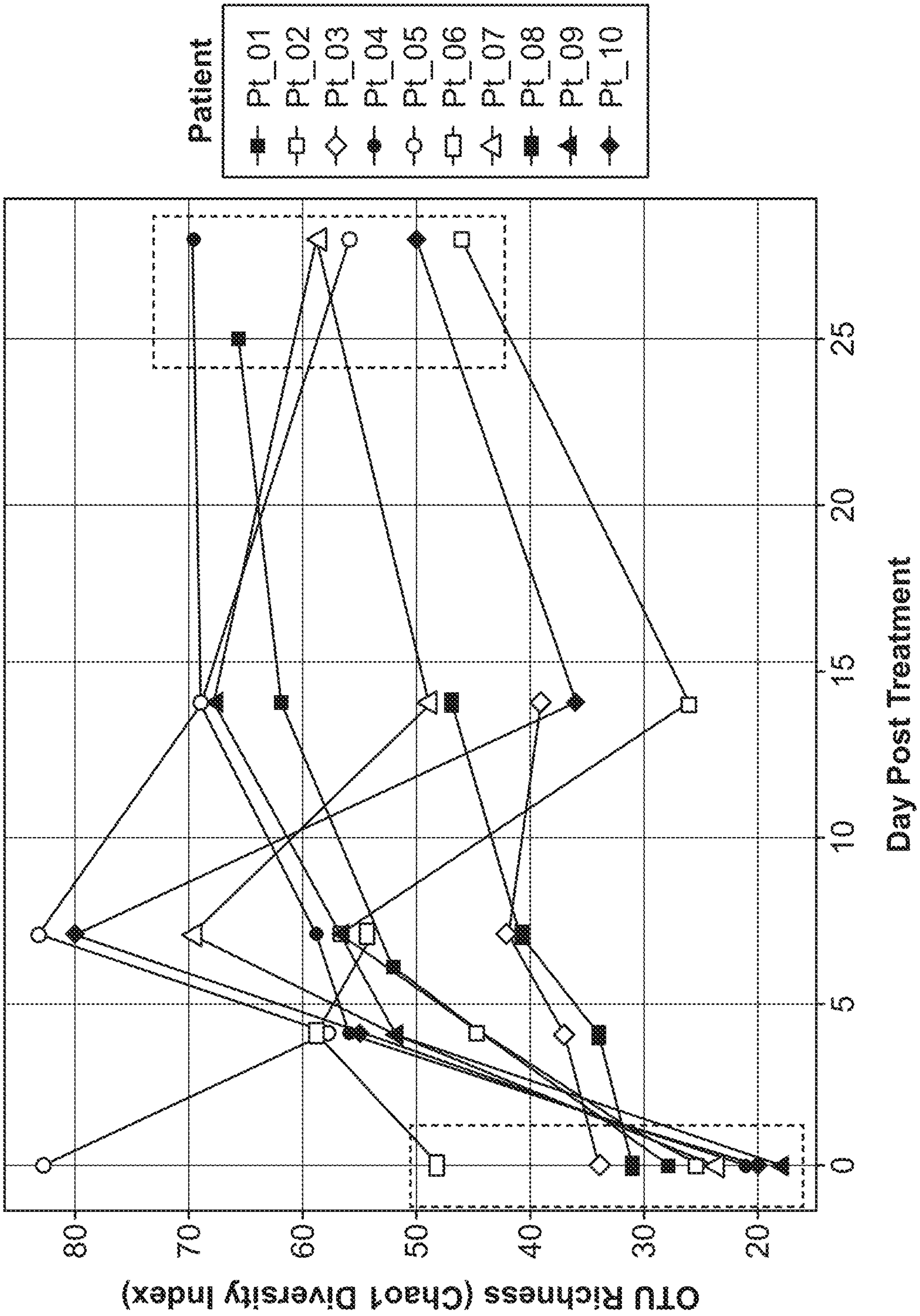
FIG. 6 shows the increase in the total microbial diversity (measured using the Chao-1 diversity index) in the gut of human subjects with recurrent *Clostridium difficile* associated disease pretreatment and post-treatment with a microbial spore ecology.
Figure 7:
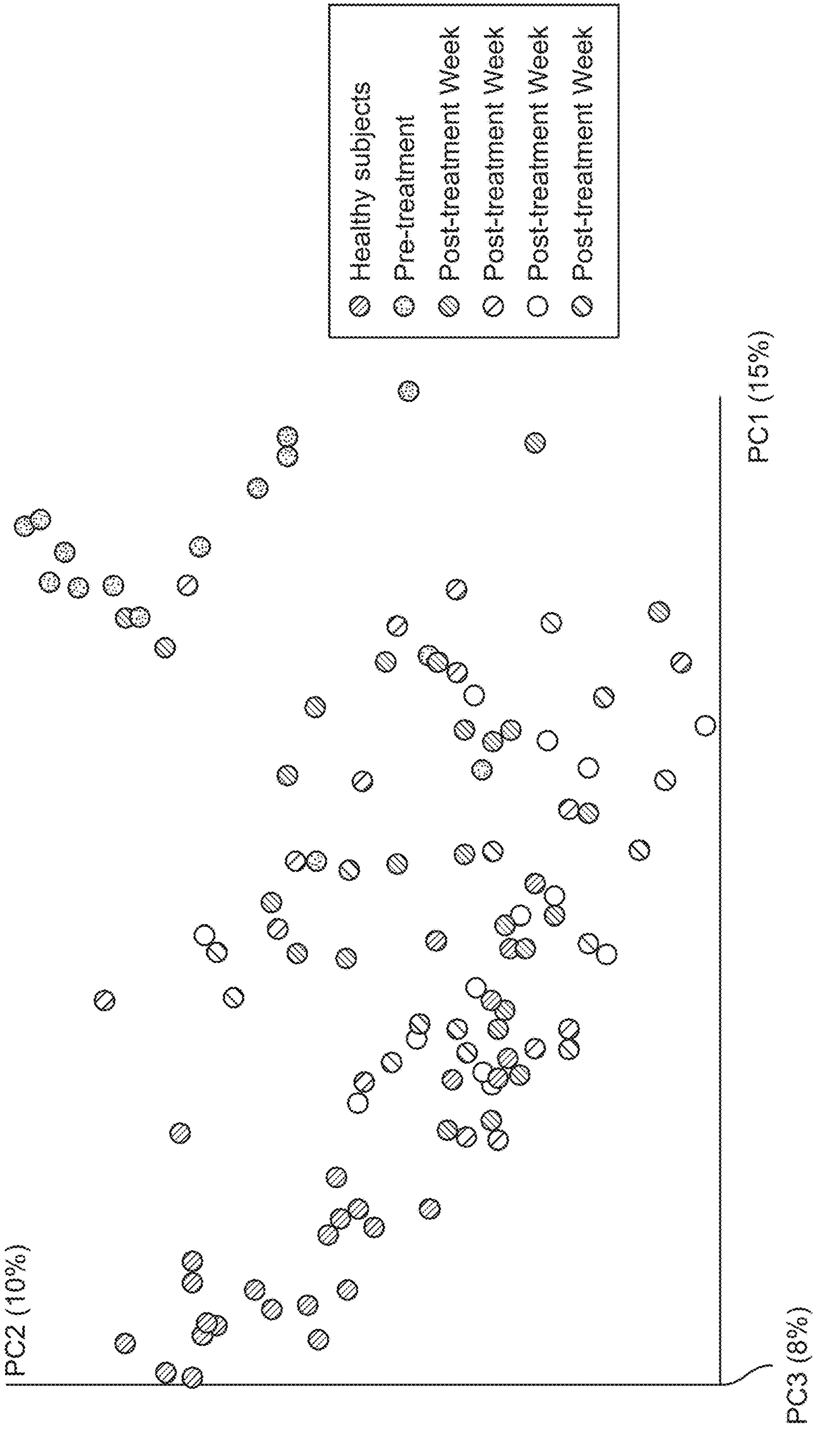
FIG. 7 shows the compositional change in the microbiome (measured using the Bray-Curtis PCoA metric) in the gut of human subjects with recurrent *Clostridium difficile* associated disease pretreatment and post-treatment with a microbial spore ecology.

Non-limiting exemplary OTUs and clades of the spore forming microbes identified in the initial compositions are provided in Table 11. OTUs and clades in the spore ecology treatment were observed in 1 to 15 of the initial 15 subjects treated (Table 11) and in subsequently treated subjects. Treatment of the subjects with the microbial spore ecology resolved *C. difficile* associated disease (CDAD) in all subjects treated. In addition, treatment with the microbial spore composition led to the reduction or removal of Gram(−) and Gram(+) pathobionts including but not limited to pathobionts with multi-drug resistance such as but not limited to vancomycin-resistant Enterococci (VRE) and carbapenem- or imipenem resistant bacteria. Additionally, treatment led to an increase in the total microbial diversity of the subjects gut microbiome (FIG. 6) and the resulting microbial community that established as the result of treatment with the microbial spore ecology was different from the microbiome pretreatment and more closely represented that of a healthy individual than that of an individual with CDAD (FIG. 7).

Using novel computational approaches, applicants delineated bacterial OTUs associated with engraftment and ecological augmentation and establishment of a more diverse microbial ecology in patients treated with an ethanol-treated spore preparation (Table 11). OTUs that comprise an augmented ecology are those below the limit of detection in the patient prior to treatment and/or exist at extremely low frequencies such that they do not comprise a significant fraction of the total microbial carriage and are not detectable by genomic and/or microbiological assay methods in the bacterial composition. OTUs that are members of the engrafting and augmented ecologies were identified by characterizing the OTUs that increase in their relative abundance post treatment and that respectively are: (i) present in the ethanol-treated spore preparation and not detectable in the patient pretreatment (engrafting OTUs), or (ii) absent in the ethanol-treated spore preparation, but increase in their relative abundance in the patient through time post treatment with the preparation due to the formation of favorable growth conditions by the treatment (augmenting OTUs). Augmenting OTUs can grow from low frequency reservoirs in the patient, or can be introduced from exogenous sources such as diet.

Notably, 16S sequences of isolates of a given OTU are phylogenetically placed within their respective clades despite that the actual taxonomic assignment of species and genus may suggest they are taxonomically distinct from other members of the clades in which they fall. Discrepancies between taxonomic names given to an OTU is based on microbiological characteristics versus genetic sequencing are known to exist from the literature. The OTUs footnoted in this table are known to be discrepant between the different methods for assigning a taxonomic name.

Rational Design of Therapeutic Compositions from Core Ecologies

To define the Core Ecology underlying the remarkable clinical efficacy of the microbial spore bacterial the following analysis was carried out. The OTU composition of the microbial spore ecology was determined by 16S-V4 rDNA sequencing and computational assignment of OTUs per Example 13. A requirement to detect at least ten sequence reads in the microbial spore ecology was set as a conservative threshold to define only OTUs that were highly unlikely to arise from errors during amplification or sequencing. Methods routinely employed by those familiar to the art of genomic-based microbiome characterization use a read relative abundance threshold of 0.005% (see e.g., Bokulich et al. 2013. Quality-filtering vastly improves diversity estimates from Illumina amplicon sequencing. Nature Methods 10: 57-59), which would equate to 22 reads given the sequencing depth obtained for the samples analyzed in this example, as cut-off which is substantially lower than the ≥10 reads used in this analysis. All taxonomic and clade assignments were made for each OTU as described in Example 13. The resulting list of OTUs, clade assignments, and frequency of detection in the spore preparations are shown in Table 11.

In one embodiment, OTUs that comprise a "core" bacterial composition of a microbial spore ecology, augmented ecology or engrafted ecology can be defined by the percentage of total subjects in which they are observed; the greater this percentage the more likely they are to be part of a core ecology responsible for catalyzing a shift away from a dysbiotic ecology. In one embodiment, therapeutic bacterial compositions are rationally designed by identifying the OTUs that occur in the greatest number of subjects evaluated. In one embodiment OTUs that occur in 100% of subjects define a therapeutic bacterial composition. In other embodiments, OTUs that are defined to occur in ≥90%, ≥80%, ≥70%, ≥60%, or ≥50% of the subjects evaluated comprise the therapeutic bacterial composition. In a further embodiment, OTUs that are in either 100%, ≥90%, ≥80%, 270%, ≥60%, or 50% are further refined to rationally design a therapeutic bacterial composition using phylogenetic parameters or other features such as but not limited to their capacity to metabolize secondary bile acids, illicit TH17 immune signaling, or produce short-chain fatty acids.

In an additional embodiment, the dominant OTUs in an ecology can be identified using several methods including but not limited to defining the OTUs that have the greatest relative abundance in either the augmented or engrafted ecologies and defining a total relative abundance threshold. As example, the dominant OTUs in the augmented ecology of Patient-1 were identified by defining the OTUs with the greatest relative abundance, which together comprise 60% of the microbial carriage in this patient's augmented ecology by day 25 post-treatment.

In a further embodiment, an OTU is assigned to be a member of the Core Ecology of the bacterial composition, that OTU must be shown to engraft in a patient. Engraftment is important for at least two reasons. First, engraftment is believed to be a sine qua non of the mechanism to reshape the microbiome and eliminate *C. difficile* colonization. OTUs that engraft with higher frequency are highly likely to be a component of the Core Ecology of the spore preparation or broadly speaking a set bacterial composition. Second, OTUs detected by sequencing a bacterial composition may include non-viable cells or other contaminant DNA molecules not associated with the composition. The requirement that an OTU must be shown to engraft in the patient eliminates OTUs that represent non-viable cells or contaminating sequences. OTUs that are present in a large percentage of the bacterial composition, e.g., ethanol spore preparations analyzed and that engraft in a large number of patients represent a subset of the Core Ecology that are highly likely to catalyze the shift from a dysbiotic disease ecology to a healthy microbiome. OTUs from which to define such therapeutic bacterial compositions derived of OTUs that engraft are denoted in Table 11.

A third lens was applied to further refine discoveries into the Core Ecology of the bacterial composition (e.g., microbial spore ecology). Computational-based, network analysis has enabled the description of microbial ecologies that are present in the microbiota of a broad population of healthy individuals. These network ecologies are comprised of multiple OTUs, some of which are defined as Keystone OTUs. Keystone OTUs are computationally defined OTUs that occur in a large percentage of computed networks and meet the networks in which they occur are highly prevalent in the population of subjects evaluated. Keystone OTUs form a foundation to the microbially ecologies in that they are found and as such are central to the function of network ecologies in healthy subjects. Keystone OTUs associated with microbial ecologies associated with healthy subjects are often are missing or exist at reduced levels in subjects with disease. Keystone OTUs may exist in low, moderate, or high abundance in subjects.

There are several important findings from these data. A relatively small number of species, 11 in total, are detected in all of the spore preparations from 6 donors and 10 donations. This is surprising because the HMP database (www.hmpdacc.org) describes the enormous variability of commensal species across healthy individuals. The presence of a small number of consistent OTUs lends support to the concept of a Core Ecology and Backbone Networks. The engraftment data further supports this conclusion.

In another embodiment, three factors—prevalence in the bacterial composition such as but not limited to a spore preparation, frequency of engraftment, and designation as a Keystone OTUs—enabled the creation of a "Core Ecology Score" (CES) to rank individual OTUs. CES was defined as follows:

- 40% weighting for presence of OTU in spore preparation
  - multiplier of 1 for presence in 1-3 spore preparations
  - multiplier of 2.5 for presence in 4-8 spore preparations
  - multiplier of 5 for presences in ≥9 spore preparations
- 40% weighting for engraftment in a patient
  - multiplier of 1 for engraftment in 1-4 patients
  - multiplier of 2.5 for engraftment in 5-6 patients
  - multiplier of 5 for engraftment in ≥7 patients
- 20% weighting to Keystone OTUs
  - multiplier of 1 for a Keystone OTU
  - multiplier of 0 for a non-Keystone OTU Using this guide, the CES has a maximum possible score of 5 and a minimum possible score of 0.8. As an example, an OTU found in 8 of the 10 bacterial composition such as but not limited to a spore preparations that engrafted in 3 patients and was a Keystone OTU would be assigned the follow CES:

$$CES=(0.4\times2.5)+(0.4\times1)+(0.2\times1)=1.6$$

Table 11 provides a rank of OTUs by CES. Bacterial compositions rationally designed using a CES score are highly likely to catalyze the shift from a dysbiotic disease ecology to a healthy microbiome. In additional embodiments, the CES score can be combined with other factors to refine the rational design of a therapeutic bacterial composition. Such factors include but are not limited to: using phylogenetic parameters or other features such as but not limited to their capacity to metabolize secondary bile acids, illicit TH17 immune signaling, or produce short-chain fatty acids. In an additional embodiment, refinement can be done by identifying the OTUs that have the greatest relative abundance in either the augmented or engrafted ecologies and defining a total relative abundance threshold.

The number of organisms in the human gastrointestinal tract, as well as the diversity between healthy individuals, is indicative of the functional redundancy of a healthy gut microbiome ecology (see The Human Microbiome Consortia. 2012. Structure, function and diversity of the healthy human microbiome. Nature 486: 207-214). This redundancy makes it highly likely that subsets of the Core Ecology describe therapeutically beneficial components of the bacterial composition such as but not limited to an ethanol-treated spore preparation and that such subsets may themselves be useful compositions for populating the GI tract and for the treatment of *C. difficile* infection given the ecologies functional characteristics. Using the CES, as well as other key metrics as defined above, individual OTUs can be prioritized for evaluation as an efficacious subset of the Core Ecology.

Another aspect of functional redundancy is that evolutionarily related organisms (i.e., those close to one another on the phylogenetic tree, e.g., those grouped into a single clade) will also be effective substitutes in the Core Ecology or a subset thereof for treating *C. difficile.*

To one skilled in the art, the selection of appropriate OTU subsets for testing in vitro or in vivo is straightforward. Subsets may be selected by picking any 2, 3, 4, 5, 6, 7, 8, 9, 10, or more than 10 OTUs from Table 11, typically selecting those with higher CES. In addition, using the clade relationships defined in Example 13 above and Table 11, related OTUs can be selected as substitutes for OTUs with acceptable CES values. These organisms can be cultured anaerobically in vitro using the appropriate media, and then combined in a desired ratio. A typical experiment in the mouse *C. difficile* model utilizes at least 104 and preferably at least 105, 106, 107, 108, 109 or more than 109 colony forming units of a each microbe in the composition. In some compositions, organisms are combined in unequal ratios, for example, due to variations in culture yields, e.g., 1:10, 1:100, 1:1,000, 1:10,000, 1:100,000, or greater than 1:100,000. What is important in these compositions is that each strain be provided in a minimum amount so that the strain's contribution to the efficacy of the Core Ecology subset can be therapeutically effective, and in some cases, measured. Using the principles and instructions described here, one of skill in the art can make clade-based substitutions to test the efficacy of subsets of the Core Ecology. Table 11 and Table 2 describe the clades for each OTU from which such substitutions can be derived.

Rational Design of Therapeutic Compositions by Integration of In Vitro and Clinical Microbiome Data In one embodiment, efficacious subsets of the treatment microbial spore ecology as well as subsets of the microbial ecology of the subject post-treatment are defined by rationally interrogating and the composition of these ecologies with respect to compositions comprising 2, 3, 4, 5, 6, 7, 8, 9, 10, or some larger number of OTUs. In one embodiment, the bacterial compositions that have demonstrated efficacy in an in vitro pathogen inhibition assay and that are additionally identified as constituents of the ecology of the treatment itself and/or the microbial ecology of 100%, ≥90%, ≥80%, ≥70%, ≥60%, or ≥50% of the subject's can by an individual with ordinary skill in the art be prioritize for functional screening. Functional screens can include but are not limited to in vivo screens using various pathogen or non-pathogen models (as example, murine models, hamster models, primate models, or human). Table 12 provides bacterial compositions that exhibited inhibition against *C. difficile* as measured by a mean log inhibition greater than the 99% confidence interval (C.I) of the null hypothesis (see Example 6, ++++) and that are identified in at least one spore ecology treatment or subject post-treatment. In another embodiment compositions found in the 95%, 90%, or 80% confidence intervals (C.I.) and occurring in the treatment and post-treatment ecologies are selected. In other embodiments, bacterial compositions are selected for screening for therapeutic potential by selecting OTUs that occur in the treatment or post-treatment ecologies and the measured growth inhibition of the composition is ranked ≥ the 75th percentile of all growth inhibition scores. In other embodiments, compositions ranked ≥ the 50th, 60th, 70th, 80th, 90th, 95th, or 99th percentiles are selected. In another embodiment, compositions demonstrated to have synergistic inhibition are selected (see Example 7). In yet a further embodiment, compositions selected to screen for efficacy in in vivo models are selected using a combination of growth inhibition metrics. As non-limiting example: (i) compositions are first selected based on their log inhibition being greater than the 99% confidence interval (C.I.) of the null hypothesis, (ii) then this subset of compositions further selected to represent those that are ranked ≥ the 75th percentile in the distribution of all inhibition scores, (iii) this subset is then further selected based on compositions that demonstrate synergistic inhibition. In some embodiments, different confidence intervals (C.I.) and percentiles are used to subset and rationally select the compositions. In yet another embodiment, bacterial compositions are further rationally defined for their therapeutic potential using phylogenetic criteria, such as but not limited to, the presence of particular phylogenetic clade, or other features such as but not limited to their capacity to metabolize secondary bile acids, illicit TH17 immune signaling, or produce short-chain fatty acids.

In a related embodiment, all unique bacterial compositions that can be delineated in silico using the OTUs that occur in 100% of the dose spore ecologies are defined; exemplary bacterial compositions are denoted in Table 13. In other embodiments, compositions are derived form OTUs that occur in ≥90%, ≥80%, ≥70%, ≥60%, or ≥50% of the dose spore ecology or the subject's post-treatment ecologies. One with ordinary skill in the art can interrogate the resulting bacterial compositions and using various metrics including, but not limited to the percentage of spore formers, the presence of keystone OTUs, phylogenetic composition, or the OTUs' ability to metabolize secondary bile acids or the ability to produce short-chain fatty acids to rationally define bacterial compositions with suspected efficacy and suitability for further screening.

Example 24. Computational Analysis of Administered Spore Ecology Dose Compositions, and Augmentation and Engraftment Following Administration of Spore Ecology Doses The clinical trial described in Example 23 enrolled 15 additional subjects. Further analyses were carried out on information combining data from all subjects responding to treatment in the trial (29 of 30 subjects). The treatment was with a complex formulation of microbes derived from human stool. Analyses of these results are provided in Tables 14-21. Table 22 is provided for convenience, and lists alternative names for certain organisms. Typically, the presence of an OTU is made using a method known in the art, for example, using qPCR under conditions known in the art and described herein.

The set of doses used in the trial is the collection of doses that was provided to at least one patient. Thus, a dose is implicitly a member of the set of doses. Consequently, the set of all OTUs in doses is defined as the unique set of OTUs such that each OTU is present in at least one dose.

As described herein, an engrafting OTU is an OTU that is not detectable in a patient, e.g., in their stool, pre-treatment, but is present in the composition delivered to the subject and is detected in the subject, (e.g., in the subject's stool) in at least one post-treatment sample from the subject. The set of all engrafting OTUs is defined as the unique set of engrafting OTUs found in at least one subject. An augmenting OTU is an OTU detected in a subject that is not engrafting and has an abundance ten times greater than the pre-treatment abundance at some post-treatment time point. The set of all augmenting OTUs is the unique set of augmenting OTUs found in at least one subject. The set of all augmenting and engrafting OTUs is defined as the unique set of OTUs that either augment or engraft in at least one subject.

The set of all unique ternary combinations can be generated from the experimentally derived set of OTUs by considering the all combinations of OTUs such that 1) each OTU of the ternary is different and 2) the three OTUs were not used together previously. A computer program can be used to generate such combinations.

Table 14 is generated from the set of all augmenting and engrafting OTUs and provides the OTUs that either were found to engraft or augment in at least one subject after they were treated with the composition. Each listed ternary combination is either in all doses provided to subjects or were detected together in all patients for at least one post-treatment time point. Typically, a useful composition includes at least one of the ternary compositions. In some embodiments, all three members of the ternary composition either engraft or augment in at least, e.g., 68%, 70%, 71%, 75%, 79%, 86%, 89%, 93%, or 100% of subjects. Because all subjects analyzed responded to treatment, the ternaries listed in the Table are useful in compositions for treatment of a dysbiosis.

Table 15 provides the list of unique ternary combinations of OTUs that were present in at least 95% of doses (rounding to the nearest integer) and that engrafted in at least one subject. Note that ternary combinations that were present in 100% of doses are listed in Table 14. Compositions that include a ternary combination are useful in compositions for treating a dysbiosis.

Table 16 provides the set of all unique ternary combinations of augmenting OTUs such that each ternary combination was detected in at least 75% of the subjects at a post-treatment time point.

Table 17 provides the set of all unique ternary combinations that were present in at least 75% of doses and for which the subject receiving the dose containing the ternary combination had Clostridiales sp. SM4/1 present as either an engrafting or augmenting OTU. Accordingly, in some embodiments, a composition consisting of, consisting essentially of, or comprising a ternary combination selected from Table 17 is useful for increasing Clostridiales sp. SM4/1 in a subject.

Table 18 provides the set of all unique ternary combinations generated from the set of all OTUs in doses such that each ternary is present at least 75% of the doses and for which the subject receiving the dose containing the ternary combination had Clostridiales sp. SSC/2 present as either an engrafting or augmenting OTU after treatment. Accordingly, in some embodiments, a composition consisting of, consisting essentially of, or comprising a ternary combination selected from Table 18 is useful for increasing Clostridiales sp. SSC/2 in a subject.

Table 19 provides the set of all unique ternary combinations generated from the set of all OTUs present in doses such that each ternary is present at least 75% of the doses and for which the subject to whom the doses containing the ternary combination was administered had *Clostridium* sp. NML 04A032 present as either an engrafting or augmenting OTU after treatment. Accordingly, in some embodiments, a composition consisting of, consisting essentially of, or comprising a ternary combination selected from Table 19 is useful for increasing *Clostridium* sp. NML 04A032 in a subject.

Table 20 provides the set of all unique ternary combinations generated from the set of all OTUs in doses such that the ternary is present at least 75% of the doses and for which the subject to whom the dose containing the ternary was administered had *Clostridium* sp. NML 04A032, *Ruminococcus lactaris*, and *Ruminococcus torques* present as either an engrafting or augmenting OTUs. Accordingly, in some embodiments, a composition consisting of, consisting essentially of, or comprising a ternary combination selected from Table 20 is useful for increasing *Clostridium* sp. NML 04A032, *Ruminococcus lactaris*, and *Ruminococcus torques* in a subject.

Table 21 shows the set of all unique ternary combinations generated from the set of all OTUs in doses such that each ternary is present at least 75% of the doses and for which the subject to whom the dose containing the ternary combination was administered has *Eubacterium rectale, Faecalibacterium prausnitzii*, Oscillibacter sp. G2, *Ruminococcus lactaris*, and *Ruminococcus torques* present as either an engrafting or augmenting OTU. Accordingly, in some embodiments, a composition consisting of, consisting essentially of, or comprising a ternary combination selected from Table 21 is useful for increasing *Eubacterium rectale, Faecalibacterium prausnitzii*, Oscillibacter sp. G2, *Ruminococcus lactaris*, and *Ruminococcus torques* in a subject.

Other embodiments will be apparent to those skilled in the art from consideration of the specification and practice of the embodiments. Consider the specification and examples as exemplary only, with a true scope and spirit being indicated by the following claims.

TABLES

TABLE 1

| OTU | SEQ ID Number | Public DB Accession | Phylogenetic Clade | Spore Former | Pathogen Status |
|---|---|---|---|---|---|
| *Corynebacterium coyleae* | 697 | X96497 | clade_100 | N | N |
| *Corynebacterium mucifaciens* | 711 | NR_026396 | clade_100 | N | N |
| *Corynebacterium ureicelerivorans* | 733 | AM397636 | clade_100 | N | N |
| *Corynebacterium appendicis* | 684 | NR_028951 | clade_102 | N | N |
| *Corynebacterium genitalium* | 698 | ACLJ01000031 | clade_102 | N | N |
| *Corynebacterium glaucum* | 699 | NR_028971 | clade_102 | N | N |
| *Corynebacterium imitans* | 703 | AF537597 | clade_102 | N | N |
| *Corynebacterium riegelii* | 719 | EU848548 | clade_102 | N | N |
| *Corynebacterium* sp. L_2012475 | 723 | HE575405 | clade_102 | N | N |
| *Corynebacterium* sp. NML 93_0481 | 724 | GU238409 | clade_102 | N | N |
| *Corynebacterium sundsvallense* | 728 | Y09655 | clade_102 | N | N |
| *Corynebacterium tuscaniae* | 730 | AY677186 | clade_102 | N | N |
| *Prevotella maculosa* | 1504 | AGEK01000035 | clade_104 | N | N |
| *Prevotella oris* | 1513 | ADDV01000091 | clade_104 | N | N |
| *Prevotella salivae* | 1517 | AB108826 | clade_104 | N | N |
| *Prevotella* sp. ICM55 | 1521 | HQ616399 | clade_104 | N | N |
| *Prevotella* sp. oral clone AA020 | 1528 | AY005057 | clade_104 | N | N |
| *Prevotella* sp. oral clone GI032 | 1538 | AY349396 | clade_104 | N | N |
| *Prevotella* sp. oral taxon G70 | 1558 | GU432179 | clade_104 | N | N |
| *Prevotella corporis* | 1491 | L16465 | clade_105 | N | N |
| *Bacteroides* sp. 4_1_36 | 312 | ACTC01000133 | clade_110 | N | N |
| *Bacteroides* sp. AR20 | 315 | AF139524 | clade_110 | N | N |
| *Bacteroides* sp. D20 | 319 | ACPT01000052 | clade_110 | N | N |
| *Bacteroides* sp. F_4 | 322 | AB470322 | clade_110 | N | N |
| *Bacteroides uniformis* | 329 | AB050110 | clade_110 | N | N |
| *Prevotella nanceiensis* | 1510 | JN867228 | clade_127 | N | N |
| *Prevotella* sp. oral taxon 299 | 1548 | ACWZ01000026 | clade_127 | N | N |
| *Prevotella bergensis* | 1485 | ACKS01000100 | clade_128 | N | N |
| *Prevotella buccalis* | 1489 | JN867261 | clade_129 | N | N |
| *Prevotella timonensis* | 1564 | ADEF01000012 | clade_129 | N | N |
| *Prevotella oralis* | 1512 | AEPE01000021 | clade_130 | N | N |
| *Prevotella* sp. SEQ072 | 1525 | JN867238 | clade_130 | N | N |
| *Leuconostoc carnosum* | 1177 | NR_040811 | clade_135 | N | N |
| *Leuconostoc gasicomitatum* | 1179 | FN822744 | clade_135 | N | N |
| *Leuconostoc inhae* | 1180 | NR_025204 | clade_135 | N | N |
| *Leuconostoc kimchii* | 1181 | NR_075014 | clade_135 | N | N |
| *Edwardsiella tarda* | 777 | CP002154 | clade_139 | N | N |
| *Photorhabdus asymbiotica* | 1466 | Z76752 | clade_139 | N | N |
| *Psychrobacter arcticus* | 1607 | CP000082 | clade_141 | N | N |
| *Psychrobacter cibarius* | 1608 | HQ698586 | clade_141 | N | N |
| *Psychrobacter cryohalolentis* | 1609 | CP000323 | clade_141 | N | N |
| *Psychrobacter faecalis* | 1610 | HQ698566 | clade_141 | N | N |
| *Psychrobacter nivimaris* | 1611 | HQ698587 | clade_141 | N | N |
| *Psychrobacter pulmonis* | 1612 | HQ698582 | clade_141 | N | N |
| *Pseudomonas aeruginosa* | 1592 | AABQ07000001 | clade_154 | N | N |
| *Pseudomonas* sp. 2_1_26 | 1600 | ACWU01000257 | clade_154 | N | N |
| *Corynebacterium confusum* | 691 | Y15886 | clade_158 | N | N |
| *Corynebacterium propinquum* | 712 | NR_037038 | clade_158 | N | N |
| *Corynebacterium pseudodiphtheriticum* | 713 | X84258 | clade_158 | N | N |
| *Bartonella bacilliformis* | 338 | NC_008783 | clade_159 | N | N |
| *Bartonella grahamii* | 339 | CP001562 | clade_159 | N | N |
| *Bartonella henselae* | 340 | NC_005956 | clade_159 | N | N |
| *Bartonella quintana* | 341 | BX897700 | clade_159 | N | N |
| *Bartonella tamiae* | 342 | EF672728 | clade_159 | N | N |
| *Bartonella washoensis* | 343 | FJ719017 | clade_159 | N | N |
| *Brucella abortus* | 430 | ACBJ01000075 | clade_159 | N | Category-B |
| *Brucella canis* | 431 | NR_044652 | clade_159 | N | Category-B |
| *Brucella ceti* | 432 | ACJD01000006 | clade_159 | N | Category-B |
| *Brucella melitensis* | 433 | AE009462 | clade_159 | N | Category-B |
| *Brucella microti* | 434 | NR_042549 | clade_159 | N | Category-B |
| *Brucella ovis* | 435 | NC_009504 | clade_159 | N | Category-B |
| *Brucella* sp. 83_13 | 436 | ACBQ01000040 | clade_159 | N | Category-B |
| *Brucella* sp. BO1 | 437 | EU053207 | clade_159 | N | Category-B |
| *Brucella suis* | 438 | ACBK01000034 | clade_159 | N | Category-B |
| *Ochrobactrum anthropi* | 1360 | NC_009667 | clade_159 | N | N |
| *Ochrobactrum intermedium* | 1361 | ACQA01000001 | clade_159 | N | N |
| *Ochrobactrum pseudintermedium* | 1362 | DQ365921 | clade_159 | N | N |
| *Prevotella* genomosp. C2 | 1496 | AY278625 | clade_164 | N | N |
| *Prevotella multisaccharivorax* | 1509 | AFJE01000016 | clade_164 | N | N |
| *Prevotella* sp. oral clone IDR_CEC_0055 | 1543 | AY550997 | clade_164 | N | N |
| *Prevotella* sp. oral taxon 292 | 1547 | GQ422735 | clade_164 | N | N |
| *Prevotella* sp. oral taxon 300 | 1549 | GU409549 | clade_164 | N | N |
| *Prevotella marshii* | 1505 | AEEI01000070 | clade_166 | N | N |
| *Prevotella* sp. oral clone IK053 | 1544 | AY349401 | clade_166 | N | N |

TABLE 1-continued

| OTU | SEQ ID Number | Public DB Accession | Phylogenetic Clade | Spore Former | Pathogen Status |
|---|---|---|---|---|---|
| *Prevotella* sp. oral taxon 781 | 1554 | GQ422744 | clade_166 | N | N |
| *Prevotella stercorea* | 1562 | AB244774 | clade_166 | N | N |
| *Prevotella brevis* | 1487 | NR_041954 | clade_167 | N | N |
| *Prevotella ruminicola* | 1516 | CP002006 | clade_167 | N | N |
| *Prevotella* sp. sp24 | 1560 | AB003384 | clade_167 | N | N |
| *Prevotella* sp. sp34 | 1561 | AB003385 | clade_167 | N | N |
| *Prevotella albensis* | 1483 | NR_025300 | clade_168 | N | N |
| *Prevotella copri* | 1490 | ACBX02000014 | clade_168 | N | N |
| *Prevotella oulorum* | 1514 | L16472 | clade_168 | N | N |
| *Prevotella* sp. BI_42 | 1518 | AJ581354 | clade_168 | N | N |
| *Prevotella* sp. oral clone P4PB_83 P2 | 1546 | AY207050 | clade_168 | N | N |
| *Prevotella* sp. oral taxon G60 | 1557 | GU432133 | clade_168 | N | N |
| *Prevotella amnii* | 1484 | AB547670 | clade_169 | N | N |
| *Bacteroides caccae* | 268 | EU136686 | clade_170 | N | N |
| *Bacteroides finegoldii* | 277 | AB222699 | clade_170 | N | N |
| *Bacteroides intestinalis* | 283 | ABJL02000006 | clade_171 | N | N |
| *Bacteroides* sp. XB44A | 326 | AM230649 | clade_171 | N | N |
| Bifidobacteriaceae genomosp. C1 | 345 | AY278612 | clade_172 | N | N |
| *Bifidobacterium adolescentis* | 346 | AAXD02000018 | clade_172 | N | N |
| *Bifidobacterium angulatum* | 347 | ABYS02000004 | clade_172 | N | N |
| *Bifidobacterium animalis* | 348 | CP001606 | clade_172 | N | N |
| *Bifidobacterium breve* | 350 | CP002743 | clade_172 | N | N |
| *Bifidobacterium catenulatum* | 351 | ABXY01000019 | clade_172 | N | N |
| *Bifidobacterium dentium* | 352 | CP001750 | clade_172 | N | OP |
| *Bifidobacterium gallicum* | 353 | ABXB03000004 | clade_172 | N | N |
| *Bifidobacterium infantis* | 354 | AY151398 | clade_172 | N | N |
| *Bifidobacterium kashiwanohense* | 355 | AB491757 | clade_172 | N | N |
| *Bifidobacterium longum* | 356 | ABQQ01000041 | clade_172 | N | N |
| *Bifidobacterium pseudocatenulatum* | 357 | ABXX02000002 | clade_172 | N | N |
| *Bifidobacterium pseudolongum* | 358 | NR_043442 | clade_172 | N | N |
| *Bifidobacterium scardovii* | 359 | AJ307005 | clade_172 | N | N |
| *Bifidobacterium* sp. HM2 | 360 | AB425276 | clade_172 | N | N |
| *Bifidobacterium* sp. HMLN12 | 361 | JF519685 | clade_172 | N | N |
| *Bifidobacterium* sp. M45 | 362 | HM626176 | clade_172 | N | N |
| *Bifidobacterium* sp. MSX5B | 363 | HQ616382 | clade_172 | N | N |
| *Bifidobacterium* sp. TM_7 | 364 | AB218972 | clade_172 | N | N |
| *Bifidobacterium thermophilum* | 365 | DQ340557 | clade_172 | N | N |
| *Leuconostoc citreum* | 1178 | AM157444 | clade_175 | N | N |
| *Leuconostoc lactis* | 1182 | NR_040823 | clade_175 | N | N |
| *Eubacterium saburreum* | 858 | AB525414 | clade_178 | Y | N |
| *Eubacterium* sp. oral clone IR009 | 866 | AY349376 | clade_178 | Y | N |
| Lachnospiraceae bacterium ICM62 | 1061 | HQ616401 | clade_178 | Y | N |
| Lachnospiraceae bacterium MSX33 | 1062 | HQ616384 | clade_178 | Y | N |
| Lachnospiraceae bacterium oral taxon 107 | 1063 | ADDS01000069 | clade_178 | Y | N |
| *Alicyclobacillus acidocaldarius* | 122 | NR_074721 | clade_179 | Y | N |
| *Alicyclobacillus acidoterrestris* | 123 | NR_040844 | clade_179 | N | N |
| *Alicyclobacillus cycloheptanicus* | 125 | NR_024754 | clade_179 | N | N |
| *Acinetobacter baumannii* | 27 | ACYQ01000014 | clade_181 | N | N |
| *Acinetobacter calcoaceticus* | 28 | AM157426 | clade_181 | N | N |
| *Acinetobacter* genomosp. C1 | 29 | AY278636 | clade_181 | N | N |
| *Acinetobacter haemolyticus* | 30 | ADMT01000017 | clade_181 | N | N |
| *Acinetobacter johnsonii* | 31 | ACPL01000162 | clade_181 | N | N |
| *Acinetobacter junii* | 32 | ACPM01000135 | clade_181 | N | N |
| *Acinetobacter lwoffii* | 33 | ACPN01000204 | clade_181 | N | N |
| *Acinetobacter parvus* | 34 | AIEB01000124 | clade_181 | N | N |
| *Acinetobacter schindleri* | 36 | NR_025412 | clade_181 | N | N |
| *Acinetobacter* sp. 56A1 | 37 | GQ178049 | clade_181 | N | N |
| *Acinetobacter* sp. CIP 101934 | 38 | JQ638573 | clade_181 | N | N |
| *Acinetobacter* sp. CIP 102143 | 39 | JQ638578 | clade_181 | N | N |
| *Acinetobacter* sp. M16_22 | 41 | HM366447 | clade_181 | N | N |
| *Acinetobacter* sp. RUH2624 | 42 | ACQF01000094 | clade_181 | N | N |
| *Acinetobacter* sp. SH024 | 43 | ADCH01000068 | clade_181 | N | N |
| *Lactobacillus jensenii* | 1092 | ACQD01000066 | clade_182 | N | N |
| *Alcaligenes faecalis* | 119 | AB680368 | clade_183 | N | N |
| *Alcaligenes* sp. CO14 | 120 | DQ643040 | clade_183 | N | N |
| *Alcaligenes* sp. S3 | 121 | HQ262549 | clade_183 | N | N |
| *Oligella ureolytica* | 1366 | NR_041998 | clade_183 | N | N |
| *Oligella urethralis* | 1367 | NR_041753 | clade_183 | N | N |
| *Eikenella corrodens* | 784 | ACEA01000028 | clade_185 | N | N |
| *Kingella denitrificans* | 1019 | AEWV01000047 | clade_185 | N | N |
| *Kingella* genomosp. P1 oral cone MB2_C20 | 1020 | DQ003616 | clade_185 | N | N |
| *Kingella kingae* | 1021 | AFHS01000073 | clade_185 | N | N |
| *Kingella oralis* | 1022 | ACJW02000005 | clade_185 | N | N |
| *Kingella* sp. oral clone ID059 | 1023 | AY349381 | clade_185 | N | N |
| *Neisseria elongate* | 1330 | ADBF01000003 | clade_185 | N | N |

TABLE 1-continued

| OTU | SEQ ID Number | Public DB Accession | Phylogenetic Clade | Spore Former | Pathogen Status |
|---|---|---|---|---|---|
| *Neisseria* genomosp. P2 oral clone MB5_P15 | 1332 | DQ003630 | clade_185 | N | N |
| *Neisseria* sp. oral clone JC012 | 1345 | AY349388 | clade_185 | N | N |
| *Neisseria* sp. SMC_A9199 | 1342 | FJ763637 | clade_185 | N | N |
| *Simonsiella muelleri* | 1731 | ADCY01000105 | clade_185 | N | N |
| *Corynebacterium glucuronolyticum* | 700 | ABYP01000081 | clade_193 | N | N |
| *Corynebacterium pyruviciproducens* | 716 | FJ185225 | clade_193 | N | N |
| *Rothia aeria* | 1649 | DQ673320 | clade_194 | N | N |
| *Rothia dentocariosa* | 1650 | ADDW01000024 | clade_194 | N | N |
| *Rothia* sp. oral taxon 188 | 1653 | GU470892 | clade_194 | N | N |
| *Corynebacterium accolens* | 681 | ACGD01000048 | clade_195 | N | N |
| *Corynebacterium macginleyi* | 707 | AB359393 | clade_195 | N | N |
| *Corynebacterium pseudogenitalium* | 714 | ABYQ01000237 | clade_195 | N | N |
| *Corynebacterium tuberculostearicum* | 729 | ACVP01000009 | clade_195 | N | N |
| *Lactobacillus casei* | 1074 | CP000423 | clade_198 | N | N |
| *Lactobacillus paracasei* | 1106 | ABQV01000067 | clade_198 | N | N |
| *Lactobacillus zeae* | 1143 | NR_037122 | clade_198 | N | N |
| *Prevotella dentalis* | 1492 | AB547678 | clade_205 | N | N |
| *Prevotella* sp. oral clone ASCG10 | 1529 | AY923148 | clade_206 | N | N |
| *Prevotella* sp. oral clone HF050 | 1541 | AY349399 | clade_206 | N | N |
| *Prevotella* sp. oral clone ID019 | 1542 | AY349400 | clade_206 | N | N |
| *Prevotella* sp. oral clone IK062 | 1545 | AY349402 | clade_206 | N | N |
| *Prevotella* genomosp. P9 oral clone MB7_G16 | 1499 | DQ003633 | clade_207 | N | N |
| *Prevotella* sp. oral clone AU069 | 1531 | AY005062 | clade_207 | N | N |
| *Prevotella* sp. oral clone CY006 | 1532 | AY005063 | clade_207 | N | N |
| *Prevotella* sp. oral clone FL019 | 1534 | AY349392 | clade_207 | N | N |
| *Actinomyces* genomosp. C1 | 56 | AY278610 | clade_212 | N | N |
| *Actinomyces* genomosp. C2 | 57 | AY278611 | clade_212 | N | N |
| *Actinomyces* genomosp. P1 oral clone MB6_C03 | 58 | DQ003632 | clade_212 | N | N |
| *Actinomyces georgiae* | 59 | GU561319 | clade_212 | N | N |
| *Actinomyces israelii* | 60 | AF479270 | clade_212 | N | N |
| *Actinomyces massiliensis* | 61 | AB545934 | clade_212 | N | N |
| *Actinomyces meyeri* | 62 | GU561321 | clade_212 | N | N |
| *Actinomyces odontolyticus* | 66 | ACYT01000123 | clade_212 | N | N |
| *Actinomyces orihominis* | 68 | AJ575186 | clade_212 | N | N |
| *Actinomyces* sp. CCUG 37290 | 71 | AJ234058 | clade_212 | N | N |
| *Actinomyces* sp. ICM34 | 75 | HQ616391 | clade_212 | N | N |
| *Actinomyces* sp. ICM41 | 76 | HQ616392 | clade_212 | N | N |
| *Actinomyces* sp. ICM47 | 77 | HQ616395 | clade_212 | N | N |
| *Actinomyces* sp. ICM54 | 78 | HQ616398 | clade_212 | N | N |
| *Actinomyces* sp. oral clone IP081 | 87 | AY349366 | clade_212 | N | N |
| *Actinomyces* sp. oral taxon 178 | 91 | AEUH01000060 | clade_212 | N | N |
| *Actinomyces* sp. oral taxon 180 | 92 | AEPP01000041 | clade_212 | N | N |
| *Actinomyces* sp. TeJ5 | 80 | GU561315 | clade_212 | N | N |
| *Haematobacter* sp. BC14248 | 968 | GU396991 | clade_213 | N | N |
| *Paracoccus denitrificans* | 1424 | CP000490 | clade_213 | N | N |
| *Paracoccus marcusii* | 1425 | NR_044922 | clade_213 | N | N |
| *Grimontia hollisae* | 967 | ADAQ01000013 | clade_216 | N | N |
| *Shewanella putrefaciens* | 1723 | CP002457 | clade_216 | N | N |
| *Afipia* genomosp. 4 | 111 | EU117385 | clade_217 | N | N |
| *Rhodopseudomonas palustris* | 1626 | CP000301 | clade_217 | N | N |
| *Methylobacterium extorquens* | 1223 | NC_010172 | clade_218 | N | N |
| *Methylobacterium podarium* | 1224 | AY468363 | clade_218 | N | N |
| *Methylobacterium radiotolerans* | 1225 | GU294320 | clade_218 | N | N |
| *Methylobacterium* sp. 1sub | 1226 | AY468371 | clade_218 | N | N |
| *Methylobacterium* sp. MM4 | 1227 | AY468370 | clade_218 | N | N |
| *Clostridium baratii* | 555 | NR_029229 | clade_223 | Y | N |
| *Clostridium colicanis* | 576 | FJ957863 | clade_223 | Y | N |
| *Clostridium paraputrificum* | 611 | AB536771 | clade_223 | Y | N |
| *Clostridium sardiniense* | 621 | NR_041006 | clade_223 | Y | N |
| *Eubacterium budayi* | 837 | NR_024682 | clade_223 | Y | N |
| *Eubacterium moniliforme* | 851 | HF558373 | clade_223 | Y | N |
| *Eubacterium multiforme* | 852 | NR_024683 | clade_223 | Y | N |
| *Eubacterium nitritogenes* | 853 | NR_024684 | clade_223 | Y | N |
| *Achromobacter denitrificans* | 18 | NR_042021 | clade_224 | N | N |
| *Achromobacter piechaudii* | 19 | ADMS01000149 | clade_224 | N | N |
| *Achromobacter xylosoxidans* | 20 | ACRC01000072 | clade_224 | N | N |
| *Bordetella bronchiseptica* | 384 | NR_025949 | clade_224 | N | OP |
| *Bordetella holmesii* | 385 | AB683187 | clade_224 | N | OP |
| *Bordetella parapertussis* | 386 | NR_025950 | clade_224 | N | OP |
| *Bordetella pertussis* | 387 | BX640418 | clade_224 | N | OP |
| *Microbacterium chocolatum* | 1230 | NR_037045 | clade_225 | N | N |
| *Microbacterium flavescens* | 1231 | EU714363 | clade_225 | N | N |
| *Microbacterium lacticum* | 1233 | EU714351 | clade_225 | N | N |
| *Microbacterium oleivorans* | 1234 | EU714381 | clade_225 | N | N |

TABLE 1-continued

| OTU | SEQ ID Number | Public DB Accession | Phylogenetic Clade | Spore Former | Pathogen Status |
|---|---|---|---|---|---|
| *Microbacterium oxydans* | 1235 | EU714348 | clade_225 | N | N |
| *Microbacterium paraoxydans* | 1236 | AJ491806 | clade_225 | N | N |
| *Microbacterium phyllosphaerae* | 1237 | EU714359 | clade_225 | N | N |
| *Microbacterium schleiferi* | 1238 | NR_044936 | clade_225 | N | N |
| *Microbacterium* sp. 768 | 1239 | EU714378 | clade_225 | N | N |
| *Microbacterium* sp. oral strain C24KA | 1240 | AF287752 | clade_225 | N | N |
| *Microbacterium testaceum* | 1241 | EU714365 | clade_225 | N | N |
| *Corynebacterium atypicum* | 686 | NR_025540 | clade_229 | N | N |
| *Corynebacterium mastitidis* | 708 | AB359395 | clade_229 | N | N |
| *Corynebacterium* sp. NML 97_0186 | 725 | GU238411 | clade_229 | N | N |
| *Mycobacterium elephantis* | 1275 | AF385898 | clade_237 | N | OP |
| *Mycobacterium paraterrae* | 1288 | EU919229 | clade_237 | N | OP |
| *Mycobacterium phlei* | 1289 | GU142920 | clade_237 | N | OP |
| *Mycobacterium* sp. 1776 | 1293 | EU703152 | clade_237 | N | N |
| *Mycobacterium* sp. 1781 | 1294 | EU703147 | clade_237 | N | N |
| *Mycobacterium* sp. AQ1GA4 | 1297 | HM210417 | clade_237 | N | N |
| *Mycobacterium* sp. GN_10546 | 1299 | FJ497243 | clade_237 | N | N |
| *Mycobacterium* sp. GN_10827 | 1300 | FJ497247 | clade_237 | N | N |
| *Mycobacterium* sp. GN_11124 | 1301 | FJ652846 | clade_237 | N | N |
| *Mycobacterium* sp. GN_9188 | 1302 | FJ497240 | clade_237 | N | N |
| *Mycobacterium* sp. GR_2007_210 | 1303 | FJ555538 | clade_237 | N | N |
| *Anoxybacillus contaminans* | 172 | NR_029006 | clade_238 | N | N |
| *Anoxybacillus flavithermus* | 173 | NR_074667 | clade_238 | Y | N |
| *Bacillus aeolius* | 195 | NR_025557 | clade_238 | N | N |
| *Bacillus aerophilus* | 196 | NR_042339 | clade_238 | Y | N |
| *Bacillus aestuarii* | 197 | GQ980243 | clade_238 | Y | N |
| *Bacillus amyloliquefaciens* | 199 | NR_075005 | clade_238 | Y | N |
| *Bacillus anthracis* | 200 | AAEN01000020 | clade_238 | Y | Category-A |
| *Bacillus atrophaeus* | 201 | NR_075016 | clade_238 | Y | OP |
| *Bacillus badius* | 202 | NR_036893 | clade_238 | Y | OP |
| *Bacillus cereus* | 203 | ABDJ01000015 | clade_238 | Y | OP |
| *Bacillus circulans* | 204 | AB271747 | clade_238 | Y | OP |
| *Bacillus firmus* | 207 | NR_025842 | clade_238 | Y | OP |
| *Bacillus flexus* | 208 | NR_024691 | clade_238 | Y | OP |
| *Bacillus fordii* | 209 | NR_025786 | clade_238 | Y | OP |
| *Bacillus halmapalus* | 211 | NR_026144 | clade_238 | Y | OP |
| *Bacillus herbersteinensis* | 213 | NR_042286 | clade_238 | Y | OP |
| *Bacillus idriensis* | 215 | NR_043268 | clade_238 | Y | OP |
| *Bacillus lentus* | 216 | NR_040792 | clade_238 | Y | OP |
| *Bacillus licheniformis* | 217 | NC_006270 | clade_238 | Y | OP |
| *Bacillus megaterium* | 218 | GU252124 | clade_238 | Y | OP |
| *Bacillus nealsonii* | 219 | NR_044546 | clade_238 | Y | OP |
| *Bacillus niabensis* | 220 | NR_043334 | clade_238 | Y | OP |
| *Bacillus niacini* | 221 | NR_024695 | clade_238 | Y | OP |
| *Bacillus pocheonensis* | 222 | NR_041377 | clade_238 | Y | OP |
| *Bacillus pumilus* | 223 | NR_074977 | clade_238 | Y | OP |
| *Bacillus safensis* | 224 | JQ624766 | clade_238 | Y | OP |
| *Bacillus simplex* | 225 | NR_042136 | clade_238 | Y | OP |
| *Bacillus sonorensis* | 226 | NR_025130 | clade_238 | Y | OP |
| *Bacillus* sp. 10403023 MM10403188 | 227 | CAET01000089 | clade_238 | Y | OP |
| *Bacillus* sp. 2_A_57_CT2 | 230 | ACWD01000095 | clade_238 | Y | OP |
| *Bacillus* sp. 2008724126 | 228 | GU252108 | clade_238 | Y | OP |
| *Bacillus* sp. 2008724139 | 229 | GU252111 | clade_238 | Y | OP |
| *Bacillus* sp. 7_16AIA | 231 | FN397518 | clade_238 | Y | OP |
| *Bacillus* sp. AP8 | 233 | JX101689 | clade_238 | Y | OP |
| *Bacillus* sp. B27(2008) | 234 | EU362173 | clade_238 | Y | OP |
| *Bacillus* sp. BT1B_CT2 | 235 | ACWC01000034 | clade_238 | Y | OP |
| *Bacillus* sp. GB1.1 | 236 | FJ897765 | clade_238 | Y | OP |
| *Bacillus* sp. GB9 | 237 | FJ897766 | clade_238 | Y | OP |
| *Bacillus* sp. HU19.1 | 238 | FJ897769 | clade_238 | Y | OP |
| *Bacillus* sp. HU29 | 239 | FJ897771 | clade_238 | Y | OP |
| *Bacillus* sp. HU33.1 | 240 | FJ897772 | clade_238 | Y | OP |
| *Bacillus* sp. JC6 | 241 | JF824800 | clade_238 | Y | OP |
| *Bacillus* sp. oral taxon F79 | 248 | HM099654 | clade_238 | Y | OP |
| *Bacillus* sp. SRC_DSF1 | 243 | GU797283 | clade_238 | Y | OP |
| *Bacillus* sp. SRC_DSF10 | 242 | GU797292 | clade_238 | Y | OP |
| *Bacillus* sp. SRC_DSF2 | 244 | GU797284 | clade_238 | Y | OP |
| *Bacillus* sp. SRC_DSF6 | 245 | GU797288 | clade_238 | Y | OP |
| *Bacillus* sp. tc09 | 249 | HQ844242 | clade_238 | Y | OP |
| *Bacillus* sp. zh168 | 250 | FJ851424 | clade_238 | Y | OP |
| *Bacillus sphaericus* | 251 | DQ286318 | clade_238 | Y | OP |
| *Bacillus sporothermodurans* | 252 | NR_026010 | clade_238 | Y | OP |
| *Bacillus subtilis* | 253 | EU627588 | clade_238 | Y | OP |
| *Bacillus thermoamylovorans* | 254 | NR_029151 | clade_238 | Y | OP |
| *Bacillus thuringiensis* | 255 | NC_008600 | clade_238 | Y | OP |
| *Bacillus weihenstephanensis* | 256 | NR_074926 | clade_238 | Y | OP |
| *Brevibacterium frigoritolerans* | 422 | NR_042639 | clade_238 | N | N |

TABLE 1-continued

| OTU | SEQ ID Number | Public DB Accession | Phylogenetic Clade | Spore Former | Pathogen Status |
|---|---|---|---|---|---|
| *Geobacillus kaustophilus* | 933 | NR_074989 | clade_238 | Y | N |
| *Geobacillus* sp. E263 | 934 | DQ647387 | clade_238 | N | N |
| *Geobacillus* sp. WCH70 | 935 | CP001638 | clade_238 | N | N |
| *Geobacillus stearothermophilus* | 936 | NR_040794 | clade_238 | Y | N |
| *Geobacillus thermocatenulatus* | 937 | NR_043020 | clade_238 | N | N |
| *Geobacillus thermodenitrificans* | 938 | NR_074976 | clade_238 | Y | N |
| *Geobacillus thermoglucosidasius* | 939 | NR_043022 | clade_238 | Y | N |
| *Geobacillus thermoleovorans* | 940 | NR_074931 | clade_238 | N | N |
| *Lysinibacillus fusiformis* | 1192 | FN397522 | clade_238 | N | N |
| *Lysinibacillus sphaericus* | 1193 | NR_074883 | clade_238 | Y | N |
| *Planomicrobium koreense* | 1468 | NR_025011 | clade_238 | N | N |
| *Sporosarcina newyorkensis* | 1754 | AFPZ01000142 | clade_238 | N | N |
| *Sporosarcina* sp. 2681 | 1755 | GU994081 | clade_238 | N | N |
| *Ureibacillus composti* | 1968 | NR_043746 | clade_238 | N | N |
| *Ureibacillus suwonensis* | 1969 | NR_043232 | clade_238 | N | N |
| *Ureibacillus terrenus* | 1970 | NR_025394 | clade_238 | N | N |
| *Ureibacillus thermophilus* | 1971 | NR_043747 | clade_238 | N | N |
| *Ureibacillus thermosphaericus* | 1972 | NR_040961 | clade_238 | N | N |
| *Prevotella micans* | 1507 | AGWK01000061 | clade_239 | N | N |
| *Prevotella* sp. oral clone DA058 | 1533 | AY005065 | clade_239 | N | N |
| *Prevotella* sp. SEQ053 | 1523 | JN867222 | clade_239 | N | N |
| *Treponema socranskii* | 1937 | NR_024868 | clade_240 | N | OP |
| *Treponema* sp. 6:H:D15A_4 | 1938 | AY005083 | clade_240 | N | N |
| *Treponema* sp. oral taxon 265 | 1953 | GU408850 | clade_240 | N | N |
| *Treponema* sp. oral taxon G85 | 1958 | GU432215 | clade_240 | N | N |
| *Porphyromonas endodontalis* | 1472 | ACNN01000021 | clade_241 | N | N |
| *Porphyromonas* sp. oral clone BB134 | 1478 | AY005068 | clade_241 | N | N |
| *Porphyromonas* sp. oral clone F016 | 1479 | AY005069 | clade_241 | N | N |
| *Porphyromonas* sp. oral clone P2PB_52 P1 | 1480 | AY207054 | clade_241 | N | N |
| *Porphyromonas* sp. oral clone P4GB_100 P2 | 1481 | AY207057 | clade_241 | N | N |
| *Acidovorax* sp. 98_63833 | 26 | AY258065 | clade_245 | N | N |
| Comamonadaceae bacterium NML000135 | 663 | JN585335 | clade_245 | N | N |
| Comamonadaceae bacterium NML790751 | 664 | JN585331 | clade_245 | N | N |
| Comamonadaceae bacterium NML910035 | 665 | JN585332 | clade_245 | N | N |
| Comamonadaceae bacterium NML910036 | 666 | JN585333 | clade_245 | N | N |
| *Comamonas* sp. NSP5 | 668 | AB076850 | clade_245 | N | N |
| *Delftia acidovorans* | 748 | CP000884 | clade_245 | N | N |
| *Xenophilus aerolatus* | 2018 | JN585329 | clade_245 | N | N |
| Clostridiales sp. SS3/4 | 543 | AY305316 | clade_246 | Y | N |
| *Oribacfcerium* sp. oral taxon 078 | 1380 | ACIQ02000009 | clade_246 | N | N |
| *Oribacterium* sp. oral taxon 102 | 1381 | GQ422713 | clade_246 | N | N |
| *Weissella cibaria* | 2007 | NR_036924 | clade_247 | N | N |
| *Weissella confusa* | 2008 | NR_040816 | clade_247 | N | N |
| *Weissella hellenica* | 2009 | AB680902 | clade_247 | N | N |
| *Weissella kandleri* | 2010 | NR_044659 | clade_247 | N | N |
| *Weissella koreensis* | 2011 | NR_075058 | clade_247 | N | N |
| *Weissella paramesenteroides* | 2012 | ACKU01000017 | clade_247 | N | N |
| *Weissella* sp. KLDS 7.0701 | 2013 | EU600924 | clade_247 | N | N |
| *Mobiluncus curtisii* | 1251 | AEPZ01000013 | clade_249 | N | N |
| *Clostridium beijerinckii* | 557 | NR_074434 | clade_252 | Y | N |
| *Clostridium botulinum* | 560 | NC_010723 | clade_252 | Y | Category-A |
| *Clostridium butyricum* | 561 | ABDT01000017 | clade_252 | Y | N |
| *Clostridium chauvoei* | 568 | EU106372 | clade_252 | Y | N |
| *Clostridium favososporum* | 582 | X76749 | clade_252 | Y | N |
| *Clostridium histolyticum* | 592 | HF558362 | clade_252 | Y | N |
| *Clostridium isatidis* | 597 | NR_026347 | clade_252 | Y | N |
| *Clostridium limosum* | 602 | FR870444 | clade_252 | Y | N |
| *Clostridium sartagoforme* | 622 | NR_026490 | clade_252 | Y | N |
| *Clostridium septicum* | 624 | NR_026020 | clade_252 | Y | N |
| *Clostridium* sp. 7_2_43FAA | 626 | ACDK01000101 | clade_252 | Y | N |
| *Clostridium sporogenes* | 645 | ABKW02000003 | clade_252 | Y | N |
| *Clostridium tertium* | 653 | Y18174 | clade_252 | Y | N |
| *Clostridium carnis* | 564 | NR_044716 | clade_253 | Y | N |
| *Clostridium celatum* | 565 | X77844 | clade_253 | Y | N |
| *Clostridium disporicum* | 579 | NR_026491 | clade_253 | Y | N |
| *Clostridium gasigenes* | 585 | NR_024945 | clade_253 | Y | N |
| *Clostridium quinii* | 616 | NR_026149 | clade_253 | Y | N |
| *Enhydrobacter aerosaccus* | 785 | ACYI01000081 | clade_256 | N | N |
| *Moraxella osloensis* | 1262 | JN175341 | clade_256 | N | N |
| *Moraxella* sp. GM2 | 1264 | JF837191 | clade_256 | N | N |
| *Brevibacterium casei* | 420 | JF951998 | clade_257 | N | N |
| *Brevibacterium epidermidis* | 421 | NR_029262 | clade_257 | N | N |
| *Brevibacterium sanguinis* | 426 | NR_028016 | clade_257 | N | N |
| *Brevibacterium* sp. H15 | 427 | AB177640 | clade_257 | N | N |
| *Clostridium hylemonae* | 593 | AB023973 | clade_260 | Y | N |
| *Clostridium scindens* | 623 | AF262238 | clade_260 | Y | N |

TABLE 1-continued

| OTU | SEQ ID Number | Public DB Accession | Phylogenetic Clade | Spore Former | Pathogen Status |
|---|---|---|---|---|---|
| Lachnospiraceae bacterium 5_1_57FAA | 1054 | ACTR01000020 | clade_260 | Y | N |
| *Acinetobacter radioresistens* | 35 | ACVR01000010 | clade_261 | N | N |
| *Clostridium glycyrrhizinilyticum* | 588 | AB233029 | clade_262 | Y | N |
| *Clostridium nexile* | 607 | X73443 | clade_262 | Y | N |
| *Coprococcus comes* | 674 | ABVR01000038 | clade_262 | Y | N |
| Lachnospiraceae bacterium 1_1_57FAA | 1048 | ACTM01000065 | clade_262 | Y | N |
| Lachnospiraceae bacterium 1_4_56FAA | 1049 | ACTN01000028 | clade_262 | Y | N |
| Lachnospiraceae bacterium 8_1_57FAA | 1057 | ACWQ01000079 | clade_262 | Y | N |
| *Ruminococcus lactaris* | 1663 | ABOU02000049 | clade_262 | Y | N |
| *Ruminococcus torques* | 1670 | AAVP02000002 | clade_262 | Y | N |
| *Lactobacillus alimentarius* | 1068 | NR_044701 | clade_263 | N | N |
| *Lactobacillus farciminis* | 1082 | NR_044707 | clade_263 | N | N |
| *Lactobacillus kimchii* | 1097 | NR_025045 | clade_263 | N | N |
| *Lactobacillus nodensis* | 1101 | NR_041629 | clade_263 | N | N |
| *Lactobacillus tucceti* | 1138 | NR_042194 | clade_263 | N | N |
| *Pseudomonas mendocina* | 1595 | AAUL01000021 | clade_265 | N | N |
| *Pseudomonas pseudoalcaligenes* | 1598 | NR_037000 | clade_265 | N | N |
| *Pseudomonas* sp. NP522b | 1602 | EU723211 | clade_265 | N | N |
| *Pseudomonas stutzeri* | 1603 | AM905854 | clade_265 | N | N |
| *Paenibacillus barcinonensis* | 1390 | NR_042272 | clade_270 | N | N |
| *Paenibacillus barengoltzii* | 1391 | NR_042756 | clade_270 | N | N |
| *Paenibacillus chibensis* | 1392 | NR_040885 | clade_270 | N | N |
| *Paenibacillus cookii* | 1393 | NR_025372 | clade_270 | N | N |
| *Paenibacillus durus* | 1394 | NR_037017 | clade_270 | N | N |
| *Paenibacillus glucanolyticus* | 1395 | D78470 | clade_270 | N | N |
| *Paenibacillus lactis* | 1396 | NR_025739 | clade_270 | N | N |
| *Paenibacillus lautus* | 1397 | NR_040882 | clade_270 | Y | N |
| *Paenibacillus pabuli* | 1398 | NR_040853 | clade_270 | N | N |
| *Paenibacillus polymyxa* | 1399 | NR_037006 | clade_270 | Y | N |
| *Paenibacillus popilliae* | 1400 | NR_040888 | clade_270 | N | N |
| *Paenibacillus* sp. CIP 101062 | 1401 | HM212646 | clade_270 | N | N |
| *Paenibacillus* sp. HGF5 | 1402 | AEXS01000095 | clade_270 | Y | N |
| *Paenibacillus* sp. HGF7 | 1403 | AFDH01000147 | clade_270 | Y | N |
| *Paenibacillus* sp. JC66 | 1404 | JF824808 | clade_270 | N | N |
| *Paenibacillus* sp. R_27413 | 1405 | HE586333 | clade_270 | N | N |
| *Paenibacillus* sp. R_27422 | 1406 | HE586338 | clade_270 | N | N |
| *Paenibacillus timonensis* | 1408 | NR_042844 | clade_270 | N | N |
| *Rothia mucilaginosa* | 1651 | ACVO01000020 | clade_271 | N | N |
| *Rothia nasimurium* | 1652 | NR_025310 | clade_271 | N | N |
| *Prevotella* sp. oral taxon 302 | 1550 | ACZK01000043 | clade_280 | N | N |
| *Prevotella* sp. oral taxon F68 | 1556 | HM099652 | clade_280 | N | N |
| *Prevotella tannerae* | 1563 | ACIJ02000018 | clade_280 | N | N |
| Prevotellaceae bacterium P4P_62 P1 | 1566 | AY207061 | clade_280 | N | N |
| *Porphyromonas asaccharolytica* | 1471 | AENO01000048 | clade_281 | N | N |
| *Porphyromonas gingivails* | 1473 | AE015924 | clade_281 | N | N |
| *Porphyromonas macacae* | 1475 | NR_025908 | clade_281 | N | N |
| *Porphyromonas* sp. UQD 301 | 1477 | EU012301 | clade_281 | N | N |
| *Porphyromonas uenonis* | 1482 | ACLR01000152 | clade_281 | N | N |
| *Leptotrichia buccalis* | 1165 | CP001685 | clade_282 | N | N |
| *Leptotrichia hofstadii* | 1168 | ACVB02000032 | clade_282 | N | N |
| *Leptotrichia* sp. oral clone HE012 | 1173 | AY349386 | clade_282 | N | N |
| *Leptotrichia* sp. oral taxon 223 | 1176 | GU408547 | clade_282 | N | N |
| *Bacteroides fluxus* | 278 | AFBN01000029 | clade_285 | N | N |
| *Bacteroides helcogenes* | 281 | CP002352 | clade_285 | N | N |
| *Parabacteroides johnsonii* | 1419 | ABYH01000014 | clade_286 | N | N |
| *Parabacteroides merdae* | 1420 | EU136685 | clade_286 | N | N |
| *Treponema denticola* | 1926 | ADEC01000002 | clade_288 | N | OP |
| *Treponema* genomosp. P5 oral clone MB3_P23 | 1929 | DQ003624 | clade_288 | N | N |
| *Treponema putidum* | 1935 | AJ543428 | clade_288 | N | OP |
| *Treponema* sp. oral clone P2PB_53 P3 | 1942 | AY207055 | clade_288 | N | N |
| *Treponema* sp. oral taxon 247 | 1949 | GU408748 | clade_288 | N | N |
| *Treponema* sp. oral taxon 250 | 1950 | GU408776 | clade_288 | N | N |
| *Treponema* sp. oral taxon 251 | 1951 | GU408781 | clade_288 | N | N |
| *Anaerococcus hydrogenalis* | 144 | ABXA01000039 | clade_289 | N | N |
| *Anaerococcus* sp. 8404299 | 148 | HM587318 | clade_289 | N | N |
| *Anaerococcus* sp. gpac215 | 156 | AM176540 | clade_289 | N | N |
| *Anaerococcus vaginalis* | 158 | ACXU01000016 | clade_289 | N | N |
| *Propionibacterium acidipropionici* | 1569 | NC_019395 | clade_290 | N | N |
| *Propionibacterium avidum* | 1571 | AJ003055 | clade_290 | N | N |
| *Propionibacterium granulosum* | 1573 | FJ785716 | clade_290 | N | N |
| *Propionibacterium jensenii* | 1574 | NR_042269 | clade_290 | N | N |
| *Propionibacterium propionicum* | 1575 | NR_025277 | clade_290 | N | N |
| *Propionibacterium* sp. H456 | 1577 | AB177643 | clade_290 | N | N |
| *Propionibacterium thoenii* | 1581 | NR_042270 | clade_290 | N | N |
| *Bifidobacterium bifidum* | 349 | ABQP01000027 | clade_293 | N | N |
| *Leuconostoc mesenteroides* | 1183 | ACKV01000113 | clade_295 | N | N |

TABLE 1-continued

| OTU | SEQ ID Number | Public DB Accession | Phylogenetic Clade | Spore Former | Pathogen Status |
|---|---|---|---|---|---|
| *Leuconostoc pseudomesenteroides* | 1184 | NR_040814 | clade_295 | N | N |
| *Eubacterium* sp. oral clone JI012 | 868 | AY349379 | clade_298 | Y | N |
| *Johnsonella ignava* | 1016 | X87152 | clade_298 | N | N |
| *Propionibacterium acnes* | 1570 | ADJM01000010 | clade_299 | N | N |
| *Propionibacterium* sp. 434_HC2 | 1576 | AFIL01000035 | clade_299 | N | N |
| *Propionibacterium* sp. LG | 1578 | AY354921 | clade_299 | N | N |
| *Propionibacterium* sp. S555a | 1579 | AB264622 | clade_299 | N | N |
| *Alicyclobacillus contaminans* | 124 | NR_041475 | clade_301 | Y | N |
| *Alicyclobacillus herbarius* | 126 | NR_024753 | clade_301 | Y | N |
| *Alicyclobacillus pomorum* | 127 | NR_024801 | clade_301 | Y | N |
| *Alicyclobacillus* sp. CCUG 53762 | 128 | HE613268 | clade_301 | N | N |
| *Actinomyces cardiffensis* | 53 | GU470888 | clade_303 | N | N |
| *Actinomyces funkei* | 55 | HQ906497 | clade_303 | N | N |
| *Actinomyces* sp. HKU31 | 74 | HQ335393 | clade_303 | N | N |
| *Actinomyces* sp. oral taxon C55 | 94 | HM099646 | clade_303 | N | N |
| *Kerstersia gyiorum* | 1018 | NR_025669 | clade_307 | N | N |
| *Pigmentiphaga daeguensis* | 1467 | JN585327 | clade_307 | N | N |
| *Aeromonas allosaccharophila* | 104 | S39232 | clade_308 | N | N |
| *Aeromonas enteropelogenes* | 105 | X71121 | clade_308 | N | N |
| *Aeromonas hydrophila* | 106 | NC_008570 | clade_308 | N | N |
| *Aeromonas jandaei* | 107 | X60413 | clade_308 | N | N |
| *Aeromonas salmonicida* | 108 | NC_009348 | clade_308 | N | N |
| *Aeromonas trota* | 109 | X60415 | clade_308 | N | N |
| *Aeromonas veronii* | 110 | NR_044845 | clade_308 | N | N |
| *Blautia coccoides* | 373 | AB571656 | clade_309 | Y | N |
| *Blautia glucerasea* | 374 | AB588023 | clade_309 | Y | N |
| *Blautia glucerasei* | 375 | AB439724 | clade_309 | Y | N |
| *Blautia hansenii* | 376 | ABYU02000037 | clade_309 | Y | N |
| *Blautia luti* | 378 | AB691576 | clade_309 | Y | N |
| *Blautia producta* | 379 | AB600998 | clade_309 | Y | N |
| *Blautia schinkii* | 380 | NR_026312 | clade_309 | Y | N |
| *Blautia* sp. M25 | 381 | HM626178 | clade_309 | Y | N |
| *Blautia stercoris* | 382 | HM626177 | clade_309 | Y | N |
| *Blautia wexlerae* | 383 | EF036467 | clade_309 | Y | N |
| *Bryantella formatexigens* | 439 | ACCL02000018 | clade_309 | Y | N |
| *Clostridium coccoides* | 573 | EF025906 | clade_309 | Y | N |
| *Eubacterium cellulosolvens* | 839 | AY178842 | clade_309 | Y | N |
| Lachnospiraceae bacterium 6_1_63FAA | 1056 | ACTV01000014 | clade_309 | Y | N |
| *Marvinbryantia formatexigens* | 1196 | AJ505973 | clade_309 | N | N |
| *Ruminococcus hansenii* | 1662 | M59114 | clade_309 | Y | N |
| *Ruminococcus obeum* | 1664 | AY169419 | clade_309 | Y | N |
| *Ruminococcus* sp. 5_1_39BFAA | 1666 | ACII01000172 | clade_309 | Y | N |
| *Ruminococcus* sp. K_1 | 1669 | AB222208 | clade_309 | Y | N |
| *Syntrophococcus sucromutans* | 1911 | NR_036869 | clade_309 | Y | N |
| *Rhodobacter* sp. oral taxon C30 | 1620 | HM099648 | clade_310 | N | N |
| *Rhodobacter sphaeroides* | 1621 | CP000144 | clade_310 | N | N |
| *Lactobacillus antri* | 1071 | ACLL01000037 | clade_313 | N | N |
| *Lactobacillus coleohominis* | 1076 | ACOH01000030 | clade_313 | N | N |
| *Lactobacillus fermentum* | 1083 | CP002033 | clade_313 | N | N |
| *Lactobacillus gastricus* | 1085 | AICN01000060 | clade_313 | N | N |
| *Lactobacillus mucosae* | 1099 | FR693800 | clade_313 | N | N |
| *Lactobacillus oris* | 1103 | AEKL01000077 | clade_313 | N | N |
| *Lactobacillus pontis* | 1111 | HM218420 | clade_313 | N | N |
| *Lactobacillus reuteri* | 1112 | ACGW02000012 | clade_313 | N | N |
| *Lactobacillus* sp. KLDS 1.0707 | 1127 | EU600911 | clade_313 | N | N |
| *Lactobacillus* sp. KLDS 1.0709 | 1128 | EU600913 | clade_313 | N | N |
| *Lactobacillus* sp. KLDS 1.0711 | 1129 | EU600915 | clade_313 | N | N |
| *Lactobacillus* sp. KLDS 1.0713 | 1131 | EU600917 | clade_313 | N | N |
| *Lactobacillus* sp. KLDS 1.0716 | 1132 | EU600921 | clade_313 | N | N |
| *Lactobacillus* sp. KLDS 1.0718 | 1133 | EU600922 | clade_313 | N | N |
| *Lactobacillus* sp. oral taxon 052 | 1137 | GQ422710 | clade_313 | N | N |
| *Lactobacillus vaginalis* | 1140 | ACGV01000168 | clade_313 | N | N |
| *Brevibacterium aurantiacum* | 419 | NR_044854 | clade_314 | N | N |
| *Brevibacterium linens* | 423 | AJ315491 | clade_314 | N | N |
| *Lactobacillus pentosus* | 1108 | JN813103 | clade_315 | N | N |
| *Lactobacillus plantarum* | 1110 | ACGZ02000033 | clade_315 | N | N |
| *Lactobacillus* sp. KLDS 1.0702 | 1123 | EU600906 | clade_315 | N | N |
| *Lactobacillus* sp. KLDS 1.0703 | 1124 | EU600907 | clade_315 | N | N |
| *Lactobacillus* sp. KLDS 1.0704 | 1125 | EU600908 | clade_315 | N | N |
| *Lactobacillus* sp. KLDS 1.0705 | 1126 | EU600909 | clade_315 | N | N |
| *Agrobacterium radiobacter* | 115 | CP000628 | clade_316 | N | N |
| *Agrobacterium tumefaciens* | 116 | AJ389893 | clade_316 | N | N |
| *Corynebacterium argentoratense* | 685 | EF463055 | clade_317 | N | N |
| *Corynebacterium diphtheriae* | 693 | NC_002935 | clade_317 | N | OP |
| *Corynebacterium pseudotuberculosis* | 715 | NR_037070 | clade_317 | N | N |
| *Corynebacterium renale* | 717 | NR_037069 | clade_317 | N | N |
| *Corynebacterium ulcerans* | 731 | NR_074467 | clade_317 | N | N |

TABLE 1-continued

| OTU | SEQ ID Number | Public DB Accession | Phylogenetic Clade | Spore Former | Pathogen Status |
|---|---|---|---|---|---|
| *Aurantimonas coralicida* | 191 | AY065627 | clade_318 | N | N |
| *Aureimonas altamirensis* | 192 | FN658986 | clade_318 | N | N |
| *Lactobacillus acidipiscis* | 1066 | NR_024718 | clade_320 | N | N |
| *Lactobacillus salivarius* | 1117 | AEBA01000145 | clade_320 | N | N |
| *Lactobacillus* sp. KLDS 1.0719 | 1134 | EU600923 | clade_320 | N | N |
| *Lactobacillus buchneri* | 1073 | ACGH01000101 | clade_321 | N | N |
| *Lactobacillus* genomosp. C1 | 1086 | AY278619 | clade_321 | N | N |
| *Lactobacillus* genomosp. C2 | 1087 | AY278620 | clade_321 | N | N |
| *Lactobacillus hilgardii* | 1089 | ACGP01000200 | clade_321 | N | N |
| *Lactobacillus kefiri* | 1096 | NR_042230 | clade_321 | N | N |
| *Lactobacillus parabuchneri* | 1105 | NR_041294 | clade_321 | N | N |
| *Lactobacillus parakefiri* | 1107 | NR_029039 | clade_321 | N | N |
| *Lactobacillus curvatus* | 1079 | NR_042437 | clade_322 | N | N |
| *Lactobacillus sakei* | 1116 | DQ989236 | clade_322 | N | N |
| *Aneurinibacillus aneurinilyticus* | 167 | AB101592 | clade_323 | N | N |
| *Aneurinibacillus danicus* | 168 | NR_028657 | clade_323 | N | N |
| *Aneurinibacillus migulanus* | 169 | NR_036799 | clade_323 | N | N |
| *Aneurinibacillus terranovensis* | 170 | NR_042271 | clade_323 | N | N |
| *Staphylococcus aureus* | 1757 | CP002643 | clade_325 | N | Category-B |
| *Staphylococcus auricularis* | 1758 | JQ624774 | clade_325 | N | N |
| *Staphylococcus capitis* | 1759 | ACFR01000029 | clade_325 | N | N |
| *Staphylococcus caprae* | 1760 | ACRH01000033 | clade_325 | N | N |
| *Staphylococcus carnosus* | 1761 | NR_075003 | clade_325 | N | N |
| *Staphylococcus cohnii* | 1762 | JN175375 | clade_325 | N | N |
| *Staphylococcus condimenti* | 1763 | NR_029345 | clade_325 | N | N |
| *Staphylococcus epidermidis* | 1764 | ACHE01000056 | clade_325 | N | N |
| *Staphylococcus equorum* | 1765 | NR_027520 | clade_325 | N | N |
| *Staphylococcus haemolyticus* | 1767 | NC_007168 | clade_325 | N | N |
| *Staphylococcus hominis* | 1768 | AM157418 | clade_325 | N | N |
| *Staphylococcus lugdunensis* | 1769 | AEQA01000024 | clade_325 | N | N |
| *Staphylococcus pasteuri* | 1770 | FJ189773 | clade_325 | N | N |
| *Staphylococcus pseudintermedius* | 1771 | CP002439 | clade_325 | N | N |
| *Staphylococcus saccharolyticus* | 1772 | NR_029158 | clade_325 | N | N |
| *Staphylococcus saprophyticus* | 1773 | NC_007350 | clade_325 | N | N |
| *Staphylococcus* sp. clone bottae7 | 1777 | AF467424 | clade_325 | N | N |
| *Staphylococcus* sp. H292 | 1775 | AB177642 | clade_325 | N | N |
| *Staphylococcus* sp. H780 | 1776 | AB177644 | clade_325 | N | N |
| *Staphylococcus succinus* | 1778 | NR_028667 | clade_325 | N | N |
| *Staphylococcus warneri* | 1780 | ACPZ01000009 | clade_325 | N | N |
| *Staphylococcus xylosus* | 1781 | AY395016 | clade_325 | N | N |
| *Cardiobacterium hominis* | 490 | ACKY01000036 | clade_326 | N | N |
| *Cardiobacterium valvarum* | 491 | NR_028847 | clade_326 | N | N |
| *Pseudomonas fluorescens* | 1593 | AY622220 | clade_326 | N | N |
| *Pseudomonas gessardii* | 1594 | FJ943496 | clade_326 | N | N |
| *Pseudomonas monteilii* | 1596 | NR_024910 | clade_326 | N | N |
| *Pseudomonas poae* | 1597 | GU188951 | clade_326 | N | N |
| *Pseudomonas putida* | 1599 | AF094741 | clade_326 | N | N |
| *Pseudomonas* sp. G1229 | 1601 | DQ910482 | clade_326 | N | N |
| *Pseudomonas tolaasii* | 1604 | AF320988 | clade_326 | N | N |
| *Pseudomonas viridiflava* | 1605 | NR_042764 | clade_326 | N | N |
| *Bacillus alcalophilus* | 198 | X76436 | clade_327 | Y | N |
| *Bacillus clausii* | 205 | FN397477 | clade_327 | Y | OP |
| *Bacillus gelatini* | 210 | NR_025595 | clade_327 | Y | OP |
| *Bacillus halodurans* | 212 | AY144582 | clade_327 | Y | OP |
| *Bacillus* sp. oral taxon F26 | 246 | HM099642 | clade_327 | Y | OP |
| *Listeria grayi* | 1185 | ACCR02000003 | clade_328 | N | OP |
| *Listeria innocua* | 1186 | JF967625 | clade_328 | N | N |
| *Listeria ivanovii* | 1187 | X56151 | clade_328 | N | N |
| *Listeria monocytogenes* | 1188 | CP002003 | clade_328 | N | Category-B |
| *Listeria welshimeri* | 1189 | AM263198 | clade_328 | N | OP |
| *Capnocytophaga* sp. oral clone ASCH05 | 484 | AY923149 | clade_333 | N | N |
| *Capnocytophaga sputigena* | 489 | ABZV01000054 | clade_333 | N | N |
| *Leptotrichia* genomosp. C1 | 1166 | AY278621 | clade_334 | N | N |
| *Leptotrichia shahii* | 1169 | AY029806 | clade_334 | N | N |
| *Leptotrichia* sp. neutropenicPatient | 1170 | AF189244 | clade_334 | N | N |
| *Leptotrichia* sp. oral clone GT018 | 1171 | AY349384 | clade_334 | N | N |
| *Leptotrichia* sp. oral clone GT020 | 1172 | AY349385 | clade_334 | N | N |
| *Bacteroides* sp. 20_3 | 296 | ACRQ01000064 | clade_335 | N | N |
| *Bacteroides* sp. 3_1_19 | 307 | ADCJ01000062 | clade_335 | N | N |
| *Bacteroides* sp. 3_2_5 | 311 | ACIB01000079 | clade_335 | N | N |
| *Parabacteroides distasonis* | 1416 | CP000140 | clade_335 | N | N |
| *Parabacteroides goldsteinii* | 1417 | AY974070 | clade_335 | N | N |
| *Parabacteroides gordonii* | 1418 | AB470344 | clade_335 | N | N |
| *Parabacteroides* sp. D13 | 1421 | ACPW01000017 | clade_335 | N | N |
| *Capnocytophaga* genomosp. C1 | 477 | AY278613 | clade_336 | N | N |
| *Capnocytophaga ochracea* | 480 | AEOH01000054 | clade_336 | N | N |
| *Capnocytophaga* sp. GEJ8 | 481 | GU561335 | clade_336 | N | N |

TABLE 1-continued

| OTU | SEQ ID Number | Public DB Accession | Phylogenetic Clade | Spore Former | Pathogen Status |
|---|---|---|---|---|---|
| *Capnocytophaga* sp. oral strain A47ROY | 486 | AY005077 | clade_336 | N | N |
| *Capnocytophaga* sp. S1b | 482 | U42009 | clade_336 | N | N |
| *Paraprevotella clara* | 1426 | AFFY01000068 | clade_336 | N | N |
| *Bacteroides heparinolyticus* | 282 | JN867284 | clade_338 | N | N |
| *Prevotella heparinolytica* | 1500 | GQ422742 | clade_338 | N | N |
| *Treponema* genomosp. P4 oral clone MB2_G19 | 1928 | DQ003618 | clade_339 | N | N |
| *Treponema* genomosp. P6 oral clone MB4_G11 | 1930 | DQ003625 | clade_339 | N | N |
| *Treponema* sp. oral taxon 254 | 1952 | GU408803 | clade_339 | N | N |
| *Treponema* sp. oral taxon 508 | 1956 | GU413616 | clade_339 | N | N |
| *Treponema* sp. oral taxon 518 | 1957 | GU413640 | clade_339 | N | N |
| *Chlamydia muridarum* | 502 | AE002160 | clade_341 | N | OP |
| *Chlamydia trachomatis* | 504 | U68443 | clade_341 | N | OP |
| *Chlamydia psittaci* | 503 | NR_036864 | clade_342 | N | Category-B |
| *Chiamydophila pneumoniae* | 509 | NC_002179 | clade_342 | N | OP |
| *Chlamydophila psittaci* | 510 | D85712 | clade_342 | N | OP |
| *Anaerococcus octavius* | 146 | NR_026360 | clade_343 | N | N |
| *Anaerococcus* sp. 8405254 | 149 | HM587319 | clade_343 | N | N |
| *Anaerococcus* sp. 9401487 | 150 | HM587322 | clade_343 | N | N |
| *Anaerococcus* sp. 9403502 | 151 | HM587325 | clade_343 | N | N |
| *Gardnerella vaginalis* | 923 | CP001849 | clade_344 | N | N |
| *Campylobacter lari* | 466 | CP000932 | clade_346 | N | OP |
| *Anaerobiospirillum succiniciproducens* | 142 | NR_026075 | clade_347 | N | N |
| *Anaerobiospirillum thomasii* | 143 | AJ420985 | clade_347 | N | N |
| *Ruminobacter amylophilus* | 1654 | NR_026450 | clade_347 | N | N |
| *Succinatimonas hippei* | 1897 | AEVO01000027 | clade_347 | N | N |
| *Actinomyces europaeus* | 54 | NR_026363 | clade_348 | N | N |
| *Actinomyces* sp. oral clone GU009 | 82 | AY349361 | clade_348 | N | N |
| *Moraxella catarrhalis* | 1260 | CP002005 | clade_349 | N | N |
| *Moraxella lincolnii* | 1261 | FR822735 | clade_349 | N | N |
| *Moraxella* sp. 16285 | 1263 | JF682466 | clade_349 | N | N |
| *Psychrobacter* sp. 13983 | 1613 | HM212668 | clade_349 | N | N |
| *Actinobaculum massiliae* | 49 | AF487679 | clade_350 | N | N |
| *Actinobaculum schaalii* | 50 | AY957507 | clade_350 | N | N |
| *Actinobaculum* sp. BM#101342 | 51 | AY282578 | clade_350 | N | N |
| *Actinobaculum* sp. P2P_19 P1 | 52 | AY207066 | clade_350 | N | N |
| *Actinomyces* sp. oral clone IO076 | 84 | AY349363 | clade_350 | N | N |
| *Actinomyces* sp. oral taxon 848 | 93 | ACUY01000072 | clade_350 | N | N |
| *Clostridium innocuum* | 595 | M23732 | clade_351 | Y | N |
| *Clostridium* sp. HGF2 | 628 | AENW01000022 | clade_351 | Y | N |
| *Actinomyces neuii* | 65 | X71862 | clade_352 | N | N |
| *Mobiluncus mulieris* | 1252 | ACKW01000035 | clade_352 | N | N |
| *Clostridium perfringens* | 612 | ABDW01000023 | clade_353 | Y | Category-B |
| *Sarcina ventriculi* | 1687 | NR_026146 | clade_353 | Y | N |
| *Clostridium bartlettii* | 556 | ABEZ02000012 | clade_354 | Y | N |
| *Clostridium bifermentans* | 558 | X73437 | clade_354 | Y | N |
| *Clostridium ghonii* | 586 | AB542933 | clade_354 | Y | N |
| *Clostridium glycolicum* | 587 | FJ384385 | clade_354 | Y | N |
| *Clostridium mayombei* | 605 | FR733682 | clade_354 | Y | N |
| *Clostridium sordellii* | 625 | AB448946 | clade_354 | Y | N |
| *Clostridium* sp. MT4 E | 635 | FJ159523 | clade_354 | Y | N |
| *Eubacterium tenue* | 872 | M59118 | clade_354 | Y | N |
| *Clostridium argentinense* | 553 | NR_029232 | clade_355 | Y | N |
| *Clostridium* sp. JC122 | 630 | CAEV01000127 | clade_355 | Y | N |
| *Clostridium* sp. NMBHI_1 | 636 | JN093130 | clade_355 | Y | N |
| *Clostridium subterminale* | 650 | NR_041795 | clade_355 | Y | N |
| *Clostridium sulfidigenes* | 651 | NR_044161 | clade_355 | Y | N |
| *Blastomonas natatoria* | 372 | NR_040824 | clade_356 | N | N |
| *Novospbingobium aromaticivorans* | 1357 | AAAV03000008 | clade_356 | N | N |
| *Sphingomonas* sp. oral clone FI012 | 1745 | AY349411 | clade_356 | N | N |
| *Sphingopyxis alaskensis* | 1749 | CP000356 | clade_356 | N | N |
| *Oxalobacter formigenes* | 1389 | ACDQ01000020 | clade_357 | N | N |
| *Veillonella atypica* | 1974 | AEDS01000059 | clade_358 | N | N |
| *Veillonella dispar* | 1975 | ACIK02000021 | clade_358 | N | N |
| *Veillonella* genomosp. P1 oral clone MB5_P17 | 1976 | DQ003631 | clade_358 | N | N |
| *Veillonella parvula* | 1978 | ADFU01000009 | clade_358 | N | N |
| *Veillonella* sp. 3_1_44 | 1979 | ADCV01000019 | clade_358 | N | N |
| *Veillonella* sp. 6_1_27 | 1980 | ADCW01000016 | clade_358 | N | N |
| *Veillonella* sp. ACP1 | 1981 | HQ616359 | clade_358 | N | N |
| *Veillonella* sp. AS16 | 1982 | HQ616365 | clade_358 | N | N |
| *Veillonella* sp. BS32b | 1983 | HQ616368 | clade_358 | N | N |
| *Veillonella* sp. ICM51a | 1984 | HQ616396 | clade_358 | N | N |
| *Veillonella* sp. MSA12 | 1985 | HQ616381 | clade_358 | N | N |
| *Veillonella* sp. NVG 100cf | 1986 | EF108443 | clade_358 | N | N |
| *Veillonella* sp. OK11 | 1987 | JN695650 | clade_358 | N | N |

TABLE 1-continued

| OTU | SEQ ID Number | Public DB Accession | Phylogenetic Clade | Spore Former | Pathogen Status |
|---|---|---|---|---|---|
| *Veillonella* sp. oral clone ASCG01 | 1990 | AY923144 | clade_358 | N | N |
| *Veillonella* sp. oral clone ASCG02 | 1991 | AY953257 | clade_358 | N | N |
| *Veillonella* sp. oral clone OH1A | 1992 | AY947495 | clade_358 | N | N |
| *Veillonella* sp. oral taxon 158 | 1993 | AENU01000007 | clade_358 | N | N |
| *Dorea formicigenerans* | 773 | AAXA02000006 | clade_360 | Y | N |
| *Dorea longicatena* | 774 | AJ132842 | clade_360 | Y | N |
| Lachnospiraceae bacterium 2_1_46FAA | 1050 | ADLB01000035 | clade_360 | Y | N |
| Lachnospiraceae bacterium 2_1_58FAA | 1051 | ACTO01000052 | clade_360 | Y | N |
| Lachnospiraceae bacterium 4_1_37FAA | 1053 | ADCR01000030 | clade_360 | Y | N |
| Lachnospiraceae bacterium 9_1_43BFAA | 1058 | ACTX01000023 | clade_360 | Y | N |
| *Ruminococcus gnavus* | 1661 | X94967 | clade_360 | Y | N |
| *Ruminococcus* sp. ID8 | 1668 | AY960564 | clade_360 | Y | N |
| *Kocuria marina* | 1040 | GQ260086 | clade_365 | N | N |
| *Kocuria rhizophila* | 1042 | AY030315 | clade_365 | N | N |
| *Kocuria rosea* | 1043 | X87756 | clade_365 | N | N |
| *Kocuria varians* | 1044 | AF542074 | clade_365 | N | N |
| *Blautia hydrogenotrophica* | 377 | ACBZ01000217 | clade_368 | Y | N |
| Clostridiaceae bacterium END_2 | 531 | EF451053 | clade_368 | N | N |
| *Lactonifactor longoviformis* | 1147 | DQ100449 | clade_368 | Y | N |
| *Robinsoniella peoriensis* | 1633 | AF445258 | clade_368 | Y | N |
| *Micrococcus antarcticus* | 1242 | NR_025285 | clade_371 | N | N |
| *Micrococcus luteus* | 1243 | NR_075062 | clade_371 | N | N |
| *Micrococcus lylae* | 1244 | NR_026200 | clade_371 | N | N |
| *Micrococcus* sp. 185 | 1245 | EU714334 | clade_371 | N | N |
| *Lactobacillus brevis* | 1072 | EU194349 | clade_372 | N | N |
| *Lactobacillus parabrevis* | 1104 | NR_042456 | clade_372 | N | N |
| *Pediococcus acidilactici* | 1436 | ACXB01000026 | clade_372 | N | N |
| *Pediococcus pentosaceus* | 1437 | NR_075052 | clade_372 | N | N |
| *Lactobacillus dextrinicus* | 1081 | NR_036861 | clade_373 | N | N |
| *Lactobacillus perolens* | 1109 | NR_029360 | clade_373 | N | N |
| *Lactobacillus rhamnosus* | 1113 | ABWJ01000068 | clade_373 | N | N |
| *Lactobacillus saniviri* | 1118 | AB602569 | clade_373 | N | N |
| *Lactobacillus* sp. BT6 | 1121 | HQ616370 | clade_373 | N | N |
| *Mycobacterium mageritense* | 1282 | FR798914 | clade_374 | N | OP |
| *Mycobacterium neoaurum* | 1286 | AF268445 | clade_374 | N | OP |
| *Mycobacterium smegmatis* | 1291 | CP000480 | clade_374 | N | OP |
| *Mycobacterium* sp. HE5 | 1304 | AJ012738 | clade_374 | N | N |
| *Dysgonomonas gadei* | 775 | ADLV01000001 | clade_377 | N | N |
| *Dysgonomonas mossii* | 776 | ADLW01000023 | clade_377 | N | N |
| *Porphyromonas levii* | 1474 | NR_025907 | clade_377 | N | N |
| *Porphyromonas somerae* | 1476 | AB547667 | clade_377 | N | N |
| *Bacteroides barnesiae* | 267 | NR_041446 | clade_378 | N | N |
| *Bacteroides coprocola* | 272 | ABIY02000050 | clade_378 | N | N |
| *Bacteroides coprophilus* | 273 | ACBW01000012 | clade_378 | N | N |
| *Bacteroides dorei* | 274 | ABWZ01000093 | clade_378 | N | N |
| *Bacteroides massiliensis* | 284 | AB200226 | clade_378 | N | N |
| *Bacteroides plebeius* | 289 | AB200218 | clade_378 | N | N |
| *Bacteroides* sp. 3_1_33FAA | 309 | ACPS01000085 | clade_378 | N | N |
| *Bacteroides* sp. 3_1_40A | 310 | ACRT01000136 | clade_378 | N | N |
| *Bacteroides* sp. 4_3_47FAA | 313 | ACDR02000029 | clade_378 | N | N |
| *Bacteroides* sp. 9_1_42FAA | 314 | ACAA01000096 | clade_378 | N | N |
| *Bacteroides* sp. NB_8 | 323 | AB117565 | clade_378 | N | N |
| *Bacteroides vulgatus* | 331 | CP000139 | clade_378 | N | N |
| *Bacteroides ovatus* | 287 | ACWH01000036 | clade_38 | N | N |
| *Bacteroides* sp. 1_1_30 | 294 | ADCL01000128 | clade_38 | N | N |
| *Bacteroides* sp. 2_1_22 | 297 | ACPQ01000117 | clade_38 | N | N |
| *Bacteroides* sp. 2_2_4 | 299 | ABZZ01000168 | clade_38 | N | N |
| *Bacteroides* sp. 3_1_23 | 308 | ACRS01000081 | clade_38 | N | N |
| *Bacteroides* sp. D1 | 318 | ACAB02000030 | clade_38 | N | N |
| *Bacteroides* sp. D2 | 321 | ACGA01000077 | clade_38 | N | N |
| *Bacteroides* sp. D22 | 320 | ADCK01000151 | clade_38 | N | N |
| *Bacteroides xylanisolvens* | 332 | ADKP01000087 | clade_38 | N | N |
| *Treponema lecithinolyticum* | 1931 | NR_026247 | clade_380 | N | OP |
| *Treponema parvum* | 1933 | AF302937 | clade_380 | N | OP |
| *Treponema* sp. oral clone JU025 | 1940 | AY349417 | clade_380 | N | N |
| *Treponema* sp. oral taxon 270 | 1954 | GQ422733 | clade_380 | N | N |
| *Parascardovia denticolens* | 1428 | ADEB01000020 | clade_381 | N | N |
| *Scardovia inopinata* | 1688 | AB029087 | clade_381 | N | N |
| *Scardovia wiggsiae* | 1689 | AY278626 | clade_381 | N | N |
| Clostridiales bacterium 9400853 | 533 | HM587320 | clade_384 | N | N |
| *Eubacterium infirmum* | 849 | U13039 | clade_384 | Y | N |
| *Eubacterium* sp. WAL 14571 | 864 | FJ687606 | clade_384 | Y | N |
| *Mogibacterium diversum* | 1254 | NR_027191 | clade_384 | N | N |
| *Mogibacterium neglectum* | 1255 | NR_027203 | clade_384 | N | N |
| *Mogibacterium pumilum* | 1256 | NR_028608 | clade_384 | N | N |
| *Mogibacterium timidum* | 1257 | Z36296 | clade_384 | N | N |
| Erysipeiotrichaceae bacterium 5_2_54FAA | 823 | ACZW01000054 | clade_385 | Y | N |

TABLE 1-continued

| OTU | SEQ ID Number | Public DB Accession | Phylogenetic Clade | Spore Former | Pathogen Status |
|---|---|---|---|---|---|
| *Eubacterium biforme* | 835 | ABYT01000002 | clade_385 | Y | N |
| *Eubacterium cylindroides* | 842 | FP929041 | clade_385 | Y | N |
| *Eubacterium dolichum* | 844 | L34682 | clade_385 | Y | N |
| *Eubacterium* sp. 3_1_31 | 861 | ACTL01000045 | clade_385 | Y | N |
| *Eubacterium tortuosum* | 873 | NR_044648 | clade_385 | Y | N |
| *Borrelia burgdorferi* | 389 | ABGI01000001 | clade_386 | N | OP |
| *Borrelia garinii* | 392 | ABJV01000001 | clade_386 | N | OP |
| *Borrelia* sp. NE49 | 397 | AJ224142 | clade_386 | N | OP |
| *Caldimonas manganoxidans* | 457 | NR_040787 | clade_387 | N | N |
| Comamonadaceae bacterium oral taxon F47 | 667 | HM099651 | clade_387 | N | N |
| *Lautropia mirabilis* | 1149 | AEQP01000026 | clade_387 | N | N |
| *Lautropia* sp. oral clone AP009 | 1150 | AY005030 | clade_387 | N | N |
| *Bulleidia extructa* | 441 | ADFR01000011 | clade_388 | Y | N |
| *Solobacterium moorei* | 1739 | AECQ01000039 | clade_388 | Y | N |
| *Peptoniphilus asaccharolyticus* | 1441 | D14145 | clade_389 | N | N |
| *Peptoniphilus duerdenii* | 1442 | EU526290 | clade_389 | N | N |
| *Peptoniphilus harei* | 1443 | NR_026358 | clade_389 | N | N |
| *Peptoniphilus indolicus* | 1444 | AY153431 | clade_389 | N | N |
| *Peptoniphilus lacrimalis* | 1446 | ADDO01000050 | clade_389 | N | N |
| *Peptoniphilus* sp. gpac077 | 1450 | AM176527 | clade_389 | N | N |
| *Peptoniphilus* sp. JC140 | 1447 | JF824803 | clade_389 | N | N |
| *Peptoniphilus* sp. oral taxon 386 | 1452 | ADCS01000031 | clade_389 | N | N |
| *Peptoniphilus* sp. oral taxon 836 | 1453 | AEAA01000090 | clade_389 | N | N |
| Peptostreptococcaceae bacterium ph1 | 1454 | JN837495 | clade_389 | N | N |
| *Dialister pneumosintes* | 765 | HM596297 | clade_390 | N | N |
| *Dialister* sp. oral taxon 502 | 767 | GQ422739 | clade_390 | N | N |
| *Cupriavidus metallidurans* | 741 | GU230889 | clade_391 | N | N |
| *Herbaspirillum seropedicae* | 1001 | CP002039 | clade_391 | N | N |
| *Herbaspirillum* sp. JC206 | 1002 | JN657219 | clade_391 | N | N |
| *Janthinobacterium* sp. SY12 | 1015 | EF455530 | clade_391 | N | N |
| *Massilia* sp. CCUG 43427A | 1197 | FR773700 | clade_391 | N | N |
| *Ralstonia pickettii* | 1615 | NC_010682 | clade_391 | N | N |
| *Ralstonia* sp. 5_7_47FAA | 1616 | ACUF01000076 | clade_391 | N | N |
| *Francisella novicida* | 889 | ABSS01000002 | clade_392 | N | N |
| *Francisella philomiragia* | 890 | AY928394 | clade_392 | N | N |
| *Francisella tularensis* | 891 | ABAZ01000082 | clade_392 | N | Category-A |
| *Ignatzschineria indica* | 1009 | HQ823562 | clade_392 | N | N |
| *Ignatzschineria* sp. NML 95_0260 | 1010 | HQ823559 | clade_392 | N | N |
| *Coprococcus catus* | 673 | EU266552 | clade_393 | Y | N |
| Lachnospiraceae bacterium oral taxon F15 | 1064 | HM099641 | clade_393 | Y | N |
| *Streptococcus mutans* | 1814 | AP010655 | clade_394 | N | N |
| *Clostridium cochlearium* | 574 | NR_044717 | clade_395 | Y | N |
| *Clostridium malenominatum* | 604 | FR749893 | clade_395 | Y | N |
| *Clostridium tetani* | 654 | NC_004557 | clade_395 | Y | N |
| *Acetivibrio ethanolgignens* | 6 | FR749897 | clade_396 | Y | N |
| *Anaerosporobacter mobilis* | 161 | NR_042953 | clade_396 | Y | N |
| *Bacteroides pectinophilus* | 288 | ABVQ01000036 | clade_396 | Y | N |
| *Clostridium aminovalericum* | 551 | NR_029245 | clade_396 | Y | N |
| *Clostridium phytofermentans* | 613 | NR_074652 | clade_396 | Y | N |
| *Eubacterium hallii* | 848 | L34621 | clade_396 | Y | N |
| *Eubacterium xylanophilum* | 875 | L34628 | clade_396 | Y | N |
| *Lactobacillus gasseri* | 1084 | ACOZ01000018 | clade_398 | N | N |
| *Lactobacillus hominis* | 1090 | FR681902 | clade_398 | N | N |
| *Lactobacillus iners* | 1091 | AEKJ01000002 | clade_398 | N | N |
| *Lactobacillus johnsonii* | 1093 | AE017198 | clade_398 | N | N |
| *Lactobacillus senioris* | 1119 | AB602570 | clade_398 | N | N |
| *Lactobacillus* sp. oral clone HT002 | 1135 | AY349382 | clade_398 | N | N |
| *Weissella beninensis* | 2006 | EU439435 | clade_398 | N | N |
| *Sphingomonas echinoides* | 1744 | NR_024700 | clade_399 | N | N |
| *Sphingomonas* sp. oral taxon A09 | 1747 | HM099639 | clade_399 | N | N |
| *Sphingomonas* sp. oral taxon F71 | 1748 | HM099645 | clade_399 | N | N |
| *Zymomonas mobilis* | 2032 | NR_074274 | clade_399 | N | N |
| *Arcanobacterium haemolyticum* | 174 | NR_025347 | clade_400 | N | N |
| *Arcanobacterium pyogenes* | 175 | GU585578 | clade_400 | N | N |
| *Trueperella pyogenes* | 1962 | NR_044858 | clade_400 | N | N |
| *Lactococcus garvieae* | 1144 | AF061005 | clade_401 | N | N |
| *Lactococcus lactis* | 1145 | CP002365 | clade_401 | N | N |
| *Brevibacterium mcbrellneri* | 424 | ADNU01000076 | clade_402 | N | N |
| *Brevibacterium paucivorans* | 425 | EU086796 | clade_402 | N | N |
| *Brevibacterium* sp. JC43 | 428 | JF824806 | clade_402 | N | N |
| *Selenomonas artemidis* | 1692 | HM596274 | clade_403 | N | N |
| *Selenomonas* sp. FOBRC9 | 1704 | HQ616378 | clade_403 | N | N |
| *Selenomonas* sp. oral taxon 137 | 1715 | AENV01000007 | clade_403 | N | N |
| *Desmospora activa* | 751 | AM940019 | clade_404 | N | N |
| *Desmospora* sp. 8437 | 752 | AFHT01000143 | clade_404 | N | N |
| *Paenibacillus* sp. oral taxon F45 | 1407 | HM099647 | clade_404 | N | N |

TABLE 1-continued

| OTU | SEQ ID Number | Public DB Accession | Phylogenetic Clade | Spore Former | Pathogen Status |
|---|---|---|---|---|---|
| *Corynebacterium ammoniagenes* | 682 | ADNS01000011 | clade_405 | N | N |
| *Corynebacterium aurimucosum* | 687 | ACLH01000041 | clade_405 | N | N |
| *Corynebacterium bovis* | 688 | AF537590 | clade_405 | N | N |
| *Corynebacterium canis* | 689 | GQ871934 | clade_405 | N | N |
| *Corynebacterium casei* | 690 | NR_025101 | clade_405 | N | N |
| *Corynebacterium durum* | 694 | Z97069 | clade_405 | N | N |
| *Corynebacterium efficiens* | 695 | ACLI01000121 | clade_405 | N | N |
| *Corynebacterium falsenii* | 696 | Y13024 | clade_405 | N | N |
| *Corynebacterium flavescens* | 697 | NR_037040 | clade_405 | N | N |
| *Corynebacterium glutamicum* | 701 | BA000036 | clade_405 | N | N |
| *Corynebacterium jeikeium* | 704 | ACYW01000001 | clade_405 | N | OP |
| *Corynebacterium kroppenstedtii* | 705 | NR_026380 | clade_405 | N | N |
| *Corynebacterium lipophiloflavum* | 706 | ACHJ01000075 | clade_405 | N | N |
| *Corynebacterium matruchotii* | 709 | ACSH02000003 | clade_405 | N | N |
| *Corynebacterium minutissimum* | 710 | X82064 | clade_405 | N | N |
| *Corynebacterium resistens* | 718 | ADGN01000058 | clade_405 | N | N |
| *Corynebacterium simulans* | 720 | AF537604 | clade_405 | N | N |
| *Corynebacterium singulare* | 721 | NR_026394 | clade_405 | N | N |
| *Corynebacterium* sp. 1 ex sheep | 722 | Y13427 | clade_405 | N | N |
| *Corynebacterium* sp. NML 99_0018 | 726 | GU238413 | clade_405 | N | N |
| *Corynebacterium striatum* | 727 | ACGE01000001 | clade_405 | N | OP |
| *Corynebacterium urealyticum* | 732 | X81913 | clade_405 | N | OP |
| *Corynebacterium variabile* | 734 | NR_025314 | clade_405 | N | N |
| *Ruminococcus callidus* | 1658 | NR_029160 | clade_406 | Y | N |
| *Ruminococcus champanellensis* | 1659 | FP929052 | clade_406 | Y | N |
| *Ruminococcus* sp. 18P13 | 1665 | AJ515913 | clade_406 | Y | N |
| *Ruminococcus* sp. 9SE51 | 1667 | FM954974 | clade_406 | Y | N |
| *Aerococcus sanguinicola* | 98 | AY837833 | clade_407 | N | N |
| *Aerococcus urinae* | 99 | CP002512 | clade_407 | N | N |
| *Aerococcus urinaeequi* | 100 | NR_043443 | clade_407 | N | N |
| *Aerococcus viridans* | 101 | ADNT01000041 | clade_407 | N | N |
| *Anaerostipes caccae* | 162 | ABAX03000023 | clade_408 | Y | N |
| *Anaerostipes* sp. 3_2_56FAA | 163 | ACWB01000002 | clade_408 | Y | N |
| Clostridiales bacterium 1_7_47FAA | 541 | ABQR01000074 | clade_408 | Y | N |
| Clostridiales sp. SM4_1 | 542 | FP929060 | clade_408 | Y | N |
| Clostridiales sp. SSC_2 | 544 | FP929061 | clade_408 | Y | N |
| *Clostridium aerotolerans* | 546 | X76163 | clade_408 | Y | N |
| *Clostridium aldenense* | 547 | NR_043680 | clade_408 | Y | N |
| *Clostridium algidixylanolyticum* | 550 | NR_028726 | clade_408 | Y | N |
| *Clostridium amygdalinum* | 552 | AY353957 | clade_408 | Y | N |
| *Clostridium asparagiforme* | 554 | ACCJ01000522 | clade_408 | Y | N |
| *Clostridium bolteae* | 559 | ABCC02000039 | clade_408 | Y | N |
| *Clostridium celerecrescens* | 566 | JQ246092 | clade_408 | Y | N |
| *Clostridium citroniae* | 569 | ADLJ01000059 | clade_408 | Y | N |
| *Clostridium clostridiiformes* | 571 | M59089 | clade_408 | Y | N |
| *Clostridium clostridioforme* | 572 | NR_044715 | clade_408 | Y | N |
| *Clostridium hathewayi* | 590 | AY552788 | clade_408 | Y | N |
| *Clostridium indolis* | 594 | AF028351 | clade_408 | Y | N |
| *Clostridium lavalense* | 600 | EF564277 | clade_408 | Y | N |
| *Clostridium saccharolyticum* | 620 | CP002109 | clade_408 | Y | N |
| *Clostridium* sp. M62_1 | 633 | ACFX02000046 | clade_408 | Y | N |
| *Clostridium* sp. SS2_1 | 638 | ABGC03000041 | clade_408 | Y | N |
| *Clostridium sphenoides* | 643 | X73449 | clade_408 | Y | N |
| *Clostridium symbiosum* | 652 | ADLQ01000114 | clade_408 | Y | N |
| *Clostridium xylanolyticum* | 658 | NR_037068 | clade_408 | Y | N |
| *Eubacterium hadrum* | 847 | FR749933 | clade_408 | Y | N |
| *Fusobacterium naviforme* | 898 | HQ223106 | clade_408 | N | N |
| Lachnospiraceae bacterium 3_1_57FAA | 1052 | ACTP01000124 | clade_408 | Y | N |
| Lachnospiraceae bacterium 5_1_63FAA | 1055 | ACTS01000081 | clade_408 | Y | N |
| Lachnospiraceae bacterium A4 | 1059 | DQ789118 | clade_408 | Y | N |
| Lachnospiraceae bacterium DJF VP30 | 1060 | EU728771 | clade_408 | Y | N |
| Lachnospiraceae genomosp. C1 | 1065 | AY278618 | clade_408 | Y | N |
| *Moryella indoligenes* | 1268 | AF527773 | clade_408 | N | N |
| *Clostridium difficile* | 578 | NC_013315 | clade_409 | Y | OP |
| *Selenomonas* genomosp. P5 | 1697 | AY341820 | clade_410 | N | N |
| *Selenomonas* sp. oral clone IQ048 | 1710 | AY349408 | clade_410 | N | N |
| *Selenomonas sputigena* | 1717 | ACKP02000033 | clade_410 | N | N |
| *Hyphomicrobium sulfonivorans* | 1007 | AY468372 | clade_411 | N | N |
| *Methylocella silvestris* | 1228 | NR_074237 | clade_411 | N | N |
| *Legionella pneumophila* | 1153 | NC_002942 | clade_412 | N | OP |
| *Lactobacillus coryniformis* | 1077 | NR_044705 | clade_413 | N | N |
| *Arthrobacter agilis* | 178 | NR_026198 | clade_414 | N | N |
| *Arthrobacter arilaitensis* | 179 | NR_074608 | clade_414 | N | N |
| *Arthrobacter bergerei* | 180 | NR_025612 | clade_414 | N | N |
| *Arthrobacter globiformis* | 181 | NR_026187 | clade_414 | N | N |
| *Arthrobacter nicotianae* | 182 | NR_026190 | clade_414 | N | N |
| *Mycobacterium abscessus* | 1269 | AGQU01000002 | clade_418 | N | OP |

TABLE 1-continued

| OTU | SEQ ID Number | Public DB Accession | Phylogenetic Clade | Spore Former | Pathogen Status |
|---|---|---|---|---|---|
| *Mycobacterium chelonae* | 1273 | AB548610 | clade_418 | N | OP |
| *Bacteroides salanitronis* | 291 | CP002530 | clade_419 | N | N |
| *Paraprevotella xylaniphila* | 1427 | AFBR01000011 | clade_419 | N | N |
| *Barnesiella intestinihominis* | 336 | AB370251 | clade_420 | N | N |
| *Barnesiella viscericola* | 337 | NR_041508 | clade_420 | N | N |
| *Parabacteroides* sp. NS31_3 | 1422 | JN029805 | clade_420 | N | N |
| Porphyromonadaceae bacterium NML 060648 | 1470 | EF184292 | clade_420 | N | N |
| *Tannerella forsythia* | 1913 | CP003191 | clade_420 | N | N |
| *Tannerella* sp. 6_1_58FAA_CT1 | 1914 | ACWX01000068 | clade_420 | N | N |
| *Mycoplasma amphoriforme* | 1311 | AY531656 | clade_421 | N | N |
| *Mycoplasma genitalium* | 1317 | L43967 | clade_421 | N | N |
| *Mycoplasma pneumoniae* | 1322 | NC_000912 | clade_421 | N | N |
| *Mycoplasma penetrans* | 1321 | NC_004432 | clade_422 | N | N |
| *Ureaplasma parvum* | 1966 | AE002127 | clade_422 | N | N |
| *Ureaplasma urealyticum* | 1967 | AAYN01000002 | clade_422 | N | N |
| *Treponema* genomosp. P1 | 1927 | AY341822 | clade_425 | N | N |
| *Treponema* sp. oral taxon 228 | 1943 | GU408580 | clade_425 | N | N |
| *Treponema* sp. oral taxon 230 | 1944 | GU408603 | clade_425 | N | N |
| *Treponema* sp. oral taxon 231 | 1945 | GU408631 | clade_425 | N | N |
| *Treponema* sp. oral taxon 232 | 1946 | GU408646 | clade_425 | N | N |
| *Treponema* sp. oral taxon 235 | 1947 | GU408673 | clade_425 | N | N |
| *Treponema* sp. ovine footrot | 1959 | AJ010951 | clade_425 | N | N |
| *Treponema vincentii* | 1960 | ACYH01000036 | clade_425 | N | OP |
| *Eubacterium* sp. AS15b | 862 | HQ616364 | clade_428 | Y | N |
| *Eubacterium* sp. OBRC9 | 863 | HQ616354 | clade_428 | Y | N |
| *Eubacterium* sp. oral clone OH3A | 871 | AY947497 | clade_428 | Y | N |
| *Eubacterium yurii* | 876 | AEES01000073 | clade_428 | Y | N |
| *Clostridium acetobutylicum* | 545 | NR_074511 | clade_430 | Y | N |
| *Clostridium algidicarnis* | 549 | NR_041746 | clade_430 | Y | N |
| *Clostridium cadaveris* | 562 | AB542932 | clade_430 | Y | N |
| *Clostridium carboxidivorans* | 563 | FR733710 | clade_430 | Y | N |
| *Clostridium estertheticum* | 580 | NR_042153 | clade_430 | Y | N |
| *Clostridium fallax* | 581 | NR_044714 | clade_430 | Y | N |
| *Clostridium felsineum* | 583 | AF270502 | clade_430 | Y | N |
| *Clostridium frigidicarnis* | 584 | NR_024919 | clade_430 | Y | N |
| *Clostridium kluyveri* | 598 | NR_074165 | clade_430 | Y | N |
| *Clostridium magnum* | 603 | X77835 | clade_430 | Y | N |
| *Clostridium putrefaciens* | 615 | NR_024995 | clade_430 | Y | N |
| *Clostridium* sp. HPB_46 | 629 | AY862516 | clade_430 | Y | N |
| *Clostridium tyrobutyricum* | 656 | NR_044718 | clade_430 | Y | N |
| *Burkholderiales bacterium* 1_1_47 | 452 | ADCQ01000066 | clade_432 | N | OP |
| *Parasutterella excrementihominis* | 1429 | AFBP01000029 | clade_432 | N | N |
| *Parasutterella secunda* | 1430 | AB491209 | clade_432 | N | N |
| *Sutterella morbirenis* | 1898 | AJ832129 | clade_432 | N | N |
| *Sutterella parvirubra* | 1899 | AB300989 | clade_432 | Y | N |
| *Sutterella sanguinus* | 1900 | AJ748647 | clade_432 | N | N |
| *Sutterella* sp. YIT 12072 | 1901 | AB491210 | clade_432 | N | N |
| *Sutterella stercoricanis* | 1902 | NR_025600 | clade_432 | N | N |
| *Sutterella wadsworthensis* | 1903 | ADMF01000048 | clade_432 | N | N |
| *Propionibacterium freudenreichii* | 1572 | NR_036972 | clade_433 | N | N |
| *Propionibacterium* sp. oral taxon 192 | 1580 | GQ422728 | clade_433 | N | N |
| *Tessaracoccus* sp. oral taxon F04 | 1917 | HM099640 | clade_433 | N | N |
| *Peptoniphilus ivorii* | 1445 | Y07840 | clade_434 | N | N |
| *Peptoniphilus* sp. gpac007 | 1448 | AM176517 | clade_434 | N | N |
| *Peptoniphilus* sp. gpac018A | 1449 | AM176519 | clade_434 | N | N |
| *Peptoniphilus* sp. gpac148 | 1451 | AM176535 | clade_434 | N | N |
| *Flexispira rappini* | 887 | AY126479 | clade_436 | N | N |
| *Helicobacter bilis* | 993 | ACDN01000023 | clade_436 | N | N |
| *Helicobacter cinaedi* | 995 | ABQT01000054 | clade_436 | N | N |
| *Helicobacter* sp. None | 998 | U44756 | clade_436 | N | N |
| *Brevundimonas subvibrioides* | 429 | CP002102 | clade_438 | N | N |
| *Hyphomonas neptunium* | 1008 | NR_074092 | clade_438 | N | N |
| *Phenylobacterium zucineum* | 1465 | AY628697 | clade_438 | N | N |
| *Acetanaerobaeterium elongatum* | 4 | NR_042930 | clade_439 | Y | N |
| *Clostridium cellulosi* | 567 | NR_044624 | clade_439 | Y | N |
| *Ethanoligenens harbinense* | 832 | AY675965 | clade_439 | Y | N |
| *Streptococcus downei* | 1793 | AEKN01000002 | clade_441 | N | N |
| *Streptococcus* sp. SHV515 | 1848 | Y07601 | clade_441 | N | N |
| *Acinetobacter* sp. CIP 53.82 | 40 | JQ638584 | clade_443 | N | N |
| *Halomonas elongata* | 990 | NR_074782 | clade_443 | N | N |
| *Halomonas johnsoniae* | 991 | FR775979 | clade_443 | N | N |
| *Butyrivibrio fibrisolvens* | 456 | U41172 | clade_444 | N | N |
| *Eubacterium rectale* | 856 | FP929042 | clade_444 | Y | N |
| *Eubacterium* sp. oral clone GI038 | 865 | AY349374 | clade_444 | Y | N |
| *Lachnobacterium bovis* | 1045 | GU324407 | clade_444 | Y | N |
| *Roseburia cecicola* | 1634 | GU233441 | clade_444 | Y | N |

TABLE 1-continued

| OTU | SEQ ID Number | Public DB Accession | Phylogenetic Clade | Spore Former | Pathogen Status |
|---|---|---|---|---|---|
| *Roseburia faecalis* | 1635 | AY804149 | clade_444 | Y | N |
| *Roseburia faecis* | 1636 | AY305310 | clade_444 | Y | N |
| *Roseburia hominis* | 1637 | AJ270482 | clade_444 | Y | N |
| *Roseburia intestinalis* | 1638 | FP929050 | clade_444 | Y | N |
| *Roseburia inulinivorans* | 1639 | AJ270473 | clade_444 | Y | N |
| *Roseburia* sp. 11SE37 | 1640 | FM954975 | clade_444 | N | N |
| *Roseburia* sp. 11SE38 | 1641 | FM954976 | clade_444 | N | N |
| *Shuttleworthia satelles* | 1728 | ACIP02000004 | clade_444 | N | N |
| *Shuttleworthia* sp. MSX8B | 1729 | HQ616383 | clade_444 | N | N |
| *Shuttleworthia* sp. oral taxon G69 | 1730 | GU432167 | clade_444 | N | N |
| *Bdellovibrio* sp. MPA | 344 | AY294215 | clade_445 | N | N |
| *Desulfobulbus* sp. oral clone CH031 | 755 | AY005036 | clade_445 | N | N |
| *Desulfovibrio desulfuricans* | 757 | DQ092636 | clade_445 | N | N |
| *Desulfovibrio fairfieldensis* | 758 | U42221 | clade_445 | N | N |
| *Desulfovibrio piger* | 759 | AF192152 | clade_445 | N | N |
| *Desulfovibrio* sp. 3_1_syn3 | 760 | ADDR01000239 | clade_445 | N | N |
| *Geobacter bemidjiensis* | 941 | CP001124 | clade_445 | N | N |
| *Brachybacterium alimentarium* | 401 | NR_026269 | clade_446 | N | N |
| *Brachybacterium conglomeratum* | 402 | AB537169 | clade_446 | N | N |
| *Brachybacterium tyrofermentans* | 403 | NR_026272 | clade_446 | N | N |
| *Dermabacter hominis* | 749 | FJ263375 | clade_446 | N | N |
| *Aneurinibacillus thermoaerophilus* | 171 | NR_029303 | clade_448 | N | N |
| *Brevibacillus agri* | 409 | NR_040983 | clade_448 | N | N |
| *Brevibacillus brevis* | 410 | NR_041524 | clade_448 | Y | N |
| *Brevibacillus centrosporus* | 411 | NR_043414 | clade_448 | N | N |
| *Brevibacillus choshinensis* | 412 | NR_040980 | clade_448 | N | N |
| *Brevibacillus invocatus* | 413 | NR_041836 | clade_448 | N | N |
| *Brevibacillus laterosporus* | 414 | NR_037005 | clade_448 | Y | N |
| *Brevibacillus parabrevis* | 415 | NR_040981 | clade_448 | N | N |
| *Brevibacillus reuszeri* | 416 | NR_040982 | clade_448 | N | N |
| *Brevibacillus* sp. phR | 417 | JN837488 | clade_448 | N | N |
| *Brevibacillus thermoruber* | 418 | NR_026514 | clade_448 | N | N |
| *Lactobacillus murinus* | 1100 | NR_042231 | clade_449 | N | N |
| *Lactobacillus oeni* | 1102 | NR_043095 | clade_449 | N | N |
| *Lactobacillus ruminis* | 1115 | ACGS02000043 | clade_449 | N | N |
| *Lactobacillus vini* | 1141 | NR_042196 | clade_449 | N | N |
| *Gemella haemolysans* | 924 | ACDZ02000012 | clade_450 | N | N |
| *Gemella morbillorum* | 925 | NR_025904 | clade_450 | N | N |
| *Gemella morbillorum* | 926 | ACRX01000010 | clade_450 | N | N |
| *Gemella sanguinis* | 927 | ACRY01000057 | clade_450 | N | N |
| *Gemella* sp. oral clone ASCE02 | 929 | AY923133 | clade_450 | N | N |
| *Gemella* sp. oral clone ASCF04 | 930 | AY923139 | clade_450 | N | N |
| *Gemella* sp. oral clone ASCF12 | 931 | AY923143 | clade_450 | N | N |
| *Gemella* sp. WAL 1945J | 928 | EU427463 | clade_450 | N | N |
| *Bacillus coagulans* | 206 | DQ297928 | clade_451 | Y | OP |
| *Sporolactobacillus inulinus* | 1752 | NR_040962 | clade_451 | Y | N |
| *Sporolactobacillus nakayamae* | 1753 | NR_042247 | clade_451 | N | N |
| *Gluconacetobacter entanii* | 945 | NR_028909 | clade_452 | N | N |
| *Gluconacetobacter europaeus* | 946 | NR_026513 | clade_452 | N | N |
| *Gluconacetobacter hansenii* | 947 | NR_026133 | clade_452 | N | N |
| *Gluconacetobacter oboediens* | 949 | NR_041295 | clade_452 | N | N |
| *Gluconacetobacter xylinus* | 950 | NR_074338 | clade_452 | N | N |
| *Auritibacter ignavus* | 193 | FN554542 | clade_453 | N | N |
| *Dermacoccus* sp. Ellin185 | 750 | AEIQ01000090 | clade_453 | N | N |
| *Janibacter limosus* | 1013 | NR_026362 | clade_453 | N | N |
| *Janibacter melonis* | 1014 | EF063716 | clade_453 | N | N |
| *Kocuria palustris* | 1041 | EU333884 | clade_453 | Y | N |
| *Acetobacter aceti* | 7 | NR_026121 | clade_454 | N | N |
| *Acetobacter fabarum* | 8 | NR_042678 | clade_454 | N | N |
| *Acetobacter lovaniensis* | 9 | NR_040832 | clade_454 | N | N |
| *Acetobacter malorum* | 10 | NR_025513 | clade_454 | N | N |
| *Acetobacter orientalis* | 11 | NR_028625 | clade_454 | N | N |
| *Acetobacter pasteurianus* | 12 | NR_026107 | clade_454 | N | N |
| *Acetobacter pomorum* | 13 | NR_042112 | clade_454 | N | N |
| *Acetobacter syzygii* | 14 | NR_040868 | clade_454 | N | N |
| *Acetobacter tropicalis* | 15 | NR_036881 | clade_454 | N | N |
| *Gluconacetobacter azotocaptans* | 943 | NR_028767 | clade_454 | N | N |
| *Gluconacetobacter diazotrophicus* | 944 | NR_074292 | clade_454 | N | N |
| *Gluconacetobacter johannae* | 948 | NR_024959 | clade_454 | N | N |
| *Nocardia brasiliensis* | 1351 | AIHV01000038 | clade_455 | N | N |
| *Nocardia cyriacigeorgica* | 1352 | HQ009486 | clade_455 | N | N |
| *Nocardia farcinica* | 1353 | NC_006361 | clade_455 | Y | N |
| *Nocardia puris* | 1354 | NR_028994 | clade_455 | N | N |
| *Nocardia* sp. 01_Je_025 | 1355 | GU574059 | clade_455 | N | N |
| *Rhodococcus equi* | 1623 | ADNW01000058 | clade_455 | N | N |
| *Bacillus* sp. oral taxon F28 | 247 | HM099650 | clade_456 | Y | OP |
| *Oceanobacillus caeni* | 1358 | NR_041533 | clade_456 | N | N |

TABLE 1-continued

| OTU | SEQ ID Number | Public DB Accession | Phylogenetic Clade | Spore Former | Pathogen Status |
|---|---|---|---|---|---|
| *Oceanobacillus* sr. Ndiop | 1359 | CAER01000083 | clade_456 | N | N |
| *Ornithinibacillus bavariensis* | 1384 | NR_044923 | clade_456 | N | N |
| *Ornithinibacillus* sp. 7_10AIA | 1385 | FN397526 | clade_456 | N | N |
| *Virgibacillus proomii* | 2005 | NR_025308 | clade_456 | N | N |
| *Corynebacterium amycolatum* | 683 | ABZU01000033 | clade_457 | N | OP |
| *Corynebacterium hansenii* | 702 | AM946639 | clade_457 | N | N |
| *Corynebacterium xerosis* | 735 | FN179330 | clade_457 | N | OP |
| Staphylococcaceae bacterium NML *92* _0017 | 1756 | AY841362 | clade_458 | N | N |
| *Staphylococcus fleurettii* | 1766 | NR_041326 | clade_458 | N | N |
| *Staphylococcus sciuri* | 1774 | NR_025520 | clade_458 | N | N |
| *Staphylococcus vitulinus* | 1779 | NR_024670 | clade_458 | N | N |
| *Stenotrophomonas maltophilia* | 1782 | AAVZ01000005 | clade_459 | N | N |
| *Stenotrophomonas* sp. FG_6 | 1783 | EF017810 | clade_459 | N | N |
| *Mycobacterium africanum* | 1270 | AF480605 | clade_46 | N | OP |
| *Mycobacterium alsiensis* | 1271 | AJ938169 | clade_46 | N | OP |
| *Mycobacterium avium* | 1272 | CP000479 | clade_46 | N | OP |
| *Mycobacterium colombiense* | 1274 | AM062764 | clade_46 | N | OP |
| *Mycobacterium gordonae* | 1276 | GU142930 | clade_46 | N | OP |
| *Mycobacterium intracellulare* | 1277 | GQ153276 | clade_46 | N | OP |
| *Mycobacterium kansasii* | 1278 | AF480601 | clade_46 | N | OP |
| *Mycobacterium lacus* | 1279 | NR_025175 | clade_46 | N | OP |
| *Mycobacterium leprae* | 1280 | FM211192 | clade_46 | N | OP |
| *Mycobacterium lepromatosis* | 1281 | EU203590 | clade_46 | N | OP |
| *Mycobacterium mantenii* | 1283 | FJ042897 | clade_46 | N | OP |
| *Mycobacterium marinum* | 1284 | NC_010612 | clade_46 | N | OP |
| *Mycobacterium microti* | 1285 | NR_025234 | clade_46 | N | OP |
| *Mycobacterium parascrofulaceum* | 1287 | ADNV01000350 | clade_46 | N | OP |
| *Mycobacterium seoulense* | 1290 | DQ536403 | clade_46 | N | OP |
| *Mycobacterium* sp. 1761 | 1292 | EU703150 | clade_46 | N | N |
| *Mycobacterium* sp. 1791 | 1295 | EU703148 | clade_46 | N | N |
| *Mycobacterium* sp. 1797 | 1296 | EU703149 | clade_46 | N | N |
| *Mycobacterium* sp. B10_07.09.0206 | 1298 | HQ174245 | clade_46 | N | N |
| *Mycobacterium* sp. NLA001000736 | 1305 | HM627011 | clade_46 | N | N |
| *Mycobacterium* sp. W | 1306 | DQ437715 | clade_46 | N | N |
| *Mycobacterium tuberculosis* | 1307 | CP001658 | clade_46 | N | Category-C |
| *Mycobacterium ulcerans* | 1308 | AB548725 | clade_46 | N | OP |
| *Mycobacterium vulneris* | 1309 | EU834055 | clade_46 | N | OP |
| *Xanthomonas campestris* | 2016 | EF101975 | clade_461 | N | N |
| *Xanthomonas* sp. kmd_489 | 2017 | EU723184 | clade_461 | N | N |
| *Dietzia natronolimnaea* | 769 | GQ870426 | clade_462 | N | N |
| *Dietzia* sp. BBDP51 | 770 | DQ337512 | clade_462 | N | N |
| *Dietzia* sp. CA149 | 771 | GQ870422 | clade_462 | N | N |
| *Dietzia timorensis* | 772 | GQ870424 | clade_462 | N | N |
| *Gordonia bronchialis* | 951 | NR_027594 | clade_463 | N | N |
| *Gordonia polyisoprenivorans* | 952 | DQ385609 | clade_463 | N | N |
| *Gordonia* sp. KTR9 | 953 | DQ068383 | clade_463 | N | N |
| *Gordonia sputi* | 954 | FJ536304 | clade_463 | N | N |
| *Gordonia terrae* | 955 | GQ848239 | clade_463 | N | N |
| *Leptotrichia goodfellowii* | 1167 | ADAD01000110 | clade_465 | N | N |
| *Leptotrichia* sp. oral clone IK040 | 1174 | AY349387 | clade_465 | N | N |
| *Leptotrichia* sp. oral clone P2PB_51 P1 | 1175 | AY207053 | clade_465 | N | N |
| Bacteroidales genomosp. P7 oral clone MB3_P19 | 264 | DQ003623 | clade_466 | N | N |
| *Butyricimonas virosa* | 454 | AB443949 | clade_466 | N | N |
| *Odoribacter laneus* | 1363 | AB490805 | clade_466 | N | N |
| *Odoribacter splanchnicus* | 1364 | CP002544 | clade_466 | N | N |
| *Capnocytophaga gingivalis* | 478 | ACLQ01000011 | clade_467 | N | N |
| *Capnocytophaga granulosa* | 479 | X97248 | clade_467 | N | N |
| *Capnocytophaga* sp. oral clone AH015 | 483 | AY005074 | clade_467 | N | N |
| *Copnocytophoga* sp. oral strain S3 | 487 | AY005073 | clade_467 | N | N |
| *Copnocytophoga* sp. oral taxon 338 | 488 | AEXX01000050 | clade_467 | N | N |
| *Capnocytophaga canimorsus* | 476 | CP002113 | clade_468 | N | N |
| *Copnocytophoga* sp. oral clone ID062 | 485 | AY349368 | clade_468 | N | N |
| *Catenibacterium mitsuokai* | 495 | AB030224 | clade_469 | Y | N |
| *Clostridium* sp. TM_40 | 640 | AB249652 | clade_469 | Y | N |
| *Coprobacillus cateniformis* | 670 | AB030218 | clade_469 | Y | N |
| *Coprobacillus* sp. 29_1 | 671 | ADKX01000057 | clade_469 | Y | N |
| *Lactobacillus catenaformis* | 1075 | M23729 | clade_469 | N | N |
| *Lactobacillus vitulinus* | 1142 | NR_041305 | clade_469 | N | N |
| *Cetobacterium somerae* | 501 | AJ438155 | clade_470 | N | N |
| *Clostridium rectum* | 618 | NR_029271 | clade_470 | Y | N |
| *Fusobacterium gonidiaformans* | 896 | ACET01000043 | clade_470 | N | N |
| *Fusobacterium mortiferum* | 897 | ACDB02000034 | clade_470 | N | N |
| *Fusobacterium necrogenes* | 899 | X55408 | clade_470 | N | N |
| *Fusobacterium necrophorum* | 900 | AM905356 | clade_470 | N | N |
| *Fusobacterium* sp. 12_1B | 905 | AGWJ01000070 | clade_470 | N | N |

TABLE 1-continued

| OTU | SEQ ID Number | Public DB Accession | Phylogenetic Clade | Spore Former | Pathogen Status |
|---|---|---|---|---|---|
| *Fusobacterium* sp. 3_1_5R | 911 | ACDD01000078 | clade_470 | N | N |
| *Fusobacterium* sp. D12 | 918 | ACDG02000036 | clade_470 | N | N |
| *Fusobacterium ulcerans* | 921 | ACDH01000090 | clade_470 | N | N |
| *Fusobacterium varium* | 922 | ACIE01000009 | clade_470 | N | N |
| *Mycoplasma arthritidis* | 1312 | NC_011025 | clade_473 | N | N |
| *Mycoplasma faucium* | 1314 | NR_024983 | clade_473 | N | N |
| *Mycoplasma hominis* | 1318 | AF443616 | clade_473 | N | N |
| *Mycoplasma orale* | 1319 | AY796060 | clade_473 | N | N |
| *Mycoplasma salivarium* | 1324 | M24661 | clade_473 | N | N |
| *Mitsuokella jalaludinii* | 1247 | NR_028840 | clade_474 | N | N |
| *Mitsuokella multacida* | 1248 | ABWK02000005 | clade_474 | N | N |
| *Mitsuokella* sp. oral taxon 521 | 1249 | GU413658 | clade_474 | N | N |
| *Mitsuokella* sp. oral taxon G68 | 1250 | GU432166 | clade_474 | N | N |
| *Selenomonas* genomosp. C1 | 1695 | AY278627 | clade_474 | N | N |
| *Selenomonas* genomosp. P8 oral clone MB5_P06 | 1700 | DQ003628 | clade_474 | N | N |
| *Selenomonas ruminantium* | 1703 | NR_075026 | clade_474 | N | N |
| Veillonellaceae bacterium oral taxon 131 | 1994 | GU402916 | clade_474 | N | N |
| *Alloscardoria omnicolens* | 139 | NR_042583 | clade_475 | N | N |
| *Alloscardovia* sp. OB7196 | 140 | AB425070 | clade_475 | N | N |
| *Bifidobacterium urinalis* | 366 | AJ278695 | clade_475 | N | N |
| *Eubacterium nodatum* | 854 | U13041 | clade_476 | Y | N |
| *Eubacterium saphenum* | 859 | NR_026031 | clade_476 | Y | N |
| *Eubacterium* sp. oral clone JH012 | 867 | AY349373 | clade_476 | Y | N |
| *Eubacterium* sp. oral clone JS001 | 870 | AY349378 | clade_476 | Y | N |
| *Faecalibacterium prausnitzii* | 880 | ACOP02000011 | clade_478 | Y | N |
| *Gemmiger formicilis* | 932 | GU562446 | clade_478 | Y | N |
| *Subdoligranulum variabile* | 1896 | AJ518869 | clade_478 | Y | N |
| Clostridiaceae bacterium JC13 | 532 | JF824807 | clade_479 | Y | N |
| *Clostridium* sp. MLG055 | 634 | AF304435 | clade_479 | Y | N |
| Erysipelotrichaceae bacterium 3_1_53 | 822 | ACTJ01000113 | clade_479 | Y | N |
| *Prevotella loescheii* | 1503 | JN867231 | clade_48 | N | N |
| *Prevotella* sp. oral clone ASCG12 | 1530 | DQ272511 | clade_48 | N | N |
| *Prevotella* sp. oral clone GU027 | 1540 | AY349398 | clade_48 | N | N |
| *Prevotella* sp. oral taxon 472 | 1553 | ACZS01000106 | clade_48 | N | N |
| *Selenomonas dianae* | 1693 | GQ422719 | clade_480 | N | N |
| *Selenomonas flueggei* | 1694 | AF287803 | clade_480 | N | N |
| *Selenomonas* genomosp. C2 | 1696 | AY278628 | clade_480 | N | N |
| *Selenomonas* genomosp. P6 oral clone MB3_C41 | 1698 | DQ003636 | clade_480 | N | N |
| *Selenomonas* genomosp. P7 oral clone MB5_C08 | 1699 | DQ003627 | clade_480 | N | N |
| *Selenomonas infelix* | 1701 | AF287802 | clade_480 | N | N |
| *Selenomonas noxia* | 1702 | GU470909 | clade_480 | N | N |
| *Selenomonas* sp. oral clone FT050 | 1705 | AY349403 | clade_480 | N | N |
| *Selenomonas* sp. oral clone GI064 | 1706 | AY349404 | clade_480 | N | N |
| *Selenomonas* sp. oral clone GT010 | 1707 | AY349405 | clade_480 | N | N |
| *Selenomonas* sp. oral clone HU051 | 1708 | AY349406 | clade_480 | N | N |
| *Selenomonas* sp. oral clone IK004 | 1709 | AY349407 | clade_480 | N | N |
| *Selenomonas* sp. oral clone JI021 | 1711 | AY349409 | clade_480 | N | N |
| *Selenomonas* sp. oral clone JS031 | 1712 | AY349410 | clade_480 | N | N |
| *Selenomonas* sp. oral clone OH4A | 1713 | AY947498 | clade_480 | N | N |
| *Selenomonas* sp. oral clone P2PA_80 P4 | 1714 | AY207052 | clade_480 | N | N |
| *Selenomonas* sp. oral taxon 149 | 1716 | AEEJ01000007 | clade_480 | N | N |
| Veillonellaceae bacterium oral taxon 155 | 1995 | GU470897 | clade_480 | N | N |
| *Clostridium cocleatum* | 575 | NR_026495 | clade_481 | Y | N |
| *Clostridium ramosum* | 617 | M23731 | clade_481 | Y | N |
| *Clostridium saccharogumia* | 619 | DQ100445 | clade_481 | Y | N |
| *Clostridium spiroforme* | 644 | X73441 | clade_481 | Y | N |
| *Coprobacillus* sp. D7 | 672 | ACDT01000199 | clade_481 | Y | N |
| Clostridiales bacterium SY8519 | 535 | AB477431 | clade_482 | Y | N |
| *Clostridium* sp. SY8519 | 639 | AP012212 | clade_482 | Y | N |
| *Eubacterium ramulus* | 855 | AJ011522 | clade_482 | Y | N |
| *Agrococcus jenensis* | 117 | NR_026275 | clade_484 | Y | N |
| *Microbacterium gubbeenense* | 1232 | NR_025098 | clade_484 | N | N |
| *Pseudoclavibacter* sp. Timone | 1590 | FJ375951 | clade_484 | N | N |
| *Tropheryma whipplei* | 1961 | BX251412 | clade_484 | N | N |
| *Zimmermannella bifida* | 2031 | AB012592 | clade_484 | N | N |
| *Erysipelothrix inopinata* | 819 | NR_025594 | clade_485 | Y | N |
| *Erysipelothrix rhusiopathiae* | 820 | ACLK01000021 | clade_485 | Y | N |
| *Erysipelothrix tonsillarum* | 821 | NR_040871 | clade_485 | Y | N |
| *Holdemania filiformis* | 1004 | Y11466 | clade_485 | Y | N |
| *Mollicutes bacterium pACH93* | 1258 | AY297808 | clade_485 | Y | N |
| *Coxiella burnetii* | 736 | CP000890 | clade_486 | Y | Category-B |
| *Legionella hackeliae* | 1151 | M36028 | clade_486 | N | OP |
| *Legionella longbeachae* | 1152 | M36029 | clade_486 | N | OP |
| *Legionella* sp. D3923 | 1154 | JN380999 | clade_486 | N | OP |

TABLE 1-continued

| OTU | SEQ ID Number | Public DB Accession | Phylogenetic Clade | Spore Former | Pathogen Status |
|---|---|---|---|---|---|
| *Legionella* sp. D4088 | 1155 | JN381012 | clade_486 | N | OP |
| *Legionella* sp. H63 | 1156 | JF831047 | clade_486 | N | OP |
| *Legionella* sp. NML 93L054 | 1157 | GU062706 | clade_486 | N | OP |
| *Legionella steelei* | 1158 | HQ398202 | clade_486 | N | OP |
| *Tatlockia micdadei* | 1915 | M36032 | clade_486 | N | N |
| *Clostridium hiranonis* | 591 | AB023970 | clade_487 | Y | N |
| *Clostridium irregulare* | 596 | NR_029249 | clade_487 | Y | N |
| *Helicobacter pullorum* | 996 | ABQU01000097 | clade_489 | N | N |
| Acetobacteraceae bacterium AT_5844 | 16 | AGEZ01000040 | clade_490 | N | N |
| *Roseomonas cervicalis* | 1643 | ADVL01000363 | clade_490 | N | N |
| *Roseomonas mucosa* | 1644 | NR_028857 | clade_490 | N | N |
| *Roseomonas* sp. NML94_0193 | 1645 | AF533357 | clade_490 | N | N |
| *Roseomonas* sp. NML97_0121 | 1646 | AF533359 | clade_490 | N | N |
| *Roseornonas* sp. NML98_0009 | 1647 | AF533358 | clade_490 | N | N |
| *Roseomonas* sp. NML98_0157 | 1648 | AF533360 | clade_490 | N | N |
| *Rickettsia akari* | 1627 | CP000847 | clade_492 | N | OP |
| *Rickettsia conorii* | 1628 | AE008647 | clade_492 | N | OP |
| *Rickettsia prowazekii* | 1629 | M21789 | clade_492 | N | Category-B |
| *Rickettsia rickettsii* | 1630 | NC_010263 | clade_492 | N | OP |
| *Rickettsia slovaca* | 1631 | L36224 | clade_492 | N | OP |
| *Rickettsia typhi* | 1632 | AE017197 | clade_492 | N | OP |
| *Anaeroglobus geminatus* | 160 | AGCJ01000054 | clade_493 | N | N |
| *Megasphaera* genomosp. C1 | 1201 | AY278622 | clade_493 | N | N |
| *Megasphaera micronuciformis* | 1203 | AECS01000020 | clade_493 | N | N |
| *Clostridium orbiscindens* | 609 | Y18187 | clade_494 | Y | N |
| *Clostridium* sp. NML 04A032 | 637 | EU815224 | clade_494 | Y | N |
| *Flavonifractor plautii* | 886 | AY724678 | clade_494 | Y | N |
| *Pseudoflavonifractor capillosus* | 1591 | AY136666 | clade_494 | Y | N |
| Ruminococcaceae bacterium D16 | 1655 | ADDX01000083 | clade_494 | Y | N |
| *Acetivibrio cellulolyticus* | 5 | NR_025917 | clade_495 | Y | N |
| Clostridiales genomosp. BVAB3 | 540 | CP001850 | clade_495 | N | N |
| *Clostridium aldrichii* | 548 | NR_026099 | clade_495 | Y | N |
| *Clostridium clariflavum* | 570 | NR_041235 | clade_495 | Y | N |
| *Clostridium stercorarium* | 647 | NR_025100 | clade_495 | Y | N |
| *Clostridium straminisolvens* | 649 | NR_024829 | clade_495 | Y | N |
| *Clostridium thermocellum* | 655 | NR_074629 | clade_495 | Y | N |
| *Tsukamurella paurometabola* | 1963 | X80628 | clade_496 | N | N |
| *Tsukamurella tyrosinosolvens* | 1964 | AB478958 | clade_496 | N | N |
| *Abiotrophia* para_adiacens | 2 | AB022027 | clade_497 | N | N |
| *Carnobacterium divergens* | 492 | NR_044706 | clade_497 | N | N |
| *Carnobacterium maltaromaticum* | 493 | NC_019425 | clade_497 | N | N |
| *Enterococcus avium* | 800 | AF133535 | clade_497 | N | N |
| *Enterococcus caccae* | 801 | AY943820 | clade_497 | N | N |
| *Enterococcus casseliflavus* | 802 | AEWT01000047 | clade_497 | N | N |
| *Enterococcus durans* | 803 | AJ276354 | clade_497 | N | N |
| *Enterococcus faecalis* | 804 | AE016830 | clade_497 | N | N |
| *Enterococcus faecium* | 805 | AM157434 | clade_497 | N | N |
| *Enterococcus gallinarum* | 806 | AB269767 | clade_497 | N | N |
| *Enterococcus gilvus* | 807 | AY033814 | clade_497 | N | N |
| *Enterococcus hawaiiensis* | 808 | AY321377 | clade_497 | N | N |
| *Enterococcus hirae* | 809 | AF061011 | clade_497 | N | N |
| *Enterococcus italicus* | 810 | AEPV01000109 | clade_497 | N | N |
| *Enterococcus mundtii* | 811 | NR_024906 | clade_497 | N | N |
| *Enterococcus raffinosus* | 812 | FN600541 | clade_497 | N | N |
| *Enterococcus* sp. BV2CASA2 | 813 | JN809766 | clade_497 | N | N |
| *Enterococcus* sp. CCRI 16620 | 814 | GU457263 | clade_497 | N | N |
| *Enterococcus* sp. F95 | 815 | FJ463817 | clade_497 | N | N |
| *Enterococcus* sp. RfL6 | 816 | AJ133478 | clade_497 | N | N |
| *Enterococcus thailandicus* | 817 | AY321376 | clade_497 | N | N |
| *Fusobacterium canifelinum* | 893 | AY162222 | clade_497 | N | N |
| *Fusobacterium* genomosp. C1 | 894 | AY278616 | clade_497 | N | N |
| *Fusobacterium* genomosp. C2 | 895 | AY278617 | clade_497 | N | N |
| *Fusobacterium nucleatum* | 901 | ADVK01000034 | clade_497 | Y | N |
| *Fusobacterium periodonticum* | 902 | ACJY01000002 | clade_497 | N | N |
| *Fusobacterium* sp. 1_1_41FAA | 906 | ADGG01000053 | clade_497 | N | N |
| *Fusobacterium* sp. 11_3_2 | 904 | ACUO01000052 | clade_497 | N | N |
| *Fusobacterium* sp. 2_1_31 | 907 | ACDC02000018 | clade_497 | N | N |
| *Fusobacterium* sp. 3_1_27 | 908 | ADGF01000045 | clade_497 | N | N |
| *Fusobacterium* sp. 3_1_33 | 909 | ACQE01000178 | clade_497 | N | N |
| *Fusobacterium* sp. 3_1_36A2 | 910 | ACPU01000044 | clade_497 | N | N |
| *Fusobacterium* sp. AC18 | 912 | HQ616357 | clade_497 | N | N |
| *Fusobacterium* sp. ACB2 | 913 | HQ616358 | clade_497 | N | N |
| *Fusobacterium* sp. AS2 | 914 | HQ616361 | clade_497 | N | N |
| *Fusobacterium* sp. CM1 | 915 | HQ616371 | clade_497 | N | N |
| *Fusobacterium* sp. CM21 | 916 | HQ616375 | clade_497 | N | N |
| *Fusobacterium* sp. CM22 | 917 | HQ616376 | clade_497 | N | N |
| *Fusobacterium* sp. oral clone ASCF06 | 919 | AY923141 | clade_497 | N | N |

TABLE 1-continued

| OTU | SEQ ID Number | Public DB Accession | Phylogenetic Clade | Spore Former | Pathogen Status |
|---|---|---|---|---|---|
| *Fusobacterium* sp. oral clone ASCF11 | 920 | AY953256 | clade_497 | N | N |
| *Granulicatella adiacens* | 959 | ACKZ01000002 | clade_497 | N | N |
| *Granulicatella elegans* | 960 | AB252689 | clade_497 | N | N |
| *Granulicatella paradiacens* | 961 | AY879298 | clade_497 | N | N |
| *Granulicatella* sp. oral clone ASC02 | 963 | AY923126 | clade_497 | N | N |
| *Granulicatella* sp. oral clone ASCA05 | 964 | DQ341469 | clade_497 | N | N |
| *Granulicatella* sp. oral clone ASCB09 | 965 | AY953251 | clade_497 | N | N |
| *Granulicatella* sp. oral. clone ASCG05 | 966 | AY923146 | clade_497 | N | N |
| *Tetragenococcus halophilus* | 1918 | NR_075020 | clade_497 | N | N |
| *Tetragenococcus koreensis* | 1919 | NR_043113 | clade_497 | N | N |
| *Vagococcus fluvialis* | 1973 | NR_026489 | clade_497 | N | N |
| *Chryseobacterium anthropi* | 514 | AM982793 | clade_498 | N | N |
| *Chryseobacterium gleum* | 515 | ACKQ02000003 | clade_498 | N | N |
| *Chryseobacterium hominis* | 516 | NR_042517 | clade_498 | N | N |
| *Treponema refringens* | 1936 | AF426101 | clade_499 | N | OP |
| *Treponema* sp. oral clone JU031 | 1941 | AY349416 | clade_499 | N | N |
| *Treponema* sp. oral taxon 239 | 1948 | GU408738 | clade_499 | N | N |
| *Treponema* sp. oral taxon 271 | 1955 | GU408871 | clade_499 | N | N |
| *Alistipes finegoldii* | 129 | NR_043064 | clade_500 | N | N |
| *Alistipes onderdonkii* | 131 | NR_043318 | clade_500 | N | N |
| *Alistipes putredinis* | 132 | ABFK02000017 | clade_500 | N | N |
| *Alistipes shahii* | 133 | FP929032 | clade_500 | N | N |
| *Alistipes* sp. HGB5 | 134 | AENZ01000082 | clade_500 | N | N |
| *Alistipes* sp. JC50 | 135 | JF824804 | clade_500 | N | N |
| *Alistipes* sp. RMA 9912 | 136 | GQ140629 | clade_500 | N | N |
| *Mycoplasma agalactiae* | 1310 | AF010477 | clade_501 | N | N |
| *Mycoplasma bovoculi* | 1313 | NR_025987 | clade_501 | N | N |
| *Mycoplasma fermentans* | 1315 | CP002458 | clade_501 | N | N |
| *Mycoplasma flocculare* | 1316 | X62699 | clade_501 | N | N |
| *Mycoplasma ovipneumoniae* | 1320 | NR_025989 | clade_501 | N | N |
| *Arcobacter butzleri* | 176 | AEPT01000071 | clade_502 | N | N |
| *Arcobacter cryaerophilus* | 177 | NR_025905 | clade_502 | N | N |
| *Campylobacter curvus* | 461 | NC_009715 | clade_502 | N | OP |
| *Campylobacter rectus* | 467 | ACFU01000050 | clade_502 | N | OP |
| *Campylobacter showae* | 468 | ACVQ01000030 | clade_502 | N | OP |
| *Campylobacter* sp. FOBRC14 | 469 | HQ616379 | clade_502 | N | OP |
| *Campylobacter* sp. FOBRC15 | 470 | HQ616380 | clade_502 | N | OP |
| *Campylobacter* sp. oral clone BB120 | 471 | AY005038 | clade_502 | N | OP |
| *Campylobacter sputorum* | 472 | NR_044839 | clade_502 | N | OP |
| *Bacteroides ureolyticus* | 330 | GQ167666 | clade_504 | N | N |
| *Campylobacter gracilis* | 463 | ACYG01000026 | clade_504 | N | OP |
| *Campylobacter hominis* | 464 | NC_009714 | clade_504 | N | OP |
| *Dialister invisus* | 762 | ACIM02000001 | clade_506 | N | N |
| *Dialister micraerophilus* | 763 | AFBB01000028 | clade_506 | N | N |
| *Dialister microaerophilus* | 764 | AENT01000008 | clade_506 | N | N |
| *Dialister propionicifaciens* | 766 | NR_043231 | clade_506 | N | N |
| *Dialister succinatiphilus* | 768 | AB370249 | clade_506 | N | N |
| *Megasphaera elsdenii* | 1200 | AY038996 | clade_506 | N | N |
| *Megasphaera* genomosp. type_1 | 1202 | ADGP01000010 | clade_506 | N | N |
| *Megasphaera* sp. BLPYG_07 | 1204 | HM990964 | clade_506 | N | N |
| *Megasphaera* sp. UPII 199_6 | 1205 | AFIJ01000040 | clade_506 | N | N |
| *Chromobacterium violaceum* | 513 | NC_005085 | clade_507 | N | N |
| *Laribacter hongkongensis* | 1148 | CP001154 | clade_507 | N | N |
| *Methylophilus* sp. ECd5 | 1279 | AY436794 | clade_507 | N | N |
| *Finegoldia magna* | 883 | ACHM02000001 | clade_509 | N | N |
| *Parvimonas micra* | 1431 | AB729072 | clade_509 | N | N |
| *Parvimonas* sp. oral taxon 110 | 1432 | AFII01000002 | clade_509 | N | N |
| *Peptostreptococcus micros* | 1456 | AM176538 | clade_509 | N | N |
| *Peptostreptococcus* sp. oral clone FJ023 | 1460 | AY349390 | clade_509 | N | N |
| *Peptostreptococcus* sp. P4P_31 P3 | 1458 | AY207059 | clade_509 | N | N |
| *Helicobacter pylori* | 997 | CP00001.2 | clade_510 | N | OP |
| *Anaplasma marginale* | 165 | ABOR01000019 | clade_511 | N | N |
| *Anaplasma phagocytophilum* | 166 | NC_007797 | clade_511 | N | N |
| *Ehrlichia chaffeensis* | 783 | AAIF01000035 | clade_511 | N | OP |
| *Neorickettsia risticii* | 1349 | CP001431 | clade_511 | N | N |
| *Neorickettsia sennetsu* | 1350 | NC_007798 | clade_511 | N | N |
| *Eubacterium barkeri* | 834 | NR_044661 | clade_512 | Y | N |
| *Eubacterium callanderi* | 838 | NR_026310 | clade_512 | N | N |
| *Eubacterium limosum* | 850 | CP002273 | clade_512 | Y | N |
| *Pseudoramibacter alactolyticus* | 1606 | AB036759 | clade_512 | N | N |
| *Veillonella montpellierensis* | 1977 | AF473836 | clade_513 | N | N |
| *Veillonella* sp. oral clone ASCA08 | 1988 | AY923118 | clade_513 | N | N |
| *Veillonella* sp. oral clone ASCB03 | 1989 | AY923122 | clade_513 | N | N |
| *Inquilinus limosus* | 1012 | NR_029046 | clade_514 | N | N |
| *Sphingomonas* sp. oral clone FZ016 | 1746 | AY349412 | clade_514 | N | N |
| *Anaerococcus lactolyticus* | 145 | ABYO01000217 | clade_515 | N | N |
| *Anaerococcus prevotii* | 147 | CP001708 | clade_515 | N | N |

TABLE 1-continued

| OTU | SEQ ID Number | Public DB Accession | Phylogenetic Clade | Spore Former | Pathogen Status |
|---|---|---|---|---|---|
| *Anaerococcus* sp. gpac104 | 152 | AM176528 | clade_515 | N | N |
| *Anaerococcus* sp. gpac126 | 153 | AM176530 | clade_515 | N | N |
| *Anaerococcus* sp. gpac155 | 154 | AM176536 | clade_515 | N | N |
| *Anaerococcus* sp. gpac199 | 155 | AM176539 | clade_515 | N | N |
| *Anaerococcus tetradius* | 157 | ACGC01000107 | clade_515 | N | N |
| *Bacteroides coagulans* | 271 | AB547639 | clade_515 | N | N |
| Clostridiales bacterium 9403326 | 534 | HM587324 | clade_515 | N | N |
| Clostridiales bacterium ph2 | 539 | JN837487 | clade_515 | N | N |
| *Peptostreptococcus* sp. 9succ1 | 1457 | X90471 | clade_515 | N | N |
| *Peptostreptococcus* sp. oral clone AP24 | 1459 | AB175072 | clade_515 | N | N |
| *Tissierella praeacuta* | 1924 | NR_044860 | clade_515 | N | N |
| *Anaerotruncus colihominis* | 164 | ABGD02000021 | clade_516 | Y | N |
| *Clostridium methylpentosum* | 606 | ACEC01000059 | clade_516 | Y | N |
| *Clostridium* sp. YIT 12070 | 642 | AB491208 | clade_516 | Y | N |
| *Hydrogenoanaerobacterium saccharovorans* | 1005 | NR_044425 | clade_516 | Y | N |
| *Ruminococcus albus* | 1656 | AY445600 | clade_516 | Y | N |
| *Ruminococcus flavefaciens* | 1660 | NR_025931 | clade_516 | Y | N |
| *Clostridium haemolyticum* | 589 | NR_024749 | clade_517 | Y | N |
| *Clostridium novyi* | 608 | NR_074343 | clade_517 | Y | N |
| *Clostridium* sp. LMG 16094 | 632 | X95274 | clade_517 | Y | N |
| *Helicobacter canadensis* | 994 | ABQS01000108 | clade_518 | N | N |
| *Eubacterium ventriosum* | 874 | L34421 | clade_519 | Y | N |
| *Peptostreptococcus anaerobius* | 1455 | AY326462 | clade_520 | N | N |
| *Peptostreptococcus stomatis* | 1461 | ADGQ01000048 | clade_520 | N | N |
| *Bilophila wadsworthia* | 367 | ADCP01000166 | clade_521 | N | N |
| *Desulfovibrio vulgaris* | 761 | NR_074897 | clade_521 | N | N |
| *Bacteroides galacturonicus* | 280 | DQ497994 | clade_522 | Y | N |
| *Eubacterium eligens* | 845 | CP001104 | clade_522 | Y | N |
| *Lachnospira multipara* | 1046 | FR733699 | clade_522 | Y | N |
| *Lachnospira pectinoschiza* | 1047 | L14675 | clade_522 | Y | N |
| *Lactobacillus rogosae* | 1114 | GU269544 | clade_522 | Y | N |
| *Actinomyces nasicola* | 64 | AJ508455 | clade_523 | N | N |
| *Cellulosimicrobium funkei* | 500 | AY501364 | clade_523 | N | N |
| *Lactococcus raffinolactis* | 1146 | NR_044359 | clade_524 | N | N |
| *Bacillus horti* | 214 | NR_036860 | clade_527 | Y | OP |
| *Bacillus* sp. 9_3AIA | 232 | FN397519 | clade_527 | Y | OP |
| Bacteroidales genomosp. P1 | 258 | AY341819 | clade_529 | N | N |
| Bacteroidales genomosp. P2 oral clone MB1_G13 | 259 | DQ003613 | clade_529 | N | N |
| Bacteroidales genomosp. P3 oral clone MB1_G34 | 260 | DQ003615 | clade_529 | N | N |
| Bacteroidales genomosp. P4 oral clone MB2_G17 | 261 | DQ003617 | clade_529 | N | N |
| Bacteroidales genomosp. P5 oral clone MB2_P04 | 262 | DQ003619 | clade_529 | N | N |
| Bacteroidales genomosp. P6 oral clone MB3_C19 | 263 | DQ003634 | clade_529 | N | N |
| Bacteroidales genomosp. P8 oral clone MB4_G15 | 265 | DQ003626 | clade_529 | N | N |
| Bacteroidetes bacterium oral taxon D27 | 333 | HM099638 | clade_530 | N | N |
| Bacteroidetes bacterium oral taxon F31 | 334 | HM099643 | clade_530 | N | N |
| Bacteroidetes bacterium oral taxon F44 | 335 | HM099649 | clade_530 | N | N |
| *Flavobacterium* sp. NF2_1 | 885 | FJ195988 | clade_530 | N | N |
| *Myroides odoratimimus* | 1326 | NR_042354 | clade_530 | N | N |
| *Myroides* sp. MY15 | 1327 | GU253339 | clade_530 | N | N |
| Chlamydiales bacterium NS16 | 507 | JN606076 | clade_531 | N | N |
| *Chlamydophila pecorum* | 508 | D88317 | clade_531 | N | OP |
| *Parachlamydia* sp. UWE25 | 1423 | BX908798 | clade_531 | N | N |
| *Fusobacterium russii* | 903 | NR_044687 | clade_532 | N | N |
| *Streptobacillus moniliformis* | 1784 | NR_027615 | clade_532 | N | N |
| Eubacteriaceae bacterium P4P_50 P4 | 833 | AY207060 | clade_533 | N | N |
| *Eubacterium brachy* | 836 | U13038 | clade_533 | Y | N |
| *Filifactor alocis* | 881 | CP002390 | clade_533 | Y | N |
| *Filifactor villosus* | 882 | NR_041928 | clade_533 | Y | N |
| *Abiotrophia defectiva* | 1 | ACIN02000016 | clade_534 | N | N |
| *Abiotrophia* sp. oral clone P4PA_155 P1 | 3 | AY207063 | clade_534 | N | N |
| *Catonella* genomosp. P1 oral clone MB5_P12 | 496 | DQ003629 | clade_534 | N | N |
| *Catonella morbi* | 497 | ACIL02000016 | clade_534 | N | N |
| *Catonella* sp. oral clone FL037 | 498 | AY349369 | clade_534 | N | N |
| *Eremococcus coleocola* | 818 | AENN01000008 | clade_534 | N | N |
| *Facklamia hominis* | 879 | Y10772 | clade_534 | N | N |
| *Granulicatella* sp. M658_99_3 | 962 | AJ271861 | clade_534 | N | N |
| *Campylobacter coli* | 459 | AAFL01000004 | clade_535 | N | OP |
| *Campylobacter concisus* | 460 | CP000792 | clade_535 | N | OP |
| *Campylobacter fetus* | 462 | ACLG01001177 | clade_535 | N | OP |
| *Campylobacter jejuni* | 465 | AL139074 | clade_535 | N | Category-B |

TABLE 1-continued

| OTU | SEQ ID Number | Public DB Accession | Phylogenetic Clade | Spore Former | Pathogen Status |
|---|---|---|---|---|---|
| *Campylobacter upsaliensis* | 473 | AEPU01000040 | clade_535 | N | OP |
| *Clostridium leptum* | 601 | AJ305238 | clade_537 | Y | N |
| *Clostridium* sp. YIT 12069 | 641 | AB491207 | clade_537 | Y | N |
| *Clostridium sporosphaeroides* | 646 | NR_044835 | clade_537 | Y | N |
| *Eubacterium coprostanoligenes* | 841 | HM037995 | clade_537 | Y | N |
| *Ruminococcus bromii* | 1657 | EU266549 | clade_537 | Y | N |
| *Eubacterium siraeum* | 860 | ABCA03000054 | clade_538 | Y | N |
| *Atopobium minutum* | 183 | HM007583 | clade_539 | N | N |
| *Atopobium parvulum* | 184 | CP001721 | clade_539 | N | N |
| *Atopobium rimae* | 185 | ACFE01000007 | clade_539 | N | N |
| *Atopobium* sp. BS2 | 186 | HQ616367 | clade_539 | N | N |
| *Atopobium* sp. F0209 | 187 | EU592966 | clade_539 | N | N |
| *Atopobium* sp. ICM42b10 | 188 | HQ616393 | clade_539 | N | N |
| *Atopobium* sp. ICM57 | 189 | HQ616400 | clade_539 | N | N |
| *Atopobium vaginae* | 190 | AEDQ01000024 | clade_539 | N | N |
| Coriobacteriaceae bacterium BV3Ac1 | 677 | JN809768 | clade_539 | N | N |
| *Actinomyces naeslundii* | 63 | X81062 | clade_54 | N | N |
| *Actinomyces oricola* | 67 | NR_025559 | clade_54 | N | N |
| *Actinomyces oris* | 69 | BABV01000070 | clade_54 | N | N |
| *Actinomyces* sp. 7400942 | 70 | EU484334 | clade_54 | N | N |
| *Actinomyces* sp. ChDC B197 | 72 | AF543275 | clade_54 | N | N |
| *Actinomyces* sp. GEJ15 | 73 | GU561313 | clade_54 | N | N |
| *Actinomyces* sp. M2231_94_1 | 79 | AJ234063 | clade_54 | N | N |
| *Actinomyces* sp. oral clone GU067 | 83 | AY349362 | clade_54 | N | N |
| *Actinomyces* sp. oral clone IO077 | 85 | AY349364 | clade_54 | N | N |
| *Actinomyces* sp. oral clone IP073 | 86 | AY349365 | clade_54 | N | N |
| *Actinomyces* sp. oral clone JA063 | 88 | AY349367 | clade_54 | N | N |
| *Actinomyces* sp. oral taxon 170 | 89 | AFBL01000010 | clade_54 | N | N |
| *Actinomyces* sp. oral taxon 171 | 90 | AECW01000034 | clade_54 | N | N |
| *Actinomyces urogenitalis* | 95 | ACFH01000038 | clade_54 | N | N |
| *Actinomyces viscosus* | 96 | ACRE01000096 | clade_54 | N | N |
| *Clostridium viride* | 657 | NR_026204 | clade_540 | Y | N |
| *Oscillibacter* sp. G2 | 1386 | HM626173 | clade_540 | Y | N |
| *Oscillibacter valericigenes* | 1387 | NR_074793 | clade_540 | Y | N |
| *Oscillospira guilliermondii* | 1388 | AB040495 | clade_540 | Y | N |
| *Orientia tsutsugamushi* | 1383 | AP008981 | clade_541 | N | OP |
| *Megamonas funiformis* | 1198 | AB300988 | clade_542 | N | N |
| *Megamonas hypermegale* | 1199 | AJ420107 | clade_542 | N | N |
| *Butyrivibrio crossotus* | 455 | ABWN01000012 | clade_543 | Y | N |
| *Clostridium* sp. L2_50 | 631 | AAYW02000018 | clade_543 | Y | N |
| *Coprococcus eutactus* | 675 | EF031543 | clade_543 | Y | N |
| *Coprococcus* sp. ART55_1 | 676 | AY350746 | clade_543 | Y | N |
| *Eubacterium ruminantium* | 857 | NR_024661 | clade_543 | Y | N |
| *Aeromicrobium marinum* | 102 | NR_025681 | clade_544 | N | N |
| *Aeromicrobium* sp. JC14 | 103 | JF824798 | clade_544 | N | N |
| *Luteococcus sanguinis* | 1190 | NR_025507 | clade_544 | N | N |
| Propionibacteriaceae bacterium NML 02_0265 | 1568 | EF599122 | clade_544 | N | N |
| *Rhodococcus corynebacterioides* | 1622 | X80615 | clade_546 | N | N |
| *Rhodococcus erythropolis* | 1624 | ACNO01000030 | clade_546 | N | N |
| *Rhodococcus fascians* | 1625 | NR_037021 | clade_546 | N | N |
| *Segniliparus rotundus* | 1690 | CP001958 | clade_546 | N | N |
| *Segniliparus rugosus* | 1691 | ACZI01000025 | clade_546 | N | N |
| *Exiguobacterium acetylicum* | 878 | FJ970034 | clade_547 | N | N |
| *Micrococcus caseolyticus* | 1194 | NR_074941 | clade_547 | N | N |
| *Streptomyces* sp. 1 AIP_2009 | 1890 | FJ176782 | clade_548 | N | N |
| *Streptomyces* sp. SD 524 | 1892 | EU544234 | clade_548 | N | N |
| *Streptomyces* sp. SD 528 | 1893 | EU544233 | clade_548 | N | N |
| *Streptomyces thermoviolaceus* | 1895 | NR_027616 | clade_548 | N | N |
| *Borrelia afzelii* | 388 | ABCU01000001 | clade_549 | N | OP |
| *Borrelia crocidurae* | 390 | DQ057990 | clade_549 | N | OP |
| *Borrelia duttonii* | 391 | NC_011229 | clade_549 | N | OP |
| *Borrelia hermsii* | 393 | AY597657 | clade_549 | N | OP |
| *Borrelia hispanica* | 394 | DQ057988 | clade_549 | N | OP |
| *Borrelia persica* | 395 | HM161645 | clade_549 | N | OP |
| *Borrelia recurrentis* | 396 | AF107367 | clade_549 | N | OP |
| *Borrelia spielmanii* | 398 | ABKB01000002 | clade_549 | N | OP |
| *Borrelia turicatae* | 399 | NC_008710 | clade_549 | N | OP |
| *Borrelia valaisiana* | 400 | ABCY01000002 | clade_549 | N | OP |
| *Providencia alcalifaciens* | 1586 | ABXW01000071 | clade_55 | N | N |
| *Providencia rettgeri* | 1587 | AM040492 | clade_55 | N | N |
| *Providencia rustigianii* | 1588 | AM040489 | clade_55 | N | N |
| *Providencia stuartii* | 1589 | AF008581 | clade_55 | N | N |
| *Treponema pallidum* | 1932 | CP001752 | clade_550 | N | OP |
| *Treponema phagedenis* | 1934 | AEFH01000172 | clade_550 | N | N |
| *Treponema* sp. clone DDKL_4 | 1939 | Y08894 | clade_550 | N | N |
| *Acholeplasma laidlawii* | 17 | NR_074448 | clade_551 | N | N |

TABLE 1-continued

| OTU | SEQ ID Number | Public DB Accession | Phylogenetic Clade | Spore Former | Pathogen Status |
|---|---|---|---|---|---|
| *Mycoplasma putrefaciens* | 1323 | U26055 | clade_551 | N | N |
| Mycoplasmataceae genomosp P1 oral clone | 1325 | DQ003614 | clade_551 | N | N |
| *Spiroplasma insolitum* | 1750 | NR_025705 | clade_551 | N | N |
| *Collinsella aerofaciens* | 659 | AAVN02000007 | clade_553 | Y | N |
| *Collinsella intestinalis* | 660 | ABXH02000037 | clade_553 | N | N |
| *Collinsella stercoris* | 661 | ABXJ01000150 | clade_553 | N | N |
| *Collinsella tanakaei* | 662 | AB490807 | clade_553 | N | N |
| *Alkaliphilus metalliredigenes* | 137 | AY137848 | clade_554 | Y | N |
| *Alkaliphilus oremlandii* | 138 | NR_043674 | clade_554 | Y | N |
| *Caminicella sporogenes* | 458 | NR_025485 | clade_554 | N | N |
| *Clostridium sticklandii* | 648 | L04167 | clade_554 | Y | N |
| *Turicibacter sanguinis* | 1965 | AF349724 | clade_555 | Y | N |
| *Acidaminococcus fermentans* | 21 | CP001859 | clade_556 | N | N |
| *Acidaminococcus intestini* | 22 | CP003058 | clade_556 | N | N |
| *Acidaminococcus* sp. D21 | 23 | ACGB01000071 | clade_556 | N | N |
| *Phascolarctobacterium faecium* | 1462 | NR_026111 | clade_556 | N | N |
| *Phascolarctobacterium* sp. YIT 12068 | 1463 | AB490812 | clade_556 | N | N |
| *Phascolarctobacterium succinatutens* | 1464 | AB490811 | clade_556 | N | N |
| *Acidithiobacillus ferrivorans* | 25 | NR_074660 | clade_557 | N | N |
| *Fulvimonas* sp. NML 060897 | 892 | EF589680 | clade_557 | Y | N |
| Xanthomonadaceae bacterium NML 03_0222 | 2015 | EU313791 | clade_557 | N | N |
| *Catabacter hongkongensis* | 494 | AB671763 | clade_558 | N | N |
| *Christensenella minuta* | 512 | AB490809 | clade_558 | N | N |
| Clostridiales bacterium oral clone P4PA | 536 | AY207065 | clade_558 | N | N |
| Clostridiales bacterium oral taxon 093 | 537 | GQ422712 | clade_558 | N | N |
| *Desulfitobacterium frappieri* | 753 | AJ276701 | clade_560 | Y | N |
| *Desulfitobacterium hafniense* | 754 | NR_074996 | clade_560 | Y | N |
| *Desulfotomaculum nigrificans* | 756 | NR_044832 | clade_560 | Y | N |
| *Heliobacterium modesticaldum* | 1000 | NR_074517 | clade_560 | N | N |
| *Alistipes indistinctus* | 130 | AB490804 | clade_561 | N | N |
| Bacteroidales bacterium ph8 | 257 | JN837494 | clade_561 | N | N |
| *Candidatus Sulcia muelleri* | 475 | CP002163 | clade_561 | N | N |
| *Cytophaga xylanolytica* | 742 | FR733683 | clade_561 | N | N |
| Flavobacteriaceae genomosp. C1 | 884 | AY278614 | clade_561 | N | N |
| *Gramella forsetii* | 958 | NR_074707 | clade_561 | N | N |
| *Sphingobacterium faecium* | 1740 | NR_025537 | clade_562 | N | N |
| *Sphingobacterium mizutaii* | 1741 | JF708889 | clade_562 | N | N |
| *Sphingobacterium multivorum* | 1742 | NR_040953 | clade_562 | N | N |
| *Sphingobacterium spiritivorum* | 1743 | ACHA02000013 | clade_562 | N | N |
| *Jonquetella anthropi* | 1017 | ACOO02000004 | clade_563 | N | N |
| *Pyramidobacter piscolens* | 1614 | AY207056 | clade_563 | N | N |
| Synergistes genomosp. C1 | 1904 | AY278615 | clade_563 | N | N |
| Synergistes sp. RMA 14551 | 1905 | DQ412722 | clade_563 | N | N |
| Synergistetes bacterium ADV897 | 1906 | GQ258968 | clade_563 | N | N |
| *Candidatus Arthromitus* sp. SFB_mouse_Yit | 474 | NR_074460 | clade_564 | N | N |
| *Gracilibacter thermotolerans* | 957 | NR_043559 | clade_564 | N | N |
| *Lutispora thermophila* | 1191 | NR_041236 | clade_564 | Y | N |
| *Brachyspira aalborgi* | 404 | FM178386 | clade_565 | N | N |
| *Brachyspira pilosicoli* | 405 | NR_075069 | clade_565 | Y | N |
| *Brachyspira* sp. HIS3 | 406 | FM178387 | clade_565 | N | N |
| *Brachyspira* sp. HIS4 | 407 | FM178388 | clade_565 | N | N |
| *Brachyspira* sp. HIS5 | 408 | FM178389 | clade_565 | N | N |
| *Adlercreutzia equolifaciens* | 97 | AB306661 | clade_566 | N | N |
| Coriobacteriaceae bacterium JC110 | 678 | CAEM01000062 | clade_566 | N | N |
| Coriobacteriaceae bacterium phI | 679 | JN837493 | clade_566 | N | N |
| *Cryptobacterium curtum* | 740 | GQ422741 | clade_566 | N | N |
| *Eggerthella lenta* | 778 | AF292375 | clade_566 | Y | N |
| *Eggerthella sinensis* | 779 | AY321958 | clade_566 | N | N |
| *Eggerthella* sp. 1_3_56FAA | 780 | ACWN01000099 | clade_566 | N | N |
| *Eggerthella* sp. HGA1 | 781 | AEXR01000021 | clade_566 | N | N |
| *Eggerthella* sp. YY7918 | 782 | AP012211 | clade_566 | N | N |
| *Gordonibacter pamelaeae* | 680 | AM886059 | clade_566 | N | N |
| *Gordonibacter pamelaeae* | 956 | FP929047 | clade_566 | N | N |
| *Slackia equolifaciens* | 1732 | EU377663 | clade_566 | N | N |
| *Slackia exigua* | 1733 | ACUX01000029 | clade_566 | N | N |
| *Slackia faecicanis* | 1734 | NR_042220 | clade_566 | N | N |
| *Slackia heliotrinireducens* | 1735 | NR_074439 | clade_566 | N | N |
| *Slackia isoflavoniconvertens* | 1736 | AB566418 | clade_566 | N | N |
| *Slackia piriformis* | 1737 | AB490806 | clade_566 | N | N |
| *Slackia* sp. NATTS | 1738 | AB505075 | clade_566 | N | N |
| *Streptomyces albus* | 1888 | AJ697941 | clade_566 | Y | N |
| Chlamydiales bacterium NS11 | 505 | JN606074 | clade_567 | Y | N |
| Chlamydiales bacterium NS13 | 506 | JN606075 | clade_567 | N | N |
| Victivallaceae bacterium NML 080035 | 2003 | FJ394915 | clade_567 | N | N |
| *Victivallis vadensis* | 2004 | ABDE02000010 | clade_567 | N | N |

TABLE 1-continued

| OTU | SEQ ID Number | Public DB Accession | Phylogenetic Clade | Spore Former | Pathogen Status |
|---|---|---|---|---|---|
| *Anaerofustis stercorihominis* | 159 | ABIL02000005 | clade_570 | Y | N |
| *Butyricicoccus pullicaecorum* | 453 | HH793440 | clade_572 | Y | N |
| *Eubacterium desmolans* | 843 | NR_044644 | clade_572 | Y | N |
| *Papillibacter cinnamivorans* | 1415 | NR_025025 | clade_572 | Y | N |
| *Sporobacter termitidis* | 1751 | NR_044972 | clade_572 | Y | N |
| *Streptomyces griseus* | 1889 | NR_074787 | clade_573 | N | N |
| *Streptomyces* sp. SD 511 | 1891 | EU544231 | clade_573 | N | N |
| *Streptomyces* sp. SD 534 | 1894 | EU544232 | clade_573 | N | N |
| *Cloacibacillus evryensis* | 530 | GQ258966 | clade_575 | N | N |
| *Deferribacteres* sp. oral clone JV001 | 743 | AY349370 | clade_575 | N | N |
| *Deferribacteres* sp. oral clone JV006 | 744 | AY349371 | clade_575 | Y | N |
| *Deferribacteres* sp. oral clone JV023 | 745 | AY349372 | clade_575 | N | N |
| Synergistetes bacterium LBVCM1157 | 1907 | GQ258969 | clade_575 | N | N |
| Synergistetes bacterium oral taxon 362 | 1909 | GU410752 | clade_575 | N | N |
| Synergistetes bacterium oral taxon D48 | 1910 | GU430992 | clade_575 | N | N |
| *Clostridium colinum* | 577 | NR_026151 | clade_576 | Y | N |
| *Clostridium lactatifermentans* | 599 | NR_025651 | clade_576 | Y | N |
| *Clostridium piliforme* | 614 | D14639 | clade_576 | Y | N |
| *Peptococcus* sp. oral clone JM048 | 1439 | AY349389 | clade_576 | N | N |
| *Helicobacter winghamensis* | 999 | ACDO01000013 | clade_577 | N | N |
| *Wolinella succinogenes* | 2014 | BX571657 | clade_577 | N | N |
| *Olsenella* genomosp. C1 | 1368 | AY278623 | clade_578 | N | N |
| *Olsenella profusa* | 1369 | FN178466 | clade_578 | N | N |
| *Olsenella* sp. F0004 | 1370 | EU592964 | clade_578 | N | N |
| *Olsenella* sp. oral taxon 809 | 1371 | ACVE01000002 | clade_578 | N | N |
| *Olsenella uli* | 1372 | CP002106 | clade_578 | N | N |
| *Nocardiopsis dassonvillei* | 1356 | CP002041 | clade_579 | N | N |
| *Saccharomonospora viridis* | 1671 | X54286 | clade_579 | Y | N |
| *Thermobifida fusca* | 1921 | NC_007333 | clade_579 | Y | N |
| *Peptococcus niger* | 1438 | NR_029221 | clade_580 | N | N |
| *Peptococcus* sp. oral taxon 167 | 1440 | GQ422727 | clade_580 | N | N |
| *Akkermansia muciniphila* | 118 | CP001071 | clade_583 | N | N |
| *Opitutus terrae* | 1373 | NR_074978 | clade_583 | N | N |
| Clostridiales bacterium oral taxon F32 | 538 | HM099644 | clade_584 | N | N |
| *Leptospira borgpetersenii* | 1161 | NC_008508 | clade_585 | N | OP |
| *Leptospira broomii* | 1162 | NR_043200 | clade_585 | N | OP |
| *Leptospira interrogans* | 3163 | NC_005823 | clade_585 | N | OP |
| *Leptospira licerasiae* | 1164 | EF612284 | clade_585 | Y | OP |
| *Methanobrevibacter gottschalkii* | 1213 | NR_044789 | clade_587 | N | N |
| *Methanobrevibacter millerae* | 1214 | NR_042785 | clade_587 | N | N |
| *Methanobrevibacter oralis* | 1216 | HE654003 | clade_587 | N | N |
| *Methanobrevibacter thaueri* | 1219 | NR_044787 | clade_587 | N | N |
| *Methanobrevibacter smithii* | 1218 | ABYV02000002 | clade_588 | N | N |
| *Deinococcus radiodurans* | 746 | AE000513 | clade_589 | N | N |
| *Deinococcus* sp. R_43890 | 747 | FR682752 | clade_589 | N | N |
| *Thermus aquaticus* | 1923 | NR_025900 | clade_589 | N | N |
| *Actinomyces* sp. c109 | 81 | AB167239 | clade_590 | N | N |
| *Moorella thermoacetica* | 1259 | NR_075001 | clade_590 | Y | N |
| Syntrophomonadaceae genomosp. P1 | 1912 | AY341821 | clade_590 | N | N |
| *Thermoanaerobacter pseudethanolicus* | 1920 | CP000924 | clade_590 | Y | N |
| *Anaerobaculum hydrogeniformans* | 141 | ACJX02000009 | clade_591 | N | N |
| *Flexistipes sinusarabici* | 888 | NR_074881 | clade_591 | Y | N |
| *Microcystis aeruginosa* | 1246 | NC_010296 | clade_592 | N | N |
| *Prochlorococcus marinus* | 1567 | CP000551 | clade_592 | N | N |
| *Methanobrevibacter acididurans* | 1208 | NR_028779 | clade_593 | N | N |
| *Methanobrevibacter arboriphilus* | 1209 | NR_042783 | clade_593 | N | N |
| *Methanobrevibacter curvatus* | 1210 | NR_044796 | clade_593 | N | N |
| *Methanobrevibacter cuticularis* | 1211 | NR_044776 | clade_593 | N | N |
| *Methanobrevibacter filiformis* | 1212 | NR_044801 | clade_593 | N | N |
| *Methanobrevibacter woesei* | 1220 | NR_044788 | clade_593 | N | N |
| *Roseiflexus castenholzii* | 1642 | CP000804 | clade_594 | N | N |
| *Methanobrevibacter olleyae* | 1215 | NR_043024 | clade_595 | N | N |
| *Methanobrevibacter ruminantium* | 1217 | NR_042784 | clade_595 | N | N |
| *Methanobrevibacter wolinii* | 1221 | NR_044790 | clade_595 | N | N |
| *Methanosphaera stadtmanae* | 1222 | AY196684 | clade_595 | N | N |
| Chloroflexi genomosp. P1 | 511 | AY331414 | clade_596 | N | N |
| *Gloeobacter violaceus* | 942 | NR_074282 | clade_596 | Y | N |
| *Halorubrum lipolyticum* | 992 | AB477978 | clade_597 | N | N |
| *Methanobacterium formicicum* | 1207 | NR_025028 | clade_597 | N | N |
| *Acidilobus saccharovorans* | 24 | AY350586 | clade_598 | N | N |
| *Hyperthermus butylicus* | 1006 | CP000493 | clade_598 | N | N |
| *Ignicoccus islandicus* | 1011 | X99562 | clade_598 | N | N |
| *Metallosphaera sedula* | 1206 | D26491 | clade_598 | N | N |
| *Thermofilum pendens* | 1922 | X14835 | clade_598 | N | N |
| *Prevotella melaninogenica* | 1506 | CP002122 | clade_6 | N | N |
| *Prevotella* sp. ICM1 | 1520 | HQ616385 | clade_6 | N | N |
| *Prevotella* sp. oral clone FU048 | 1535 | AY349393 | clade_6 | N | N |

TABLE 1-continued

| OTU | SEQ ID Number | Public DB Accession | Phylogenetic Clade | Spore Former | Pathogen Status |
|---|---|---|---|---|---|
| *Prevotella* sp. oral done GI030 | 1537 | AY349395 | clade_6 | N | N |
| *Prevotella* sp. SEQ116 | 1526 | JN867246 | clade_6 | N | N |
| *Streptococcus anginosus* | 1787 | AECT01000011 | clade_60 | N | N |
| *Streptococcus milleri* | 1812 | X81023 | clade_60 | N | N |
| *Streptococcus* sp. 16362 | 1829 | JN590019 | clade_60 | N | N |
| *Streptococcus* sp. 69130 | 1832 | X78825 | clade_60 | N | N |
| *Streptococcus* sp. AC15 | 1833 | HQ616356 | clade_60 | N | N |
| *Streptococcus* sp. CM7 | 1839 | HQ616373 | clade_60 | N | N |
| *Streptococcus* sp. OBRC6 | 1847 | HQ616352 | clade_60 | N | N |
| *Burkholderia ambifaria* | 442 | AAUZ01000009 | clade_61 | N | OP |
| *Burkholderia cenocepacia* | 443 | AAHI001000060 | clade_61 | N | OP |
| *Burkholderia cepacia* | 444 | NR_041719 | clade_61 | N | OP |
| *Burkholderia mallei* | 445 | CP000547 | clade_61 | N | Category-B |
| *Burkholderia multivorans* | 446 | NC_010086 | clade_61 | N | OP |
| *Burkholderia oklahomensis* | 447 | DQ108388 | clade_61 | N | OP |
| *Burkholderia pseudomallei* | 448 | CP001408 | clade_61 | N | Category-B |
| *Burkholderia rhizoxinica* | 449 | HQ005410 | clade_61 | N | OP |
| *Burkholderia* sp. 383 | 450 | CP000151 | clade_61 | N | OP |
| *Burkholderia xenovorans* | 451 | U86373 | clade_61 | N | OP |
| *Prevotella buccae* | 1488 | ACRB01000001 | clade_62 | N | N |
| *Prevotella* genomosp. P8 oral clone MB3_P13 | 1498 | DQ003622 | clade_62 | N | N |
| *Prevotella* sp. oral clone FW035 | 1536 | AY349394 | clade_62 | N | N |
| *Prevotella bivia* | 1486 | ADFO01000096 | clade_63 | N | N |
| *Prevotella disiens* | 1494 | AEDO01000026 | clade_64 | N | N |
| *Bacteroides faecis* | 276 | GQ496624 | clade_65 | N | N |
| *Bacteroides fragilis* | 279 | AP006841 | clade_65 | N | N |
| *Bacteroides nordii* | 285 | NR_043017 | clade_65 | N | N |
| *Bacteroides salyersiae* | 292 | EU136690 | clade_65 | N | N |
| *Bacteroides* sp. 1_1_14 | 293 | ACRP01000155 | clade_65 | N | N |
| *Bacteroides* sp. 1_1_6 | 295 | ACIC01000215 | clade_65 | N | N |
| *Bacteroides* sp. 2_1_56FAA | 298 | ACWI01000065 | clade_65 | N | N |
| *Bacteroides* sp. AR29 | 316 | AF139525 | clade_65 | N | N |
| *Bacteroides* sp. B2 | 317 | EU722733 | clade_65 | N | N |
| *Bacteroides thetaiotaomicron* | 328 | NR_074277 | clade_65 | N | N |
| *Actinobacillus minor* | 45 | ACFT01000025 | clade_69 | N | N |
| *Haemophilus parasuis* | 978 | GU226366 | clade_69 | N | N |
| *Vibrio cholerae* | 1996 | AAUR01000095 | clade_71 | N | Category-B |
| *Vibrio fluvialis* | 1997 | X76335 | clade_71 | N | Category-B |
| *Vibrio furnissii* | 1998 | CP002377 | clade_71 | N | Category-B |
| *Vibrio mimicus* | 1999 | ADAF01000001 | clade_71 | N | Category-B |
| *Vibrio parahaemolyticus* | 2000 | AAWQ01000116 | clade_71 | N | Category-B |
| *Vibrio* sp. RC341 | 2001 | ACZT01000024 | clade_71 | N | Category-B |
| *Vibrio vulnificus* | 2002 | AE016796 | clade_71 | N | Category-B |
| *Lactobacillus acidophilus* | 1067 | CP000033 | clade_72 | N | N |
| *Lactobacillus amylolyticus* | 1069 | ADNY01000006 | clade_72 | N | N |
| *Lactobacillus amylovorus* | 1070 | CP002338 | clade_72 | N | N |
| *Lactobacillus crispatus* | 1078 | ACOG01000151 | clade_72 | N | N |
| *Lactobacillus delbrueckii* | 1080 | CP002341 | clade_72 | N | N |
| *Lactobacillus helveticus* | 1088 | ACLM01000202 | clade_72 | N | N |
| *Lactobacillus kalixensis* | 1094 | NR_029083 | clade_72 | N | N |
| *Lactobacillus kefiranofaciens* | 1095 | NR_042440 | clade_72 | N | N |
| *Lactobacillus leichmannii* | 1098 | JX986966 | clade_72 | N | N |
| *Lactobacillus* sp. 66c | 1120 | FR681900 | clade_72 | N | N |
| *Lactobacillus* sp. KLDS 1.0701 | 1122 | EU600905 | clade_72 | N | N |
| *Lactobacillus* sp. KLDS 1.0712 | 1130 | EU600916 | clade_72 | N | N |
| *Lactobacillus* sp. oral clone HT070 | 1136 | AY349383 | clade_72 | N | N |
| *Lactobacillus ultunensis* | 1139 | ACGU01000081 | clade_72 | N | N |
| *Prevotella intermedia* | 1502 | AF414829 | clade_81 | N | N |
| *Prevotella nigrescens* | 1511 | AFPX01000069 | clade_81 | N | N |
| *Prevotella pallens* | 1515 | AFPY01000135 | clade_81 | N | N |
| *Prevotella* sp. oral taxon 310 | 1551 | GQ422737 | clade_81 | N | N |
| *Prevotella* genomosp. C1 | 1495 | AY278624 | clade_82 | N | N |
| *Prevotella* sp. CM38 | 1519 | HQ610181 | clade_82 | N | N |
| *Prevotella* sp. oral taxon 317 | 1552 | ACQH01000158 | clade_82 | N | N |
| *Prevotella* sp. SG12 | 1527 | GU561343 | clade_82 | N | N |
| *Prevotella denticola* | 1493 | CP002589 | clade_83 | N | N |
| *Prevotella* genomosp. P7 oral clone MB2_P31 | 1497 | DQ003620 | clade_83 | N | N |
| *Prevotella histicola* | 1501 | JN867315 | clade_83 | N | N |
| *Prevotella multiformis* | 1508 | AEWX01000054 | clade_83 | N | N |
| *Prevotella* sp. JCM 6330 | 1522 | AB547699 | clade_83 | N | N |
| *Prevotella* sp. oral clone GI059 | 1539 | AY349397 | clade_83 | N | N |
| *Prevotella* sp. oral taxon 782 | 1555 | GQ422745 | clade_83 | N | N |
| *Prevotella* sp. oral taxon G71 | 1559 | GU432180 | clade_83 | N | N |
| *Prevotella* sp. SEQ065 | 1524 | JN867234 | clade_83 | N | N |
| *Prevotella veroralis* | 1565 | ACVA01000027 | clade_83 | N | N |

TABLE 1-continued

| OTU | SEQ ID Number | Public DB Accession | Phylogenetic Clade | Spore Former | Pathogen Status |
|---|---|---|---|---|---|
| *Bacteroides acidifaciens* | 266 | NR_028607 | clade_85 | N | N |
| *Bacteroides cellulosilyticus* | 269 | ACCH01000108 | clade_85 | N | N |
| *Bacteroides clarus* | 270 | AFBM01000011 | clade_85 | N | N |
| *Bacteroides eggerthii* | 275 | ACWG01000065 | clade_85 | N | N |
| *Bacteroides oleiciplenus* | 286 | AB547644 | clade_85 | N | N |
| *Bacteroides pyogenes* | 290 | NR_041280 | clade_85 | N | N |
| *Bacteroides* sp. 315_5 | 300 | FJ848547 | clade_85 | N | N |
| *Bacteroides* sp. 31SF15 | 301 | AJ583248 | clade_85 | N | N |
| *Bacteroides* sp. 31SF18 | 302 | AJ583249 | clade_85 | N | N |
| *Bacteroides* sp. 35AE31 | 303 | AJ583244 | clade_85 | N | N |
| *Bacteroides* sp. 35AE37 | 304 | AJ583245 | clade_85 | N | N |
| *Bacteroides* sp. 35BE34 | 305 | AJ583246 | clade_85 | N | N |
| *Bacteroides* sp. 35BE35 | 306 | AJ583247 | clade_85 | N | N |
| *Bacteroides* sp. WH2 | 324 | AY895180 | clade_85 | N | N |
| *Bacteroides* sp. XB12B | 325 | AM230648 | clade_85 | N | N |
| *Bacteroides stercoris* | 327 | ABFZ02000022 | clade_85 | N | N |
| *Actinobacillus pleuropneumoniae* | 46 | NR_074857 | clade_88 | N | N |
| *Actinobacillus ureae* | 48 | AEVG01000167 | clade_88 | N | N |
| *Haemophilus aegyptius* | 969 | AFBC01000053 | clade_88 | N | N |
| *Haemophilus ducreyi* | 970 | AE017143 | clade_88 | N | OP |
| *Haemophilus haemolyticus* | 973 | JN175335 | clade_88 | N | N |
| *Haemophilus influenzae* | 974 | AADP01000001 | clade_88 | N | OP |
| *Haemophilus parahaemolyticus* | 975 | GU561425 | clade_88 | N | N |
| *Haemophilus parainfluenzae* | 976 | AEWU01000024 | clade_88 | N | N |
| *Haemophilus paraphrophaemolyticus* | 977 | M75076 | clade_88 | N | N |
| *Haemophilus somnus* | 979 | NC_008309 | clade_88 | N | N |
| *Haemophilus* sp. 70334 | 980 | HQ680854 | clade_88 | N | N |
| *Haemophilus* sp. HK445 | 981 | FJ685624 | clade_88 | N | N |
| *Haemophilus* sp. oral clone ASCA07 | 982 | AY923117 | clade_88 | N | N |
| *Haemophilus* sp. oral clone ASCG06 | 983 | AY923147 | clade_88 | N | N |
| *Haemophilus* sp. oral clone BJ021 | 984 | AY005034 | clade_88 | N | N |
| *Haemophilus* sp. oral clone BJ095 | 985 | AY005033 | clade_88 | N | N |
| *Haemophilus* sp. oral taxon 851 | 987 | AGRK01000004 | clade_88 | N | N |
| *Haemophilus sputorum* | 988 | AFNK01000005 | clade_88 | N | N |
| *Histophilus somni* | 1003 | AF549387 | clade_88 | N | N |
| *Mannheimia haemolytica* | 1195 | ACZX01000102 | clade_88 | N | N |
| *Pasteurella bettyae* | 1433 | L06088 | clade_88 | N | N |
| *Moellerella wisconsensis* | 1253 | JN175344 | clade_89 | N | N |
| *Morganella morganii* | 1265 | AJ301681 | clade_89 | N | N |
| *Morganella* sp. JB_T16 | 1266 | AJ781005 | clade_89 | N | N |
| *Proteus mirabilis* | 1582 | ACLE01000013 | clade_89 | N | N |
| *Proteus penneri* | 1583 | ABVP01000020 | clade_89 | N | N |
| *Proteus* sp. HS7514 | 1584 | DQ512963 | clade_89 | N | N |
| *Proteus vulgaris* | 1585 | AJ233425 | clade_89 | N | N |
| *Eubacterium* sp. oral clone JN088 | 869 | AY349377 | clade_90 | Y | N |
| *Oribacterium sinus* | 1374 | ACKX01000142 | clade_90 | N | N |
| *Oribacterium* sp. ACB1 | 1375 | HM120210 | clade_90 | N | N |
| *Oribacterium* sp. ACB7 | 1376 | HM120211 | clade_90 | N | N |
| *Oribacterium* sp. CM12 | 1377 | HQ616374 | clade_90 | N | N |
| *Oribacterium* sp. ICM51 | 1378 | HQ616397 | clade_90 | N | N |
| *Oribacterium* sp. OBRC12 | 1379 | HQ616355 | clade_90 | N | N |
| *Oribacterium* sp. oral taxon 108 | 1382 | AFIH01000001 | clade_90 | N | N |
| *Actinobacillus actinomycetemcomitans* | 44 | AY362885 | clade_92 | N | N |
| *Actinobacillus succinogenes* | 47 | CP000746 | clade_92 | N | N |
| *Aggregatibacter actinomycetemcomitans* | 112 | CP001733 | clade_92 | N | N |
| *Aggregatibacter aphrophilus* | 113 | CP001607 | clade_92 | N | N |
| *Aggregatibacter segnis* | 114 | AEPS01000017 | clade_92 | N | N |
| *Averyella dalhousiensis* | 194 | DQ481464 | clade_92 | N | N |
| Bisgaard Taxon | 368 | AY683487 | clade_92 | N | N |
| Bisgaard Taxon | 369 | AY683489 | clade_92 | N | N |
| Bisgaard Taxon | 370 | AY683491 | clade_92 | N | N |
| Bisgaard Taxon | 371 | AY683492 | clade_92 | N | N |
| *Buchnera aphidicola* | 440 | NR_074609 | clade_92 | N | N |
| *Cedecea davisae* | 499 | AF493976 | clade_92 | N | N |
| *Citrobacter amalonaticus* | 517 | FR870441 | clade_92 | N | N |
| *Citrobacter braakii* | 518 | NR_028687 | clade_92 | N | N |
| *Citrobacter farmeri* | 519 | AF025371 | clade_92 | N | N |
| *Citrobacter freundii* | 520 | NR_028894 | clade_92 | N | N |
| *Citrobacter gillenii* | 521 | AF025367 | clade_92 | N | N |
| *Citrobacter koseri* | 522 | NC_009792 | clade_92 | N | N |
| *Citrobacter murliniae* | 523 | AF025369 | clade_92 | N | N |
| *Citrobacter rodentium* | 524 | NR_074903 | clade_92 | N | N |
| *Citrobacter sedlakii* | 525 | AF025364 | clade_92 | N | N |
| *Citrobacter* sp. 30_2 | 526 | ACDJ01000053 | clade_92 | N | N |
| *Citrobacter* sp. KMSI_3 | 527 | GQ468398 | clade_92 | N | N |
| *Citrobacter werkmanii* | 528 | AF025373 | clade_92 | N | N |
| *Citrobacter youngae* | 529 | ABWL02000011 | clade_92 | N | N |

TABLE 1-continued

| OTU | SEQ ID Number | Public DB Accession | Phylogenetic Clade | Spore Former | Pathogen Status |
|---|---|---|---|---|---|
| *Cronobacter malonaticus* | 737 | GU122174 | clade_92 | N | N |
| *Cronobacter sakazakii* | 738 | NC_009778 | clade_92 | N | N |
| *Cronobacter turicensis* | 739 | FN543093 | clade_92 | N | N |
| *Enterobacter aerogenes* | 786 | AJ251468 | clade_92 | N | N |
| *Enterobacter asburiae* | 787 | NR_024640 | clade_92 | N | N |
| *Enterobacter cancerogenus* | 788 | Z96078 | clade_92 | N | N |
| *Enterobacter cloacae* | 789 | FP929040 | clade_92 | N | N |
| *Enterobacter cowanii* | 790 | NR_025566 | clade_92 | N | N |
| *Enterobacter hormaechei* | 791 | AFHR01000079 | clade_92 | N | N |
| *Enterobacter* sp. 247BMC | 792 | HQ122932 | clade_92 | N | N |
| *Enterobacter* sp. 638 | 793 | NR_074777 | clade_92 | N | N |
| *Enterobacter* sp. JC163 | 794 | JN657217 | clade_92 | N | N |
| *Enterobacter* sp. SCSS | 795 | HM007811 | clade_92 | N | N |
| *Enterobacter* sp. TSE38 | 796 | HM156134 | clade_92 | N | N |
| Enterobacteriaceae bacterium 9_2_54FAA | 797 | ADCU01000033 | clade_92 | N | N |
| Enterobacteriaceae bacterium CF01Ent_1 | 798 | AJ489826 | clade_92 | N | N |
| Enterobacteriaceae bacterium Smarlab 3302238 | 799 | AY538694 | clade_92 | N | N |
| *Escherichia albertii* | 824 | ABKX01000012 | clade_92 | N | N |
| *Escherichia coli* | 825 | NC_008563 | clade_92 | N | Category-B |
| *Escherichia fergusonii* | 826 | CU928158 | clade_92 | N | N |
| *Escherichia hermannii* | 827 | HQ407266 | clade_92 | N | N |
| *Escherichia* sp. 1_1_43 | 828 | ACID01000033 | clade_92 | N | N |
| *Escherichia* sp. 4_1_40B | 829 | ACDM02000056 | clade_92 | N | N |
| *Escherichia* sp. B4 | 830 | EU722735 | clade_92 | N | N |
| *Escherichia vulneris* | 831 | NR_041927 | clade_92 | N | N |
| *Ewingella americana* | 877 | JN175329 | clade_92 | N | N |
| *Haemophilus* genomosp. P2 oral clone MB3_C24 | 971 | DQ003621 | clade_92 | N | N |
| *Haemophilus* genomosp. P3 oral clone MB3_C38 | 972 | DQ003635 | clade_92 | N | N |
| *Haemophilus* sp. oral clone JM053 | 986 | AY349380 | clade_92 | N | N |
| *Hafnia alvei* | 989 | DQ412565 | clade_92 | N | N |
| *Klebsiella oxytoca* | 1024 | AY292871 | clade_92 | N | OP |
| *Klebsiella pneumoniae* | 1025 | CP000647 | clade_92 | N | OP |
| *Klebsiella* sp. AS10 | 1026 | HQ616362 | clade_92 | N | N |
| *Klebsiella* sp. Co9935 | 1027 | DQ068764 | clade_92 | N | N |
| *Klebsiella* sp. enrichment culture clone *SRC* _DSD25 | 1036 | HM195210 | clade_92 | N | N |
| *Klebsiella* sp. OBRC7 | 1028 | HQ616353 | clade_92 | N | N |
| *Klebsiella* sp. SP_BA | 1029 | FJ999767 | clade_92 | N | N |
| *Klebsiella* sp. SRC_DSD1 | 1033 | GU797254 | clade_92 | N | N |
| *Klebsiella* sp. SRC_DSD11 | 1030 | GU797263 | clade_92 | N | N |
| *Klebsiella* sp. SRC_DSD12 | 1031 | GU797264 | clade_92 | N | N |
| *Klebsiella* sp. SRC_DSD15 | 1032 | GU797267 | clade_92 | N | N |
| *Klebsiella* sp. SRC_DSD2 | 1034 | GU797253 | clade_92 | N | N |
| *Klebsiella* sp. SRC_DSD6 | 1035 | GU797258 | clade_92 | N | N |
| *Klebsiella variicola* | 1037 | CP001891 | clade_92 | N | N |
| *Kluyvera ascorbata* | 1038 | NR_028677 | clade_92 | N | N |
| *Kluyvera cryocrescens* | 1039 | NR_028803 | clade_92 | N | N |
| *Leminorella grimontii* | 1159 | AJ233421 | clade_92 | N | N |
| *Leminorella richardii* | 1160 | HF558368 | clade_92 | N | N |
| *Pantoea agglomerans* | 1409 | AY335552 | clade_92 | N | N |
| *Pantoea ananatis* | 1410 | CP001875 | clade_92 | N | N |
| *Pantoea brenneri* | 1411 | EU216735 | clade_92 | N | N |
| *Pantoea citrea* | 1412 | EF688008 | clade_92 | N | N |
| *Pantoea conspicua* | 1413 | EU216737 | clade_92 | N | N |
| *Pantoea septica* | 1414 | EU216734 | clade_92 | N | N |
| *Pasteurella dagmatis* | 1434 | ACZR01000003 | clade_92 | N | N |
| *Pasteurella multocida* | 1435 | NC_002663 | clade_92 | N | N |
| *Plesiomonas shigelloides* | 1469 | X60418 | clade_92 | N | N |
| *Raoultella ornithinolytica* | 1617 | AB364958 | clade_92 | N | N |
| *Raoultella planticola* | 1618 | AF129443 | clade_92 | N | N |
| *Raoultella terrigena* | 1619 | NR_037085 | clade_92 | N | N |
| *Salmonella bongori* | 1683 | NR_041699 | clade_92 | N | Category-B |
| *Salmonella enterica* | 1672 | NC_011149 | clade_92 | N | Category-B |
| *Salmonella enterica* | 1673 | NC_011205 | clade_92 | N | Category-B |
| *Salmonella enterica* | 1674 | DQ344532 | clade_92 | N | Category-B |
| *Salmonella enterica* | 1675 | ABEH02000004 | clade_92 | N | Category-B |
| *Salmonella enterica* | 1676 | ABAK02000001 | clade_92 | N | Category-B |
| *Salmonella enterica* | 1677 | NC_011080 | clade_92 | N | Category-B |
| *Salmonella enterica* | 1678 | EU118094 | clade_92 | N | Category-B |
| *Salmonella enterica* | 1679 | NC_011094 | clade_92 | N | Category-B |
| *Salmonella enterica* | 1680 | AE014613 | clade_92 | N | Category-B |
| *Salmonella enterica* | 1682 | ABFH02000001 | clade_92 | N | Category-B |
| *Salmonella enterica* | 1684 | ABEM01000001 | clade_92 | N | Category-B |
| *Salmonella enterica* | 1685 | ABAM02000001 | clade_92 | N | Category-B |

TABLE 1-continued

| OTU | SEQ ID Number | Public DB Accession | Phylogenetic Clade | Spore Former | Pathogen Status |
|---|---|---|---|---|---|
| *Salmonella typhimurium* | 1681 | DQ344533 | clade_92 | N | Category-B |
| *Salmonella typhimurium* | 1686 | AF170176 | clade_92 | N | Category-B |
| *Serratia fonticola* | 1718 | NR_025339 | clade_92 | N | N |
| *Serratia liquefaciens* | 1719 | NR_042062 | clade_92 | N | N |
| *Serratia marcescens* | 1720 | GU826157 | clade_92 | N | N |
| *Serratia odorifera* | 1721 | ADBY01000001 | clade_92 | N | N |
| *Serratia proteamaculans* | 1722 | AAUN01000015 | clade_92 | N | N |
| *Shigella boydii* | 1724 | AAKA01000007 | clade_92 | N | Category-B |
| *Shigella dysenteriae* | 1725 | NC_007606 | clade_92 | N | Category-B |
| *Shigella flexneri* | 1726 | AE005674 | clade_92 | N | Category-B |
| *Shigella sonnei* | 1727 | NC_007384 | clade_92 | N | Category-B |
| *Tatumella ptyseos* | 1916 | NR_025342 | clade_92 | N | N |
| *Trabulsiella guamensis* | 1925 | AY373830 | clade_92 | N | N |
| *Yersinia aldovae* | 2019 | AJ871363 | clade_92 | N | OP |
| *Yersinia aleksiciae* | 2020 | AJ627597 | clade_92 | N | OP |
| *Yersinia bercovieri* | 2021 | AF366377 | clade_92 | N | OP |
| *Yersinia enterocolitica* | 2022 | FR729477 | clade_92 | N | Category-B |
| *Yersinia frederiksenii* | 2023 | AF366379 | clade_92 | N | OP |
| *Yersinia intermedia* | 2024 | AF366380 | clade_92 | N | OP |
| *Yersinia kristensenii* | 2025 | ACCA01000078 | clade_92 | N | OP |
| *Yersinia mollaretii* | 2026 | NR_027546 | clade_92 | N | OP |
| *Yersinia pestis* | 2027 | AE013632 | clade_92 | N | Category-A |
| *Yersinia pseudotuberculosis* | 2028 | NC_009708 | clade_92 | N | OP |
| *Yersinia rohdei* | 2029 | ACCD01000071 | clade_92 | N | OP |
| *Yokenella regensburgei* | 2030 | AB273739 | clade_92 | N | N |
| *Conchiformibius kuhniae* | 669 | NR_041821 | clade_94 | N | N |
| *Morococcus cerebrosus* | 1267 | JN175352 | clade_94 | N | N |
| *Neisseria bacilliformis* | 1328 | AFAY01000058 | clade_94 | N | N |
| *Neisseria cinerea* | 1329 | ACDY01000037 | clade_94 | N | N |
| *Neisseria flavescens* | 1331 | ACQV01000025 | clade_94 | N | N |
| *Neisseria gonorrhoeae* | 1333 | CP002440 | clade_94 | N | OP |
| *Neisseria lactamica* | 1334 | ACEQ01000095 | clade_94 | N | N |
| *Neisseria macacae* | 1335 | AFQE01000146 | clade_94 | N | N |
| *Neisseria meningitidis* | 1336 | NC_003112 | clade_94 | N | OP |
| *Neisseria mucosa* | 1337 | ACDX01000110 | clade_94 | N | N |
| *Neisseria pharyngis* | 1338 | AJ239281 | clade_94 | N | N |
| *Neisseria polysaccharea* | 1339 | ADBE01000137 | clade_94 | N | N |
| *Neisseria sicca* | 1340 | ACKO02000016 | clade_94 | N | N |
| *Neisseria* sp. KEM232 | 1341 | GQ203291 | clade_94 | N | N |
| *Neisseria* sp. oral clone AP132 | 1344 | AY005027 | clade_94 | N | N |
| *Neisseria* sp. oral strain B33KA | 1346 | AY005028 | clade_94 | N | N |
| *Neisseria* sp. oral taxon 014 | 1347 | ADEA01000039 | clade_94 | N | N |
| *Neisseria* sp. TM10_1 | 1343 | DQ279352 | clade_94 | N | N |
| *Neisseria subflava* | 1348 | ACEO01000067 | clade_94 | N | N |
| *Clostridium oroticum* | 610 | FR749922 | clade_96 | Y | N |
| *Clostridium* sp. D5 | 627 | ADBG01000142 | clade_96 | Y | N |
| *Eubacterium contortum* | 840 | FR749946 | clade_96 | Y | N |
| *Eubacterium fissicatena* | 846 | FR749935 | clade_96 | Y | N |
| *Okadaella gastrococcus* | 1365 | HQ699465 | clade_98 | N | N |
| *Streptococcus agalactiae* | 1785 | AAJO01000130 | clade_98 | N | N |
| *Streptococcus alactolyticus* | 1786 | NR_041781 | clade_98 | N | N |
| *Streptococcus australis* | 1788 | AEQR01000024 | clade_98 | N | N |
| *Streptococcus bovis* | 1789 | AEEL01000030 | clade_98 | N | N |
| *Streptococcus canis* | 1790 | AJ413203 | clade_98 | N | N |
| *Streptococcus constellatus* | 1791 | AY277942 | clade_98 | N | N |
| *Streptococcus cristatus* | 1792 | AEVC01000028 | clade_98 | N | N |
| *Streptococcus dysgalactiae* | 1794 | AP010935 | clade_98 | N | N |
| *Streptococcus equi* | 1795 | CP001129 | clade_98 | N | N |
| *Streptococcus equinus* | 1796 | AEVB01000043 | clade_98 | N | N |
| *Streptococcus gallolyticus* | 1797 | FR824043 | clade_98 | N | N |
| *Streptococcus* genomosp. C1 | 1798 | AY278629 | clade_98 | N | N |
| *Streptococcus* genomosp. C2 | 1799 | AY278630 | clade_98 | N | N |
| *Streptococcus* genomosp. C3 | 1800 | AY278631 | clade_98 | N | N |
| *Streptococcus* genomosp. C4 | 1801 | AY278632 | clade_98 | N | N |
| *Streptococcus* genomosp. C5 | 1802 | AY278633 | clade_98 | N | N |
| *Streptococcus* genomosp. C6 | 1803 | AY278634 | clade_98 | N | N |
| *Streptococcus* genomosp. C7 | 1804 | AY278635 | clade_98 | N | N |
| *Streptococcus* genomosp. C8 | 1805 | AY278609 | clade_98 | N | N |
| *Streptococcus gordonii* | 1806 | NC_009785 | clade_98 | N | N |
| *Streptococcus infantarius* | 1807 | ABJK02000017 | clade_98 | N | N |
| *Streptococcus infantis* | 1808 | AFNN01000024 | clade_98 | N | N |
| *Streptococcus intermedius* | 1809 | NR_028736 | clade_98 | N | N |
| *Streptococcus lutetiensis* | 1810 | NR_037096 | clade_98 | N | N |
| *Streptococcus massiliensis* | 1811 | AY769997 | clade_98 | N | N |
| *Streptococcus mitis* | 1813 | AM157420 | clade_98 | N | N |
| *Streptococcus oligofermentans* | 1815 | AY099095 | clade_98 | N | N |
| *Streptococcus oralis* | 1816 | ADMV01000001 | clade_98 | N | N |

TABLE 1-continued

| OTU | SEQ ID Number | Public DB Accession | Phylogenetic Clade | Spore Former | Pathogen Status |
|---|---|---|---|---|---|
| *Streptococcus parasanguinis* | 1817 | AEKM01000012 | clade_98 | N | N |
| *Streptococcus pasteurianus* | 1818 | AP012054 | clade_98 | N | N |
| *Streptococcus peroris* | 1819 | AEVF01000016 | clade_98 | N | N |
| *Streptococcus pneumoniae* | 1820 | AE008537 | clade_98 | N | N |
| *Streptococcus porcinus* | 1821 | EF121439 | clade_98 | N | N |
| *Streptococcus pseudopneumoniae* | 1822 | FJ827123 | clade_98 | N | N |
| *Streptococcus pseudoporcinus* | 1823 | AENS01000003 | clade_98 | N | N |
| *Streptococcus pyogenes* | 1824 | AE006496 | clade_98 | N | OP |
| *Streptococcus ratti* | 1825 | X58304 | clade_98 | N | N |
| *Streptococcus salivarius* | 1826 | AGBV01000001 | clade_98 | N | N |
| *Streptococcus sanguinis* | 1827 | NR_074974 | clade_98 | N | N |
| *Streptococcus sinensis* | 1828 | AF432857 | clade_98 | N | N |
| *Streptococcus* sp. 2_1_36FAA | 1831 | ACOI01000028 | clade_98 | N | N |
| *Streptococcus* sp. 2285_97 | 1830 | AJ131965 | clade_98 | N | N |
| *Streptococcus* sp. ACS2 | 1834 | HQ616360 | clade_98 | N | N |
| *Streptococcus* sp. AS20 | 1835 | HQ616366 | clade_98 | N | N |
| *Streptococcus* sp. BS35a | 1836 | HQ616369 | clade_98 | N | N |
| *Streptococcus* sp. C150 | 1837 | ACRI01000045 | clade_98 | N | N |
| *Streptococcus* sp. CM6 | 1838 | HQ616372 | clade_98 | N | N |
| *Streptococcus* sp. ICM10 | 1840 | HQ616389 | clade_98 | N | N |
| *Streptococcus* sp. ICM12 | 1841 | HQ616390 | clade_98 | N | N |
| *Streptococcus* sp. ICM2 | 1842 | HQ616386 | clade_98 | N | N |
| *Streptococcus* sp. ICM4 | 1844 | HQ616387 | clade_98 | N | N |
| *Streptococcus* sp. ICM45 | 1843 | HQ616394 | clade_98 | N | N |
| *Streptococcus* sp. M143 | 1845 | ACRK01000025 | clade_98 | N | N |
| *Streptococcus* sp. M334 | 1846 | ACRL01000052 | clade_98 | N | N |
| *Streptococcus* sp. oral clone ASB02 | 1849 | AY923121 | clade_98 | N | N |
| *Streptococcus* sp. oral clone ASCA03 | 1850 | DQ272504 | clade_98 | N | N |
| *Streptococcus* sp. oral clone ASCA04 | 1851 | AY923116 | clade_98 | N | N |
| *Streptococcus* sp. oral clone ASCA09 | 1852 | AY923119 | clade_98 | N | N |
| *Streptococcus* sp. oral clone ASCB04 | 1853 | AY923123 | clade_98 | N | N |
| *Streptococcus* sp. oral clone ASCB06 | 1854 | AY923124 | clade_98 | N | N |
| *Streptococcus* sp. oral clone ASCC04 | 1855 | AY923127 | clade_98 | N | N |
| *Streptococcus* sp. oral clone ASCC05 | 1856 | AY923128 | clade_98 | N | N |
| *Streptococcus* sp. oral clone ASCC12 | 1857 | DQ272507 | clade_98 | N | N |
| *Streptococcus* sp. oral clone ASCD01 | 1858 | AY923129 | clade_98 | N | N |
| *Streptococcus* sp. oral clone ASCD09 | 1859 | AY923130 | clade_98 | N | N |
| *Streptococcus* sp. oral clone ASCD10 | 1860 | DQ272509 | clade_98 | N | N |
| *Streptococcus* sp. oral clone ASCE03 | 1861 | AY923134 | clade_98 | N | N |
| *Streptococcus* sp. oral clone ASCE04 | 1862 | AY953253 | clade_98 | N | N |
| *Streptococcus* sp. oral clone ASCE05 | 1863 | DQ272510 | clade_98 | N | N |
| *Streptococcus* sp. oral clone ASCE06 | 1864 | AY923135 | clade_98 | N | N |
| *Streptococcus* sp. oral clone ASCE09 | 1865 | AY923136 | clade_98 | N | N |
| *Streptococcus* sp. oral clone ASCE10 | 1866 | AY923137 | clade_98 | N | N |
| *Streptococcus* sp. oral clone ASCE12 | 1867 | AY923138 | clade_98 | N | N |
| *Streptococcus* sp. oral clone ASCF05 | 1868 | AY923140 | clade_98 | N | N |
| *Streptococcus* sp. oral clone ASCF07 | 1869 | AY953255 | clade_98 | N | N |
| *Streptococcus* sp. oral clone ASCF09 | 1870 | AY923142 | clade_98 | N | N |
| *Streptococcus* sp. oral clone ASCG04 | 1871 | AY923145 | clade_98 | N | N |
| *Streptococcus* sp. oral clone BW009 | 1872 | AY005042 | clade_98 | N | N |
| *Streptococcus* sp. oral clone CH016 | 1873 | AY005044 | clade_98 | N | N |
| *Streptococcus* sp. oral clone GK051 | 1874 | AY349413 | clade_98 | N | N |
| *Streptococcus* sp. oral clone GM006 | 1875 | AY349414 | clade_98 | N | N |
| *Streptococcus* sp. oral clone P2PA_41 P2 | 1876 | AY207051 | clade_98 | N | N |
| *Streptococcus* sp. oral clone P4PA_30 P4 | 1877 | AY207064 | clade_98 | N | N |
| *Streptococcus* sp. oral taxon 071 | 1878 | AEEP01000019 | clade_98 | N | N |
| *Streptococcus* sp. oral taxon G59 | 1879 | GU432132 | clade_98 | N | N |
| *Streptococcus* sp. oral taxon G62 | 1880 | GU432146 | clade_98 | N | N |
| *Streptococcus* sp. oral taxon G63 | 1881 | GU432150 | clade_98 | N | N |
| *Streptococcus suis* | 1882 | FM252032 | clade_98 | N | N |
| *Streptococcus thermophilus* | 1883 | CP000419 | clade_98 | N | N |
| *Streptococcus uberis* | 1884 | HQ391900 | clade_98 | N | N |
| *Streptococcus urinalis* | 1885 | DQ303194 | clade_98 | N | N |
| *Streptococcus vestibularis* | 1886 | AEKO01000008 | clade_98 | N | N |
| *Streptococcus viridans* | 1887 | AF076036 | clade_98 | N | N |
| *Synergistetes bacterium* oral clone 03 5 D05 | 1908 | GU227192 | clade_98 | N | N |

TABLE 2

| Phylogenetic Clade | OTUs in clade |
|---|---|
| clade_172 | Bifidobacteriaceae genomosp. C1, *Bifidobacterium adolescentis*, *Bifidobacterium angulatum*, *Bifidobacterium animalis*, *Bifidobacterium breve*, *Bifidobacterium catenulatum*, *Bifidobacterium dentium*, *Bifidobacterium gallicuin*, *Bifidobacterium infantis*, *Bifidobacterium kashiwanohense*, *Bifidobacterium longum*, *Bifidobacterium pseudocatenulatum*, *Bifidobacterium pseudolongum*, *Bifidobacterium scardovii*, *Bifidobacterium* sp. HM2, *Bifidobacterium* sp. HMLN12, *Bifidobacterium* sp. M45, *Bifidobacterium* sp. MSX5B, *Bifidobacterium* sp. TM_7, *Bifidobacterium thermophilum* |
| clade_172i | Bifidobacteriaceae genomosp. C1, *Bifidobacterium angulatum*, *Bifidobacterium animalis*, *Bifidobacterium breve*, *Bifidobacterium catenulatum*, *Bifidobacterium dentium*, *Bifidobacterium gallicum*, *Bifidobacterium infantis*, *Bifidobacterium kashiwanohense*, *Bifidobacterium pseudocatenulatum*, *Bifidobacterium pseudolongum*, *Bifidobacterium scardovii*, *Bifidobacterium* sp. HM2, *Bifidobacterium* sp. HMLN12, *Bifidobacterium* sp. M45, *Bifidobacterium* sp. MSX5B, *Bifidobacterium* sp. TM 7, *Bifidobacterium thermophilum* |
| clade_198 | *Lactobacillus casei*, *Lactobacillus paracasei*, *Lactobacillus zeae* |
| clade_198i | *Lactobacillus zeae* |
| clade_260 | *Clostridium hylemonae*, *Clostridium scindens*, Lachnospiraceae bacterium 5_1_57FAA |
| clade_260c | *Clostridium hylemonae*, Lachnospiraceae bacterium 5_1_57FAA |
| clade_260g | *Clostridium hylemonae*, Lachnospiraceae bacterium 5_1_57FAA |
| clade_260h | *Clostridium hylemonae*, Lachnospiraceae bacterium 5_1_57FAA |
| clade_262 | *Clostridium glycyrrhizinilyticum*, *Clostridium nexile*, *Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, *Rummococcus torques* |
| clade_262i | *Clostridium glycyrrhizinilyticum*, *Clostridium nexile*, *Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris* |
| clade_309 | *Blautia coccoides*, *Blautia glucerasea*, *Blautia glucerasei*, *Blautia hansenii*, *Blautia luti*, *Blautia producta*, *Blautia schinkii*, *Blautia* sp. M25, *Blautia stercoris*, *Blautia wexlerae*, *Bryantella formatexigens*, *Clostridium coccoides*, *Eubacterium cellulosolveris*, Lachnospiraceae bacterium 6_1_63FAA, *Marvinbryantia formatexigens*, *Ruminococcus hansenii*, *Ruminococcus obeum*, *Ruminococcus* sp. 5_1_39BFAA, *Ruminococcus* sp. K_1, *Syntrophococcus sucromutans* |
| clade_309c | *Blautia coccoides*, *Blautia glucerasea*, *Blautia glucerasei*, *Blautia hansenii*, *Blautia luti*, *Blautia schinkii*, *Blautia* sp. M25, *Blautia stercoris*, *Blautia wexlerae*, *Bryantella formatexigens*, *Clostridium coccoides*, *Eubacterium cellulosolvens*, Lachnospiraceae bacterium 6_1_63FAA, *Marvinbryantia formatexigens*, *Ruminococcus hansenii*, *Ruminococcus obeum*, *Ruminococcus* sp. 5_1_39BFAA, *Ruminococcus* sp. K_1, *Syntrophococcus sucromutans* |
| clade_309e | *Blautia coccoides*, *Blautia glucerasea*, *Blautia glucerasei*, *Blautia hansenii*, *Blautia luti*, *Blautia schinkii*, *Blautia* sp. M25, *Blautia stercoris*, *Blautia wexlerae*, *Bryantella formatexigens*, *Clostridium coccoides*, *Eubacterium cellulosolvens*, Lachnospiraceae bacterium 6_1_63FAA, *Marvinbryantia formatexigens*, *Ruminococcus hansenii*, *Ruminococcus obeum*, *Ruminococcus* sp. 5_1_39BFAA, *Ruminococcus* sp. K_1, *Syntrophococcus sucromutans* |
| clade_309g | *Blautia coccoides*, *Blautia glucerasea*, *Blautia glucerasei*, *Blautia hansenii*, *Blautia luti*, *Blautia schinkii*, *Blautia* sp. M25, *Blautia stercoris*, *Blautia wexlerae*, *Bryantella formatexigens*, *Clostridium coccoides*, *Eubacterium cellulosolvens*, Lachnospiraceae bacterium 6_1_63FAA, *Marvinbryantia formatexigens*, *Ruminococcus hansenii*, *Ruminococcus obeum*, *Ruminococcus* sp. 5_1_39BFAA, *Ruminococcus* sp. K_1, *Syntrophococcus sucromutans* |
| clade_309h | *Blautia coccoides*, *Blautia glucerasea*, *Blautia glucerasei*, *Blautia hansenii*, *Blautia luti*, *Blautia schinkii*, *Blautia* sp. M25, *Blautia stercoris*, *Blautia wexlerae*, *Bryantella formatexigens*, *Clostridium coccoides*, *Eubacterium cellulosolvens*, Lachnospiraceae bacterium 6_1_63FAA, *Marvinbryantia formatexigens*, *Ruminococcus hansenii*, *Ruminococcus obeum*, *Ruminococcus* sp. 5_1_39BFAA, *Ruminococcus* sp. K_1, *Syntrophococcus sucromutans* |
| clade_309i | *Blautia coccoides*, *Blautia glucerasea*, *Blautia glucerasei*, *Blautia hansenii*, *Blautia luti*, *Blautia schinkii*, *Blautia* sp. M25, *Blautia stercoris*, *Blautia wexlerae*, *Bryantella formatexigens*, *Clostridium coccoides*, *Eubacterium cellulosolvens*, Lachnospiraceae bacterium 6_1_63FAA, *Marvinbryantia formatexigens*, *Ruminococcus hansenii*, *Ruminococcus* sp. 5_1_39BFAA, *Ruminococcus* sp. K_1, *Syntrophococcus sucromutans* |
| clade_313 | *Lactobacillus antri*, *Lactobacillus coleohominis*, *Lactobacillus fermentum*, *Lactobacillus gastricus*, *Lactobacillus mucosae*, *Lactobacillus oris*, *Lactobacillus pontis*, *Lactobacillus reuteri*, *Lactobacillus* sp. KLDS 1.0707, *Lactobacillus* sp. KLDS 1.0709, *Lactobacillus* sp. KLDS 1.0711, *Lactobacillus* sp. KLDS 1.0713, *Lactobacillus* sp. KLDS 1.0716, *Lactobacillus* sp. KLDS 1.0718, *Lactobacillus* sp. oral taxon 052, *Lactobacillus vaginalis* |
| clade_313f | *Lactobacillus antri*, *Lactobacillus coleohominis*, *Lactobacillus fermentum*, *Lactobacillus gastricus*, *Lactobacillus mucosae*, *Lactobacillus oris*, *Lactobacillus pontis*, *Lactobacillus* sp. KLDS 1.0707, *Lactobacillus* sp. KLDS 1.0709, *Lactobacillus* sp. KLDS 1.0711, *Lactobacillus* sp. KLDS 1.0713, *Lactobacillus* sp. KLDS 1.0716, *Lactobacillus* sp. KLDS 1.0718, *Lactobacillus* sp. oral taxon 052, *Lactobacillus vaginalis* |
| clade_325 | *Staphylococcus aureus*, *Staphylococcus auricularis*, *Staphylococcus capitis*, *Staphylococcus caprae*, *Staphylococcus carnosus*, *Staphylococcus cohnii*, *Staphylococcus condimenti*, *Staphylococcus epidermidis*, *Staphylococcus equorum*, *Staphylococcus haemolyticus*, *Staphylococcus hominis*, *Staphylococcus lugdunensis*, *Staphylococcus pasteuri*, *Staphylococcus pseudintermedius*, *Staphylococcus saccharolyticus*, *Staphylococcus saprophyticus*, *Staphylococcus* sp. H292, *Staphylococcus* sp. H780, *Staphylococcus* sp. clone bottae7, *Staphylococcus succinus*, *Staphylococcus warneri*, *Staphylococcus xylosus* |
| clade_325f | *Staphylococcus aureus*, *Staphylococcus auricularis*, *Staphylococcus capitis*, *Staphylococcus caprae*, *Staphylococcus carnosus*, *Staphylococcus cohnii*, *Staphylococcus condimenti*, *Staphylococcus epidermidis*, *Staphylococcus equorum*, *Staphylococcus haemolyticus*, *Staphylococcus hominis*, *Staphylococcus lugdunensis*, *Staphylococcus pseudintermedius*, *Staphylococcus saccharolyticus*, *Staphylococcus saprophyticus*, *Staphylococcus* sp. H292, *Staphylococcus* sp. H780, *Staphylococcus* sp. clone bottae7, *Staphylococcus succinus*, *Staphylococcus xylosus* |

TABLE 2-continued

| Phylogenetic Clade | OTUs in clade |
|---|---|
| clade_335 | *Bacteroides* sp. 20_3, *Bacteroides* sp. 3_1_19, *Bacteroides* sp. 3_2_5, *Parabacteroides distasonis*, *Parabacteroides goldsteinii*, *Parabacteroides gordonii*, *Parabacteroides* sp. D13 |
| clade_335i | *Bacteroides* sp. 20_3, *Bacteroides* sp. 3_1_19, *Bacteroides* sp. 3_2_5, *Parabacteroides goldsteinii*, *Parabacteroides gordonii*, *Parabacteroides* sp. D13 |
| clade_351 | *Clostridium innocuum*, *Clostridium* sp. HGF2 |
| clade_351e | *Clostridium* sp. HGF2 |
| clade_354 | *Clostridium bartlettii*, *Clostridium bifermentans*, *Clostridium ghonii*, *Clostridium glycolicum*, *Clostridium mayombei*, *Clostridium sordellii*, *Clostridium* sp. MT4 E, *Eubacterium tenue* |
| clade_354e | *Clostridium bartlettii*, *Clostridium ghonii*, *Clostridium glycolicum*, *Clostridium mayombei*, *Clostridium sordellii*, *Clostridium* sp. MT4 E, *Eubacterium tenue* |
| clade_360 | *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, *Ruminococcus* sp. ID8 |
| clade_360c | *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus* |
| clade_360g | *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus* |
| clade_360h | *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus* |
| clade_360i | *Dorea formicigenerans*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, *Ruminococcus* sp. ID8 |
| clade_378 | *Bacteroides barnesiae*, *Bacteroides coprocola*, *Bacteroides coprophilus*, *Bacteroides dorei*, *Bacteroides massiliensis*, *Bacteroides plebeius*, *Bacteroides* sp. 3_1_33FAA, *Bacteroides* sp. 3_1_40A, *Bacteroides* sp. 4_3_47FAA, *Bacteroides* sp. 9_1_42FAA, *Bacteroides* sp. NB_8, *Bacteroides vulgatus* |
| clade_378e | *Bacteroides barnesiae*, *Bacteroides coprocola*, *Bacteroides coprophilus*, *Bacteroides dorei*, *Bacteroides massiliensis*, *Bacteroides plebeius*, *Bacteroides* sp. 3_1_33FAA, *Bacteroides* sp. 3_1_40A, *Bacteroides* sp. 4_3_47FAA, *Bacteroides* sp. 9_1_42FAA, *Bacteroides* sp. NB_8 |
| clade_38 | *Bacteroides ovatus*, *Bacteroides* sp. 1_1_30, *Bacteroides* sp. 2_1_22, *Bacteroides* sp. 2_2_4, *Bacteroides* sp. 3_1_23, *Bacteroides* sp. D1, *Bacteroides* sp. D2, *Bacteroides* sp. D22, *Bacteroides xylanisolvens* |
| clade_38e | *Bacteroides* sp. 1_1_30, *Bacteroides* sp. 2_1_22, *Bacteroides* sp. 2_2_4, *Bacteroides* sp. 3_1_23, *Bacteroides* sp. D1, *Bacteroides* sp. D2, *Bacteroides* sp. D22, *Bacteroides xylanisolvens* |
| clade_38i | *Bacteroides* sp. 1_1_30, *Bacteroides* sp. 2_1_22, *Bacteroides* sp. 2_2_4, *Bacteroides* sp. 3_1_23, *Bacteroides* sp. D1, *Bacteroides* sp. D2, *Bacteroides* sp. D22, *Bacteroides xylanisolvens* |
| clade_408 | *Anaerostipes caccae*, *Anaerostipes* sp. 3_2_56FAA, Clostridiales bacterium 1_7_47FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium asparagiforme*, *Clostridium bolteae*, *Clostridium celerecrescens*, *Clostridium citroniae*, *Clostridium clostridiiformes*, *Clostridium clostridioforme*, *Clostridium hathewayi*, *Clostridium indolis*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 3_1_57FAA, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_408b | *Anaerostipes caccae*, *Anaerostipes* sp. 3_2_56FAA, Clostridiales bacterium 1_7_47FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium asparagiforme*, *Clostridium bolteae*, *Clostridium celerecrescens*, *Clostridium citroniae*, *Clostridium clostridiiformes*, *Clostridium clostridioforme*, *Clostridium indolis*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_408d | *Anaerostipes caccae*, *Anaerostipes* sp. 3_2_56FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium celerecrescens*, *Clostridium citroniae*, *Clostridium clostridiiformes*, *Clostridium clostridioforme*, *Clostridium hathewayi*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 3_1_57FAA, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_408f | *Anaerostipes* sp. 3_2_56FAA, Clostridiales bacterium 1_7_47FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium asparagiforme*, *Clostridium bolteae*, *Clostridium celerecrescens*, *Clostridium citroniae*, *Clostridium clostridiiformes*, *Clostridium clostridioforme*, *Clostridium hathewayi*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 3_1_57FAA, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_408g | *Anaerostipes caccae*, *Anaerostipes* sp. 3_2_56FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium celerecrescens*, *Clostridium citroniae*, *Clostridium clostridiiformes*, |

TABLE 2-continued

| Phylogenetic Clade | OTUs in clade |
|---|---|
| | *Clostridium clostridioforme*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_408h | *Anaerostipes caccae*, *Anaerostipes* sp. 3_2_56FAA, Clostridiales sp. SM4_1, Clostridiales sp. SSC_2, *Clostridium aerotolerans*, *Clostridium aldenense*, *Clostridium algidixylanolyticum*, *Clostridium amygdalinum*, *Clostridium celerecrescens*, *Clostridium citroniae*, *Clostridium clostridiiformes*, *Clostridium clostridioforme*, *Clostridium lavalense*, *Clostridium saccharolyticum*, *Clostridium* sp. M62_1, *Clostridium* sp. SS2_1, *Clostridium sphenoides*, *Clostridium symbiosum*, *Clostridium xylanolyticum*, *Eubacterium hadrum*, *Fusobacterium naviforme*, Lachnospiraceae bacterium 5_1_63FAA, Lachnospiraceae bacterium A4, Lachnospiraceae bacterium DJF VP30, Lachnospiraceae genomosp. C1, *Moryella indoligenes* |
| clade_420 | *Barnesiella intestinihominis*, *Barnesiella viscericola*, *Parabacteroides* sp. NS31_3, Porphyromonadaceae bacterium NML 060648, *Tannerella forsythia*, *Tannerella* sp. 6_1_58FAA_CT1 |
| clade_420f | *Barnesiella viscericola*, *Parabacteroides* sp. NS31_3. Porphyromonadaceae bacterium NML 060648, *Tannerella forsythia*, *Tannerella* sp. 6_1_58FAA_CT1 |
| clade_444 | *Butyrivibrio fibrisolvens*, *Eubacterium rectale*, *Eubacterium* sp. oral clone GI038, *Lachnobacterium bovis*, *Roseburia cecicola*, *Roseburia faecalis*, *Roseburia faecis*, *Roseburia hominis*, *Roseburia intestinalis*, *Roseburia inulinivorans*, *Roseburia* sp. 11SE37, *Roseburia* sp. 11SE38, *Shuttleworthia satelles*, *Shuttleworthia* sp. MSX8B, *Shuttleworthia* sp. oral taxon G69 |
| clade_444i | *Butyrivibrio fibrisolvens*, *Eubacterium* sp. oral clone GI038, *Lachnobacterium bovis*, *Roseburia cecicola*, *Roseburia faecis*, *Roseburia hominis*, *Roseburia inulinivorans*, *Roseburia* sp. 11SE37, *Roseburia* sp. 11SE38, *Shuttleworthia satelles*, *Shuttleworthia* sp. MSX8B, *Shuttleworthia* sp. oral taxon G69 |
| clade_478 | *Faecalibacterium prausnitzii*, *Gemmiger formicilis*, *Subdoligranulum variabile* |
| clade_478i | *Gemmiger formicilis*, *Subdoligranulum variabile* |
| clade_479 | Clostridiaceae bacterium JC13, *Clostridium* sp. MLG055, Erysipelotrichaceae bacterium 3_1_53 |
| clade_479c | *Clostridium* sp. MLG055, Erysipelotrichaceae bacterium 3_1_53 |
| clade_479g | *Clostridium* sp. MLG055, Erysipelotrichaceae bacterium 3_1_53 |
| clade_479h | *Clostridium* sp. MLG055, Erysipelotrichaceae bacterium 3_1_53 |
| clade_481 | *Clostridium cocleatum*, *Clostridium ramosum*, *Clostridium saccharogumia*, *Clostridium spiroforme*, *Coprobacillus* sp. D7 |
| clade_481a | *Clostridium cocleatum*, *Clostridium spiroforme*, *Coprobacillus* sp. D7 |
| clade_481b | *Clostridium cocleatum*, *Clostridium ramosum*, *Clostridium spiroforme*, *Coprobacillus* sp. D7 |
| clade_481e | *Clostridium cocleatum*, *Clostridium saccharogumia*, *Clostridium spiroforme*, *Coprobacillus* sp. D7 |
| clade_481g | *Clostridium cocleatum*, *Clostridium spiroforme*, *Coprobacillus* sp. D7 |
| clade_481h | *Clostridium cocleatum*, *Clostridium spiroforme*, *Coprobacillus* sp. D7 |
| clade_481i | *Clostridium ramosum*, *Clostridium saccharogumia*, *Clostridium spiroforme*, *Coprobacillus* sp. D7 |
| clade_497 | *Abiotrophia para_adiacens*, *Carnobacterium divergens*, *Carnobacterium maltaromaticum*, *Enterococcus avium*, *Enterococcus caccae*, *Enterococcus casseliflavus*, *Enterococcus durans*, *Enterococcus faecalis*, *Enterococcus faecium*, *Enterococcus gallinarum*, *Enterococcus gilvus*, *Enterococcus hawaiiensis*, *Enterococcus hirae*, *Enterococcus italicus*, *Enterococcus mundtii*, *Enterococcus raffinosus*, *Enterococcus* sp. BV2CASA2, *Enterococcus* sp. CCRI 16620, *Enterococcus* sp. F95, *Enterococcus* sp. RfL6, *Enterococcus thailandieus*, *Fusobacterium canifelinum*, *Fusobacterium* genomosp. C1, *Fusobacterium* genomosp. C2, *Fusobacterium nucleatum*, *Fusobacterium periodonticum*, *Fusobacterium* sp. 11_3_2, *Fusobacterium* sp. 1_1_41FAA, *Fusobacterium* sp. 2_1_31, *Fusobacterium* sp. 3_1_27, *Fusobacterium* sp. 3_1_33, *Fusobacterium* sp. 3_1_36A2, *Fusobacterium* sp. AC18, *Fusobacterium* sp. ACB2, *Fusobacterium* sp. AS2, *Fusobacterium* sp. CM1, *Fusobacterium* sp. CM21, *Fusobacterium* sp. CM22, *Fusobacterium* sp. oral clone ASCF06, *Fusobacterium* sp. oral clone ASCF11, *Granulicatella adiacens*, *Granulicatella elegans*, *Granulicatella paradiacens*, *Granulicatella* sp. oral clone ASC02, *Granulicatella* sp. oral clone ASCA05, *Granulicatella* sp. oral clone ASCB09, *Granulicatella* sp. oral clone ASCG05, *Tetragenococcus halophilus*, *Tetragenococcus koreensis*, *Vagococcus fluvialis* |
| clade_497e | *Abiotrophia para_adiacens*, *Carnobacterium divergens*, *Carnobacterium maltaromaticum*, *Enterococcus avium*, *Enterococcus caccae*, *Enterococcus casseliflavus*, *Enterococcus durans*, *Enterococcus faecium*, *Enterococcus gallinarum*, *Enterococcus gilvus*, *Enterococcus hawaiiensis*, *Enterococcus hirae*, *Enterococcus italicus*, *Enterococcus mundtii*, *Enterococcus raffinosus*, *Enterococcus* sp. BV2CASA2, *Enterococcus* sp. CCRI 16620, *Enterococcus* sp. F95, *Enterococcus* sp. RfL6, *Enterococcus thailandicus*, *Fusobacterium canifelinum*, *Fusobacterium* genomosp. C1, *Fusobacterium* genomosp. C2, *Fusobacterium nucleatum*, *Fusobacterium periodonticum*, *Fusobacterium* sp. 11_3_2, *Fusobacterium* sp. 1_1_41FAA, *Fusobacterium* sp. 2_1_31, *Fusobacterium* sp. 3_1_27, *Fusobacterium* sp. 3_1_33, *Fusobacterium* sp. 3_1_36A2, *Fusobacterium* sp. AC18, *Fusobacterium* sp. ACB2, *Fusobacterium* sp. AS2, *Fusobacterium* sp. CM1, *Fusobacterium* sp. CM21, *Fusobacterium* sp. CM22, *Fusobacterium* sp. oral clone ASCF06, *Fusobacterium* sp. oral clone ASCF11, *Granulicatella adiacens*, *Granulicatella elegans*, *Granulicatella paradiacens*, *Granulicatella* sp. oral clone ASC02, *Granulicatella* sp. oral clone ASCA05, *Granulicatella* sp. oral clone ASCB09, *Granulicatella* sp. oral clone ASCG05, *Tetragenococcus halophilus*, *Tetragenococcus koreensis*, *Vagococcus fluvialis* |
| clade_497f | *Abiotrophia para_adiacens*, *Carnobacterium divergens*, *Carnobacterium maltaromaticum*, *Enterococcus avium*, *Enterococcus caccae*, *Enterococcus casseliflavus*, *Enterococcus faecalis*, *Enterococcus gallinarum*, *Enterococcus gilvus*, *Enterococcus hawaiiensis*, *Enterococcus italicus*, *Enterococcus mundtii*, *Enterococcus raffinosus*, *Enterococcus* sp. BV2CASA2, *Enterococcus* sp. CCRI 16620, *Enterococcus* sp. F95, *Enterococcus* sp. RfL6, *Enterococcus thailandicus*, *Fusobacterium canifelinum*, *Fusobacterium* genomosp. C1, *Fusobacterium* genomosp. C2, *Fusobacterium nucleatum*, *Fusobacterium periodonticum*, *Fusobacterium* sp. 11_3_2, *Fusobacterium* sp. 1_1_41FAA, *Fusobacterium* sp. 2_1_31, *Fusobacterium* sp. 3_1_27, *Fusobacterium* sp. 3_1_33, *Fusobacterium* sp. 3_1_36A2, *Fusobacterium* sp. AC18, *Fusobacterium* sp. ACB2, *Fusobacterium* sp. AS2, *Fusobacterium* sp. CM1, *Fusobacterium* sp. CM21, *Fusobacterium* sp. CM22, *Fusobacterium* sp. oral clone ASCF06, *Fusobacterium* sp. oral clone |

TABLE 2-continued

| Phylogenetic Clade | OTUs in clade |
|---|---|
| | ASCF11, *Granulicatella adiacens*, *Granulicatella elegans*, *Granulicatella paradiacens*, *Granulicatella* sp. oral clone ASC02, *Granulicatella* sp. oral clone ASCA05, *Granulicatella* sp. oral clone ASCB09, *Granulicatella* sp. oral clone ASCG05, *Tetragenococcus halophilus*, *Tetragenococcus koreensis*, *Vagococcus fluvialis* |
| clade_512 | *Eubacterium barkeri*, *Eubacterium callanderi*, *Eubacterium limosum*, *Pseudoramibacter alactolyticus* |
| clade_512i | *Eubacterium barkeri*, *Eubacterium callanderi*, *Pseudoramibacter alactolyticus* |
| clade_516 | *Anaerotruncus colihominis*, *Clostridium methylpentosum*, *Clostridium* sp. YIT 12070, *Hydrogenoanaerobacterium saccharovorans*, *Ruminococcus albus*, *Ruminococcus flavefaciens* |
| clade_516c | *Clostridium methylpentosum*, *Clostridium* sp. YIT 12070, *Hydrogenoanaerobacterium saccharovorans*, *Ruminococcus albus*, *Ruminococcus flavefaciens* |
| clade_516g | *Clostridium methylpentosum*, *Clostridium* sp. YIT 12070, *Hydrogenoanaerobacterium saccharovorans*, *Ruminococcus albus*, *Ruminococcus flavefaciens* |
| clade_516h | *Clostridium methylpentosum*, *Clostridium* sp. YIT 12070, *Hydrogenoanaerobacterium saccharovorans*, *Ruminococcus albus*, *Ruminococcus flavefaciens* |
| clade_519 | *Eubacterium ventriosum* |
| clade_522 | *Bacteroides galacturonicus*, *Eubacterium eligens*, *Lachnospira multipara*, *Lachnospira pectinoschiza*, *Lactobacillus rogosae* |
| clade_522i | *Bacteroides galacturonicus*, *Lachnospira multipara*, *Lachnospira pectinoschiza*, *Lactobacillus rogosae* |
| clade_553 | *Collinsella aerofaciens*, *Collinsella intestinalis*, *Collinsella stercoris*, *Collinsella tanakaei* |
| clade_553i | *Collinsella intestinalis*, *Collinsella stercoris*, *Collinsella tanakaei* |
| clade_566 | *Adlercreutzia equolifaciens*, Coriobacteriaceae bacterium JC110, Coriobacteriaceae bacterium phI, *Cryptobacterium curtum*, *Eggerthella lenta*, *Eggerthella sinensis*, *Eggerthella* sp. 1_3_56FAA, *Eggerthella* sp. HGA1, *Eggerthella* sp. YY7918, *Gordonibacter pamelaeae*, *Slackia equolifaciens*, *Slackia exigua*, *Slackia faecicanis*, *Slackia heliotrinireducens*, *Slackia isoflavoniconvertens*, *Slackia piriformis*, *Slackia* sp. NATTS, *Streptomyces albus* |
| clade_566f | Coriobacteriaceae bacterium JC110, Coriobacteriaceae bacterium phI, *Cryptobacterium curtum*, *Eggerthella lenta*, *Eggerthella sinensis*, *Eggerthella* sp. 1_3_56FAA, *Eggerthella* sp. HGA1, *Eggerthella* sp. YY7918, *Gordonibacter pamelaeae*, *Slackia equolifaciens*, *Slackia exigua*, *Slackia faecicanis*, *Slackia heliotrinireducens*, *Slackia isoflavoniconvertens*, *Slackia piriformis*, *Slackia* sp. NATTS, *Streptomyces albus* |
| clade_572 | *Butyricicoccus pullicaecorum*, *Eubacterium desmolans*, *Papillibacter cinnamivorans*, *Sporobacter termitidis* |
| clade_572i | *Butyricicoccus pullicaecorum*, *Papillibacter cinnamivorans*, *Sporobacter termitidis* |
| clade_65 | *Bacteroides faecis*, *Bacteroides fragilis*, *Bacteroides nordii*, *Bacteroides salyersiae*, *Bacteroides* sp. 1_1_14, *Bacteroides* sp. 1_1_6, *Bacteroides* sp. 2_1_56FAA, *Bacteroides* sp. AR29, *Bacteroides* sp. B2, *Bacteroides thetaiotaomicron* |
| clade_65e | *Bacteroides faecis*, *Bacteroides fragilis*, *Bacteroides nordii*, *Bacteroides salyersiae*, *Bacteroides* sp. 1_1_14, *Bacteroides* sp. 1_1_6, *Bacteroides* sp. 2_1_56FAA, *Bacteroides* sp. AR29, *Bacteroides* sp. B2 |
| clade_92 | *Actinobacillus actinomycetemcomitans*, *Actinobacillus succinogenes*, *Aggregatibacter actinomycetemcomitans*, *Aggregatibacter aphrophilus*, *Aggregatibacter segnis*, *Averyella dalhousiensis*, Bisgaard Taxon, *Buchnera aphidicola*, *Cedecea davisae*, *Citrobacter amalonaticus*, *Citrobacter braakii*, *Citrobacter farmeri*, *Citrobacter freundii*, *Citrobacter gillenii*, *Citrobacter koseri*, *Citrobacter murliniae*, *Citrobacter rodentium*, *Citrobacter sedlakii*, *Citrobacter* sp. 30_2, *Citrobacter* sp. KMSI_3, *Citrobacter werkmanii*, *Citrobacter youngae*, *Cronobacter malonaticus*, *Cronobacter sakazakii*, *Cronobacter turicensis*, *Enterobacter aerogenes*, *Enterobacter asburiae*, *Enterobacter cancerogenus*, *Enterobacter cloacae*, *Enterobacter cowanii*, *Enterobacter hormaechei*, *Enterobacter* sp. 247BMC, *Enterobacter* sp. 638, *Enterobacter* sp. JC163, *Enterobacter* sp. SCSS, *Enterobacter* sp. TSE38, Enterobacteriaceae bacterium 9_2_54FAA, Enterobacteriaceae bacterium CF01Ent_1, Enterobacteriaceae bacterium Smarlab 3302238, *Escherichia albertii*, *Escherichia coli*, *Escherichia fergusonii*, *Escherichia hermannii*, *Escherichia* sp. 1_1_43, *Escherichia* sp. 4_1_40B, *Escherichia* sp. B4, *Escherichia vulneris*, *Ewingella americana*, *Haemophilus* genomosp. P2 oral clone MB3_C24, *Haemophilus* genomosp. P3 oral clone MB3_C38, *Haemophilus* sp. oral clone JM053, *Hafnia alvei*, *Klebsiella oxytoca*, *Klebsiella pneumoniae*, *Klebsiella* sp. AS10, *Klebsiella* sp. Co9935, *Klebsiella* sp. OBRC7, *Klebsiella* sp. SP_BA, *Klebsiella* sp. SRC_DSD1, *Klebsiella* sp. SRC_DSD11, *Klebsiella* sp. SRC_DSD12, *Klebsiella* sp. SRC_DSD15, *Klebsiella* sp. SRC_DSD2, *Klebsiella* sp. SRC_DSD6, *Klebsiella* sp. enrichment culture clone SRC_DSD25, *Klebsiella variicola*, *Kluyvera ascorbata*, *Kluyvera cryocrescens*, *Leminorella grimontii*, *Leminorella richardii*, *Pantoea agglomerans*, *Pantoea ananatis*, *Pantoea brenneri*, *Pantoea citrea*, *Pantoea conspicua*, *Pantoea septica*, *Pasteurella dagmatis*, *Pasteurella multocida*, *Plesiomonas shigelloides*, *Raoultella ornithinolytica*, *Raoultella planticola*, *Raoultella terrigena*, *Salmonella bongori*, *Salmonella enterica*, *Salmonella typhimurium*, *Serratia fonticola*, *Serratia liquefaciens*, *Serratia marcescens*, *Serratia odorifera*, *Serratia proteamaculans*, *Shigella boydii*, *Shigella dysenteriae*, *Shigella flexneri*, *Shigella sonnei*, *Tatumella ptyseos*, *Trabulsiella guamensis*, *Yersinia aldovae*, *Yersinia aleksiciae*, *Yersinia bercovieri*, *Yersinia enterocolitica*, *Yersinia frederiksenii*, *Yersinia intermedia*, *Yersinia kristensenii*, *Yersinia mollaretii*, *Yersinia pestis*, *Yersinia pseudotuberculosis*, *Yersinia rohdei*, *Yokenella regensburgei* |
| clade_92e | *Actinobacillus actinomycetemcomitans*, *Actinobacillus succinogenes*, *Aggregatibacter actinomycetemcomitans*, *Aggregatibacter aphrophilus*, *Aggregatibacter segnis*, *Averyella dalhousiensis*, Bisgaard Taxon, *Buchnera aphidicola*, *Cedecea davisae*, *Citrobacter amalonaticus*, *Citrobacter braakii*, *Citrobacter farmeri*, *Citrobacter freundii*, *Citrobacter gillenii*, *Citrobacter koseri*, *Citrobacter murliniae*, *Citrobacter rodentium*, *Citrobacter sedlakii*, *Citrobacter* sp. 30_2, *Citrobacter* sp. KMSI_3, *Citrobacter werkmanii*, *Citrobacter youngae*, *Cronobacter malonaticus*, *Cronobacter sakazakii*, *Cronobacter turicensis*, *Enterobacter aerogenes*, *Enterobacter asburiae*, *Enterobacter cancerogenus*, *Enterobacter cloacae*, *Enterobacter cowanii*, *Enterobacter hormaechei*, *Enterobacter* sp. 247BMC, *Enterobacter* sp. 638, *Enterobacter* sp. JC163, *Enterobacter* sp. SCSS, *Enterobacter* sp. TSE38, Enterobacteriaceae bacterium 9_2_54FAA, Enterobacteriaceae bacterium CF01Ent_1, Enterobacteriaceae bacterium Smarlab 3302238, *Escherichia albertii*, *Escherichia fergusonii*, *Escherichia hermannii*, *Escherichia* sp. 1_1_43, *Escherichia* sp. 4_1_40B, *Escherichia* sp. B4, *Escherichia vulneris*, *Ewingella americana*, |

TABLE 2-continued

| Phylogenetic Clade | OTUs in clade |
|---|---|
| | *Haemophilus* genomosp. P2 oral clone MB3_C24, *Haemophilus* genomosp. P3 oral clone MB3_C38, *Haemophilus* sp. oral clone JM053, *Hafnia alvei*, *Klebsiella oxytoca*, *Klebsiella pneumoniae*, *Klebsiella* sp. AS10, *Klebsiella* sp. Co9935, *Klebsiella* sp. OBRC7, *Klebsiella* sp. SP_BA, *Klebsiella* sp. SRC_DSD1, *Klebsiella* sp. SRC_DSD11, *Klebsiella* sp. SRC_DSD12, *Klebsiella* sp. SRC_DSD15, *Klebsiella* sp. SRC_DSD2, *Klebsiella* sp. SRC_DSD6, *Klebsiella* sp. enrichment culture clone SRC_DSD25, *Klebsiella variicola*, *Kluyvera ascorbata*, *Kluyvera cryocrescens*, *Leminorella grimontii*, *Leminorella richardii*, *Pantoea agglomerans*, *Pantoea ananatis*, *Pantoea brenneri*, *Pantoea citrea*, *Pantoea conspicua*, *Pantoea septica*, *Pasteurella dagmatis*, *Pasteurella multocida*, *Plesiomonas shigelloides*, *Raoultella ornithinolytica*, *Raoultella planticola*, *Raoultella terrigena*, *Salmonella bongori*, *Salmonella enterica*, *Salmonella typhimurium*, *Serratia fonticola*, *Serratia liquefaciens*, *Serratia marcescens*, *Serratia odorifera*, *Serratia proteamaculans*, *Shigella boydii*, *Shigella dysenteriae*, *Shigella flexneri*, *Shigella sonnei*, *Tatumella ptyseos*, *Trabulsiella guamensis*, *Yersinia aldovae*, *Yersinia aleksiciae*, *Yersinia bercovieri*, *Yersinia enterocolitica*, *Yersinia frederiksenii*, *Yersinia intermedia*, *Yersinia kristensenii*, *Yersinia mollaretii*, *Yersinia pestis*, *Yersinia pseudotuberculosis*, *Yersinia rohdei*, *Yokenella regensburgei* |
| clade_92i | *Actinobacillus actinomycetemcomitans*, *Actinobacillus succinogenes*, *Aggregatibacter actinomycetemcomitans*, *Aggregatibacter aphrophilus*, *Aggregatibacter segnis*, *Averyella dalhousiensis*, Bisgaard Taxon, *Buchnera aphidicola*, *Cedecea davisae*, *Citrobacter amalonaticus*, *Citrobacter braakii*, *Citrobacter farmeri*, *Citrobacter freundii*, *Citrobacter gillenii*, *Citrobacter koseri*, *Citrobacter murliniae*, *Citrobacter rodentium*, *Citrobacter sedlakii*, *Citrobacter* sp. 30_2, *Citrobacter* sp. KMSI_3, *Citrobacter werkmanii*, *Citrobacter youngae*, *Cronobacter malonaticus*, *Cronobacter sakazakii*, *Cronobacter turicensis*, *Enterobacter aerogenes*, *Enterobacter asburiae*, *Enterobacter cancerogenus*, *Enterobacter cloacae*, *Enterobacter cowanii*, *Enterobacter hormaechei*, *Enterobacter* sp. 247BMC, *Enterobacter* sp. 638, *Enterobacter* sp. JC163, *Enterobacter* sp. SCSS, *Enterobacter* sp. TSE38, Enterobacteriaceae bacterium 9_2_54FAA, Enterobacteriaceae bacterium CF01Ent_1, Enterobacteriaceae bacterium Smarlab 3302238, *Escherichia albertii*, *Escherichia fergusonii*, *Escherichia hermannii*, *Escherichia* sp. 1_1_43, *Escherichia* sp. 4_1_40B, *Escherichia* sp. B4, *Escherichia vulneris*, *Ewingella americana*, *Haemophilus* genomosp. P2 oral clone MB3_C24, *Haemophilus* genomosp. P3 oral clone MB3_C38, *Haemophilus* sp. oral clone JM053, *Hafnia alvei*, *Klebsiella oxytoca*, *Klebsiella pneumoniae*, *Klebsiella* sp. AS10, *Klebsiella* sp. Co9935, *Klebsiella* sp. OBRC7, *Klebsiella* sp. SP_BA, *Klebsiella* sp. SRC_DSD1, *Klebsiella* sp. SRC_DSD11, *Klebsiella* sp. SRC_DSD12, *Klebsiella* sp. SRC_DSD15, *Klebsiella* sp. SRC_DSD2, *Klebsiella* sp. SRC_DSD6, *Klebsiella* sp. enrichment culture clone SRC_DSD25, *Klebsiella variicola*, *Kluyvera ascorbata*, *Kluyvera cryocrescens*, *Leminorella grimontii*, *Leminorella richardii*, *Pantoea agglomerans*, *Pantoea ananatis*, *Pantoea brenneri*, *Pantoea citrea*, *Pantoea conspicua*, *Pantoea septica*, *Pasteurella dagmatis*, *Pasteurella multocida*, *Plesiomonas shigelloides*, *Raoultella ornithinolytica*, *Raoultella planticola*, *Raoultella terrigena*, *Salmonella bongori*, *Salmonella enterica*, *Salmonella typhimurium*, *Serratia fonticola*, *Serratia liquefaciens*, *Serratia marcescens*, *Serratia odorifera*, *Serratia proteamaculans*, *Shigella boydii*, *Shigella dysenteriae*, *Shigella flexneri*, *Shigella sonnei*, *Tatumella ptyseos*, *Trabulsiella guamensis*, *Yersinia aldovae*, *Yersinia aleksiciae*, *Yersinia bercovieri*, *Yersinia enterocolitica*, *Yersinia frederiksenii*, *Yersinia intermedia*, *Yersinia kristensenii*, *Yersinia mollaretii*, *Yersinia pestis*, *Yersinia pseudotuberculosis*, *Yersinia rohdei*, *Yokenella regensburgei* |
| clade_96 | *Clostridium oroticum*, *Clostridium* sp. D5, *Eubacterium contortum*, *Eubacterium fissicatena* |
| clade_96g | *Clostridium oroticum*, *Clostridium* sp. D5, *Eubacterium fissicatena* |
| clade_96h | *Clostridium oroticum*, *Clostridium* sp. D5, *Eubacterium fissicatena* |
| clade_98 | *Okadaella gastrococcus*, *Streptococcus agalactiae*, *Streptococcus alactolyticus*, *Streptococcus australis*, *Streptococcus bovis*, *Streptococcus canis*, *Streptococcus constellatus*, *Streptococcus cristatus*, *Streptococcus dysgalactiae*, *Streptococcus equi*, *Streptococcus equinus*, *Streptococcus gallolyticus*, *Streptococcus* genomosp. C1, *Streptococcus* genomosp. C2, *Streptococcus* genomosp. C3, *Streptococcus* genomosp. C4, *Streptococcus* genomosp. C5, *Streptococcus* genomosp. C6, *Streptococcus* genomosp. C7, *Streptococcus* genomosp. C8, *Streptococcus gordonii*, *Streptococcus infantarius*, *Streptococcus infantis*, *Streptococcus intermedius*, *Streptococcus lutetiensis*, *Streptococcus massiliensis*, *Streptococcus mitis*, *Streptococcus oligofermentans*, *Streptococcus oralis*, *Streptococcus parasanguinis*, *Streptococcus pasteurianus*, *Streptococcus peroris*, *Streptococcus pneumoniae*, *Streptococcus porcinus*, *Streptococcus pseudopneumoniae*, *Streptococcus pseudoporcinus*, *Streptococcus pyogenes*, *Streptococcus ratti*, *Streptococcus salivarius*, *Streptococcus sanguinis*, *Streptococcus sinensis*, *Streptococcus* sp. 2285_97, *Streptococcus* sp. 2_1_36FAA, *Streptococcus* sp. ACS2, *Streptococcus* sp. AS20, *Streptococcus* sp. BS35a, *Streptococcus* sp. C150, *Streptococcus* sp. CM6, *Streptococcus* sp. ICM10, *Streptococcus* sp. ICM12, *Streptococcus* sp. ICM2, *Streptococcus* sp. ICM4, *Streptococcus* sp. ICM45, *Streptococcus* sp. M143, *Streptococcus* sp. M334, *Streptococcus* sp. oral clone ASB02, *Streptococcus* sp. oral clone ASCA03, *Streptococcus* sp. oral clone ASCA04, *Streptococcus* sp. oral clone ASCA09, *Streptococcus* sp. oral clone ASCB04, *Streptococcus* sp. oral clone ASCB06, *Streptococcus* sp. oral clone ASCC04, *Streptococcus* sp. oral clone ASCC05, *Streptococcus* sp. oral clone ASCC12, *Streptococcus* sp. oral clone ASCD01, *Streptococcus* sp. oral clone ASCD09, *Streptococcus* sp. oral clone ASCD10, *Streptococcus* sp. oral clone ASCE03, *Streptococcus* sp. oral clone ASCE04, *Streptococcus* sp. oral clone ASCE05, *Streptococcus* sp. oral clone ASCE06, *Streptococcus* sp. oral clone ASCE09, *Streptococcus* sp. oral clone ASCE10, *Streptococcus* sp. oral clone ASCE12, *Streptococcus* sp. oral clone ASCF05, *Streptococcus* sp. oral clone ASCF07, *Streptococcus* sp. oral clone ASCF09, *Streptococcus* sp. oral clone ASCG04, *Streptococcus* sp. oral clone RW009, *Streptococcus* sp. oral clone CH016, *Streptococcus* sp. oral clone GK051, *Streptococcus* sp. oral clone GM006, *Streptococcus* sp. oral clone P2PA_41 P2, *Streptococcus* sp. oral clone P4PA_30 P4, *Streptococcus* sp. oral taxon 071, *Streptococcus* sp. oral taxon G59, *Streptococcus* sp. oral taxon G62, *Streptococcus* sp. oral taxon G63, *Streptococcus suis*, *Streptococcus thermophilus*, *Streptococcus uberis*, *Streptococcus urinalis*, *Streptococcus vestibularis*, *Streptococcus viridans*, Synergistetes bacterium oral clone 03 5 D05 |
| clade_98i | *Okadaella gastrococcus*, *Streptococcus agalactiae*, *Streptococcus alactolyticus*, *Streptococcus australis*, *Streptococcus bovis*, *Streptococcus canis*, *Streptococcus constellatus*, *Streptococcus cristatus*, *Streptococcus dysgalactiae*, *Streptococcus equi*, *Streptococcus equinus*, *Streptococcus gallolyticus*, |

TABLE 2-continued

| Phylogenetic Clade | OTUs in clade |
|---|---|
| | *Streptococcus* genomosp. C1, *Streptococcus* genomosp. C2, *Streptococcus* genomosp. C3, *Streptococcus* genomosp. C4, *Streptococcus* genomosp. C5, *Streptococcus* genomosp. C6, *Streptococcus* genomosp. C7, *Streptococcus* genomosp. C8, *Streptococcus gordonii*, *Streptococcus infantarius*, *Streptococcus infantis*, *Streptococcus intermedius*, *Streptococcus lutetiensis*, *Streptococcus massiliensis*, *Streptococcus oligofermentans*, *Streptococcus oralis*, *Streptococcus parasanguinis*, *Streptococcus pasteurianus*, *Streptococcus peroris*, *Streptococcus pneumoniae*, *Streptococcus porcinus*, *Streptococcus pseudopneumoniae*, *Streptococcus pseudoporcinus*, *Streptococcus pyogenes*, *Streptococcus ratti*, *Streptococcus salivarius*, *Streptococcus sanguinis*, *Streptococcus sinensis*, *Streptococcus* sp. 2285_97, *Streptococcus* sp. 2_1_36FAA, *Streptococcus* sp. ACS2, *Streptococcus* sp. AS20, *Streptococcus* sp. BS35a, *Streptococcus* sp. C150, *Streptococcus* sp. CM6, *Streptococcus* sp. ICM10, *Streptococcus* sp. ICM12, *Streptococcus* sp. ICM2, *Streptococcus* sp. ICM4, *Streptococcus* sp. ICM45, *Streptococcus* sp. M143, *Streptococcus* sp. M334, *Streptococcus* sp. oral clone ASB02, *Streptococcus* sp. oral clone ASCA03, *Streptococcus* sp. oral clone ASCA04, *Streptococcus* sp. oral clone ASCA09, *Streptococcus* sp. oral clone ASCB04, *Streptococcus* sp. oral clone ASCB06, *Streptococcus* sp. oral clone ASCC04, *Streptococcus* sp. oral clone ASCC05, *Streptococcus* sp. oral clone ASCC12, *Streptococcus* sp. oral clone ASCD01, *Streptococcus* sp. oral clone ASCD09, *Streptococcus* sp. oral clone ASCD10, *Streptococcus* sp. oral clone ASCE03, *Streptococcus* sp. oral clone ASCE04, *Streptococcus* sp. oral clone ASCE05, *Streptococcus* sp. oral clone ASCE06, *Streptococcus* sp. oral clone ASCE09, *Streptococcus* sp. oral clone ASCE10, *Streptococcus* sp. oral clone ASCE12, *Streptococcus* sp. oral clone ASCF05, *Streptococcus* sp. oral clone ASCF07, *Streptococcus* sp. oral clone ASCF09, *Streptococcus* sp. oral clone ASCG04, *Streptococcus* sp. oral clone BW009, *Streptococcus* sp. oral clone CH016, *Streptococcus* sp. oral clone GK051, *Streptococcus* sp. oral clone GM006, *Streptococcus* sp. oral clone P2PA_41 P2, *Streptococcus* sp. oral clone P4PA_30 P4, *Streptococcus* sp. oral taxon 071, *Streptococcus* sp. oral taxon G59, *Streptococcus* sp. oral taxon G62, *Streptococcus* sp. oral taxon G63, *Streptococcus suis*, *Streptococcus thermophilus*, *Streptococcus uberis*, *Streptococcus urinalis*, *Streptococcus vestibularis*, *Streptococcus viridans*, Synergistetes bacterium oral clone 03 5 D05 |

TABLE 3

| Disease Indication |
|---|
| Abdominal cavity inflammation |
| *Absidia* infection |
| *Acinetobacter baumanii* infection |
| *Acinetobacter* infection |
| *Acinetobacter lwoffii* infection |
| Acne |
| *Actinomyces israelii* infection |
| Adenovirus infection |
| Adult varicella zoster virus infection |
| Aging |
| Alcoholism (and effects) |
| Allergic conjunctivitis |
| Allergic rhinitis |
| Allergy |
| ALS |
| Alzheimers disease |
| Amoeba infection |
| Anal cancer |
| Antibiotic treatment |
| Antitbiotic associated diarrhea |
| Arteriosclerosis |
| Arthritis |
| *Aspergillus fumigatus* infection |
| *Aspergillus* infection |
| Asthma |
| Atherosclerosis |
| Atopic dermatitis |
| Atopy/Allergic Sensitivity |
| Autism |
| Autoimmune disease |
| *Bacillus anthracis* infection |
| *Bacillus* infection |
| Bacterial endocarditis |
| Bacterial eye infection |
| Bacterial infection |
| Bacterial meningitis |
| Bacterial pneumonia |
| Bacterial respiratory tract infection |
| Bacterial skin infection |
| Bacterial susceptibility |
| Bacterial urinary tract infection |
| Bacterial vaginosis |
| *Bacteroides caccae* infection |

TABLE 3-continued

| Disease Indication |
|---|
| *Bacteroides fragilis* infection |
| *Bacteroides* infection |
| *Bacteroides thetaiotaomicron* infection |
| *Bacteroides uniformis* infection |
| *Bacteroides vulgatus* infection |
| *Bartonella bacilliformis* infection |
| *Bartonella* infection |
| *Bifidobacterium* infection |
| Biliary cancer |
| Biliary cirrhosis |
| Biliary tract disease |
| Biliary tract infection |
| Biliary tumor |
| BK virus infection |
| *Blastomyces* infection |
| Bone and joint infection |
| Bone infection |
| *Bordetella pertussis* infection |
| *Borrelia burgdorferi* infection |
| *Borrelia recurrentis* infection |
| *Brucella* infection |
| *Burkholderia* infection |
| Cachexia |
| *Campylobacter* fetus infection |
| *Campylobacter* infection |
| *Campylobacter jejuni* infection |
| Cancer |
| *Candida albicans* infection |
| *Candida* infection |
| *Candida krusei* infection |
| Celiac Disease |
| Cervix infection |
| Chemotherapy-induced diarrhea |
| *Chlamydia* infection |
| *Chlamydia pneumoniae* infection |
| *Chlamydia trachomatis* infection |
| Chlamydiae infection |
| Chronic fatigue syndrome |
| Chronic infection |
| Chronic inflammatory demyelinating polyneuropathy |
| Chronic Polio Shedders |
| Circadian rhythm sleep disorder |
| Cirrhosis |

TABLE 3-continued

| Disease Indication |
|---|
| *Citrobacter* infection |
| *Cladophialophora* infection |
| Clostridiaceae infection |
| *Clostridium botulinum* infection |
| *Clostridium difficile* infection |
| *Clostridium* infection |
| *Clostridium tetani* infection |
| *Coccidioides* infection |
| Colitis |
| Colon cancer |
| Colorectal cancer |
| Common cold |
| Compensated liver cirrhosis |
| Complicated skin and skin structure infection |
| Complicated urinary tract infection |
| Constipation |
| Constipation predominant irritable bowel syndrome |
| *Corynebacterium diphtheriae* infection |
| *Corynebacterium* infection |
| *Coxiella* infection |
| carbapenem-resistant Enterobacteriaceae (CRE) infection |
| Crohns disease |
| *Cryptococcus* infection |
| *Cryptococcus neoformans* infection |
| *Cryptosporidium* infection |
| Cutaneous lupus erythematosus |
| Cystic fibrosis |
| Cystitis |
| Cytomegalovirus infection |
| Dementia |
| Dengue virus infection |
| Depression |
| Dermatitis |
| Diabetes mellitus |
| Diabetic complication |
| Diabetic foot ulcer |
| Diarrhea |
| Diarrhea predominant irritable bowel syndrome |
| Discoid lupus erythematosus |
| Diverticulitis |
| DNA virus infection |
| Duodenal ulcer |
| Ebola virus infection |
| *Entamoeba histolytica* infection |
| *Enterobacter aerogenes* infection |
| *Enterobacter cloacae* infection |
| *Enterobacter* infection |
| Enterobacteriaceae infection |
| *Enterococcus faecalis* infection |
| *Enterococcus faecium* infection |
| *Enterococcus* infection |
| Enterocolitis |
| Enterovirus 71 infection |
| *Epidermophyton* infection |
| Epstein Barr virus infection |
| ESBL (Extended Spectrum Beta Lactamase) Producing Bacterial Infection |
| *Escherichia coli* infection |
| Esophageal cancer |
| *Exophiala* infection |
| Familial cold autoinflammatory syndrome |
| *Fasciola hepatica* infection |
| Female genital tract infection |
| Female genital tract tumor |
| Female infertility |
| Fibrosis |
| Flavivirus infection |
| Food Allergy |
| *Francisella tularensis* infection |
| Functional bowel disorder |
| Fungal infection |
| Fungal respiratory tract infection |
| Fungal urinary tract infection |
| *Fusarium* infection |
| *Fusobacterium* infection |
| Gastric ulcers |
| Gastrointestinal infection |
| Gastrointestinal pain |

TABLE 3-continued

| Disease Indication |
|---|
| Gastrointestinal ulcer |
| Genital tract infection |
| Genitourinary disease |
| Genitourinary tract rumor |
| Gestational diabetes |
| *Giardia lamblia* infection |
| Gingivitis |
| Gram negative bacterium infection |
| Gram positive bacterium infection |
| *Haemophilus aegyptus* infection |
| *Haemophilus ducreyi* infection |
| *Haemophilus* infection |
| *Haemophilus influenzae* infection |
| *Haemophilus parainfluenzae* infection |
| Hantavirus infection |
| *Helicobacter pylori* infection |
| Helminth infection |
| Hepatitis A virus infection |
| Hepatitis B virus infection |
| Hepatitis C virus infection |
| Hepatitis D virus infection |
| Hepatitis E virus infection |
| Hepatitis virus infection |
| Herpes simplex virus infection |
| Herpesvirus infection |
| *Histoplasma* infection |
| HIV infection |
| HIV-1 infection |
| HIV-2 infection |
| HSV-1 infection |
| HSV-2 infection |
| Human T cell leukemia virus 1 infection |
| Hypercholesterolemia |
| Hyperoxaluria |
| Hypertension |
| Infectious arthritis |
| Infectious disease |
| Infectious endocarditis |
| Infertility |
| Inflammatory bowel disease |
| Inflammatory disease |
| Influenza virus A infection |
| Influenza virus B infection |
| Influenza virus infection |
| Insomnia |
| Insulin dependent diabetes |
| Intestine infection |
| Irritable bowel syndrome |
| Japanese encephalitis virus infection |
| Joint infection |
| Juvenile rheumatoid arthritis |
| *Klebsiella granulomatis* infection |
| *Klebsiella* infection |
| *Klebsiella pneumoniae* infection |
| *Legionella* infection |
| *Legionella pneumophila* infection |
| *Leishmania braziliensis* infection |
| *Leishmania donovani* infection |
| *Leishmania* infection |
| *Leishmania tropica* infection |
| Leptospiraceae infection |
| *Listeria monocytogenes* infection |
| Listerosis |
| Liver cirrhosis |
| Liver fibrosis |
| Lower respiratory tract infection |
| Lung infection |
| Lung inflammation |
| Lupus erythematosus panniculitis |
| Lupus nephritis |
| Lyme disease |
| Male infertility |
| Marburg virus infection |
| Measles virus infection |
| Metabolic disorder |
| Metabolic Syndrome |
| Metastatic colon cancer |
| Metastatic colorectal cancer |

TABLE 3-continued

| Disease Indication |
| --- |
| Metastatic esophageal cancer |
| Metastatic gastrointestinal cancer |
| Metastatic stomach cancer |
| Micrococcaceae infection |
| *Micrococcus* infection |
| Microsporidial infection |
| *Microsporum* infection |
| *Molluscum contagiosum* infection |
| Monkeypox virus infection |
| *Moraxella catarrhalis* infection |
| *Moraxella* infection |
| *Morganella* infection |
| *Morganella morganii* infection |
| MRSA infection |
| Mucor infection |
| Multidrug resistant infection |
| Multiple sclerosis |
| Mumps virus infection |
| Musculoskeletal system inflammation |
| *Mycobacterium* infection |
| *Mycobacterium leprae* infection |
| *Mycobacterium tuberculosis* infection |
| *Mycoplasma* infection |
| *Mycoplasma pneumoniae* infection |
| Necrotizing enterocolitis |
| Necrotizing Pancreatitis |
| *Neisseria gonorrhoeae* infection |
| *Neisseria* infection |
| *Neisseria meningitidis* infection |
| Nematode infection |
| Non alcoholic fatty liver disease |
| Non-alcoholic steatohepatitis |
| Non-insulin dependent diabetes |
| Obesity |
| Ocular infection |
| Ocular inflammation |
| Orbital inflammatory disease |
| Osteoarthritis |
| Otorhinolaryngological infection |
| Pain |
| Papillomavirus infection |
| Parasitic infection |
| Parkinsons disease |
| Pediatric varicella zoster virus infection |
| Pelvic inflammatory disease |
| *Peptostreptococcus* infection |
| Perennial allergic rhinitis |
| Periarthritis |
| Pink eye infection |
| *Plasmodium falciparum* infection |
| *Plasmodium* infection |
| *Plasmodium malariae* infection |
| *Plasmodium vivax* infection |
| *Pneumocystis carinii* infection |
| Poliovirus infection |
| Polyomavirus infection |
| Post-surgical bacterial leakage |
| Pouchitis |
| *Prevotella* infection |
| Primary biliary cirrhosis |
| Primary sclerosing cholangitis |
| *Propionibacterium acnes* infection |
| *Propionibacterium* infection |
| Prostate cancer |
| *Proteus* infection |
| *Proteus mirabilis* infection |
| Protozoal infection |
| *Providencia* infection |
| *Pseudomonas aeruginosa* infection |
| *Pseudomonas* infection |
| Psoriasis |
| Psoriatic arthritis |
| Pulmonary fibrosis |
| Rabies virus infection |
| Rectal cancer |
| Respiratory syncytial virus infection |
| Respiratory tract infection |
| Respiratory tract inflammation |

TABLE 3-continued

| Disease Indication |
| --- |
| Rheumatoid arthritis |
| Rhinitis |
| *Rhizomucor* infection |
| *Rhizopus* infection |
| *Rickettsia* infection |
| Ross River virus infection |
| Rotavirus infection |
| Rubella virus infection |
| *Salmonella* infection |
| *Salmonella typhi* infection |
| Sarcopenia |
| SARS coronavirus infection |
| Scabies infection |
| *Scedosporium* infection |
| Scleroderma |
| Seasonal allergic rhinitis |
| *Serratia* infection |
| *Serratia marcescens* infection |
| *Shigella boydii* infection |
| *Shigella dysenteriae* infection |
| *Shigella flexneri* infection |
| *Shigella* infection |
| *Shigella sonnei* infection |
| Short bowel syndrome |
| Skin allergy |
| Skin cancer |
| Skin infection |
| Skin Inflammatory disease |
| Sleep disorder |
| Spondylarthritis |
| *Staphylococcus aureus* infection |
| *Staphylococcus epidermidis* infection |
| *Staphylococcus* infection |
| *Staphylococcus saprophyticus* infection |
| *Stenotrophomonas maltophilia* infection |
| Stomach cancer |
| Stomach infection |
| Stomach ulcer |
| *Streptococcus agalactiae* infection |
| *Streptococcus constellatus* infection |
| *Streptococcus* infection |
| *Streptococcus intermedius* infection |
| *Streptococcus mitis* infection |
| *Streptococcus oralis* infection |
| *Streptococcus pneumoniae* infection |
| *Streptococcus pyogenes* infection |
| Systemic lupus erythematosus |
| Traveler's diarrhea |
| Trench mouth |
| *Treponema* infection |
| *Treponema pallidum* infection |
| *Trichomonas* infection |
| *Trichophyton* infection |
| *Trypanosoma brucei* infection |
| *Trypanosoma cruzi* infection |
| Type 1 Diabetes |
| Type 2 Diabetes |
| Ulcerative colitis |
| Upper respiratory tract infection |
| *Ureaplasma urealyticum* infection |
| Urinary tract disease |
| Urinary tract infection |
| Urinary tract tumor |
| Urogenital tract infection |
| Uterus infection |
| Vaccinia virus infection |
| Vaginal infection |
| Varicella zoster virus infection |
| Variola virus infection |
| *Vibrio cholerae* infection |
| Viral eye infection |
| Viral infection |
| Viral respiratory tract infection |
| Viridans group *Streptococcus* infection |
| Vancomycin-Resistant *Enterococcus* infection |
| Wasting Syndrome |
| Weight loss |
| West Nile virus infection |

TABLE 3-continued

| Disease Indication |
| --- |
| Whipple's disease |
| Xenobiotic metabolism |
| Yellow fever virus infection |
| *Yersinia pestis* infection |
| Flatulence |
| Gastrointestinal Disorder |
| General Inflammation |

TABLE 4a

| OTU1 of Composition | OTU2 of Composition | OTU3 of Composition | Strain ID OTU1 |
| --- | --- | --- | --- |
| *Escherichia_coli* | *Escherichia_coli* | | SPC00001 |
| *Escherichia_coli* | *Bacteroides_vulgatus* | | SPC00001 |
| *Escherichia_coli* | *Bacteroides*_sp_1_1_6 | | SPC00001 |
| *Escherichia_coli* | *Bacteroides*_sp_3_1_23 | | SPC00001 |
| *Escherichia_coli* | *Enterococcus_faecalis* | | SPC00001 |
| *Escherichia_coli* | *Coprobacillus*_sp_D7 | | SPC00001 |
| *Escherichia_coli* | *Streptococcus_thermophilus* | | SPC00001 |
| *Escherichia_coli* | *Dorea_formicigenerans* | | SPC00001 |
| *Escherichia_coli* | *Blautia_producta* | | SPC00001 |
| *Escherichia_coli* | *Eubacterium_eligens* | | SPC00001 |
| *Escherichia_coli* | *Clostridium_nexile* | | SPC00001 |
| *Escherichia_coli* | *Clostridium*_sp_HGF2 | | SPC00001 |
| *Escherichia_coli* | *Faecalibacterium_prausnitzii* | | SPC00001 |
| *Escherichia_coli* | *Odoribacter_splanchnicus* | | SPC00001 |
| *Escherichia_coli* | *Dorea_longicatena* | | SPC00001 |
| *Escherichia_coli* | *Roseburia_intestinalis* | | SPC00001 |
| *Escherichia_coli* | *Coprococcus_catus* | | SPC00001 |
| *Escherichia_coli* | Erysipelotrichaceae_*bacterium*_3_1_53 | | SPC00001 |
| *Escherichia_coli* | *Bacteroides*_sp_D20 | | SPC00001 |
| *Escherichia_coli* | *Bacteroides_ovatus* | | SPC00001 |
| *Escherichia_coli* | *Parabacteroides_merdae* | | SPC00001 |
| *Escherichia_coli* | *Bacteroides_vulgatus* | | SPC00001 |
| *Escherichia_coli* | *Collinsella_aerofaciens* | | SPC00001 |
| *Escherichia_coli* | *Escherichia_coli* | | SPC00001 |
| *Escherichia_coli* | *Ruminococcus_obeum* | | SPC00001 |
| *Escherichia_coli* | *Bacteroides_caccae* | | SPC00001 |
| *Escherichia_coli* | *Bacteroides_eggerthii* | | SPC00001 |
| *Escherichia_coli* | *Ruminococcus_torques* | | SPC00001 |
| *Escherichia_coli* | *Clostridium_hathewayi* | | SPC00001 |
| *Escherichia_coli* | *Bifidobacterium_pseudocatenulatum* | | SPC00001 |
| *Escherichia_coli* | *Bifidobacterium_adolescentis* | | SPC00001 |
| *Escherichia_coli* | *Coprococcus_comes* | | SPC00001 |
| *Escherichia_coli* | *Clostridium_symbiosum* | | SPC00001 |
| *Escherichia_coli* | *Eubacterium_rectale* | | SPC00001 |
| *Escherichia_coli* | *Faecalibacterium_prausnitzii* | | SPC00001 |
| *Escherichia_coli* | *Odoribacter_splanchnicus* | | SPC00001 |
| *Escherichia_coli* | Lachnospiraceae_*bacterium*_5_1_57FAA | | SPC00001 |
| *Escherichia_coli* | *Blautia_schinkii* | | SPC00001 |
| *Escherichia_coli* | *Alistipes_shahii* | | SPC00001 |
| *Escherichia_coli* | *Blautia_producta* | | SPC00001 |
| *Bacteroides_vulgatus* | *Bacteroides_vulgatus* | | SPC00005 |
| *Bacteroides_vulgatus* | *Bacteroides*_sp_1_1_6 | | SPC00005 |
| *Bacteroides_vulgatus* | *Bacteroides*_sp_3_1_23 | | SPC00005 |
| *Bacteroides_vulgatus* | *Enterococcus_faecalis* | | SPC00005 |
| *Bacteroides_vulgatus* | *Coprobacillus*_sp_D7 | | SPC00005 |
| *Bacteroides_vulgatus* | *Streptococcus_thermophilus* | | SPC00005 |
| *Bacteroides_vulgatus* | *Dorea_formicigenerans* | | SPC00005 |
| *Bacteroides_vulgatus* | *Blautia_producta* | | SPC00005 |
| *Bacteroides_vulgatus* | *Eubacterium_eligens* | | SPC00005 |
| *Bacteroides_vulgatus* | *Clostridium_nexile* | | SPC00005 |
| *Bacteroides_vulgatus* | *Clostridium*_sp_HGF2 | | SPC00005 |
| *Bacteroides_vulgatus* | *Faecalibacterium_prausnitzii* | | SPC00005 |
| *Bacteroides_vulgatus* | *Odoribacter_splanchnicus* | | SPC00005 |
| *Bacteroides_vulgatus* | *Dorea_longicatena* | | SPC00005 |
| *Bacteroides_vulgatus* | *Roseburia_intestinalis* | | SPC00005 |
| *Bacteroides_vulgatus* | *Coprococcus_catus* | | SPC00005 |
| *Bacteroides_vulgatus* | Erysipelotrichaceae_*bacterium*_3_1_53 | | SPC00005 |
| *Bacteroides_vulgatus* | *Bacteroides*_sp_D20 | | SPC00005 |
| *Bacteroides_vulgatus* | *Bacteroides_ovatus* | | SPC00005 |
| *Bacteroides_vulgatus* | *Parabacteroides_merdae* | | SPC00005 |
| *Bacteroides_vulgatus* | *Bacteroides_vulgatus* | | SPC00005 |
| *Bacteroides_vulgatus* | *Collinsella_aerofaciens* | | SPC00005 |
| *Bacteroides_vulgatus* | *Escherichia_coli* | | SPC00005 |
| *Bacteroides_vulgatus* | *Ruminococcus_obeum* | | SPC00005 |
| *Bacteroides_vulgatus* | *Bacteroides_caccae* | | SPC00005 |
| *Bacteroides_vulgatus* | *Bacteroides_eggerthii* | | SPC00005 |

TABLE 4a-continued

| | | |
|---|---|---|
| *Bacteroides_vulgatus* | *Ruminococcus_torques* | SPC00005 |
| *Bacteroides_vulgatus* | *Clostridium_hathewayi* | SPC00005 |
| *Bacteroides_vulgatus* | *Bifidobacterium_pseudocatenulatum* | SPC00005 |
| *Bacteroides_vulgatus* | *Bifidobacterium_adolescentis* | SPC00005 |
| *Bacteroides_vulgatus* | *Coprococcus_comes* | SPC00005 |
| *Bacteroides_vulgatus* | *Clostridium_symbiosum* | SPC00005 |
| *Bacteroides_vulgatus* | *Eubacterium_rectale* | SPC00005 |
| *Bacteroides_vulgatus* | *Faecalibacterium_prausnitzii* | SPC00005 |
| *Bacteroides_vulgatus* | *Odoribacter_splanchnicus* | SPC00005 |
| *Bacteroides_vulgatus* | Lachnospiraceae_*bacterium*_5_1_57FAA | SPC00005 |
| *Bacteroides_vulgatus* | *Blautia_schinkii* | SPC00005 |
| *Bacteroides_vulgatus* | *Alistipes_shahii* | SPC00005 |
| *Bacteroides_vulgatus* | *Blautia_producta* | SPC00005 |
| *Bacteroides*_sp_1_1_6 | *Bacteroides*_sp_1_1_6 | SPC00006 |
| *Bacteroides*_sp_1_1_6 | *Bacteroides*_sp_3_1_23 | SPC00006 |
| *Bacteroides*_sp_1_1_6 | *Enterococcus_faecalis* | SPC00006 |
| *Bacteroides*_sp_1_1_6 | *Coprobacillus*_sp_D7 | SPC00006 |
| *Bacteroides*_sp_1_1_6 | *Streptococcus_thermophilus* | SPC00006 |
| *Bacteroides*_sp_1_1_6 | *Dorea_formicigenerans* | SPC00006 |
| *Bacteroides*_sp_1_1_6 | *Blautia_producta* | SPC00006 |
| *Bacteroides*_sp_1_1_6 | *Eubacterium_eligens* | SPC00006 |
| *Bacteroides*_sp_1_1_6 | *Clostridium_nexile* | SPC00006 |
| *Bacteroides*_sp_1_1_6 | *Clostridium*_sp_HGF2 | SPC00006 |
| *Bacteroides*_sp_1_1_6 | *Faecalibacterium_prausnitzii* | SPC00006 |
| *Bacteroides*_sp_1_1_6 | *Odoribacter_splanchnicus* | SPC00006 |
| *Bacteroides*_sp_1_1_6 | *Dorea_longicatena* | SPC00006 |
| *Bacteroides*_sp_1_1_6 | *Roseburia_intestinalis* | SPC00006 |
| *Bacteroides*_sp_1_1_6 | *Coprococcus_catus* | SPC00006 |
| *Bacteroides*_sp_1_1_6 | Erysipelotrichaceae_*bacterium*_3_1_53 | SPC00006 |
| *Bacteroides*_sp_1_1_6 | *Bacteroides*_sp_D20 | SPC00006 |
| *Bacteroides*_sp_1_1_6 | *Bacteroides_ovatus* | SPC00006 |
| *Bacteroides*_sp_1_1_6 | *Parabacteroides_merdae* | SPC00006 |
| *Bacteroides*_sp_1_1_6 | *Bacteroides_vulgatus* | SPC00006 |
| *Bacteroides*_sp_1_1_6 | *Collinsella_aerofaciens* | SPC00006 |
| *Bacteroides*_sp_1_1_6 | *Escherichia_coli* | SPC00006 |
| *Bacteroides*_sp_1_1_6 | *Ruminococcus_obeum* | SPC00006 |
| *Bacteroides*_sp_1_1_6 | *Bacteroides_caccae* | SPC00006 |
| *Bacteroides*_sp_1_1_6 | *Bacteroides_eggerthii* | SPC00006 |
| *Bacteroides*_sp_1_1_6 | *Ruminococcus_torques* | SPC00006 |
| *Bacteroides*_sp_1_1_6 | *Clostridium_hathewayi* | SPC00006 |
| *Bacteroides*_sp_1_1_6 | *Bifidobacterium_pseudocatenulatum* | SPC00006 |
| *Bacteroides*_sp_1_1_6 | *Bifidobacterium_adolescentis* | SPC00006 |
| *Bacteroides*_sp_1_1_6 | *Coprococcus_comes* | SPC00006 |
| *Bacteroides*_sp_1_1_6 | *Clostridium_symbiosum* | SPC00006 |
| *Bacteroides*_sp_1_1_6 | *Eubacterium_rectale* | SPC00006 |
| *Bacteroides*_sp_1_1_6 | *Faecalibacterium_prausnitzii* | SPC00006 |
| *Bacteroides*_sp_1_1_6 | *Odoribacter_splanchnicus* | SPC00006 |
| *Bacteroides*_sp_1_1_6 | Lachnospiraceae_*bacterium*_5_1_57FAA | SPC00006 |
| *Bacteroides*_sp_1_1_6 | *Blautia_schinkii* | SPC00006 |
| *Bacteroides*_sp_1_1_6 | *Alistipes_shahii* | SPC00006 |
| *Bacteroides*_sp_1_1_6 | *Blautia_producta* | SPC00006 |
| *Bacteroides*_sp_3_1_23 | *Bacteroides*_sp_3_1_23 | SPC00007 |
| *Bacteroides*_sp_3_1_23 | *Enterococcus_faecalis* | SPC00007 |
| *Bacteroides*_sp_3_1_23 | *Coprobacillus*_sp_D7 | SPC00007 |
| *Bacteroides*_sp_3_1_23 | *Streptococcus_thermophilus* | SPC00007 |
| *Bacteroides*_sp_3_1_23 | *Dorea_formicigenerans* | SPC00007 |
| *Bacteroides*_sp_3_1_23 | *Blautia_producta* | SPC00007 |
| *Bacteroides*_sp_3_1_23 | *Eubacterium_eligens* | SPC00007 |
| *Bacteroides*_sp_3_1_23 | *Clostridium_nexile* | SPC00007 |
| *Bacteroides*_sp_3_1_23 | *Clostridium*_sp_HGF2 | SPC00007 |
| *Bacteroides*_sp_3_1_23 | *Faecalibacterium_prausnitzii* | SPC00007 |
| *Bacteroides*_sp_3_1_23 | *Odoribacter_splanchnicus* | SPC00007 |
| *Bacteroides*_sp_3_1_23 | *Dorea_longicatena* | SPC00007 |
| *Bacteroides*_sp_3_1_23 | *Roseburia_intestinalis* | SPC00007 |
| *Bacteroides*_sp_3_1_23 | *Coprococcus_catus* | SPC00007 |
| *Bacteroides*_sp_3_1_23 | Erysipelotrichaceae_*bacterium*_3_1_53 | SPC00007 |
| *Bacteroides*_sp_3_1_23 | *Bacteroides*_sp_D20 | SPC00007 |
| *Bacteroides*_sp_3_1_23 | *Bacteroides_ovatus* | SPC00007 |
| *Bacteroides*_sp_3_1_23 | *Parabacteroides_merdae* | SPC00007 |
| *Bacteroides*_sp_3_1_23 | *Bacteroides_vulgatus* | SPC00007 |
| *Bacteroides*_sp_3_1_23 | *Collinsella_aerofaciens* | SPC00007 |
| *Bacteroides*_sp_3_1_23 | *Escherichia_coli* | SPC00007 |
| *Bacteroides*_sp_3_1_23 | *Ruminococcus_obeum* | SPC00007 |
| *Bacteroides*_sp_3_1_23 | *Bacteroides_caccae* | SPC00007 |
| *Bacteroides*_sp_3_1_23 | *Bacteroides_eggerthii* | SPC00007 |
| *Bacteroides*_sp_3_1_23 | *Ruminococcus_torques* | SPC00007 |
| *Bacteroides*_sp_3_1_23 | *Clostridium_hathewayi* | SPC00007 |
| *Bacteroides*_sp_3_1_23 | *Bifidobacterium_pseudocatenulatum* | SPC00007 |
| *Bacteroides*_sp_3_1_23 | *Bifidobacterium_adolescentis* | SPC00007 |
| *Bacteroides*_sp_3_1_23 | *Coprococcus_comes* | SPC00007 |

TABLE 4a-continued

| | | |
|---|---|---|
| *Bacteroides*_sp_3_1_23 | *Clostridium_symbiosum* | SPC00007 |
| *Bacteroides*_sp_3_1_23 | *Eubacterium_rectale* | SPC00007 |
| *Bacteroides*_sp_3_1_23 | *Faecalibacterium_prausnitzii* | SPC00007 |
| *Bacteroides*_sp_3_1_23 | *Odoribacter_splanchnicus* | SPC00007 |
| *Bacteroides*_sp_3_1_23 | Lachnospiraceae_*bacterium*_5_1_57FAA | SPC00007 |
| *Bacteroides*_sp_3_1_23 | *Blautia_schinkii* | SPC00007 |
| *Bacteroides*_sp_3_1_23 | *Alistipes_shahii* | SPC00007 |
| *Bacteroides*_sp_3_1_23 | *Blautia_producta* | SPC00007 |
| *Enterococcus_faecalis* | *Enterococcus_faecalis* | SPC00008 |
| *Enterococcus_faecalis* | *Coprobacillus*_sp_D7 | SPC00008 |
| *Enterococcus_faecalis* | *Streptococcus_thermophilus* | SPC00008 |
| *Enterococcus_faecalis* | *Dorea_formicigenerans* | SPC00008 |
| *Enterococcus_faecalis* | *Blautia_producta* | SPC00008 |
| *Enterococcus_faecalis* | *Eubacterium_eligens* | SPC00008 |
| *Enterococcus_faecalis* | *Clostridium_nexile* | SPC00008 |
| *Enterococcus_faecalis* | *Clostridium*_sp_HGF2 | SPC00008 |
| *Enterococcus_faecalis* | *Faecalibacterium_prausnitzii* | SPC00008 |
| *Enterococcus_faecalis* | *Odoribacter_splanchnicus* | SPC00008 |
| *Enterococcus_faecalis* | *Dorea_longicatena* | SPC00008 |
| *Enterococcus_faecalis* | *Roseburia_intestinalis* | SPC00008 |
| *Enterococcus_faecalis* | *Coprococcus_catus* | SPC00008 |
| *Enterococcus_faecalis* | Erysipelotrichaceae_*bacterium*_3_1_53 | SPC00008 |
| *Enterococcus_faecalis* | *Bacteroides*_sp_D20 | SPC00008 |
| *Enterococcus_faecalis* | *Bacteroides_ovatus* | SPC00008 |
| *Enterococcus_faecalis* | *Parabacteroides_merdae* | SPC00008 |
| *Enterococcus_faecalis* | *Bacteroides_vulgatus* | SPC00008 |
| *Enterococcus_faecalis* | *Collinsella_aerofaciens* | SPC00008 |
| *Enterococcus_faecalis* | *Escherichia_coli* | SPC00008 |
| *Enterococcus_faecalis* | *Ruminococcus_obeum* | SPC00008 |
| *Enterococcus_faecalis* | *Bacteroides_caccae* | SPC00008 |
| *Enterococcus_faecalis* | *Bacteroides_eggerthii* | SPC00008 |
| *Enterococcus_faecalis* | *Ruminococcus_torques* | SPC00008 |
| *Enterococcus_faecalis* | *Clostridium_hathewayi* | SPC00008 |
| *Enterococcus_faecalis* | *Bifidobacterium_pseudocatenulatum* | SPC00008 |
| *Enterococcus_faecalis* | *Bifidobacterium_adolescentis* | SPC00008 |
| *Enterococcus_faecalis* | *Coprococcus_comes* | SPC00008 |
| *Enterococcus_faecalis* | *Clostridium_symbiosum* | SPC00008 |
| *Enterococcus_faecalis* | *Eubacterium_rectale* | SPC00008 |
| *Enterococcus_faecalis* | *Faecalibacterium_prausnitzii* | SPC00008 |
| *Enterococcus_faecalis* | *Odoribacter_splanchnicus* | SPC00008 |
| *Enterococcus_faecalis* | Lachnospiraceae_*bacterium*_5_1_57FAA | SPC00008 |
| *Enterococcus_faecalis* | *Blautia_schinkii* | SPC00008 |
| *Enterococcus_faecalis* | *Alistipes_shahii* | SPC00008 |
| *Enterococcus_faecalis* | *Blautia_producta* | SPC00008 |
| *Coprobacillus*_sp_D7 | *Coprobacillus*_sp_D7 | SPC00009 |
| *Coprobacillus*_sp_D7 | *Streptococcus_thermophilus* | SPC00009 |
| *Coprobacillus*_sp_D7 | *Dorea_formicigenerans* | SPC00009 |
| *Coprobacillus*_sp_D7 | *Blautia_producta* | SPC00009 |
| *Coprobacillus*_sp_D7 | *Eubacterium_eligens* | SPC00009 |
| *Coprobacillus*_sp_D7 | *Clostridium_nexile* | SPC00009 |
| *Coprobacillus*_sp_D7 | *Clostridium*_sp_HGF2 | SPC00009 |
| *Coprobacillus*_sp_D7 | *Faecalibacterium_prausnitzii* | SPC00009 |
| *Coprobacillus*_sp_D7 | *Odoribacter_splanchnicus* | SPC00009 |
| *Coprobacillus*_sp_D7 | *Dorea_longicatena* | SPC00009 |
| *Coprobacillus*_sp_D7 | *Roseburia_intestinalis* | SPC00009 |
| *Coprobacillus*_sp_D7 | *Coprococcus_catus* | SPC00009 |
| *Coprobacillus*_sp_D7 | Erysipelotrichaceae_*bacterium*_3_1_53 | SPC00009 |
| *Coprobacillus*_sp_D7 | *Bacteroides*_sp_D20 | SPC00009 |
| *Coprobacillus*_sp_D7 | *Bacteroides_ovatus* | SPC00009 |
| *Coprobacillus*_sp_D7 | *Parabacteroides_merdae* | SPC00009 |
| *Coprobacillus*_sp_D7 | *Bacteroides_vulgatus* | SPC00009 |
| *Coprobacillus*_sp_D7 | *Collinsella_aerofaciens* | SPC00009 |
| *Coprobacillus*_sp_D7 | *Escherichia_coli* | SPC00009 |
| *Coprobacillus*_sp_D7 | *Ruminococcus_obeum* | SPC00009 |
| *Coprobacillus*_sp_D7 | *Bacteroides_caccae* | SPC00009 |
| *Coprobacillus*_sp_D7 | *Bacteroides_eggerthii* | SPC00009 |
| *Coprobacillus*_sp_D7 | *Ruminococcus_torques* | SPC00009 |
| *Coprobacillus*_sp_D7 | *Clostridium_hathewayi* | SPC00009 |
| *Coprobacillus*_sp_D7 | *Bifidobacterium_pseudocatenulatum* | SPC00009 |
| *Coprobacillus*_sp_D7 | *Bifidobacterium_adolescentis* | SPC00009 |
| *Coprobacillus*_sp_D7 | *Coprococcus_comes* | SPC00009 |
| *Coprobacillus*_sp_D7 | *Clostridium_symbiosum* | SPC00009 |
| *Coprobacillus*_sp_D7 | *Eubacterium_rectale* | SPC00009 |
| *Coprobacillus*_sp_D7 | *Faecalibacterium_prausnitzii* | SPC00009 |
| *Coprobacillus*_sp_D7 | *Odoribacter_splanchnicus* | SPC00009 |
| *Coprobacillus*_sp_D7 | Lachnospiraceae_*bacterium*_5_1_57FAA | SPC00009 |
| *Coprobacillus*_sp_D7 | *Blautia_schinkii* | SPC00009 |
| *Coprobacillus*_sp_D7 | *Alistipes_shahii* | SPC00009 |
| *Coprobacillus*_sp_D7 | *Blautia_producta* | SPC00009 |
| *Streptococcus_thermophilus* | *Streptococcus_thermophilus* | SPC00015 |

TABLE 4a-continued

| | | |
|---|---|---|
| *Streptococcus_thermophilus* | *Dorea_formicigenerans* | SPC00015 |
| *Streptococcus_thermophilus* | *Blautia_producta* | SPC00015 |
| *Streptococcus_thermophilus* | *Eubacterium_eligens* | SPC00015 |
| *Streptococcus_thermophilus* | *Clostridium_nexile* | SPC00015 |
| *Streptococcus_thermophilus* | *Clostridium*_sp_HGF2 | SPC00015 |
| *Streptococcus_thermophilus* | *Faecalibacterium_prausnitzii* | SPC00015 |
| *Streptococcus_thermophilus* | *Odoribacter_splanchnicus* | SPC00015 |
| *Streptococcus_thermophilus* | *Dorea_longicatena* | SPC00015 |
| *Streptococcus_thermophilus* | *Roseburia_intestinalis* | SPC00015 |
| *Streptococcus_thermophilus* | *Coprococcus_catus* | SPC00015 |
| *Streptococcus_thermophilus* | Erysipelotrichaceae_*bacterium*_3_1_53 | SPC00015 |
| *Streptococcus_thermophilus* | *Bacteroides*_sp_D20 | SPC00015 |
| *Streptococcus_thermophilus* | *Bacteroides_ovatus* | SPC00015 |
| *Streptococcus_thermophilus* | *Parabacteroides_merdae* | SPC00015 |
| *Streptococcus_thermophilus* | *Bacteroides_vulgatus* | SPC00015 |
| *Streptococcus_thermophilus* | *Collinsella_aerofaciens* | SPC00015 |
| *Streptococcus_thermophilus* | *Escherichia_coli* | SPC00015 |
| *Streptococcus_thermophilus* | *Ruminococcus_obeum* | SPC00015 |
| *Streptococcus_thermophilus* | *Bacteroides_caccae* | SPC00015 |
| *Streptococcus_thermophilus* | *Bacteroides_eggerthii* | SPC00015 |
| *Streptococcus_thermophilus* | *Ruminococcus_torques* | SPC00015 |
| *Streptococcus_thermophilus* | *Clostridium_hathewayi* | SPC00015 |
| *Streptococcus_thermophilus* | *Bifidobacterium_pseudocatenulatum* | SPC00015 |
| *Streptococcus_thermophilus* | *Bifidobacterium_adolescentis* | SPC00015 |
| *Streptococcus_thermophilus* | *Coprococcus_comes* | SPC00015 |
| *Streptococcus_thermophilus* | *Clostridium_symbiosum* | SPC00015 |
| *Streptococcus_thermophilus* | *Eubacterium_rectale* | SPC00015 |
| *Streptococcus_thermophilus* | *Faecalibacterium_prausnitzii* | SPC00015 |
| *Streptococcus_thermophilus* | *Odoribacter_splanchnicus* | SPC00015 |
| *Streptococcus_thermophilus* | Lachnospiraceae_*bacterium*_5_1_57FAA | SPC00015 |
| *Streptococcus_thermophilus* | *Blautia_schinkii* | SPC00015 |
| *Streptococcus_thermophilus* | *Alistipes_shahii* | SPC00015 |
| *Streptococcus_thermophilus* | *Blautia_producta* | SPC00015 |
| *Dorea_formicigenerans* | *Dorea_formicigenerans* | SPC00018 |
| *Dorea_formicigenerans* | *Blautia_producta* | SPC00018 |
| *Dorea_formicigenerans* | *Eubacterium_eligens* | SPC00018 |
| *Dorea_formicigenerans* | *Clostridium_nexile* | SPC00018 |
| *Dorea_formicigenerans* | *Clostridium*_sp_HGF2 | SPC00018 |
| *Dorea_formicigenerans* | *Faecalibacterium_prausnitzii* | SPC00018 |
| *Dorea_formicigenerans* | *Odoribacter_splanchnicus* | SPC00018 |
| *Dorea_formicigenerans* | *Dorea_longicatena* | SPC00018 |
| *Dorea_formicigenerans* | *Roseburia_intestinalis* | SPC00018 |
| *Dorea_formicigenerans* | *Coprococcus_catus* | SPC00018 |
| *Dorea_formicigenerans* | Erysipelotrichaceae_*bacterium*_3_1_53 | SPC00018 |
| *Dorea_formicigenerans* | *Bacteroides*_sp_D20 | SPC00018 |
| *Dorea_formicigenerans* | *Bacteroides_ovatus* | SPC00018 |
| *Dorea_formicigenerans* | *Parabacteroides_merdae* | SPC00018 |
| *Dorea_formicigenerans* | *Bacteroides_vulgatus* | SPC00018 |
| *Dorea_formicigenerans* | *Collinsella_aerofaciens* | SPC00018 |
| *Dorea_formicigenerans* | *Escherichia_coli* | SPC00018 |
| *Dorea_formicigenerans* | *Ruminococcus_obeum* | SPC00018 |
| *Dorea_formicigenerans* | *Bacteroides_caccae* | SPC00018 |
| *Dorea_formicigenerans* | *Bacteroides_eggerthii* | SPC00018 |
| *Dorea_formicigenerans* | *Ruminococcus_torques* | SPC00018 |
| *Dorea_formicigenerans* | *Clostridium_hathewayi* | SPC00018 |
| *Dorea_formicigenerans* | *Bifidobacterium_pseudocatenulatum* | SPC00018 |
| *Dorea_formicigenerans* | *Bifidobacterium_adolescentis* | SPC00018 |
| *Dorea_formicigenerans* | *Coprococcus_comes* | SPC00018 |
| *Dorea_formicigenerans* | *Clostridium_symbiosum* | SPC00018 |
| *Dorea_formicigenerans* | *Eubacterium_rectale* | SPC00018 |
| *Dorea_formicigenerans* | *Faecalibacterium_prausnitzii* | SPC00018 |
| *Dorea_formicigenerans* | *Odoribacter_splanchnicus* | SPC00018 |
| *Dorea_formicigenerans* | Lachnospiraceae_*bacterium*_5_1_57FAA | SPC00018 |
| *Dorea_formicigenerans* | *Blautia_schinkii* | SPC00018 |
| *Dorea_formicigenerans* | *Alistipes_shahii* | SPC00018 |
| *Dorea_formicigenerans* | *Blautia_producta* | SPC00018 |
| *Blautia_producta* | *Blautia_producta* | SPC00021 |
| *Blautia_producta* | *Eubacterium_eligens* | SPC00021 |
| *Blautia_producta* | *Clostridium_nexile* | SPC00021 |
| *Blautia_producta* | *Clostridium*_sp_HGF2 | SPC00021 |
| *Blautia_producta* | *Faecalibacterium_prausnitzii* | SPC00021 |
| *Blautia_producta* | *Odoribacter_splanchnicus* | SPC00021 |
| *Blautia_producta* | *Dorea_longicatena* | SPC00021 |
| *Blautia_producta* | *Roseburia_intestinalis* | SPC00021 |
| *Blautia_producta* | *Coprococcus_catus* | SPC00021 |
| *Blautia_producta* | Erysipelotrichaceae_*bacterium*_3_1_53 | SPC00021 |
| *Blautia_producta* | *Bacteroides*_sp_D20 | SPC00021 |
| *Blautia_producta* | *Bacteroides_ovatus* | SPC00021 |
| *Blautia_producta* | *Parabacteroides_merdae* | SPC00021 |
| *Blautia_producta* | *Bacteroides_vulgatus* | SPC00021 |

TABLE 4a-continued

| | | |
|---|---|---|
| *Blautia_producta* | *Collinsella_aerofaciens* | SPC00021 |
| *Blautia_producta* | *Escherichia_coli* | SPC00021 |
| *Blautia_producta* | *Ruminococcus_obeum* | SPC00021 |
| *Blautia_producta* | *Bacteroides_caccae* | SPC00021 |
| *Blautia_producta* | *Bacteroides_eggerthii* | SPC00021 |
| *Blautia_producta* | *Ruminococcus_torques* | SPC00021 |
| *Blautia_producta* | *Clostridium_hathewayi* | SPC00021 |
| *Blautia_producta* | *Bifidobacterium_pseudocatenulatum* | SPC00021 |
| *Blautia_producta* | *Bifidobacterium_adolescentis* | SPC00021 |
| *Blautia_producta* | *Coprococcus_comes* | SPC00021 |
| *Blautia_producta* | *Clostridium_symbiosum* | SPC00021 |
| *Blautia_producta* | *Eubacterium_rectale* | SPC00021 |
| *Blautia_producta* | *Faecalibacterium_prausnitzii* | SPC00021 |
| *Blautia_producta* | *Odoribacter_splanchnicus* | SPC00021 |
| *Blautia_producta* | Lachnospiraceae_*bacterium*_5_1_57FAA | SPC00021 |
| *Blautia_producta* | *Blautia_schinkii* | SPC00021 |
| *Blautia_producta* | *Alistipes_shahii* | SPC00021 |
| *Blautia_producta* | *Blautia_producta* | SPC00021 |
| *Eubacterium_eligens* | *Eubacterium_eligens* | SPC00022 |
| *Eubacterium_eligens* | *Clostridium_nexile* | SPC00022 |
| *Eubacterium_eligens* | *Clostridium*_sp_HGF2 | SPC00022 |
| *Eubacterium_eligens* | *Faecalibacterium_prausnitzii* | SPC00022 |
| *Eubacterium_eligens* | *Odoribacter_splanchnicus* | SPC00022 |
| *Eubacterium_eligens* | *Dorea_longicatena* | SPC00022 |
| *Eubacterium_eligens* | *Roseburia_intestinalis* | SPC00022 |
| *Eubacterium_eligens* | *Coprococcus_catus* | SPC00022 |
| *Eubacterium_eligens* | Erysipelotrichaceae_*bacterium*_3_1_53 | SPC00022 |
| *Eubacterium_eligens* | *Bacteroides*_sp_D20 | SPC00022 |
| *Eubacterium_eligens* | *Bacteroides_ovatus* | SPC00022 |
| *Eubacterium_eligens* | *Parabacteroides_merdae* | SPC00022 |
| *Eubacterium_eligens* | *Bacteroides_vulgatus* | SPC00022 |
| *Eubacterium_eligens* | *Collinsella_aerofaciens* | SPC00022 |
| *Eubacterium_eligens* | *Escherichia_coli* | SPC00022 |
| *Eubacterium_eligens* | *Ruminococcus_obeum* | SPC00022 |
| *Eubacterium_eligens* | *Bacteroides_caccae* | SPC00022 |
| *Eubacterium_eligens* | *Bacteroides_eggerthii* | SPC00022 |
| *Eubacterium_eligens* | *Ruminococcus_torques* | SPC00022 |
| *Eubacterium_eligens* | *Clostridium_hathewayi* | SPC00022 |
| *Eubacterium_eligens* | *Bifidobacterium_pseudocatenulatum* | SPC00022 |
| *Eubacterium_eligens* | *Bifidobacterium_adolescentis* | SPC00022 |
| *Eubacterium_eligens* | *Coprococcus_comes* | SPC00022 |
| *Eubacterium_eligens* | *Clostridium_symbiosum* | SPC00022 |
| *Eubacterium_eligens* | *Eubacterium_rectale* | SPC00022 |
| *Eubacterium_eligens* | *Faecalibacterium_prausnitzii* | SPC00022 |
| *Eubacterium_eligens* | *Odoribacter_splanchnicus* | SPC00022 |
| *Eubacterium_eligens* | Lachnospiraceae_*bacterium*_5_1_57FAA | SPC00022 |
| *Eubacterium_eligens* | *Blautia_schinkii* | SPC00022 |
| *Eubacterium_eligens* | *Alistipes_shahii* | SPC00022 |
| *Eubacterium_eligens* | *Blautia_producta* | SPC00022 |
| *Clostridium_nexile* | *Clostridium_nexile* | SPC00026 |
| *Clostridium_nexile* | *Clostridium*_sp_HGF2 | SPC00026 |
| *Clostridium_nexile* | *Faecalibacterium_prausnitzii* | SPC00026 |
| *Clostridium_nexile* | *Odoribacter_splanchnicus* | SPC00026 |
| *Clostridium_nexile* | *Dorea_longicatena* | SPC00026 |
| *Clostridium_nexile* | *Roseburia_intestinalis* | SPC00026 |
| *Clostridium_nexile* | *Coprococcus_catus* | SPC00026 |
| *Clostridium_nexile* | Erysipelotrichaceae_*bacterium*_3_1_53 | SPC00026 |
| *Clostridium_nexile* | *Bacteroides*_sp_D20 | SPC00026 |
| *Clostridium_nexile* | *Bacteroides_ovatus* | SPC00026 |
| *Clostridium_nexile* | *Parabacteroides_merdae* | SPC00026 |
| *Clostridium_nexile* | *Bacteroides_vulgatus* | SPC00026 |
| *Clostridium_nexile* | *Collinsella_aerofaciens* | SPC00026 |
| *Clostridium_nexile* | *Escherichia_coli* | SPC00026 |
| *Clostridium_nexile* | *Ruminococcus_obeum* | SPC00026 |
| *Clostridium_nexile* | *Bacteroides_caccae* | SPC00026 |
| *Clostridium_nexile* | *Bacteroides_eggerthii* | SPC00026 |
| *Clostridium_nexile* | *Ruminococcus_torques* | SPC00026 |
| *Clostridium_nexile* | *Clostridium_hathewayi* | SPC00026 |
| *Clostridium_nexile* | *Bifidobacterium_pseudocatenulatum* | SPC00026 |
| *Clostridium_nexile* | *Bifidobacterium_adolescentis* | SPC00026 |
| *Clostridium_nexile* | *Coprococcus_comes* | SPC00026 |
| *Clostridium_nexile* | *Clostridium_symbiosum* | SPC00026 |
| *Clostridium_nexile* | *Eubacterium_rectale* | SPC00026 |
| *Clostridium_nexile* | *Faecalibacterium_prausnitzii* | SPC00026 |
| *Clostridium_nexile* | *Odoribacter_splanchnicus* | SPC00026 |
| *Clostridium_nexile* | Lachnospiraceae_*bacterium*_5_1_57FAA | SPC00026 |
| *Clostridium_nexile* | *Blautia_schinkii* | SPC00026 |
| *Clostridium_nexile* | *Alistipes_shahii* | SPC00026 |
| *Clostridium_nexile* | *Blautia_producta* | SPC00026 |
| *Clostridium*_sp_HGF2 | *Clostridium*_sp_HGF2 | SPC00027 |

TABLE 4a-continued

| | | |
|---|---|---|
| Clostridium_sp_HGF2 | Faecalibacterium_prausnitzii | SPC00027 |
| Clostridium_sp_HGF2 | Odoribacter_splanchnicus | SPC00027 |
| Clostridium_sp_HGF2 | Dorea_longicatena | SPC00027 |
| Clostridium_sp_HGF2 | Roseburia_intestinalis | SPC00027 |
| Clostridium_sp_HGF2 | Coprococcus_catus | SPC00027 |
| Clostridium_sp_HGF2 | Erysipelotrichaceae_bacterium_3_1_53 | SPC00027 |
| Clostridium_sp_HGF2 | Bacteroides_sp_D20 | SPC00027 |
| Clostridium_sp_HGF2 | Bacteroides_ovatus | SPC00027 |
| Clostridium_sp_HGF2 | Parabacteroides_merdae | SPC00027 |
| Clostridium_sp_HGF2 | Bacteroides_vulgatus | SPC00027 |
| Clostridium_sp_HGF2 | Collinsella_aerofaciens | SPC00027 |
| Clostridium_sp_HGF2 | Escherichia_coli | SPC00027 |
| Clostridium_sp_HGF2 | Ruminococcus_obeum | SPC00027 |
| Clostridium_sp_HGF2 | Bacteroides_caccae | SPC00027 |
| Clostridium_sp_HGF2 | Bacteroides_eggerthii | SPC00027 |
| Clostridium_sp_HGF2 | Ruminococcus_torques | SPC00027 |
| Clostridium_sp_HGF2 | Clostridium_hathewayi | SPC00027 |
| Clostridium_sp_HGF2 | Bifidobacterium_pseudocatenulatum | SPC00027 |
| Clostridium_sp_HGF2 | Bifidobacterium_adolescentis | SPC00027 |
| Clostridium_sp_HGF2 | Coprococcus_comes | SPC00027 |
| Clostridium_sp_HGF2 | Clostridium_symbiosum | SPC00027 |
| Clostridium_sp_HGF2 | Eubacterium_rectale | SPC00027 |
| Clostridium_sp_HGF2 | Faecalibacterium_prausnitzii | SPC00027 |
| Clostridium_sp_HGF2 | Odoribacter_splanchnicus | SPC00027 |
| Clostridium_sp_HGF2 | Lachnospiraceae_bacterium_5_1_57FAA | SPC00027 |
| Clostridium_sp_HGF2 | Blautia_schinkii | SPC00027 |
| Clostridium_sp_HGF2 | Alistipes_shahii | SPC00027 |
| Clostridium_sp_HGF2 | Blautia_producta | SPC00027 |
| Faecalibacterium_prausnitzii | Faecalibacterium_prausnitzii | SPC00054 |
| Faecalibacterium_prausnitzii | Odoribacter_splanchnicus | SPC00054 |
| Faecalibacterium_prausnitzii | Dorea_longicatena | SPC00054 |
| Faecalibacterium_prausnitzii | Roseburia_intestinalis | SPC00054 |
| Faecalibacterium_prausnitzii | Coprococcus_catus | SPC00054 |
| Faecalibacterium_prausnitzii | Erysipelotrichaceae_bacterium_3_1_53 | SPC00054 |
| Faecalibacterium_prausnitzii | Bacteroides_sp_D20 | SPC00054 |
| Faecalibacterium_prausnitzii | Bacteroides_ovatus | SPC00054 |
| Faecalibacterium_prausnitzii | Parabacteroides_merdae | SPC00054 |
| Faecalibacterium_prausnitzii | Bacteroides_vulgatus | SPC00054 |
| Faecalibacterium_prausnitzii | Collinsella_aerofaciens | SPC00054 |
| Faecalibacterium_prausnitzii | Escherichia_coli | SPC00054 |
| Faecalibacterium_prausnitzii | Ruminococcus_obeum | SPC00054 |
| Faecalibacterium_prausnitzii | Bacteroides_caccae | SPC00054 |
| Faecalibacterium_prausnitzii | Bacteroides_eggerthii | SPC00054 |
| Faecalibacterium_prausnitzii | Ruminococcus_torques | SPC00054 |
| Faecalibacterium_prausnitzii | Clostridium_hathewayi | SPC00054 |
| Faecalibacterium_prausnitzii | Bifidobacterium_pseudocatenulatum | SPC00054 |
| Faecalibacterium_prausnitzii | Bifidobacterium_adolescentis | SPC00054 |
| Faecalibacterium_prausnitzii | Coprococcus_comes | SPC00054 |
| Faecalibacterium_prausnitzii | Clostridium_symbiosum | SPC00054 |
| Faecalibacterium_prausnitzii | Eubacterium_rectale | SPC00054 |
| Faecalibacterium_prausnitzii | Faecalibacterium_prausnitzii | SPC00054 |
| Faecalibacterium_prausnitzii | Odoribacter_splanchnicus | SPC00054 |
| Faecalibacterium_prausnitzii | Lachnospiraceae_bacterium_5_1_57FAA | SPC00054 |
| Faecalibacterium_prausnitzii | Blautia_schinkii | SPC00054 |
| Faecalibacterium_prausnitzii | Alistipes_shahii | SPC00054 |
| Faecalibacterium_prausnitzii | Blautia_producta | SPC00054 |
| Odoribacter_splanchnicus | Odoribacter_splanchnicus | SPC00056 |
| Odoribacter_splanchnicus | Dorea_longicatena | SPC00056 |
| Odoribacter_splanchnicus | Roseburia_intestinalis | SPC00056 |
| Odoribacter_splanchnicus | Coprococcus_catus | SPC00056 |
| Odoribacter_splanchnicus | Erysipelotrichaceae_bacterium_3_1_53 | SPC00056 |
| Odoribacter_splanchnicus | Bacteroides_sp_D20 | SPC00056 |
| Odoribacter_splanchnicus | Bacteroides_ovatus | SPC00056 |
| Odoribacter_splanchnicus | Parabacteroides_merdae | SPC00056 |
| Odoribacter_splanchnicus | Bacteroides_vulgatus | SPC00056 |
| Odoribacter_splanchnicus | Collinsella_aerofaciens | SPC00056 |
| Odoribacter_splanchnicus | Escherichia_coli | SPC00056 |
| Odoribacter_splanchnicus | Ruminococcus_obeum | SPC00056 |
| Odoribacter_splanchnicus | Bacteroides_caccae | SPC00056 |
| Odoribacter_splanchnicus | Bacteroides_eggerthii | SPC00056 |
| Odoribacter_splanchnicus | Ruminococcus_torques | SPC00056 |
| Odoribacter_splanchnicus | Clostridium_hathewayi | SPC00056 |
| Odoribacter_splanchnicus | Bifidobacterium_pseudocatenulatum | SPC00056 |
| Odoribacter_splanchnicus | Bifidobacterium_adolescentis | SPC00056 |
| Odoribacter_splanchnicus | Coprococcus_comes | SPC00056 |
| Odoribacter_splanchnicus | Clostridium_symbiosum | SPC00056 |
| Odoribacter_splanchnicus | Eubacterium_rectale | SPC00056 |
| Odoribacter_splanchnicus | Faecalibacterium_prausnitzii | SPC00056 |
| Odoribacter_splanchnicus | Odoribacter_splanchnicus | SPC00056 |
| Odoribacter_splanchnicus | Lachnospiraceae_bacterium_5_1_57FAA | SPC00056 |

TABLE 4a-continued

| | | |
|---|---|---|
| Odoribacter_splanchnicus | Blautia_schinkii | SPC00056 |
| Odoribacter_splanchnicus | Alistipes_shahii | SPC00056 |
| Odoribacter_splanchnicus | Blautia_producta | SPC00056 |
| Dorea_longicatena | Dorea_longicatena | SPC00057 |
| Dorea_longicatena | Roseburia_intestinalis | SPC00057 |
| Dorea_longicatena | Coprococcus_catus | SPC00057 |
| Dorea_longicatena | Erysipelotrichaceae_bacterium_3_1_53 | SPC00057 |
| Dorea_longicatena | Bacteroides_sp_D20 | SPC00057 |
| Dorea_longicatena | Bacteroides_ovatus | SPC00057 |
| Dorea_longicatena | Parabacteroides_merdae | SPC00057 |
| Dorea_longicatena | Bacteroides_vulgatus | SPC00057 |
| Dorea_longicatena | Collinsella_aerofaciens | SPC00057 |
| Dorea_longicatena | Escherichia_coli | SPC00057 |
| Dorea_longicatena | Ruminococcus_obeum | SPC00057 |
| Dorea_longicatena | Bacteroides_caccae | SPC00057 |
| Dorea_longicatena | Bacteroides_eggerthii | SPC00057 |
| Dorea_longicatena | Ruminococcus_torques | SPC00057 |
| Dorea_longicatena | Clostridium_hathewayi | SPC00057 |
| Dorea_longicatena | Bifidobacterium_pseudocatenulatum | SPC00057 |
| Dorea_longicatena | Bifidobacterium_adolescentis | SPC00057 |
| Dorea_longicatena | Coprococcus_comes | SPC00057 |
| Dorea_longicatena | Clostridium_symbiosum | SPC00057 |
| Dorea_longicatena | Eubacterium_rectale | SPC00057 |
| Dorea_longicatena | Faecalibacterium_prausnitzii | SPC00057 |
| Dorea_longicatena | Odoribacter_splanchnicus | SPC00057 |
| Dorea_longicatena | Lachnospiraceae_bacterium_5_1_57FAA | SPC00057 |
| Dorea_longicatena | Blautia_schinkii | SPC00057 |
| Dorea_longicatena | Alistipes_shahii | SPC00057 |
| Dorea_longicatena | Blautia_producta | SPC00057 |
| Roseburia_intestinalis | Roseburia_intestinalis | SPC00061 |
| Roseburia_intestinalis | Coprococcus_catus | SPC00061 |
| Roseburia_intestinalis | Erysipelotrichaceae_bacterium_3_1_53 | SPC00061 |
| Roseburia_intestinalis | Bacteroides_sp_D20 | SPC00061 |
| Roseburia_intestinalis | Bacteroides_ovatus | SPC00061 |
| Roseburia_intestinalis | Parabacteroides_merdae | SPC00061 |
| Roseburia_intestinalis | Bacteroides_vulgatus | SPC00061 |
| Roseburia_intestinalis | Collinsella_aerofaciens | SPC00061 |
| Roseburia_intestinalis | Escherichia_coli | SPC00061 |
| Roseburia_intestinalis | Ruminococcus_obeum | SPC00061 |
| Roseburia_intestinalis | Bacteroides_caccae | SPC00061 |
| Roseburia_intestinalis | Bacteroides_eggerthii | SPC00061 |
| Roseburia_intestinalis | Ruminococcus_torques | SPC00061 |
| Roseburia_intestinalis | Clostridium_hathewayi | SPC00061 |
| Roseburia_intestinalis | Bifidobacterium_pseudocatenulatum | SPC00061 |
| Roseburia_intestinalis | Bifidobacterium_adolescentis | SPC00061 |
| Roseburia_intestinalis | Coprococcus_comes | SPC00061 |
| Roseburia_intestinalis | Clostridium_symbiosum | SPC00061 |
| Roseburia_intestinalis | Eubacterium_rectale | SPC00061 |
| Roseburia_intestinalis | Faecalibacterium_prausnitzii | SPC00061 |
| Roseburia_intestinalis | Odoribacter_splanchnicus | SPC00061 |
| Roseburia_intestinalis | Lachnospiraceae_bacterium_5_1_57FAA | SPC00061 |
| Roseburia_intestinalis | Blautia_schinkii | SPC00061 |
| Roseburia_intestinalis | Alistipes_shahii | SPC00061 |
| Roseburia_intestinalis | Blautia_producta | SPC00061 |
| Coprococcus_catus | Coprococcus_catus | SPC00080 |
| Coprococcus_catus | Erysipelotricliaceae_bacterium_3_1_53 | SPC00080 |
| Coprococcus_catus | Bacteroides_sp_D20 | SPC00080 |
| Coprococcus_catus | Bacteroides_ovatus | SPC00080 |
| Coprococcus_catus | Parabacteroides_merdae | SPC00080 |
| Coprococcus_catus | Bacteroides_vulgatus | SPC00080 |
| Coprococcus_catus | Collinsella_aerofaciens | SPC00080 |
| Coprococcus_catus | Escherichia_coli | SPC00080 |
| Coprococcus_catus | Ruminococcus_obeum | SPC00080 |
| Coprococcus_catus | Bacteroides_caccae | SPC00080 |
| Coprococcus_catus | Bacteroides_eggerthii | SPC00080 |
| Coprococcus_catus | Ruminococcus_torques | SPC00080 |
| Coprococcus_catus | Clostridium_hathewayi | SPC00080 |
| Coprococcus_catus | Bifidobacterium_pseudocatenulatum | SPC00080 |
| Coprococcus_catus | Bifidobacterium_adolescentis | SPC00080 |
| Coprococcus_catus | Coprococcus_comes | SPC00080 |
| Coprococcus_catus | Clostridium_symbiosum | SPC00080 |
| Coprococcus_catus | Eubacterium_rectale | SPC00080 |
| Coprococcus_catus | Faecalibacterium_prausnitzii | SPC00080 |
| Coprococcus_catus | Odoribacter_splanchnicus | SPC00080 |
| Coprococcus_catus | Lachnospiraceae_bacterium_5_1_57FAA | SPC00080 |
| Coprococcus_catus | Blautia_schinkii | SPC00080 |
| Coprococcus_catus | Alistipes_shahii | SPC00080 |
| Coprococcus_catus | Blautia_producta | SPC00080 |
| Erysipelotrichaceae_bacterium_3_1_53 | Erysipelotrichaceae_bacterium_3_1_53 | SPC10001 |
| Erysipelotrichaceae_bacterium_3_1_53 | Bacteroides_sp_D20 | SPC10001 |

TABLE 4a-continued

| | | |
|---|---|---|
| Erysipelotrichaceae_*bacterium*_3_1_53 | *Bacteroides_ovatus* | SPC10001 |
| Erysipelotrichaceae_*bacterium*_3_1_53 | *Parabacteroides_merdae* | SPC10001 |
| Erysipelotrichaceae_*bacterium*_3_1_53 | *Bacteroides_vulgatus* | SPC10001 |
| Erysipelotrichaceae_*bacterium*_3_1_53 | *Collinsella_aerofaciens* | SPC10001 |
| Erysipelotrichaceae_*bacterium*_3_1_53 | *Escherichia_coli* | SPC10001 |
| Erysipelotrichaceae_*bacterium*_3_1_53 | *Ruminococcus_obeum* | SPC10001 |
| Erysipelotrichaceae_*bacterium*_3_1_53 | *Bacteroides_caccae* | SPC10001 |
| Erysipelotrichaceae_*bacterium*_3_1_53 | *Bacteroides_eggerthii* | SPC10001 |
| Erysipelotrichaceae_*bacterium*_3_1_53 | *Ruminococcus_torques* | SPC10001 |
| Erysipelotrichaceae_*bacterium*_3_1_53 | *Clostridium_hathewayi* | SPC10001 |
| Erysipelotrichaceae_*bacterium*_3_1_53 | *Bifidobacterium_pseudocatenulatum* | SPC10001 |
| Erysipelotrichaceae_*bacterium*_3_1_53 | *Bifidobacterium_adolescentis* | SPC10001 |
| Erysipelotrichaceae_*bacterium*_3_1_53 | *Coprococcus_comes* | SPC10001 |
| Erysipelotrichaceae_*bacterium*_3_1_53 | *Clostridium_symbiosum* | SPC10001 |
| Erysipelotrichaceae_*bacterium*_3_1_53 | *Eubacterium_rectale* | SPC10001 |
| Erysipelotrichaceae_*bacterium*_3_1_53 | *Faecalibacterium_prausnitzii* | SPC10001 |
| Erysipelotrichaceae_*bacterium*_3_1_53 | *Odoribacter_splanchnicus* | SPC10001 |
| Erysipelotrichaceae_*bacterium*_3_1_53 | Lachnospiraceae_*bacterium*_5_1_57FAA | SPC10001 |
| Erysipelotrichaceae_*bacterium*_3_1_53 | *Blautia_schinkii* | SPC10001 |
| Erysipelotrichaceae_*bacterium*_3_1_53 | *Alistipes_shahii* | SPC10001 |
| Erysipelotrichaceae_*bacterium*_3_1_53 | *Blautia_producta* | SPC10001 |
| *Bacteroides*_sp_D20 | *Bacteroides*_sp_D20 | SPC10019 |
| *Bacteroides*_sp_D20 | *Bacteroides_ovatus* | SPC10019 |
| *Bacteroides*_sp_D20 | *Parabacteroides_merdae* | SPC10019 |
| *Bacteroides*_sp_D20 | *Bacteroides_vulgatus* | SPC10019 |
| *Bacteroides*_sp_D20 | *Collinsella_aerofaciens* | SPC10019 |
| *Bacteroides*_sp_D20 | *Escherichia_coli* | SPC10019 |
| *Bacteroides*_sp_D20 | *Ruminococcus_obeum* | SPC10019 |
| *Bacteroides*_sp_D20 | *Bacteroides_caccae* | SPC10019 |
| *Bacteroides*_sp_D20 | *Bacteroides_eggerthii* | SPC10019 |
| *Bacteroides*_sp_D20 | *Ruminococcus_torques* | SPC10019 |
| *Bacteroides*_sp_D20 | *Clostridium_hathewayi* | SPC10019 |
| *Bacteroides*_sp_D20 | *Bifidobacterium_pseudocatenulatum* | SPC10019 |
| *Bacteroides*_sp_D20 | *Bifidobacterium_adolescentis* | SPC10019 |
| *Bacteroides*_sp_D20 | *Coprococcus_comes* | SPC10019 |
| *Bacteroides*_sp_D20 | *Clostridium_symbiosum* | SPC10019 |
| *Bacteroides*_sp_D20 | *Eubacterium_rectale* | SPC10019 |
| *Bacteroides*_sp_D20 | *Faecalibacterium_prausnitzii* | SPC10019 |
| *Bacteroides*_sp_D20 | *Odoribacter_splanchnicus* | SPC10019 |
| *Bacteroides*_sp_D20 | Lachnospiraceae_*bacterium*_5_1_57FAA | SPC10019 |
| *Bacteroides*_sp_D20 | *Blautia_schinkii* | SPC10019 |
| *Bacteroides*_sp_D20 | *Alistipes_shahii* | SPC10019 |
| *Bacteroides*_sp_D20 | *Blautia_producta* | SPC10019 |
| *Bacteroides_ovatus* | *Bacteroides_ovatus* | SPC10030 |
| *Bacteroides_ovatus* | *Parabacteroides_merdae* | SPC10030 |
| *Bacteroides_ovatus* | *Bacteroides_vulgatus* | SPC10030 |
| *Bacteroides_ovatus* | *Collinsella_aerofaciens* | SPC10030 |
| *Bacteroides_ovatus* | *Escherichia_coli* | SPC10030 |
| *Bacteroides_ovatus* | *Ruminococcus_obeum* | SPC10030 |
| *Bacteroides_ovatus* | *Bacteroides_caccae* | SPC10030 |
| *Bacteroides_ovatus* | *Bacteroides_eggerthii* | SPC10030 |
| *Bacteroides_ovatus* | *Ruminococcus_torques* | SPC10030 |
| *Bacteroides_ovatus* | *Clostridium_hathewayi* | SPC10030 |
| *Bacteroides_ovatus* | *Bifidobacterium_pseudocatenulatum* | SPC10030 |
| *Bacteroides_ovatus* | *Bifidobacterium_adolescentis* | SPC10030 |
| *Bacteroides_ovatus* | *Coprococcus_comes* | SPC10030 |
| *Bacteroides_ovatus* | *Clostridium_symbiosum* | SPC10030 |
| *Bacteroides_ovatus* | *Eubacterium_rectale* | SPC10030 |
| *Bacteroides_ovatus* | *Faecalibacterium_prausnitzii* | SPC10030 |
| *Bacteroides_ovatus* | *Odoribacter_splanchnicus* | SPC10030 |
| *Bacteroides_ovatus* | Lachnospiraceae_*bacterium*_5_1_57FAA | SPC10030 |
| *Bacteroides_ovatus* | *Blautia_schinkii* | SPC10030 |
| *Bacteroides_ovatus* | *Alistipes_shahii* | SPC10030 |
| *Bacteroides_ovatus* | *Blautia_producta* | SPC10030 |
| *Parabacteroides_merdae* | *Parabacteroides_merdae* | SPC10048 |
| *Parabacteroides_merdae* | *Bacteroides_vulgatus* | SPC10048 |
| *Parabacteroides_merdae* | *Collinsella_aerofaciens* | SPC10048 |
| *Parabacteroides_merdae* | *Escherichia_coli* | SPC10048 |
| *Parabacteroides_merdae* | *Ruminococcus_obeum* | SPC10048 |
| *Parabacteroides_merdae* | *Bacteroides_caccae* | SPC10048 |
| *Parabacteroides_merdae* | *Bacteroides_eggerthii* | SPC10048 |
| *Parabacteroides_merdae* | *Ruminococcus_torques* | SPC10048 |
| *Parabacteroides_merdae* | *Clostridium_hathewayi* | SPC10048 |
| *Parabacteroides_merdae* | *Bifidobacterium_pseudocatenulatum* | SPC10048 |
| *Parabacteroides_merdae* | *Bifidobacterium_adolescentis* | SPC10048 |
| *Parabacteroides_merdae* | *Coprococcus_comes* | SPC10048 |
| *Parabacteroides_merdae* | *Clostridium_symbiosum* | SPC10048 |
| *Parabacteroides_merdae* | *Eubacterium_rectale* | SPC10048 |
| *Parabacteroides_merdae* | *Faecalibacterium_prausnitzii* | SPC10048 |
| *Parabacteroides_merdae* | *Odoribacter_splanchnicus* | SPC10048 |

TABLE 4a-continued

| | | |
|---|---|---|
| *Parabacteroides_merdae* | Lachnospiraceae_*bacterium*_5_1_57FAA | SPC10048 |
| *Parabacteroides_merdae* | *Blautia_schinkii* | SPC10048 |
| *Parabacteroides_merdae* | *Alistipes_shahii* | SPC10048 |
| *Parabacteroides_merdae* | *Blautia_producta* | SPC10048 |
| *Bacteroides_vulgatus* | *Bacteroides_vulgatus* | SPC10081 |
| *Bacteroides_vulgatus* | *Collinsella_aerofaciens* | SPC10081 |
| *Bacteroides_vulgatus* | *Escherichia_coli* | SPC10081 |
| *Bacteroides_vulgatus* | *Ruminococcus_obeum* | SPC10081 |
| *Bacteroides_vulgatus* | *Bacteroides_caccae* | SPC10081 |
| *Bacteroides_vulgatus* | *Bacteroides_eggerthii* | SPC10081 |
| *Bacteroides_vulgatus* | *Ruminococcus_torques* | SPC10081 |
| *Bacteroides_vulgatus* | *Clostridium_hathewayi* | SPC10081 |
| *Bacteroides_vulgatus* | *Bifidobacterium_pseudocatenulatum* | SPC10081 |
| *Bacteroides_vulgatus* | *Bifidobacterium_adolescentis* | SPC10081 |
| *Bacteroides_vulgatus* | *Coprococcus_comes* | SPC10081 |
| *Bacteroides_vulgatus* | *Clostridium_symbiosum* | SPC10081 |
| *Bacteroides_vulgatus* | *Eubacterium_rectale* | SPC10081 |
| *Bacteroides_vulgatus* | *Faecalibacterium_prausnitzii* | SPC10081 |
| *Bacteroides_vulgatus* | *Odoribacter_splanchnicus* | SPC10081 |
| *Bacteroides_vulgatus* | Lachnospiraceae_*bacterium*_5_1_57FAA | SPC10081 |
| *Bacteroides_vulgatus* | *Blautia_schinkii* | SPC10081 |
| *Bacteroides_vulgatus* | *Alistipes_shahii* | SPC10081 |
| *Bacteroides_vulgatus* | *Blautia_producta* | SPC10081 |
| *Collinsella_aerofaciens* | *Collinsella_aerofaciens* | SPC10097 |
| *Collinsella_aerofaciens* | *Escherichia_coli* | SPC10097 |
| *Collinsella_aerofaciens* | *Ruminococcus_obeum* | SPC10097 |
| *Collinsella_aerofaciens* | *Bacteroides_caccae* | SPC10097 |
| *Collinsella_aerofaciens* | *Bacteroides_eggerthii* | SPC10097 |
| *Collinsella_aerofaciens* | *Ruminococcus_torques* | SPC10097 |
| *Collinsella_aerofaciens* | *Clostridium_hathewayi* | SPC10097 |
| *Collinsella_aerofaciens* | *Bifidobacterium_pseudocatenulatum* | SPC10097 |
| *Collinsella_aerofaciens* | *Bifidobacterium_adolescentis* | SPC10097 |
| *Collinsella_aerofaciens* | *Coprococcus_comes* | SPC10097 |
| *Collinsella_aerofaciens* | *Clostridium_symbiosum* | SPC10097 |
| *Collinsella_aerofaciens* | *Eubacterium_rectale* | SPC10097 |
| *Collinsella_aerofaciens* | *Faecalibacterium_prausnitzii* | SPC10097 |
| *Collinsella_aerofaciens* | *Odoribacter_splanchnicus* | SPC10097 |
| *Collinsella_aerofaciens* | Lachnospiraceae_*bacterium*_5_1_57FAA | SPC10097 |
| *Collinsella_aerofaciens* | *Blautia_schinkii* | SPC10097 |
| *Collinsella_aerofaciens* | *Alistipes_shahii* | SPC10097 |
| *Collinsella_aerofaciens* | *Blautia_producta* | SPC10097 |
| *Escherichia_coli* | *Escherichia_coli* | SPC10110 |
| *Escherichia_coli* | *Ruminococcus_obeum* | SPC10110 |
| *Escherichia_coli* | *Bacteroides_caccae* | SPC10110 |
| *Escherichia_coli* | *Bacteroides_eggerthii* | SPC10110 |
| *Escherichia_coli* | *Ruminococcus_torques* | SPC10110 |
| *Escherichia_coli* | *Clostridium_hathewayi* | SPC10110 |
| *Escherichia_coli* | *Bifidobacterium_pseudocatenulatum* | SPC10110 |
| *Escherichia_coli* | *Bifidobacterium_adolescentis* | SPC10110 |
| *Escherichia_coli* | *Coprococcus_comes* | SPC10110 |
| *Escherichia_coli* | *Clostridium_symbiosum* | SPC10110 |
| *Escherichia_coli* | *Eubacterium_rectale* | SPC10110 |
| *Escherichia_coli* | *Faecalibacterium_prausnitzii* | SPC10110 |
| *Escherichia_coli* | *Odoribacter_splanchnicus* | SPC10110 |
| *Escherichia_coli* | Lachnospiraceae_*bacterium*_5_1_57FAA | SPC10110 |
| *Escherichia_coli* | *Blautia_schinkii* | SPC10110 |
| *Escherichia_coli* | *Alistipes_shahii* | SPC10110 |
| *Escherichia_coli* | *Blautia_producta* | SPC10110 |
| *Ruminococcus_obeum* | *Ruminococcus_obeum* | SPC10197 |
| *Ruminococcus_obeum* | *Bacteroides_caccae* | SPC10197 |
| *Ruminococcus_obeum* | *Bacteroides_eggerthii* | SPC10197 |
| *Ruminococcus_obeum* | *Ruminococcus_torques* | SPC10197 |
| *Ruminococcus_obeum* | *Clostridium_hathewayi* | SPC10197 |
| *Ruminococcus_obeum* | *Bifidobacterium_pseudocatenulatum* | SPC10197 |
| *Ruminococcus_obeum* | *Bifidobacterium_adolescentis* | SPC10197 |
| *Ruminococcus_obeum* | *Coprococcus_comes* | SPC10197 |
| *Ruminococcus_obeum* | *Clostridium_symbiosum* | SPC10197 |
| *Ruminococcus_obeum* | *Eubacterium_rectale* | SPC10197 |
| *Ruminococcus_obeum* | *Faecalibacterium_prausnitzii* | SPC10197 |
| *Ruminococcus_obeum* | *Odoribacter_splanchnicus* | SPC10197 |
| *Ruminococcus_obeum* | Lachnospiraceae_*bacterium*_5_1_57FAA | SPC10197 |
| *Ruminococcus_obeum* | *Blautia_schinkii* | SPC10197 |
| *Ruminococcus_obeum* | *Alistipes_shahii* | SPC10197 |
| *Ruminococcus_obeum* | *Blautia_producta* | SPC10197 |
| *Bacteroides_caccae* | *Bacteroides_caccae* | SPC10211 |
| *Bacteroides_caccae* | *Bacteroides_eggerthii* | SPC10211 |
| *Bacteroides_caccae* | *Ruminococcus_torques* | SPC10211 |
| *Bacteroides_caccae* | *Clostridium_hathewayi* | SPC10211 |
| *Bacteroides_caccae* | *Bifidobacterium_pseudocatenulatum* | SPC10211 |
| *Bacteroides_caccae* | *Bifidobacterium_adolescentis* | SPC10211 |

TABLE 4a-continued

| | | |
|---|---|---|
| *Bacteroides_caccae* | *Coprococcus_comes* | SPC10211 |
| *Bacteroides_caccae* | *Clostridium_symbiosum* | SPC10211 |
| *Bacteroides_caccae* | *Eubacterium_rectale* | SPC10211 |
| *Bacteroides_caccae* | *Faecalibacterium_prausnitzii* | SPC10211 |
| *Bacteroides_caccae* | *Odoribacter_splanchnicus* | SPC10211 |
| *Bacteroides_caccae* | Lachnospiraceae_*bacterium*_5_1_57FAA | SPC10211 |
| *Bacteroides_caccae* | *Blautia_schinkii* | SPC10211 |
| *Bacteroides_caccae* | *Alistipes_shahii* | SPC10211 |
| *Bacteroides_caccae* | *Blautia_producta* | SPC10211 |
| *Bacteroides_eggerthii* | *Bacteroides_eggerthii* | SPC10213 |
| *Bacteroides_eggerthii* | *Ruminococcus_torques* | SPC10213 |
| *Bacteroides_eggerthii* | *Clostridium_hathewayi* | SPC10213 |
| *Bacteroides_eggerthii* | *Bifidobacterium_pseudocatenulatum* | SPC10213 |
| *Bacteroides_eggerthii* | *Bifidobacterium_adolescentis* | SPC10213 |
| *Bacteroides_eggerthii* | *Coprococcus_comes* | SPC10213 |
| *Bacteroides_eggerthii* | *Clostridium_symbiosum* | SPC10213 |
| *Bacteroides_eggerthii* | *Eubacterium_rectale* | SPC10213 |
| *Bacteroides_eggerthii* | *Faecalibacterium_prausnitzii* | SPC10213 |
| *Bacteroides_eggerthii* | *Odoribacter_splanchnicus* | SPC10213 |
| *Bacteroides_eggerthii* | Lachnospiraceae_*bacterium*_5_1_57FAA | SPC10213 |
| *Bacteroides_eggerthii* | *Blautia_schinkii* | SPC10213 |
| *Bacteroides_eggerthii* | *Alistipes_shahii* | SPC10213 |
| *Bacteroides_eggerthii* | *Blautia_producta* | SPC10213 |
| *Ruminococcus_torques* | *Ruminococcus_torques* | SPC10233 |
| *Ruminococcus_torques* | *Clostridium_hathewayi* | SPC10233 |
| *Ruminococcus_torques* | *Bifidobacterium_pseudocatenulatum* | SPC10233 |
| *Ruminococcus_torques* | *Bifidobacterium_adolescentis* | SPC10233 |
| *Ruminococcus_torques* | *Coprococcus_comes* | SPC10233 |
| *Ruminococcus_torques* | *Clostridium_symbiosum* | SPC10233 |
| *Ruminococcus_torques* | *Eubacterium_rectale* | SPC10233 |
| *Ruminococcus_torques* | *Faecalibacterium_prausnitzii* | SPC10233 |
| *Ruminococcus_torques* | *Odoribacter_splanchnicus* | SPC10233 |
| *Ruminococcus_torques* | Lachnospiraceae_*bacterium*_5_1_57FAA | SPC10233 |
| *Ruminococcus_torques* | *Blautia_schinkii* | SPC10233 |
| *Ruminococcus_torques* | *Alistipes_shahii* | SPC10233 |
| *Ruminococcus_torques* | *Blautia_producta* | SPC10233 |
| *Clostridium_hathewayi* | *Clostridium_hathewayi* | SPC10243 |
| *Clostridium_hathewayi* | *Bifidobacterium_pseudocatenulatum* | SPC10243 |
| *Clostridium_hathewayi* | *Bifidobacterium_adolescentis* | SPC10243 |
| *Clostridium_hathewayi* | *Coprococcus_comes* | SPC10243 |
| *Clostridium_hathewayi* | *Clostridium_symbiosum* | SPC10243 |
| *Clostridium_hathewayi* | *Eubacterium_rectale* | SPC10243 |
| *Clostridium_hathewayi* | *Faecalibacterium_prausnitzii* | SPC10243 |
| *Clostridium_hathewayi* | *Odoribacter_splanchnicus* | SPC10243 |
| *Clostridium_hathewayi* | Lachospiraceae_*bacterium*_5_1_57FAA | SPC10243 |
| *Clostridium_hathewayi* | *Blautia_schinkii* | SPC10243 |
| *Clostridium_hathewayi* | *Alistipes_shahii* | SPC10243 |
| *Clostridium_hathewayi* | *Blautia_producta* | SPC10243 |
| *Bifidobacterium_pseudocatenulatum* | *Bifidobacterium_pseudocatenulatum* | SPC10298 |
| *Bifidobacterium_pseudocatenulatum* | *Bifidobacterium_adolescentis* | SPC10298 |
| *Bifidobacterium_pseudocatenulatum* | *Coprococcus_comes* | SPC10298 |
| *Bifidobacterium_pseudocatenulatum* | *Clostridium_symbiosum* | SPC10298 |
| *Bifidobacterium_pseudocatenulatum* | *Eubacterium_rectale* | SPC10298 |
| *Bifidobacterium_pseudocatenulatum* | *Faecalibacterium_prausnitzii* | SPC10298 |
| *Bifidobacterium_pseudocatenulatum* | *Odoribacter_splanchnicus* | SPC10298 |
| *Bifidobacterium_pseudocatenulatum* | Lachnospiraceae_*bacterium*_5_1_57FAA | SPC10298 |
| *Bifidobacterium_pseudocatenulatum* | *Blautia_schinkii* | SPC10298 |
| *Bifidobacterium_pseudocatenulatum* | *Alistipes_shahii* | SPC10298 |
| *Bifidobacterium_pseudocatenulatum* | *Blautia_producta* | SPC10298 |
| *Bifidobacterium_adolescentis* | *Bifidobacterium_adolescentis* | SPC10301 |
| *Bifidobacterium_adolescentis* | *Coprococcus_comes* | SPC10301 |
| *Bifidobacterium_adolescentis* | *Clostridium_symbiosum* | SPC10301 |
| *Bifidobacterium_adolescentis* | *Eubacterium_rectale* | SPC10301 |
| *Bifidobacterium_adolescentis* | *Faecalibacterium_prausnitzii* | SPC10301 |
| *Bifidobacterium_adolescentis* | *Odoribacter_splanchnicus* | SPC10301 |
| *Bifidobacterium_adolescentis* | Lachnospiraceae_*bacterium*_5_1_57FAA | SPC10301 |
| *Bifidobacterium_adolescentis* | *Blautia_schinkii* | SPC10301 |
| *Bifidobacterium_adolescentis* | *Alistipes_shahii* | SPC10301 |
| *Bifidobacterium_adolescentis* | *Blautia_producta* | SPC10301 |
| *Coprococcus_comes* | *Coprococcus_comes* | SPC10304 |
| *Coprococcus_comes* | *Clostridium_symbiosum* | SPC10304 |
| *Coprococcus_comes* | *Eubacterium_rectale* | SPC10304 |
| *Coprococcus_comes* | *Faecalibacterium_prausnitzii* | SPC10304 |
| *Coprococcus_comes* | *Odoribacter_splanchnicus* | SPC10304 |
| *Coprococcus_comes* | Lachnospiraceae_*bacterium*_5_1_57FAA | SPC10304 |
| *Coprococcus_comes* | *Blautia_schinkii* | SPC10304 |
| *Coprococcus_comes* | *Alistipes_shahii* | SPC10304 |
| *Coprococcus_comes* | *Blautia_producta* | SPC10304 |
| *Clostridium_symbiosum* | *Clostridium_symbiosum* | SPC10355 |
| *Clostridium_symbiosum* | *Eubacterium_rectale* | SPC10355 |

TABLE 4a-continued

| | | |
|---|---|---|
| *Clostridium_symbiosum* | *Faecalibacterium_prausnitzii* | SPC10355 |
| *Clostridium_symbiosum* | *Odoribacter_splanchnicus* | SPC10355 |
| *Clostridium_symbiosum* | Lachnospiraceae_*bacterium*_5_1_57FAA | SPC10355 |
| *Clostridium_symbiosum* | *Blautia_schinkii* | SPC10355 |
| *Clostridium_symbiosum* | *Alistipes_shahii* | SPC10355 |
| *Clostridium_symbiosum* | *Blautia_producta* | SPC10355 |
| *Eubacterium_rectale* | *Eubacterium_rectale* | SPC10363 |
| *Eubacterium_rectale* | *Faecalibacterium_prausnitzii* | SPC10363 |
| *Eubacterium_rectale* | *Odoribacter_splanchnicus* | SPC10363 |
| *Eubacterium_rectale* | Lachnospiraceae_*bacterium*_5_1_57FAA | SPC10363 |
| *Eubacterium_rectale* | *Blautia_schinkii* | SPC10363 |
| *Eubacterium_rectale* | *Alistipes_shahii* | SPC10363 |
| *Eubacterium_rectale* | *Blautia_producta* | SPC10363 |
| *Faecalibacterium_prausnitzii* | *Faecalibacterium_prausnitzii* | SPC10386 |
| *Faecalibacterium_prausnitzii* | *Odoribacter_splanchnicus* | SPC10386 |
| *Faecalibacterium_prausnitzii* | Lachnospiraceae_*bacterium*_5_1_57FAA | SPC10386 |
| *Faecalibacterium_prausnitzii* | *Blautia_schinkii* | SPC10386 |
| *Faecalibacterium_prausnitzii* | *Alistipes_shahii* | SPC10386 |
| *Faecalibacterium_prausnitzii* | *Blautia_producta* | SPC10386 |
| *Odoribacter_splanchnicus* | *Odoribacter_splanchnicus* | SPC10388 |
| *Odoribacter_splanchnicus* | Lachnospiraceae_*bacterium*_5_1_57FAA | SPC10388 |
| *Odoribacter_splanchnicus* | *Blautia_schinkii* | SPC10388 |
| *Odoribacter_splanchnicus* | *Alistipes_shahii* | SPC10388 |
| *Odoribacter_splanchnicus* | *Blautia_producta* | SPC10388 |
| Lachnospiraceae_*bacterium*_5_1_57FAA | Lachnospiraceae_*bacterium*_5_1_57FAA | SPC10390 |
| Lachnospiraceae_*bacterium*_5_1_57FAA | *Blautia_schinkii* | SPC10390 |
| Lachnospiraceae_*bacterium*_5_1_57FAA | *Alistipes_shahii* | SPC10390 |
| Lachnospiraceae_*bacterium*_5_1_57FAA | *Blautia_producta* | SPC10390 |
| *Blautia_schinkii* | *Blautia_schinkii* | SPC10403 |
| *Blautia_schinkii* | *Alistipes_shahii* | SPC10403 |
| *Blautia_schinkii* | *Blautia_producta* | SPC10403 |
| *Alistipes_shahii* | *Alistipes_shahii* | SPC10414 |
| *Alistipes_shahii* | *Blautia_producta* | SPC10414 |
| *Blautia_producta* | *Blautia_producta* | SPC10415 |
| *Collinsella_aerofaciens* | *Clostridium_tertium* | SPC10097 |
| *Collinsella_aerofaciens* | *Clostridium_disporicum* | SPC10097 |
| *Collinsella_aerofaciens* | *Clostridium_innocuum* | SPC10097 |
| *Collinsella_aerofaciens* | *Clostridium_mayombei* | SPC10097 |
| *Collinsella_aerofaciens* | *Clostridium_butyricum* | SPC10097 |
| *Collinsella_aerofaciens* | *Clostridium_hylemonae* | SPC10097 |
| *Collinsella_aerofaciens* | *Clostridium_bolteae* | SPC10097 |
| *Collinsella_aerofaciens* | *Clostridium_orbiscindens* | SPC10097 |
| *Collinsella_aerofaciens* | *Ruminococcus_gnavus* | SPC10097 |
| *Collinsella_aerofaciens* | *Ruminococcus_bromii* | SPC10097 |
| *Collinsella_aerofaciens* | *Eubacterium_rectale* | SPC10097 |
| *Clostridium_tertium* | *Collinsella_aerofaciens* | SPC10155 |
| *Clostridium_tertium* | *Clostridium_tertium* | SPC10155 |
| *Clostridium_tertium* | *Clostridium_disporicum* | SPC10155 |
| *Clostridium_tertium* | *Clostridium_innocuum* | SPC10155 |
| *Clostridium_tertium* | *Clostridium_mayombei* | SPC10155 |
| *Clostridium_tertium* | *Clostridium_butyricum* | SPC10155 |
| *Clostridium_tertium* | *Coprococcus_comes* | SPC10155 |
| *Clostridium_tertium* | *Clostridium_hylemonae* | SPC10155 |
| *Clostridium_tertium* | *Clostridium_bolteae* | SPC10155 |
| *Clostridium_tertium* | *Clostridium_symbiosum* | SPC10155 |
| *Clostridium_tertium* | *Clostridium_orbiscindens* | SPC10155 |
| *Clostridium_tertium* | *Faecalibacterium_prausnitzii* | SPC10155 |
| *Clostridium_tertium* | Lachnospiraceae_*bacterium*_5_1_57FAA | SPC10155 |
| *Clostridium_tertium* | *Blautia_producta* | SPC10155 |
| *Clostridium_tertium* | *Ruminococcus_gnavus* | SPC10155 |
| *Clostridium_tertium* | *Ruminococcus_bromii* | SPC10155 |
| *Clostridium_tertium* | *Eubacterium_rectale* | SPC10155 |
| *Clostridium_disporicum* | *Clostridium_tertium* | SPC10167 |
| *Clostridium_disporicum* | *Clostridium_disporicum* | SPC10167 |
| *Clostridium_disporicum* | *Clostridium_innocuum* | SPC10167 |
| *Clostridium_disporicum* | *Clostridium_mayombei* | SPC10167 |
| *Clostridium_disporicum* | *Clostridium_butyricum* | SPC10167 |
| *Clostridium_disporicum* | *Coprococcus_comes* | SPC10167 |
| *Clostridium_disporicum* | *Clostridium_hylemonae* | SPC10167 |
| *Clostridium_disporicum* | *Clostridium_bolteae* | SPC10167 |
| *Clostridium_disporicum* | *Clostridium_symbiosum* | SPC10167 |
| *Clostridium_disporicum* | *Clostridium_orbiscindens* | SPC10167 |
| *Clostridium_disporicum* | *Faecalibacterium_prausnitzii* | SPC10167 |
| *Clostridium_disporicum* | Lachnospiraceae_*bacterium*_5_1_57FAA | SPC10167 |
| *Clostridium_disporicum* | *Blautia_producta* | SPC10167 |
| *Clostridium_disporicum* | *Ruminococcus_gnavus* | SPC10167 |
| *Clostridium_disporicum* | *Ruminococcus_bromii* | SPC10167 |
| *Clostridium_disporicum* | *Eubacterium_rectale* | SPC10167 |
| *Clostridium_innocuum* | *Clostridium_disporicum* | SPC10202 |
| *Clostridium_innocuum* | *Clostridium_innocuum* | SPC10202 |

TABLE 4a-continued

| | | |
|---|---|---|
| *Clostridium_innocuum* | *Clostridium_mayombei* | SPC10202 |
| *Clostridium_innocuum* | *Clostridium_butyricum* | SPC10202 |
| *Clostridium_innocuum* | *Coprococcus_comes* | SPC10202 |
| *Clostridium_innocuum* | *Clostridium_hylemonae* | SPC10202 |
| *Clostridium_innocuum* | *Clostridium_bolteae* | SPC10202 |
| *Clostridium_innocuum* | *Clostridium_symbiosum* | SPC10202 |
| *Clostridium_innocuum* | *Clostridium_orbiscindens* | SPC10202 |
| *Clostridium_innocuum* | *Faecalibacterium_prausnitzii* | SPC10202 |
| *Clostridium_innocuum* | Lachnospiraceae_*bacterium*_5_1_57FAA | SPC10202 |
| *Clostridium_innocuum* | *Blautia_producta* | SPC10202 |
| *Clostridium_innocuum* | *Ruminococcus_gnavus* | SPC10202 |
| *Clostridium_innocuum* | *Ruminococcus_bromii* | SPC10202 |
| *Clostridium_innocuum* | *Eubacterium_rectale* | SPC10202 |
| *Clostridium_mayombei* | *Clostridium_innocuum* | SPC10238 |
| *Clostridium_mayombei* | *Clostridium_mayombei* | SPC10238 |
| *Clostridium_mayombei* | *Clostridium_butyricum* | SPC10238 |
| *Clostridium_mayombei* | *Coprococcus_comes* | SPC10238 |
| *Clostridium_mayombei* | *Clostridium_hylemonae* | SPC10238 |
| *Clostridium_mayombei* | *Clostridium_bolteae* | SPC10238 |
| *Clostridium_mayombei* | *Clostridium_symbiosum* | SPC10238 |
| *Clostridium_mayombei* | *Clostridium_orbiscindens* | SPC10238 |
| *Clostridium_mayombei* | *Faecalibacterium_prausnitzii* | SPC10238 |
| *Clostridium_mayombei* | Lachnospiraceae_*bacterium*_5_1_57FAA | SPC10238 |
| *Clostridium_mayombei* | *Blautia_producta* | SPC10238 |
| *Clostridium_mayombei* | *Ruminococcus_gnavus* | SPC10238 |
| *Clostridium_mayombei* | *Ruminococcus_bromii* | SPC10238 |
| *Clostridium_mayombei* | *Eubacterium_rectale* | SPC10238 |
| *Clostridium_butyricum* | *Clostridium_mayombei* | SPC10256 |
| *Clostridium_butyricum* | *Clostridium_butyricum* | SPC10256 |
| *Clostridium_butyricum* | *Coprococcus_comes* | SPC10256 |
| *Clostridium_butyricum* | *Clostridium_hylemonae* | SPC10256 |
| *Clostridium_butyricum* | *Clostridium_bolteae* | SPC10256 |
| *Clostridium_butyricum* | *Clostridium_symbiosum* | SPC10256 |
| *Clostridium_butyricum* | *Clostridium_orbiscindens* | SPC10256 |
| *Clostridium_butyricum* | *Faecalibacterium_prausnitzii* | SPC10256 |
| *Clostridium_butyricum* | Lachnospiraceae_*bacterium*_5_1_57FAA | SPC10256 |
| *Clostridium_butyricum* | *Blautia_producta* | SPC10256 |
| *Clostridium_butyricum* | *Ruminococcus_gnavus* | SPC10256 |
| *Clostridium_butyricum* | *Ruminococcus_bromii* | SPC10256 |
| *Clostridium_butyricum* | *Eubacterium_rectale* | SPC10256 |
| *Coprococcus_comes* | *Clostridium_butyricum* | SPC10304 |
| *Coprococcus_comes* | *Clostridium_hylemonae* | SPC10304 |
| *Coprococcus_comes* | *Clostridium_bolteae* | SPC10304 |
| *Coprococcus_comes* | *Clostridium_orbiscindens* | SPC10304 |
| *Coprococcus_comes* | *Ruminococcus_gnavus* | SPC10304 |
| *Coprococcus_comes* | *Ruminococcus_bromii* | SPC10304 |
| *Coprococcus_comes* | *Eubacterium_rectale* | SPC10304 |
| *Clostridium_hylemonae* | *Coprococcus_comes* | SPC10313 |
| *Clostridium_hylemonae* | *Clostridium_hylemonae* | SPC10313 |
| *Clostridium_hylemonae* | *Clostridium_bolteae* | SPC10313 |
| *Clostridium_hylemonae* | *Clostridium_symbiosum* | SPC10313 |
| *Clostridium_hylemonae* | *Clostridium_orbiscindens* | SPC10313 |
| *Clostridium_hylemonae* | *Faecalibacterium_prausnitzii* | SPC10313 |
| *Clostridium_hylemonae* | Lachnospiraceae_*bacterium*_5_1_57FAA | SPC10313 |
| *Clostridium_hylemonae* | *Blautia_producta* | SPC10313 |
| *Clostridium_hylemonae* | *Ruminococcus_gnavus* | SPC10313 |
| *Clostridium_hylemonae* | *Ruminococcus_bromii* | SPC10313 |
| *Clostridium_hylemonae* | *Eubacterium_rectale* | SPC10313 |
| *Clostridium_bolteae* | *Clostridium_hylemonae* | SPC10325 |
| *Clostridium_bolteae* | *Clostridium_bolteae* | SPC10325 |
| *Clostridium_bolteae* | *Clostridium_symbiosum* | SPC10325 |
| *Clostridium_bolteae* | *Clostridium_orbiscindens* | SPC10325 |
| *Clostridium_bolteae* | *Faecalibacterium_prausnitzii* | SPC10325 |
| *Clostridium_bolteae* | Lachnospiraceae_*bacterium*_5_1_57FAA | SPC10325 |
| *Clostridium_bolteae* | *Blautia_producta* | SPC10325 |
| *Clostridium_bolteae* | *Ruminococcus_gnavus* | SPC10325 |
| *Clostridium_bolteae* | *Ruminococcus_bromii* | SPC10325 |
| *Clostridium_bolteae* | *Eubacterium_rectale* | SPC10325 |
| *Clostridium_symbiosum* | *Clostridium_bolteae* | SPC10355 |
| *Clostridium_symbiosum* | *Clostridium_orbiscindens* | SPC10355 |
| *Clostridium_symbiosum* | *Ruminococcus_gnavus* | SPC10355 |
| *Clostridium_symbiosum* | *Ruminococcus_bromii* | SPC10355 |
| *Clostridium_symbiosum* | *Eubacterium_rectale* | SPC10355 |
| *Clostridium_orbiscindens* | *Clostridium_symbiosum* | SPC10358 |
| *Clostridium_orbiscindens* | *Clostridium_orbiscindens* | SPC10358 |
| *Clostridium_orbiscindens* | *Faecalibacterium_prausnitzii* | SPC10358 |
| *Clostridium_orbiscindens* | Lachnospiraceae_*bacterium*_5_1_57FAA | SPC10358 |
| *Clostridium_orbiscindens* | *Blautia_producta* | SPC10358 |
| *Clostridium_orbiscindens* | *Ruminococcus_gnavus* | SPC10358 |
| *Clostridium_orbiscindens* | *Ruminococcus_bromii* | SPC10358 |

TABLE 4a-continued

| | | | |
|---|---|---|---|
| *Clostridium_orbiscindens* | *Eubacterium_rectale* | | SPC10358 |
| *Faecalibacterium_prausnitzii* | *Clostridium_orbiscindens* | | SPC10386 |
| *Faecalibacterium_prausnitzii* | *Ruminococcus_gnavus* | | SPC10386 |
| *Faecalibacterium_prausnitzii* | *Ruminococcus_bromii* | | SPC10386 |
| *Faecalibacterium_prausnitzii* | *Eubacterium_rectale* | | SPC10386 |
| Lachnospiraceae_*bacterium*_5_1_57FAA | *Ruminococcus_gnavus* | | SPC10390 |
| Lachnospiraceae_*bacterium*_5_1_57FAA | *Ruminococcus_bromii* | | SPC10390 |
| Lachnospiraceae_*bacterium*_5_1_57FAA | *Eubacterium_rectale* | | SPC10390 |
| *Blautia_producta* | *Ruminococcus_gnavus* | | SPC10415 |
| *Blautia_producta* | *Ruminococcus_bromii* | | SPC10415 |
| *Blautia_producta* | *Eubacterium_rectale* | | SPC10415 |
| *Ruminococcus_gnavus* | *Blautia_producta* | | SPC10468 |
| *Ruminococcus_gnavus* | *Ruminococcus_gnavus* | | SPC10468 |
| *Ruminococcus_gnavus* | *Ruminococcus_bromii* | | SPC10468 |
| *Ruminococcus_gnavus* | *Eubacterium_rectale* | | SPC10468 |
| *Ruminococcus_bromii* | *Ruminococcus_gnavus* | | SPC10470 |
| *Ruminococcus_bromii* | *Ruminococcus_bromii* | | SPC10470 |
| *Ruminococcus_bromii* | *Eubacterium_rectale* | | SPC10470 |
| *Eubacterium_rectale* | *Ruminococcus_bromii* | | SPC10567 |
| *Eubacterium_rectale* | *Eubacterium_rectale* | | SPC10567 |
| *Collinsella_aerofaciens* | *Collinsella_aerofaciens* | *Collinsella_aerofaciens* | SPC10097 |
| *Collinsella_aerofaciens* | *Collinsella_aerofaciens* | *Coprococcus_comes* | SPC10097 |
| *Collinsella_aerofaciens* | *Collinsella_aerofaciens* | *Clostridium_bolteae* | SPC10097 |
| *Collinsella_aerofaciens* | *Collinsella_aerofaciens* | *Clostridium_symbiosum* | SPC10097 |
| *Collinsella_aerofaciens* | *Collinsella_aerofaciens* | *Faecalibacterium_prausnitzii* | SPC10097 |
| *Collinsella_aerofaciens* | *Collinsella_aerofaciens* | Lachnospiraceae_*bacterium*_5_1_57FAA | SPC10097 |
| *Collinsella_aerofaciens* | *Collinsella_aerofaciens* | *Blautia_producta* | SPC10097 |
| *Collinsella_aerofaciens* | *Collinsella_aerofaciens* | *Eubacterium_rectale* | SPC10097 |
| *Collinsella_aerofaciens* | *Coprococcus_comes* | *Coprococcus_comes* | SPC10097 |
| *Collinsella_aerofaciens* | *Coprococcus_comes* | *Clostridium_bolteae* | SPC10097 |
| *Collinsella_aerofaciens* | *Coprococcus_comes* | *Clostridium_symbiosum* | SPC10097 |
| *Collinsella_aerofaciens* | *Coprococcus_comes* | *Faecalibacterium_prausnitzii* | SPC10097 |
| *Collinsella_aerofaciens* | *Coprococcus_comes* | Lachnospiraceae_*bacterium*_5_1_57FAA | SPC10097 |
| *Collinsella_aerofaciens* | *Coprococcus_comes* | *Blautia_producta* | SPC10097 |
| *Collinsella_aerofaciens* | *Coprococcus_comes* | *Eubacterium_rectale* | SPC10097 |
| *Collinsella_aerofaciens* | *Clostridium_bolteae* | *Clostridium_bolteae* | SPC10097 |
| *Collinsella_aerofaciens* | *Clostridium_bolteae* | *Clostridium_symbiosum* | SPC10097 |
| *Collinsella_aerofaciens* | *Clostridium_bolteae* | *Faecalibacterium_prausnitzii* | SPC10097 |
| *Collinsella_aerofaciens* | *Clostridium_bolteae* | Lachnospiraceae_*bacterium*_5_1_57FAA | SPC10097 |
| *Collinsella_aerofaciens* | *Clostridium_bolteae* | *Blautia_producta* | SPC10097 |
| *Collinsella_aerofaciens* | *Clostridium_bolteae* | *Eubacterium_rectale* | SPC10097 |
| *Collinsella_aerofaciens* | *Clostridium_symbiosum* | *Clostridium_symbiosum* | SPC10097 |
| *Collinsella_aerofaciens* | *Clostridium_symbiosum* | *Faecalibacterium_prausnitzii* | SPC10097 |
| *Collinsella_aerofaciens* | *Clostridium_symbiosum* | Lachnospiraceae_*bacterium*_5_1_57FAA | SPC10097 |
| *Collinsella_aerofaciens* | *Clostridium_symbiosum* | *Blautia_producta* | SPC10097 |
| *Collinsella_aerofaciens* | *Clostridium_symbiosum* | *Eubacterium_rectale* | SPC10097 |
| *Collinsella_aerofaciens* | *Faecalibacterium_prausnitzii* | *Faecalibacterium_prausnitzii* | SPC10097 |
| *Collinsella_aerofaciens* | *Faecalibacterium_prausnitzii* | Lachnospiraceae_*bacterium*_5_1_57FAA | SPC10097 |
| *Collinsella_aerofaciens* | *Faecalibacterium_prausnitzii* | *Blautia_producta* | SPC10097 |
| *Collinsella_aerofaciens* | *Faecalibacterium_prausnitzii* | *Eubacterium_rectale* | SPC10097 |
| *Collinsella_aerofaciens* | Lachnospiraceae_*bacterium*_5_1_57FAA | Lachnospiraceae_*bacterium*_5_1_57FAA | SPC10097 |
| *Collinsella_aerofaciens* | Lachnospiraceae_*bacterium*_5_1_57FAA | *Blautia_producta* | SPC10097 |
| *Collinsella_aerofaciens* | Lachnospiraceae_*bacterium*_5_1_57FAA | *Eubacterium_rectale* | SPC10097 |
| *Collinsella_aerofaciens* | *Blautia_producta* | *Blautia_producta* | SPC10097 |
| *Collinsella_aerofaciens* | *Blautia_producta* | *Eubacterium_rectale* | SPC10097 |
| *Collinsella_aerofaciens* | *Eubacterium_rectale* | *Eubacterium_rectale* | SPC10097 |
| *Coprococcus_comes* | *Coprococcus_comes* | *Coprococcus_comes* | SPC10304 |
| *Coprococcus_comes* | *Coprococcus_comes* | *Clostridium_bolteae* | SPC10304 |
| *Coprococcus_comes* | *Coprococcus_comes* | *Clostridium_symbiosum* | SPC10304 |
| *Coprococcus_comes* | *Coprococcus_comes* | *Faecalibacterium_prausnitzii* | SPC10304 |
| *Coprococcus_comes* | *Coprococcus_comes* | Lachnospiraceae_*bacterium*_5_1_57FAA | SPC10304 |
| *Coprococcus_comes* | *Coprococcus_comes* | *Blautia_producta* | SPC10304 |
| *Coprococcus_comes* | *Coprococcus_comes* | *Eubacterium_rectale* | SPC10304 |
| *Coprococcus_comes* | *Clostridium_bolteae* | *Clostridium_bolteae* | SPC10304 |
| *Coprococcus_comes* | *Clostridium_bolteae* | *Clostridium_symbiosum* | SPC10304 |
| *Coprococcus_comes* | *Clostridium_bolteae* | *Faecalibacterium_prausnitzii* | SPC10304 |
| *Coprococcus_comes* | *Clostridium_bolteae* | Lachnospiraceae_*bacterium*_5_1_57FAA | SPC10304 |
| *Coprococcus_comes* | *Clostridium_bolteae* | *Blautia_producta* | SPC10304 |
| *Coprococcus_comes* | *Clostridium_bolteae* | *Eubacterium_rectale* | SPC10304 |
| *Coprococcus_comes* | *Clostridium_symbiosum* | *Clostridium_symbiosum* | SPC10304 |
| *Coprococcus_comes* | *Clostridium_symbiosum* | *Faecalibacterium_prausnitzii* | SPC10304 |
| *Coprococcus_comes* | *Clostridium_symbiosum* | Lachnospiraceae_*bacterium*_5_1_57FAA | SPC10304 |
| *Coprococcus_comes* | *Clostridium_symbiosum* | *Blautia_producta* | SPC10304 |
| *Coprococcus_comes* | *Clostridium_symbiosum* | *Eubacterium_rectale* | SPC10304 |
| *Coprococcus_comes* | *Faecalibacterium_prausnitzii* | *Faecalibacterium_prausnitzii* | SPC10304 |
| *Coprococcus_comes* | *Faecalibacterium_prausnitzii* | Lachnospiraceae_*bacterium*_5_1_57FAA | SPC10304 |
| *Coprococcus_comes* | *Faecalibacterium_prausnitzii* | *Blautia_producta* | SPC10304 |
| *Coprococcus_comes* | *Faecalibacterium_prausnitzii* | *Eubacterium_rectale* | SPC10304 |
| *Coprococcus_comes* | Lachnospiraceae_*bacterium*_5_1_57FAA | Lachnospiraceae_*bacterium*_5_1_57FAA | SPC10304 |
| *Coprococcus_comes* | Lachnospiraceae_*bacterium*_5_1_57FAA | *Blautia_producta* | SPC10304 |

TABLE 4a-continued

| | | | |
|---|---|---|---|
| *Coprococcus_comes* | Lachnospiraceae_*bacterium*_5_1_57FAA | *Eubacterium_rectale* | SPC10304 |
| *Coprococcus_comes* | *Blautia_producta* | *Blautia_producta* | SPC10304 |
| *Coprococcus_comes* | *Blautia_producta* | *Eubacterium_rectale* | SPC10304 |
| *Coprococcus_comes* | *Eubacterium_rectale* | *Eubacterium_rectale* | SPC10304 |
| *Clostridium_bolteae* | *Clostridium_bolteae* | *Clostridium_bolteae* | SPC10325 |
| *Clostridium_bolteae* | *Clostridium_bolteae* | *Clostridium_symbiosum* | SPC10325 |
| *Clostridium_bolteae* | *Clostridium_bolteae* | *Faecalibacterium_prausnitzii* | SPC10325 |
| *Clostridium_bolteae* | *Clostridium_bolteae* | Lachnospiraceae_*bacterium*_5_1_57FAA | SPC10325 |
| *Clostridium_bolteae* | *Clostridium_bolteae* | *Blautia_producta* | SPC10325 |
| *Clostridium_bolteae* | *Clostridium_bolteae* | *Eubacterium_rectale* | SPC10325 |
| *Clostridium_bolteae* | *Clostridium_symbiosum* | *Clostridium_symbiosum* | SPC10325 |
| *Clostridium_bolteae* | *Clostridium_symbiosum* | *Faecalibacterium_prausnitzii* | SPC10325 |
| *Clostridium_bolteae* | *Clostridium_symbiosum* | Lachnospiraceae_*bacterium*_5_1_57FAA | SPC10325 |
| *Clostridium_bolteae* | *Clostridium_symbiosum* | *Blautia_producta* | SPC10325 |
| *Clostridium_bolteae* | *Clostridium_symbiosum* | *Eubacterium_rectale* | SPC10325 |
| *Clostridium_bolteae* | *Faecalibacterium_prausnitzii* | *Faecalibacterium_prausnitzii* | SPC10325 |
| *Clostridium_bolteae* | *Faecalibacterium_prausnitzii* | Lachnospiraceae_*bacterium*_5_1_57FAA | SPC10325 |
| *Clostridium_bolteae* | *Faecalibacterium_prausnitzii* | *Blautia_producta* | SPC10325 |
| *Clostridium_bolteae* | *Faecalibacterium_prausnitzii* | *Eubacterium_rectale* | SPC10325 |
| *Clostridium_bolteae* | Lachnospiraceae_*bacterium*_5_1_57FAA | Lachnospiraceae_*bacterium*_5_1_57FAA | SPC10325 |
| *Clostridium_bolteae* | Lachnospiraceae_*bacterium*_5_1_57FAA | *Blautia_producta* | SPC10325 |
| *Clostridium_bolteae* | Lachnospiraceae_*bacterium*_5_1_57FAA | *Eubacterium_rectale* | SPC10325 |
| *Clostridium_bolteae* | *Blautia_producta* | *Blautia_producta* | SPC10325 |
| *Clostridium_bolteae* | *Blautia_producta* | *Eubacterium_rectale* | SPC10325 |
| *Clostridium_bolteae* | *Eubacterium_rectale* | *Eubacterium_rectale* | SPC10325 |
| *Clostridium_symbiosum* | *Clostridium_symbiosum* | *Clostridium_symbiosum* | SPC10355 |
| *Clostridium_symbiosum* | *Clostridium_symbiosum* | *Faecalibacterium_prausnitzii* | SPC10355 |
| *Clostridium_symbiosum* | *Clostridium_symbiosum* | Lachnospiraceae_*bacterium*_5_1_57FAA | SPC10355 |
| *Clostridium_symbiosum* | *Clostridium_symbiosum* | *Blautia_producta* | SPC10355 |
| *Clostridium_symbiosum* | *Clostridium_symbiosum* | *Eubacterium_rectale* | SPC10355 |
| *Clostridium_symbiosum* | *Faecalibacterium_prausnitzii* | *Faecalibacterium_prausnitzii* | SPC10355 |
| *Clostridium_symbiosum* | *Faecalibacterium_prausnitzii* | Lachnospiraceae_*bacterium*_5_1_57FAA | SPC10355 |
| *Clostridium_symbiosum* | *Faecalibacterium_prausnitzii* | *Blautia_producta* | SPC10355 |
| *Clostridium_symbiosum* | *Faecalibacterium_prausnitzii* | *Eubacterium_rectale* | SPC10355 |
| *Clostridium_symbiosum* | Lachnospiraceae_*bacterium*_5_1_57FAA | Lachnospiraceae_*bacterium*_5_1_57FAA | SPC10355 |
| *Clostridium_symbiosum* | Lachnospiraceae_*bacterium*_5_1_57FAA | *Blautia_producta* | SPC10355 |
| *Clostridium_symbiosum* | Lachnospiraceae_*bacterium*_5_1_57FAA | *Eubacterium_rectale* | SPC10355 |
| *Clostridium_symbiosum* | *Blautia_producta* | *Blautia_producta* | SPC10355 |
| *Clostridium_symbiosum* | *Blautia_producta* | *Eubacterium_rectale* | SPC10355 |
| *Clostridium_symbiosum* | *Eubacterium_rectale* | *Eubacterium_rectale* | SPC10355 |
| *Faecalibacterium_prausnitzii* | *Faecalibacterium_prausnitzii* | *Faecalibacterium_prausnitzii* | SPC10386 |
| *Faecalibacterium_prausnitzii* | *Faecalibacterium_prausnitzii* | Lachnospiraceae_*bacterium*_5_1_57FAA | SPC10386 |
| *Faecalibacterium_prausnitzii* | *Faecalibacterium_prausnitzii* | *Blautia_producta* | SPC10386 |
| *Faecalibacterium_prausnitzii* | *Faecalibacterium_prausnitzii* | *Eubacterium_rectale* | SPC10386 |
| *Faecalibacterium_prausnitzii* | Lachnospiraceae_*bacterium*_5_1_57FAA | Lachnospiraceae_*bacterium*_5_1_57FAA | SPC10386 |
| *Faecalibacterium_prausnitzii* | Lachnospiraceae_*bacterium*_5_1_57FAA | *Blautia_producta* | SPC10386 |
| *Faecalibacterium_prausnitzii* | Lachnospiraceae_*bacterium*_5_1_57FAA | *Eubacterium_rectale* | SPC10386 |
| *Faecalibacterium_prausnitzii* | *Blautia_producta* | *Blautia_producta* | SPC10386 |
| *Faecalibacterium_prausnitzii* | *Blautia_producta* | *Eubacterium_rectale* | SPC10386 |
| *Faecalibacterium_prausnitzii* | *Eubacterium_rectale* | *Eubacterium_rectale* | SPC10386 |
| Lachnospiraceae_*bacterium*_5_1_57FAA | Lachnospiraceae_*bacterium*_5_1_57FAA | Lachnospiraceae_*bacterium*_5_1_57FAA | SPC10390 |
| Lachnospiraceae_*bacterium*_5_1_57FAA | Lachnospiraceae_*bacterium*_5_1_57FAA | *Blautia_producta* | SPC10390 |
| Lachnospiraceae_*bacterium*_5_1_57FAA | Lachnospiraceae_*bacterium*_5_1_57FAA | *Eubacterium_rectale* | SPC10390 |
| Lachnospiraceae_*bacterium*_5_1_57FAA | *Blautia_producta* | *Blautia_producta* | SPC10390 |
| Lachnospiraceae_*bacterium*_5_1_57FAA | *Blautia_producta* | *Eubacterium_rectale* | SPC10390 |
| Lachnospiraceae_*bacterium*_5_1_57FAA | *Eubacterium_rectale* | *Eubacterium_rectale* | SPC10390 |
| *Blautia_producta* | *Blautia_producta* | *Blautia_producta* | SPC10415 |
| *Blautia_producta* | *Blautia_producta* | *Eubacterium_rectale* | SPC10415 |
| *Blautia_producta* | *Eubacterium_rectale* | *Eubacterium_rectale* | SPC10415 |
| *Eubacterium_rectale* | *Eubacterium_rectale* | *Eubacterium_rectale* | SPC10567 |
| *Collinsella_aerofaciens* | *Clostridium_tertium* | *Clostridium_tertium* | SPC10097 |
| *Collinsella_aerofaciens* | *Clostridium_tertium* | *Clostridium_disporicum* | SPC10097 |
| *Collinsella_aerofaciens* | *Clostridium_tertium* | *Clostridium_innocuum* | SPC10097 |
| *Collinsella_aerofaciens* | *Clostridium_tertium* | *Clostridium_mayombei* | SPC10097 |
| *Collinsella_aerofaciens* | *Clostridium_tertium* | *Clostridium_butyricum* | SPC10097 |
| *Collinsella_aerofaciens* | *Clostridium_tertium* | *Clostridium_hylemonae* | SPC10097 |
| *Collinsella_aerofaciens* | *Clostridium_tertium* | *Clostridium_orbiscindens* | SPC10097 |
| *Collinsella_aerofaciens* | *Clostridium_tertium* | *Ruminococcus_gnavus* | SPC10097 |
| *Collinsella_aerofaciens* | *Clostridium_tertium* | *Ruminococcus_bromii* | SPC10097 |
| *Collinsella_aerofaciens* | *Clostridium_tertium* | *Blautia*_sp_M25 | SPC10097 |
| *Collinsella_aerofaciens* | *Clostridium_disporicum* | *Clostridium_disporicum* | SPC10097 |
| *Collinsella_aerofaciens* | *Clostridium_disporicum* | *Clostridium_innocuum* | SPC10097 |
| *Collinsella_aerofaciens* | *Clostridium_disporicum* | *Clostridium_mayombei* | SPC10097 |
| *Collinsella_aerofaciens* | *Clostridium_disporicum* | *Clostridium_butyricum* | SPC10097 |
| *Collinsella_aerofaciens* | *Clostridium_disporicum* | *Clostridium_hylemonae* | SPC10097 |
| *Collinsella_aerofaciens* | *Clostridium_disporicum* | *Clostridium_orbiscindens* | SPC10097 |
| *Collinsella_aerofaciens* | *Clostridium_disporicum* | *Ruminococcus_gnavus* | SPC10097 |
| *Collinsella_aerofaciens* | *Clostridium_disporicum* | *Ruminococcus_bromii* | SPC10097 |
| *Collinsella_aerofaciens* | *Clostridium_disporicum* | *Blautia*_sp_M25 | SPC10097 |
| *Collinsella_aerofaciens* | *Clostridium_innocuum* | *Clostridium_innocuum* | SPC10097 |

TABLE 4a-continued

| | | | |
|---|---|---|---|
| *Collinsella_aerofaciens* | *Clostridium_innocuum* | *Clostridium_mayombei* | SPC10097 |
| *Collinsella_aerofaciens* | *Clostridium_innocuum* | *Clostridium_butyricum* | SPC10097 |
| *Collinsella_aerofaciens* | *Clostridium_innocuum* | *Clostridium_hylemonae* | SPC10097 |
| *Collinsella_aerofaciens* | *Clostridium_innocuum* | *Clostridium_orbiscindens* | SPC10097 |
| *Collinsella_aerofaciens* | *Clostridium_innocuum* | *Ruminococcus_gnavus* | SPC10097 |
| *Collinsella_aerofaciens* | *Clostridium_innocuum* | *Ruminococcus_bromii* | SPC10097 |
| *Collinsella_aerofaciens* | *Clostridium_innocuum* | *Blautia*_sp_M25 | SPC10097 |
| *Collinsella_aerofaciens* | *Clostridium_mayombei* | *Clostridium_mayombei* | SPC10097 |
| *Collinsella_aerofaciens* | *Clostridium_mayombei* | *Clostridium_butyricum* | SPC10097 |
| *Collinsella_aerofaciens* | *Clostridium_mayombei* | *Clostridium_hylemonae* | SPC10097 |
| *Collinsella_aerofaciens* | *Clostridium_mayombei* | *Clostridium_orbiscindens* | SPC10097 |
| *Collinsella_aerofaciens* | *Clostridium_mayombei* | *Ruminococcus_gnavus* | SPC10097 |
| *Collinsella_aerofaciens* | *Clostridium_mayombei* | *Ruminococcus_bromii* | SPC10097 |
| *Collinsella_aerofaciens* | *Clostridium_mayombei* | *Blautia*_sp_M25 | SPC10097 |
| *Collinsella_aerofaciens* | *Clostridium_butyricum* | *Clostridium_butyricum* | SPC10097 |
| *Collinsella_aerofaciens* | *Clostridium_butyricum* | *Clostridium_hylemonae* | SPC10097 |
| *Collinsella_aerofaciens* | *Clostridium_butyricum* | *Clostridium_orbiscindens* | SPC10097 |
| *Collinsella_aerofaciens* | *Clostridium_butyricum* | *Ruminococcus_gnavus* | SPC10097 |
| *Collinsella_aerofaciens* | *Clostridium_butyricum* | *Ruminococcus_bromii* | SPC10097 |
| *Collinsella_aerofaciens* | *Clostridium_butyricum* | *Blautia*_sp_M25 | SPC10097 |
| *Collinsella_aerofaciens* | *Clostridium_hylemonae* | *Clostridium_hylemonae* | SPC10097 |
| *Collinsella_aerofaciens* | *Clostridium_hylemonae* | *Clostridium_orbiscindens* | SPC10097 |
| *Collinsella_aerofaciens* | *Clostridium_hylemonae* | *Ruminococcus_gnavus* | SPC10097 |
| *Collinsella_aerofaciens* | *Clostridium_hylemonae* | *Ruminococcus_bromii* | SPC10097 |
| *Collinsella_aerofaciens* | *Clostridium_hylemonae* | *Blautia*_sp_M25 | SPC10097 |
| *Collinsella_aerofaciens* | *Clostridium_orbiscindens* | *Clostridium_orbiscindens* | SPC10097 |
| *Collinsella_aerofaciens* | *Clostridium_orbiscindens* | *Ruminococcus_gnavus* | SPC10097 |
| *Collinsella_aerofaciens* | *Clostridium_orbiscindens* | *Ruminococcus_bromii* | SPC10097 |
| *Collinsella_aerofaciens* | *Clostridium_orbiscindens* | *Blautia*_sp_M25 | SPC10097 |
| *Collinsella_aerofaciens* | *Ruminococcus_gnavus* | *Ruminococcus_gnavus* | SPC10097 |
| *Collinsella_aerofaciens* | *Ruminococcus_gnavus* | *Ruminococcus_bromii* | SPC10097 |
| *Collinsella_aerofaciens* | *Ruminococcus_gnavus* | *Blautia*_sp_M25 | SPC10097 |
| *Coprococcus_comes* | *Clostridium_tertium* | *Clostridium_tertium* | SPC10304 |
| *Coprococcus_comes* | *Clostridium_tertium* | *Clostridium_disporicum* | SPC10304 |
| *Coprococcus_comes* | *Clostridium_tertium* | *Clostridium_innocuum* | SPC10304 |
| *Coprococcus_comes* | *Clostridium_tertium* | *Clostridium_mayombei* | SPC10304 |
| *Coprococcus_comes* | *Clostridium_tertium* | *Clostridium_butyricum* | SPC10304 |
| *Coprococcus_comes* | *Clostridium_tertium* | *Clostridium_hylemonae* | SPC10304 |
| *Coprococcus_comes* | *Clostridium_tertium* | *Clostridium_orbiscindens* | SPC10304 |
| *Coprococcus_comes* | *Clostridium_tertium* | *Ruminococcus_gnavus* | SPC10304 |
| *Coprococcus_comes* | *Clostridium_tertium* | *Ruminococcus_bromii* | SPC10304 |
| *Coprococcus_comes* | *Clostridium_tertium* | *Blautia*_sp_M25 | SPC10304 |
| *Coprococcus_comes* | *Clostridium_disporicum* | *Clostridium_disporicum* | SPC10304 |
| *Coprococcus_comes* | *Clostridium_disporicum* | *Clostridium_innocuum* | SPC10304 |
| *Coprococcus_comes* | *Clostridium_disporicum* | *Clostridium_mayombei* | SPC10304 |
| *Coprococcus_comes* | *Clostridium_disporicum* | *Clostridium_butyricum* | SPC10304 |
| *Coprococcus_comes* | *Clostridium_disporicum* | *Clostridium_hylemonae* | SPC10304 |
| *Coprococcus_comes* | *Clostridium_disporicum* | *Clostridium_orbiscindens* | SPC10304 |
| *Coprococcus_comes* | *Clostridium_disporicum* | *Ruminococcus_gnavus* | SPC10304 |
| *Coprococcus_comes* | *Clostridium_disporicum* | *Ruminococcus_bromii* | SPC10304 |
| *Coprococcus_comes* | *Clostridium_disporicum* | *Blautia*_sp_M25 | SPC10304 |
| *Coprococcus_comes* | *Clostridium_innocuum* | *Clostridium_innocuum* | SPC10304 |
| *Coprococcus_comes* | *Clostridium_innocuum* | *Clostridium_mayombei* | SPC10304 |
| *Coprococcus_comes* | *Clostridium_innocuum* | *Clostridium_butyricum* | SPC10304 |
| *Coprococcus_comes* | *Clostridium_innocuum* | *Clostridium_hylemonae* | SPC10304 |
| *Coprococcus_comes* | *Clostridium_innocuum* | *Clostridium_orbiscindens* | SPC10304 |
| *Coprococcus_comes* | *Clostridium_innocuum* | *Ruminococcus_gnavus* | SPC10304 |
| *Coprococcus_comes* | *Clostridium_innocuum* | *Ruminococcus_bromii* | SPC10304 |
| *Coprococcus_comes* | *Clostridium_innocuum* | *Blautia*_sp_M25 | SPC10304 |
| *Coprococcus_comes* | *Clostridium_mayombei* | *Clostridium_mayombei* | SPC10304 |
| *Coprococcus_comes* | *Clostridium_mayombei* | *Clostridium_butyricum* | SPC10304 |
| *Coprococcus_comes* | *Clostridium_mayombei* | *Clostridium_hylemonae* | SPC10304 |
| *Coprococcus_comes* | *Clostridium_mayombei* | *Clostridium_orbiscindens* | SPC10304 |
| *Coprococcus_comes* | *Clostridium_mayombei* | *Ruminococcus_gnavus* | SPC10304 |
| *Coprococcus_comes* | *Clostridium_mayombei* | *Ruminococcus_bromii* | SPC10304 |
| *Coprococcus_comes* | *Clostridium_mayombei* | *Blautia*_sp_M25 | SPC10304 |
| *Coprococcus_comes* | *Clostridium_butyricum* | *Clostridium_butyricum* | SPC10304 |
| *Coprococcus_comes* | *Clostridium_butyricum* | *Clostridium_hylemonae* | SPC10304 |
| *Coprococcus_comes* | *Clostridium_butyricum* | *Clostridium_orbiscindens* | SPC10304 |
| *Coprococcus_comes* | *Clostridium_butyricum* | *Ruminococcus_gnavus* | SPC10304 |
| *Coprococcus_comes* | *Clostridium_butyricum* | *Ruminococcus_bromii* | SPC10304 |
| *Coprococcus_comes* | *Clostridium_butyricum* | *Blautia*_sp_M25 | SPC10304 |
| *Coprococcus_comes* | *Clostridium_hylemonae* | *Clostridium_hylemonae* | SPC10304 |
| *Coprococcus_comes* | *Clostridium_hylemonae* | *Clostridium_orbiscindens* | SPC10304 |
| *Coprococcus_comes* | *Clostridium_hylemonae* | *Ruminococcus_gnavus* | SPC10304 |
| *Coprococcus_comes* | *Clostridium_hylemonae* | *Ruminococcus_bromii* | SPC10304 |
| *Coprococcus_comes* | *Clostridium_hylemonae* | *Blautia*_sp_M25 | SPC10304 |
| *Coprococcus_comes* | *Clostridium_orbiscindens* | *Clostridium_orbiscindens* | SPC10304 |
| *Coprococcus_comes* | *Clostridium_orbiscindens* | *Ruminococcus_gnavus* | SPC10304 |
| *Coprococcus_comes* | *Clostridium_orbiscindens* | *Ruminococcus_bromii* | SPC10304 |

TABLE 4a-continued

| | | | |
|---|---|---|---|
| *Coprococcus_comes* | *Clostridium_orbiscindens* | *Blautia*_sp_M25 | SPC10304 |
| *Coprococcus_comes* | *Ruminococcus_gnavus* | *Ruminococcus_gnavus* | SPC10304 |
| *Coprococcus_comes* | *Ruminococcus_gnavus* | *Ruminococcus_bromii* | SPC10304 |
| *Coprococcus_comes* | *Ruminococcus_gnavus* | *Blautia*_sp_M25 | SPC10304 |
| *Clostridium_bolteae* | *Clostridium_tertium* | *Clostridium_tertium* | SPC10325 |
| *Clostridium_bolteae* | *Clostridium_tertium* | *Clostridium_disporicum* | SPC10325 |
| *Clostridium_bolteae* | *Clostridium_tertium* | *Clostridium_innocuum* | SPC10325 |
| *Clostridium_bolteae* | *Clostridium_tertium* | *Clostridium_mayombei* | SPC10325 |
| *Clostridium_bolteae* | *Clostridium_tertium* | *Clostridium_butyricum* | SPC10325 |
| *Clostridium_bolteae* | *Clostridium_tertium* | *Clostridium_hylemonae* | SPC10325 |
| *Clostridium_bolteae* | *Clostridium_tertium* | *Clostridium_orbiscindens* | SPC10325 |
| *Clostridium_bolteae* | *Clostridium_tertium* | *Ruminococcus_gnavus* | SPC10325 |
| *Clostridium_bolteae* | *Clostridium_tertium* | *Ruminococcus_bromii* | SPC10325 |
| *Clostridium_bolteae* | *Clostridium_tertium* | *Blautia*_sp_M25 | SPC10325 |
| *Clostridium_bolteae* | *Clostridium_disporicum* | *Clostridium_disporicum* | SPC10325 |
| *Clostridium_bolteae* | *Clostridium_disporicum* | *Clostridium_innocuum* | SPC10325 |
| *Clostridium_bolteae* | *Clostridium_disporicum* | *Clostridium_mayombei* | SPC10325 |
| *Clostridium_bolteae* | *Clostridium_disporicum* | *Clostridium_butyricum* | SPC10325 |
| *Clostridium_bolteae* | *Clostridium_disporicum* | *Clostridium_hylemonae* | SPC10325 |
| *Clostridium_bolteae* | *Clostridium_disporicum* | *Clostridium_orbiscindens* | SPC10325 |
| *Clostridium_bolteae* | *Clostridium_disporicum* | *Ruminococcus_gnavus* | SPC10325 |
| *Clostridium_bolteae* | *Clostridium_disporicum* | *Ruminococcus_bromii* | SPC10325 |
| *Clostridium_bolteae* | *Clostridium_disporicum* | *Blautia*_sp_M25 | SPC10325 |
| *Clostridium_bolteae* | *Clostridium_innocuum* | *Clostridium_innocuum* | SPC10325 |
| *Clostridium_bolteae* | *Clostridium_innocuum* | *Clostridium_mayombei* | SPC10325 |
| *Clostridium_bolteae* | *Clostridium_innocuum* | *Clostridium_butyricum* | SPC10325 |
| *Clostridium_bolteae* | *Clostridium_innocuum* | *Clostridium_hylemonae* | SPC10325 |
| *Clostridium_bolteae* | *Clostridium_innocuum* | *Clostridium_orbiscindens* | SPC10325 |
| *Clostridium_bolteae* | *Clostridium_innocuum* | *Ruminococcus_gnavus* | SPC10325 |
| *Clostridium_bolteae* | *Clostridium_innocuum* | *Ruminococcus_bromii* | SPC10325 |
| *Clostridium_bolteae* | *Clostridium_innocuum* | *Blautia*_sp_M25 | SPC10325 |
| *Clostridium_bolteae* | *Clostridium_mayombei* | *Clostridium_mayombei* | SPC10325 |
| *Clostridium_bolteae* | *Clostridium_mayombei* | *Clostridium_butyricum* | SPC10325 |
| *Clostridium_bolteae* | *Clostridium_mayombei* | *Clostridium_hylemonae* | SPC10325 |
| *Clostridium_bolteae* | *Clostridium_mayombei* | *Clostridium_orbiscindens* | SPC10325 |
| *Clostridium_bolteae* | *Clostridium_mayombei* | *Ruminococcus_gnavus* | SPC10325 |
| *Clostridium_bolteae* | *Clostridium_mayombei* | *Ruminococcus_bromii* | SPC10325 |
| *Clostridium_bolteae* | *Clostridium_mayombei* | *Blautia*_sp_M25 | SPC10325 |
| *Clostridium_bolteae* | *Clostridium_butyricum* | *Clostridium_butyricum* | SPC10325 |
| *Clostridium_bolteae* | *Clostridium_butyricum* | *Clostridium_hylemonae* | SPC10325 |
| *Clostridium_bolteae* | *Clostridium_butyricum* | *Clostridium_orbiscindens* | SPC10325 |
| *Clostridium_bolteae* | *Clostridium_butyricum* | *Ruminococcus_gnavus* | SPC10325 |
| *Clostridium_bolteae* | *Clostridium_butyricum* | *Ruminococcus_bromii* | SPC10325 |
| *Clostridium_bolteae* | *Clostridium_butyricum* | *Blautia*_sp_M25 | SPC10325 |
| *Clostridium_bolteae* | *Clostridium_hylemonae* | *Clostridium_hylemonae* | SPC10325 |
| *Clostridium_bolteae* | *Clostridium_hylemonae* | *Clostridium_orbiscindens* | SPC10325 |
| *Clostridium_bolteae* | *Clostridium_hylemonae* | *Ruminococcus_gnavus* | SPC10325 |
| *Clostridium_bolteae* | *Clostridium_hylemonae* | *Ruminococcus_bromii* | SPC10325 |
| *Clostridium_bolteae* | *Clostridium_hylemonae* | *Blautia*_sp_M25 | SPC10325 |
| *Clostridium_bolteae* | *Clostridium_orbiscindens* | *Clostridium_orbiscindens* | SPC10325 |
| *Clostridium_bolteae* | *Clostridium_orbiscindens* | *Ruminococcus_gnavus* | SPC10325 |
| *Clostridium_bolteae* | *Clostridium_orbiscindens* | *Ruminococcus_bromii* | SPC10325 |
| *Clostridium_bolteae* | *Clostridium_orbiscindens* | *Blautia*_sp_M25 | SPC10325 |
| *Clostridium_bolteae* | *Ruminococcus_gnavus* | *Ruminococcus_gnavus* | SPC10325 |
| *Clostridium_bolteae* | *Ruminococcus_gnavus* | *Ruminococcus_bromii* | SPC10325 |
| *Clostridium_bolteae* | *Ruminococcus_gnavus* | *Blautia*_sp_M25 | SPC10325 |
| *Clostridium_symbiosum* | *Clostridium_tertium* | *Clostridium_tertium* | SPC10355 |
| *Clostridium_symbiosum* | *Clostridium_tertium* | *Clostridium_disporicum* | SPC10355 |
| *Clostridium_symbiosum* | *Clostridium_tertium* | *Clostridium_innocuum* | SPC10355 |
| *Clostridium_symbiosum* | *Clostridium_tertium* | *Clostridium_mayombei* | SPC10355 |
| *Clostridium_symbiosum* | *Clostridium_tertium* | *Clostridium_butyricum* | SPC10355 |
| *Clostridium_symbiosum* | *Clostridium_tertium* | *Clostridium_hylemonae* | SPC10355 |
| *Clostridium_symbiosum* | *Clostridium_tertium* | *Clostridium_orbiscindens* | SPC10355 |
| *Clostridium_symbiosum* | *Clostridium_tertium* | *Ruminococcus_gnavus* | SPC10355 |
| *Clostridium_symbiosum* | *Clostridium_tertium* | *Ruminococcus_bromii* | SPC10355 |
| *Clostridium_symbiosum* | *Clostridium_tertium* | *Blautia*_sp_M25 | SPC10355 |
| *Clostridium_symbiosum* | *Clostridium_disporicum* | *Clostridium_disporicum* | SPC10355 |
| *Clostridium_symbiosum* | *Clostridium_disporicum* | *Clostridium_innocuum* | SPC10355 |
| *Clostridium_symbiosum* | *Clostridium_disporicum* | *Clostridium_mayombei* | SPC10355 |
| *Clostridium_symbiosum* | *Clostridium_disporicum* | *Clostridium_butyricum* | SPC10355 |
| *Clostridium_symbiosum* | *Clostridium_disporicum* | *Clostridium_hylemonae* | SPC10355 |
| *Clostridium_symbiosum* | *Clostridium_disporicum* | *Clostridium_orbiscindens* | SPC10355 |
| *Clostridium_symbiosum* | *Clostridium_disporicum* | *Ruminococcus_gnavus* | SPC10355 |
| *Clostridium_symbiosum* | *Clostridium_disporicum* | *Ruminococcus_bromii* | SPC10355 |
| *Clostridium_symbiosum* | *Clostridium_disporicum* | *Blautia*_sp_M25 | SPC10355 |
| *Clostridium_symbiosum* | *Clostridium_innocuum* | *Clostridium_innocuum* | SPC10355 |
| *Clostridium_symbiosum* | *Clostridium_innocuum* | *Clostridium_mayombei* | SPC10355 |
| *Clostridium_symbiosum* | *Clostridium_innocuum* | *Clostridium_butyricum* | SPC10355 |
| *Clostridium_symbiosum* | *Clostridium_innocuum* | *Clostridium_hylemonae* | SPC10355 |
| *Clostridium_symbiosum* | *Clostridium_innocuum* | *Clostridium_orbiscindens* | SPC10355 |

TABLE 4a-continued

| | | | |
|---|---|---|---|
| *Clostridium_symbiosum* | *Clostridium_innocuum* | *Ruminococcus_gnavus* | SPC10355 |
| *Clostridium_symbiosum* | *Clostridium_innocuum* | *Ruminococcus_bromii* | SPC10355 |
| *Clostridium_symbiosum* | *Clostridium_innocuum* | *Blautia*_sp_M25 | SPC10355 |
| *Clostridium_symbiosum* | *Clostridium_mayombei* | *Clostridium_mayombei* | SPC10355 |
| *Clostridium_symbiosum* | *Clostridium_mayombei* | *Clostridium_butyricum* | SPC10355 |
| *Clostridium_symbiosum* | *Clostridium_mayombei* | *Clostridium_hylemonae* | SPC10355 |
| *Clostridium_symbiosum* | *Clostridium_mayombei* | *Clostridium_orbiscindens* | SPC10355 |
| *Clostridium_symbiosum* | *Clostridium_mayombei* | *Ruminococcus_gnavus* | SPC10355 |
| *Clostridium_symbiosum* | *Clostridium_mayombei* | *Ruminococcus_bromii* | SPC10355 |
| *Clostridium_symbiosum* | *Clostridium_mayombei* | *Blautia*_sp_M25 | SPC10355 |
| *Clostridium_symbiosum* | *Clostridium_butyricum* | *Clostridium_butyricum* | SPC10355 |
| *Clostridium_symbiosum* | *Clostridium_butyricum* | *Clostridium_hylemonae* | SPC10355 |
| *Clostridium_symbiosum* | *Clostridium_butyricum* | *Clostridium_orbiscindens* | SPC10355 |
| *Clostridium_symbiosum* | *Clostridium_butyricum* | *Ruminococcus_gnavus* | SPC10355 |
| *Clostridium_symbiosum* | *Clostridium_butyricum* | *Ruminococcus_bromii* | SPC10355 |
| *Clostridium_symbiosum* | *Clostridium_butyricum* | *Blautia*_sp_M25 | SPC10355 |
| *Clostridium_symbiosum* | *Clostridium_hylemonae* | *Clostridium_hylemonae* | SPC10355 |
| *Clostridium_symbiosum* | *Clostridium_hylemonae* | *Clostridium_orbiscindens* | SPC10355 |
| *Clostridium_symbiosum* | *Clostridium_hylemonae* | *Ruminococcus_gnavus* | SPC10355 |
| *Clostridium_symbiosum* | *Clostridium_hylemonae* | *Ruminococcus_bromii* | SPC10355 |
| *Clostridium_symbiosum* | *Clostridium_hylemonae* | *Blautia*_sp_M25 | SPC10355 |
| *Clostridium_symbiosum* | *Clostridium_orbiscindens* | *Clostridium_orbiscindens* | SPC10355 |
| *Clostridium_symbiosum* | *Clostridium_orbiscindens* | *Ruminococcus_gnavus* | SPC10355 |
| *Clostridium_symbiosum* | *Clostridium_orbiscindens* | *Ruminococcus_bromii* | SPC10355 |
| *Clostridium_symbiosum* | *Clostridium_orbiscindens* | *Blautia*_sp_M25 | SPC10355 |
| *Clostridium_symbiosum* | *Ruminococcus_gnavus* | *Ruminococcus_gnavus* | SPC10355 |
| *Clostridium_symbiosum* | *Ruminococcus_gnavus* | *Ruminococcus_bromii* | SPC10355 |
| *Clostridium_symbiosum* | *Ruminococcus_gnavus* | *Blautia*_sp_M25 | SPC10355 |
| *Faecalibacterium_prausnitzii* | *Clostridium_tertium* | *Clostridium_tertium* | SPC10386 |
| *Faecalibacterium_prausnitzii* | *Clostridium_tertium* | *Clostridium_disporicum* | SPC10386 |
| *Faecalibacterium_prausnitzii* | *Clostridium_tertium* | *Clostridium_innocuum* | SPC10386 |
| *Faecalibacterium_prausnitzii* | *Clostridium_tertium* | *Clostridium_mayombei* | SPC10386 |
| *Faecalibacterium_prausnitzii* | *Clostridium_tertium* | *Clostridium_butyricum* | SPC10386 |
| *Faecalibacterium_prausnitzii* | *Clostridium_tertium* | *Clostridium_hylemonae* | SPC10386 |
| *Faecalibacterium_prausnitzii* | *Clostridium_tertium* | *Clostridium_orbiscindens* | SPC10386 |
| *Faecalibacterium_prausnitzii* | *Clostridium_tertium* | *Ruminococcus_gnavus* | SPC10386 |
| *Faecalibacterium_prausnitzii* | *Clostridium_tertium* | *Ruminococcus_bromii* | SPC10386 |
| *Faecalibacterium_prausnitzii* | *Clostridium_tertium* | *Blautia*_sp_M25 | SPC10386 |
| *Faecalibacterium_prausnitzii* | *Clostridium_disporicum* | *Clostridium_disporicum* | SPC10386 |
| *Faecalibacterium_prausnitzii* | *Clostridium_disporicum* | *Clostridium_innocuum* | SPC10386 |
| *Faecalibacterium_prausnitzii* | *Clostridium_disporicum* | *Clostridium_mayombei* | SPC10386 |
| *Faecalibacterium_prausnitzii* | *Clostridium_disporicum* | *Clostridium_butyricum* | SPC10386 |
| *Faecalibacterium_prausnitzii* | *Clostridium_disporicum* | *Clostridium_hylemonae* | SPC10386 |
| *Faecalibacterium_prausnitzii* | *Clostridium_disporicum* | *Clostridium_orbiscindens* | SPC10386 |
| *Faecalibacterium_prausnitzii* | *Clostridium_disporicum* | *Ruminococcus_gnavus* | SPC10386 |
| *Faecalibacterium_prausnitzii* | *Clostridium_disporicum* | *Ruminococcus_bromii* | SPC10386 |
| *Faecalibacterium_prausnitzii* | *Clostridium_disporicum* | *Blautia*_sp_M25 | SPC10386 |
| *Faecalibacterium_prausnitzii* | *Clostridium_innocuum* | *Clostridium_innocuum* | SPC10386 |
| *Faecalibacterium_prausnitzii* | *Clostridium_innocuum* | *Clostridium_mayombei* | SPC10386 |
| *Faecalibacterium_prausnitzii* | *Clostridium_innocuum* | *Clostridium_butyricum* | SPC10386 |
| *Faecalibacterium_prausnitzii* | *Clostridium_innocuum* | *Clostridium_hylemonae* | SPC10386 |
| *Faecalibacterium_prausnitzii* | *Clostridium_innocuum* | *Clostridium_orbiscindens* | SPC10386 |
| *Faecalibacterium_prausnitzii* | *Clostridium_innocuum* | *Ruminococcus_gnavus* | SPC10386 |
| *Faecalibacterium_prausnitzii* | *Clostridium_innocuum* | *Ruminococcus_bromii* | SPC10386 |
| *Faecalibacterium_prausnitzii* | *Clostridium_innocuum* | *Blautia*_sp_M25 | SPC10386 |
| *Faecalibacterium_prausnitzii* | *Clostridium_mayombei* | *Clostridium_mayombei* | SPC10386 |
| *Faecalibacterium_prausnitzii* | *Clostridium_mayombei* | *Clostridium_butyricum* | SPC10386 |
| *Faecalibacterium_prausnitzii* | *Clostridium_mayombei* | *Clostridium_hylemonae* | SPC10386 |
| *Faecalibacterium_prausnitzii* | *Clostridium_mayombei* | *Clostridium_orbiscindens* | SPC10386 |
| *Faecalibacterium_prausnitzii* | *Clostridium_mayombei* | *Ruminococcus_gnavus* | SPC10386 |
| *Faecalibacterium_prausnitzii* | *Clostridium_mayombei* | *Ruminococcus_bromii* | SPC10386 |
| *Faecalibacterium_prausnitzii* | *Clostridium_mayombei* | *Blautia*_sp_M25 | SPC10386 |
| *Faecalibacterium_prausnitzii* | *Clostridium_butyricum* | *Clostridium_butyricum* | SPC10386 |
| *Faecalibacterium_prausnitzii* | *Clostridium_butyricum* | *Clostridium_hylemonae* | SPC10386 |
| *Faecalibacterium_prausnitzii* | *Clostridium_butyricum* | *Clostridium_orbiscindens* | SPC10386 |
| *Faecalibacterium_prausnitzii* | *Clostridium_butyricum* | *Ruminococcus_gnavus* | SPC10386 |
| *Faecalibacterium_prausnitzii* | *Clostridium_butyricum* | *Ruminococcus_bromii* | SPC10386 |
| *Faecalibacterium_prausnitzii* | *Clostridium_butyricum* | *Blautia*_sp_M25 | SPC10386 |
| *Faecalibacterium_prausnitzii* | *Clostridium_hylemonae* | *Clostridium_hylemonae* | SPC10386 |
| *Faecalibacterium_prausnitzii* | *Clostridium_hylemonae* | *Clostridium_orbiscindens* | SPC10386 |
| *Faecalibacterium_prausnitzii* | *Clostridium_hylemonae* | *Ruminococcus_gnavus* | SPC10386 |
| *Faecalibacterium_prausnitzii* | *Clostridium_hylemonae* | *Ruminococcus_bromii* | SPC10386 |
| *Faecalibacterium_prausnitzii* | *Clostridium_hylemonae* | *Blautia*_sp_M25 | SPC10386 |
| *Faecalibacterium_prausnitzii* | *Clostridium_orbiscindens* | *Clostridium_orbiscindens* | SPC10386 |
| *Faecalibacterium_prausnitzii* | *Clostridium_orbiscindens* | *Ruminococcus_gnavus* | SPC10386 |
| *Faecalibacterium_prausnitzii* | *Clostridium_orbiscindens* | *Ruminococcus_bromii* | SPC10386 |
| *Faecalibacterium_prausnitzii* | *Clostridium_orbiscindens* | *Blautia*_sp_M25 | SPC10386 |
| *Faecalibacterium_prausnitzii* | *Ruminococcus_gnavus* | *Ruminococcus_gnavus* | SPC10386 |
| *Faecalibacterium_prausnitzii* | *Ruminococcus_gnavus* | *Ruminococcus_bromii* | SPC10386 |
| *Faecalibacterium_prausnitzii* | *Ruminococcus_gnavus* | *Blautia*_sp_M25 | SPC10386 |

TABLE 4a-continued

| | | | |
|---|---|---|---|
| Lachnospiraceae_*bacterium*_5_1_57FAA | *Clostridium_tertium* | *Clostridium_tertium* | SPC10390 |
| Lachnospiraceae_*bacterium*_5_1_57FAA | *Clostridium_tertium* | *Clostridium_disporicum* | SPC10390 |
| Lachnospiraceae_*bacterium*_5_1_57FAA | *Clostridium_tertium* | *Clostridium_innocuum* | SPC10390 |
| Lachnospiraceae_*bacterium*_5_1_57FAA | *Clostridium_tertium* | *Clostridium_mayombei* | SPC10390 |
| Lachnospiraceae_*bacterium*_5_1_57FAA | *Clostridium_tertium* | *Clostridium_butyricum* | SPC10390 |
| Lachnospiraceae_*bacterium*_5_1_57FAA | *Clostridium_tertium* | *Clostridium_hylemonae* | SPC10390 |
| Lachnospiraceae_*bacterium*_5_1_57FAA | *Clostridium_tertium* | *Clostridium_orbiscindens* | SPC10390 |
| Lachnospiraceae_*bacterium*_5_1_57FAA | *Clostridium_tertium* | *Ruminococcus_gnavus* | SPC10390 |
| Lachnospiraceae_*bacterium*_5_1_57FAA | *Clostridium_tertium* | *Ruminococcus_bromii* | SPC10390 |
| Lachnospiraceae_*bacterium*_5_1_57FAA | *Clostridium_tertium* | *Blautia*_sp_M25 | SPC10390 |
| Lachnospiraceae_*bacterium*_5_1_57FAA | *Clostridium_disporicum* | *Clostridium_disporicum* | SPC10390 |
| Lachnospiraceae_*bacterium*_5_1_57FAA | *Clostridium_disporicum* | *Clostridium_innocuum* | SPC10390 |
| Lachnospiraceae_*bacterium*_5_1_57FAA | *Clostridium_disporicum* | *Clostridium_mayombei* | SPC10390 |
| Lachnospiraceae_*bacterium*_5_1_57FAA | *Clostridium_disporicum* | *Clostridium_butyricum* | SPC10390 |
| Lachnospiraceae_*bacterium*_5_1_57FAA | *Clostridium_disporicum* | *Clostridium_hylemonae* | SPC10390 |
| Lachnospiraceae_*bacterium*_5_1_57FAA | *Clostridium_disporicum* | *Clostridium_orbiscindens* | SPC10390 |
| Lachnospiraceae_*bacterium*_5_1_57FAA | *Clostridium_disporicum* | *Ruminococcus_gnavus* | SPC10390 |
| Lachnospiraceae_*bacterium*_5_1_57FAA | *Clostridium_disporicum* | *Ruminococcus_bromii* | SPC10390 |
| Lachnospiraceae_*bacterium*_5_1_57FAA | *Clostridium_disporicum* | *Blautia*_sp_M25 | SPC10390 |
| Lachnospiraceae_*bacterium*_5_1_57FAA | *Clostridium_innocuum* | *Clostridium_innocuum* | SPC10390 |
| Lachnospiraceae_*bacterium*_5_1_57FAA | *Clostridium_innocuum* | *Clostridium_mayombei* | SPC10390 |
| Lachnospiraceae_*bacterium*_5_1_57FAA | *Clostridium_innocuum* | *Clostridium_butyricum* | SPC10390 |
| Lachnospiraceae_*bacterium*_5_1_57FAA | *Clostridium_innocuum* | *Clostridium_hylemonae* | SPC10390 |
| Lachnospiraceae_*bacterium*_5_1_57FAA | *Clostridium_innocuum* | *Clostridium_orbiscindens* | SPC10390 |
| Lachnospiraceae_*bacterium*_5_1_57FAA | *Clostridium_innocuum* | *Ruminococcus_gnavus* | SPC10390 |
| Lachnospiraceae_*bacterium*_5_1_57FAA | *Clostridium_innocuum* | *Ruminococcus_bromii* | SPC10390 |
| Lachnospiraceae_*bacterium*_5_1_57FAA | *Clostridium_innocuum* | *Blautia*_sp_M25 | SPC10390 |
| Lachnospiraceae_*bacterium*_5_1_57FAA | *Clostridium_mayombei* | *Clostridium_mayombei* | SPC10390 |
| Lachnospiraceae_*bacterium*_5_1_57FAA | *Clostridium_mayombei* | *Clostridium_butyricum* | SPC10390 |
| Lachnospiraceae_*bacterium*_5_1_57FAA | *Clostridium_mayombei* | *Clostridium_hylemonae* | SPC10390 |
| Lachnospiraceae_*bacterium*_5_1_57FAA | *Clostridium_mayombei* | *Clostridium_orbiscindens* | SPC10390 |
| Lachnospiraceae_*bacterium*_5_1_57FAA | *Clostridium_mayombei* | *Ruminococcus_gnavus* | SPC10390 |
| Lachnospiraceae_*bacterium*_5_1_57FAA | *Clostridium_mayombei* | *Ruminococcus_bromii* | SPC10390 |
| Lachnospiraceae_*bacterium*_5_1_57FAA | *Clostridium_mayombei* | *Blautia*_sp_M25 | SPC10390 |
| Lachnospiraceae_*bacterium*_5_1_57FAA | *Clostridium_butyricum* | *Clostridium_butyricum* | SPC10390 |
| Lachnospiraceae_*bacterium*_5_1_57FAA | *Clostridium_butyricum* | *Clostridium_hylemonae* | SPC10390 |
| Lachnospiraceae_*bacterium*_5_1_57FAA | *Clostridium_butyricum* | *Clostridium_orbiscindens* | SPC10390 |
| Lachnospiraceae_*bacterium*_5_1_57FAA | *Clostridium_butyricum* | *Ruminococcus_gnavus* | SPC10390 |
| Lachnospiraceae_*bacterium*_5_1_57FAA | *Clostridium_butyricum* | *Ruminococcus_bromii* | SPC10390 |
| Lachnospiraceae_*bacterium*_5_1_57FAA | *Clostridium_butyricum* | *Blautia*_sp_M25 | SPC10390 |
| Lachnospiraceae_*bacterium*_5_1_57FAA | *Clostridium_hylemonae* | *Clostridium_hylemonae* | SPC10390 |
| Lachnospiraceae_*bacterium*_5_1_57FAA | *Clostridium_hylemonae* | *Clostridium_orbiscindens* | SPC10390 |
| Lachnospiraceae_*bacterium*_5_1_57FAA | *Clostridium_hylemonae* | *Ruminococcus_gnavus* | SPC10390 |
| Lachnospiraceae_*bacterium*_5_1_57FAA | *Clostridium_hylemonae* | *Ruminococcus_bromii* | SPC10390 |
| Lachnospiraceae_*bacterium*_5_1_57FAA | *Clostridium_hylemonae* | *Blautia*_sp_M25 | SPC10390 |
| Lachnospiraceae_*bacterium*_5_1_57FAA | *Clostridium_orbiscindens* | *Clostridium_orbiscindens* | SPC10390 |
| Lachnospiraceae_*bacterium*_5_1_57FAA | *Clostridium_orbiscindens* | *Ruminococcus_gnavus* | SPC10390 |
| Lachnospiraceae_*bacterium*_5_1_57FAA | *Clostridium_orbiscindens* | *Ruminococcus_bromii* | SPC10390 |
| Lachnospiraceae_*bacterium*_5_1_57FAA | *Clostridium_orbiscindens* | *Blautia*_sp_M25 | SPC10390 |
| Lachnospiraceae_*bacterium*_5_1_57FAA | *Ruminococcus_gnavus* | *Ruminococcus_gnavus* | SPC10390 |
| Lachnospiraceae_*bacterium*_5_1_57FAA | *Ruminococcus_gnavus* | *Ruminococcus_bromii* | SPC10390 |
| Lachnospiraceae_*bacterium*_5_1_57FAA | *Ruminococcus_gnavus* | *Blautia*_sp_M25 | SPC10390 |
| *Blautia_producta* | *Clostridium_tertium* | *Clostridium_tertium* | SPC10415 |
| *Blautia_producta* | *Clostridium_tertium* | *Clostridium_disporicum* | SPC10415 |
| *Blautia_producta* | *Clostridium_tertium* | *Clostridium_innocuum* | SPC10415 |
| *Blautia_producta* | *Clostridium_tertium* | *Clostridium_mayombei* | SPC10415 |
| *Blautia_producta* | *Clostridium_tertium* | *Clostridium_butyricum* | SPC10415 |
| *Blautia_producta* | *Clostridium_tertium* | *Clostridium_hylemonae* | SPC10415 |
| *Blautia_producta* | *Clostridium_tertium* | *Clostridium_orbiscindens* | SPC10415 |
| *Blautia_producta* | *Clostridium_tertium* | *Ruminococcus_gnavus* | SPC10415 |
| *Blautia_producta* | *Clostridium_tertium* | *Ruminococcus_bromii* | SPC10415 |
| *Blautia_producta* | *Clostridium_tertium* | *Blautia*_sp_M25 | SPC10415 |
| *Blautia_producta* | *Clostridium_disporicum* | *Clostridium_disporicum* | SPC10415 |
| *Blautia_producta* | *Clostridium_disporicum* | *Clostridium_innocuum* | SPC10415 |
| *Blautia_producta* | *Clostridium_disporicum* | *Clostridium_mayombei* | SPC10415 |
| *Blautia_producta* | *Clostridium_disporicum* | *Clostridium_butyricum* | SPC10415 |
| *Blautia_producta* | *Clostridium_disporicum* | *Clostridium_hylemonae* | SPC10415 |
| *Blautia_producta* | *Clostridium_disporicum* | *Clostridium_orbiscindens* | SPC10415 |
| *Blautia_producta* | *Clostridium_disporicum* | *Ruminococcus_gnavus* | SPC10415 |
| *Blautia_producta* | *Clostridium_disporicum* | *Ruminococcus_bromii* | SPC10415 |
| *Blautia_producta* | *Clostridium_disporicum* | *Blautia*_sp_M25 | SPC10415 |
| *Blautia_producta* | *Clostridium_innocuum* | *Clostridium_innocuum* | SPC10415 |
| *Blautia_producta* | *Clostridium_innocuum* | *Clostridium_mayombei* | SPC10415 |
| *Blautia_producta* | *Clostridium_innocuum* | *Clostridium_butyricum* | SPC10415 |
| *Blautia_producta* | *Clostridium_innocuum* | *Clostridium_hylemonae* | SPC10415 |
| *Blautia_producta* | *Clostridium_innocuum* | *Clostridium_orbiscindens* | SPC10415 |
| *Blautia_producta* | *Clostridium_innocuum* | *Ruminococcus_gnavus* | SPC10415 |
| *Blautia_producta* | *Clostridium_innocuum* | *Ruminococcus_bromii* | SPC10415 |
| *Blautia_producta* | *Clostridium_innocuum* | *Blautia*_sp_M25 | SPC10415 |
| *Blautia_producta* | *Clostridium_mayombei* | *Clostridium_mayombei* | SPC10415 |

TABLE 4a-continued

| | | | |
|---|---|---|---|
| *Blautia_producta* | *Clostridium_mayombei* | *Clostridium_butyricum* | SPC10415 |
| *Blautia_producta* | *Clostridium_mayombei* | *Clostridium_hylemonae* | SPC10415 |
| *Blautia_producta* | *Clostridium_mayombei* | *Clostridium_orbiscindens* | SPC10415 |
| *Blautia_producta* | *Clostridium_mayombei* | *Ruminococcus_gnavus* | SPC10415 |
| *Blautia_producta* | *Clostridium_mayombei* | *Ruminococcus_bromii* | SPC10415 |
| *Blautia_producta* | *Clostridium_mayombei* | *Blautia*_sp_M25 | SPC10415 |
| *Blautia_producta* | *Clostridium_butyricum* | *Clostridium_butyricum* | SPC10415 |
| *Blautia_producta* | *Clostridium_butyricum* | *Clostridium_hylemonae* | SPC10415 |
| *Blautia_producta* | *Clostridium_butyricum* | *Clostridium_orbiscindens* | SPC10415 |
| *Blautia_producta* | *Clostridium_butyricum* | *Ruminococcus_gnavus* | SPC10415 |
| *Blautia_producta* | *Clostridium_butyricum* | *Ruminococcus_bromii* | SPC10415 |
| *Blautia_producta* | *Clostridium_butyricum* | *Blautia*_sp_M25 | SPC10415 |
| *Blautia_producta* | *Clostridium_hylemonae* | *Clostridium_hylemonae* | SPC10415 |
| *Blautia_producta* | *Clostridium_hylemonae* | *Clostridium_orbiscindens* | SPC10415 |
| *Blautia_producta* | *Clostridium_hylemonae* | *Ruminococcus_gnavus* | SPC10415 |
| *Blautia_producta* | *Clostridium_hylemonae* | *Ruminococcus_bromii* | SPC10415 |
| *Blautia_producta* | *Clostridium_hylemonae* | *Blautia*_sp_M25 | SPC10415 |
| *Blautia_producta* | *Clostridium_orbiscindens* | *Clostridium_orbiscindens* | SPC10415 |
| *Blautia_producta* | *Clostridium_orbiscindens* | *Ruminococcus_gnavus* | SPC10415 |
| *Blautia_producta* | *Clostridium_orbiscindens* | *Ruminococcus_bromii* | SPC10415 |
| *Blautia_producta* | *Clostridium_orbiscindens* | *Blautia*_sp_M25 | SPC10415 |
| *Blautia_producta* | *Ruminococcus_gnavus* | *Ruminococcus_gnavus* | SPC10415 |
| *Blautia_producta* | *Ruminococcus_gnavus* | *Ruminococcus_bromii* | SPC10415 |
| *Blautia_producta* | *Ruminococcus_gnavus* | *Blautia*_sp_M25 | SPC10415 |
| *Eubacterium_rectale* | *Clostridium_tertium* | *Clostridium_tertium* | SPC10567 |
| *Eubacterium_rectale* | *Clostridium_tertium* | *Clostridium_disporicum* | SPC10567 |
| *Eubacterium_rectale* | *Clostridium_tertium* | *Clostridium_innocuum* | SPC10567 |
| *Eubacterium_rectale* | *Clostridium_tertium* | *Clostridium_mayombei* | SPC10567 |
| *Eubacterium_rectale* | *Clostridium_tertium* | *Clostridium_butyricum* | SPC10567 |
| *Eubacterium_rectale* | *Clostridium_tertium* | *Clostridium_hylemonae* | SPC10567 |
| *Eubacterium_rectale* | *Clostridium_tertium* | *Clostridium_orbiscindens* | SPC10567 |
| *Eubacterium_rectale* | *Clostridium_tertium* | *Ruminococcus_gnavus* | SPC10567 |
| *Eubacterium_rectale* | *Clostridium_tertium* | *Ruminococcus_bromii* | SPC10567 |
| *Eubacterium_rectale* | *Clostridium_tertium* | *Blautia*_sp_M25 | SPC10567 |
| *Eubacterium_rectale* | *Clostridium_disporicum* | *Clostridium_disporicum* | SPC10567 |
| *Eubacterium_rectale* | *Clostridium_disporicum* | *Clostridium_innocuum* | SPC10567 |
| *Eubacterium_rectale* | *Clostridium_disporicum* | *Clostridium_mayombei* | SPC10567 |
| *Eubacterium_rectale* | *Clostridium_disporicum* | *Clostridium_butyricum* | SPC10567 |
| *Eubacterium_rectale* | *Clostridium_disporicum* | *Clostridium_hylemonae* | SPC10567 |
| *Eubacterium_rectale* | *Clostridium_disporicum* | *Clostridium_orbiscindens* | SPC10567 |
| *Eubacterium_rectale* | *Clostridium_disporicum* | *Ruminococcus_gnavus* | SPC10567 |
| *Eubacterium_rectale* | *Clostridium_disporicum* | *Ruminococcus_bromii* | SPC10567 |
| *Eubacterium_rectale* | *Clostridium_disporicum* | *Blautia*_sp_M25 | SPC10567 |
| *Eubacterium_rectale* | *Clostridium_innocuum* | *Clostridium_innocuum* | SPC10567 |
| *Eubacterium_rectale* | *Clostridium_innocuum* | *Clostridium_mayombei* | SPC10567 |
| *Eubacterium_rectale* | *Clostridium_innocuum* | *Clostridium_butyricum* | SPC10567 |
| *Eubacterium_rectale* | *Clostridium_innocuum* | *Clostridium_hylemonae* | SPC10567 |
| *Eubacterium_rectale* | *Clostridium_innocuum* | *Clostridium_orbiscindens* | SPC10567 |
| *Eubacterium_rectale* | *Clostridium_innocuum* | *Ruminococcus_gnavus* | SPC10567 |
| *Eubacterium_rectale* | *Clostridium_innocuum* | *Ruminococcus_bromii* | SPC10567 |
| *Eubacterium_rectale* | *Clostridium_innocuum* | *Blautia*_sp_M25 | SPC10567 |
| *Eubacterium_rectale* | *Clostridium_mayombei* | *Clostridium_mayombei* | SPC10567 |
| *Eubacterium_rectale* | *Clostridium_mayombei* | *Clostridium_butyricum* | SPC10567 |
| *Eubacterium_rectale* | *Clostridium_mayombei* | *Clostridium_hylemonae* | SPC10567 |
| *Eubacterium_rectale* | *Clostridium_mayombei* | *Clostridium_orbiscindens* | SPC10567 |
| *Eubacterium_rectale* | *Clostridium_mayombei* | *Ruminococcus_gnavus* | SPC10567 |
| *Eubacterium_rectale* | *Clostridium_mayombei* | *Ruminococcus_bromii* | SPC10567 |
| *Eubacterium_rectale* | *Clostridium_mayombei* | *Blautia*_sp_M25 | SPC10567 |
| *Eubacterium_rectale* | *Clostridium_butyricum* | *Clostridium_butyricum* | SPC10567 |
| *Eubacterium_rectale* | *Clostridium_butyricum* | *Clostridium_hylemonae* | SPC10567 |
| *Eubacterium_rectale* | *Clostridium_butyricum* | *Clostridium_orbiscindens* | SPC10567 |
| *Eubacterium_rectale* | *Clostridium_butyricum* | *Ruminococcus_gnavus* | SPC10567 |
| *Eubacterium_rectale* | *Clostridium_butyricum* | *Ruminococcus_bromii* | SPC10567 |
| *Eubacterium_rectale* | *Clostridium_butyricum* | *Blautia*_sp_M25 | SPC10567 |
| *Eubacterium_rectale* | *Clostridium_hylemonae* | *Clostridium_hylemonae* | SPC10567 |
| *Eubacterium_rectale* | *Clostridium_hylemonae* | *Clostridium_orbiscindens* | SPC10567 |
| *Eubacterium_rectale* | *Clostridium_hylemonae* | *Ruminococcus_gnavus* | SPC10567 |
| *Eubacterium_rectale* | *Clostridium_hylemonae* | *Ruminococcus_bromii* | SPC10567 |
| *Eubacterium_rectale* | *Clostridium_hylemonae* | *Blautia*_sp_M25 | SPC10567 |
| *Eubacterium_rectale* | *Clostridium_orbiscindens* | *Clostridium_orbiscindens* | SPC10567 |
| *Eubacterium_rectale* | *Clostridium_orbiscindens* | *Ruminococcus_gnavus* | SPC10567 |
| *Eubacterium_rectale* | *Clostridium_orbiscindens* | *Ruminococcus_bromii* | SPC10567 |
| *Eubacterium_rectale* | *Clostridium_orbiscindens* | *Blautia*_sp_M25 | SPC10567 |
| *Eubacterium_rectale* | *Ruminococcus_gnavus* | *Ruminococcus_gnavus* | SPC10567 |
| *Eubacterium_rectale* | *Ruminococcus_gnavus* | *Ruminococcus_bromii* | SPC10567 |
| *Eubacterium_rectale* | *Ruminococcus_gnavus* | *Blautia*_sp_M25 | SPC10567 |
| *Clostridium_tertium* | *Collinsella_aerofaciens* | *Collinsella_aerofaciens* | SPC10155 |
| *Clostridium_tertium* | *Collinsella_aerofaciens* | *Coprococcus_comes* | SPC10155 |
| *Clostridium_tertium* | *Collinsella_aerofaciens* | *Clostridium_bolteae* | SPC10155 |
| *Clostridium_tertium* | *Collinsella_aerofaciens* | *Clostridium_symbiosum* | SPC10155 |

TABLE 4a-continued

| | | | |
|---|---|---|---|
| *Clostridium_tertium* | *Collinsella_aerofaciens* | *Faecalibacterium_prausnitzii* | SPC10155 |
| *Clostridium_tertium* | *Collinsella_aerofaciens* | Lachnospiraceae_*bacterium_5_1_57FAA* | SPC10155 |
| *Clostridium_tertium* | *Collinsella_aerofaciens* | *Blautia_producta* | SPC10155 |
| *Clostridium_tertium* | *Collinsella_aerofaciens* | *Eubacterium_rectale* | SPC10155 |
| *Clostridium_tertium* | *Coprococcus_comes* | *Coprococcus_comes* | SPC10155 |
| *Clostridium_tertium* | *Coprococcus_comes* | *Clostridium_bolteae* | SPC10155 |
| *Clostridium_tertium* | *Coprococcus_comes* | *Clostridium_symbiosum* | SPC10155 |
| *Clostridium_tertium* | *Coprococcus_comes* | *Faecalibacterium_prausnitzii* | SPC10155 |
| *Clostridium_tertium* | *Coprococcus_comes* | Lachnospiraceae_*bacterium_5_1_57FAA* | SPC10155 |
| *Clostridium_tertium* | *Coprococcus_comes* | *Blautia_producta* | SPC10155 |
| *Clostridium_tertium* | *Coprococcus_comes* | *Eubacterium_rectale* | SPC10155 |
| *Clostridium_tertium* | *Clostridium_bolteae* | *Clostridium_bolteae* | SPC10155 |
| *Clostridium_tertium* | *Clostridium_bolteae* | *Clostridium_symbiosum* | SPC10155 |
| *Clostridium_tertium* | *Clostridium_bolteae* | *Faecalibacterium_prausnitzii* | SPC10155 |
| *Clostridium_tertium* | *Clostridium_bolteae* | Lachnospiraceae_*bacterium_5_1_57FAA* | SPC10155 |
| *Clostridium_tertium* | *Clostridium_bolteae* | *Blautia_producta* | SPC10155 |
| *Clostridium_tertium* | *Clostridium_bolteae* | *Eubacterium_rectale* | SPC10155 |
| *Clostridium_tertium* | *Clostridium_symbiosum* | *Clostridium_symbiosum* | SPC10155 |
| *Clostridium_tertium* | *Clostridium_symbiosum* | *Faecalibacterium_prausnitzii* | SPC10155 |
| *Clostridium_tertium* | *Clostridium_symbiosum* | Lachnospiraceae_*bacterium_5_1_57FAA* | SPC10155 |
| *Clostridium_tertium* | *Clostridium_symbiosum* | *Blautia_producta* | SPC10155 |
| *Clostridium_tertium* | *Clostridium_symbiosum* | *Eubacterium_rectale* | SPC10155 |
| *Clostridium_tertium* | *Faecalibacterium_prausnitzii* | *Faecalibacterium_prausnitzii* | SPC10155 |
| *Clostridium_tertium* | *Faecalibacterium_prausnitzii* | Lachnospiraceae_*bacterium_5_1_57FAA* | SPC10155 |
| *Clostridium_tertium* | *Faecalibacterium_prausnitzii* | *Blautia_producta* | SPC10155 |
| *Clostridium_tertium* | *Faecalibacterium_prausnitzii* | *Eubacterium_rectale* | SPC10155 |
| *Clostridium_tertium* | Lachnospiraceae_*bacterium_5_1_57FAA* | Lachnospiraceae_*bacterium_5_1_57FAA* | SPC10155 |
| *Clostridium_tertium* | Lachnospiraceae_*bacterium_5_1_57FAA* | *Blautia_producta* | SPC10155 |
| *Clostridium_tertium* | Lachnospiraceae_*bacterium_5_1_57FAA* | *Eubacterium_rectale* | SPC10155 |
| *Clostridium_tertium* | *Blautia_producta* | *Blautia_producta* | SPC10155 |
| *Clostridium_tertium* | *Blautia_producta* | *Eubacterium_rectale* | SPC10155 |
| *Clostridium_tertium* | *Eubacterium_rectale* | *Eubacterium_rectale* | SPC10155 |
| *Clostridium_disporicum* | *Collinsella_aerofaciens* | *Collinsella_aerofaciens* | SPC10167 |
| *Clostridium_disporicum* | *Collinsella_aerofaciens* | *Coprococcus_comes* | SPC10167 |
| *Clostridium_disporicum* | *Collinsella_aerofaciens* | *Clostridium_bolteae* | SPC10167 |
| *Clostridium_disporicum* | *Collinsella_aerofaciens* | *Clostridium_symbiosum* | SPC10167 |
| *Clostridium_disporicum* | *Collinsella_aerofaciens* | *Faecalibacterium_prausnitzii* | SPC10167 |
| *Clostridium_disporicum* | *Collinsella_aerofaciens* | Lachnospiraceae_*bacterium_5_1_57FAA* | SPC10167 |
| *Clostridium_disporicum* | *Collinsella_aerofaciens* | *Blautia_producta* | SPC10167 |
| *Clostridium_disporicum* | *Collinsella_aerofaciens* | *Eubacterium_rectale* | SPC10167 |
| *Clostridium_disporicum* | *Coprococcus_comes* | *Coprococcus_comes* | SPC10167 |
| *Clostridium_disporicum* | *Coprococcus_comes* | *Clostridium_bolteae* | SPC10167 |
| *Clostridium_disporicum* | *Coprococcus_comes* | *Clostridium_symbiosum* | SPC10167 |
| *Clostridium_disporicum* | *Coprococcus_comes* | *Faecalibacterium_prausnitzii* | SPC10167 |
| *Clostridium_disporicum* | *Coprococcus_comes* | Lachnospiraceae_*bacterium_5_1_57FAA* | SPC10167 |
| *Clostridium_disporicum* | *Coprococcus_comes* | *Blautia_producta* | SPC10167 |
| *Clostridium_disporicum* | *Coprococcus_comes* | *Eubacterium_rectale* | SPC10167 |
| *Clostridium_disporicum* | *Clostridium_bolteae* | *Clostridium_bolteae* | SPC10167 |
| *Clostridium_disporicum* | *Clostridium_bolteae* | *Clostridium_symbiosum* | SPC10167 |
| *Clostridium_disporicum* | *Clostridium_bolteae* | *Faecalibacterium_prausnitzii* | SPC10167 |
| *Clostridium_disporicum* | *Clostridium_bolteae* | Lachnospiraceae_*bacterium_5_1_57FAA* | SPC10167 |
| *Clostridium_disporicum* | *Clostridium_bolteae* | *Blautia_producta* | SPC10167 |
| *Clostridium_disporicum* | *Clostridium_bolteae* | *Eubacterium_rectale* | SPC10167 |
| *Clostridium_disporicum* | *Clostridium_symbiosum* | *Clostridium_symbiosum* | SPC10167 |
| *Clostridium_disporicum* | *Clostridium_symbiosum* | *Faecalibacterium_prausnitzii* | SPC10167 |
| *Clostridium_disporicum* | *Clostridium_symbiosum* | Lachnospiraceae_*bacterium_5_1_57FAA* | SPC10167 |
| *Clostridium_disporicum* | *Clostridium_symbiosum* | *Blautia_producta* | SPC10167 |
| *Clostridium_disporicum* | *Clostridium_symbiosum* | *Eubacterium_rectale* | SPC10167 |
| *Clostridium_disporicum* | *Faecalibacterium_prausnitzii* | *Faecalibacterium_prausnitzii* | SPC10167 |
| *Clostridium_disporicum* | *Faecalibacterium_prausnitzii* | Lachnospiraceae_*bacterium_5_1_57FAA* | SPC10167 |
| *Clostridium_disporicum* | *Faecalibacterium_prausnitzii* | *Blautia_producta* | SPC10167 |
| *Clostridium_disporicum* | *Faecalibacterium_prausnitzii* | *Eubacterium_rectale* | SPC10167 |
| *Clostridium_disporicum* | Lachnospiraceae_*bacterium_5_1_57FAA* | Lachnospiraceae_*bacterium_5_1_57FAA* | SPC10167 |
| *Clostridium_disporicum* | Lachnospiraceae_*bacterium_5_1_57FAA* | *Blautia_producta* | SPC10167 |
| *Clostridium_disporicum* | Lachnospiraceae_*bacterium_5_1_57FAA* | *Eubacterium_rectale* | SPC10167 |
| *Clostridium_disporicum* | *Blautia_producta* | *Blautia_producta* | SPC10167 |
| *Clostridium_disporicum* | *Blautia_producta* | *Eubacterium_rectale* | SPC10167 |
| *Clostridium_disporicum* | *Eubacterium_rectale* | *Eubacterium_rectale* | SPC10167 |
| *Clostridium_innocuum* | *Collinsella_aerofaciens* | *Collinsella_aerofaciens* | SPC10202 |
| *Clostridium_innocuum* | *Collinsella_aerofaciens* | *Coprococcus_comes* | SPC10202 |
| *Clostridium_innocuum* | *Collinsella_aerofaciens* | *Clostridium_bolteae* | SPC10202 |
| *Clostridium_innocuum* | *Collinsella_aerofaciens* | *Clostridium_symbiosum* | SPC10202 |
| *Clostridium_innocuum* | *Collinsella_aerofaciens* | *Faecalibacterium_prausnitzii* | SPC10202 |
| *Clostridium_innocuum* | *Collinsella_aerofaciens* | Lachnospiraceae_*bacterium_5_1_57FAA* | SPC10202 |
| *Clostridium_innocuum* | *Collinsella_aerofaciens* | *Blautia_producta* | SPC10202 |
| *Clostridium_innocuum* | *Collinsella_aerofaciens* | *Eubacterium_rectale* | SPC10202 |
| *Clostridium_innocuum* | *Coprococcus_comes* | *Coprococcus_comes* | SPC10202 |
| *Clostridium_innocuum* | *Coprococcus_comes* | *Clostridium_bolteae* | SPC10202 |
| *Clostridium_innocuum* | *Coprococcus_comes* | *Clostridium_symbiosum* | SPC10202 |
| *Clostridium_innocuum* | *Coprococcus_comes* | *Faecalibacterium_prausnitzii* | SPC10202 |

TABLE 4a-continued

| | | | |
|---|---|---|---|
| *Clostridium_innocuum* | *Coprococcus_comes* | Lachnospiraceae_*bacterium*_5_1_57FAA | SPC10202 |
| *Clostridium_innocuum* | *Coprococcus_comes* | *Blautia_producta* | SPC10202 |
| *Clostridium_innocuum* | *Coprococcus_comes* | *Eubacterium_rectale* | SPC10202 |
| *Clostridium_innocuum* | *Clostridium_bolteae* | *Clostridium_bolteae* | SPC10202 |
| *Clostridium_innocuum* | *Clostridium_bolteae* | *Clostridium_symbiosum* | SPC10202 |
| *Clostridium_innocuum* | *Clostridium_bolteae* | *Faecalibacterium_prausnitzii* | SPC10202 |
| *Clostridium_innocuum* | *Clostridium_bolteae* | Lachnospiraceae_*bacterium*_5_1_57FAA | SPC10202 |
| *Clostridium_innocuum* | *Clostridium_bolteae* | *Blautia_producta* | SPC10202 |
| *Clostridium_innocuum* | *Clostridium_bolteae* | *Eubacterium_rectale* | SPC10202 |
| *Clostridium_innocuum* | *Clostridium_symbiosum* | *Clostridium_symbiosum* | SPC10202 |
| *Clostridium_innocuum* | *Clostridium_symbiosum* | *Faecalibacterium_prausnitzii* | SPC10202 |
| *Clostridium_innocuum* | *Clostridium_symbiosum* | Lachnospiraceae_*bacterium*_5_1_57FAA | SPC10202 |
| *Clostridium_innocuum* | *Clostridium_symbiosum* | *Blautia_producta* | SPC10202 |
| *Clostridium_innocuum* | *Clostridium_symbiosum* | *Eubacterium_rectale* | SPC10202 |
| *Clostridium_innocuum* | *Faecalibacterium_prausnitzii* | *Faecalibacterium_prausnitzii* | SPC10202 |
| *Clostridium_innocuum* | *Faecalibacterium_prausnitzii* | Lachnospiraceae_*bacterium*_5_1_57FAA | SPC10202 |
| *Clostridium_innocuum* | *Faecalibacterium_prausnitzii* | *Blautia_producta* | SPC10202 |
| *Clostridium_innocuum* | *Faecalibacterium_prausnitzii* | *Eubacterium_rectale* | SPC10202 |
| *Clostridium_innocuum* | Lachnospiraceae_*bacterium*_5_1_57FAA | Lachnospiraceae_*bacterium*_5_1_57FAA | SPC10202 |
| *Clostridium_innocuum* | Lachnospiraceae_*bacterium*_5_1_57FAA | *Blautia_producta* | SPC10202 |
| *Clostridium_innocuum* | Lachnospiraceae_*bacterium*_5_1_57FAA | *Eubacterium_rectale* | SPC10202 |
| *Clostridium_innocuum* | *Blautia_producta* | *Blautia_producta* | SPC10202 |
| *Clostridium_innocuum* | *Blautia_producta* | *Eubacterium_rectale* | SPC10202 |
| *Clostridium_innocuum* | *Eubacterium_rectale* | *Eubacterium_rectale* | SPC10202 |
| *Clostridium_mayombei* | *Collinsella_aerofaciens* | *Collinsella_aerofaciens* | SPC10238 |
| *Clostridium_mayombei* | *Collinsella_aerofaciens* | *Coprococcus_comes* | SPC10238 |
| *Clostridium_mayombei* | *Collinsella_aerofaciens* | *Clostridium_bolteae* | SPC10238 |
| *Clostridium_mayombei* | *Collinsella_aerofaciens* | *Clostridium_symbiosum* | SPC10238 |
| *Clostridium_mayombei* | *Collinsella_aerofaciens* | *Faecalibacterium_prausnitzii* | SPC10238 |
| *Clostridium_mayombei* | *Collinsella_aerofaciens* | Lachnospiraceae_*bacterium*_5_1_57FAA | SPC10238 |
| *Clostridium_mayombei* | *Collinsella_aerofaciens* | *Blautia_producta* | SPC10238 |
| *Clostridium_mayombei* | *Collinsella_aerofaciens* | *Eubacterium_rectale* | SPC10238 |
| *Clostridium_mayombei* | *Coprococcus_comes* | *Coprococcus_comes* | SPC10238 |
| *Clostridium_mayombei* | *Coprococcus_comes* | *Clostridium_bolteae* | SPC10238 |
| *Clostridium_mayombei* | *Coprococcus_comes* | *Clostridium_symbiosum* | SPC10238 |
| *Clostridium_mayombei* | *Coprococcus_comes* | *Faecalibacterium_prausnitzii* | SPC10238 |
| *Clostridium_mayombei* | *Coprococcus_comes* | Lachnospiraceae_*bacterium*_5_1_57FAA | SPC10238 |
| *Clostridium_mayombei* | *Coprococcus_comes* | *Blautia_producta* | SPC10238 |
| *Clostridium_mayombei* | *Coprococcus_comes* | *Eubacterium_rectale* | SPC10238 |
| *Clostridium_mayombei* | *Clostridium_bolteae* | *Clostridium_bolteae* | SPC10238 |
| *Clostridium_mayombei* | *Clostridium_bolteae* | *Clostridium_symbiosum* | SPC10238 |
| *Clostridium_mayombei* | *Clostridium_bolteae* | *Faecalibacterium_prausnitzii* | SPC10238 |
| *Clostridium_mayombei* | *Clostridium_bolteae* | Lachnospiraceae_*bacterium*_5_1_57FAA | SPC10238 |
| *Clostridium_mayombei* | *Clostridium_bolteae* | *Blautia_producta* | SPC10238 |
| *Clostridium_mayombei* | *Clostridium_bolteae* | *Eubacterium_rectale* | SPC10238 |
| *Clostridium_mayombei* | *Clostridium_symbiosum* | *Clostridium_symbiosum* | SPC10238 |
| *Clostridium_mayombei* | *Clostridium_symbiosum* | *Faecalibacterium_prausnitzii* | SPC10238 |
| *Clostridium_mayombei* | *Clostridium_symbiosum* | Lachnospiraceae_*bacterium*_5_1_57FAA | SPC10238 |
| *Clostridium_mayombei* | *Clostridium_symbiosum* | *Blautia_producta* | SPC10238 |
| *Clostridium_mayombei* | *Clostridium_symbiosum* | *Eubacterium_rectale* | SPC10238 |
| *Clostridium_mayombei* | *Faecalibacterium_prausnitzii* | *Faecalibacterium_prausnitzii* | SPC10238 |
| *Clostridium_mayombei* | *Faecalibacterium_prausnitzii* | Lachnospiraceae_*bacterium*_5_1_57FAA | SPC10238 |
| *Clostridium_mayombei* | *Faecalibacterium_prausnitzii* | *Blautia_producta* | SPC10238 |
| *Clostridium_mayombei* | *Faecalibacterium_prausnitzii* | *Eubacterium_rectale* | SPC10238 |
| *Clostridium_mayombei* | Lachnospiraceae_*bacterium*_5_1_57FAA | Lachnospiraceae_*bacterium*_5_1_57FAA | SPC10238 |
| *Clostridium_mayombei* | Lachnospiraceae_*bacterium*_5_1_57FAA | *Blautia_producta* | SPC10238 |
| *Clostridium_mayombei* | Lachnospiraceae_*bacterium*_5_1_57FAA | *Eubacterium_rectale* | SPC10238 |
| *Clostridium_mayombei* | *Blautia_producta* | *Blautia_producta* | SPC10238 |
| *Clostridium_mayombei* | *Blautia_producta* | *Eubacterium_rectale* | SPC10238 |
| *Clostridium_mayombei* | *Eubacterium_rectale* | *Eubacterium_rectale* | SPC10238 |
| *Clostridium_butyricum* | *Collinsella_aerofaciens* | *Collinsella_aerofaciens* | SPC10256 |
| *Clostridium_butyricum* | *Collinsella_aerofaciens* | *Coprococcus_comes* | SPC10256 |
| *Clostridium_butyricum* | *Collinsella_aerofaciens* | *Clostridium_bolteae* | SPC10256 |
| *Clostridium_butyricum* | *Collinsella_aerofaciens* | *Clostridium_symbiosum* | SPC10256 |
| *Clostridium_butyricum* | *Collinsella_aerofaciens* | *Faecalibacterium_prausnitzii* | SPC10256 |
| *Clostridium_butyricum* | *Collinsella_aerofaciens* | Lachnospiraceae_*bacterium*_5_1_57FAA | SPC10256 |
| *Clostridium_butyricum* | *Collinsella_aerofaciens* | *Blautia_producta* | SPC10256 |
| *Clostridium_butyricum* | *Collinsella_aerofaciens* | *Eubacterium_rectale* | SPC10256 |
| *Clostridium_butyricum* | *Coprococcus_comes* | *Coprococcus_comes* | SPC10256 |
| *Clostridium_butyricum* | *Coprococcus_comes* | *Clostridium_bolteae* | SPC10256 |
| *Clostridium_butyricum* | *Coprococcus_comes* | *Clostridium_symbiosum* | SPC10256 |
| *Clostridium_butyricum* | *Coprococcus_comes* | *Faecalibacterium_prausnitzii* | SPC10256 |
| *Clostridium_butyricum* | *Coprococcus_comes* | Lachnospiraceae_*bacterium*_5_1_57FAA | SPC10256 |
| *Clostridium_butyricum* | *Coprococcus_comes* | *Blautia_producta* | SPC10256 |
| *Clostridium_butyricum* | *Coprococcus_comes* | *Eubacterium_rectale* | SPC10256 |
| *Clostridium_butyricum* | *Clostridium_bolteae* | *Clostridium_bolteae* | SPC10256 |
| *Clostridium_butyricum* | *Clostridium_bolteae* | *Clostridium_symbiosum* | SPC10256 |
| *Clostridium_butyricum* | *Clostridium_bolteae* | *Faecalibacterium_prausnitzii* | SPC10256 |
| *Clostridium_butyricum* | *Clostridium_bolteae* | Lachnospiraceae_*bacterium*_5_1_57FAA | SPC10256 |
| *Clostridium_butyricum* | *Clostridium_bolteae* | *Blautia_producta* | SPC10256 |

TABLE 4a-continued

| | | | |
|---|---|---|---|
| *Clostridium_butyricum* | *Clostridium_bolteae* | *Eubacterium_rectale* | SPC10256 |
| *Clostridium_butyricum* | *Clostridium_symbiosum* | *Clostridium_symbiosum* | SPC10256 |
| *Clostridium_butyricum* | *Clostridium_symbiosum* | *Faecalibacterium_prausnitzii* | SPC10256 |
| *Clostridium_butyricum* | *Clostridium_symbiosum* | Lachnospiraceae_*bacterium*_5_1_57FAA | SPC10256 |
| *Clostridium_butyricum* | *Clostridium_symbiosum* | *Blautia_producta* | SPC10256 |
| *Clostridium_butyricum* | *Clostridium_symbiosum* | *Eubacterium_rectale* | SPC10256 |
| *Clostridium_butyricum* | *Faecalibacterium_prausnitzii* | *Faecalibacterium_prausnitzii* | SPC10256 |
| *Clostridium_butyricum* | *Faecalibacterium_prausnitzii* | Lachnospiraceae_*bacterium*_5_1_57FAA | SPC10256 |
| *Clostridium_butyricum* | *Faecalibacterium_prausnitzii* | *Blautia_producta* | SPC10256 |
| *Clostridium_butyricum* | *Faecalibacterium_prausnitzii* | *Eubacterium_rectale* | SPC10256 |
| *Clostridium_butyricum* | Lachnospiraceae_*bacterium*_5_1_57FAA | Lachnospiraceae_*bacterium*_5_1_57FAA | SPC10256 |
| *Clostridium_butyricum* | Lachnospiraceae_*bacterium*_5_1_57FAA | *Blautia_producta* | SPC10256 |
| *Clostridium_butyricum* | Lachnospiraceae_*bacterium*_5_1_57FAA | *Eubacterium_rectale* | SPC10256 |
| *Clostridium_butyricum* | *Blautia_producta* | *Blautia_producta* | SPC10256 |
| *Clostridium_butyricum* | *Blautia_producta* | *Eubacterium_rectale* | SPC10256 |
| *Clostridium_butyricum* | *Eubacterium_rectale* | *Eubacterium_rectale* | SPC10256 |
| *Clostridium_hylemonae* | *Collinsella_aerofaciens* | *Collinsella_aerofaciens* | SPC10313 |
| *Clostridium_hylemonae* | *Collinsella_aerofaciens* | *Coprococcus_comes* | SPC10313 |
| *Clostridium_hylemonae* | *Collinsella_aerofaciens* | *Clostridium_bolteae* | SPC10313 |
| *Clostridium_hylemonae* | *Collinsella_aerofaciens* | *Clostridium_symbiosum* | SPC10313 |
| *Clostridium_hylemonae* | *Collinsella_aerofaciens* | *Faecalibacterium_prausnitzii* | SPC10313 |
| *Clostridium_hylemonae* | *Collinsella_aerofaciens* | Lachnospiraceae_*bacterium*_5_1_57FAA | SPC10313 |
| *Clostridium_hylemonae* | *Collinsella_aerofaciens* | *Blautia_producta* | SPC10313 |
| *Clostridium_hylemonae* | *Collinsella_aerofaciens* | *Eubacterium_rectale* | SPC10313 |
| *Clostridium_hylemonae* | *Coprococcus_comes* | *Coprococcus_comes* | SPC10313 |
| *Clostridium_hylemonae* | *Coprococcus_comes* | *Clostridium_bolteae* | SPC10313 |
| *Clostridium_hylemonae* | *Coprococcus_comes* | *Clostridium_symbiosum* | SPC10313 |
| *Clostridium_hylemonae* | *Coprococcus_comes* | *Faecalibacterium_prausnitzii* | SPC10313 |
| *Clostridium_hylemonae* | *Coprococcus_comes* | Lachnospiraceae_*bacterium*_5_1_57FAA | SPC10313 |
| *Clostridium_hylemonae* | *Coprococcus_comes* | *Blautia_producta* | SPC10313 |
| *Clostridium_hylemonae* | *Coprococcus_comes* | *Eubacterium_rectale* | SPC10313 |
| *Clostridium_hylemonae* | *Clostridium_bolteae* | *Clostridium_bolteae* | SPC10313 |
| *Clostridium_hylemonae* | *Clostridium_bolteae* | *Clostridium_symbiosum* | SPC10313 |
| *Clostridium_hylemonae* | *Clostridium_bolteae* | *Faecalibacterium_prausnitzii* | SPC10313 |
| *Clostridium_hylemonae* | *Clostridium_bolteae* | Lachnospiraceae_*bacterium*_5_1_57FAA | SPC10313 |
| *Clostridium_hylemonae* | *Clostridium_bolteae* | *Blautia_producta* | SPC10313 |
| *Clostridium_hylemonae* | *Clostridium_bolteae* | *Eubacterium_rectale* | SPC10313 |
| *Clostridium_hylemonae* | *Clostridium_symbiosum* | *Clostridium_symbiosum* | SPC10313 |
| *Clostridium_hylemonae* | *Clostridium_symbiosum* | *Faecalibacterium_prausnitzii* | SPC10313 |
| *Clostridium_hylemonae* | *Clostridium_symbiosum* | Lachnospiraceae_*bacterium*_5_1_57FAA | SPC10313 |
| *Clostridium_hylemonae* | *Clostridium_symbiosum* | *Blautia_producta* | SPC10313 |
| *Clostridium_hylemonae* | *Clostridium_symbiosum* | *Eubacterium_rectale* | SPC10313 |
| *Clostridium_hylemonae* | *Faecalibacterium_prausnitzii* | *Faecalibacterium_prausnitzii* | SPC10313 |
| *Clostridium_hylemonae* | *Faecalibacterium_prausnitzii* | Lachnospiraceae_*bacterium*_5_1_57FAA | SPC10313 |
| *Clostridium_hylemonae* | *Faecalibacterium_prausnitzii* | *Blautia_producta* | SPC10313 |
| *Clostridium_hylemonae* | *Faecalibacterium_prausnitzii* | *Eubacterium_rectale* | SPC10313 |
| *Clostridium_hylemonae* | Lachnospiraceae_*bacterium*_5_1_57FAA | Lachnospiraceae_*bacterium*_5_1_57FAA | SPC10313 |
| *Clostridium_hylemonae* | Lachnospiraceae_*bacterium*_5_1_57FAA | *Blautia_producta* | SPC10313 |
| *Clostridium_hylemonae* | Lachnospiraceae_*bacterium*_5_1_57FAA | *Eubacterium_rectale* | SPC10313 |
| *Clostridium_hylemonae* | *Blautia_producta* | *Blautia_producta* | SPC10313 |
| *Clostridium_hylemonae* | *Blautia_producta* | *Eubacterium_rectale* | SPC10313 |
| *Clostridium_hylemonae* | *Eubacterium_rectale* | *Eubacterium_rectale* | SPC10313 |
| *Clostridium_orbiscindens* | *Collinsella_aerofaciens* | *Collinsella_aerofaciens* | SPC10358 |
| *Clostridium_orbiscindens* | *Collinsella_aerofaciens* | *Coprococcus_comes* | SPC10358 |
| *Clostridium_orbiscindens* | *Collinsella_aerofaciens* | *Clostridium_bolteae* | SPC10358 |
| *Clostridium_orbiscindens* | *Collinsella_aerofaciens* | *Clostridium_symbiosum* | SPC10358 |
| *Clostridium_orbiscindens* | *Collinsella_aerofaciens* | *Faecalibacterium_prausnitzii* | SPC10358 |
| *Clostridium_orbiscindens* | *Collinsella_aerofaciens* | Lachnospiraceae_*bacterium*_5_1_57FAA | SPC10358 |
| *Clostridium_orbiscindens* | *Collinsella_aerofaciens* | *Blautia_producta* | SPC10358 |
| *Clostridium_orbiscindens* | *Collinsella_aerofaciens* | *Eubacterium_rectale* | SPC10358 |
| *Clostridium_orbiscindens* | *Coprococcus_comes* | *Coprococcus_comes* | SPC10358 |
| *Clostridium_orbiscindens* | *Coprococcus_comes* | *Clostridium_bolteae* | SPC10358 |
| *Clostridium_orbiscindens* | *Coprococcus_comes* | *Clostridium_symbiosum* | SPC10358 |
| *Clostridium_orbiscindens* | *Coprococcus_comes* | *Faecalibacterium_prausnitzii* | SPC10358 |
| *Clostridium_orbiscindens* | *Coprococcus_comes* | Lachnospiraceae_*bacterium*_5_1_57FAA | SPC10358 |
| *Clostridium_orbiscindens* | *Coprococcus_comes* | *Blautia_producta* | SPC10358 |
| *Clostridium_orbiscindens* | *Coprococcus_comes* | *Eubacterium_rectale* | SPC10358 |
| *Clostridium_orbiscindens* | *Clostridium_bolteae* | *Clostridium_bolteae* | SPC10358 |
| *Clostridium_orbiscindens* | *Clostridium_bolteae* | *Clostridium_symbiosum* | SPC10358 |
| *Clostridium_orbiscindens* | *Clostridium_bolteae* | *Faecalibacterium_prausnitzii* | SPC10358 |
| *Clostridium_orbiscindens* | *Clostridium_bolteae* | Lachnospiraceae_*bacterium*_5_1_57FAA | SPC10358 |
| *Clostridium_orbiscindens* | *Clostridium_bolteae* | *Blautia_producta* | SPC10358 |
| *Clostridium_orbiscindens* | *Clostridium_bolteae* | *Eubacterium_rectale* | SPC10358 |
| *Clostridium_orbiscindens* | *Clostridium_symbiosum* | *Clostridium_symbiosum* | SPC10358 |
| *Clostridium_orbiscindens* | *Clostridium_symbiosum* | *Faecalibacterium_prausnitzii* | SPC10358 |
| *Clostridium_orbiscindens* | *Clostridium_symbiosum* | Lachnospiraceae_*bacterium*_5_1_57FAA | SPC10358 |
| *Clostridium_orbiscindens* | *Clostridium_symbiosum* | *Blautia_producta* | SPC10358 |
| *Clostridium_orbiscindens* | *Clostridium_symbiosum* | *Eubacterium_rectale* | SPC10358 |
| *Clostridium_orbiscindens* | *Faecalibacterium_prausnitzii* | *Faecalibacterium_prausnitzii* | SPC10358 |
| *Clostridium_orbiscindens* | *Faecalibacterium_prausnitzii* | Lachnospiraceae_*bacterium*_5_1_57FAA | SPC10358 |

TABLE 4a-continued

| | | | |
|---|---|---|---|
| *Clostridium_orbiscindens* | *Faecalibacterium_prausnitzii* | *Blautia_producta* | SPC10358 |
| *Clostridium_orbiscindens* | *Faecalibacterium_prausnitzii* | *Eubacterium_rectale* | SPC10358 |
| *Clostridium_orbiscindens* | Lachnospiraceae_*bacterium*_5_1_57FAA | Lachnospiraceae_*bacterium*_5_1_57FAA | SPC10358 |
| *Clostridium_orbiscindens* | Lachnospiraceae_*bacterium*_5_1_57FAA | *Blautia_producta* | SPC10358 |
| *Clostridium_orbiscindens* | Lachnospiraceae_*bacterium*_5_1_57FAA | *Eubacterium_rectale* | SPC10358 |
| *Clostridium_orbiscindens* | *Blautia_producta* | *Blautia_producta* | SPC10358 |
| *Clostridium_orbiscindens* | *Blautia_producta* | *Eubacterium_rectale* | SPC10358 |
| *Clostridium_orbiscindens* | *Eubacterium_rectale* | *Eubacterium_rectale* | SPC10358 |
| *Ruminococcus_gnavus* | *Collinsella_aerofaciens* | *Collinsella_aerofaciens* | SPC10468 |
| *Ruminococcus_gnavus* | *Collinsella_aerofaciens* | *Coprococcus_comes* | SPC10468 |
| *Ruminococcus_gnavus* | *Collinsella_aerofaciens* | *Clostridium_bolteae* | SPC10468 |
| *Ruminococcus_gnavus* | *Collinsella_aerofaciens* | *Clostridium_symbiosum* | SPC10468 |
| *Ruminococcus_gnavus* | *Collinsella_aerofaciens* | *Faecalibacterium_prausnitzii* | SPC10468 |
| *Ruminococcus_gnavus* | *Collinsella_aerofaciens* | Lachnospiraceae_*bacterium*_5_1_57FAA | SPC10468 |
| *Ruminococcus_gnavus* | *Collinsella_aerofaciens* | *Blautia_producta* | SPC10468 |
| *Ruminococcus_gnavus* | *Collinsella_aerofaciens* | *Eubacterium_rectale* | SPC10468 |
| *Ruminococcus_gnavus* | *Coprococcus_comes* | *Coprococcus_comes* | SPC10468 |
| *Ruminococcus_gnavus* | *Coprococcus_comes* | *Clostridium_bolteae* | SPC10468 |
| *Ruminococcus_gnavus* | *Coprococcus_comes* | *Clostridium_symbiosum* | SPC10468 |
| *Ruminococcus_gnavus* | *Coprococcus_comes* | *Faecalibacterium_prausnitzii* | SPC10468 |
| *Ruminococcus_gnavus* | *Coprococcus_comes* | Lachnospiraceae_*bacterium*_5_1_57FAA | SPC10468 |
| *Ruminococcus_gnavus* | *Coprococcus_comes* | *Blautia_producta* | SPC10468 |
| *Ruminococcus_gnavus* | *Coprococcus_comes* | *Eubacterium_rectale* | SPC10468 |
| *Ruminococcus_gnavus* | *Clostridium_bolteae* | *Clostridium_bolteae* | SPC10468 |
| *Ruminococcus_gnavus* | *Clostridium_bolteae* | *Clostridium_symbiosum* | SPC10468 |
| *Ruminococcus_gnavus* | *Clostridium_bolteae* | *Faecalibacterium_prausnitzii* | SPC10468 |
| *Ruminococcus_gnavus* | *Clostridium_bolteae* | Lachnospiraceae_*bacterium*_5_1_57FAA | SPC10468 |
| *Ruminococcus_gnavus* | *Clostridium_bolteae* | *Blautia_producta* | SPC10468 |
| *Ruminococcus_gnavus* | *Clostridium_bolteae* | *Eubacterium_rectale* | SPC10468 |
| *Ruminococcus_gnavus* | *Clostridium_symbiosum* | *Clostridium_symbiosum* | SPC10468 |
| *Ruminococcus_gnavus* | *Clostridium_symbiosum* | *Faecalibacterium_prausnitzii* | SPC10468 |
| *Ruminococcus_gnavus* | *Clostridium_symbiosum* | Lachnospiraceae_*bacterium*_5_1_57FAA | SPC10468 |
| *Ruminococcus_gnavus* | *Clostridium_symbiosum* | *Blautia_producta* | SPC10468 |
| *Ruminococcus_gnavus* | *Clostridium_symbiosum* | *Eubacterium_rectale* | SPC10468 |
| *Ruminococcus_gnavus* | *Faecalibacterium_prausnitzii* | *Faecalibacterium_prausnitzii* | SPC10468 |
| *Ruminococcus_gnavus* | *Faecalibacterium_prausnitzii* | Lachnospiraceae_*bacterium*_5_1_57FAA | SPC10468 |
| *Ruminococcus_gnavus* | *Faecalibacterium_prausnitzii* | *Blautia_producta* | SPC10468 |
| *Ruminococcus_gnavus* | *Faecalibacterium_prausnitzii* | *Eubacterium_rectale* | SPC10468 |
| *Ruminococcus_gnavus* | Lachnospiraceae_*bacterium*_5_1_57FAA | Lachnospiraceae_*bacterium*_5_1_57FAA | SPC10468 |
| *Ruminococcus_gnavus* | Lachnospiraceae_*bacterium*_5_1_57FAA | *Blautia_producta* | SPC10468 |
| *Ruminococcus_gnavus* | Lachnospiraceae_*bacterium*_5_1_57FAA | *Eubacterium_rectale* | SPC10468 |
| *Ruminococcus_gnavus* | *Blautia_producta* | *Blautia_producta* | SPC10468 |
| *Ruminococcus_gnavus* | *Blautia_producta* | *Eubacterium_rectale* | SPC10468 |
| *Ruminococcus_gnavus* | *Eubacterium_rectale* | *Eubacterium_rectale* | SPC10468 |

| Strain ID OTU2 | Strain ID OTU3 (if applicable) | Clade of OTU1 | Clade of OTU2 | Clade of OTU3 (if applicable) | Hetero/ Semi/ Homo | *C. diff* Inhibition Score | 75th Percentile of *C. diff* Inhibition Score | *C. diff* Inhibition Synergy | VRE Inhibition Score | 75th Percentile of VRE Inhibition Score |
|---|---|---|---|---|---|---|---|---|---|---|
| SPC00001 | | clade_92 | clade_92 | | homo | +++ | FALSE | | | |
| SPC00005 | | clade_92 | clade_378 | | hetero | ++++ | FALSE | TRUE | | |
| SPC00006 | | clade_92 | clade_65 | | hetero | ++++ | TRUE | TRUE | | |
| SPC00007 | | clade_92 | clade_38 | | hetero | ++++ | TRUE | TRUE | | |
| SPC00008 | | clade_92 | clade_497 | | hetero | ++++ | TRUE | TRUE | | |
| SPC00009 | | clade_92 | clade_481 | | hetero | + | FALSE | TRUE | | |
| SPC00015 | | clade_92 | clade_98 | | hetero | + | FALSE | FALSE | | |
| SPC00018 | | clade_92 | clade_360 | | hetero | + | FALSE | TRUE | | |
| SPC00021 | | clade_92 | clade_309 | | hetero | ++++ | FALSE | FALSE | | |
| SPC00022 | | clade_92 | clade_522 | | hetero | + | FALSE | TRUE | | |
| SPC00026 | | clade_92 | clade_262 | | hetero | ++++ | TRUE | TRUE | | |
| SPC00027 | | clade_92 | clade_351 | | hetero | ++++ | FALSE | TRUE | | |
| SPC00054 | | clade_92 | clade_478 | | hetero | ++++ | TRUE | TRUE | | |
| SPC00056 | | clade_92 | clade_466 | | hetero | ++++ | TRUE | TRUE | | |
| SPC00057 | | clade_92 | clade_360 | | hetero | ++++ | TRUE | TRUE | | |
| SPC00061 | | clade_92 | clade_444 | | hetero | ++++ | FALSE | TRUE | | |
| SPC00080 | | clade_92 | clade_393 | | hetero | ++++ | FALSE | TRUE | | |
| SPC10001 | | clade_92 | clade_479 | | hetero | +++ | FALSE | TRUE | | |
| SPC10019 | | clade_92 | clade_110 | | hetero | ++++ | TRUE | TRUE | | |
| SPC10030 | | clade_92 | clade_38 | | hetero | ++++ | TRUE | TRUE | | |
| SPC10048 | | clade_92 | clade_286 | | hetero | +++ | FALSE | FALSE | | |
| SPC10081 | | clade_92 | clade_378 | | hetero | ++++ | TRUE | TRUE | | |
| SPC10097 | | clade_92 | clade_553 | | hetero | ++++ | FALSE | TRUE | | |
| SPC10110 | | clade_92 | clade_92 | | hetero | +++ | FALSE | FALSE | | |
| SPC10197 | | clade_92 | clade_309 | | hetero | +++ | FALSE | FALSE | | |
| SPC10211 | | clade_92 | clade_170 | | hetero | ++++ | TRUE | TRUE | | |
| SPC10213 | | clade_92 | clade_85 | | hetero | ++++ | TRUE | TRUE | | |
| SPC10233 | | clade_92 | clade_262 | | hetero | ++++ | FALSE | FALSE | | |
| SPC10243 | | clade_92 | clade_408 | | hetero | ++++ | FALSE | FALSE | | |

TABLE 4a-continued

| | | | | | | |
|---|---|---|---|---|---|---|
| SPC10298 | clade_92 | clade_172 | hetero | ++++ | TRUE | TRUE |
| SPC10301 | clade_92 | clade_172 | hetero | ++++ | TRUE | TRUE |
| SPC10304 | clade_92 | clade_262 | hetero | ++++ | FALSE | TRUE |
| SPC10355 | clade_92 | clade_408 | hetero | ++++ | TRUE | TRUE |
| SPC10363 | clade_92 | clade_444 | hetero | ++++ | TRUE | TRUE |
| SPC10386 | clade_92 | clade_478 | hetero | ++++ | FALSE | TRUE |
| SPC10388 | clade_92 | clade_466 | hetero | +++ | FALSE | TRUE |
| SPC10390 | clade_92 | clade_260 | hetero | ++++ | TRUE | TRUE |
| SPC10403 | clade_92 | clade_309 | hetero | ++++ | TRUE | TRUE |
| SPC10414 | clade_92 | clade_500 | hetero | ++++ | TRUE | TRUE |
| SPC10415 | clade_92 | clade_309 | hetero | ++++ | FALSE | FALSE |
| SPC00005 | clade_378 | clade_378 | homo | | FALSE | |
| SPC00006 | clade_378 | clade_65 | hetero | +++ | FALSE | TRUE |
| SPC00007 | clade_378 | clade_38 | hetero | +++ | FALSE | TRUE |
| SPC00008 | clade_378 | clade_497 | hetero | ++++ | TRUE | TRUE |
| SPC00009 | clade_378 | clade_481 | hetero | + | FALSE | TRUE |
| SPC00015 | clade_378 | clade_98 | hetero | + | FALSE | TRUE |
| SPC00018 | clade_378 | clade_360 | hetero | + | FALSE | TRUE |
| SPC00021 | clade_378 | clade_309 | hetero | ++++ | TRUE | TRUE |
| SPC00022 | clade_378 | clade_522 | hetero | ++ | FALSE | TRUE |
| SPC00026 | clade_378 | clade_262 | hetero | +++ | FALSE | TRUE |
| SPC00027 | clade_378 | clade_351 | hetero | + | FALSE | FALSE |
| SPC00054 | clade_378 | clade_478 | hetero | +++ | FALSE | TRUE |
| SPC00056 | clade_378 | clade_466 | hetero | ++ | FALSE | TRUE |
| SPC00057 | clade_378 | clade_360 | hetero | ++++ | FALSE | TRUE |
| SPC00061 | clade_378 | clade_444 | hetero | + | FALSE | TRUE |
| SPC00080 | clade_378 | clade_393 | hetero | | FALSE | TRUE |
| SPC10001 | clade_378 | clade_479 | hetero | | FALSE | TRUE |
| SPC10019 | clade_378 | clade_110 | hetero | | FALSE | TRUE |
| SPC10030 | clade_378 | clade_38 | hetero | | FALSE | FALSE |
| SPC10048 | clade_378 | clade_286 | hetero | ++++ | FALSE | TRUE |
| SPC10081 | clade_378 | clade_378 | hetero | + | FALSE | TRUE |
| SPC10097 | clade_378 | clade_553 | hetero | ++++ | TRUE | TRUE |
| SPC10110 | clade_378 | clade_92 | hetero | +++ | FALSE | TRUE |
| SPC10197 | clade_378 | clade_309 | hetero | ++++ | FALSE | TRUE |
| SPC10211 | clade_378 | clade_170 | hetero | ++++ | TRUE | TRUE |
| SPC10213 | clade_378 | clade_85 | hetero | ++++ | FALSE | TRUE |
| SPC10233 | clade_378 | clade_262 | hetero | ++++ | TRUE | TRUE |
| SPC10243 | clade_378 | clade_408 | hetero | ++++ | TRUE | TRUE |
| SPC10298 | clade_378 | clade_172 | hetero | ++++ | TRUE | TRUE |
| SPC10301 | clade_378 | clade_172 | hetero | ++++ | TRUE | TRUE |
| SPC10304 | clade_378 | clade_262 | hetero | ++++ | TRUE | TRUE |
| SPC10355 | clade_378 | clade_408 | hetero | ++ | FALSE | TRUE |
| SPC10363 | clade_378 | clade_444 | hetero | ++++ | FALSE | TRUE |
| SPC10386 | clade_378 | clade_478 | hetero | ++ | FALSE | TRUE |
| SPC10388 | clade_378 | clade_466 | hetero | ++ | FALSE | TRUE |
| SPC10390 | clade_378 | clade_260 | hetero | ++ | FALSE | TRUE |
| SPC10403 | clade_378 | clade_309 | hetero | + | FALSE | TRUE |
| SPC10414 | clade_378 | clade_500 | hetero | ++ | FALSE | TRUE |
| SPC10415 | clade_378 | clade_309 | hetero | ++++ | FALSE | TRUE |
| SPC00006 | clade_65 | clade_65 | homo | ++++ | TRUE | |
| SPC00007 | clade_65 | clade_38 | hetero | +++ | FALSE | FALSE |
| SPC00008 | clade_65 | clade_497 | hetero | ++++ | TRUE | TRUE |
| SPC00009 | clade_65 | clade_481 | hetero | ++ | FALSE | TRUE |
| SPC00015 | clade_65 | clade_98 | hetero | ++ | FALSE | FALSE |
| SPC00018 | clade_65 | clade_360 | hetero | ++ | FALSE | TRUE |
| SPC00021 | clade_65 | clade_309 | hetero | ++++ | TRUE | TRUE |
| SPC00022 | clade_65 | clade_522 | hetero | +++ | FALSE | TRUE |
| SPC00026 | clade_65 | clade_262 | hetero | +++ | FALSE | FALSE |
| SPC00027 | clade_65 | clade_351 | hetero | ++++ | TRUE | TRUE |
| SPC00054 | clade_65 | clade_478 | hetero | ++++ | TRUE | TRUE |
| SPC00056 | clade_65 | clade_466 | hetero | ++++ | FALSE | TRUE |
| SPC00057 | clade_65 | clade_360 | hetero | ++++ | TRUE | TRUE |
| SPC00061 | clade_65 | clade_444 | hetero | ++++ | FALSE | TRUE |
| SPC00080 | clade_65 | clade_393 | hetero | +++ | FALSE | TRUE |
| SPC10001 | clade_65 | clade_479 | hetero | ++++ | FALSE | TRUE |
| SPC10019 | clade_65 | clade_110 | hetero | ++++ | FALSE | TRUE |
| SPC10030 | clade_65 | clade_38 | hetero | +++ | FALSE | FALSE |
| SPC10048 | clade_65 | clade_286 | hetero | +++ | FALSE | FALSE |
| SPC10081 | clade_65 | clade_378 | hetero | | FALSE | FALSE |
| SPC10097 | clade_65 | clade_553 | hetero | ++++ | TRUE | TRUE |
| SPC10110 | clade_65 | clade_92 | hetero | +++ | FALSE | FALSE |
| SPC10197 | clade_65 | clade_309 | hetero | ++ | FALSE | FALSE |
| SPC10211 | clade_65 | clade_170 | hetero | +++ | FALSE | FALSE |
| SPC10213 | clade_65 | clade_85 | hetero | +++ | FALSE | FALSE |
| SPC10233 | clade_65 | clade_262 | hetero | ++++ | TRUE | FALSE |
| SPC10243 | clade_65 | clade_408 | hetero | ++++ | FALSE | FALSE |
| SPC10298 | clade_65 | clade_172 | hetero | ++++ | TRUE | TRUE |
| SPC10301 | clade_65 | clade_172 | hetero | ++++ | TRUE | TRUE |
| SPC10304 | clade_65 | clade_262 | hetero | ++ | FALSE | FALSE |

TABLE 4a-continued

| | | | | | | |
|---|---|---|---|---|---|---|
| SPC10355 | clade_65 | clade_408 | hetero | ++++ | TRUE | TRUE |
| SPC10363 | clade_65 | clade_444 | hetero | ++++ | FALSE | TRUE |
| SPC10386 | clade_65 | clade_478 | hetero | +++ | FALSE | FALSE |
| SPC10388 | clade_65 | clade_466 | hetero | + | FALSE | FALSE |
| SPC10390 | clade_65 | clade_260 | hetero | ++ | FALSE | FALSE |
| SPC10403 | clade_65 | clade_309 | hetero | ++ | FALSE | FALSE |
| SPC10414 | clade_65 | clade_500 | hetero | +++ | FALSE | TRUE |
| SPC10415 | clade_65 | clade_309 | hetero | +++ | FALSE | FALSE |
| SPC00007 | clade_38 | clade_38 | homo | | FALSE | |
| SPC00008 | clade_38 | clade_497 | hetero | ++++ | TRUE | TRUE |
| SPC00009 | clade_38 | clade_481 | hetero | | FALSE | TRUE |
| SPC00015 | clade_38 | clade_98 | hetero | ++ | FALSE | TRUE |
| SPC00018 | clade_38 | clade_360 | hetero | | FALSE | TRUE |
| SPC00021 | clade_38 | clade_309 | hetero | ++++ | TRUE | TRUE |
| SPC00022 | clade_38 | clade_522 | hetero | | FALSE | TRUE |
| SPC00026 | clade_38 | clade_262 | hetero | ++++ | TRUE | TRUE |
| SPC00027 | clade_38 | clade_351 | hetero | +++ | FALSE | TRUE |
| SPC00054 | clade_38 | clade_478 | hetero | + | FALSE | TRUE |
| SPC00056 | clade_38 | clade_466 | hetero | | FALSE | TRUE |
| SPC00057 | clade_38 | clade_360 | hetero | ++ | FALSE | TRUE |
| SPC00061 | clade_38 | clade_444 | hetero | | FALSE | TRUE |
| SPC00080 | clade_38 | clade_393 | hetero | | FALSE | FALSE |
| SPC10001 | clade_38 | clade_479 | hetero | | FALSE | FALSE |
| SPC10019 | clade_38 | clade_110 | hetero | +++ | FALSE | TRUE |
| SPC10030 | clade_38 | clade_38 | hetero | | FALSE | FALSE |
| SPC10048 | clade_38 | clade_286 | hetero | ++ | FALSE | TRUE |
| SPC10081 | clade_38 | clade_378 | hetero | | FALSE | FALSE |
| SPC10097 | clade_38 | clade_553 | hetero | ++++ | TRUE | TRUE |
| SPC10110 | clade_38 | clade_92 | hetero | ++++ | TRUE | TRUE |
| SPC10197 | clade_38 | clade_309 | hetero | ++ | FALSE | FALSE |
| SPC10211 | clade_38 | clade_170 | hetero | ++ | FALSE | FALSE |
| SPC10213 | clade_38 | clade_85 | hetero | + | FALSE | FALSE |
| SPC10233 | clade_38 | clade_262 | hetero | +++ | FALSE | FALSE |
| SPC10243 | clade_38 | clade_408 | hetero | +++ | FALSE | FALSE |
| SPC10298 | clade_38 | clade_172 | hetero | ++++ | TRUE | TRUE |
| SPC10301 | clade_38 | clade_172 | hetero | ++++ | TRUE | TRUE |
| SPC10304 | clade_38 | clade_262 | hetero | +++ | FALSE | TRUE |
| SPC10355 | clade_38 | clade_408 | hetero | ++++ | TRUE | TRUE |
| SPC10363 | clade_38 | clade_444 | hetero | ++ | FALSE | TRUE |
| SPC10386 | clade_38 | clade_478 | hetero | | FALSE | FALSE |
| SPC10388 | clade_38 | clade_466 | hetero | | FALSE | FALSE |
| SPC10390 | clade_38 | clade_260 | hetero | | FALSE | FALSE |
| SPC10403 | clade_38 | clade_309 | hetero | | FALSE | TRUE |
| SPC10414 | clade_38 | clade_500 | hetero | | FALSE | TRUE |
| SPC10415 | clade_38 | clade_309 | hetero | + | FALSE | FALSE |
| SPC00008 | clade_497 | clade_497 | homo | ++++ | TRUE | |
| SPC00009 | clade_497 | clade_481 | hetero | ++++ | TRUE | TRUE |
| SPC00015 | clade_497 | clade_98 | hetero | ++++ | TRUE | TRUE |
| SPC00018 | clade_497 | clade_360 | hetero | ++++ | TRUE | TRUE |
| SPC00021 | clade_497 | clade_309 | hetero | ++++ | TRUE | TRUE |
| SPC00022 | clade_497 | clade_522 | hetero | ++++ | TRUE | TRUE |
| SPC00026 | clade_497 | clade_262 | hetero | ++++ | TRUE | TRUE |
| SPC00027 | clade_497 | clade_351 | hetero | ++++ | TRUE | TRUE |
| SPC00054 | clade_497 | clade_478 | hetero | ++++ | TRUE | TRUE |
| SPC00056 | clade_497 | clade_466 | hetero | ++++ | TRUE | TRUE |
| SPC00057 | clade_497 | clade_360 | hetero | ++++ | TRUE | TRUE |
| SPC00061 | clade_497 | clade_444 | hetero | ++++ | TRUE | TRUE |
| SPC00080 | clade_497 | clade_393 | hetero | ++++ | TRUE | TRUE |
| SPC10001 | clade_497 | clade_479 | hetero | ++++ | TRUE | TRUE |
| SPC10019 | clade_497 | clade_110 | hetero | ++++ | TRUE | TRUE |
| SPC10030 | clade_497 | clade_38 | hetero | ++++ | TRUE | TRUE |
| SPC10048 | clade_497 | clade_286 | hetero | ++++ | TRUE | TRUE |
| SPC10081 | clade_497 | clade_378 | hetero | ++++ | TRUE | TRUE |
| SPC10097 | clade_497 | clade_553 | hetero | ++++ | TRUE | TRUE |
| SPC10110 | clade_497 | clade_92 | hetero | +++ | FALSE | FALSE |
| SPC10197 | clade_497 | clade_309 | hetero | ++++ | TRUE | TRUE |
| SPC10211 | clade_497 | clade_170 | hetero | ++++ | TRUE | TRUE |
| SPC10213 | clade_497 | clade_85 | hetero | ++++ | TRUE | TRUE |
| SPC10233 | clade_497 | clade_262 | hetero | ++++ | TRUE | TRUE |
| SPC10243 | clade_497 | clade_408 | hetero | ++++ | TRUE | TRUE |
| SPC10298 | clade_497 | clade_172 | hetero | ++++ | TRUE | TRUE |
| SPC10301 | clade_497 | clade_172 | hetero | ++++ | TRUE | TRUE |
| SPC10304 | clade_497 | clade_262 | hetero | ++++ | TRUE | TRUE |
| SPC10355 | clade_497 | clade_408 | hetero | ++++ | TRUE | TRUE |
| SPC10363 | clade_497 | clade_444 | hetero | ++++ | TRUE | TRUE |
| SPC10386 | clade_497 | clade_478 | hetero | ++++ | TRUE | TRUE |
| SPC10388 | clade_497 | clade_466 | hetero | ++++ | TRUE | TRUE |
| SPC10390 | clade_497 | clade_260 | hetero | ++++ | TRUE | TRUE |
| SPC10403 | clade_497 | clade_309 | hetero | ++++ | TRUE | TRUE |
| SPC10414 | clade_497 | clade_500 | hetero | ++++ | TRUE | TRUE |

TABLE 4a-continued

| | | | | | | |
|---|---|---|---|---|---|---|
| SPC10415 | clade_497 | clade_309 | hetero | ++++ | TRUE | TRUE |
| SPC00009 | clade_481 | clade_481 | homo | | FALSE | |
| SPC00015 | clade_481 | clade_98 | hetero | | FALSE | TRUE |
| SPC00018 | clade_481 | clade_360 | hetero | | FALSE | TRUE |
| SPC00021 | clade_481 | clade_309 | hetero | ++++ | TRUE | TRUE |
| SPC00022 | clade_481 | clade_522 | hetero | | FALSE | TRUE |
| SPC00026 | clade_481 | clade_262 | hetero | | FALSE | FALSE |
| SPC00027 | clade_481 | clade_351 | hetero | | FALSE | FALSE |
| SPC00054 | clade_481 | clade_478 | hetero | −− | FALSE | FALSE |
| SPC00056 | clade_481 | clade_466 | hetero | | FALSE | FALSE |
| SPC00057 | clade_481 | clade_360 | hetero | | FALSE | TRUE |
| SPC00061 | clade_481 | clade_444 | hetero | | FALSE | FALSE |
| SPC00080 | clade_481 | clade_393 | hetero | −− | FALSE | FALSE |
| SPC10001 | clade_481 | clade_479 | hetero | | FALSE | TRUE |
| SPC10019 | clade_481 | clade_110 | hetero | | FALSE | TRUE |
| SPC10030 | clade_481 | clade_38 | hetero | | FALSE | FALSE |
| SPC10048 | clade_481 | clade_286 | hetero | − | FALSE | FALSE |
| SPC10081 | clade_481 | clade_378 | hetero | | FALSE | FALSE |
| SPC10097 | clade_481 | clade_553 | hetero | ++ | FALSE | TRUE |
| SPC10110 | clade_481 | clade_92 | hetero | + | FALSE | TRUE |
| SPC10197 | clade_481 | clade_309 | hetero | + | FALSE | FALSE |
| SPC10211 | clade_481 | clade_170 | hetero | ++ | FALSE | FALSE |
| SPC10213 | clade_481 | clade_85 | hetero | | FALSE | FALSE |
| SPC10233 | clade_481 | clade_262 | hetero | +++ | FALSE | FALSE |
| SPC10243 | clade_481 | clade_408 | hetero | +++ | FALSE | TRUE |
| SPC10298 | clade_481 | clade_172 | hetero | +++ | FALSE | TRUE |
| SPC10301 | clade_481 | clade_172 | hetero | ++++ | TRUE | TRUE |
| SPC10304 | clade_481 | clade_262 | hetero | ++ | FALSE | TRUE |
| SPC10355 | clade_481 | clade_408 | hetero | | FALSE | TRUE |
| SPC10363 | clade_481 | clade_444 | hetero | ++ | FALSE | TRUE |
| SPC10386 | clade_481 | clade_478 | hetero | | FALSE | TRUE |
| SPC10388 | clade_481 | clade_466 | hetero | ++ | FALSE | TRUE |
| SPC10390 | clade_481 | clade_260 | hetero | +++ | FALSE | TRUE |
| SPC10403 | clade_481 | clade_309 | hetero | ++++ | FALSE | TRUE |
| SPC10414 | clade_481 | clade_500 | hetero | +++ | FALSE | TRUE |
| SPC10415 | clade_481 | clade_309 | hetero | ++++ | TRUE | TRUE |
| SPC00015 | clade_98 | clade_98 | homo | | FALSE | |
| SPC00018 | clade_98 | clade_360 | hetero | | FALSE | TRUE |
| SPC00021 | clade_98 | clade_309 | hetero | ++++ | TRUE | TRUE |
| SPC00022 | clade_98 | clade_522 | hetero | | FALSE | TRUE |
| SPC00026 | clade_98 | clade_262 | hetero | + | FALSE | TRUE |
| SPC00027 | clade_98 | clade_351 | hetero | | FALSE | FALSE |
| SPC00054 | clade_98 | clade_478 | hetero | | FALSE | FALSE |
| SPC00056 | clade_98 | clade_466 | hetero | | FALSE | FALSE |
| SPC00057 | clade_98 | clade_360 | hetero | | FALSE | TRUE |
| SPC00061 | clade_98 | clade_444 | hetero | | FALSE | FALSE |
| SPC00080 | clade_98 | clade_393 | hetero | | FALSE | FALSE |
| SPC10001 | clade_98 | clade_479 | hetero | | FALSE | FALSE |
| SPC10019 | clade_98 | clade_110 | hetero | + | FALSE | TRUE |
| SPC10030 | clade_98 | clade_38 | hetero | + | FALSE | TRUE |
| SPC10048 | clade_98 | clade_286 | hetero | | FALSE | FALSE |
| SPC10081 | clade_98 | clade_378 | hetero | − | FALSE | FALSE |
| SPC10097 | clade_98 | clade_553 | hetero | | FALSE | TRUE |
| SPC10110 | clade_98 | clade_92 | hetero | ++ | FALSE | FALSE |
| SPC10197 | clade_98 | clade_309 | hetero | ++ | FALSE | FALSE |
| SPC10211 | clade_98 | clade_170 | hetero | + | FALSE | FALSE |
| SPC10213 | clade_98 | clade_85 | hetero | | FALSE | FALSE |
| SPC10233 | clade_98 | clade_262 | hetero | | FALSE | FALSE |
| SPC10243 | clade_98 | clade_408 | hetero | + | FALSE | FALSE |
| SPC10298 | clade_98 | clade_172 | hetero | ++++ | TRUE | TRUE |
| SPC10301 | clade_98 | clade_172 | hetero | ++++ | FALSE | FALSE |
| SPC10304 | clade_98 | clade_262 | hetero | + | FALSE | TRUE |
| SPC10355 | clade_98 | clade_408 | hetero | | FALSE | FALSE |
| SPC10363 | clade_98 | clade_444 | hetero | | FALSE | FALSE |
| SPC10386 | clade_98 | clade_478 | hetero | | FALSE | TRUE |
| SPC10388 | clade_98 | clade_466 | hetero | | FALSE | TRUE |
| SPC10390 | clade_98 | clade_260 | hetero | | FALSE | FALSE |
| SPC10403 | clade_98 | clade_309 | hetero | | FALSE | TRUE |
| SPC10414 | clade_98 | clade_500 | hetero | | FALSE | FALSE |
| SPC10415 | clade_98 | clade_309 | hetero | | FALSE | FALSE |
| SPC00018 | clade_360 | clade_360 | homo | | FALSE | |
| SPC00021 | clade_360 | clade_309 | hetero | ++++ | FALSE | TRUE |
| SPC00022 | clade_360 | clade_522 | hetero | − | FALSE | FALSE |
| SPC00026 | clade_360 | clade_262 | hetero | | FALSE | TRUE |
| SPC00027 | clade_360 | clade_351 | hetero | | FALSE | FALSE |
| SPC00054 | clade_360 | clade_478 | hetero | | FALSE | TRUE |
| SPC00056 | clade_360 | clade_466 | hetero | | FALSE | TRUE |
| SPC00057 | clade_360 | clade_360 | hetero | + | FALSE | TRUE |
| SPC00061 | clade_360 | clade_444 | hetero | | FALSE | TRUE |
| SPC00080 | clade_360 | clade_393 | hetero | | FALSE | TRUE |

TABLE 4a-continued

| | | | | | | |
|---|---|---|---|---|---|---|
| SPC10001 | clade_360 | clade_479 | hetero | – | FALSE | FALSE |
| SPC10019 | clade_360 | clade_110 | hetero | | FALSE | TRUE |
| SPC10030 | clade_360 | clade_38 | hetero | | FALSE | FALSE |
| SPC10048 | clade_360 | clade_286 | hetero | | FALSE | TRUE |
| SPC10081 | clade_360 | clade_378 | hetero | | FALSE | TRUE |
| SPC10097 | clade_360 | clade_553 | hetero | + | FALSE | TRUE |
| SPC10110 | clade_360 | clade_92 | hetero | +++ | FALSE | TRUE |
| SPC10197 | clade_360 | clade_309 | hetero | +++ | FALSE | TRUE |
| SPC10211 | clade_360 | clade_170 | hetero | ++ | FALSE | TRUE |
| SPC10213 | clade_360 | clade_85 | hetero | | FALSE | FALSE |
| SPC10233 | clade_360 | clade_262 | hetero | +++ | FALSE | FALSE |
| SPC10243 | clade_360 | clade_408 | hetero | +++ | FALSE | TRUE |
| SPC10298 | clade_360 | clade_172 | hetero | ++ | FALSE | TRUE |
| SPC10301 | clade_360 | clade_172 | hetero | ++++ | TRUE | TRUE |
| SPC10304 | clade_360 | clade_262 | hetero | | FALSE | TRUE |
| SPC10355 | clade_360 | clade_408 | hetero | | FALSE | FALSE |
| SPC10363 | clade_360 | clade_444 | hetero | | FALSE | FALSE |
| SPC10386 | clade_360 | clade_478 | hetero | –– | FALSE | FALSE |
| SPC10388 | clade_360 | clade_466 | hetero | | FALSE | FALSE |
| SPC10390 | clade_360 | clade_260 | hetero | – | FALSE | FALSE |
| SPC10403 | clade_360 | clade_309 | hetero | | FALSE | FALSE |
| SPC10414 | clade_360 | clade_500 | hetero | ––– | FALSE | FALSE |
| SPC10415 | clade_360 | clade_309 | hetero | – | FALSE | FALSE |
| SPC00021 | clade_309 | clade_309 | homo | ++++ | TRUE | |
| SPC00022 | clade_309 | clade_522 | hetero | ++++ | TRUE | TRUE |
| SPC00026 | clade_309 | clade_262 | hetero | ++++ | TRUE | TRUE |
| SPC00027 | clade_309 | clade_351 | hetero | ++++ | TRUE | TRUE |
| SPC00054 | clade_309 | clade_478 | hetero | ++++ | TRUE | TRUE |
| SPC00056 | clade_309 | clade_466 | hetero | ++++ | TRUE | TRUE |
| SPC00057 | clade_309 | clade_360 | hetero | ++++ | TRUE | TRUE |
| SPC00061 | clade_309 | clade_444 | hetero | ++++ | TRUE | TRUE |
| SPC00080 | clade_309 | clade_393 | hetero | ++++ | FALSE | TRUE |
| SPC10001 | clade_309 | clade_479 | hetero | ++++ | FALSE | TRUE |
| SPC10019 | clade_309 | clade_110 | hetero | ++++ | FALSE | TRUE |
| SPC10030 | clade_309 | clade_38 | hetero | +++ | FALSE | FALSE |
| SPC10048 | clade_309 | clade_286 | hetero | ++++ | TRUE | TRUE |
| SPC10081 | clade_309 | clade_378 | hetero | ++++ | TRUE | TRUE |
| SPC10097 | clade_309 | clade_553 | hetero | ++++ | TRUE | TRUE |
| SPC10110 | clade_309 | clade_92 | hetero | ++++ | TRUE | TRUE |
| SPC10197 | clade_309 | clade_309 | hetero | ++++ | TRUE | FALSE |
| SPC10211 | clade_309 | clade_170 | hetero | ++++ | TRUE | TRUE |
| SPC10213 | clade_309 | clade_85 | hetero | ++++ | FALSE | FALSE |
| SPC10233 | clade_309 | clade_262 | hetero | ++++ | TRUE | FALSE |
| SPC10243 | clade_309 | clade_408 | hetero | ++++ | TRUE | FALSE |
| SPC10298 | clade_309 | clade_172 | hetero | | FALSE | FALSE |
| SPC10301 | clade_309 | clade_172 | hetero | ++++ | TRUE | TRUE |
| SPC10304 | clade_309 | clade_262 | hetero | ++++ | TRUE | TRUE |
| SPC10355 | clade_309 | clade_408 | hetero | ++++ | TRUE | TRUE |
| SPC10363 | clade_309 | clade_444 | hetero | ++++ | TRUE | TRUE |
| SPC10386 | clade_309 | clade_478 | hetero | ++++ | TRUE | TRUE |
| SPC10388 | clade_309 | clade_466 | hetero | ++++ | TRUE | TRUE |
| SPC10390 | clade_309 | clade_260 | hetero | ++++ | TRUE | TRUE |
| SPC10403 | clade_309 | clade_309 | hetero | ++++ | TRUE | TRUE |
| SPC10414 | clade_309 | clade_500 | hetero | ++++ | TRUE | TRUE |
| SPC10415 | clade_309 | clade_309 | hetero | ++++ | TRUE | TRUE |
| SPC00022 | clade_522 | clade_522 | homo | | FALSE | |
| SPC00026 | clade_522 | clade_262 | hetero | | FALSE | TRUE |
| SPC00027 | clade_522 | clade_351 | hetero | | FALSE | FALSE |
| SPC00054 | clade_522 | clade_478 | hetero | | FALSE | FALSE |
| SPC00056 | clade_522 | clade_466 | hetero | | FALSE | FALSE |
| SPC00057 | clade_522 | clade_360 | hetero | + | FALSE | TRUE |
| SPC00061 | clade_522 | clade_444 | hetero | | FALSE | TRUE |
| SPC00080 | clade_522 | clade_393 | hetero | | FALSE | FALSE |
| SPC10001 | clade_522 | clade_479 | hetero | – | FALSE | FALSE |
| SPC10019 | clade_522 | clade_110 | hetero | – | FALSE | FALSE |
| SPC10030 | clade_522 | clade_38 | hetero | | FALSE | FALSE |
| SPC10048 | clade_522 | clade_286 | hetero | | FALSE | FALSE |
| SPC10081 | clade_522 | clade_378 | hetero | | FALSE | FALSE |
| SPC10097 | clade_522 | clade_553 | hetero | ++ | FALSE | TRUE |
| SPC10110 | clade_522 | clade_92 | hetero | ++++ | FALSE | TRUE |
| SPC10197 | clade_522 | clade_309 | hetero | | FALSE | FALSE |
| SPC10211 | clade_522 | clade_170 | hetero | + | FALSE | FALSE |
| SPC10213 | clade_522 | clade_85 | hetero | | FALSE | FALSE |
| SPC10233 | clade_522 | clade_262 | hetero | + | FALSE | FALSE |
| SPC10243 | clade_522 | clade_408 | hetero | + | FALSE | FALSE |
| SPC10298 | clade_522 | clade_172 | hetero | ++++ | FALSE | TRUE |
| SPC10301 | clade_522 | clade_172 | hetero | ++++ | FALSE | TRUE |
| SPC10304 | clade_522 | clade_262 | hetero | + | FALSE | TRUE |
| SPC10355 | clade_522 | clade_408 | hetero | | FALSE | TRUE |
| SPC10363 | clade_522 | clade_444 | hetero | | FALSE | FALSE |

TABLE 4a-continued

| | | | | | | |
|---|---|---|---|---|---|---|
| SPC10386 | clade_522 | clade_478 | hetero | | FALSE | TRUE |
| SPC10388 | clade_522 | clade_466 | hetero | | FALSE | FALSE |
| SPC10390 | clade_522 | clade_260 | hetero | | FALSE | FALSE |
| SPC10403 | clade_522 | clade_309 | hetero | | FALSE | FALSE |
| SPC10414 | clade_522 | clade_500 | hetero | − | FALSE | FALSE |
| SPC10415 | clade_522 | clade_309 | hetero | −− | FALSE | FALSE |
| SPC00026 | clade_262 | clade_262 | homo | + | FALSE | |
| SPC00027 | clade_262 | clade_351 | hetero | +++ | FALSE | TRUE |
| SPC00054 | clade_262 | clade_478 | hetero | | FALSE | FALSE |
| SPC00056 | clade_262 | clade_466 | hetero | | FALSE | FALSE |
| SPC00057 | clade_262 | clade_360 | hetero | | FALSE | TRUE |
| SPC00061 | clade_262 | clade_444 | hetero | | FALSE | FALSE |
| SPC00080 | clade_262 | clade_393 | hetero | | FALSE | FALSE |
| SPC10001 | clade_262 | clade_479 | hetero | | FALSE | FALSE |
| SPC10019 | clade_262 | clade_110 | hetero | | FALSE | FALSE |
| SPC10030 | clade_262 | clade_38 | hetero | | FALSE | FALSE |
| SPC10048 | clade_262 | clade_286 | hetero | + | FALSE | FALSE |
| SPC10081 | clade_262 | clade_378 | hetero | | FALSE | FALSE |
| SPC10097 | clade_262 | clade_553 | hetero | | FALSE | FALSE |
| SPC10110 | clade_262 | clade_92 | hetero | +++ | FALSE | FALSE |
| SPC10197 | clade_262 | clade_309 | hetero | | FALSE | FALSE |
| SPC10211 | clade_262 | clade_170 | hetero | | FALSE | FALSE |
| SPC10213 | clade_262 | clade_85 | hetero | | FALSE | FALSE |
| SPC10233 | clade_262 | clade_262 | hetero | | FALSE | FALSE |
| SPC10243 | clade_262 | clade_408 | hetero | | FALSE | FALSE |
| SPC10298 | clade_262 | clade_172 | hetero | ++++ | TRUE | TRUE |
| SPC10301 | clade_262 | clade_172 | hetero | ++++ | TRUE | FALSE |
| SPC10304 | clade_262 | clade_262 | hetero | | FALSE | FALSE |
| SPC10355 | clade_262 | clade_408 | hetero | + | FALSE | FALSE |
| SPC10363 | clade_262 | clade_444 | hetero | − | FALSE | FALSE |
| SPC10386 | clade_262 | clade_478 | hetero | − | FALSE | FALSE |
| SPC10388 | clade_262 | clade_466 | hetero | −− | FALSE | FALSE |
| SPC10390 | clade_262 | clade_260 | hetero | − | FALSE | FALSE |
| SPC10403 | clade_262 | clade_309 | hetero | − | FALSE | FALSE |
| SPC10414 | clade_262 | clade_500 | hetero | | FALSE | FALSE |
| SPC10415 | clade_262 | clade_309 | hetero | | FALSE | FALSE |
| SPC00027 | clade_351 | clade_351 | homo | ++ | FALSE | |
| SPC00054 | clade_351 | clade_478 | hetero | + | FALSE | FALSE |
| SPC00056 | clade_351 | clade_466 | hetero | | FALSE | FALSE |
| SPC00057 | clade_351 | clade_360 | hetero | − | FALSE | FALSE |
| SPC00061 | clade_351 | clade_444 | hetero | −− | FALSE | FALSE |
| SPC00080 | clade_351 | clade_393 | hetero | −− | FALSE | FALSE |
| SPC10001 | clade_351 | clade_479 | hetero | − | FALSE | FALSE |
| SPC10019 | clade_351 | clade_110 | hetero | | FALSE | FALSE |
| SPC10030 | clade_351 | clade_38 | hetero | | FALSE | FALSE |
| SPC10048 | clade_351 | clade_286 | hetero | ++ | FALSE | FALSE |
| SPC10081 | clade_351 | clade_378 | hetero | ++ | FALSE | TRUE |
| SPC10097 | clade_351 | clade_553 | hetero | +++ | FALSE | TRUE |
| SPC10110 | clade_351 | clade_92 | hetero | +++ | FALSE | FALSE |
| SPC10197 | clade_351 | clade_309 | hetero | − | FALSE | FALSE |
| SPC10211 | clade_351 | clade_170 | hetero | | FALSE | FALSE |
| SPC10213 | clade_351 | clade_85 | hetero | | FALSE | FALSE |
| SPC10233 | clade_351 | clade_262 | hetero | | FALSE | FALSE |
| SPC10243 | clade_351 | clade_408 | hetero | | FALSE | FALSE |
| SPC10298 | clade_351 | clade_172 | hetero | ++ | FALSE | FALSE |
| SPC10301 | clade_351 | clade_172 | hetero | ++++ | FALSE | FALSE |
| SPC10304 | clade_351 | clade_262 | hetero | | FALSE | FALSE |
| SPC10355 | clade_351 | clade_408 | hetero | | FALSE | FALSE |
| SPC10363 | clade_351 | clade_444 | hetero | − | FALSE | FALSE |
| SPC10386 | clade_351 | clade_478 | hetero | − | FALSE | FALSE |
| SPC10388 | clade_351 | clade_466 | hetero | −−− | FALSE | FALSE |
| SPC10390 | clade_351 | clade_260 | hetero | | FALSE | FALSE |
| SPC10403 | clade_351 | clade_309 | hetero | | FALSE | FALSE |
| SPC10414 | clade_351 | clade_500 | hetero | | FALSE | FALSE |
| SPC10415 | clade_351 | clade_309 | hetero | | FALSE | FALSE |
| SPC00054 | clade_478 | clade_478 | homo | | FALSE | |
| SPC00056 | clade_478 | clade_466 | hetero | | FALSE | FALSE |
| SPC00057 | clade_478 | clade_360 | hetero | − | FALSE | FALSE |
| SPC00061 | clade_478 | clade_444 | hetero | | FALSE | FALSE |
| SPC00080 | clade_478 | clade_393 | hetero | | FALSE | FALSE |
| SPC10001 | clade_478 | clade_479 | hetero | − | FALSE | FALSE |
| SPC10019 | clade_478 | clade_110 | hetero | | FALSE | FALSE |
| SPC10030 | clade_478 | clade_38 | hetero | | FALSE | FALSE |
| SPC10048 | clade_478 | clade_286 | hetero | | FALSE | FALSE |
| SPC10081 | clade_478 | clade_378 | hetero | | FALSE | FALSE |
| SPC10097 | clade_478 | clade_553 | hetero | ++ | FALSE | TRUE |
| SPC10110 | clade_478 | clade_92 | hetero | +++ | FALSE | FALSE |
| SPC10197 | clade_478 | clade_309 | hetero | | FALSE | FALSE |
| SPC10211 | clade_478 | clade_170 | hetero | | FALSE | FALSE |
| SPC10213 | clade_478 | clade_85 | hetero | | FALSE | FALSE |

TABLE 4a-continued

| | | | | | | |
|---|---|---|---|---|---|---|
| SPC10233 | clade_478 | clade_262 | hetero | | FALSE | FALSE |
| SPC10243 | clade_478 | clade_408 | hetero | | FALSE | FALSE |
| SPC10298 | clade_478 | clade_172 | hetero | + | FALSE | FALSE |
| SPC10301 | clade_478 | clade_172 | hetero | | FALSE | FALSE |
| SPC10304 | clade_478 | clade_262 | hetero | | FALSE | FALSE |
| SPC10355 | clade_478 | clade_408 | hetero | | FALSE | FALSE |
| SPC10363 | clade_478 | clade_444 | hetero | – | FALSE | FALSE |
| SPC10386 | clade_478 | clade_478 | hetero | | FALSE | FALSE |
| SPC10388 | clade_478 | clade_466 | hetero | | FALSE | FALSE |
| SPC10390 | clade_478 | clade_260 | hetero | | FALSE | FALSE |
| SPC10403 | clade_478 | clade_309 | hetero | | FALSE | FALSE |
| SPC10414 | clade_478 | clade_500 | hetero | | FALSE | FALSE |
| SPC10415 | clade_478 | clade_309 | hetero | | FALSE | FALSE |
| SPC00056 | clade_466 | clade_466 | homo | | FALSE | |
| SPC00057 | clade_466 | clade_360 | hetero | | FALSE | TRUE |
| SPC00061 | clade_466 | clade_444 | hetero | | FALSE | FALSE |
| SPC00080 | clade_466 | clade_393 | hetero | | FALSE | FALSE |
| SPC10001 | clade_466 | clade_479 | hetero | | FALSE | FALSE |
| SPC10019 | clade_466 | clade_110 | hetero | | FALSE | FALSE |
| SPC10030 | clade_466 | clade_38 | hetero | | FALSE | FALSE |
| SPC10048 | clade_466 | clade_286 | hetero | | FALSE | FALSE |
| SPC10081 | clade_466 | clade_378 | hetero | | FALSE | FALSE |
| SPC10097 | clade_466 | clade_553 | hetero | ++ | FALSE | TRUE |
| SPC10110 | clade_466 | clade_92 | hetero | ++ | FALSE | TRUE |
| SPC10197 | clade_466 | clade_309 | hetero | – | FALSE | FALSE |
| SPC10211 | clade_466 | clade_170 | hetero | | FALSE | FALSE |
| SPC10213 | clade_466 | clade_85 | hetero | | FALSE | FALSE |
| SPC10233 | clade_466 | clade_262 | hetero | | FALSE | FALSE |
| SPC10243 | clade_466 | clade_408 | hetero | | FALSE | FALSE |
| SPC10298 | clade_466 | clade_172 | hetero | | FALSE | FALSE |
| SPC10301 | clade_466 | clade_172 | hetero | +++ | FALSE | FALSE |
| SPC10304 | clade_466 | clade_262 | hetero | | FALSE | FALSE |
| SPC10355 | clade_466 | clade_408 | hetero | | FALSE | FALSE |
| SPC10363 | clade_466 | clade_444 | hetero | – | FALSE | FALSE |
| SPC10386 | clade_466 | clade_478 | hetero | – | FALSE | FALSE |
| SPC10388 | clade_466 | clade_466 | hetero | –– | FALSE | FALSE |
| SPC10390 | clade_466 | clade_260 | hetero | – | FALSE | FALSE |
| SPC10403 | clade_466 | clade_309 | hetero | – | FALSE | FALSE |
| SPC10414 | clade_466 | clade_500 | hetero | | FALSE | FALSE |
| SPC10415 | clade_466 | clade_309 | hetero | – | FALSE | FALSE |
| SPC00057 | clade_360 | clade_360 | homo | | FALSE | |
| SPC00061 | clade_360 | clade_444 | hetero | | FALSE | FALSE |
| SPC00080 | clade_360 | clade_393 | hetero | | FALSE | TRUE |
| SPC10001 | clade_360 | clade_479 | hetero | | FALSE | TRUE |
| SPC10019 | clade_360 | clade_110 | hetero | | FALSE | TRUE |
| SPC10030 | clade_360 | clade_38 | hetero | | FALSE | FALSE |
| SPC10048 | clade_360 | clade_286 | hetero | | FALSE | FALSE |
| SPC10081 | clade_360 | clade_378 | hetero | | FALSE | FALSE |
| SPC10097 | clade_360 | clade_553 | hetero | +++ | FALSE | TRUE |
| SPC10110 | clade_360 | clade_92 | hetero | ++++ | TRUE | TRUE |
| SPC10197 | clade_360 | clade_309 | hetero | | FALSE | FALSE |
| SPC10211 | clade_360 | clade_170 | hetero | | FALSE | FALSE |
| SPC10213 | clade_360 | clade_85 | hetero | | FALSE | FALSE |
| SPC10233 | clade_360 | clade_262 | hetero | | FALSE | FALSE |
| SPC10243 | clade_360 | clade_408 | hetero | + | FALSE | FALSE |
| SPC10298 | clade_360 | clade_172 | hetero | ++++ | FALSE | TRUE |
| SPC10301 | clade_360 | clade_172 | hetero | +++ | FALSE | FALSE |
| SPC10304 | clade_360 | clade_262 | hetero | | FALSE | FALSE |
| SPC10355 | clade_360 | clade_408 | hetero | ++++ | TRUE | TRUE |
| SPC10363 | clade_360 | clade_444 | hetero | ++++ | FALSE | TRUE |
| SPC10386 | clade_360 | clade_478 | hetero | ++ | FALSE | TRUE |
| SPC10388 | clade_360 | clade_466 | hetero | ++++ | FALSE | TRUE |
| SPC10390 | clade_360 | clade_260 | hetero | +++ | FALSE | TRUE |
| SPC10403 | clade_360 | clade_309 | hetero | ++ | FALSE | TRUE |
| SPC10414 | clade_360 | clade_500 | hetero | +++ | FALSE | TRUE |
| SPC10415 | clade_360 | clade_309 | hetero | ++ | FALSE | TRUE |
| SPC00061 | clade_444 | clade_444 | homo | | FALSE | |
| SPC00080 | clade_444 | clade_393 | hetero | | FALSE | TRUE |
| SPC10001 | clade_444 | clade_479 | hetero | | FALSE | FALSE |
| SPC10019 | clade_444 | clade_110 | hetero | | FALSE | FALSE |
| SPC10030 | clade_444 | clade_38 | hetero | | FALSE | FALSE |
| SPC10048 | clade_444 | clade_286 | hetero | | FALSE | FALSE |
| SPC10081 | clade_444 | clade_378 | hetero | | FALSE | FALSE |
| SPC10097 | clade_444 | clade_553 | hetero | + | FALSE | TRUE |
| SPC10110 | clade_444 | clade_92 | hetero | + | FALSE | TRUE |
| SPC10197 | clade_444 | clade_309 | hetero | | FALSE | FALSE |
| SPC10211 | clade_444 | clade_170 | hetero | | FALSE | FALSE |
| SPC10213 | clade_444 | clade_85 | hetero | | FALSE | FALSE |
| SPC10233 | clade_444 | clade_262 | hetero | + | FALSE | FALSE |
| SPC10243 | clade_444 | clade_408 | hetero | + | FALSE | FALSE |

TABLE 4a-continued

| | | | | | | |
|---|---|---|---|---|---|---|
| SPC10298 | clade_444 | clade_172 | hetero | ++ | FALSE | FALSE |
| SPC10301 | clade_444 | clade_172 | hetero | ++ | FALSE | FALSE |
| SPC10304 | clade_444 | clade_262 | hetero | | FALSE | FALSE |
| SPC10355 | clade_444 | clade_408 | hetero | − | FALSE | FALSE |
| SPC10363 | clade_444 | clade_444 | hetero | −−− | FALSE | FALSE |
| SPC10386 | clade_444 | clade_478 | hetero | | FALSE | FALSE |
| SPC10388 | clade_444 | clade_466 | hetero | | FALSE | FALSE |
| SPC10390 | clade_444 | clade_260 | hetero | | FALSE | FALSE |
| SPC10403 | clade_444 | clade_309 | hetero | − | FALSE | FALSE |
| SPC10414 | clade_444 | clade_500 | hetero | | FALSE | FALSE |
| SPC10415 | clade_444 | clade_309 | hetero | − | FALSE | FALSE |
| SPC00080 | clade_393 | clade_393 | homo | | FALSE | |
| SPC10001 | clade_393 | clade_479 | hetero | | FALSE | TRUE |
| SPC10019 | clade_393 | clade_110 | hetero | | FALSE | TRUE |
| SPC10030 | clade_393 | clade_38 | hetero | | FALSE | FALSE |
| SPC10048 | clade_393 | clade_286 | hetero | ++ | FALSE | TRUE |
| SPC10081 | clade_393 | clade_378 | hetero | + | FALSE | TRUE |
| SPC10097 | clade_393 | clade_553 | hetero | +++ | FALSE | TRUE |
| SPC10110 | clade_393 | clade_92 | hetero | ++++ | FALSE | TRUE |
| SPC10197 | clade_393 | clade_309 | hetero | | FALSE | FALSE |
| SPC10211 | clade_393 | clade_170 | hetero | +++ | FALSE | TRUE |
| SPC10213 | clade_393 | clade_85 | hetero | | FALSE | FALSE |
| SPC10233 | clade_393 | clade_262 | hetero | + | FALSE | FALSE |
| SPC10243 | clade_393 | clade_408 | hetero | ++ | FALSE | FALSE |
| SPC10298 | clade_393 | clade_172 | hetero | | FALSE | FALSE |
| SPC10301 | clade_393 | clade_172 | hetero | | FALSE | FALSE |
| SPC10304 | clade_393 | clade_262 | hetero | − | FALSE | FALSE |
| SPC10355 | clade_393 | clade_408 | hetero | | FALSE | FALSE |
| SPC10363 | clade_393 | clade_444 | hetero | −− | FALSE | FALSE |
| SPC10386 | clade_393 | clade_478 | hetero | −− | FALSE | FALSE |
| SPC10388 | clade_393 | clade_466 | hetero | − | FALSE | FALSE |
| SPC10390 | clade_393 | clade_260 | hetero | | FALSE | FALSE |
| SPC10403 | clade_393 | clade_309 | hetero | −− | FALSE | FALSE |
| SPC10414 | clade_393 | clade_500 | hetero | | FALSE | FALSE |
| SPC10415 | clade_393 | clade_309 | hetero | −−− | FALSE | FALSE |
| SPC10001 | clade_479 | clade_479 | homo | | FALSE | |
| SPC10019 | clade_479 | clade_110 | hetero | | FALSE | TRUE |
| SPC10030 | clade_479 | clade_38 | hetero | | FALSE | FALSE |
| SPC10048 | clade_479 | clade_286 | hetero | | FALSE | FALSE |
| SPC10081 | clade_479 | clade_378 | hetero | | FALSE | TRUE |
| SPC10097 | clade_479 | clade_553 | hetero | +++ | FALSE | TRUE |
| SPC10110 | clade_479 | clade_92 | hetero | ++++ | FALSE | TRUE |
| SPC10197 | clade_479 | clade_309 | hetero | | FALSE | FALSE |
| SPC10211 | clade_479 | clade_170 | hetero | + | FALSE | FALSE |
| SPC10213 | clade_479 | clade_85 | hetero | | FALSE | FALSE |
| SPC10233 | clade_479 | clade_262 | hetero | | FALSE | FALSE |
| SPC10243 | clade_479 | clade_408 | hetero | +++ | FALSE | FALSE |
| SPC10298 | clade_479 | clade_172 | hetero | | FALSE | FALSE |
| SPC10301 | clade_479 | clade_172 | hetero | ++++ | TRUE | TRUE |
| SPC10304 | clade_479 | clade_262 | hetero | | FALSE | FALSE |
| SPC10355 | clade_479 | clade_408 | hetero | | FALSE | FALSE |
| SPC10363 | clade_479 | clade_444 | hetero | | FALSE | FALSE |
| SPC10386 | clade_479 | clade_478 | hetero | − | FALSE | FALSE |
| SPC10388 | clade_479 | clade_466 | hetero | − | FALSE | FALSE |
| SPC10390 | clade_479 | clade_260 | hetero | −− | FALSE | FALSE |
| SPC10403 | clade_479 | clade_309 | hetero | −−− | FALSE | FALSE |
| SPC10414 | clade_479 | clade_500 | hetero | −− | FALSE | FALSE |
| SPC10415 | clade_479 | clade_309 | hetero | −− | FALSE | FALSE |
| SPC10019 | clade_110 | clade_110 | homo | | FALSE | |
| SPC10030 | clade_110 | clade_38 | hetero | | FALSE | FALSE |
| SPC10048 | clade_110 | clade_286 | hetero | | FALSE | FALSE |
| SPC10081 | clade_110 | clade_378 | hetero | | FALSE | TRUE |
| SPC10097 | clade_110 | clade_553 | hetero | ++++ | TRUE | TRUE |
| SPC10110 | clade_110 | clade_92 | hetero | ++++ | TRUE | TRUE |
| SPC10197 | clade_110 | clade_309 | hetero | | FALSE | FALSE |
| SPC10211 | clade_110 | clade_170 | hetero | ++ | FALSE | FALSE |
| SPC10213 | clade_110 | clade_85 | hetero | | FALSE | FALSE |
| SPC10233 | clade_110 | clade_262 | hetero | + | FALSE | FALSE |
| SPC10243 | clade_110 | clade_408 | hetero | +++ | FALSE | TRUE |
| SPC10298 | clade_110 | clade_172 | hetero | − | FALSE | FALSE |
| SPC10301 | clade_110 | clade_172 | hetero | ++++ | TRUE | TRUE |
| SPC10304 | clade_110 | clade_262 | hetero | | FALSE | FALSE |
| SPC10355 | clade_110 | clade_408 | hetero | | FALSE | FALSE |
| SPC10363 | clade_110 | clade_444 | hetero | − | FALSE | FALSE |
| SPC10386 | clade_110 | clade_478 | hetero | − | FALSE | FALSE |
| SPC10388 | clade_110 | clade_466 | hetero | −− | FALSE | FALSE |
| SPC10390 | clade_110 | clade_260 | hetero | −−− | FALSE | FALSE |
| SPC10403 | clade_110 | clade_309 | hetero | − | FALSE | FALSE |
| SPC10414 | clade_110 | clade_500 | hetero | | FALSE | FALSE |
| SPC10415 | clade_110 | clade_309 | hetero | | FALSE | FALSE |

TABLE 4a-continued

| | | | | | | |
|---|---|---|---|---|---|---|
| SPC10030 | clade_38 | clade_38 | homo | + | FALSE | |
| SPC10048 | clade_38 | clade_286 | hetero | | FALSE | FALSE |
| SPC10081 | clade_38 | clade_378 | hetero | | FALSE | FALSE |
| SPC10097 | clade_38 | clade_553 | hetero | ++++ | TRUE | TRUE |
| SPC10110 | clade_38 | clade_92 | hetero | ++++ | TRUE | TRUE |
| SPC10197 | clade_38 | clade_309 | hetero | | FALSE | FALSE |
| SPC10211 | clade_38 | clade_170 | hetero | | FALSE | FALSE |
| SPC10213 | clade_38 | clade_85 | hetero | | FALSE | FALSE |
| SPC10233 | clade_38 | clade_262 | hetero | ++++ | TRUE | FALSE |
| SPC10243 | clade_38 | clade_408 | hetero | +++ | FALSE | FALSE |
| SPC10298 | clade_38 | clade_172 | hetero | ++++ | TRUE | TRUE |
| SPC10301 | clade_38 | clade_172 | hetero | ++++ | TRUE | TRUE |
| SPC10304 | clade_38 | clade_262 | hetero | | FALSE | FALSE |
| SPC10355 | clade_38 | clade_408 | hetero | | FALSE | FALSE |
| SPC10363 | clade_38 | clade_444 | hetero | | FALSE | FALSE |
| SPC10386 | clade_38 | clade_478 | hetero | | FALSE | FALSE |
| SPC10388 | clade_38 | clade_466 | hetero | – | FALSE | FALSE |
| SPC10390 | clade_38 | clade_260 | hetero | – | FALSE | FALSE |
| SPC10403 | clade_38 | clade_309 | hetero | | FALSE | FALSE |
| SPC10414 | clade_38 | clade_500 | hetero | | FALSE | FALSE |
| SPC10415 | clade_38 | clade_309 | hetero | | FALSE | FALSE |
| SPC10048 | clade_286 | clade_286 | homo | + | FALSE | |
| SPC10081 | clade_286 | clade_378 | hetero | | FALSE | FALSE |
| SPC10097 | clade_286 | clade_553 | hetero | ++++ | FALSE | TRUE |
| SPC10110 | clade_286 | clade_92 | hetero | ++++ | FALSE | TRUE |
| SPC10197 | clade_286 | clade_309 | hetero | | FALSE | FALSE |
| SPC10211 | clade_286 | clade_170 | hetero | | FALSE | FALSE |
| SPC10213 | clade_286 | clade_85 | hetero | | FALSE | FALSE |
| SPC10233 | clade_286 | clade_262 | hetero | + | FALSE | FALSE |
| SPC10243 | clade_286 | clade_408 | hetero | + | FALSE | FALSE |
| SPC10298 | clade_286 | clade_172 | hetero | ++++ | TRUE | TRUE |
| SPC10301 | clade_286 | clade_172 | hetero | ++++ | TRUE | FALSE |
| SPC10304 | clade_286 | clade_262 | hetero | | FALSE | FALSE |
| SPC10355 | clade_386 | clade_408 | hetero | | FALSE | FALSE |
| SPC10363 | clade_286 | clade_444 | hetero | | FALSE | FALSE |
| SPC10386 | clade_286 | clade_478 | hetero | – | FALSE | FALSE |
| SPC10388 | clade_286 | clade_466 | hetero | | FALSE | FALSE |
| SPC10390 | clade_386 | clade_380 | hetero | | FALSE | FALSE |
| SPC10403 | clade_286 | clade_309 | hetero | | FALSE | FALSE |
| SPC10414 | clade_386 | clade_500 | hetero | | FALSE | FALSE |
| SPC10415 | clade_386 | clade_309 | hetero | ++ | FALSE | FALSE |
| SPC10081 | clade_378 | clade_378 | homo | | FALSE | |
| SPC10097 | clade_378 | clade_553 | hetero | +++ | FALSE | TRUE |
| SPC10110 | clade_378 | clade_92 | hetero | ++++ | TRUE | TRUE |
| SPC10197 | clade_378 | clade_309 | hetero | | FALSE | FALSE |
| SPC10211 | clade_378 | clade_170 | hetero | | FALSE | FALSE |
| SPC10213 | clade_378 | clade_85 | hetero | | FALSE | FALSE |
| SPC10233 | clade_378 | clade_262 | hetero | +++ | FALSE | FALSE |
| SPC10243 | clade_378 | clade_408 | hetero | ++++ | FALSE | TRUE |
| SPC10298 | clade_378 | clade_172 | hetero | ++++ | FALSE | TRUE |
| SPC10301 | clade_378 | clade_172 | hetero | ++++ | TRUE | TRUE |
| SPC10304 | clade_378 | clade_262 | hetero | | FALSE | FALSE |
| SPC10355 | clade_378 | clade_408 | hetero | | FALSE | FALSE |
| SPC10363 | clade_378 | clade_444 | hetero | | FALSE | FALSE |
| SPC10386 | clade_378 | clade_478 | hetero | –– | FALSE | FALSE |
| SPC10388 | clade_378 | clade_466 | hetero | | FALSE | FALSE |
| SPC10390 | clade_378 | clade_260 | hetero | – | FALSE | FALSE |
| SPC10403 | clade_378 | clade_309 | hetero | | FALSE | FALSE |
| SPC10414 | clade_378 | clade_500 | hetero | | FALSE | TRUE |
| SPC10415 | clade_378 | clade_309 | hetero | +++ | FALSE | TRUE |
| SPC10097 | clade_553 | clade_553 | homo | ++ | FALSE | |
| SPC10110 | clade_553 | clade_92 | hetero | ++++ | TRUE | TRUE |
| SPC10197 | clade_553 | clade_309 | hetero | ++++ | FALSE | FALSE |
| SPC10211 | clade_553 | clade_170 | hetero | ++++ | FALSE | FALSE |
| SPC10213 | clade_553 | clade_85 | hetero | ++++ | FALSE | TRUE |
| SPC10233 | clade_553 | clade_262 | hetero | ++++ | TRUE | FALSE |
| SPC10243 | clade_553 | clade_408 | hetero | ++++ | TRUE | TRUE |
| SPC10298 | clade_553 | clade_172 | hetero | ++++ | TRUE | TRUE |
| SPC10301 | clade_553 | clade_172 | hetero | ++++ | TRUE | TRUE |
| SPC10304 | clade_553 | clade_262 | hetero | ++++ | FALSE | TRUE |
| SPC10355 | clade_553 | clade_408 | hetero | ++++ | FALSE | TRUE |
| SPC10363 | clade_553 | clade_444 | hetero | +++ | FALSE | TRUE |
| SPC10386 | clade_553 | clade_478 | hetero | ++++ | FALSE | TRUE |
| SPC10388 | clade_553 | clade_466 | hetero | ++++ | FALSE | TRUE |
| SPC10390 | clade_553 | clade_260 | hetero | ++++ | FALSE | TRUE |
| SPC10403 | clade_553 | clade_309 | hetero | +++ | FALSE | TRUE |
| SPC10414 | clade_553 | clade_500 | hetero | ++++ | FALSE | TRUE |
| SPC10415 | clade_553 | clade_309 | hetero | ++++ | TRUE | TRUE |
| SPC10110 | clade_92 | clade_92 | homo | +++ | FALSE | |
| SPC10197 | clade_92 | clade_309 | hetero | +++ | FALSE | FALSE |

TABLE 4a-continued

| | | | | | | |
|---|---|---|---|---|---|---|
| SPC10211 | clade_92 | clade_170 | hetero | ++++ | TRUE | TRUE |
| SPC10213 | clade_92 | clade_85 | hetero | ++++ | TRUE | TRUE |
| SPC10233 | clade_92 | clade_262 | hetero | ++++ | FALSE | FALSE |
| SPC10243 | clade_92 | clade_408 | hetero | ++++ | FALSE | FALSE |
| SPC10298 | clade_92 | clade_172 | hetero | ++++ | TRUE | TRUE |
| SPC10301 | clade_92 | clade_172 | hetero | ++++ | TRUE | FALSE |
| SPC10304 | clade_92 | clade_262 | hetero | +++ | FALSE | TRUE |
| SPC10355 | clade_92 | clade_408 | hetero | ++++ | FALSE | TRUE |
| SPC10363 | clade_92 | clade_444 | hetero | ++++ | FALSE | TRUE |
| SPC10386 | clade_92 | clade_478 | hetero | + | FALSE | FALSE |
| SPC10388 | clade_92 | clade_466 | hetero | +++ | FALSE | TRUE |
| SPC10390 | clade_92 | clade_260 | hetero | ++++ | FALSE | TRUE |
| SPC10403 | clade_92 | clade_309 | hetero | +++ | FALSE | TRUE |
| SPC10414 | clade_92 | clade_500 | hetero | ++++ | TRUE | TRUE |
| SPC10415 | clade_92 | clade_309 | hetero | ++++ | FALSE | FALSE |
| SPC10197 | clade_309 | clade_309 | homo | ++++ | TRUE | |
| SPC10211 | clade_309 | clade_170 | hetero | ++++ | TRUE | FALSE |
| SPC10213 | clade_309 | clade_85 | hetero | ++++ | TRUE | FALSE |
| SPC10233 | clade_309 | clade_262 | hetero | ++++ | TRUE | FALSE |
| SPC10243 | clade_309 | clade_408 | hetero | ++++ | TRUE | TRUE |
| SPC10298 | clade_309 | clade_172 | hetero | +++ | FALSE | FALSE |
| SPC10301 | clade_309 | clade_172 | hetero | ++++ | TRUE | FALSE |
| SPC10304 | clade_309 | clade_262 | hetero | ++++ | FALSE | TRUE |
| SPC10355 | clade_309 | clade_408 | hetero | +++ | FALSE | FALSE |
| SPC10363 | clade_309 | clade_444 | hetero | + | FALSE | FALSE |
| SPC10386 | clade_309 | clade_478 | hetero | | FALSE | FALSE |
| SPC10388 | clade_309 | clade_466 | hetero | | FALSE | FALSE |
| SPC10390 | clade_309 | clade_260 | hetero | | FALSE | FALSE |
| SPC10403 | clade_309 | clade_309 | hetero | | FALSE | FALSE |
| SPC10414 | clade_309 | clade_500 | hetero | | FALSE | FALSE |
| SPC10415 | clade_309 | clade_309 | hetero | | FALSE | FALSE |
| SPC10211 | clade_170 | clade_170 | homo | ++++ | TRUE | |
| SPC10213 | clade_170 | clade_85 | hetero | ++++ | TRUE | FALSE |
| SPC10233 | clade_170 | clade_262 | hetero | ++++ | TRUE | FALSE |
| SPC10243 | clade_170 | clade_408 | hetero | ++++ | FALSE | FALSE |
| SPC10298 | clade_170 | clade_172 | hetero | ++++ | FALSE | FALSE |
| SPC10301 | clade_170 | clade_172 | hetero | ++++ | TRUE | FALSE |
| SPC10304 | clade_170 | clade_262 | hetero | +++ | FALSE | FALSE |
| SPC10355 | clade_170 | clade_408 | hetero | ++ | FALSE | FALSE |
| SPC10363 | clade_170 | clade_444 | hetero | | FALSE | FALSE |
| SPC10386 | clade_170 | clade_478 | hetero | | FALSE | FALSE |
| SPC10388 | clade_170 | clade_466 | hetero | | FALSE | FALSE |
| SPC10390 | clade_170 | clade_260 | hetero | | FALSE | FALSE |
| SPC10403 | clade_170 | clade_309 | hetero | | FALSE | FALSE |
| SPC10414 | clade_170 | clade_500 | hetero | | FALSE | FALSE |
| SPC10415 | clade_170 | clade_309 | hetero | | FALSE | FALSE |
| SPC10213 | clade_85 | clade_85 | homo | +++ | FALSE | |
| SPC10233 | clade_85 | clade_262 | hetero | ++++ | TRUE | FALSE |
| SPC10243 | clade_85 | clade_408 | hetero | ++++ | TRUE | FALSE |
| SPC10298 | clade_85 | clade_172 | hetero | ++++ | FALSE | FALSE |
| SPC10301 | clade_85 | clade_172 | hetero | ++++ | TRUE | FALSE |
| SPC10304 | clade_85 | clade_262 | hetero | ++ | FALSE | FALSE |
| SPC10355 | clade_85 | clade_408 | hetero | +++ | FALSE | FALSE |
| SPC10363 | clade_85 | clade_444 | hetero | | FALSE | FALSE |
| SPC10386 | clade_85 | clade_478 | hetero | | FALSE | FALSE |
| SPC10388 | clade_85 | clade_466 | hetero | | FALSE | FALSE |
| SPC10390 | clade_38 | clade_260 | hetero | | FALSE | FALSE |
| SPC10403 | clade_38 | clade_309 | hetero | − | FALSE | FALSE |
| SPC10414 | clade_85 | clade_500 | hetero | − | FALSE | FALSE |
| SPC10415 | clade_38 | clade_309 | hetero | | FALSE | FALSE |
| SPC10233 | clade_262 | clade_262 | homo | ++++ | TRUE | |
| SPC10243 | clade_262 | clade_408 | hetero | ++++ | TRUE | TRUE |
| SPC10298 | clade_262 | clade_172 | hetero | ++++ | TRUE | FALSE |
| SPC10301 | clade_262 | clade_172 | hetero | ++++ | TRUE | FALSE |
| SPC10304 | clade_262 | clade_262 | hetero | ++++ | FALSE | FALSE |
| SPC10355 | clade_262 | clade_408 | hetero | + | FALSE | FALSE |
| SPC10363 | clade_262 | clade_444 | hetero | | FALSE | FALSE |
| SPC10386 | clade_262 | clade_478 | hetero | | FALSE | FALSE |
| SPC10388 | clade_262 | clade_466 | hetero | | FALSE | FALSE |
| SPC10390 | clade_262 | clade_260 | hetero | | FALSE | FALSE |
| SPC10403 | clade_262 | clade_309 | hetero | | FALSE | FALSE |
| SPC10414 | clade_262 | clade_500 | hetero | | FALSE | FALSE |
| SPC10415 | clade_262 | clade_309 | hetero | | FALSE | FALSE |
| SPC10243 | clade_408 | clade_408 | homo | ++++ | TRUE | |
| SPC10298 | clade_408 | clade_172 | hetero | ++++ | TRUE | FALSE |
| SPC10301 | clade_408 | clade_172 | hetero | ++++ | TRUE | TRUE |
| SPC10304 | clade_408 | clade_262 | hetero | ++++ | FALSE | TRUE |
| SPC10355 | clade_408 | clade_408 | hetero | +++ | FALSE | FALSE |
| SPC10363 | clade_408 | clade_444 | hetero | ++++ | FALSE | TRUE |
| SPC10386 | clade_408 | clade_478 | hetero | ++ | FALSE | FALSE |

TABLE 4a-continued

| | | | | | | |
|---|---|---|---|---|---|---|
| SPC10388 | clade_408 | clade_466 | hetero | +++ | FALSE | FALSE |
| SPC10390 | clade_408 | clade_260 | hetero | +++ | FALSE | FALSE |
| SPC10403 | clade_408 | clade_309 | hetero | +++ | FALSE | FALSE |
| SPC10414 | clade_408 | clade_500 | hetero | +++ | FALSE | FALSE |
| SPC10415 | clade_408 | clade_309 | hetero | ++ | FALSE | FALSE |
| SPC10298 | clade_172 | clade_172 | homo | ++++ | TRUE | |
| SPC10301 | clade_172 | clade_172 | hetero | ++++ | TRUE | TRUE |
| SPC10304 | clade_172 | clade_262 | hetero | ++++ | FALSE | TRUE |
| SPC10355 | clade_172 | clade_408 | hetero | + | FALSE | FALSE |
| SPC10363 | clade_172 | clade_444 | hetero | | FALSE | FALSE |
| SPC10386 | clade_172 | clade_478 | hetero | | FALSE | FALSE |
| SPC10388 | clade_172 | clade_466 | hetero | ++ | FALSE | FALSE |
| SPC10390 | clade_172 | clade_260 | hetero | | FALSE | FALSE |
| SPC10403 | clade_172 | clade_309 | hetero | | FALSE | FALSE |
| SPC10414 | clade_172 | clade_500 | hetero | | FALSE | FALSE |
| SPC10415 | clade_172 | clade_309 | hetero | | FALSE | FALSE |
| SPC10301 | clade_172 | clade_172 | homo | ++++ | TRUE | |
| SPC10304 | clade_172 | clade_262 | hetero | ++++ | TRUE | TRUE |
| SPC10355 | clade_172 | clade_408 | hetero | ++++ | FALSE | FALSE |
| SPC10363 | clade_172 | clade_444 | hetero | ++++ | TRUE | TRUE |
| SPC10386 | clade_172 | clade_478 | hetero | | FALSE | FALSE |
| SPC10388 | clade_172 | clade_466 | hetero | ++++ | TRUE | FALSE |
| SPC10390 | clade_172 | clade_260 | hetero | ++++ | FALSE | FALSE |
| SPC10403 | clade_172 | clade_309 | hetero | + | FALSE | FALSE |
| SPC10414 | clade_172 | clade_500 | hetero | +++ | FALSE | FALSE |
| SPC10415 | clade_172 | clade_309 | hetero | +++ | FALSE | FALSE |
| SPC10304 | clade_262 | clade_262 | homo | | FALSE | |
| SPC10355 | clade_262 | clade_408 | hetero | ++ | FALSE | FALSE |
| SPC10363 | clade_262 | clade_444 | hetero | + | FALSE | TRUE |
| SPC10386 | clade_262 | clade_478 | hetero | + | FALSE | TRUE |
| SPC10388 | clade_262 | clade_466 | hetero | | FALSE | FALSE |
| SPC10390 | clade_262 | clade_260 | hetero | ++++ | FALSE | TRUE |
| SPC10403 | clade_262 | clade_309 | hetero | | FALSE | TRUE |
| SPC10414 | clade_262 | clade_380 | hetero | | FALSE | FALSE |
| SPC10415 | clade_262 | clade_309 | hetero | ++++ | TRUE | TRUE |
| SPC10355 | clade_408 | clade_408 | homo | ++ | FALSE | |
| SPC10363 | clade_408 | clade_444 | hetero | + | FALSE | FALSE |
| SPC10386 | clade_408 | clade_478 | hetero | +++ | FALSE | TRUE |
| SPC10388 | clade_408 | clade_466 | hetero | + | FALSE | FALSE |
| SPC10390 | clade_408 | clade_260 | hetero | +++ | FALSE | FALSE |
| SPC10403 | clade_408 | clade_309 | hetero | | FALSE | FALSE |
| SPC10414 | clade_408 | clade_500 | hetero | | FALSE | FALSE |
| SPC10415 | clade_408 | clade_309 | hetero | ++++ | TRUE | TRUE |
| SPC10363 | clade_444 | clade_444 | homo | + | FALSE | |
| SPC10386 | clade_444 | clade_478 | hetero | + | FALSE | TRUE |
| SPC10388 | clade_444 | clade_466 | hetero | + | FALSE | FALSE |
| SPC10390 | clade_444 | clade_260 | hetero | | FALSE | FALSE |
| SPC10403 | clade_444 | clade_309 | hetero | | FALSE | FALSE |
| SPC10414 | clade_444 | clade_500 | hetero | | FALSE | FALSE |
| SPC10415 | clade_444 | clade_309 | hetero | + | FALSE | FALSE |
| SPC10386 | clade_478 | clade_478 | homo | | FALSE | |
| SPC10388 | clade_478 | clade_466 | hetero | + | FALSE | TRUE |
| SPC10390 | clade_478 | clade_260 | hetero | ++ | FALSE | TRUE |
| SPC10403 | clade_478 | clade_309 | hetero | | FALSE | TRUE |
| SPC10414 | clade_478 | clade_500 | hetero | | FALSE | TRUE |
| SPC10415 | clade_478 | clade_309 | hetero | ++++ | TRUE | TRUE |
| SPC10388 | clade_466 | clade_466 | homo | | FALSE | |
| SPC10390 | clade_466 | clade_260 | hetero | | FALSE | FALSE |
| SPC10403 | clade_466 | clade_309 | hetero | | FALSE | FALSE |
| SPC10414 | clade_466 | clade_500 | hetero | | FALSE | TRUE |
| SPC10415 | clade_466 | clade_309 | hetero | | FALSE | FALSE |
| SPC10390 | clade_260 | clade_260 | homo | ++ | FALSE | |
| SPC10403 | clade_260 | clade_309 | hetero | | FALSE | FALSE |
| SPC10414 | clade_260 | clade_500 | hetero | | FALSE | FALSE |
| SPC10415 | clade_260 | clade_309 | hetero | ++++ | TRUE | TRUE |
| SPC10403 | clade_309 | clade_309 | homo | | FALSE | |
| SPC10414 | clade_309 | clade_500 | hetero | | FALSE | TRUE |
| SPC10415 | clade_309 | clade_309 | hetero | | FALSE | FALSE |
| SPC10414 | clade_500 | clade_500 | homo | | FALSE | |
| SPC10415 | clade_500 | clade_309 | hetero | | FALSE | FALSE |
| SPC10415 | clade_309 | clade_309 | homo | ++++ | TRUE | |
| SPC10155 | clade_553 | clade_252 | hetero | | FALSE | FALSE |
| SPC10167 | clade_553 | clade_253 | hetero | – | FALSE | FALSE |
| SPC10202 | clade_553 | clade_351 | hetero | ++ | FALSE | FALSE |
| SPC10238 | clade_553 | clade_354 | hetero | ++++ | TRUE | TRUE |
| SPC10256 | clade_553 | clade_252 | hetero | ++++ | TRUE | TRUE |
| SPC10313 | clade_553 | clade_260 | hetero | +++ | FALSE | TRUE |
| SPC10325 | clade_553 | clade_408 | hetero | ++++ | FALSE | TRUE |
| SPC10358 | clade_553 | clade_494 | hetero | ++++ | TRUE | TRUE |
| SPC10468 | clade_553 | clade_360 | hetero | ++++ | FALSE | TRUE |

TABLE 4a-continued

| | | | | | | |
|---|---|---|---|---|---|---|
| SPC10470 | clade_553 | clade_537 | hetero | ++++ | FALSE | TRUE |
| SPC10567 | clade_553 | clade_444 | hetero | ++++ | FALSE | TRUE |
| SPC10097 | clade_252 | clade_553 | hetero | | FALSE | FALSE |
| SPC10155 | clade_252 | clade_252 | homo | ++ | FALSE | |
| SPC10167 | clade_252 | clade_253 | hetero | ++++ | FALSE | TRUE |
| SPC10202 | clade_252 | clade_351 | hetero | ++++ | TRUE | TRUE |
| SPC10238 | clade_252 | clade_354 | hetero | ++++ | TRUE | TRUE |
| SPC10256 | clade_252 | clade_252 | hetero | ++++ | TRUE | TRUE |
| SPC10304 | clade_252 | clade_262 | hetero | ++++ | TRUE | TRUE |
| SPC10313 | clade_252 | clade_260 | hetero | ++++ | TRUE | TRUE |
| SPC10325 | clade_252 | clade_408 | hetero | ++++ | TRUE | TRUE |
| SPC10355 | clade_252 | clade_408 | hetero | + | FALSE | FALSE |
| SPC10358 | clade_252 | clade_494 | hetero | ++++ | TRUE | TRUE |
| SPC10386 | clade_252 | clade_478 | hetero | ++++ | TRUE | TRUE |
| SPC10390 | clade_252 | clade_260 | hetero | ++++ | TRUE | TRUE |
| SPC10415 | clade_252 | clade_309 | hetero | ++++ | TRUE | TRUE |
| SPC10468 | clade_252 | clade_360 | hetero | ++++ | TRUE | TRUE |
| SPC10470 | clade_252 | clade_537 | hetero | ++++ | TRUE | TRUE |
| SPC10567 | clade_252 | clade_444 | hetero | ++++ | TRUE | TRUE |
| SPC10155 | clade_253 | clade_252 | hetero | ++++ | FALSE | TRUE |
| SPC10167 | clade_253 | clade_253 | homo | + | FALSE | |
| SPC10202 | clade_253 | clade_351 | hetero | ++ | FALSE | FALSE |
| SPC10238 | clade_253 | clade_354 | hetero | ++++ | TRUE | TRUE |
| SPC10256 | clade_253 | clade_252 | hetero | ++++ | TRUE | TRUE |
| SPC10304 | clade_253 | clade_262 | hetero | ++++ | FALSE | TRUE |
| SPC10313 | clade_253 | clade_260 | hetero | | FALSE | FALSE |
| SPC10325 | clade_253 | clade_408 | hetero | ++++ | FALSE | TRUE |
| SPC10355 | clade_253 | clade_408 | hetero | +++ | FALSE | TRUE |
| SPC10358 | clade_253 | clade_494 | hetero | ++++ | TRUE | TRUE |
| SPC10386 | clade_253 | clade_478 | hetero | | FALSE | FALSE |
| SPC10390 | clade_253 | clade_260 | hetero | ++++ | FALSE | TRUE |
| SPC10415 | clade_253 | clade_309 | hetero | ++++ | TRUE | TRUE |
| SPC10468 | clade_253 | clade_360 | hetero | ++++ | TRUE | TRUE |
| SPC10470 | clade_253 | clade_537 | hetero | | FALSE | FALSE |
| SPC10567 | clade_253 | clade_444 | hetero | ++++ | TRUE | TRUE |
| SPC10167 | clade_351 | clade_253 | hetero | ++ | FALSE | FALSE |
| SPC10202 | clade_351 | clade_351 | homo | +++ | FALSE | |
| SPC10238 | clade_351 | clade_354 | hetero | ++++ | TRUE | TRUE |
| SPC10256 | clade_351 | clade_252 | hetero | ++++ | TRUE | TRUE |
| SPC10304 | clade_351 | clade_262 | hetero | ++++ | FALSE | TRUE |
| SPC10313 | clade_351 | clade_260 | hetero | +++ | FALSE | TRUE |
| SPC10325 | clade_351 | clade_408 | hetero | ++++ | FALSE | TRUE |
| SPC10355 | clade_351 | clade_408 | hetero | ++++ | FALSE | TRUE |
| SPC10358 | clade_351 | clade_494 | hetero | ++++ | FALSE | TRUE |
| SPC10386 | clade_351 | clade_478 | hetero | ++++ | TRUE | TRUE |
| SPC10390 | clade_351 | clade_260 | hetero | ++++ | TRUE | TRUE |
| SPC10415 | clade_351 | clade_309 | hetero | ++++ | TRUE | TRUE |
| SPC10468 | clade_351 | clade_360 | hetero | ++++ | TRUE | TRUE |
| SPC10470 | clade_351 | clade_537 | hetero | ++++ | TRUE | TRUE |
| SPC10567 | clade_351 | clade_444 | hetero | ++++ | TRUE | TRUE |
| SPC10202 | clade_354 | clade_351 | hetero | ++++ | TRUE | TRUE |
| SPC10238 | clade_354 | clade_354 | homo | ++++ | TRUE | |
| SPC10256 | clade_354 | clade_252 | hetero | ++++ | TRUE | TRUE |
| SPC10304 | clade_354 | clade_262 | hetero | ++++ | TRUE | TRUE |
| SPC10313 | clade_354 | clade_260 | hetero | ++++ | TRUE | TRUE |
| SPC10325 | clade_354 | clade_408 | hetero | ++++ | TRUE | TRUE |
| SPC10355 | clade_354 | clade_408 | hetero | ++++ | TRUE | TRUE |
| SPC10358 | clade_354 | clade_494 | hetero | ++++ | TRUE | TRUE |
| SPC10386 | clade_354 | clade_478 | hetero | ++++ | TRUE | TRUE |
| SPC10390 | clade_354 | clade_260 | hetero | ++++ | TRUE | TRUE |
| SPC10415 | clade_354 | clade_309 | hetero | ++++ | TRUE | TRUE |
| SPC10468 | clade_354 | clade_360 | hetero | ++++ | TRUE | TRUE |
| SPC10470 | clade_354 | clade_537 | hetero | ++++ | TRUE | TRUE |
| SPC10567 | clade_354 | clade_444 | hetero | ++++ | TRUE | TRUE |
| SPC10238 | clade_252 | clade_354 | hetero | ++++ | TRUE | TRUE |
| SPC10256 | clade_252 | clade_252 | homo | ++++ | TRUE | |
| SPC10304 | clade_252 | clade_262 | hetero | ++++ | TRUE | TRUE |
| SPC10313 | clade_252 | clade_260 | hetero | ++++ | TRUE | TRUE |
| SPC10325 | clade_252 | clade_408 | hetero | ++++ | TRUE | TRUE |
| SPC10355 | clade_252 | clade_408 | hetero | ++++ | TRUE | TRUE |
| SPC10358 | clade_252 | clade_494 | hetero | ++++ | TRUE | TRUE |
| SPC10386 | clade_252 | clade_478 | hetero | ++++ | TRUE | TRUE |
| SPC10390 | clade_252 | clade_260 | hetero | ++++ | TRUE | TRUE |
| SPC10415 | clade_252 | clade_309 | hetero | ++++ | TRUE | TRUE |
| SPC10468 | clade_252 | clade_360 | hetero | ++++ | TRUE | TRUE |
| SPC10470 | clade_252 | clade_537 | hetero | ++++ | TRUE | TRUE |
| SPC10567 | clade_252 | clade_444 | hetero | ++++ | TRUE | TRUE |
| SPC10256 | clade_262 | clade_252 | hetero | ++++ | TRUE | TRUE |
| SPC10313 | clade_262 | clade_260 | hetero | | FALSE | TRUE |
| SPC10325 | clade_262 | clade_408 | hetero | +++ | FALSE | TRUE |

TABLE 4a-continued

| | | | | | | | | |
|---|---|---|---|---|---|---|---|---|
| SPC10358 | | clade_262 | clade_494 | | hetero | ++++ | FALSE | TRUE |
| SPC10468 | | clade_262 | clade_360 | | hetero | ++++ | TRUE | TRUE |
| SPC10470 | | clade_262 | clade_537 | | hetero | ++++ | FALSE | TRUE |
| SPC10567 | | clade_262 | clade_444 | | hetero | ++++ | FALSE | TRUE |
| SPC10304 | | clade_260 | clade_262 | | hetero | | FALSE | TRUE |
| SPC10313 | | clade_260 | clade_260 | | homo | | FALSE | |
| SPC10325 | | clade_260 | clade_408 | | hetero | | FALSE | FALSE |
| SPC10355 | | clade_260 | clade_408 | | hetero | ++ | FALSE | TRUE |
| SPC10358 | | clade_260 | clade_494 | | hetero | | FALSE | TRUE |
| SPC10386 | | clade_260 | clade_478 | | hetero | | FALSE | TRUE |
| SPC10390 | | clade_260 | clade_260 | | hetero | ++++ | TRUE | TRUE |
| SPC10415 | | clade_260 | clade_309 | | hetero | ++++ | TRUE | TRUE |
| SPC10468 | | clade_260 | clade_360 | | hetero | ++ | FALSE | TRUE |
| SPC10470 | | clade_260 | clade_537 | | hetero | | FALSE | TRUE |
| SPC10567 | | clade_260 | clade_444 | | hetero | | FALSE | TRUE |
| SPC10313 | | clade_408 | clade_260 | | hetero | | FALSE | FALSE |
| SPC10325 | | clade_408 | clade_408 | | homo | ++ | FALSE | |
| SPC10355 | | clade_408 | clade_408 | | hetero | +++ | FALSE | TRUE |
| SPC10358 | | clade_408 | clade_494 | | hetero | +++ | FALSE | TRUE |
| SPC10386 | | clade_408 | clade_478 | | hetero | + | FALSE | FALSE |
| SPC10390 | | clade_408 | clade_260 | | hetero | ++++ | TRUE | TRUE |
| SPC10415 | | clade_408 | clade_309 | | hetero | ++++ | TRUE | TRUE |
| SPC10468 | | clade_408 | clade_360 | | hetero | ++++ | FALSE | TRUE |
| SPC10470 | | clade_408 | clade_537 | | hetero | ++ | FALSE | TRUE |
| SPC10567 | | clade_408 | clade_444 | | hetero | + | FALSE | TRUE |
| SPC10325 | | clade_408 | clade_408 | | hetero | +++ | FALSE | TRUE |
| SPC10358 | | clade_408 | clade_494 | | hetero | +++ | FALSE | TRUE |
| SPC10468 | | clade_408 | clade_360 | | hetero | ++++ | FALSE | TRUE |
| SPC10470 | | clade_408 | clade_537 | | hetero | ++++ | FALSE | TRUE |
| SPC10567 | | clade_408 | clade_444 | | hetero | + | FALSE | TRUE |
| SPC10355 | | clade_494 | clade_408 | | hetero | +++ | FALSE | TRUE |
| SPC10358 | | clade_494 | clade_494 | | homo | | FALSE | |
| SPC10386 | | clade_494 | clade_478 | | hetero | | FALSE | FALSE |
| SPC10390 | | clade_494 | clade_260 | | hetero | +++ | FALSE | TRUE |
| SPC10415 | | clade_494 | clade_309 | | hetero | ++++ | TRUE | TRUE |
| SPC10468 | | clade_494 | clade_360 | | hetero | ++++ | TRUE | TRUE |
| SPC10470 | | clade_494 | clade_537 | | hetero | | FALSE | FALSE |
| SPC10567 | | clade_494 | clade_444 | | hetero | | FALSE | TRUE |
| SPC10358 | | clade_478 | clade_494 | | hetero | | FALSE | FALSE |
| SPC10468 | | clade_478 | clade_360 | | hetero | ++++ | FALSE | TRUE |
| SPC10470 | | clade_478 | clade_537 | | hetero | | FALSE | FALSE |
| SPC10567 | | clade_478 | clade_444 | | hetero | | FALSE | TRUE |
| SPC10468 | | clade_260 | clade_360 | | hetero | ++++ | FALSE | TRUE |
| SPC10470 | | clade_260 | clade_537 | | hetero | +++ | FALSE | TRUE |
| SPC10567 | | clade_260 | clade_444 | | hetero | ++ | FALSE | TRUE |
| SPC10468 | | clade_309 | clade_360 | | hetero | ++++ | TRUE | TRUE |
| SPC10470 | | clade_309 | clade_537 | | hetero | ++++ | TRUE | TRUE |
| SPC10567 | | clade_309 | clade_444 | | hetero | ++++ | TRUE | TRUE |
| SPC10415 | | clade_360 | clade_309 | | hetero | ++++ | TRUE | TRUE |
| SPC10468 | | clade_360 | clade_360 | | homo | + | FALSE | |
| SPC10470 | | clade_360 | clade_537 | | hetero | +++ | FALSE | TRUE |
| SPC10567 | | clade_360 | clade_444 | | hetero | +++ | FALSE | TRUE |
| SPC10468 | | clade_537 | clade_360 | | hetero | +++ | FALSE | TRUE |
| SPC10470 | | clade_537 | clade_537 | | homo | | FALSE | |
| SPC10567 | | clade_537 | clade_444 | | hetero | | FALSE | TRUE |
| SPC10470 | | clade_444 | clade_537 | | hetero | | FALSE | TRUE |
| SPC10567 | | clade_444 | clade_444 | | homo | | FALSE | |
| SPC10097 | SPC10097 | clade_553 | clade_553 | clade_553 | homo | ++ | FALSE | |
| SPC10097 | SPC10304 | clade_553 | clade_553 | clade_262 | semi | ++ | FALSE | FALSE |
| SPC10097 | SPC10325 | clade_553 | clade_553 | clade_408 | semi | ++++ | FALSE | FALSE |
| SPC10097 | SPC10355 | clade_553 | clade_553 | clade_408 | semi | +++ | FALSE | FALSE |
| SPC10097 | SPC10386 | clade_553 | clade_553 | clade_478 | semi | ++++ | FALSE | TRUE |
| SPC10097 | SPC10390 | clade_553 | clade_553 | clade_260 | semi | +++ | FALSE | FALSE |
| SPC10097 | SPC10415 | clade_553 | clade_553 | clade_309 | semi | ++++ | FALSE | TRUE |
| SPC10097 | SPC10567 | clade_553 | clade_553 | clade_444 | semi | | FALSE | FALSE |
| SPC10304 | SPC10304 | clade_553 | clade_262 | clade_262 | semi | | FALSE | FALSE |
| SPC10304 | SPC10325 | clade_553 | clade_262 | clade_408 | hetero | ++++ | FALSE | FALSE |
| SPC10304 | SPC10355 | clade_553 | clade_262 | clade_408 | hetero | +++ | FALSE | FALSE |
| SPC10304 | SPC10386 | clade_553 | clade_262 | clade_478 | hetero | ++++ | FALSE | TRUE |
| SPC10304 | SPC10390 | clade_553 | clade_262 | clade_260 | hetero | +++ | FALSE | FALSE |
| SPC10304 | SPC10415 | clade_553 | clade_262 | clade_309 | hetero | ++++ | FALSE | TRUE |
| SPC10304 | SPC10567 | clade_553 | clade_262 | clade_444 | hetero | +++ | FALSE | TRUE |
| SPC10325 | SPC10325 | clade_553 | clade_408 | clade_408 | semi | +++ | FALSE | FALSE |
| SPC10325 | SPC10355 | clade_553 | clade_408 | clade_408 | hetero | ++++ | FALSE | FALSE |
| SPC10325 | SPC10386 | clade_553 | clade_408 | clade_478 | hetero | ++++ | FALSE | TRUE |
| SPC10325 | SPC10390 | clade_553 | clade_408 | clade_260 | hetero | ++++ | FALSE | FALSE |
| SPC10325 | SPC10415 | clade_553 | clade_408 | clade_309 | hetero | ++++ | FALSE | TRUE |
| SPC10325 | SPC10567 | clade_553 | clade_408 | clade_444 | hetero | ++++ | FALSE | FALSE |
| SPC10355 | SPC10355 | clade_553 | clade_408 | clade_408 | semi | | FALSE | FALSE |
| SPC10355 | SPC10386 | clade_553 | clade_408 | clade_478 | hetero | | FALSE | FALSE |

TABLE 4a-continued

| | | | | | | | | |
|---|---|---|---|---|---|---|---|---|
| SPC10355 | SPC10390 | clade_553 | clade_408 | clade_260 | hetero | + | FALSE | FALSE |
| SPC10355 | SPC10415 | clade_553 | clade_408 | clade_309 | hetero | ++++ | FALSE | TRUE |
| SPC10355 | SPC10567 | clade_553 | clade_408 | clade_444 | hetero | | FALSE | FALSE |
| SPC10386 | SPC10386 | clade_553 | clade_478 | clade_478 | semi | ++++ | FALSE | TRUE |
| SPC10386 | SPC10390 | clade_553 | clade_478 | clade_260 | hetero | +++ | FALSE | FALSE |
| SPC10386 | SPC10415 | clade_553 | clade_478 | clade_309 | hetero | ++++ | TRUE | TRUE |
| SPC10386 | SPC10567 | clade_553 | clade_478 | clade_444 | hetero | +++ | FALSE | TRUE |
| SPC10390 | SPC10390 | clade_553 | clade_260 | clade_260 | semi | +++ | FALSE | FALSE |
| SPC10390 | SPC10415 | clade_553 | clade_260 | clade_309 | hetero | ++++ | FALSE | TRUE |
| SPC10390 | SPC10567 | clade_553 | clade_260 | clade_444 | hetero | ++++ | FALSE | FALSE |
| SPC10415 | SPC10415 | clade_553 | clade_309 | clade_309 | semi | ++++ | FALSE | FALSE |
| SPC10415 | SPC10567 | clade_553 | clade_309 | clade_444 | hetero | ++++ | FALSE | TRUE |
| SPC10567 | SPC10567 | clade_553 | clade_444 | clade_444 | semi | + | FALSE | TRUE |
| SPC10304 | SPC10304 | clade_262 | clade_262 | clade_262 | homo | | FALSE | |
| SPC10304 | SPC10325 | clade_262 | clade_262 | clade_408 | semi | | FALSE | FALSE |
| SPC10304 | SPC10355 | clade_262 | clade_262 | clade_408 | semi | | FALSE | FALSE |
| SPC10304 | SPC10386 | clade_262 | clade_262 | clade_478 | semi | | FALSE | FALSE |
| SPC10304 | SPC10390 | clade_262 | clade_262 | clade_260 | semi | | FALSE | FALSE |
| SPC10304 | SPC10415 | clade_262 | clade_262 | clade_309 | semi | ++++ | FALSE | TRUE |
| SPC10304 | SPC10567 | clade_262 | clade_262 | clade_444 | semi | −− | FALSE | FALSE |
| SPC10325 | SPC10325 | clade_262 | clade_408 | clade_408 | semi | ++ | FALSE | FALSE |
| SPC10325 | SPC10355 | clade_262 | clade_408 | clade_408 | hetero | | FALSE | FALSE |
| SPC10325 | SPC10386 | clade_262 | clade_408 | clade_478 | hetero | +++ | FALSE | FALSE |
| SPC10325 | SPC10390 | clade_262 | clade_408 | clade_260 | hetero | +++ | FALSE | FALSE |
| SPC10325 | SPC10415 | clade_262 | clade_408 | clade_309 | hetero | ++++ | FALSE | FALSE |
| SPC10325 | SPC10567 | clade_262 | clade_408 | clade_444 | hetero | −− | FALSE | FALSE |
| SPC10355 | SPC10355 | clade_262 | clade_408 | clade_408 | semi | | FALSE | FALSE |
| SPC10355 | SPC10386 | clade_262 | clade_408 | clade_478 | hetero | | FALSE | FALSE |
| SPC10355 | SPC10390 | clade_262 | clade_408 | clade_260 | hetero | | FALSE | FALSE |
| SPC10355 | SPC10415 | clade_262 | clade_408 | clade_309 | hetero | ++++ | FALSE | FALSE |
| SPC10355 | SPC10567 | clade_262 | clade_408 | clade_444 | hetero | −−− | FALSE | FALSE |
| SPC10386 | SPC10386 | clade_262 | clade_478 | clade_478 | semi | −−− | FALSE | FALSE |
| SPC10386 | SPC10390 | clade_262 | clade_478 | clade_260 | hetero | | FALSE | FALSE |
| SPC10386 | SPC10415 | clade_262 | clade_478 | clade_309 | hetero | ++++ | FALSE | TRUE |
| SPC10386 | SPC10567 | clade_262 | clade_478 | clade_444 | hetero | − | FALSE | FALSE |
| SPC10390 | SPC10390 | clade_262 | clade_260 | clade_260 | semi | + | FALSE | FALSE |
| SPC10390 | SPC10415 | clade_262 | clade_260 | clade_309 | hetero | ++++ | FALSE | TRUE |
| SPC10390 | SPC10567 | clade_262 | clade_260 | clade_444 | hetero | | FALSE | FALSE |
| SPC10415 | SPC10415 | clade_262 | clade_309 | clade_309 | semi | ++++ | FALSE | FALSE |
| SPC10415 | SPC10567 | clade_262 | clade_309 | clade_444 | hetero | ++++ | FALSE | TRUE |
| SPC10567 | SPC10567 | clade_262 | clade_444 | clade_444 | semi | − | FALSE | FALSE |
| SPC10325 | SPC10325 | clade_408 | clade_408 | clade_408 | homo | | FALSE | |
| SPC10325 | SPC10355 | clade_408 | clade_408 | clade_408 | semi | | FALSE | FALSE |
| SPC10325 | SPC10386 | clade_408 | clade_408 | clade_478 | semi | ++ | FALSE | FALSE |
| SPC10325 | SPC10390 | clade_408 | clade_408 | clade_260 | semi | ++ | FALSE | FALSE |
| SPC10325 | SPC10415 | clade_408 | clade_408 | clade_309 | semi | ++++ | FALSE | FALSE |
| SPC10325 | SPC10567 | clade_408 | clade_408 | clade_444 | semi | | FALSE | FALSE |
| SPC10355 | SPC10355 | clade_408 | clade_408 | clade_408 | semi | − | FALSE | FALSE |
| SPC10355 | SPC10386 | clade_408 | clade_408 | clade_478 | hetero | − | FALSE | FALSE |
| SPC10355 | SPC10390 | clade_408 | clade_408 | clade_260 | hetero | | FALSE | FALSE |
| SPC10355 | SPC10415 | clade_408 | clade_408 | clade_309 | hetero | ++++ | FALSE | FALSE |
| SPC10355 | SPC10567 | clade_408 | clade_408 | clade_444 | hetero | − | FALSE | FALSE |
| SPC10386 | SPC10386 | clade_408 | clade_478 | clade_478 | semi | | FALSE | FALSE |
| SPC10386 | SPC10390 | clade_408 | clade_478 | clade_260 | hetero | ++++ | FALSE | FALSE |
| SPC10386 | SPC10415 | clade_408 | clade_478 | clade_309 | hetero | ++++ | FALSE | TRUE |
| SPC10386 | SPC10567 | clade_408 | clade_478 | clade_444 | hetero | | FALSE | FALSE |
| SPC10390 | SPC10390 | clade_408 | clade_260 | clade_260 | semi | ++ | FALSE | FALSE |
| SPC10390 | SPC10415 | clade_408 | clade_260 | clade_309 | hetero | ++++ | FALSE | FALSE |
| SPC10390 | SPC10567 | clade_408 | clade_260 | clade_444 | hetero | + | FALSE | FALSE |
| SPC10415 | SPC10415 | clade_408 | clade_309 | clade_309 | semi | ++++ | FALSE | FALSE |
| SPC10415 | SPC10567 | clade_408 | clade_309 | clade_444 | hetero | ++++ | FALSE | TRUE |
| SPC10567 | SPC10567 | clade_408 | clade_444 | clade_444 | semi | −− | FALSE | FALSE |
| SPC10355 | SPC10355 | clade_408 | clade_408 | clade_408 | homo | | FALSE | |
| SPC10355 | SPC10386 | clade_408 | clade_408 | clade_478 | semi | | FALSE | FALSE |
| SPC10355 | SPC10390 | clade_408 | clade_408 | clade_260 | semi | + | FALSE | FALSE |
| SPC10355 | SPC10415 | clade_408 | clade_408 | clade_309 | semi | ++++ | FALSE | FALSE |
| SPC10355 | SPC10567 | clade_408 | clade_408 | clade_444 | semi | | FALSE | FALSE |
| SPC10386 | SPC10386 | clade_408 | clade_478 | clade_478 | semi | − | FALSE | FALSE |
| SPC10386 | SPC10390 | clade_408 | clade_478 | clade_260 | hetero | + | FALSE | FALSE |
| SPC10386 | SPC10415 | clade_408 | clade_478 | clade_309 | hetero | ++++ | FALSE | TRUE |
| SPC10386 | SPC10567 | clade_408 | clade_478 | clade_444 | hetero | | FALSE | FALSE |
| SPC10390 | SPC10390 | clade_408 | clade_260 | clade_260 | semi | +++ | FALSE | FALSE |
| SPC10390 | SPC10415 | clade_408 | clade_260 | clade_309 | hetero | ++++ | FALSE | TRUE |
| SPC10390 | SPC10567 | clade_408 | clade_260 | clade_444 | hetero | | FALSE | FALSE |
| SPC10415 | SPC10415 | clade_408 | clade_309 | clade_309 | semi | ++++ | FALSE | FALSE |
| SPC10415 | SPC10567 | clade_408 | clade_309 | clade_444 | hetero | ++++ | FALSE | TRUE |
| SPC10567 | SPC10567 | clade_408 | clade_444 | clade_444 | semi | | FALSE | FALSE |
| SPC10386 | SPC10386 | clade_478 | clade_478 | clade_478 | homo | − | FALSE | |
| SPC10386 | SPC10390 | clade_478 | clade_478 | clade_260 | semi | | FALSE | FALSE |
| SPC10386 | SPC10415 | clade_478 | clade_478 | clade_309 | semi | ++++ | FALSE | TRUE |

TABLE 4a-continued

| | | | | | | | | |
|---|---|---|---|---|---|---|---|---|
| SPC10386 | SPC10567 | clade_478 | clade_478 | clade_444 | semi | −−− | FALSE | FALSE |
| SPC10390 | SPC10390 | clade_478 | clade_260 | clade_260 | semi | +++ | FALSE | FALSE |
| SPC10390 | SPC10415 | clade_478 | clade_260 | clade_309 | hetero | ++++ | FALSE | TRUE |
| SPC10390 | SPC10567 | clade_478 | clade_260 | clade_444 | hetero | | FALSE | FALSE |
| SPC10415 | SPC10415 | clade_478 | clade_309 | clade_309 | semi | ++++ | FALSE | TRUE |
| SPC10415 | SPC10567 | clade_478 | clade_309 | clade_444 | hetero | ++++ | FALSE | TRUE |
| SPC10567 | SPC10567 | clade_478 | clade_444 | clade_444 | semi | − | FALSE | FALSE |
| SPC10390 | SPC10390 | clade_260 | clade_260 | clade_260 | homo | +++ | FALSE | |
| SPC10390 | SPC10415 | clade_260 | clade_260 | clade_309 | semi | ++++ | FALSE | TRUE |
| SPC10390 | SPC10567 | clade_260 | clade_260 | clade_444 | semi | + | FALSE | FALSE |
| SPC10415 | SPC10415 | clade_260 | clade_309 | clade_309 | semi | | FALSE | FALSE |
| SPC10415 | SPC10567 | clade_260 | clade_309 | clade_444 | hetero | ++++ | FALSE | TRUE |
| SPC10567 | SPC10567 | clade_260 | clade_444 | clade_444 | semi | | FALSE | FALSE |
| SPC10415 | SPC10415 | clade_309 | clade_309 | clade_309 | homo | ++++ | FALSE | |
| SPC10415 | SPC10567 | clade_309 | clade_309 | clade_444 | semi | ++++ | FALSE | TRUE |
| SPC10567 | SPC10567 | clade_309 | clade_444 | clade_444 | semi | ++++ | FALSE | TRUE |
| SPC10567 | SPC10567 | clade_444 | clade_444 | clade_444 | homo | | FALSE | |
| SPC10155 | SPC10155 | clade_553 | clade_252 | clade_252 | semi | ++++ | FALSE | FALSE |
| SPC10155 | SPC10167 | clade_553 | clade_382 | clade_253 | hetero | ++++ | FALSE | FALSE |
| SPC10155 | SPC10202 | clade_553 | clade_252 | clade_351 | hetero | ++++ | FALSE | FALSE |
| SPC10155 | SPC10238 | clade_553 | clade_252 | clade_354 | hetero | ++++ | FALSE | FALSE |
| SPC10155 | SPC10256 | clade_553 | clade_252 | clade_252 | hetero | ++++ | TRUE | TRUE |
| SPC10155 | SPC10313 | clade_553 | clade_252 | clade_260 | hetero | ++++ | FALSE | TRUE |
| SPC10155 | SPC10358 | clade_553 | clade_252 | clade_494 | hetero | ++++ | FALSE | TRUE |
| SPC10155 | SPC10468 | clade_553 | clade_252 | clade_360 | hetero | ++++ | FALSE | TRUE |
| SPC10155 | SPC10470 | clade_553 | clade_252 | clade_537 | hetero | ++++ | FALSE | FALSE |
| SPC10155 | SPC10613 | clade_553 | clade_382 | clade_309 | hetero | ++++ | FALSE | |
| SPC10167 | SPC10167 | clade_553 | clade_253 | clade_253 | semi | +++ | FALSE | FALSE |
| SPC10167 | SPC10202 | clade_553 | clade_253 | clade_351 | hetero | ++++ | FALSE | FALSE |
| SPC10167 | SPC10238 | clade_553 | clade_253 | clade_354 | hetero | ++++ | FALSE | TRUE |
| SPC10167 | SPC10256 | clade_553 | clade_253 | clade_252 | hetero | ++++ | TRUE | TRUE |
| SPC10167 | SPC10313 | clade_553 | clade_253 | clade_260 | hetero | ++++ | FALSE | FALSE |
| SPC10167 | SPC10358 | clade_553 | clade_253 | clade_494 | hetero | ++++ | FALSE | TRUE |
| SPC10167 | SPC10468 | clade_553 | clade_253 | clade_360 | hetero | ++++ | FALSE | FALSE |
| SPC10167 | SPC10470 | clade_553 | clade_253 | clade_537 | hetero | ++++ | FALSE | FALSE |
| SPC10167 | SPC10613 | clade_553 | clade_253 | clade_309 | hetero | ++++ | FALSE | |
| SPC10202 | SPC10202 | clade_553 | clade_351 | clade_351 | semi | ++++ | FALSE | FALSE |
| SPC10202 | SPC10238 | clade_553 | clade_351 | clade_354 | hetero | ++++ | FALSE | FALSE |
| SPC10202 | SPC10256 | clade_553 | clade_351 | clade_252 | hetero | ++++ | TRUE | TRUE |
| SPC10202 | SPC10313 | clade_553 | clade_351 | clade_260 | hetero | ++++ | FALSE | FALSE |
| SPC10202 | SPC10358 | clade_553 | clade_351 | clade_494 | hetero | ++++ | FALSE | TRUE |
| SPC10202 | SPC10468 | clade_553 | clade_351 | clade_360 | hetero | ++++ | FALSE | FALSE |
| SPC10202 | SPC10470 | clade_553 | clade_351 | clade_537 | hetero | ++++ | FALSE | TRUE |
| SPC10202 | SPC10613 | clade_553 | clade_351 | clade_309 | hetero | ++++ | FALSE | |
| SPC10238 | SPC10238 | clade_553 | clade_354 | clade_354 | semi | ++++ | FALSE | FALSE |
| SPC10238 | SPC10256 | clade_553 | clade_354 | clade_252 | hetero | ++++ | TRUE | FALSE |
| SPC10238 | SPC10313 | clade_553 | clade_354 | clade_260 | hetero | ++++ | FALSE | FALSE |
| SPC10238 | SPC10358 | clade_553 | clade_354 | clade_494 | hetero | ++++ | FALSE | TRUE |
| SPC10238 | SPC10468 | clade_553 | clade_354 | clade_360 | hetero | ++++ | FALSE | FALSE |
| SPC10238 | SPC10470 | clade_553 | clade_354 | clade_537 | hetero | ++++ | FALSE | TRUE |
| SPC10238 | SPC10613 | clade_553 | clade_354 | clade_309 | hetero | ++++ | FALSE | |
| SPC10256 | SPC10256 | clade_553 | clade_252 | clade_252 | semi | ++++ | TRUE | FALSE |
| SPC10256 | SPC10313 | clade_553 | clade_252 | clade_260 | hetero | ++++ | TRUE | TRUE |
| SPC10256 | SPC10358 | clade_553 | clade_252 | clade_494 | hetero | ++++ | TRUE | TRUE |
| SPC10256 | SPC10468 | clade_553 | clade_252 | clade_360 | hetero | ++++ | TRUE | TRUE |
| SPC10256 | SPC10470 | clade_553 | clade_252 | clade_537 | hetero | ++++ | TRUE | TRUE |
| SPC10256 | SPC10613 | clade_553 | clade_252 | clade_309 | hetero | ++++ | TRUE | |
| SPC10313 | SPC10313 | clade_553 | clade_260 | clade_260 | semi | ++ | FALSE | TRUE |
| SPC10313 | SPC10358 | clade_553 | clade_260 | clade_494 | hetero | ++++ | FALSE | TRUE |
| SPC10313 | SPC10468 | clade_553 | clade_260 | clade_360 | hetero | ++++ | FALSE | TRUE |
| SPC10313 | SPC10470 | clade_553 | clade_260 | clade_537 | hetero | ++++ | FALSE | TRUE |
| SPC10313 | SPC10613 | clade_553 | clade_260 | clade_309 | hetero | ++++ | FALSE | |
| SPC10358 | SPC10358 | clade_553 | clade_494 | clade_494 | semi | ++++ | FALSE | TRUE |
| SPC10358 | SPC10468 | clade_553 | clade_494 | clade_360 | hetero | ++++ | FALSE | TRUE |
| SPC10358 | SPC10470 | clade_553 | clade_494 | clade_537 | hetero | ++++ | FALSE | TRUE |
| SPC10358 | SPC10613 | clade_553 | clade_494 | clade_309 | hetero | ++++ | FALSE | |
| SPC10468 | SPC10468 | clade_553 | clade_360 | clade_360 | semi | ++++ | FALSE | TRUE |
| SPC10468 | SPC10470 | clade_553 | clade_360 | clade_537 | hetero | ++++ | FALSE | TRUE |
| SPC10468 | SPC10613 | clade_553 | clade_360 | clade_309 | hetero | ++++ | FALSE | |
| SPC10155 | SPC10155 | clade_262 | clade_252 | clade_252 | semi | −−−− | FALSE | FALSE |
| SPC10155 | SPC10167 | clade_262 | clade_252 | clade_253 | hetero | −−−− | FALSE | FALSE |
| SPC10155 | SPC10202 | clade_262 | clade_252 | clade_351 | hetero | | FALSE | FALSE |
| SPC10155 | SPC10238 | clade_262 | clade_252 | clade_354 | hetero | ++++ | TRUE | TRUE |
| SPC10155 | SPC10256 | clade_262 | clade_252 | clade_252 | hetero | ++++ | TRUE | TRUE |
| SPC10155 | SPC10313 | clade_262 | clade_252 | clade_260 | hetero | ++++ | FALSE | FALSE |
| SPC10155 | SPC10358 | clade_262 | clade_252 | clade_494 | hetero | ++++ | TRUE | TRUE |
| SPC10155 | SPC10468 | clade_262 | clade_252 | clade_360 | hetero | ++++ | FALSE | TRUE |
| SPC10155 | SPC10470 | clade_262 | clade_252 | clade_537 | hetero | ++ | FALSE | FALSE |
| SPC10155 | SPC10613 | clade_262 | clade_252 | clade_309 | hetero | ++++ | FALSE | |
| SPC10167 | SPC10167 | clade_262 | clade_253 | clade_253 | semi | −−−− | FALSE | FALSE |

TABLE 4a-continued

| | | | | | | | | |
|---|---|---|---|---|---|---|---|---|
| SPC10167 | SPC10202 | clade_262 | clade_553 | clade_351 | hetero | ---- | FALSE | FALSE |
| SPC10167 | SPC10238 | clade_262 | clade_253 | clade_354 | hetero | ++++ | FALSE | TRUE |
| SPC10167 | SPC10256 | clade_262 | clade_253 | clade_252 | hetero | ++++ | TRUE | TRUE |
| SPC10167 | SPC10313 | clade_262 | clade_253 | clade_260 | hetero | ---- | FALSE | FALSE |
| SPC10167 | SPC10358 | clade_262 | clade_253 | clade_494 | hetero | ---- | FALSE | FALSE |
| SPC10167 | SPC10468 | clade_262 | clade_553 | clade_360 | hetero | | FALSE | FALSE |
| SPC10167 | SPC10470 | clade_262 | clade_253 | clade_537 | hetero | ---- | FALSE | FALSE |
| SPC10167 | SPC10613 | clade_262 | clade_553 | clade_309 | hetero | ++ | FALSE | |
| SPC10202 | SPC10202 | clade_262 | clade_351 | clade_351 | semi | ---- | FALSE | FALSE |
| SPC10202 | SPC10238 | clade_262 | clade_351 | clade_354 | hetero | ++++ | FALSE | FALSE |
| SPC10202 | SPC10256 | clade_262 | clade_351 | clade_252 | hetero | ++++ | TRUE | TRUE |
| SPC10202 | SPC10313 | clade_262 | clade_351 | clade_260 | hetero | ---- | FALSE | FALSE |
| SPC10202 | SPC10358 | clade_262 | clade_351 | clade_494 | hetero | -- | FALSE | FALSE |
| SPC10202 | SPC10468 | clade_262 | clade_351 | clade_360 | hetero | ++++ | FALSE | FALSE |
| SPC10202 | SPC10470 | clade_262 | clade_351 | clade_537 | hetero | ++++ | FALSE | TRUE |
| SPC10202 | SPC10613 | clade_262 | clade_351 | clade_309 | hetero | ++++ | FALSE | |
| SPC10238 | SPC10238 | clade_262 | clade_354 | clade_354 | semi | ++++ | FALSE | FALSE |
| SPC10238 | SPC10256 | clade_262 | clade_354 | clade_252 | hetero | ++++ | TRUE | TRUE |
| SPC10238 | SPC10313 | clade_262 | clade_354 | clade_260 | hetero | ++++ | FALSE | TRUE |
| SPC10238 | SPC10358 | clade_262 | clade_354 | clade_494 | hetero | ++++ | FALSE | TRUE |
| SPC10238 | SPC10468 | clade_262 | clade_354 | clade_360 | hetero | ++++ | FALSE | FALSE |
| SPC10238 | SPC10470 | clade_262 | clade_354 | clade_537 | hetero | ++++ | FALSE | TRUE |
| SPC10238 | SPC10613 | clade_262 | clade_354 | clade_309 | hetero | ++++ | TRUE | |
| SPC10256 | SPC10256 | clade_262 | clade_252 | clade_252 | semi | ++++ | TRUE | FALSE |
| SPC10256 | SPC10313 | clade_262 | clade_252 | clade_260 | hetero | ++++ | TRUE | TRUE |
| SPC10256 | SPC10358 | clade_262 | clade_252 | clade_494 | hetero | ++++ | TRUE | TRUE |
| SPC10256 | SPC10468 | clade_262 | clade_252 | clade_360 | hetero | ++++ | TRUE | TRUE |
| SPC10256 | SPC10470 | clade_262 | clade_252 | clade_537 | hetero | ++++ | TRUE | TRUE |
| SPC10256 | SPC10613 | clade_262 | clade_252 | clade_309 | hetero | ++++ | TRUE | |
| SPC10313 | SPC10313 | clade_262 | clade_260 | clade_260 | semi | | FALSE | TRUE |
| SPC10313 | SPC10358 | clade_262 | clade_260 | clade_494 | hetero | | FALSE | FALSE |
| SPC10313 | SPC10468 | clade_262 | clade_260 | clade_360 | hetero | ++++ | FALSE | TRUE |
| SPC10313 | SPC10470 | clade_262 | clade_260 | clade_537 | hetero | + | FALSE | TRUE |
| SPC10313 | SPC10613 | clade_262 | clade_260 | clade_309 | hetero | ++++ | FALSE | |
| SPC10358 | SPC10358 | clade_262 | clade_494 | clade_494 | semi | ---- | FALSE | FALSE |
| SPC10358 | SPC10468 | clade_262 | clade_494 | clade_360 | hetero | ++++ | FALSE | FALSE |
| SPC10358 | SPC10470 | clade_262 | clade_494 | clade_537 | hetero | -- | FALSE | FALSE |
| SPC10358 | SPC10613 | clade_262 | clade_494 | clade_309 | hetero | ++++ | FALSE | |
| SPC10468 | SPC10468 | clade_262 | clade_360 | clade_360 | semi | ++++ | FALSE | FALSE |
| SPC10468 | SPC10470 | clade_262 | clade_360 | clade_537 | hetero | ++++ | FALSE | TRUE |
| SPC10468 | SPC10613 | clade_262 | clade_360 | clade_309 | hetero | ++++ | FALSE | |
| SPC10155 | SPC10155 | clade_408 | clade_252 | clade_252 | semi | ++++ | FALSE | FALSE |
| SPC10155 | SPC10167 | clade_408 | clade_252 | clade_253 | hetero | ++++ | FALSE | FALSE |
| SPC10155 | SPC10202 | clade_408 | clade_252 | clade_351 | hetero | ++++ | FALSE | FALSE |
| SPC10155 | SPC10238 | clade_408 | clade_252 | clade_354 | hetero | ++++ | TRUE | TRUE |
| SPC10155 | SPC10256 | clade_408 | clade_252 | clade_252 | hetero | ++++ | TRUE | TRUE |
| SPC10155 | SPC10313 | clade_408 | clade_252 | clade_260 | hetero | ++++ | FALSE | TRUE |
| SPC10155 | SPC10358 | clade_408 | clade_252 | clade_494 | hetero | ++++ | FALSE | TRUE |
| SPC10155 | SPC10468 | clade_408 | clade_252 | clade_360 | hetero | ++++ | FALSE | TRUE |
| SPC10155 | SPC10470 | clade_408 | clade_252 | clade_537 | hetero | ++++ | FALSE | TRUE |
| SPC10155 | SPC10613 | clade_408 | clade_252 | clade_309 | hetero | ++++ | FALSE | |
| SPC10167 | SPC10167 | clade_408 | clade_253 | clade_253 | semi | +++ | FALSE | FALSE |
| SPC10167 | SPC10202 | clade_408 | clade_253 | clade_351 | hetero | - | FALSE | FALSE |
| SPC10167 | SPC10238 | clade_408 | clade_253 | clade_354 | hetero | ++++ | FALSE | FALSE |
| SPC10167 | SPC10256 | clade_408 | clade_253 | clade_252 | hetero | ++++ | TRUE | TRUE |
| SPC10167 | SPC10313 | clade_408 | clade_253 | clade_260 | hetero | | FALSE | FALSE |
| SPC10167 | SPC10358 | clade_408 | clade_253 | clade_494 | hetero | | FALSE | FALSE |
| SPC10167 | SPC10468 | clade_408 | clade_253 | clade_360 | hetero | ++++ | FALSE | FALSE |
| SPC10167 | SPC10470 | clade_408 | clade_253 | clade_537 | hetero | ++++ | FALSE | FALSE |
| SPC10167 | SPC10613 | clade_408 | clade_253 | clade_309 | hetero | ++++ | FALSE | |
| SPC10202 | SPC10202 | clade_408 | clade_351 | clade_351 | semi | ---- | FALSE | FALSE |
| SPC10202 | SPC10238 | clade_408 | clade_351 | clade_354 | hetero | ++++ | FALSE | FALSE |
| SPC10202 | SPC10256 | clade_408 | clade_351 | clade_252 | hetero | ++++ | TRUE | TRUE |
| SPC10202 | SPC10313 | clade_408 | clade_351 | clade_260 | hetero | ---- | FALSE | FALSE |
| SPC10202 | SPC10358 | clade_408 | clade_351 | clade_494 | hetero | -- | FALSE | FALSE |
| SPC10202 | SPC10468 | clade_408 | clade_381 | clade_360 | hetero | ++++ | FALSE | FALSE |
| SPC10202 | SPC10470 | clade_408 | clade_351 | clade_537 | hetero | ++++ | FALSE | FALSE |
| SPC10202 | SPC10613 | clade_408 | clade_351 | clade_309 | hetero | ++++ | FALSE | |
| SPC10238 | SPC10238 | clade_408 | clade_354 | clade_354 | semi | ++++ | FALSE | FALSE |
| SPC10238 | SPC10256 | clade_408 | clade_354 | clade_252 | hetero | ++++ | TRUE | FALSE |
| SPC10238 | SPC10313 | clade_408 | clade_354 | clade_260 | hetero | ++++ | FALSE | FALSE |
| SPC10238 | SPC10358 | clade_408 | clade_354 | clade_494 | hetero | ++++ | FALSE | FALSE |
| SPC10238 | SPC10468 | clade_408 | clade_354 | clade_360 | hetero | ++++ | FALSE | FALSE |
| SPC10238 | SPC10470 | clade_408 | clade_354 | clade_537 | hetero | ++++ | TRUE | TRUE |
| SPC10238 | SPC10613 | clade_408 | clade_354 | clade_309 | hetero | ++++ | TRUE | |
| SPC10256 | SPC10256 | clade_408 | clade_252 | clade_252 | semi | ++++ | TRUE | FALSE |
| SPC10256 | SPC10313 | clade_408 | clade_252 | clade_260 | hetero | ++++ | TRUE | TRUE |
| SPC10256 | SPC10358 | clade_408 | clade_252 | clade_494 | hetero | ++++ | TRUE | TRUE |
| SPC10256 | SPC10468 | clade_408 | clade_252 | clade_360 | hetero | ++++ | TRUE | TRUE |
| SPC10256 | SPC10470 | clade_408 | clade_252 | clade_537 | hetero | ++++ | TRUE | TRUE |

TABLE 4a-continued

| | | | | | | | | |
|---|---|---|---|---|---|---|---|---|
| SPC10256 | SPC10613 | clade_408 | clade_252 | clade_500 | hetero | ++++ | TRUE | |
| SPC10313 | SPC10313 | clade_408 | clade_260 | clade_260 | semi | ---- | FALSE | FALSE |
| SPC10313 | SPC10358 | clade_408 | clade_260 | clade_494 | hetero | ---- | FALSE | FALSE |
| SPC10313 | SPC10468 | clade_408 | clade_260 | clade_360 | hetero | ++++ | FALSE | FALSE |
| SPC10313 | SPC10470 | clade_408 | clade_260 | clade_537 | hetero | +++ | FALSE | TRUE |
| SPC10313 | SPC10613 | clade_408 | clade_260 | clade_309 | hetero | ++++ | FALSE | |
| SPC10358 | SPC10358 | clade_408 | clade_494 | clade_494 | semi | ---- | FALSE | FALSE |
| SPC10358 | SPC10468 | clade_408 | clade_494 | clade_360 | hetero | ++++ | FALSE | FALSE |
| SPC10358 | SPC10470 | clade_408 | clade_494 | clade_537 | hetero | | FALSE | FALSE |
| SPC10358 | SPC10613 | clade_408 | clade_494 | clade_309 | hetero | ++++ | FALSE | |
| SPC10468 | SPC10468 | clade_408 | clade_360 | clade_360 | semi | | FALSE | FALSE |
| SPC10468 | SPC10470 | clade_408 | clade_360 | clade_537 | hetero | ++++ | FALSE | TRUE |
| SPC10468 | SPC10613 | clade_408 | clade_360 | clade_309 | hetero | ++++ | FALSE | |
| SPC10155 | SPC10155 | clade_408 | clade_252 | clade_252 | semi | ++++ | FALSE | TRUE |
| SPC10155 | SPC10167 | clade_408 | clade_252 | clade_253 | hetero | ++++ | FALSE | TRUE |
| SPC10155 | SPC10202 | clade_408 | clade_252 | clade_351 | hetero | ++++ | FALSE | TRUE |
| SPC10155 | SPC10238 | clade_408 | clade_252 | clade_354 | hetero | ++++ | TRUE | TRUE |
| SPC10155 | SPC10256 | clade_408 | clade_252 | clade_252 | hetero | ++++ | TRUE | TRUE |
| SPC10155 | SPC10313 | clade_408 | clade_252 | clade_260 | hetero | ++++ | FALSE | TRUE |
| SPC10155 | SPC10358 | clade_408 | clade_252 | clade_494 | hetero | ++++ | FALSE | TRUE |
| SPC10155 | SPC10468 | clade_408 | clade_252 | clade_360 | hetero | ++++ | FALSE | TRUE |
| SPC10155 | SPC10470 | clade_408 | clade_252 | clade_537 | hetero | ++++ | FALSE | FALSE |
| SPC10155 | SPC10613 | clade_408 | clade_382 | clade_309 | hetero | ++++ | FALSE | |
| SPC10167 | SPC10167 | clade_408 | clade_553 | clade_553 | semi | | FALSE | FALSE |
| SPC10167 | SPC10202 | clade_408 | clade_253 | clade_351 | hetero | --- | FALSE | FALSE |
| SPC10167 | SPC10238 | clade_408 | clade_253 | clade_354 | hetero | ++++ | FALSE | TRUE |
| SPC10167 | SPC10256 | clade_408 | clade_553 | clade_252 | hetero | ++++ | TRUE | TRUE |
| SPC10167 | SPC10313 | clade_408 | clade_253 | clade_260 | hetero | - | FALSE | FALSE |
| SPC10167 | SPC10358 | clade_408 | clade_253 | clade_494 | hetero | | FALSE | FALSE |
| SPC10167 | SPC10468 | clade_408 | clade_253 | clade_360 | hetero | ++ | FALSE | FALSE |
| SPC10167 | SPC10470 | clade_408 | clade_253 | clade_537 | hetero | ---- | FALSE | FALSE |
| SPC10167 | SPC10613 | clade_408 | clade_253 | clade_309 | hetero | --- | FALSE | |
| SPC10202 | SPC10202 | clade_408 | clade_351 | clade_351 | semi | -- | FALSE | FALSE |
| SPC10202 | SPC10238 | clade_408 | clade_351 | clade_354 | hetero | ++++ | TRUE | TRUE |
| SPC10202 | SPC10256 | clade_408 | clade_351 | clade_252 | hetero | ++++ | TRUE | TRUE |
| SPC10202 | SPC10313 | clade_408 | clade_351 | clade_260 | hetero | ---- | FALSE | FALSE |
| SPC10202 | SPC10358 | clade_408 | clade_351 | clade_494 | hetero | | FALSE | FALSE |
| SPC10202 | SPC10468 | clade_408 | clade_351 | clade_360 | hetero | +++ | FALSE | FALSE |
| SPC10202 | SPC10470 | clade_408 | clade_351 | clade_537 | hetero | +++ | FALSE | FALSE |
| SPC10202 | SPC10613 | clade_408 | clade_351 | clade_309 | hetero | ++++ | FALSE | |
| SPC10238 | SPC10238 | clade_408 | clade_354 | clade_354 | semi | ++++ | TRUE | FALSE |
| SPC10238 | SPC10256 | clade_408 | clade_354 | clade_252 | hetero | ++++ | TRUE | FALSE |
| SPC10238 | SPC10313 | clade_408 | clade_354 | clade_260 | hetero | ++++ | FALSE | TRUE |
| SPC10238 | SPC10358 | clade_408 | clade_354 | clade_494 | hetero | ++++ | TRUE | TRUE |
| SPC10238 | SPC10468 | clade_408 | clade_354 | clade_360 | hetero | ++++ | FALSE | TRUE |
| SPC10238 | SPC10470 | clade_408 | clade_354 | clade_537 | hetero | ++++ | TRUE | TRUE |
| SPC10238 | SPC10613 | clade_408 | clade_354 | clade_309 | hetero | ++++ | TRUE | |
| SPC10256 | SPC10256 | clade_408 | clade_252 | clade_252 | semi | ++++ | TRUE | FALSE |
| SPC10256 | SPC10313 | clade_408 | clade_252 | clade_260 | hetero | ++++ | TRUE | TRUE |
| SPC10256 | SPC10358 | clade_408 | clade_252 | clade_494 | hetero | ++++ | TRUE | TRUE |
| SPC10256 | SPC10468 | clade_408 | clade_252 | clade_360 | hetero | ++++ | TRUE | TRUE |
| SPC10256 | SPC10470 | clade_408 | clade_252 | clade_537 | hetero | ++++ | TRUE | TRUE |
| SPC10256 | SPC10613 | clade_408 | clade_252 | clade_309 | hetero | ++++ | TRUE | |
| SPC10313 | SPC10313 | clade_408 | clade_260 | clade_260 | semi | --- | FALSE | FALSE |
| SPC10313 | SPC10358 | clade_408 | clade_260 | clade_494 | hetero | ++ | FALSE | FALSE |
| SPC10313 | SPC10468 | clade_408 | clade_260 | clade_360 | hetero | +++ | FALSE | FALSE |
| SPC10313 | SPC10470 | clade_408 | clade_260 | clade_537 | hetero | ++++ | FALSE | TRUE |
| SPC10313 | SPC10613 | clade_408 | clade_260 | clade_309 | hetero | --- | FALSE | |
| SPC10358 | SPC10358 | clade_408 | clade_494 | clade_494 | semi | ++++ | FALSE | TRUE |
| SPC10358 | SPC10468 | clade_408 | clade_494 | clade_360 | hetero | ++++ | FALSE | TRUE |
| SPC10358 | SPC10470 | clade_408 | clade_494 | clade_537 | hetero | +++ | FALSE | FALSE |
| SPC10358 | SPC10613 | clade_408 | clade_494 | clade_309 | hetero | ++++ | FALSE | |
| SPC10468 | SPC10468 | clade_408 | clade_360 | clade_360 | semi | ++++ | FALSE | FALSE |
| SPC10468 | SPC10470 | clade_408 | clade_360 | clade_537 | hetero | ++++ | FALSE | TRUE |
| SPC10468 | SPC10613 | clade_408 | clade_360 | clade_500 | hetero | ++++ | FALSE | |
| SPC10155 | SPC10155 | clade_478 | clade_252 | clade_252 | semi | | FALSE | FALSE |
| SPC10155 | SPC10167 | clade_478 | clade_252 | clade_253 | hetero | ++++ | FALSE | FALSE |
| SPC10155 | SPC10202 | clade_478 | clade_252 | clade_351 | hetero | | FALSE | FALSE |
| SPC10155 | SPC10238 | clade_478 | clade_252 | clade_354 | hetero | ++++ | FALSE | TRUE |
| SPC10155 | SPC10256 | clade_478 | clade_252 | clade_252 | hetero | ++++ | TRUE | TRUE |
| SPC10155 | SPC10313 | clade_478 | clade_252 | clade_260 | hetero | ++++ | FALSE | TRUE |
| SPC10155 | SPC10358 | clade_478 | clade_252 | clade_494 | hetero | ++++ | FALSE | TRUE |
| SPC10155 | SPC10468 | clade_478 | clade_252 | clade_360 | hetero | ++++ | FALSE | FALSE |
| SPC10155 | SPC10470 | clade_478 | clade_252 | clade_537 | hetero | ---- | FALSE | FALSE |
| SPC10155 | SPC10613 | clade_478 | clade_252 | clade_309 | hetero | ++++ | FALSE | |
| SPC10167 | SPC10167 | clade_478 | clade_253 | clade_253 | semi | ---- | FALSE | FALSE |
| SPC10167 | SPC10202 | clade_478 | clade_253 | clade_351 | hetero | ---- | FALSE | FALSE |
| SPC10167 | SPC10238 | clade_478 | clade_253 | clade_354 | hetero | ++++ | FALSE | TRUE |
| SPC10167 | SPC10256 | clade_478 | clade_253 | clade_252 | hetero | ++++ | TRUE | TRUE |
| SPC10167 | SPC10313 | clade_478 | clade_253 | clade_260 | hetero | ---- | FALSE | FALSE |

TABLE 4a-continued

| | | | | | | | | |
|---|---|---|---|---|---|---|---|---|
| SPC10167 | SPC10358 | clade_478 | clade_253 | clade_494 | hetero | ---- | FALSE | FALSE |
| SPC10167 | SPC10468 | clade_478 | clade_253 | clade_360 | hetero | --- | FALSE | FALSE |
| SPC10167 | SPC10470 | clade_478 | clade_253 | clade_537 | hetero | ---- | FALSE | FALSE |
| SPC10167 | SPC10613 | clade_478 | clade_253 | clade_309 | hetero | --- | FALSE | |
| SPC10202 | SPC10202 | clade_478 | clade_351 | clade_351 | semi | ---- | FALSE | FALSE |
| SPC10202 | SPC10238 | clade_478 | clade_351 | clade_354 | hetero | ++++ | FALSE | FALSE |
| SPC10202 | SPC10256 | clade_478 | clade_351 | clade_252 | hetero | ++++ | TRUE | TRUE |
| SPC10202 | SPC10313 | clade_478 | clade_351 | clade_260 | hetero | ---- | FALSE | FALSE |
| SPC10202 | SPC10358 | clade_478 | clade_351 | clade_494 | hetero | ---- | FALSE | FALSE |
| SPC10202 | SPC10468 | clade_478 | clade_351 | clade_360 | hetero | - | FALSE | FALSE |
| SPC10202 | SPC10470 | clade_478 | clade_351 | clade_537 | hetero | ---- | FALSE | FALSE |
| SPC10202 | SPC10613 | clade_478 | clade_351 | clade_309 | hetero | ++++ | FALSE | |
| SPC10238 | SPC10238 | clade_478 | clade_354 | clade_354 | semi | ++++ | FALSE | FALSE |
| SPC10238 | SPC10256 | clade_478 | clade_354 | clade_252 | hetero | ++++ | TRUE | FALSE |
| SPC10238 | SPC10313 | clade_478 | clade_354 | clade_260 | hetero | ++++ | FALSE | TRUE |
| SPC10238 | SPC10358 | clade_478 | clade_354 | clade_494 | hetero | ++++ | TRUE | TRUE |
| SPC10238 | SPC10468 | clade_478 | clade_354 | clade_360 | hetero | ++++ | FALSE | TRUE |
| SPC10238 | SPC10470 | clade_478 | clade_354 | clade_537 | hetero | ++++ | FALSE | TRUE |
| SPC10238 | SPC10613 | clade_478 | clade_354 | clade_309 | hetero | ++++ | TRUE | |
| SPC10256 | SPC10256 | clade_478 | clade_252 | clade_252 | semi | ++++ | TRUE | FALSE |
| SPC10256 | SPC10313 | clade_478 | clade_252 | clade_260 | hetero | ++++ | TRUE | TRUE |
| SPC10256 | SPC10358 | clade_478 | clade_252 | clade_494 | hetero | ++++ | TRUE | TRUE |
| SPC10256 | SPC10468 | clade_478 | clade_252 | clade_360 | hetero | ++++ | TRUE | TRUE |
| SPC10256 | SPC10470 | clade_478 | clade_252 | clade_537 | hetero | ++++ | TRUE | TRUE |
| SPC10256 | SPC10613 | clade_478 | clade_252 | clade_309 | hetero | ++++ | TRUE | |
| SPC10313 | SPC10313 | clade_478 | clade_260 | clade_260 | semi | ---- | FALSE | FALSE |
| SPC10313 | SPC10358 | clade_478 | clade_260 | clade_494 | hetero | ---- | FALSE | FALSE |
| SPC10313 | SPC10468 | clade_478 | clade_260 | clade_360 | hetero | ++++ | FALSE | TRUE |
| SPC10313 | SPC10470 | clade_478 | clade_260 | clade_537 | hetero | --- | FALSE | FALSE |
| SPC10313 | SPC10613 | clade_478 | clade_260 | clade_309 | hetero | | FALSE | |
| SPC10358 | SPC10358 | clade_478 | clade_494 | clade_494 | semi | ---- | FALSE | FALSE |
| SPC10358 | SPC10468 | clade_478 | clade_494 | clade_360 | hetero | ++++ | FALSE | FALSE |
| SPC10358 | SPC10470 | clade_478 | clade_494 | clade_537 | hetero | -- | FALSE | FALSE |
| SPC10358 | SPC10613 | clade_478 | clade_494 | clade_309 | hetero | ++++ | FALSE | |
| SPC10468 | SPC10468 | clade_478 | clade_360 | clade_360 | semi | ++++ | FALSE | FALSE |
| SPC10468 | SPC10470 | clade_478 | clade_360 | clade_537 | hetero | ++++ | FALSE | TRUE |
| SPC10468 | SPC10613 | clade_478 | clade_360 | clade_309 | hetero | ++++ | FALSE | |
| SPC10155 | SPC10155 | clade_260 | clade_252 | clade_252 | semi | ++++ | FALSE | FALSE |
| SPC10155 | SPC10167 | clade_260 | clade_252 | clade_253 | hetero | ++++ | FALSE | TRUE |
| SPC10155 | SPC10202 | clade_260 | clade_252 | clade_351 | hetero | ++++ | FALSE | FALSE |
| SPC10155 | SPC10238 | clade_260 | clade_252 | clade_354 | hetero | ++++ | FALSE | FALSE |
| SPC10155 | SPC10256 | clade_260 | clade_252 | clade_252 | hetero | ++++ | TRUE | TRUE |
| SPC10155 | SPC10313 | clade_260 | clade_252 | clade_260 | hetero | ++++ | FALSE | FALSE |
| SPC10155 | SPC10358 | clade_260 | clade_252 | clade_494 | hetero | ++++ | FALSE | TRUE |
| SPC10155 | SPC10468 | clade_260 | clade_252 | clade_360 | hetero | ++++ | FALSE | TRUE |
| SPC10155 | SPC10470 | clade_260 | clade_252 | clade_537 | hetero | ++++ | FALSE | FALSE |
| SPC10155 | SPC10613 | clade_260 | clade_252 | clade_309 | hetero | ++++ | FALSE | |
| SPC10167 | SPC10167 | clade_260 | clade_253 | clade_253 | semi | ---- | FALSE | FALSE |
| SPC10167 | SPC10202 | clade_260 | clade_253 | clade_351 | hetero | ---- | FALSE | FALSE |
| SPC10167 | SPC10238 | clade_260 | clade_253 | clade_354 | hetero | ++++ | FALSE | TRUE |
| SPC10167 | SPC10256 | clade_260 | clade_253 | clade_252 | hetero | ++++ | TRUE | TRUE |
| SPC10167 | SPC10313 | clade_260 | clade_253 | clade_260 | hetero | ---- | FALSE | FALSE |
| SPC10167 | SPC10358 | clade_260 | clade_253 | clade_494 | hetero | ---- | FALSE | FALSE |
| SPC10167 | SPC10468 | clade_260 | clade_253 | clade_360 | hetero | +++ | FALSE | FALSE |
| SPC10167 | SPC10470 | clade_260 | clade_253 | clade_537 | hetero | ---- | FALSE | FALSE |
| SPC10167 | SPC10613 | clade_260 | clade_253 | clade_309 | hetero | | FALSE | |
| SPC10202 | SPC10202 | clade_260 | clade_351 | clade_351 | semi | ---- | FALSE | FALSE |
| SPC10202 | SPC10238 | clade_260 | clade_351 | clade_354 | hetero | ++++ | FALSE | FALSE |
| SPC10202 | SPC10256 | clade_260 | clade_351 | clade_252 | hetero | ++++ | TRUE | FALSE |
| SPC10202 | SPC10313 | clade_260 | clade_351 | clade_260 | hetero | ---- | FALSE | FALSE |
| SPC10202 | SPC10358 | clade_260 | clade_351 | clade_494 | hetero | --- | FALSE | FALSE |
| SPC10202 | SPC10468 | clade_260 | clade_351 | clade_360 | hetero | ++++ | FALSE | FALSE |
| SPC10202 | SPC10470 | clade_260 | clade_351 | clade_537 | hetero | ++++ | FALSE | FALSE |
| SPC10202 | SPC10613 | clade_260 | clade_351 | clade_309 | hetero | ++++ | FALSE | |
| SPC10238 | SPC10238 | clade_260 | clade_354 | clade_354 | semi | ++++ | FALSE | FALSE |
| SPC10238 | SPC10256 | clade_260 | clade_354 | clade_252 | hetero | ++++ | TRUE | FALSE |
| SPC10238 | SPC10313 | clade_260 | clade_354 | clade_260 | hetero | ++++ | FALSE | TRUE |
| SPC10238 | SPC10358 | clade_260 | clade_354 | clade_494 | hetero | ++++ | FALSE | TRUE |
| SPC10238 | SPC10468 | clade_260 | clade_354 | clade_360 | hetero | ++++ | TRUE | TRUE |
| SPC10238 | SPC10470 | clade_260 | clade_354 | clade_537 | hetero | ++++ | TRUE | TRUE |
| SPC10238 | SPC10613 | clade_260 | clade_354 | clade_309 | hetero | ++++ | TRUE | |
| SPC10256 | SPC10256 | clade_260 | clade_252 | clade_252 | semi | ++++ | TRUE | FALSE |
| SPC10256 | SPC10313 | clade_260 | clade_252 | clade_260 | hetero | ++++ | TRUE | TRUE |
| SPC10256 | SPC10358 | clade_260 | clade_252 | clade_494 | hetero | ++++ | TRUE | TRUE |
| SPC10256 | SPC10468 | clade_260 | clade_252 | clade_360 | hetero | ++++ | TRUE | TRUE |
| SPC10256 | SPC10470 | clade_260 | clade_252 | clade_537 | hetero | ++++ | TRUE | TRUE |
| SPC10256 | SPC10613 | clade_260 | clade_252 | clade_309 | hetero | ++++ | TRUE | |
| SPC10313 | SPC10313 | clade_260 | clade_260 | clade_260 | semi | ---- | FALSE | FALSE |
| SPC10313 | SPC10358 | clade_260 | clade_260 | clade_494 | hetero | ---- | FALSE | FALSE |
| SPC10313 | SPC10468 | clade_260 | clade_260 | clade_360 | hetero | ++++ | FALSE | FALSE |

TABLE 4a-continued

| | | | | | | | | | | |
|---|---|---|---|---|---|---|---|---|---|---|
| SPC10313 | SPC10470 | clade_260 | clade_260 | clade_537 | hetero | +++ | FALSE | TRUE | | |
| SPC10313 | SPC10613 | clade_260 | clade_260 | clade_309 | hetero | ++++ | FALSE | | | |
| SPC10358 | SPC10358 | clade_260 | clade_494 | clade_494 | semi | | FALSE | FALSE | | |
| SPC10358 | SPC10468 | clade_260 | clade_494 | clade_360 | hetero | ++++ | FALSE | FALSE | | |
| SPC10358 | SPC10470 | clade_260 | clade_494 | clade_537 | hetero | +++ | FALSE | FALSE | | |
| SPC10358 | SPC10613 | clade_260 | clade_494 | clade_309 | hetero | ++++ | FALSE | | | |
| SPC10468 | SPC10468 | clade_260 | clade_360 | clade_360 | semi | ++++ | FALSE | FALSE | | |
| SPC10468 | SPC10470 | clade_260 | clade_360 | clade_537 | hetero | ++++ | FALSE | TRUE | | |
| SPC10468 | SPC10613 | clade_260 | clade_360 | clade_309 | hetero | ++++ | FALSE | | | |
| SPC10155 | SPC10155 | clade_309 | clade_252 | clade_252 | semi | ++++ | TRUE | TRUE | ++++ | FALSE |
| SPC10155 | SPC10167 | clade_309 | clade_252 | clade_253 | hetero | ++++ | TRUE | TRUE | ++++ | FALSE |
| SPC10155 | SPC10202 | clade_309 | clade_252 | clade_351 | hetero | ++++ | TRUE | TRUE | ++++ | FALSE |
| SPC10155 | SPC10238 | clade_309 | clade_252 | clade_354 | hetero | ++++ | TRUE | TRUE | | FALSE |
| SPC10155 | SPC10256 | clade_309 | clade_252 | clade_252 | hetero | ++++ | TRUE | TRUE | ++++ | TRUE |
| SPC10155 | SPC10313 | clade_309 | clade_252 | clade_260 | hetero | ++++ | FALSE | TRUE | ++++ | FALSE |
| SPC10155 | SPC10358 | clade_309 | clade_252 | clade_494 | hetero | ++++ | TRUE | TRUE | ++++ | FALSE |
| SPC10155 | SPC10468 | clade_309 | clade_252 | clade_360 | hetero | ++++ | TRUE | TRUE | ++++ | FALSE |
| SPC10155 | SPC10470 | clade_309 | clade_252 | clade_537 | hetero | ++++ | TRUE | TRUE | ++++ | FALSE |
| SPC10155 | SPC10613 | clade_309 | clade_252 | clade_309 | hetero | ++++ | TRUE | | ++++ | FALSE |
| SPC10167 | SPC10167 | clade_309 | clade_253 | clade_253 | semi | ++++ | FALSE | TRUE | ++++ | FALSE |
| SPC10167 | SPC10202 | clade_309 | clade_253 | clade_351 | hetero | ++++ | FALSE | TRUE | ++++ | FALSE |
| SPC10167 | SPC10238 | clade_309 | clade_253 | clade_354 | hetero | ++++ | TRUE | TRUE | ++++ | FALSE |
| SPC10167 | SPC10256 | clade_309 | clade_253 | clade_252 | hetero | ++++ | TRUE | TRUE | ++++ | TRUE |
| SPC10167 | SPC10313 | clade_309 | clade_253 | clade_260 | hetero | ++++ | TRUE | TRUE | ++++ | FALSE |
| SPC10167 | SPC10358 | clade_309 | clade_253 | clade_494 | hetero | ++++ | TRUE | TRUE | +++ | FALSE |
| SPC10167 | SPC10468 | clade_309 | clade_253 | clade_360 | hetero | ++++ | TRUE | TRUE | ++++ | FALSE |
| SPC10167 | SPC10470 | clade_309 | clade_253 | clade_537 | hetero | ++++ | TRUE | TRUE | ++++ | FALSE |
| SPC10167 | SPC10613 | clade_309 | clade_253 | clade_309 | hetero | ++++ | TRUE | | ++++ | FALSE |
| SPC10202 | SPC10202 | clade_309 | clade_351 | clade_351 | semi | ++++ | TRUE | TRUE | ++++ | FALSE |
| SPC10202 | SPC10238 | clade_309 | clade_351 | clade_354 | hetero | ++++ | TRUE | TRUE | ++++ | FALSE |
| SPC10202 | SPC10256 | clade_309 | clade_351 | clade_252 | hetero | ++++ | TRUE | TRUE | ++++ | TRUE |
| SPC10202 | SPC10313 | clade_309 | clade_351 | clade_260 | hetero | ++++ | TRUE | TRUE | ++++ | FALSE |
| SPC10202 | SPC10358 | clade_309 | clade_351 | clade_494 | hetero | ++++ | TRUE | TRUE | ++++ | FALSE |
| SPC10202 | SPC10468 | clade_309 | clade_351 | clade_360 | hetero | ++++ | TRUE | TRUE | ++++ | FALSE |
| SPC10202 | SPC10470 | clade_309 | clade_351 | clade_537 | hetero | ++++ | TRUE | TRUE | ++++ | FALSE |
| SPC10202 | SPC10613 | clade_309 | clade_351 | clade_309 | hetero | ++++ | TRUE | | ++++ | FALSE |
| SPC10238 | SPC10238 | clade_309 | clade_354 | clade_354 | semi | ++++ | TRUE | TRUE | ++++ | TRUE |
| SPC10238 | SPC10256 | clade_309 | clade_354 | clade_252 | hetero | ++++ | TRUE | FALSE | ++++ | TRUE |
| SPC10238 | SPC10313 | clade_309 | clade_354 | clade_260 | hetero | ++++ | TRUE | TRUE | ++++ | FALSE |
| SPC10238 | SPC10358 | clade_309 | clade_354 | clade_494 | hetero | ++++ | TRUE | TRUE | ++++ | FALSE |
| SPC10238 | SPC10468 | clade_309 | clade_354 | clade_360 | hetero | ++++ | TRUE | TRUE | ++++ | FALSE |
| SPC10238 | SPC10470 | clade_309 | clade_354 | clade_537 | hetero | ++++ | TRUE | TRUE | ++++ | FALSE |
| SPC10238 | SPC10613 | clade_309 | clade_354 | clade_309 | hetero | ++++ | TRUE | | ++++ | TRUE |
| SPC10256 | SPC10256 | clade_309 | clade_252 | clade_252 | semi | ++++ | TRUE | FALSE | ++++ | TRUE |
| SPC10256 | SPC10313 | clade_309 | clade_252 | clade_260 | hetero | ++++ | TRUE | TRUE | ++++ | TRUE |
| SPC10256 | SPC10358 | clade_309 | clade_252 | clade_494 | hetero | ++++ | TRUE | TRUE | ++++ | TRUE |
| SPC10256 | SPC10468 | clade_309 | clade_252 | clade_360 | hetero | ++++ | TRUE | TRUE | ++++ | TRUE |
| SPC10256 | SPC10470 | clade_309 | clade_252 | clade_537 | hetero | ++++ | TRUE | TRUE | ++++ | TRUE |
| SPC10256 | SPC10613 | clade_309 | clade_252 | clade_309 | hetero | ++++ | TRUE | | ++++ | TRUE |
| SPC10313 | SPC10313 | clade_309 | clade_260 | clade_260 | semi | ++++ | TRUE | TRUE | ++++ | FALSE |
| SPC10313 | SPC10358 | clade_309 | clade_260 | clade_494 | hetero | ++++ | TRUE | TRUE | ++++ | FALSE |
| SPC10313 | SPC10468 | clade_309 | clade_260 | clade_360 | hetero | ++++ | TRUE | TRUE | ++++ | FALSE |
| SPC10313 | SPC10470 | clade_309 | clade_260 | clade_537 | hetero | ++++ | TRUE | TRUE | + | FALSE |
| SPC10313 | SPC10613 | clade_309 | clade_260 | clade_309 | hetero | ++++ | TRUE | | + | FALSE |
| SPC10358 | SPC10358 | clade_309 | clade_494 | clade_494 | semi | ++++ | TRUE | TRUE | ++++ | FALSE |
| SPC10358 | SPC10468 | clade_309 | clade_494 | clade_360 | hetero | ++++ | TRUE | TRUE | ++++ | FALSE |
| SPC10358 | SPC10470 | clade_309 | clade_494 | clade_537 | hetero | ++++ | TRUE | TRUE | ++++ | FALSE |
| SPC10358 | SPC10613 | clade_309 | clade_494 | clade_309 | hetero | ++++ | TRUE | | ++++ | FALSE |
| SPC10468 | SPC10468 | clade_309 | clade_360 | clade_360 | semi | ++++ | TRUE | TRUE | ++++ | TRUE |
| SPC10468 | SPC10470 | clade_309 | clade_360 | clade_537 | hetero | ++++ | TRUE | TRUE | ++++ | FALSE |
| SPC10468 | SPC10613 | clade_309 | clade_360 | clade_309 | hetero | ++++ | TRUE | | ++++ | FALSE |
| SPC10155 | SPC10155 | clade_444 | clade_252 | clade_252 | semi | ++++ | FALSE | FALSE | | |
| SPC10155 | SPC10167 | clade_444 | clade_252 | clade_253 | hetero | +++ | FALSE | FALSE | | |
| SPC10155 | SPC10202 | clade_444 | clade_252 | clade_351 | hetero | ++++ | FALSE | FALSE | | |
| SPC10155 | SPC10238 | clade_444 | clade_252 | clade_354 | hetero | ++++ | TRUE | TRUE | | |
| SPC10155 | SPC10256 | clade_444 | clade_252 | clade_252 | hetero | ++++ | TRUE | TRUE | | |
| SPC10155 | SPC10313 | clade_444 | clade_252 | clade_260 | hetero | ++++ | FALSE | TRUE | | |
| SPC10155 | SPC10358 | clade_444 | clade_252 | clade_494 | hetero | ++++ | FALSE | TRUE | | |
| SPC10155 | SPC10468 | clade_444 | clade_252 | clade_360 | hetero | ++++ | FALSE | TRUE | | |
| SPC10155 | SPC10470 | clade_444 | clade_252 | clade_537 | hetero | + | FALSE | FALSE | | |
| SPC10155 | SPC10613 | clade_444 | clade_252 | clade_309 | hetero | ++++ | FALSE | | | |
| SPC10167 | SPC10167 | clade_444 | clade_253 | clade_253 | semi | ---- | FALSE | FALSE | | |
| SPC10167 | SPC10202 | clade_444 | clade_253 | clade_351 | hetero | ---- | FALSE | FALSE | | |
| SPC10167 | SPC10238 | clade_444 | clade_253 | clade_354 | hetero | ++++ | FALSE | TRUE | | |
| SPC10167 | SPC10256 | clade_444 | clade_253 | clade_252 | hetero | ++++ | TRUE | TRUE | | |
| SPC10167 | SPC10313 | clade_444 | clade_253 | clade_260 | hetero | ---- | FALSE | FALSE | | |
| SPC10167 | SPC10358 | clade_444 | clade_253 | clade_494 | hetero | ---- | FALSE | FALSE | | |
| SPC10167 | SPC10468 | clade_444 | clade_253 | clade_360 | hetero | ++++ | FALSE | FALSE | | |
| SPC10167 | SPC10470 | clade_444 | clade_253 | clade_537 | hetero | ---- | FALSE | FALSE | | |
| SPC10167 | SPC10613 | clade_444 | clade_253 | clade_309 | hetero | ---- | FALSE | | | |

TABLE 4a-continued

| | | | | | | | | |
|---|---|---|---|---|---|---|---|---|
| SPC10202 | SPC10202 | clade_444 | clade_351 | clade_351 | semi | | FALSE | FALSE |
| SPC10202 | SPC10238 | clade_444 | clade_351 | clade_354 | hetero | ++++ | FALSE | TRUE |
| SPC10202 | SPC10256 | clade_444 | clade_351 | clade_252 | hetero | ++++ | TRUE | TRUE |
| SPC10202 | SPC10313 | clade_444 | clade_351 | clade_260 | hetero | −−−− | FALSE | FALSE |
| SPC10202 | SPC10358 | clade_444 | clade_351 | clade_494 | hetero | −−− | FALSE | FALSE |
| SPC10202 | SPC10468 | clade_444 | clade_351 | clade_360 | hetero | ++++ | FALSE | FALSE |
| SPC10202 | SPC10470 | clade_444 | clade_351 | clade 537 | hetero | | FALSE | FALSE |
| SPC10202 | SPC10613 | clade_444 | clade_351 | clade_309 | hetero | ++++ | FALSE | |
| SPC10238 | SPC10238 | clade_444 | clade_354 | clade_354 | semi | ++++ | FALSE | FALSE |
| SPC10238 | SPC10256 | clade_444 | clade_354 | clade_252 | hetero | ++++ | TRUE | FALSE |
| SPC10238 | SPC10313 | clade_444 | clade_354 | clade_260 | hetero | ++++ | TRUE | TRUE |
| SPC10238 | SPC10358 | clade_444 | clade_354 | clade_494 | hetero | ++++ | TRUE | TRUE |
| SPC10238 | SPC10468 | clade_444 | clade_354 | clade_360 | hetero | ++++ | TRUE | TRUE |
| SPC10238 | SPC10470 | clade_444 | clade_354 | clade_537 | hetero | ++++ | TRUE | TRUE |
| SPC10238 | SPC10613 | clade_444 | clade_354 | clade_309 | hetero | ++++ | TRUE | |
| SPC10256 | SPC10256 | clade_444 | clade_252 | clade_252 | semi | ++++ | TRUE | FALSE |
| SPC10256 | SPC10313 | clade_444 | clade_252 | clade_260 | hetero | ++++ | TRUE | TRUE |
| SPC10256 | SPC10358 | clade_444 | clade_252 | clade_494 | hetero | ++++ | TRUE | TRUE |
| SPC10256 | SPC10468 | clade_444 | clade_252 | clade_360 | hetero | ++++ | TRUE | TRUE |
| SPC10256 | SPC10470 | clade_444 | clade_252 | clade_537 | hetero | ++++ | TRUE | TRUE |
| SPC10256 | SPC10613 | clade_444 | clade_252 | clade_309 | hetero | ++++ | TRUE | |
| SPC10313 | SPC10313 | clade_444 | clade_260 | clade_260 | semi | −−−− | FALSE | FALSE |
| SPC10313 | SPC10358 | clade_444 | clade_260 | clade_494 | hetero | −−−− | FALSE | FALSE |
| SPC10313 | SPC10468 | clade_444 | clade_260 | clade_360 | hetero | ++ | FALSE | TRUE |
| SPC10313 | SPC10470 | clade_444 | clade_260 | clade_537 | hetero | − | FALSE | TRUE |
| SPC10313 | SPC10613 | clade_444 | clade_260 | clade_309 | hetero | ++++ | FALSE | |
| SPC10358 | SPC10358 | clade_444 | clade_494 | clade_494 | semi | − | FALSE | FALSE |
| SPC10358 | SPC10468 | clade_444 | clade_494 | clade_360 | hetero | ++++ | FALSE | FALSE |
| SPC10358 | SPC10470 | clade_444 | clade_494 | clade_537 | hetero | − | FALSE | FALSE |
| SPC10358 | SPC10613 | clade_444 | clade_494 | clade_309 | hetero | ++++ | FALSE | |
| SPC10468 | SPC10468 | clade_444 | clade_360 | clade_360 | semi | ++++ | FALSE | FALSE |
| SPC10468 | SPC10470 | clade_444 | clade_360 | clade_537 | hetero | ++++ | FALSE | TRUE |
| SPC10468 | SPC10613 | clade_444 | clade_360 | clade_309 | hetero | ++++ | FALSE | |
| SPC10097 | SPC10097 | clade_252 | clade_553 | clade_553 | semi | | FALSE | FALSE |
| SPC10097 | SPC10304 | clade_252 | clade_553 | clade_262 | hetero | ++++ | FALSE | FALSE |
| SPC10097 | SPC10325 | clade_252 | clade_553 | clade_408 | hetero | ++++ | FALSE | FALSE |
| SPC10097 | SPC10355 | clade_252 | clade_553 | clade_408 | hetero | ++++ | FALSE | FALSE |
| SPC10097 | SPC10386 | clade_252 | clade_553 | clade_478 | hetero | ++++ | FALSE | FALSE |
| SPC10097 | SPC10390 | clade_252 | clade_553 | clade_260 | hetero | +++ | FALSE | FALSE |
| SPC10097 | SPC10415 | clade_252 | clade_553 | clade_309 | hetero | ++++ | TRUE | TRUE |
| SPC10097 | SPC10567 | clade_252 | clade_553 | clade_444 | hetero | ++++ | FALSE | FALSE |
| SPC10304 | SPC10304 | clade_252 | clade_262 | clade_262 | semi | −− | FALSE | FALSE |
| SPC10304 | SPC10325 | clade_252 | clade_262 | clade_408 | hetero | ++++ | FALSE | FALSE |
| SPC10304 | SPC10355 | clade_252 | clade_262 | clade_408 | hetero | | FALSE | FALSE |
| SPC10304 | SPC10386 | clade_252 | clade_262 | clade_478 | hetero | −−−− | FALSE | FALSE |
| SPC10304 | SPC10390 | clade_252 | clade_262 | clade_260 | hetero | ++++ | FALSE | TRUE |
| SPC10304 | SPC10415 | clade_252 | clade_262 | clade_309 | hetero | ++++ | FALSE | TRUE |
| SPC10304 | SPC10567 | clade_252 | clade_262 | clade_444 | hetero | | FALSE | FALSE |
| SPC10325 | SPC10325 | clade_252 | clade_408 | clade_408 | semi | ++++ | FALSE | FALSE |
| SPC10325 | SPC10355 | clade_252 | clade_408 | clade_408 | hetero | ++++ | FALSE | FALSE |
| SPC10325 | SPC10386 | clade_252 | clade_408 | clade_478 | hetero | +++ | FALSE | FALSE |
| SPC10325 | SPC10390 | clade_252 | clade_408 | clade_260 | hetero | ++++ | FALSE | FALSE |
| SPC10325 | SPC10415 | clade_252 | clade_408 | clade_309 | hetero | ++++ | FALSE | TRUE |
| SPC10325 | SPC10567 | clade_252 | clade_408 | clade_444 | hetero | ++++ | FALSE | TRUE |
| SPC10355 | SPC10355 | clade_252 | clade_408 | clade_408 | semi | −−− | FALSE | FALSE |
| SPC10355 | SPC10386 | clade_252 | clade_408 | clade_478 | hetero | −−−− | FALSE | FALSE |
| SPC10355 | SPC10390 | clade_252 | clade_408 | clade_260 | hetero | ++++ | FALSE | TRUE |
| SPC10355 | SPC10415 | clade_252 | clade_408 | clade_309 | hetero | ++++ | FALSE | FALSE |
| SPC10355 | SPC10567 | clade_252 | clade_408 | clade_444 | hetero | +++ | FALSE | FALSE |
| SPC10386 | SPC10386 | clade_252 | clade_478 | clade_478 | semi | −− | FALSE | FALSE |
| SPC10386 | SPC10390 | clade_252 | clade_478 | clade_260 | hetero | ++++ | FALSE | FALSE |
| SPC10386 | SPC10415 | clade_252 | clade_478 | clade_309 | hetero | ++++ | FALSE | TRUE |
| SPC10386 | SPC10567 | clade_252 | clade_478 | clade_444 | hetero | | FALSE | FALSE |
| SPC10390 | SPC10390 | clade_252 | clade_260 | clade_260 | semi | ++++ | FALSE | FALSE |
| SPC10390 | SPC10415 | clade_252 | clade_260 | clade_309 | hetero | ++++ | FALSE | TRUE |
| SPC10390 | SPC10567 | clade_252 | clade_260 | clade_444 | hetero | ++++ | FALSE | TRUE |
| SPC10415 | SPC10415 | clade_252 | clade_309 | clade_309 | semi | ++++ | FALSE | TRUE |
| SPC10415 | SPC10567 | clade_252 | clade_309 | clade_444 | hetero | ++++ | TRUE | TRUE |
| SPC10567 | SPC10567 | clade_252 | clade_444 | clade_444 | semi | +++ | FALSE | TRUE |
| SPC10097 | SPC10097 | clade_253 | clade_553 | clade_553 | semi | − | FALSE | FALSE |
| SPC10097 | SPC10304 | clade_253 | clade_553 | clade_262 | hetero | | FALSE | FALSE |
| SPC10097 | SPC10325 | clade_253 | clade_553 | clade_408 | hetero | −−− | FALSE | FALSE |
| SPC10097 | SPC10355 | clade_253 | clade_553 | clade_408 | hetero | −−−− | FALSE | FALSE |
| SPC10097 | SPC10386 | clade_253 | clade_553 | clade_478 | hetero | −−− | FALSE | FALSE |
| SPC10097 | SPC10390 | clade_253 | clade_553 | clade_260 | hetero | ++ | FALSE | FALSE |
| SPC10097 | SPC10415 | clade_253 | clade_553 | clade_309 | hetero | ++++ | FALSE | TRUE |
| SPC10097 | SPC10567 | clade_253 | clade_553 | clade_444 | hetero | | FALSE | FALSE |
| SPC10304 | SPC10304 | clade_253 | clade_262 | clade_262 | semi | −−−− | FALSE | FALSE |
| SPC10304 | SPC10325 | clade_253 | clade_262 | clade_408 | hetero | | FALSE | FALSE |
| SPC10304 | SPC10355 | clade_253 | clade_262 | clade_408 | hetero | −−−− | FALSE | FALSE |

TABLE 4a-continued

| | | | | | | | | |
|---|---|---|---|---|---|---|---|---|
| SPC10304 | SPC10386 | clade_253 | clade_262 | clade_478 | hetero | –––– | FALSE | FALSE |
| SPC10304 | SPC10390 | clade_253 | clade_262 | clade_260 | hetero | ++++ | FALSE | FALSE |
| SPC10304 | SPC10415 | clade_253 | clade_262 | clade_309 | hetero | ++++ | FALSE | TRUE |
| SPC10304 | SPC10567 | clade_253 | clade_262 | clade_444 | hetero | –––– | FALSE | FALSE |
| SPC10325 | SPC10325 | clade_253 | clade_408 | clade_408 | semi | – | FALSE | FALSE |
| SPC10325 | SPC10355 | clade_253 | clade_408 | clade_408 | hetero | –––– | FALSE | FALSE |
| SPC10325 | SPC10386 | clade_253 | clade_408 | clade_478 | hetero | –––– | FALSE | FALSE |
| SPC10325 | SPC10390 | clade_253 | clade_408 | clade_360 | hetero | ++ | FALSE | FALSE |
| SPC10325 | SPC10415 | clade_253 | clade_408 | clade_309 | hetero | ++++ | FALSE | TRUE |
| SPC10325 | SPC10567 | clade_253 | clade_408 | clade_444 | hetero | ++++ | FALSE | FALSE |
| SPC10355 | SPC10355 | clade_253 | clade_408 | clade_408 | semi | –––– | FALSE | FALSE |
| SPC10355 | SPC10386 | clade_253 | clade_408 | clade_478 | hetero | –––– | FALSE | FALSE |
| SPC10355 | SPC10390 | clade_253 | clade_408 | clade_260 | hetero | ++++ | FALSE | FALSE |
| SPC10355 | SPC10415 | clade_253 | clade_408 | clade_309 | hetero | ++++ | FALSE | FALSE |
| SPC10355 | SPC10567 | clade_253 | clade_408 | clade_444 | hetero | –––– | FALSE | FALSE |
| SPC10386 | SPC10386 | clade_253 | clade_478 | clade_478 | semi | –––– | FALSE | FALSE |
| SPC10386 | SPC10390 | clade_253 | clade_478 | clade_260 | hetero | –––– | FALSE | FALSE |
| SPC10386 | SPC10415 | clade_253 | clade_478 | clade_309 | hetero | ++++ | FALSE | TRUE |
| SPC10386 | SPC10567 | clade_253 | clade_478 | clade_444 | hetero | –––– | FALSE | FALSE |
| SPC10390 | SPC10390 | clade_253 | clade_260 | clade_260 | semi | ––– | FALSE | FALSE |
| SPC10390 | SPC10415 | clade_253 | clade_260 | clade_309 | hetero | ++++ | FALSE | TRUE |
| SPC10390 | SPC10567 | clade_253 | clade_260 | clade_444 | hetero | + | FALSE | FALSE |
| SPC10415 | SPC10415 | clade_253 | clade_309 | clade_309 | semi | ++++ | FALSE | TRUE |
| SPC10415 | SPC10567 | clade_253 | clade_309 | clade_444 | hetero | ++++ | FALSE | TRUE |
| SPC10567 | SPC10567 | clade_253 | clade_444 | clade_444 | semi | –––– | FALSE | FALSE |
| SPC10097 | SPC10097 | clade_351 | clade_553 | clade_553 | semi | +++ | FALSE | FALSE |
| SPC10097 | SPC10304 | clade_351 | clade_553 | clade_262 | hetero | ++++ | FALSE | FALSE |
| SPC10097 | SPC10325 | clade_351 | clade_553 | clade_408 | hetero | +++ | FALSE | FALSE |
| SPC10097 | SPC10355 | clade_351 | clade_553 | clade_408 | hetero | ++++ | FALSE | FALSE |
| SPC10097 | SPC10386 | clade_351 | clade_553 | clade_478 | hetero | ++++ | FALSE | FALSE |
| SPC10097 | SPC10390 | clade_351 | clade_553 | clade_260 | hetero | ++++ | FALSE | TRUE |
| SPC10097 | SPC10415 | clade_351 | clade_553 | clade_309 | hetero | ++++ | FALSE | TRUE |
| SPC10097 | SPC10567 | clade_351 | clade_553 | clade_444 | hetero | ++++ | FALSE | TRUE |
| SPC10304 | SPC10304 | clade_351 | clade_262 | clade_262 | semi | ––– | FALSE | FALSE |
| SPC10304 | SPC10325 | clade_351 | clade_262 | clade_408 | hetero | ++ | FALSE | FALSE |
| SPC10304 | SPC10355 | clade_351 | clade_262 | clade_408 | hetero | –– | FALSE | FALSE |
| SPC10304 | SPC10386 | clade_351 | clade_262 | clade_478 | hetero | –––– | FALSE | FALSE |
| SPC10304 | SPC10390 | clade_351 | clade_262 | clade_260 | hetero | ++++ | FALSE | FALSE |
| SPC10304 | SPC10415 | clade_351 | clade_262 | clade_309 | hetero | ++++ | FALSE | TRUE |
| SPC10304 | SPC10567 | clade_351 | clade_262 | clade_444 | hetero | ++++ | FALSE | FALSE |
| SPC10325 | SPC10325 | clade_351 | clade_408 | clade_408 | semi | ++ | FALSE | FALSE |
| SPC10325 | SPC10355 | clade_351 | clade_408 | clade_408 | hetero | +++ | FALSE | FALSE |
| SPC10325 | SPC10386 | clade_351 | clade_408 | clade_478 | hetero | | FALSE | FALSE |
| SPC10325 | SPC10390 | clade_351 | clade_408 | clade_260 | hetero | ++++ | FALSE | FALSE |
| SPC10325 | SPC10415 | clade_351 | clade_408 | clade_309 | hetero | ++++ | FALSE | TRUE |
| SPC10325 | SPC10567 | clade_351 | clade_408 | clade_444 | hetero | ++++ | FALSE | FALSE |
| SPC10355 | SPC10355 | clade_351 | clade_408 | clade_408 | semi | – | FALSE | FALSE |
| SPC10355 | SPC10386 | clade_351 | clade_408 | clade_478 | hetero | – | FALSE | FALSE |
| SPC10355 | SPC10390 | clade_351 | clade_408 | clade_260 | hetero | +++ | FALSE | FALSE |
| SPC10355 | SPC10415 | clade_351 | clade_408 | clade_309 | hetero | ++++ | FALSE | FALSE |
| SPC10355 | SPC10567 | clade_351 | clade_408 | clade_444 | hetero | +++ | FALSE | FALSE |
| SPC10386 | SPC10386 | clade_351 | clade_478 | clade_478 | semi | ––– | FALSE | FALSE |
| SPC10386 | SPC10390 | clade_351 | clade_478 | clade_260 | hetero | +++ | FALSE | FALSE |
| SPC10386 | SPC10415 | clade_351 | clade_478 | clade_309 | hetero | ++++ | FALSE | TRUE |
| SPC10386 | SPC10567 | clade_351 | clade_478 | clade_444 | hetero | | FALSE | FALSE |
| SPC10390 | SPC10390 | clade_351 | clade_260 | clade_260 | semi | ++++ | FALSE | FALSE |
| SPC10390 | SPC10415 | clade_351 | clade_260 | clade_309 | hetero | ++++ | FALSE | TRUE |
| SPC10390 | SPC10567 | clade_351 | clade_260 | clade_444 | hetero | ++++ | FALSE | TRUE |
| SPC10415 | SPC10415 | clade_351 | clade_309 | clade_309 | semi | ++++ | FALSE | TRUE |
| SPC10415 | SPC10567 | clade_351 | clade_309 | clade_444 | hetero | ++++ | TRUE | TRUE |
| SPC10567 | SPC10567 | clade_351 | clade_444 | clade_444 | semi | +++ | FALSE | TRUE |
| SPC10097 | SPC10097 | clade_354 | clade_553 | clade_553 | semi | ++++ | FALSE | FALSE |
| SPC10097 | SPC10304 | clade_354 | clade_553 | clade_262 | hetero | ++++ | FALSE | FALSE |
| SPC10097 | SPC10325 | clade_354 | clade_553 | clade_408 | hetero | ++++ | FALSE | FALSE |
| SPC10097 | SPC10355 | clade_354 | clade_553 | clade_408 | hetero | ++++ | FALSE | TRUE |
| SPC10097 | SPC10386 | clade_354 | clade_553 | clade_478 | hetero | ++++ | FALSE | TRUE |
| SPC10097 | SPC10390 | clade_354 | clade_553 | clade_260 | hetero | ++++ | FALSE | TRUE |
| SPC10097 | SPC10415 | clade_354 | clade_553 | clade_309 | hetero | ++++ | FALSE | FALSE |
| SPC10097 | SPC10567 | clade_354 | clade_553 | clade_444 | hetero | ++++ | FALSE | TRUE |
| SPC10304 | SPC10304 | clade_354 | clade_262 | clade_262 | semi | ++++ | FALSE | FALSE |
| SPC10304 | SPC10325 | clade_354 | clade_262 | clade_408 | hetero | ++++ | FALSE | FALSE |
| SPC10304 | SPC10355 | clade_354 | clade_262 | clade_408 | hetero | ++++ | FALSE | TRUE |
| SPC10304 | SPC10386 | clade_354 | clade_262 | clade_478 | hetero | ++++ | FALSE | TRUE |
| SPC10304 | SPC10390 | clade_354 | clade_262 | clade_260 | hetero | ++++ | FALSE | FALSE |
| SPC10304 | SPC10415 | clade_354 | clade_262 | clade_309 | hetero | ++++ | FALSE | TRUE |
| SPC10304 | SPC10567 | clade_354 | clade_262 | clade_444 | hetero | ++++ | TRUE | TRUE |
| SPC10325 | SPC10325 | clade_354 | clade_408 | clade_408 | semi | ++++ | FALSE | FALSE |
| SPC10325 | SPC10355 | clade_354 | clade_408 | clade_408 | hetero | ++++ | FALSE | TRUE |
| SPC10325 | SPC10386 | clade_354 | clade_408 | clade_478 | hetero | ++++ | FALSE | TRUE |
| SPC10325 | SPC10390 | clade_354 | clade_408 | clade_260 | hetero | ++++ | FALSE | TRUE |

TABLE 4a-continued

| | | | | | | | | |
|---|---|---|---|---|---|---|---|---|
| SPC10325 | SPC10415 | clade_354 | clade_408 | clade_309 | hetero | ++++ | TRUE | TRUE |
| SPC10325 | SPC10567 | clade_354 | clade_408 | clade_444 | hetero | ++++ | TRUE | TRUE |
| SPC10355 | SPC10355 | clade_354 | clade_408 | clade_408 | semi | ++++ | FALSE | FALSE |
| SPC10355 | SPC10386 | clade_354 | clade_408 | clade_478 | hetero | ++++ | FALSE | TRUE |
| SPC10355 | SPC10390 | clade_354 | clade_408 | clade_260 | hetero | ++++ | FALSE | FALSE |
| SPC10355 | SPC10415 | clade_354 | clade_408 | clade_309 | hetero | ++++ | FALSE | FALSE |
| SPC10355 | SPC10567 | clade_354 | clade_408 | clade_444 | hetero | ++++ | TRUE | TRUE |
| SPC10386 | SPC10386 | clade_354 | clade_478 | clade_478 | semi | ++++ | FALSE | TRUE |
| SPC10386 | SPC10390 | clade_354 | clade_478 | clade_260 | hetero | ++++ | FALSE | TRUE |
| SPC10386 | SPC10415 | clade_354 | clade_478 | clade_309 | hetero | ++++ | TRUE | TRUE |
| SPC10386 | SPC10567 | clade_354 | clade_478 | clade_444 | hetero | ++++ | TRUE | TRUE |
| SPC10390 | SPC10390 | clade_354 | clade_260 | clade_260 | semi | ++++ | FALSE | TRUE |
| SPC10390 | SPC10415 | clade_354 | clade_260 | clade_309 | hetero | ++++ | TRUE | TRUE |
| SPC10390 | SPC10567 | clade_354 | clade_260 | clade_444 | hetero | ++++ | TRUE | TRUE |
| SPC10415 | SPC10415 | clade_354 | clade_309 | clade_309 | semi | ++++ | FALSE | FALSE |
| SPC10415 | SPC10567 | clade_354 | clade_309 | clade_444 | hetero | ++++ | TRUE | TRUE |
| SPC10567 | SPC10567 | clade_354 | clade_444 | clade_444 | semi | ++++ | TRUE | TRUE |
| SPC10097 | SPC10097 | clade_252 | clade_553 | clade_553 | semi | ++++ | TRUE | TRUE |
| SPC10097 | SPC10304 | clade_252 | clade_553 | clade_262 | hetero | ++++ | TRUE | TRUE |
| SPC10097 | SPC10325 | clade_252 | clade_553 | clade_408 | hetero | ++++ | TRUE | FALSE |
| SPC10097 | SPC10355 | clade_252 | clade_553 | clade_408 | hetero | ++++ | TRUE | TRUE |
| SPC10097 | SPC10386 | clade_252 | clade_553 | clade_478 | hetero | ++++ | TRUE | TRUE |
| SPC10097 | SPC10390 | clade_252 | clade_553 | clade_260 | hetero | ++++ | TRUE | TRUE |
| SPC10097 | SPC10415 | clade_252 | clade_553 | clade_309 | hetero | ++++ | TRUE | TRUE |
| SPC10097 | SPC10567 | clade_252 | clade_553 | clade_444 | hetero | ++++ | TRUE | TRUE |
| SPC10304 | SPC10304 | clade_252 | clade_262 | clade_262 | semi | ++++ | TRUE | TRUE |
| SPC10304 | SPC10325 | clade_252 | clade_262 | clade_408 | hetero | ++++ | TRUE | TRUE |
| SPC10304 | SPC10355 | clade_252 | clade_262 | clade_408 | hetero | ++++ | TRUE | TRUE |
| SPC10304 | SPC10386 | clade_252 | clade_262 | clade_478 | hetero | ++++ | TRUE | TRUE |
| SPC10304 | SPC10390 | clade_252 | clade_262 | clade_260 | hetero | ++++ | TRUE | TRUE |
| SPC10304 | SPC10415 | clade_252 | clade_262 | clade_309 | hetero | ++++ | TRUE | TRUE |
| SPC10304 | SPC10567 | clade_252 | clade_262 | clade_444 | hetero | ++++ | TRUE | TRUE |
| SPC10325 | SPC10325 | clade_252 | clade_408 | clade_408 | semi | ++++ | TRUE | TRUE |
| SPC10325 | SPC10355 | clade_252 | clade_408 | clade_408 | hetero | ++++ | TRUE | FALSE |
| SPC10325 | SPC10386 | clade_252 | clade_408 | clade_478 | hetero | ++++ | TRUE | TRUE |
| SPC10325 | SPC10390 | clade_252 | clade_408 | clade_260 | hetero | ++++ | TRUE | TRUE |
| SPC10325 | SPC10415 | clade_252 | clade_408 | clade_309 | hetero | ++++ | TRUE | TRUE |
| SPC10325 | SPC10567 | clade_252 | clade_408 | clade_444 | hetero | ++++ | TRUE | TRUE |
| SPC10355 | SPC10355 | clade_252 | clade_408 | clade_408 | semi | ++++ | TRUE | FALSE |
| SPC10355 | SPC10386 | clade_252 | clade_408 | clade_478 | hetero | ++++ | TRUE | TRUE |
| SPC10355 | SPC10390 | clade_252 | clade_408 | clade_260 | hetero | ++++ | TRUE | TRUE |
| SPC10355 | SPC10415 | clade_252 | clade_408 | clade_309 | hetero | ++++ | TRUE | FALSE |
| SPC10355 | SPC10567 | clade_252 | clade_408 | clade_444 | hetero | ++++ | TRUE | TRUE |
| SPC10386 | SPC10386 | clade_252 | clade_478 | clade_478 | semi | ++++ | TRUE | TRUE |
| SPC10386 | SPC10390 | clade_252 | clade_478 | clade_260 | hetero | ++++ | TRUE | TRUE |
| SPC10386 | SPC10415 | clade_252 | clade_478 | clade_309 | hetero | ++++ | TRUE | TRUE |
| SPC10386 | SPC10567 | clade_252 | clade_478 | clade_444 | hetero | ++++ | TRUE | TRUE |
| SPC10390 | SPC10390 | clade_252 | clade_260 | clade_260 | semi | ++++ | TRUE | TRUE |
| SPC10390 | SPC10415 | clade_252 | clade_260 | clade_309 | hetero | ++++ | TRUE | TRUE |
| SPC10390 | SPC10567 | clade_252 | clade_260 | clade_444 | hetero | ++++ | TRUE | TRUE |
| SPC10415 | SPC10415 | clade_252 | clade_309 | clade_309 | semi | ++++ | TRUE | TRUE |
| SPC10415 | SPC10567 | clade_252 | clade_309 | clade_444 | hetero | ++++ | TRUE | TRUE |
| SPC10567 | SPC10567 | clade_252 | clade_444 | clade_444 | semi | ++++ | TRUE | TRUE |
| SPC10097 | SPC10097 | clade_260 | clade_553 | clade_553 | semi | + | FALSE | FALSE |
| SPC10097 | SPC10304 | clade_260 | clade_553 | clade_262 | hetero | ++++ | FALSE | TRUE |
| SPC10097 | SPC10325 | clade_260 | clade_553 | clade_408 | hetero | ++++ | FALSE | FALSE |
| SPC10097 | SPC10355 | clade_260 | clade_553 | clade_408 | hetero | ++++ | FALSE | FALSE |
| SPC10097 | SPC10386 | clade_260 | clade_553 | clade_478 | hetero | ++++ | FALSE | TRUE |
| SPC10097 | SPC10390 | clade_260 | clade_553 | clade_260 | hetero | ++++ | FALSE | TRUE |
| SPC10097 | SPC10415 | clade_260 | clade_553 | clade_309 | hetero | ++++ | FALSE | TRUE |
| SPC10097 | SPC10567 | clade_260 | clade_553 | clade_444 | hetero | ++++ | FALSE | TRUE |
| SPC10304 | SPC10304 | clade_260 | clade_262 | clade_262 | semi | | FALSE | FALSE |
| SPC10304 | SPC10325 | clade_260 | clade_262 | clade_408 | hetero | ++++ | FALSE | TRUE |
| SPC10304 | SPC10355 | clade_260 | clade_262 | clade_408 | hetero | ++++ | FALSE | TRUE |
| SPC10304 | SPC10386 | clade_260 | clade_262 | clade_478 | hetero | | FALSE | FALSE |
| SPC10304 | SPC10390 | clade_260 | clade_262 | clade_260 | hetero | ++++ | FALSE | TRUE |
| SPC10304 | SPC10415 | clade_260 | clade_262 | clade_309 | hetero | ++++ | FALSE | TRUE |
| SPC10304 | SPC10567 | clade_260 | clade_262 | clade_444 | hetero | + | FALSE | TRUE |
| SPC10325 | SPC10325 | clade_260 | clade_408 | clade_408 | semi | ++++ | FALSE | FALSE |
| SPC10325 | SPC10355 | clade_260 | clade_408 | clade_408 | hetero | | FALSE | FALSE |
| SPC10325 | SPC10386 | clade_260 | clade_408 | clade_478 | hetero | ++++ | FALSE | TRUE |
| SPC10325 | SPC10390 | clade_260 | clade_408 | clade_260 | hetero | ++++ | FALSE | TRUE |
| SPC10325 | SPC10415 | clade_260 | clade_408 | clade_309 | hetero | ++++ | FALSE | TRUE |
| SPC10325 | SPC10567 | clade_260 | clade_408 | clade_444 | hetero | ++++ | FALSE | TRUE |
| SPC10355 | SPC10355 | clade_260 | clade_408 | clade_408 | semi | – | FALSE | FALSE |
| SPC10355 | SPC10386 | clade_260 | clade_408 | clade_478 | hetero | | FALSE | FALSE |
| SPC10355 | SPC10390 | clade_260 | clade_408 | clade_260 | hetero | ++++ | FALSE | FALSE |
| SPC10355 | SPC10415 | clade_260 | clade_408 | clade_309 | hetero | ++++ | FALSE | TRUE |
| SPC10355 | SPC10567 | clade_260 | clade_408 | clade_444 | hetero | ++++ | FALSE | TRUE |
| SPC10386 | SPC10386 | clade_260 | clade_478 | clade_478 | semi | –––– | FALSE | FALSE |

TABLE 4a-continued

| | | | | | | | | |
|---|---|---|---|---|---|---|---|---|
| SPC10386 | SPC10390 | clade_260 | clade_478 | clade_260 | hetero | ++++ | FALSE | TRUE |
| SPC10386 | SPC10415 | clade_260 | clade_478 | clade_309 | hetero | ++++ | FALSE | TRUE |
| SPC10386 | SPC10567 | clade_260 | clade_478 | clade_444 | hetero | +++ | FALSE | TRUE |
| SPC10390 | SPC10390 | clade_260 | clade_260 | clade_260 | semi | ++++ | FALSE | TRUE |
| SPC10390 | SPC10415 | clade_260 | clade_260 | clade_309 | hetero | ++++ | TRUE | TRUE |
| SPC10390 | SPC10567 | clade_260 | clade_260 | clade_444 | hetero | ++++ | FALSE | TRUE |
| SPC10415 | SPC10415 | clade_260 | clade_309 | clade_309 | semi | ++++ | TRUE | TRUE |
| SPC10415 | SPC10567 | clade_260 | clade_309 | clade_444 | hetero | ++++ | TRUE | TRUE |
| SPC10567 | SPC10567 | clade_260 | clade_444 | clade_444 | semi | ++++ | FALSE | TRUE |
| SPC10097 | SPC10097 | clade_494 | clade_553 | clade_553 | semi | ++++ | FALSE | TRUE |
| SPC10097 | SPC10304 | clade_494 | clade_553 | clade_262 | hetero | ++++ | FALSE | TRUE |
| SPC10097 | SPC10325 | clade_494 | clade_553 | clade_408 | hetero | ++++ | FALSE | TRUE |
| SPC10097 | SPC10355 | clade_494 | clade_553 | clade_408 | hetero | ++++ | FALSE | TRUE |
| SPC10097 | SPC10386 | clade_494 | clade_553 | clade_478 | hetero | ++++ | FALSE | TRUE |
| SPC10097 | SPC10390 | clade_494 | clade_553 | clade_260 | hetero | ++++ | FALSE | TRUE |
| SPC10097 | SPC10415 | clade_494 | clade_553 | clade_309 | hetero | ++++ | TRUE | TRUE |
| SPC10097 | SPC10567 | clade_494 | clade_553 | clade_444 | hetero | ++++ | FALSE | TRUE |
| SPC10304 | SPC10304 | clade_494 | clade_262 | clade_262 | semi | −−−− | FALSE | FALSE |
| SPC10304 | SPC10325 | clade_494 | clade_262 | clade_408 | hetero | + | FALSE | FALSE |
| SPC10304 | SPC10355 | clade_494 | clade_262 | clade_408 | hetero | ++ | FALSE | FALSE |
| SPC10304 | SPC10386 | clade_494 | clade_262 | clade_478 | hetero | −−−− | FALSE | FALSE |
| SPC10304 | SPC10390 | clade_494 | clade_262 | clade_260 | hetero | ++++ | FALSE | TRUE |
| SPC10304 | SPC10415 | clade_494 | clade_262 | clade_309 | hetero | ++++ | TRUE | TRUE |
| SPC10304 | SPC10567 | clade_494 | clade_262 | clade_444 | hetero | −−−− | FALSE | FALSE |
| SPC10325 | SPC10325 | clade_494 | clade_408 | clade_408 | semi | ++++ | FALSE | FALSE |
| SPC10325 | SPC10355 | clade_494 | clade_408 | clade_408 | hetero | ++ | FALSE | FALSE |
| SPC10325 | SPC10386 | clade_494 | clade_408 | clade_478 | hetero | ++++ | FALSE | FALSE |
| SPC10325 | SPC10390 | clade_494 | clade_408 | clade_260 | hetero | ++++ | FALSE | FALSE |
| SPC10325 | SPC10415 | clade_494 | clade_408 | clade_309 | hetero | ++++ | TRUE | TRUE |
| SPC10325 | SPC10567 | clade_494 | clade_408 | clade_444 | hetero | ++++ | FALSE | TRUE |
| SPC10355 | SPC10355 | clade_494 | clade_408 | clade_408 | semi | −− | FALSE | FALSE |
| SPC10355 | SPC10386 | clade_494 | clade_408 | clade_478 | hetero | −−− | FALSE | FALSE |
| SPC10355 | SPC10390 | clade_494 | clade_408 | clade_260 | hetero | ++++ | FALSE | FALSE |
| SPC10355 | SPC10415 | clade_494 | clade_408 | clade_309 | hetero | ++++ | FALSE | TRUE |
| SPC10355 | SPC10567 | clade_494 | clade_408 | clade_444 | hetero | ++ | FALSE | FALSE |
| SPC10386 | SPC10386 | clade_494 | clade_478 | clade_478 | semi | −−− | FALSE | FALSE |
| SPC10386 | SPC10390 | clade_494 | clade_478 | clade_260 | hetero | | FALSE | FALSE |
| SPC10386 | SPC10415 | clade_494 | clade_478 | clade_309 | hetero | ++++ | TRUE | TRUE |
| SPC10386 | SPC10567 | clade_494 | clade_478 | clade_444 | hetero | −−−− | FALSE | FALSE |
| SPC10390 | SPC10390 | clade_494 | clade_260 | clade_260 | semi | | FALSE | FALSE |
| SPC10390 | SPC10415 | clade_494 | clade_260 | clade_309 | hetero | ++++ | TRUE | TRUE |
| SPC10390 | SPC10567 | clade_494 | clade_260 | clade_444 | hetero | +++ | FALSE | FALSE |
| SPC10415 | SPC10415 | clade_494 | clade_309 | clade_309 | semi | ++++ | TRUE | TRUE |
| SPC10415 | SPC10567 | clade_494 | clade_309 | clade_444 | hetero | ++++ | TRUE | TRUE |
| SPC10567 | SPC10567 | clade_494 | clade_444 | clade_444 | semi | − | FALSE | FALSE |
| SPC10097 | SPC10097 | clade_360 | clade_553 | clade_553 | semi | | FALSE | FALSE |
| SPC10097 | SPC10304 | clade_360 | clade_553 | clade_262 | hetero | | FALSE | FALSE |
| SPC10097 | SPC10325 | clade_360 | clade_553 | clade_408 | hetero | + | FALSE | FALSE |
| SPC10097 | SPC10355 | clade_360 | clade_553 | clade_408 | hetero | ++++ | FALSE | FALSE |
| SPC10097 | SPC10386 | clade_360 | clade_553 | clade_478 | hetero | ++++ | FALSE | FALSE |
| SPC10097 | SPC10390 | clade_360 | clade_553 | clade_260 | hetero | ++++ | FALSE | TRUE |
| SPC10097 | SPC10415 | clade_360 | clade_553 | clade_309 | hetero | ++++ | FALSE | TRUE |
| SPC10097 | SPC10567 | clade_360 | clade_553 | clade_444 | hetero | ++++ | FALSE | TRUE |
| SPC10304 | SPC10304 | clade_360 | clade_262 | clade_262 | semi | − | FALSE | FALSE |
| SPC10304 | SPC10325 | clade_360 | clade_262 | clade_408 | hetero | | FALSE | FALSE |
| SPC10304 | SPC10355 | clade_360 | clade_262 | clade_408 | hetero | | FALSE | FALSE |
| SPC10304 | SPC10386 | clade_360 | clade_262 | clade_478 | hetero | ++++ | FALSE | FALSE |
| SPC10304 | SPC10390 | clade_360 | clade_262 | clade_260 | hetero | ++++ | FALSE | TRUE |
| SPC10304 | SPC10415 | clade_360 | clade_262 | clade_309 | hetero | ++++ | FALSE | TRUE |
| SPC10304 | SPC10567 | clade_360 | clade_262 | clade_444 | hetero | ++++ | FALSE | TRUE |
| SPC10325 | SPC10325 | clade_360 | clade_408 | clade_408 | semi | ++ | FALSE | FALSE |
| SPC10325 | SPC10355 | clade_360 | clade_408 | clade_408 | hetero | ++++ | FALSE | FALSE |
| SPC10325 | SPC10386 | clade_360 | clade_408 | clade_478 | hetero | +++ | FALSE | FALSE |
| SPC10325 | SPC10390 | clade_360 | clade_408 | clade_260 | hetero | ++++ | FALSE | FALSE |
| SPC10325 | SPC10415 | clade_360 | clade_408 | clade_309 | hetero | ++++ | TRUE | TRUE |
| SPC10325 | SPC10567 | clade_360 | clade_408 | clade_444 | hetero | ++++ | FALSE | TRUE |
| SPC10355 | SPC10355 | clade_360 | clade_408 | clade_408 | semi | | FALSE | FALSE |
| SPC10355 | SPC10386 | clade_360 | clade_408 | clade_478 | hetero | | FALSE | FALSE |
| SPC10355 | SPC10390 | clade_360 | clade_408 | clade_260 | hetero | ++++ | FALSE | TRUE |
| SPC10355 | SPC10415 | clade_360 | clade_408 | clade_309 | hetero | ++++ | FALSE | TRUE |
| SPC10355 | SPC10567 | clade_360 | clade_408 | clade_444 | hetero | ++++ | FALSE | FALSE |
| SPC10386 | SPC10386 | clade_360 | clade_478 | clade_478 | semi | | FALSE | FALSE |
| SPC10386 | SPC10390 | clade_360 | clade_478 | clade_260 | hetero | ++++ | FALSE | TRUE |
| SPC10386 | SPC10415 | clade_360 | clade_478 | clade_309 | hetero | ++++ | FALSE | TRUE |
| SPC10386 | SPC10567 | clade_360 | clade_478 | clade_444 | hetero | ++++ | FALSE | TRUE |
| SPC10390 | SPC10390 | clade_360 | clade_260 | clade_260 | semi | ++++ | FALSE | TRUE |
| SPC10390 | SPC10415 | clade_360 | clade_260 | clade_309 | hetero | ++++ | TRUE | TRUE |
| SPC10390 | SPC10567 | clade_360 | clade_260 | clade_444 | hetero | ++++ | FALSE | TRUE |

TABLE 4a-continued

| | | | | | | | | |
|---|---|---|---|---|---|---|---|---|
| SPC10415 | SPC10415 | clade_360 | clade_309 | clade_309 | semi | ++++ | TRUE | TRUE |
| SPC10415 | SPC10567 | clade_360 | clade_309 | clade_444 | hetero | ++++ | TRUE | TRUE |
| SPC10567 | SPC10567 | clade_360 | clade_444 | clade_444 | semi | ++++ | FALSE | TRUE |

TABLE 4b

| OTU1 | ID1 | OTU2 | ID2 | OTU3 | ID3 | Clade1 | Clade2 | Clade3 |
|---|---|---|---|---|---|---|---|---|
| *Bacteroides* sp. 1_1_6 | 295 | *Clostridium* sp. HGF2 | 628 | | | clade_65 | clade_351 | |
| *Bacteroides* sp. 1_1_6 | 295 | *Bifidobacterium pseudocatenulatum* | 357 | | | clade_65 | clade_172 | |
| *Bacteroides* sp. 1_1_6 | 295 | *Clostridium symbiosum* | 652 | | | clade_65 | clade_408 | |
| *Bacteroides* sp. 3_1_23 | 308 | *Clostridium nexile* | 607 | | | clade_38 | clade_262 | |
| *Bacteroides* sp. 3_1_23 | 308 | *Bifidobacterium pseudocatenulatum* | 357 | | | clade_38 | clade_172 | |
| *Bacteroides* sp. 3_1_23 | 308 | *Clostridium symbiosum* | 652 | | | clade_38 | clade_408 | |
| *Streptococcus thermophilus* | 1883 | *Bifidobacterium pseudocatenulatum* | 357 | | | clade_98 | clade_172 | |
| *Clostridium nexile* | 607 | *Bifidobacterium pseudocatenulatum* | 357 | | | clade_262 | clade_172 | |
| *Parabacteroides merdae* | 1420 | *Bifidobacterium pseudocatenulatum* | 357 | | | clade_286 | clade_172 | |
| *Clostridium tertium* | 653 | *Clostridium mayombei* | 605 | | | clade_252 | clade_354 | |
| *Clostridium tertium* | 653 | *Clostridium butyricum* | 561 | | | clade_252 | clade_252 | |
| *Clostridium tertium* | 653 | *Coprococcus comes* | 674 | | | clade_252 | clade_262 | |
| *Clostridium tertium* | 653 | *Clostridium hylemonae* | 593 | | | clade_252 | clade_260 | |
| *Clostridium tertium* | 653 | *Clostridium orbiscindens* | 609 | | | clade_252 | clade_494 | |
| *Clostridium tertium* | 653 | Lachnospiraceae *bacterium* 5_1_57FAA | 1054 | | | clade_252 | clade_260 | |
| *Clostridium tertium* | 653 | *Ruminococcus gnavus* | 1661 | | | clade_252 | clade_360 | |
| *Clostridium tertium* | 653 | *Ruminococcus bromii* | 1657 | | | clade_252 | clade_537 | |
| *Clostridium disporicum* | 579 | *Clostridium mayombei* | 605 | | | clade_253 | clade_354 | |
| *Clostridium disporicum* | 579 | *Clostridium butyricum* | 561 | | | clade_253 | clade_252 | |
| *Clostridium disporicum* | 579 | *Clostridium orbiscindens* | 609 | | | clade_253 | clade_494 | |
| *Clostridium disporicum* | 579 | *Ruminococcus gnavus* | 1661 | | | clade_253 | clade_360 | |
| *Clostridium mayombei* | 605 | *Clostridium butyricum* | 561 | | | clade_354 | clade_252 | |
| *Clostridium mayombei* | 605 | *Coprococcus comes* | 674 | | | clade_354 | clade_262 | |
| *Clostridium mayombei* | 605 | *Clostridium hylemonae* | 593 | | | clade_354 | clade_260 | |
| *Clostridium mayombei* | 605 | *Clostridium symbiosum* | 652 | | | clade_354 | clade_408 | |
| *Clostridium mayombei* | 605 | *Clostridium orbiscindens* | 609 | | | clade_354 | clade_494 | |
| *Clostridium mayombei* | 605 | Lachnospiraceae *bacterium* 5_1_57FAA | 1054 | | | clade_354 | clade_260 | |
| *Clostridium mayombei* | 605 | *Ruminococcus gnavus* | 1661 | | | clade_354 | clade_360 | |
| *Clostridium mayombei* | 605 | *Ruminococcus bromii* | 1657 | | | clade_354 | clade_537 | |
| *Clostridium butyricum* | 561 | *Clostridium mayombei* | 605 | | | clade_252 | clade_354 | |
| *Clostridium butyricum* | 561 | *Coprococcus comes* | 674 | | | clade_252 | clade_262 | |
| *Clostridium butyricum* | 561 | *Clostridium hylemonae* | 593 | | | clade_252 | clade_260 | |
| *Clostridium butyricum* | 561 | *Clostridium symbiosum* | 652 | | | clade_252 | clade_408 | |
| *Clostridium butyricum* | 561 | *Clostridium orbiscindens* | 609 | | | clade_252 | clade_494 | |
| *Clostridium butyricum* | 561 | Lachnospiraceae *bacterium* 5_1_57FAA | 1054 | | | clade_252 | clade_260 | |
| *Clostridium butyricum* | 561 | *Ruminococcus gnavus* | 1661 | | | clade_252 | clade_360 | |
| *Clostridium butyricum* | 561 | *Ruminococcus bromii* | 1657 | | | clade_252 | clade_537 | |
| *Coprococcus comes* | 674 | *Clostridium butyricum* | 561 | | | clade_262 | clade_252 | |
| *Coprococcus comes* | 674 | *Ruminococcus gnavus* | 1661 | | | clade_262 | clade_360 | |
| *Clostridium hylemonae* | 593 | Lachnospiraceae *bacterium* 5_1_57FAA | 1054 | | | clade_260 | clade_260 | |
| *Clostridium orbiscindens* | 609 | *Ruminococcus gnavus* | 1661 | | | clade_494 | clade_360 | |
| *Coprococcus comes* | 674 | *Clostridium tertium* | 653 | *Clostridium mayombei* | 605 | clade_262 | clade_252 | clade_354 |
| *Coprococcus comes* | 674 | *Clostridium tertium* | 653 | *Clostridium butyricum* | 561 | clade_262 | clade_252 | clade_252 |
| *Coprococcus comes* | 674 | *Clostridium tertium* | 653 | *Clostridium orbiscindens* | 609 | clade_262 | clade_252 | clade_494 |
| *Coprococcus comes* | 674 | *Clostridium disporicum* | 579 | *Clostridium butyricum* | 561 | clade_262 | clade_253 | clade_252 |
| *Coprococcus comes* | 674 | *Clostridium mayombei* | 605 | *Clostridium butyricum* | 561 | clade_262 | clade_354 | clade_252 |
| *Coprococcus comes* | 674 | *Clostridium butyricum* | 561 | *Clostridium hylemonae* | 593 | clade_262 | clade_252 | clade_260 |
| *Coprococcus comes* | 674 | *Clostridium butyricum* | 561 | *Clostridium orbiscindens* | 609 | clade_262 | clade_252 | clade_494 |
| *Coprococcus comes* | 674 | *Clostridium butyricum* | 561 | *Ruminococcus gnavus* | 1661 | clade_262 | clade_252 | clade_360 |
| *Coprococcus comes* | 674 | *Clostridium butyricum* | 561 | *Ruminococcus bromii* | 1657 | clade_262 | clade_252 | clade_537 |
| *Clostridium symbiosum* | 652 | *Clostridium tertium* | 653 | *Clostridium mayombei* | 605 | clade_408 | clade_252 | clade_354 |
| *Clostridium symbiosum* | 652 | *Clostridium tertium* | 653 | *Clostridium butyricum* | 561 | clade_408 | clade_252 | clade_252 |
| *Clostridium symbiosum* | 652 | *Clostridium disporicum* | 579 | *Clostridium butyricum* | 561 | clade_408 | clade_253 | clade_252 |
| *Clostridium symbiosum* | 652 | *Clostridium mayombei* | 605 | *Clostridium orbiscindens* | 609 | clade_408 | clade_354 | clade_494 |
| *Clostridium symbiosum* | 652 | *Clostridium mayombei* | 605 | *Ruminococcus bromii* | 1657 | clade_408 | clade_354 | clade_537 |
| *Clostridium symbiosum* | 652 | *Clostridium butyricum* | 561 | *Clostridium hylemonae* | 593 | clade_408 | clade_252 | clade_260 |
| *Clostridium symbiosum* | 652 | *Clostridium butyricum* | 561 | *Clostridium orbiscindens* | 609 | clade_408 | clade_252 | clade_494 |

TABLE 4b-continued

| OTU1 | ID1 | OTU2 | ID2 | OTU3 | ID3 | Clade1 | Clade2 | Clade3 |
|---|---|---|---|---|---|---|---|---|
| *Clostridium symbiosum* | 652 | *Clostridium butyricum* | 561 | *Ruminococcus gnavus* | 1661 | clade_408 | clade_252 | clade_360 |
| *Clostridium symbiosum* | 652 | *Clostridium butyricum* | 561 | *Ruminococcus bromii* | 1657 | clade_408 | clade_252 | clade_537 |
| Lachnospiraceae *bacterium* 5_1_57FAA | 1054 | *Clostridium tertium* | 653 | *Clostridium butyricum* | 561 | clade_260 | clade_252 | clade_252 |
| Lachnospiraceae *bacterium* 5_1_57FAA | 1054 | *Clostridium disporicum* | 579 | *Clostridium butyricum* | 561 | clade_260 | clade_253 | clade_252 |
| Lachnospiraceae *bacterium* 5_1_57FAA | 1054 | *Clostridium mayombei* | 605 | *Ruminococcus gnavus* | 1661 | clade_260 | clade_354 | clade_360 |
| Lachnospiraceae *bacterium* 5_1_57FAA | 1054 | *Clostridium mayombei* | 605 | *Ruminococcus bromii* | 1657 | clade_260 | clade_354 | clade_537 |
| Lachnospiraceae *bacterium* 5_1_57FAA | 1054 | *Clostridium butyricum* | 561 | *Clostridium hylemonae* | 593 | clade_260 | clade_252 | clade_260 |
| Lachnospiraceae *bacterium* 5_1_57FAA | 1054 | *Clostridium butyricum* | 561 | *Clostridium orbiscindens* | 609 | clade_260 | clade_252 | clade_494 |
| Lachnospiraceae *bacterium* 5_1_57FAA | 1054 | *Clostridium butyricum* | 561 | *Ruminococcus gnavus* | 1661 | clade_260 | clade_252 | clade_360 |
| Lachnospiraceae *bacterium* 5_1_57FAA | 1054 | *Clostridium butyricum* | 561 | *Ruminococcus bromii* | 1657 | clade_260 | clade_252 | clade_537 |
| *Clostridium butyricum* | 561 | *Coprococcus comes* | 674 | *Clostridium symbiosum* | 652 | clade_252 | clade_262 | clade_408 |
| *Clostridium butyricum* | 561 | *Coprococcus comes* | 674 | Lachnospiraceae *bacterium* 5_1_57FAA | 1054 | clade_252 | clade_262 | clade_260 |
| *Clostridium butyricum* | 561 | *Clostridium symbiosum* | 652 | Lachnospiraceae *bacterium* 5_1_57FAA | 1054 | clade_252 | clade_408 | clade_260 |

TABLE 5

| Expt. | SP Arm | Key | Seres Arm | Treatment | OTU1 | OTU2 | OTU3 | CivSim Inhibition (log10 CFU/mL) | CivSim Inhibition (Confidence) | Mean Min. Rel. Weight | Mean Max. Clin. Score | Cum. | | | |
|---|---|---|---|---|---|---|---|---|---|---|---|---|---|---|---|
| Mort. | Clade1 | Clade2 | Clade3 | | | | | | | | | | | | |
| SP427 | 1 | PBS | 1 | Vehicle | | | | n/a | n/a | 0.82 | 2.6 | 3 | | | |
| SP427 | 14 | V5F | 2 | FSV33_10pct (EMT) | | | | n/a | n/a | 0.99 | 0 | 0 | | | |
| SP427 | 6 | 79F | 3 | DE277512.1 | *Collinsella aerofaciens* | *Faecalibacterium prausnitzii* | *Blautia producta* | 1.84 | ++++ | 0.85 | 1.4 | 1 | clade_553 | clade_478 | clade_309 |
| SP427 | 12 | V7B | 4 | DE643314.1 | *Faecalibacterium prausnitzii* | *Blautia producta* | *Eubacterium rectale* | 1.27 | ++++ | 0.81 | 2 | 3 | clade_478 | clade_309 | clade_444 |
| SP427 | 5 | 699 | 5 | DE022136.1 | *Clostridium bolteae* | Lachnospiraceae *bacterium* 5_1_57FAA | *Blautia producta* | 0.81 | ++++ | 0.93 | 1 | 0 | clade_408 | clade_260 | clade_309 |
| SP427 | 10 | E4W | 6 | DE061176.1 | *Collinsella aerofaciens* | *Clostridium butyricum* | *Ruminococcus gnavus* | 2.87 | ++++ | 0.96 | 0.2 | 0 | clade_553 | clade_252 | clade_360 |
| SP427 | 7 | 852 | 7 | DE554703.1 | *Collinsella aerofaciens* | *Clostridium butyricum* | *Clostridium hylemonae* | 3.09 | ++++ | 0.78 | 1.7 | 2 | clade_553 | clade_252 | clade_260 |
| SP427 | 3 | 366 | 8 | DE705158.1 | *Coprococcus comes* | *Clostridium innocuum* | *Clostridium butyricum* | 3 | ++++ | 0.85 | 1.7 | 2 | clade_262 | clade_351 | clade_252 |
| SP427 | 9 | CE3 | 9 | DE266960.1 | *Clostridium bolteae* | *Clostridium butyricum* | *Ruminococcus gnavus* | 3.06 | ++++ | 0.91 | 1 | 0 | clade_408 | clade_252 | clade_360 |
| SP427 | 8 | BCY | 10 | DE897971.1 | *Clostridium mayombei* | *Collinsella aerofaciens* | *Clostridium symbiosum* | 1.46 | ++++ | 0.83 | 1.7 | 1 | clade_354 | clade_553 | clade_408 |
| SP427 | 13 | Y4K | 11 | DE001210.1 | *Clostridium tertium* | *Collinsella aerofaciens* | *Blautia producta* | 2 | ++++ | 0.88 | 1.1 | 0 | clade_252 | clade_553 | clade_309 |
| SP427 | 11 | FBK | 12 | DE586246.1 | *Clostridium mayombei* | Lachnospiraceae *bacterium* 5_1_57FAA | *Blautia producta* | 1.88 | ++++ | 0.94 | 1 | 0 | clade_354 | clade_260 | clade_309 |
| SP427 | 4 | 3R1 | 13 | DE844277.1 | *Coprococcus comes* | *Clostridium mayombei* | *Blautia* sp. M25 | 2.1 | ++++ | 0.88 | 1 | 0 | clade_262 | clade_354 | clade_309 |
| SP427 | 2 | 1HR | 14 | DE208485.1 | *Coprococcus comes* | *Clostridium tertium* | *Clostridium orbiscindens* | 1.8 | ++++ | 0.89 | 1.3 | 1 | clade_262 | clade_252 | clade_494 |
| SP427 | 31 | PBS NoCdiff | 31 | Naive | | | | n/a | n/a | 1 | 0 | 0 | | | |

TABLE 6

| Initial Concentration of VRE (log10 CFU/mL) | Initial Concentration of Ecobiotic ™ Composition (log10 CFU/mL/Strain) | Incu-bation Time (h) | Inhibition (log10 CFU/mL) |
|---|---|---|---|
| 3 | 6 | 15 | 3.1 |
| 3 | 4 | 15 | 1.3 |
| 2 | 6 | 15 | 5.2 |
| 2 | 4 | 15 | 1.6 |
| 3 | 6 | 24 | 2.7 |
| 3 | 4 | 24 | 0.7 |
| 2 | 6 | 24 | 4.6 |

TABLE 7

| Initial Concentration of *K. pneumoniae* (log10 CFU/mL) | Initial Concentration of Ecobiotic ™ Composition (log10 CFU/mL/Strain) | Incu-bation Time (h) | Inhibition (log10 CFU/mL) |
|---|---|---|---|
| 3 | 6 | 15 | 2.5 |
| 3 | 4 | 15 | 0.4 |
| 2 | 6 | 15 | 4.2 |
| 2 | 4 | 15 | 1.2 |
| 3 | 6 | 24 | 1.7 |

TABLE 7-continued

| Initial Concentration of *K. pneumoniae* (log10 CFU/mL) | Initial Concentration of Ecobiotic ™ Composition (log10 CFU/mL/Strain) | Incu-bation Time (h) | Inhibition (log10 CFU/mL) |
|---|---|---|---|
| 3 | 4 | 24 | 0.2 |
| 2 | 6 | 24 | 3.1 |
| 2 | 4 | 24 | 0.1 |

TABLE 8

| Initial Concentration of *M. morganii* (log10 CFU/mL) | Initial Concentration of Ecobiotic ™ Composition (log10 CFU/mL/Strain) | Incu-bation Time (h) | Inhibition (log10 CFU/mL) |
|---|---|---|---|
| 3 | 6 | 15 | 4.3 |
| 3 | 4 | 15 | 2.1 |
| 2 | 6 | 15 | 5.8 |
| 2 | 4 | 15 | 3.3 |
| 3 | 6 | 24 | 3.9 |
| 3 | 4 | 24 | 1.4 |
| 2 | 6 | 24 | 5.1 |
| 2 | 4 | 24 | 2.5 |

TABLE 9

| SP Expt. | SP Arm | Test Article | Target Dose (CFU/OTU/ mouse) | Cumulative Mortality (%) | Mean Min. Rel. Weight | Mean Max. Clin. Score (Death = 4) |
|---|---|---|---|---|---|---|
| SP-327 | 3 | Vehicle Control | | 30 | 0.89 | 2.2 |
| SP-327 | 4 | Vanco. Positive Control | | 0 | 0.99 | 1 |
| SP-327 | 12 | N1957 | 2.0E+07 | 0 | 0.87 | 0 |
| SP-327 | 13 | N1957 | 2.0E+06 | 40 | 0.86 | 2.2 |
| SP-327 | 14 | N1957 | 2.0E+05 | 50 | 0.80 | 2.8 |
| SP-338 | 1 | Vehicle Control | | 60 | 0.81 | 3.2 |
| SP-338 | 2 | Vanco. Positive Control | | 0 | 1.00 | 0 |
| SP-338 | 3 | 10% fecal suspension | | 0 | 0.95 | 1 |
| SP-338 | 5 | N1957 | 2.0E+07 | 10 | 0.80 | 2 |
| SP-338 | 6 | N1957 | 2.0E+06 | 0 | 0.97 | 1 |
| SP-338 | 7 | N1957 | 2.0E+05 | 20 | 0.85 | 1.7 |
| SP-338 | 11 | N1957 | 2.0E+07 | 20 | 0.86 | 2 |
| SP-338 | 12 | N1957 | 2.0E+06 | 30 | 0.83 | 2.5 |
| SP-338 | 13 | N1961 | 2.0E+07 | 10 | 0.93 | 1.3 |
| SP-338 | 14 | N1955 | 2.0E+07 | 0 | 0.91 | 1.2 |
| SP-338 | 15 | N1955 | 2.0E+06 | 10 | 0.90 | 1.5 |
| SP-338 | 16 | N1955 | 2.0E+05 | 10 | 0.89 | 2.7 |
| SP-338 | 17 | N1967 | 2.0E+07 | 10 | 0.94 | 1.4 |
| SP-338 | 18 | N1983 | 2.0E+07 | 0 | 0.92 | 1 |
| SP-338 | 19 | N1989 | 2.0E+07 | 10 | 0.91 | 1.3 |
| SP-338 | 20 | N1996 | 2.0E+07 | 10 | 0.93 | 1.3 |
| SP-338 | 21 | Naïve | | 0 | 1.00 | 0 |
| SP-339 | 1 | Vehicle Control | | 20 | 0.88 | 2.2 |
| SP-339 | 2 | Vanco. Positive Control | | 0 | 0.99 | 0 |
| SP-339 | 3 | 10% fecal suspension | | 0 | 0.97 | 0 |
| SP-339 | 4 | N1995 | 2.0E+07 | 20 | 0.83 | 2.1 |
| SP-339 | 5 | N1995 | 2.0E+06 | 10 | 0.91 | 1.5 |
| SP-339 | 6 | N1995 | 2.0E+05 | 0 | 0.96 | 1.2 |
| SP-339 | 7 | N1950 | 2.0E+07 | 0 | 0.94 | 1 |
| SP-339 | 8 | N1994 | 2.0E+07 | 20 | 0.87 | 1.8 |
| SP-339 | 9 | N1997 | 2.0E+07 | 0 | 0.95 | 1.2 |
| SP-339 | 10 | N1967 | 2.0E+07 | 0 | 0.93 | 1.2 |
| SP-339 | 11 | N1983 | 2.0E+07 | 10 | 0.83 | 2.2 |
| SP-339 | 12 | N1989 | 2.0E+07 | 0 | 0.88 | 1.5 |
| SP-339 | 13 | N1996 | 2.0E+07 | 0 | 0.97 | 1 |
| SP-339 | 14 | N2002 | 2.0E+07 | 20 | 0.92 | 2 |
| SP-339 | 15 | N2000 | 2.0E+07 | 0 | 0.98 | 1.2 |
| SP-339 | 21 | Naïve | | 0 | 0.98 | 0 |
| SP-342 | 1 | Vehicle Control | | 40 | 0.85 | 2.5 |
| SP-342 | 2 | Vanco. Positive Control | | 0 | 1.00 | 0 |
| SP-342 | 5 | N1957 | 2.0E+08 | 0 | 0.94 | 0.2 |

TABLE 9-continued

| SP Expt. | SP Arm | Test Article | Target Dose (CFU/OTU/ mouse) | Cumulative Mortality (%) | Mean Min. Rel. Weight | Mean Max. Clin. Score (Death = 4) |
|---|---|---|---|---|---|---|
| SP-342 | 6 | N1957 | 2.0E+07 | 0 | 0.96 | 0 |
| SP-342 | 7 | N1957 | 2.0E+06 | 10 | 0.88 | 1.3 |
| SP-342 | 8 | N1980 | 2.0E+08 | 10 | 0.92 | 1.8 |
| SP-342 | 9 | N1998 | 2.0E+08 | 20 | 0.83 | 2.8 |
| SP-342 | 10 | N1976 | 2.0E+08 | 10 | 0.92 | 1.4 |
| SP-342 | 11 | N1987 | 2.0E+08 | 10 | 0.93 | 1.6 |
| SP-342 | 12 | N2005 | 2.0E+08 | 20 | 0.86 | 2.4 |
| SP-342 | 13 | N1958 | 2.0E+08 | 0 | 0.94 | 1.5 |
| SP-342 | 14 | N2004 | 2.0E+08 | 10 | 0.93 | 1.4 |
| SP-342 | 15 | N1949 | 2.0E+08 | 10 | 0.87 | 1.5 |
| SP-342 | 18 | N1970 | 2.0E+08 | 50 | 0.81 | 3 |
| SP-342 | 21 | Naïve | | 0 | 0.99 | 0 |
| SP-361 | 1 | Vehicle Control | | 30 | 0.88 | 2.6 |
| SP-361 | 2 | 10% fecal suspension | | 0 | 0.99 | 0 |
| SP-361 | 3 | N435 | 1.0E+07 | 80 | 0.83 | 3.6 |
| SP-361 | 4 | N1979 | 1.0E+07 | 0 | 0.97 | 0 |
| SP-361 | 5 | N414 | 1.0E+07 | 0 | 0.97 | 0 |
| SP-361 | 6 | N512 | 1.0E+07 | 20 | 0.94 | 1.6 |
| SP-361 | 7 | N582 | 1.0E+07 | 10 | 0.93 | 0.9 |
| SP-361 | 8 | N571 | 1.0E+07 | 30 | 0.88 | 2.1 |
| SP-361 | 9 | N510 | 1.0E+07 | 0 | 0.93 | 0.3 |
| SP-361 | 10 | N1981 | 1.0E+07 | 40 | 0.83 | 2.8 |
| SP-361 | 11 | N1969 | 1.0E+07 | 80 | 0.82 | 3.6 |
| SP-361 | 12 | N461 | 1.0E+07 | 10 | 0.89 | 1.2 |
| SP-361 | 13 | N460 | 1.0E+07 | 0 | 0.93 | 1.1 |
| SP-361 | 14 | N1959 | 1.0E+07 | 30 | 0.89 | 1.9 |
| SP-361 | 15 | N2006 | 1.0E+07 | 30 | 0.89 | 1.9 |
| SP-361 | 16 | N1953 | 1.0E+07 | 10 | 0.83 | 2.3 |
| SP-361 | 17 | N1960 | 1.0E+07 | 0 | 0.92 | 1 |
| SP-361 | 18 | N2007 | 1.0E+07 | 10 | 0.91 | 0.9 |
| SP-361 | 19 | N1978 | 1.0E+07 | 10 | 0.91 | 1.3 |
| SP-361 | 20 | N1972 | 1.0E+07 | 30 | 0.83 | 2.6 |
| SP-361 | 21 | Naïve | | 0 | 1.00 | 0 |
| SP-363 | 1 | Vehicle Control | | 30 | 0.85 | 2.6 |
| SP-363 | 2 | 10% fecal suspension | | 0 | 0.95 | 0 |
| SP-363 | 8 | N1974 | 1.0E+07 | 60 | 0.81 | 3.2 |
| SP-363 | 9 | N582 | 1.0E+07 | 60 | 0.81 | 3.2 |
| SP-363 | 10 | N435 | 1.0E+07 | 30 | 0.86 | 2.1 |
| SP-363 | 11 | N414 | 1.0E+07 | 40 | 0.83 | 2.5 |
| SP-363 | 12 | N457 | 1.0E+07 | 30 | 0.83 | 2.2 |
| SP-363 | 13 | N511 | 1.0E+07 | 20 | 0.87 | 2 |
| SP-363 | 14 | N513 | 1.0E+07 | 0 | 0.88 | 0.2 |
| SP-363 | 15 | N682 | 1.0E+07 | 30 | 0.82 | 2.6 |
| SP-363 | 16 | N736 | 1.0E+07 | 40 | 0.82 | 2.8 |
| SP-363 | 17 | N732 | 1.0E+07 | 10 | 0.86 | 1.3 |
| SP-363 | 18 | N1948 | 1.0E+07 | 60 | 0.85 | 3.2 |
| SP-363 | 19 | N853 | 1.0E+07 | 10 | 0.85 | 2.2 |
| SP-363 | 20 | N1979 | 1.0E+07 | 60 | 0.78 | 3.2 |
| SP-363 | 21 | N879 | 1.0E+07 | 40 | 0.83 | 2.8 |
| SP-363 | 22 | N999 | 1.0E+07 | 20 | 0.88 | 2.4 |
| SP-363 | 23 | N975 | 1.0E+07 | 30 | 0.80 | 2.6 |
| SP-363 | 24 | N861 | 1.0E+07 | 50 | 0.85 | 3 |
| SP-363 | 25 | N1095 | 1.0E+07 | 80 | 0.83 | 3.6 |
| SP-363 | 26 | Naïve | | 0 | 1.00 | 0 |
| SP-364 | 1 | Vehicle Control | | 40 | 0.83 | 2.8 |
| SP-364 | 4 | N582 | 1.0E+07 | 0 | 0.81 | 0.9 |
| SP-364 | 5 | N582 | 1.0E+06 | 0 | 0.84 | 0.9 |
| SP-364 | 6 | N582 | 1.0E+05 | 40 | 0.76 | 2.5 |
| SP-364 | 13 | N414 | 1.0E+07 | 0 | 0.84 | 0 |
| SP-364 | 14 | N414 | 1.0E+06 | 30 | 0.79 | 2.4 |
| SP-364 | 15 | N414 | 1.0E+05 | 10 | 0.76 | 2 |
| SP-364 | 22 | 10% fecal suspension | | 0 | 0.97 | 0 |
| SP-364 | 23 | Nave | | 0 | 0.99 | 0 |
| SP-365 | 1 | Vehicle Control | | 40 | 0.83 | 2.8 |
| SP-365 | 4 | 10% fecal suspension | | 0 | 0.98 | 0 |
| SP-365 | 13 | N582 | 1.0E+07 | 60 | 0.80 | 3.2 |
| SP-365 | 14 | N582 | 1.0E+06 | 10 | 0.89 | 1.5 |
| SP-365 | 15 | N414 | 1.0E+07 | 20 | 0.86 | 1.7 |
| SP-365 | 16 | N414 | 1.0E+06 | 80 | 0.83 | 3.5 |
| SP-365 | 21 | Naïve | | 0 | 1.00 | 0 |
| SP-366 | 1 | Vehicle Control | | 20 | 0.82 | 2.4 |
| SP-366 | 4 | 10% fecal suspension | | 0 | 0.93 | 1 |
| SP-366 | 7 | N582 | 1.0E+07 | 0 | 0.86 | 1 |
| SP-366 | 10 | N414 | 1.0E+07 | 20 | 0.83 | 2.4 |
| SP-366 | 13 | N402 | 1.0E+07 | 30 | 0.81 | 2.1 |

TABLE 9-continued

| SP Expt. | SP Arm | Test Article | Target Dose (CFU/OTU/ mouse) | Cumulative Mortality (%) | Mean Min. Rel. Weight | Mean Max. Clin. Score (Death = 4) |
|---|---|---|---|---|---|---|
| SP-366 | 16 | N1982 | 1.0E+07 | 0 | 0.90 | 1.1 |
| SP-366 | 19 | N460 | 1.0E+07 | 10 | 0.83 | 2.2 |
| SP-366 | 22 | N513 | 6.7E+06 | 40 | 0.82 | 2.8 |
| SP-366 | 23 | N1966 | 1.0E+07 | 0 | 0.90 | 0.5 |
| SP-366 | 24 | N1977 | 1.0E+07 | 20 | 0.83 | 1.9 |
| SP-366 | 25 | N1979 | 1.0E+07 | 20 | 0.83 | 2.4 |
| SP-366 | 26 | N682 | 1.0E+07 | 20 | 0.83 | 2.3 |
| SP-366 | 27 | N1947 | 1.0E+07 | 10 | 0.82 | 1.3 |
| SP-366 | 28 | N582 | 1.0E+07 | 20 | 0.82 | 1.8 |
| SP-366 | 29 | N414 | 1.0E+07 | 0 | 0.85 | 1.5 |
| SP-366 | 30 | N603 | 1.0E+07 | 30 | 0.82 | 2.2 |
| SP-366 | 31 | Naïve | | 0 | 0.99 | 0 |
| SP-368 | 1 | Vehicle Control | | 50 | 0.85 | 2.8 |
| SP-368 | 2 | 10% fecal suspension | | 0 | 0.97 | 0 |
| SP-368 | 7 | N1966 | 1.0E+07 | 0 | 0.89 | 1 |
| SP-368 | 8 | N1966 | 1.0E+06 | 10 | 0.91 | 1.5 |
| SP-368 | 9 | N1966 | 1.0E+05 | 50 | 0.82 | 3.1 |
| SP-368 | 21 | Naïve | | 0 | 1.00 | 0 |
| SP-374 | 1 | Vehicle Control | | 100 | 0.83 | 4 |
| SP-374 | 4 | 10% fecal suspension | | 10 | 0.89 | 0.5 |
| SP-374 | 11 | N1966 | 1.0E+08 | 0 | 0.87 | 1 |
| SP-374 | 12 | N1966 | 1.0E+08 | 0 | 0.91 | 0.5 |
| SP-374 | 13 | N1966 | 1.0E+07 | 10 | 0.88 | 1.3 |
| SP-374 | 14 | N1966 | 1.0E+06 | 50 | 0.79 | 3 |
| SP-374 | 15 | N584 | 1.0E+08 | 0 | 0.89 | 1 |
| SP-374 | 16 | N584 | 1.0E+07 | 30 | 0.84 | 2.4 |
| SP-374 | 17 | N1962 | 1.0E+07 | 0 | 0.93 | 0 |
| SP-374 | 18 | N382 | 1.0E+07 | 10 | 0.85 | 1.5 |
| SP-374 | 19 | N1964 | 1.0E+07 | 20 | 0.89 | 1.8 |
| SP-374 | 20 | N1965 | 1.0E+07 | 30 | 0.85 | 2.1 |
| SP-374 | 21 | N306 | 1.0E+07 | 10 | 0.90 | 0.4 |
| SP-374 | 22 | N1988 | 1.0E+07 | 0 | 0.89 | 1 |
| SP-374 | 23 | N2003 | 1.0E+07 | 0 | 0.92 | 1.2 |
| SP-374 | 24 | N1993 | 1.0E+07 | 20 | 0.77 | 2.4 |
| SP-374 | 25 | Naïve | | 0 | 0.99 | 0 |
| SP-376 | 1 | Vehicle Control | | 60 | 0.83 | 3.2 |
| SP-376 | 2 | 10% fecal suspension | | 0 | 0.98 | 0 |
| SP-376 | 3 | N1966 | 1.0E+08 | 30 | 0.79 | 2.4 |
| SP-376 | 4 | N1966 | 1.0E+07 | 0 | 0.95 | 0 |
| SP-376 | 5 | N1966 | 1.0E+08 | 30 | 0.79 | 2.6 |
| SP-376 | 6 | N1966 | 1.0E+07 | 10 | 0.88 | 2.2 |
| SP-376 | 7 | N1986 | 1.0E+07 | 40 | 0.80 | 2.8 |
| SP-376 | 8 | N1962 | 1.0E+08 | 0 | 0.98 | 0 |
| SP-376 | 9 | N1962 | 1.0E+07 | 0 | 0.95 | 0 |
| SP-376 | 10 | N1963 | 1.0E+07 | 40 | 0.81 | 2.6 |
| SP-376 | 11 | N1984 | 1.0E+08 | 0 | 0.97 | 0 |
| SP-376 | 12 | N1984 | 1.0E+07 | 0 | 0.90 | 1.1 |
| SP-376 | 13 | N1990 | 1.0E+08 | 0 | 0.92 | 1 |
| SP-376 | 14 | N1990 | 1.0E+07 | 0 | 0.92 | 1 |
| SP-376 | 15 | N1999 | 1.0E+08 | 10 | 0.87 | 1.4 |
| SP-376 | 16 | N1999 | 1.0E+07 | 0 | 0.93 | 0 |
| SP-376 | 17 | N1968 | 1.0E+07 | 50 | 0.78 | 3 |
| SP-376 | 18 | N1951 | 1.0E+07 | 0 | 0.93 | 1 |
| SP-376 | 19 | N1991 | 1.0E+07 | 0 | 0.93 | 1.1 |
| SP-376 | 20 | N1975 | 1.0E+07 | 50 | 0.78 | 3 |
| SP-376 | 21 | Naïve | | 0 | 0.99 | 0 |
| SP-383 | 1 | Vehicle Control | | 100 | 0.83 | 4 |
| SP-383 | 2 | 10% fecal suspension | | 0 | 0.92 | 0.1 |
| SP-383 | 9 | N1962 | 1.0E+09 | 10 | 0.95 | 1.3 |
| SP-383 | 10 | N1962 | 1.0E+08 | 10 | 0.93 | 1.3 |
| SP-383 | 11 | N1962 | 1.0E+07 | 0 | 0.92 | 1 |
| SP-383 | 12 | N1984 | 1.0E+09 | 0 | 0.89 | 1 |
| SP-383 | 13 | N1984 | 1.0E+08 | 10 | 0.94 | 1.3 |
| SP-383 | 14 | N1984 | 1.0E+07 | 10 | 0.90 | 1.3 |
| SP-383 | 21 | Naïve | | 0 | 1.00 | 0 |
| SP-390 | 1 | Vehicle Control | | 80 | 0.82 | 3.6 |
| SP-390 | 2 | 10% fecal suspension | | 0 | 0.98 | 0.1 |
| SP-390 | 3 | N1962 | 2.0E+07 | 0 | 0.97 | 0 |
| SP-390 | 4 | N1962 | 2.0E+06 | 0 | 0.98 | 0 |
| SP-390 | 5 | N1984 | 2.0E+07 | 0 | 0.95 | 1 |
| SP-390 | 6 | N1984 | 2.0E+06 | 0 | 0.95 | 0.1 |
| SP-390 | 9 | N1962 | 2.0E+07 | 0 | 0.93 | 1 |
| SP-390 | 10 | N1962 | 2.0E+06 | 10 | 0.93 | 1.3 |
| SP-390 | 11 | N1984 | 2.0E+07 | 20 | 0.86 | 2.2 |
| SP-390 | 12 | N1984 | 2.0E+09 | 30 | 0.88 | 2.1 |

TABLE 9-continued

| SP Expt. | SP Arm | Test Article | Target Dose (CFU/OTU/ mouse) | Cumulative Mortality (%) | Mean Min. Rel. Weight | Mean Max. Clin. Score (Death = 4) |
|---|---|---|---|---|---|---|
| SP-390 | 13 | N1952 | 2.0E+07 | 0 | 0.89 | 1 |
| SP-390 | 14 | N2001 | 2.0E+07 | 0 | 0.95 | 0.2 |
| SP-390 | 15 | N1973 | 2.0E+07 | 10 | 0.90 | 0.7 |
| SP-390 | 16 | N1954 | 2.0E+07 | 0 | 0.94 | 1.1 |
| SP-390 | 17 | N1985 | 2.0E+07 | 10 | 0.86 | 1.8 |
| SP-390 | 18 | N1971 | 2.0E+07 | 0 | 0.89 | 0.9 |
| SP-390 | 19 | N1956 | 2.0E+07 | 0 | 0.95 | 0 |
| SP-390 | 20 | N1992 | 2.0E+07 | 0 | 0.95 | 0 |
| SP-390 | 31 | Naïve | | 0 | 0.98 | 0 |

TABLE 10

| Network Ecology ID | Exemplary Network Clades | Exemplary Network OTUs |
|---|---|---|
| N306 | clade_252, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_38 or clade_38e or clade_38i), (clade_408 or clade_408b or clade_408d or clade_408f or clade_408g or clade_408h), (clade_444 or clade_444i), (clade_478 or clade_478i), (clade_481 or clade_481a or clade_481b or clade_481e or clade_481g or clade_481h or clade_481i), clade_494, (clade_553 or clade_553i) | *Blautia producta*, *Clostridium hylemonae*, *Clostridium innocuum*, *Clostridium orbiscindens*, *Clostridium symbiosum*, *Clostridium tertium*, *Collinsella aerofaciens*, *Coprobacillus* sp. D7, *Coprococcus comes*, *Eubacterium rectale*, *Eubacterium* sp. WAL 14571, *Faecalibacterium prausnitzii*, Lachnospiraceae bacterium 5_1_57FAA, *Roseburia faecalis*, *Ruminococcus obeum*, *Ruminococcus torques* |
| N382 | clade_252, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia producta*, *Clostridium hylemonae*, *Clostridium innocuum*, *Clostridium orbiscindens*, *Clostridium symbiosum*, *Clostridium tertium*, *Collinsella aerofaciens*, *Coprococcus comes*, Lachnospiraceae bacterium 5_1_57FAA, *Ruminococcus bromii*, *Ruminococcus gnavus* |
| N402 | (clade_262 or clade_262i), clade_286, (clade_309 or clade_309c or clade_309e or clade_309g or clade_309h or clade_309i), (clade_360 or clade_360c or clade_360g or clade_360h or clade_360i), (clade_444 or clade_444i), clade_466, (clade_478 or clade_478i), clade_500 | *Alistipes shahii*, *Coprococcus comes*, *Dorea formicigenerans*, *Dorea longicatena*, *Eubacterium rectale*, *Faecalibacterium prausnitzii*, *Odoribacter splanchnicus*, *Parabacteroides merdae*, *Ruminococcus obeum*, *Ruminococcus torques* |
| N414 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), clade_466, (clade_478 or clade_478i), (clade_522 or clade_522i) | *Coprococcus comes*, *Dorea formicigenerans*, *Dorea longicatena*, *Eubacterium eligens*, *Eubacterium rectale*, *Faecalibacterium prausnitzii*, *Odoribacter splanchnicus*, *Ruminococcus obeum*, *Ruminococcus torques* |
| N435 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), clade_466, (clade_478 or clade_478i) | *Coprococcus comes*, *Dorea formicigenerans*, *Dorea longicatena*, *Eubacterium rectale*, *Faecalibacterium prausnitzii*, *Odoribacter splanchnicus*, *Ruminococcus obeum*, *Ruminococcus torques* |
| N457 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i), (clade_522 or clade_522i) | *Dorea longicatena*, *Eubacterium eligens*, *Eubacterium rectale*, *Faecalibacterium prausnitzii*, *Roseburia intestinalis*, *Ruminococcus obeum*, *Ruminococcus torques* |
| N460 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), clade_466, (clade_478 or clade_478i) | *Coprococcus comes*, *Dorea formicigenerans*, *Eubacterium rectale*, *Faecalibacterium prausnitzii*, *Odoribacter splanchnicus*, *Ruminococcus obeum*, *Ruminococcus torques* |

TABLE 10-continued

| Network Ecology ID | Exemplary Network Clades | Exemplary Network OTUs |
|---|---|---|
| N461 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i) | *Coprococcus comes*, *Dorea formicigenerans*, *Dorea longicatena*, *Eubacterium rectale*, *Faecalibacterium prausnitzii*, *Ruminococcus obeum*, *Ruminococcus torques* |
| N510 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i), (clade_522 or clade_522i) | *Dorea longicatena*, *Eubacterium eligens*, *Eubacterium rectale*, *Faecalibacterium prausnitzii*, *Ruminococcus obeum*, *Ruminococcus torques* |
| N511 | (clade_262 or clade_262i), (clade_309 or clade_309c or clade_309e or clade_309g or clade_309h or clade_309i), (clade_444 or clade_444i), (clade_478 or clade_478i) | *Coprococcus comes*, *Eubacterium rectale*, *Faecalibacterium prausnitzii*, *Roseburia intestinalis*, *Ruminococcus obeum*, *Ruminococcus torques* |
| N512 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i) | *Coprococcus comes*, *Dorea formicigenerans*, *Dorea longicatena*, *Eubacterium rectale*, *Ruminococcus obeum*, *Ruminococcus torques* |
| N513 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i) | *Coprococcus comes*, *Dorea formicigenerans*, *Eubacterium rectale*, *Faecalibacterium prausnitzii*, *Ruminococcus obeum*, *Ruminococcus torques* |
| N571 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i) | *Dorea longicatena*, *Eubacterium rectale*, *Faecalibacterium prausnitzii*, *Ruminococcus obeum*, *Ruminococcus torques* |
| N582 | (clade_262 or clade_262i), (clade_309 or clade_309c or clade_309e or clade_309g or clade_309h or clade_309i), (clade_408 or clade_408b or clade_408d or clade_408f or clade_408g or clade_408h), (clade_444 or clade_444i), (clade_478 or clade_478i) | *Clostridium symbiosum*, *Eubacterium rectale*, *Faecalibacterium prausnitzii*, *Ruminococcus obeum*, *Ruminococcus torques* |
| N584 | (clade_260 or clade_260c or clade_260g or clade_260h), (clade_262 or clade_262i), (clade_309 or clade_309c or clade_309e or clade_309g or clade_309h or clade_309i), (clade_408 or clade_408b or clade_408d or clade_408f or clade_408g or clade_408h), (clade_553 or clade_553i) | *Blautia producta*, *Clostridium symbiosum*, *Collinsella aerofaciens*, *Coprococcus comes*, Lachnospiraceae bacterium 5_1_57FAA |
| N603 | (clade_172 or clade_172i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i) | *Bifidobacterium adolescentis*, *Dorea longicatena*, *Eubacterium rectale*, *Faecalibacterium prausnitzii*, *Ruminococcus obeum* |
| N682 | clade_170, (clade_309 or clade_309c or clade_309e or clade_309g or clade_309h or clade_309i), (clade_444 or clade_444i), (clade_478 or clade_478i) | *Bacteroides caccae*, *Eubacterium rectale*, *Faecalibacterium prausnitzii*, *Ruminococcus obeum* |
| N732 | (clade_262 or clade_262i), (clade_309 or clade_309c or clade_309e or clade_309g or clade_309h or clade_309i), (clade_478 or clade_478i) | *Coprococcus comes*, *Faecalibacterium prausnitzii*, *Ruminococcus obeum*, *Ruminococcus torques* |
| N736 | (clade_262 or clade_262i), (clade_309 or clade_309c or clade_309e or clade_309g or clade_309h or clade_309i), (clade_360 or clade_360c or clade_360g or clade_360h or clade_360i), (clade_478 or clade_478i) | *Dorea longicatena*, *Faecalibacterium prausnitzii*, *Ruminococcus obeum*, *Ruminococcus torques* |
| N853 | (clade_262 or clade_262i), (clade_444 or clade_444i), (clade_478 or clade_478i) | *Eubacterium rectale*, *Faecalibacterium prausnitzii*, *Ruminococcus torques* |
| N861 | (clade_262 or clade_262i), (clade_309 or clade_309c or clade_309e or clade_309g or clade_309h or clade_309i), (clade_408 or clade_408b or clade_408d or clade_408f or clade_408g or clade_408h) | *Clostridium hathewayi*, *Ruminococcus obeum*, *Ruminococcus torques* |
| N879 | (clade_309 or clade_309c or clade_309e or clade_309g or clade_309h or clade_309i), (clade_444 or clade_444i), (clade_478 or clade_478i) | *Faecalibacterium prausnitzii*, *Roseburia intestinalis*, *Ruminococcus obeum* |

TABLE 10-continued

| Network Ecology ID | Exemplary Network Clades | Exemplary Network OTUs |
|---|---|---|
| N975 | clade__170, (clade__262 or clade__262i), (clade__360 or clade__360c or clade__360g or clade__360h clade__360i) | *Bacteroides caccae*, *Coprococcus comes*, *Dorea longicatena* |
| N999 | (clade__309 or clade__309c or clade__309e or clade__309g or clade__309h or clade__309i), (clade__360 or clade__360c or clade__360g or clade__360h or clade__360i), (clade__478 or clade__478i) | *Dorea formicigenerans*, *Faecalibacterium prausnitzii*, *Ruminococcus obeum* |
| N1095 | (clade__444 or clade__444i), (clade__522 or clade__522i) | *Eubacterium eligens*, *Eubacterium rectale* |
| N1947 | (clade__262 or clade__262i), (clade__309 or clade__309c or clade__309e or clade__309g or clade__309h or clade__309i), (clade__360 or clade__360c or clade__360g or clade__360h or clade__360i), (clade__38 or clade__38e or clade__38i), (clade__444 or clade__444i), (clade__478 or clade__478i), (clade__553 or clade__553i), (clade__92 or clade__92e or clade__92i) | *Bacteroides* sp. 3__1__23, *Collinsella aerofaciens*, *Dorea longicatena*, *Escherichia coli*, *Eubacterium rectale*, *Faecalibacterium prausnitzii*, *Roseburia intestinalis*, *Ruminococcus obeum*, *Ruminococcus torques* |
| N1948 | (clade__262 or clade__262i), (clade__38 or clade__38e or clade__38i), (clade__478 or clade__478i), (clade__65 or clade__65e) | *Bacteroides* sp. 1__1__6, *Bacteroides* sp. 3__1__23, *Faecalibacterium prausnitzii*, *Ruminococcus torques* |
| N1949 | (clade__309 or clade__309c or clade__309e or clade__309g or clade__309h or clade__309i), (clade__378 or clade__378e), (clade__38 or clade__38e or clade__38i), (clade__479 or clade__479c or clade__479g or clade__479h), (clade__497 or clade__497e or clade__497f), (clade__65 or clade__65e), (clade__92 or clade__92e or clade__92i) | *Bacteroides* sp. 1__1__6, *Bacteroides* sp. 3__1__23, *Bacteroides vulgatus*, *Blautia producta*, *Enterococcus faecalis*, Erysipelotrichaceae bacterium 3__1__53, *Escherichia coli* |
| N1950 | clade__253, (clade__309 or clade__309c or clade__309e or clade__309g or clade__309h or clade__309i), (clade__378 or clade__378e), (clade__38 or clade__38e or clade__38i), (clade__479 or clade__479c or clade__479g or clade__479h), (clade__65 or clade__65e) | *Bacteroides* sp. 1__1__6, *Bacteroides* sp. 3__1__23, *Bacteroides vulgatus*, *Blautia producta*, *Clostridium disporicum*, Erysipelotrichaceae bacterium 3__1__53 |
| N1951 | (clade__260 or clade__260c or clade__260g or clade__260h), (clade__262 or clade__262i), (clade__309 or clade__309c or clade__309e or clade__309g or clade__309h or clade__309i), (clade__360 or clade__360c or clade__360g or clade__360h or clade__360i), (clade__408 or clade__408b or clade__408d or clade__408f or clade__408g or clade__408h), (clade__444 or clade__444i) | *Blautia producta*, *Clostridium bolteae*, *Clostridium hylemonae*, *Clostridium symbiosum*, *Coprococcus comes*, *Eubacterium rectale*, Lachnospiraceae bacterium 5__1__57FAA, *Ruminococcus gnavus* |
| N1952 | clade__252, clade__253, (clade__260 or clade__260c or clade__260g or clade__260h), (clade__262 or clade__262i), (clade__309 or clade__309c or clade__309e or clade__309g or clade__309h or clade__309i), (clade__351 or clade__351e), (clade__354 or clade__354e), (clade__360 or clade__360c or clade__360g or clade__360h or clade__360i), (clade__408 or clade__408b or clade__408d or clade__408f or clade__408g or clade__408h), clade__494, clade__537, (clade__553 or clade__553i) | *Blautia producta*, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsella aerofaciens*, *Coprococcus comes*, Lachnospiraceae bacterium 5__1__57FAA, *Ruminococcus bromii*, *Ruminococcus gnavus* |
| N1953 | clade__253, (clade__262 or clade__262i), (clade__309 or clade__309c or clade__309e or clade__309g or clade__309h or clade__309i), (clade__354 or clade__354e), (clade__360 or clade__360c or clade__360g or clade__360h or clade__360i), (clade__378 or clade__378e), (clade__408 or clade__408b or clade__408d or clade__408f or clade__408g or clade__408h), (clade__444 or clade__444i), clade__466, (clade__478 or clade__478i), (clade__479 or clade__479c or clade__479g or clade__479h), (clade__481 or clade__481a or clade__481b or clade__481e or clade__481g or clade__481h or clade__481i), (clade__497 or clade__497e or clade__497f), (clade__65 or clade__65e), (clade__92 or clade__92e or clade__92i) | *Bacteroides* sp. 1__1__6, *Bacteroides vulgatus*, *Clostridium disporicum*, *Clostridium mayombei*, *Clostridium symbiosum*, *Coprobacillus* sp. D7, *Coprococcus comes*, *Dorea formicigenerans*, *Enterococcus faecalis*, Erysipelotrichaceae bacterium 3__1__53, *Escherichia coli*, *Eubacterium rectale*, *Faecalibacterium prausnitzii*, *Odoribacter splanchnicus*, *Ruminococcus obeum* |
| N1954 | clade__252, clade__253, (clade__260 or clade__260c or clade__260g or clade__260h), (clade__262 or clade__262i), (clade__309 or clade__309c or clade__309e or clade__309g or clade__309h or clade__309i), (clade__351 or | *Blautia* sp. M25, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsella* |

TABLE 10-continued

| Network Ecology ID | Exemplary Network Clades | Exemplary Network OTUs |
|---|---|---|
| | clade__351e), (clade__354 or clade__354e), (clade__360 or clade__360c or clade__360g or clade__360h or clade__360i), (clade__408 or clade__408b or clade__408d or clade__408f or clade__408g or clade__408h), clade__494, clade__537, (clade__553 or clade__553i) | *aerofaciens*, *Coprococcus comes*, Lachnospiraceae bacterium 5__1__57FAA, *Ruminococcus bromii*, *Ruminococcus gnavus* |
| N1955 | (clade__309 or clade__309c or clade__309e or clade__309g or clade__309h or clade__309i), (clade__354 or clade__354e), (clade__378 or clade__378e), (clade__38 or clade__38e or clade__38i), (clade__479 or clade__479c or clade__479g or clade__479h), (clade__481 or clade__481a or clade__481b or clade__481e or clade__481g or clade__481h or clade__481i), (clade__497 or clade__497e or clade__497f), (clade__65 or clade__65e), (clade__92 or clade__92e or clade__92i) | *Bacteroides* sp. 1__1__6, *Bacteroides* sp. 2__1__22, *Bacteroides* sp. 3__1__23, *Bacteroides vulgatus*, *Blautia producta*, *Clostridium sordellii*, *Coprobacillus* sp. D7, *Enterococcus faecalis*, *Enterococcus faecium*, Erysipelotrichaceae bacterium 3__1__53, *Escherichia coli* |
| N1956 | clade__252, clade__253, (clade__260 or clade__260c or clade__260g or clade__260h), (clade__262 or clade__262i), (clade__309 or clade__309c or clade__309e or clade__309g or clade__309h or clade__309i), (clade__351 or clade__351e), (clade__354 or clade__354e), (clade__360 or clade__360c or clade__360g or clade__360h or clade__380i), (clade__408 or clade__408b or clade__408d or clade__408f or clade__408g or clade__408h), clade__494, clade__537, (clade__553 or clade__553i) | *Blautia producta*, *Clostridium bolteae*, *Clostridium butyricum*, *Clostridium disporicum*, *Clostridium hylemonae*, *Clostridium innocuum*, *Clostridium mayombei*, *Clostridium nexile*, *Clostridium orbiscindens*, *Clostridium symbiosum*, *Clostridium tertium*, *Collinsella aerofaciens*, Lachnospiraceae bacterium 5__1__57FAA, *Ruminococcus bromii*, *Ruminococcus gnavus* |
| N1957 | (clade__309 or clade__309c or clade__309e or clade__309g or clade__309h or clade__309i), (clade__351 or clade__351e), (clade__354 or clade__354e), (clade__378 or clade__378e), (clade__38 or clade__38e or clade__38i), (clade__481 or clade__481a or clade__481b or clade__481e or clade__481g or clade__481h or clade__481i), (clade__497 or clade__497e or clade__497f), (clade__65 or clade__65e), (clade__92 or clade__92e or clade__92i) | *Bacteroides* sp. 1__1__6, *Bacteroides* sp. 3__1__23, *Bacteroides vulgatus*, *Blautia producta*, *Clostridium innocuum*, *Clostridium sordellii*, *Coprobacillus* sp. D7, *Enterococcus faecalis*, *Escherichia coli* |
| N1958 | (clade__351 or clade__351e), (clade__354 or clade__354e), (clade__481 or clade__481a or clade__481b or clade__481e or clade__481g or clade__481h or clade__481i) | *Clostridium innocuum*, *Clostridium sordellii*, *Coprobacillus* sp. D7 |
| N1959 | clade__253, (clade__262 or clade__262i), (clade__309 or clade__309c or clade__309e or clade__309g or clade__309h or clade__309i), (clade__360 or clade__360c or clade__360g or clade__360h or clade__360i), (clade__378 or clade__378e), (clade__38 or clade__38e or clade__38i), (clade__444 or clade__444i), (clade__478 or clade__478i), (clade__479 or clade__479c or clade__479g or clade__479h), (clade__497 or clade__497e or clade__497f), (clade__522 or clade__522i), (clade__65 or clade__65e), (clade__92 or clade__92e or clade__92i) | *Bacteroides* sp. 1__1__6, *Bacteroides* sp. 3__1__23, *Bacteroides vulgatus*, *Blautia producta*, *Clostridium disporicum*, *Coprococcus comes*, *Dorea formicigenerans*, *Dorea longicatena*, *Enterococcus faecalis*, Erysipelotrichaceae bacterium 3__1__53, *Escherichia coli*, *Eubacterium eligens*, *Eubacterium rectale*, *Faecalibacterium prausnitzii*, *Ruminococcus obeum*, *Ruminococcus torques* |
| N1960 | clade__253, (clade__262 or clade__262i), (clade__309 or clade__309c or clade__309e or clade__309g or clade__309h or clade__309i), (clade__354 or clade__354e), (clade__360 or clade__360c or clade__360g or clade__360h or clade__360i), (clade__408 or clade__408b or clade__408d or clade__408f or clade__408g or clade__408h), (clade__444 or clade__444i), (clade__478 or clade__478i), (clade__479 or clade__479c or clade__479g or clade__479h), (clade__481 or clade__481a or clade__481b or clade__481e or clade__481g or clade__481h or clade__481i), (clade__497 or clade__497e or clade__497f), (clade__92 or clade__92e or clade__92i) | *Clostridium disporicum*, *Clostridium mayombei*, *Clostridium symbiosum*, *Coprobacillus* sp. D7, *Coprococcus comes*, *Dorea formicigenerans*, *Enterococcus faecalis*, Erysipelotrichaceae bacterium 3__1__53, *Escherichia coli*, *Eubacterium rectale*, *Faecalibacterium prausnitzii*, *Ruminococcus obeum* |
| N1961 | (clade__309 or clade__309c or clade__309e or clade__309g or clade__309h or clade__309i), (clade__351 or clade__351e), (clade__378 or clade__378e), (clade__38 or clade__38e or clade__38i), (clade__497 or clade__497e or clade__497f), (clade__65 or clade__65e), (clade__92 or clade__92e or clade__92i) | *Bacteroides* sp. 1__1__6, *Bacteroides* sp. 3__1__23, *Bacteroides vulgatus*, *Blautia producta*, *Clostridium innocuum*, *Enterococcus faecalis*, *Escherichia coli* |

TABLE 10-continued

| Network Ecology ID | Exemplary Network Clades | Exemplary Network OTUs |
|---|---|---|
| N1962 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia producta*, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsella aerofaciens*, *Coprococcus comes*, Lachnospiraceae bacterium 5_1_S7FAA, *Ruminococcus bromii*, *Ruminococcus gnavus* |
| N1963 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia producta*, *Clostridium disporicum*, *Clostridium hylemonae*, *Clostridium innocuum*, *Clostridium orbiscindens*,*Clostridium symbiosum*, *Clostridium tertium*, *Collinsella aerofaciens*, *Coprococcus comes*, Lachnospiraceae bacterium 5_1_57FAA, *Ruminococcus bromii*, *Ruminococcus gnavus* |
| N1964 | clade_170, (clade_260 or clade_260c or clade_260g or clade_260h), (clade_262 or clade_262i), clade_286, (clade_309 or clade_309c or clade_309e or clade_309g or clade_309h or clade_309i), (clade 360 or clade_360c or clade_360g or clade_360h or clade_360i), (clade_408 or clade_408b or clade_408d or clade_408f or clade_408g or clade_408h), (clade_444 or clade_444i), clade_485, clade_500, clade_537, (clade_553 or clade_553i), clade_85 | *Alistipes shahii*, *Bacteroides caccae*, *Bacteroides stercoris*, *Blautia producta*, *Clostridium hathewayi*, *Clostridium symbiosum*, *Collinsella aerofaciens*, *Coprococcus comes*, *Dorea formicigenerans*, *Eubacterium rectale*, *Holdemania filiformis*, Lachnospiraceae bacterium 5_1_57FAA, *Parabacteroides merdae*, *Ruminococcus bromii*, *Ruminococcus obeum*, *Ruminococcus torques* |
| N1965 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_408 or clade_408b or clade_408d or clade_408f or clade_408g or clade_408h), (clade_444 or clade_444i), (clade_478 or clade_478i), clade_537, (clade_553 or clade_553i) | *Blautia products*, *Clostridium bolteae*, *Clostridium butyricum*, *Clostridium disporicum*, *Clostridium mayombel*, *Clostridium symbiosum*, *Collinsella aerofaciens*, *Coprococcus comes*, *Eubacterium rectale*, *Faecalibacterium prausnitzii*, Lachnospiraceae bacterium 5_1_57FAA, *Roseburia intestinalis*, *Ruminococcus bromii*, *Ruminococcus obeum* |
| N1966 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_408 or clade_408b or clade_408d or clade_408f or clade_408g or clade_408h), (clade_553 or clade_553i) | *Blautia producta*, *Clostridium bolteae*, *Clostridium butyricum*, *Clostridium disporicum*, *Clostridium mayombei*, *Clostridium symbiosum*, *Collinsella aerofaciens*, *Coprococcus comes*, Lachnospiraceae bacterium 5_1_57FAA |
| N1967 | (clade_309 or clade_309c or clade_309e or clade_309g or clade_309h or clade_309i), (clade_378 or clade_378e), (clade_38 or clade_38e or clade_38i), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Blautia producta*, *Enterococcus faecium*, *Escherichia coli* |
| N1968 | clade_252, clade_253, (clade_351 or clade_351e), (clade_354 or clade_354e), (clade_478 or clade_478i), clade_494, clade_537, (clade_553 or clade_553i) | *Clostridium butyricum*, *Clostridium disporicum*, *Clostridium innocuum*, *Clostridium mayombei*, *Clostridium orbiscindens*, *Clostridium tertium*, *Collinsella aerofaciens*, *Faecalibacterium prausnitzii*, *Ruminococcus bromii* |
| N1969 | clade_252, clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_479 or clade_479c or clade_479g or clade_479h) | *Blautia producta*, *Clostridium butyricum*, *Clostridium disporicum*, *Clostridium mayombei*, *Dorea formicigenerans*, Erysipelotrichaceae bacterium 3_1_53, *Ruminococcus torques* |
| N1970 | (clade_351 or clade_351e), (clade_354 or clade_354e), (clade_378 or clade_378e), (clade_38 or clade_38e or clade_38i), (clade_481 or clade_481a or clade_481b or | *Bacteroides* sp. 1_1_6, *Bacteroides* sp. 3_1_23, *Bacteroides vulgatus*, *Clostridium innocuum*, *Clostridium sordellii*, *Coprobacillus* sp. D7, *Enterococcus faecalis*, *Escherichia coli* |

TABLE 10-continued

| Network Ecology ID | Exemplary Network Clades | Exemplary Network OTUs |
|---|---|---|
| | clade_481e or clade_481g or clade_481h or clade_481i), (clade_497 or clade_497e or clade_497f), (cladc_65 or clade_65e), (clade_92 or clade_92e or clade_92i) | |
| N1971 | clade_252, clade_253, (clade_260 or clade_260c or clade_260g or clade_260h), (clade_262 or clade_262i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsessa aerofaciens*, *Coprococcus comes*, Lachnospiraceae bacterium 5_1_57FAA, *Ruminococcus bromii*, *Ruminococcus gnavus* |
| N1972 | clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_408 or clade_408b or clade_408d or clade_408f or clade_408g or clade_408h), (clade_444 or clade_444i), (clade_478 or clade_478i), (clade_479 or clade_479c or clade_479g or clade_479h), (clade_481 or clade_481a or clade_481b or clade_481e or clade_481g or clade_481h or clade_481i) | *Clostridium disporicum*, *Clostridium mayombei*, *Clostridium symbiosum*, *Coprobacillus* sp. D7, *Coprococcus comes*, *Dorea formicigenerans*, Erysipelotrichaceae bacterium 3_1_53, *Eubacterium rectale*, *Faecalibacterium prausnitzii*, *Ruminococcus obeum* |
| N1973 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537 | *Blautia producta*, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Coprococcus comes*, Lachnospiraceae bacterium 5_1_57FAA, *Ruminococcus bromii*, *Ruminococcus gnavus* |
| N1974 | (clade_262 or clade_262i), (clade_309 or clade_309c or clade_309e or clade_309g or clade_309h or clade_309f), (clade_360 or clade_360c or clade_360g or clade_360h or clade_360i), (clade_444 or clade_444i), clade_466, (clade_478 or clade_478i) | *Coprococcus comes*, *Dorea formicigenerans*, *Dorea longicatena*, *Eubacterium rectale*, *Faecalibacterium prausnitzii*, *Odoribacter splanchnicus*, *Roseburia intestinalis*, *Ruminococcus obeum*, *Ruminococcus torques* |
| N1975 | (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), (clade_444 or clade_444i), (clade_478 or clade_478i), clade_494, clade_537, (clade_553 or clade_553i) | *Blautia producta*, *Clostridium bolteae*, *Clostridium hylemonae*, *Clostridium innocuum*, *Clostridium mayombei*, *Clostridium orbiscindens*, *Clostridium symbiosum*, *Collinsella aerofaciens*, *Coprococcus comes*, *Eubacterium rectale*, *Faecalibacterium prausnitzii*, Lachnospiraceae bacterium 5_1_57FAA, *Ruminococcus bromii*, *Ruminococcus gnavus* |
| N1976 | (clade_351 or clade_351e), (clade_378 or clade_378e), (clade_38 or clade_38e or clade_38i), (clade_481 or clade_481a or clade_481b or clade_481e or clade_481g or clade_481h or clade_481i), (clade_497 or clade_497e or clade_497f), (clade_65 or clade_65e) | *Bacteroides* sp. 1_1_6, *Bacteroides* sp. 3_1_23, *Bacteroides vulgatus*, *Clostridium innocuum*, *Coprobacillus* sp. D7, *Enterococcus faecalis* |
| N1977 | clade_252, clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_479 or clade_479c or clade_479g or clade_479h) | *Blautia producta*, *Clostridium butyricum*, *Clostridium disporicum*, *Clostridium mayombei*, *Dorea formicigenerans*, Erysipelotrichaceae bacterium 3_1_53, *Eubacterium tenue*, *Ruminococcus torques* |
| N1978 | clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_378 or clade_378e), (clade_408 or clade_408b or clade_408d or clade_408f or clade_408g or clade_408h), | *Bacteroides* sp. 1_1_6, *Bacteroides vulgatus*, *Clostridium disporicum*, *Clostridium mayombei*, *Clostridium symbiosum*, *Coprobacillus* sp. D7, *Coprococcus comes*, *Dorea formicigenerans*, Erysipelotrichaceae bacterium 3_1_53, *Escherichia coli*, *Eubacterium rectale*, *Faecalibacterium prausnttzii*, *Odoribacter splanchnicus*, *Ruminococcus obeum* |

TABLE 10-continued

| Network Ecology ID | Exemplary Network Clades | Exemplary Network OTUs |
|---|---|---|
| | (clade_444 or clade_444i), clade_466, (clade_478 or clade_478i), (clade_479 or clade_479c or clade_479g or clade_479h), (clade_481 or clade_481a or clade_481b or clade_481e or clade_481g or clade_481h or clade_481i), (clade_65 or clade_65e), (clade_92 or clade_92e or clade_92i) | |
| N1979 | (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i), (clade_65 or clade_65e) | *Bacteroides* sp. 1_1_6, *Coprococcus comes*, *Dorea formicigenerans*, *Dorea longicatena*, *Eubacterium rectale*, *Faecalibacterium prausnitzii*, *Ruminococcus obeum*, *Ruminococcus torques* |
| N1980 | (clade_309 or clade_309c or clade_309e or clade_309g or clade_309h or clade_309i), (clade_351 or clade_351e), (clade_354 or clade_354e), (clade_481 or clade_481a or clade_481b or clade_481e or clade_481g or clade_481h or clade_481i), (clade_497 or clade_497e or clade_497f), (clade_92 or clade_92e or clade_92i) | *Blautia producta*, *Clostridium innocuum*, *Clostridium sordellii*, *Coprobacillus* sp. D7, *Enterococcus faecalis*, *Escherichia coli* |
| N1981 | (clade_262 or clade_262i), (clade_309 or clade_309c or clade_309e or clade_309g or clade_309h or clade_309i), (clade_360 or clade_360c or clade_360g or clade_360h or clade_360i), (clade_38 or clade_38e or clade_38i), (clade_444 or clade_444i), (clade_478 or clade_478i), (clade_522 or clade_522i) | *Bacteroides* sp. 3_1_23, *Dorea longicatena*, *Eubacterium eligens*, *Eubacterium rectale*, *Faecalibacterium prausnitzii*, *Ruminococcus obeum*, *Ruminococcus torques* |
| N1982 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_408 or clade_408b or clade_408d or clade_408f or clade_408g or clade_408h), (clade_444 or clade_444i), (clade_479 or clade_479c or clade_479g or clade_479h), (clade_553 or clade_553i) | *Blautia producta*, *Clostridium bolteae*, *Clostridium butyricum*, *Clostridium disporicum*, *Clostridium mayombei*, *Clostridium symbiosum*, *Collinsella aerofaciens*, *Coprococcus comes*, *Dorea formicigenerans*, Erysipelotrichaceae bacterium 3_1_53, *Eubacterium rectale*, Lachnospiraceae bacterium 5_1_57FAA, *Ruminococcus obeum*, *Ruminococcus torques* |
| N1983 | clade_252, clade_253, (clade_309 or clade_309c or clade_309e or clade_309g or clade_309h or clade_309i), (clade_354 or clade_354e), (clade_378 or clade_378e), (clade_38 or clade_38e or clade_38i), (clade_479 or clade_479c or clade_479g or clade_479h), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Blautia producta*, *Clostridium butyricum*, *Clostridium disporicum*, *Clostridium mayombei*, *Enterococcus faecium*, Erysipelotrichaceae bacterium 3_1_53, *Escherichia coli* |
| N1984 | clade_253, (clade_260 or clade_260c or clade_260g or clade_260h), (clade_309 or clade_309c or clade_309e or clade_309g or clade_309h or clade_309i), (clade_351 or clade_351e), (clade_354 or clade_354e), (clade_403 or clade_408b or clade_408d or clade_408f or clade_408g or clade_408h), (clade_444 or clade_444i), clade_494, (clade_553 or clade_553i) | *Blautia producta*, *Clostridium disporicum*, *Clostridium innocuum*, *Clostridium mayombei*, *Clostridium orbiscindens*, *Clostridium symbiosum*, *Collinsella aerofaciens*, *Eubacterium rectale*, Lachnospiraceae bacterium 5_1_57FAA |
| N1985 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia glucerasei*, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertiurm*, *Collinsella aerofaciens*, *Coprococcus comes*, Lachnospiraceae bacterium 5_1_57FAA, *Ruminococcus bromii*, *Ruminococcus gnavus* |
| N1986 | clade_253, (clade_260 or clade_260c or clade_260g or clade_260h), (clade_262 or clade_262i), (clade_309 or clade_309c or clade_309e or clade_309g or clade_309h or | *Blautia producta*, *Clostridium disporicum*, *Clostridium symbiosum*, *Collinsella aerofaciens*, *Coprococcus comes*, Lachnospiraceae bacterium 5_1_57FAA |

TABLE 10-continued

| Network Ecology ID | Exemplary Network Clades | Exemplary Network OTUs |
|---|---|---|
| | clade_309i), (clade_408 or clade_408b or clade_408d or clade_408f or clade_408g or clade_408h), (clade_553 or clade_553i) | |
| N1987 | (clade_309 or clade_309c or clade_309e or clade_309g or clade_309h or clade_309i), (clade_354 or clade_354e), (clade_92 or clade_92e or clade_92i) | *Blautia producta*, *Clostridium sordellii*, *Escherichia coli* |
| N1988 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_408 or clade_408b or clade_408d or clade_408f or clade_408g or clade_408h), (clade_444 or clade_444i), (clade_478 or clade_478i), clade_485, clade_500, (clade_553 or clade_553i) | *Alistipes shahii*, *Blautia producta*, *Clostridium bolteae*, *Clostridium butyricum*, *Clostridium disporicum*, *Clostridium mayombei*, *Clostridium symbiosum*, *Collinsella aerofaciens*, *Coprococcus comes*, *Eubacterium rectale*, *Faecalibacterium prausnitzii*, *Holdemania filiformis*, Lachnospiraceae bacterium 5_1_57FAA, *Roseburia intestinalis*, *Ruminococcus obeum*, *Ruminococcus torques* |
| N1989 | clade_252, clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_378 or clade_378e), (clade_38 or clade_38e or clade_38i), (clade_479 or clade_479c or clade_479g or clade_479h), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Blautia producta*, *Clostridium butyricum*, *Clostridium disporicum*, *Clostridium mayombei*, *Dorea formicigenerans*, *Enterococcus faecium*, Erysipelotrichaceae bacterium 3_1_53, *Escherichia coli*, *Eubacterium tenue*, *Ruminococcus torques* |
| N1990 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_360 or clade_360c or clade_360g or clade_360h or clade_360i), (clade_408 or clade_408b or clade_408d or clade_408f or clade_408g or clade_408h), (clade_444 or clade_444i), (clade_478 or clade_478i), clade_494, clade_537, (clade_553 or clade_553i) | *Blautia producta*, *Clostridium disporicum*, *Clostridium hylemonae*, *Clostridium innocuum*, *Clostridium orbiscindens*, *Clostridium symbiosum*, *Clostridium tertium*, *Collinsella aerofaciens*, *Coprococcus comes*, *Eubacterium rectale*, *Faecalibacterium prausnitzii*, Lachnospiraceae bacterium 5_1_57FAA, *Ruminococcus brornii*, *Ruminococcus gnavus* |
| N1991 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), (clade_444 or clade_444i), (clade_553 or clade_553i) | *Blautia producta*, *Clostridium bolteae*, *Clostridium butyricum*, *Clostrtdium disporicum*, *Clostridium hylemonae*, *Clostridium innocuum*, *Clostridium mayombei*, *Clostridium symbiosum*, *Clostridium tertium*, *Collinsella aerofaciens*, *Coprococcus comes*, *Eubacterium rectale*, Lachnospiraceae bacterium 5_1_57FAA, *Ruminococcus gnavus* |
| N1992 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia producta*, *Clostridium bolteae*, *Clostridium butyricum*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsella aerofaciens*, Lachnospiraceae bacterium 1_4_56FAA, Lachnospiraceae bacterium 5_1_57FAA, *Ruminococcus bromii*, *Ruminococcus gnavus* |
| N1993 | clade_110, clade_170, (clade_378 or clade_378e), (clade_38 or clade_38e or clade_38i), (clade_65 or clade_65e), clade_85 | *Bacteroides caccae*, *Bacteroides eggerthii*, *Bacteroides* sp. 1_1_6, *Bacteroides* sp. 3_1_23, *Bacteroides stercoris*, *Bacteroides uniformis*, *Bacteroides vulgatus* |
| N1994 | clade_253, (clade_378 or clade_378e), (clade_38 or clade_38e or clade_38i), (clade_479 or clade_479c or clade_479g or clade_479h), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Clostridium disporicum*, *Enterococcus faecium*, Erysipelotrichaceae bacterium 3_1_53, *Escherichia coli* |

TABLE 10-continued

| Network Ecology ID | Exemplary Network Clades | Exemplary Network OTUs |
|---|---|---|
| N1995 | clade_253, (clade_309 or clade_309c or clade_309e or clade_309g or clade_309h or clade_309i), (clade_378 or clade_378e), (clade_38 or clade_38e or clade_38i), (clade_479 or clade_479c or clade_479g or clade_479h), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Blautia producta*, *Clostridium disporicum*, *Enterococcus faecium*, Erysipelotrichaceae bacterium 3_1_53, *Escherichia coli* |
| N1996 | clade_253, (clade_309 or clade_309c or clade_309e or clade_309g or clade_309h or clade_309i), (clade_479 or clade_479c or clade_479g or clade_479h) | *Blautia producta*, *Clostridium disporicum*, Erysipelotrichaceae bacterium 3_1_53 |
| N1997 | clade_253, (clade_309 or clade_309c or clade_309e or clade_309g or clade_309h or clade_309i), (clade_479 or clade_479c or clade_479g or clade_479h), (clade_497 or clade_497e or clade_497f), (clade_92 or clade_92e or clade_92i) | *Blautia producta*, Clostridium disporicum, *Enterococcus faecium*, Erysipelotrichaceae bacterium 3_1_53, *Escherichia coli* |
| N1998 | (clade_378 or clade_378e), (clade_38 or clade_38e or clade_38i), (clade_65 or clade_65e) | *Bacteroides* sp. 1_1_6, *Bacteroides* sp. 3_1_23, *Bacteroides vulgatus* |
| N1999 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_408 or clade_408b or clade_408d or clade_408f or clade_408g or clade_408h), (clade_444 or clade_444i), (clade_478 or clade_478i), (clade_553 or clade_553i) | *Blautia producta*, *Clostridium bolteae*, *Clostridium butyricum*, *Clostridium disporicum*, *Clostridium mayombei*, *Clostridium symbiosum*, *Collinsella aerofaciens*, *Coprococcus comes*, *Eubacterium rectale*, *Faecalibacterium prausnitzii*, Lachnospiraceae bacterium 5_1_57FAA |
| N2000 | clade_252, clade_253, (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_479 or clade_479c or clade_479g or clade_479h) | *Blautia producta*, *Clostridium butyricum*, *Clostridium disporicum*, *Clostridium mayombei*, *Dorea formicigenerans*, Erysipelotrichaceae bacterium 3_1_53, *Eubacterium tenue*, *Ruminococcus torques* |
| N2001 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_351 or clade_351e), (clade_354 or clade_354e), (clade_360 or clade_360c or clade_360g or clade_360h or clade_360i), (clade_408 or clade_408b or clade_408d or clade_408f or clade_408g or clade_408h), clade_494, clade_537, (clade_553 or clade_553i) | *Blautia producta*, *Clostridium bolteae*, *Clostridium disporicum*, *Clostridium hylemonae*, *Clostridium innocuum*, *Clostridium mayombei*, *Clostridium orbiscindens*, *Clostridium symbiosum*, *Clostridium tertium*, *Collinsella aerofaciens*, *Coprococcus comes*, Lachnospiraceae bacterium 5_1_57FAA, *Ruminococcus bromii*, *Ruminococcus gnavus* |
| N2002 | clade_252, clade_253, (clade_309 or clade_309c or clade_309e or clade_309g or clade_309h or clade_309i), (clade_354 or clade_354e), (clade_479 or clade_479c or clade_479g or clade_479h) | *Blautia producta*, *Clostridium butyricum*, *Clostridium disporicum*, *Clostridium mayombei*, Erysipelotrichaceae bacterium 3_1_53 |
| N2003 | clade_252, clade_253, (clade_260 or clade_260c or clade_260g or clade_260h), (clade_262 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_38 or clade_38e or clade_38i), (clade_408 or clade_408b or clade_408d or clade_408f or clade_408g or clade_408h), (clade_481 or clade_481a or clade_481b or clade_481e or clade_481g or clade_481h or clade_481i), clade_537, (clade_553 or clade_553i) | *Blautia producta*, *Clostridium bolteae*, *Clostridium butyricum*, *Clostridium disporicum*, *Clostridium hylemonae*, *Clostridium mayombei*, *Clostridium sordellii*, *Clostridium symbiosum*, *Clostridium tertium*, *Collinsella aerofaciens*, *Coprobacillus* sp. D7, *Coprococcus comes*, *Eubacterium* sp. WAL 14571, Lachnospiraceae bacterium 5_1_57FAA, *Rumtinococcus bromii*, *Ruminococcus gnavus* |
| N2004 | (clade_351 or clade_351e), (clade_378 or clade_378e), (clade_38 or clade_38e or clade_38i), (clade_497 or clade_497e or clade_497f), (clade_65 or clade_65e), (clade_92 or clade_92e or clade_92i) | *Bacteroides* sp. 1_1_6, *Bacteroides* sp. 3_1_23, *Bacteroides vulgatus*, *Clostridium innocuum*, *Enterococcus faecalis*, *Escherichia coli* |
| N2005 | (clade_309 or clade_309c or dade_309e or clade_309g or clade_309h or clade_309i) (clade_378 or clade_378e), (clade_38 or | *Bacteroides* sp. 1_1_6, *Bacteroides* sp. 3_1_23, *Bacteroides vulgatus*, *Blautia producta*, *Enterococcus faecalis*, *Escherichia coli* |

TABLE 10-continued

| Network Ecology ID | Exemplary Network Clades | Exemplary Network OTUs |
|---|---|---|
| | clade_38e or clade_38i), (clade_497 or clade_497e or clade_497f), (clade_65 or clade_65e), (clade_92 or clade_92e or clade_92i) | |
| N2006 | clade_170, (clade_262 or clade_262i), (clade_309 or clade_309c or clade_309e or clade_309g or clade_309h or clade_309i), (clade_360 or clade_360c or clade_360g or clade_360h or clade_360i), (clade_444 or clade_444i), (clade_478 or clade_478i), (clade_65 or dade_65e) | *Bacteroides caccae*, *Bacteroides* sp. 1_1_6, *Coprococcus comes*, *Dorea formicigenerans*, *Dorea longicatena*, *Eubacterium rectale*, *Faecalibacterium prausnitzii*, *Ruminococcus obeum*, *Ruminococcus torques* |
| N2007 | clade_253, (clade_202 or clade_262i), (clade_309 or clade_309c or clade_309e or clade_309g or clade_309h or clade_309i), (clade_354 or clade_354e), (clade_360 or clade_360c or clade_360g or clade_360h or clade_360i), (clade_378 or clade_378e), (clade_408 or clade_408b or clade_408d or clade_408f or clade_408g or clade_408h), (clade_444 or clade_444i), clade_466, (clade_478 or clade_478i), (clade_479 or clade_479c or clade_479g or clade_479h), (clade_481 or clade_481a or clade_481b or clade_481e or clade_481g or clade_481h or clade_481i), (clade_497 or clade_497e or clade_497f), (clade_65 or clade_65e) | *Bacteroides* sp. 1_1_6, *Bacteroides vulgatus*, *Clostridium disporicum*, *Clostridium mayombei*, *Clostridium symbiosum*, *Coprobacillus* sp. D7, *Coprococcus comes*, *Dorea formicigenerans*, *Enterococcus faecalis*, Erysipelotrichaceae bacterium 3_1_53, *Eubacterium rectale*, *Faecalibacterium prausnitzii*, *Odoribacter splanchnicus*, *Ruminococcus obeum* |

TABLE 11

| OTU | Clade | Genus | Family | Order | Spore Former | Percent of Dose Ecologies Occurs | Percent of Engrafted Ecologies Occurs | Percent of Augemented Ecologies Occurs | Keystone OTU | CES |
|---|---|---|---|---|---|---|---|---|---|---|
| Blautia_luti | clade_309 | Blautia | Lachnospiraceae | Clostridiales | yes | 100 | 100 | 0 | 0 | 4.0 |
| Blautia_schinkii | clade_309 | Blautia | Lachnospiraceae | Clostridiales | yes | 100 | 93 | 7 | 0 | 4.0 |
| Blautia_sp_M25 | clade_309 | Blautia | Lachnospiraceae | Clostridiales | yes | 100 | 93 | 7 | 1 | 5.0 |
| Subdoligranulum_variabile | clade_478 | Subdoligranulum | Ruminococcaceae | Clostridiales | yes | 100 | 93 | 0 | 1 | 5.0 |
| Eubacterium_rectale | clade_444 | Eubacterium | Eubacteriaceae | Clostridiales | yes | 100 | 87 | 13 | 1 | 5.0 |
| Lachnospiraceae_bacterium_2_1_58FAA | clade_360 | unassigned | Lachnospiraceae | Clostridiales | yes | 100 | 80 | 7 | 0 | 4.0 |
| Clostridium_leptum | clade_537 | Clostridium | Clostridiaceae | Clostridiales | yes | 100 | 73 | 13 | 1 | 4.0 |
| Faecalibacterium_prausnitzii | clade_478 | Faecalibacterium | Ruminococcaceae | Clostridiales | yes | 100 | 73 | 0 | 1 | 4.0 |
| Ruminococcus_bromii | clade_537 | Ruminococcus | Ruminococcaceae | Clostridiales | yes | 100 | 67 | 7 | 1 | 4.0 |
| Clostridium_citroniae | clade_408 | Clostridium | Clostridiaceae | Clostridiales | yes | 100 | 53 | 27 | 0 | 3.0 |
| Christensenella_minuta | clade_558 | Christensenella | Christensenellaceae | Clostridiales | yes | 100 | 0 | 27 | 0 | 2.0 |
| Ruminococcus_torques | clade_262 | Blautia | Lachnospiraceae | Clostridiales | yes | 93 | 87 | 7 | 1 | 5.0 |
| Dorea_longicatena | clade_360 | Dorea | Lachnospiraceae | Clostridiales | yes | 93 | 80 | 20 | 1 | 5.0 |
| Eubacterium_hadrum | clade_408 | Anaerostipes | Lachnospiraceae | Clostridiales | yes | 93 | 80 | 7 | 1 | 5.0 |
| Blautia_hansenii | clade_309 | Blautia | Lachnospiraceae | Clostridiales | yes | 93 | 73 | 13 | 0 | 3.0 |
| Clostridium_ramosum | clade_481 | unassigned | Erysipelotrichaceae | Erysipelotrichales | yes | 93 | 73 | 13 | 0 | 3.0 |
| Ruminococcus_lactaris | clade_262 | Ruminococcus | Ruminococcaceae | Clostridiales | yes | 93 | 67 | 33 | 1 | 4.0 |
| Clostridiales_sp_SS3_4 | clade_246 | Clostridiales | unclassified | Clostridiales | yes | 86 | 73 | 20 | 0 | 3.0 |
| Dorea_formicigenerans | clade_360 | Dorea | Lachnospiraceae | Clostridiales | yes | 86 | 53 | 7 | 1 | 4.0 |
| Coprococcus_comes | clade_262 | Coprococcus | Lachnospiraceae | Clostridiales | yes | 86 | 47 | 0 | 1 | 4.0 |
| Lachnospiraceae_bacterium_A4 | clade_408 | unassigned | Lachnospiraceae | Clostridiales | yes | 86 | 40 | 20 | 0 | 2.4 |
| Eubacterium_hallii | clade_396 | Eubacterium | Eubacteriaceae | Clostridiales | yes | 86 | 40 | 7 | 1 | 3.4 |
| Eubacterium_brachy | clade_533 | Eubacterium | Eubacteriaceae | Clostridiales | yes | 86 | 13 | 0 | 0 | 2.4 |
| Ruminococcus_callidus | clade_406 | Ruminococcus | Ruminococcaceae | Clostridiales | yes | 79 | 67 | 13 | 0 | 2.3 |
| Clostridium_bartlettii | clade_354 | unassigned | Peptostreptococcaceae | Clostridiales | yes | 79 | 67 | 7 | 0 | 2.3 |
| Clostridium_sporosphaeroides | clade_537 | Clostridium | Clostridiaceae | Clostridiales | yes | 79 | 60 | 20 | 0 | 2.3 |
| Clostridium_bifermentans | clade_354 | unassigned | Peptostreptococcaceae | Clostridiales | yes | 79 | 53 | 13 | 0 | 2.3 |
| Turicibacter_sanguinis | clade_555 | Turicibacter | Erysipelotrichaceae | Erysipelotrichales | yes | 79 | 40 | 13 | 0 | 1.7 |
| Ruminococcus_albus | clade_516 | Ruminococcus | Ruminococcaceae | Clostridiales | yes | 71 | 60 | 27 | 0 | 2.3 |
| Eubacterium_ramulus | clade_482 | Eubacterium | Eubacteriaceae | Clostridiales | yes | 71 | 47 | 33 | 0 | 2.3 |
| Eubacterium_desmolans | clade_572 | Eubacterium | Eubacteriaceae | Clostridiales | yes | 71 | 40 | 27 | 0 | 1.7 |
| Coprococcus_catus | clade_393 | Coprococcus | Lachnospiraceae | Clostridiales | yes | 71 | 33 | 7 | 1 | 2.7 |
| Clostridium_oroticum | clade_96 | Clostridium | Clostridiaceae | Clostridiales | yes | 71 | 27 | 7 | 0 | 1.7 |
| Blautia_glucerasea | clade_309 | Blautia | Lachnospiraceae | Clostridiales | yes | 64 | 33 | 33 | 0 | 1.7 |
| Lachnospiraceae_bacterium_3_1_57FAA | clade_408 | unassigned | Lachnospiraceae | Clostridiales | yes | 64 | 33 | 13 | 1 | 2.7 |
| Clostridium_viride | clade_540 | Clostridium | Clostridiaceae | Clostridiales | yes | 64 | 27 | 13 | 0 | 1.7 |
| Ruminococcus_obeum | clade_309 | Blautia | Lachnospiraceae | Clostridiales | yes | 64 | 27 | 7 | 1 | 2.7 |
| Eubacterium_ruminantium | clade_543 | Eubacterium | Eubacteriaceae | Clostridiales | yes | 57 | 20 | 27 | 0 | 1.7 |
| Clostridium_thermocellum | clade_495 | Clostridium | Clostridiaceae | Clostridiales | yes | 50 | 47 | 20 | 0 | 2.3 |
| Oscillibacter_valericigenes | clade_540 | Oscillibacter | Oscillospiraceae | Clostridiales | yes | 50 | 40 | 60 | 1 | 2.7 |
| Eubacterium_coprostanoligenes | clade_537 | Eubacterium | Eubacteriaceae | Clostridiales | yes | 50 | 27 | 13 | 1 | 2.7 |
| Clostridium_disporicum | clade_253 | Clostridium | Clostridiaceae | Clostridiales | yes | 50 | 20 | 27 | 0 | 1.7 |
| Clostridium_mayombei | clade_354 | Clostridium | Clostridiaceae | Clostridiales | yes | 50 | 20 | 0 | 0 | 1.7 |
| Roseburia_faecalis | clade_444 | Roseburia | Lachnospiraceae | Clostridiales | yes | 43 | 27 | 60 | 0 | 1.7 |
| Lachnospiraceae_bacterium_1_4_56FAA | clade_262 | unassigned | Lachnospiraceae | Clostridiales | yes | 43 | 13 | 20 | 1 | 2.7 |
| Clostridium_spiroforme | clade_481 | unassigned | Erysipelotrichaceae | Erysipelotrichales | yes | 36 | 33 | 33 | 0 | 1.7 |

TABLE 11-continued

| OTU | Clade | Genus | Family | Order | Spore Former | Percent of Dose Ecologies Occurs | Percent of Engrafted Ecologies Occurs | Percent of Augemented Ecologies Occurs | Keystone OTU | CES |
|---|---|---|---|---|---|---|---|---|---|---|
| *Eubacterium_siraeum* | clade_538 | *Eubacterium* | Eubacteriaceae | Clostridiales | yes | 36 | 27 | 60 | 1 | 2.7 |
| *Lachnospira_pectinoschiza* | clade_522 | *Lachnospira* | Lachnospiraceae | Clostridiales | yes | 36 | 27 | 53 | 0 | 1.7 |
| *Papillibacter_cinnamivorans* | clade_572 | *Papillibacter* | Ruminococcaceae | Clostridiales | yes | 36 | 27 | 53 | 0 | 1.7 |
| *Clostridium_tyrobutyricum* | clade_430 | *Clostridium* | Clostridiaceae | Clostridiales | yes | 36 | 27 | 13 | 0 | 1.7 |
| *Roseburia_inulinivorans* | clade_444 | *Roseburia* | Lachnospiraceae | Clostridiales | yes | 36 | 20 | 60 | 1 | 2.7 |
| *Ethanoligenens_harbinense* | clade_439 | *Ethanoligenens* | Ruminococcaceae | Clostridiales | yes | 36 | 20 | 27 | 0 | 1.7 |
| *Eggerthella_lenta* | clade_566 | *Eggerthella* | Coriobacteriaceae | Coriobacteriales | yes | 36 | 13 | 40 | 0 | 1.7 |
| *Clostridium_orbiscindens* | clade_494 | unassigned | unassigned | Clostridiales | yes | 29 | 20 | 60 | 0 | 1.1 |
| *Eubacterium_ventriosum* | clade_519 | *Eubacterium* | Eubacteriaceae | Clostridiales | yes | 29 | 20 | 40 | 0 | 1.1 |
| *Clostridium_paraputrificum* | clade_223 | *Clostridium* | Clostridiaceae | Clostridiales | yes | 29 | 13 | 33 | 0 | 1.1 |
| *Clostridium*_sp_YIT_12069 | clade_537 | *Clostridium* | Clostridiaceae | Clostridiales | yes | 29 | 7 | 53 | 0 | 1.1 |
| *Eubacterium_barkeri* | clade_512 | *Eubacterium* | Eubacteriaceae | Clostridiales | yes | 29 | 0 | 13 | 0 | 0.7 |
| *Eubacterium_biforme* | clade_385 | unassigned | Erysipelotrichaceae | Erysipelotrichales | yes | 29 | 0 | 13 | 0 | 0.7 |
| *Alkaliphilus_oremlandii* | clade_554 | *Alkaliphilus* | Clostridiaceae | Clostridiales | yes | 29 | 0 | 7 | 0 | 0.7 |
| Lachnospiraceae_*bacterium*_5_1_57FAA | clade_260 | unassigned | Lachnospiraceae | Clostridiales | yes | 21 | 20 | 60 | 0 | 1.1 |
| *Eubacterium_eligens* | clade_522 | *Eubacterium* | Eubacteriaceae | Clostridiales | yes | 21 | 20 | 33 | 0 | 1.1 |
| *Bacillus*_sp_9_3AIA | clade_527 | *Bacillus* | Bacillaceae | Bacillales | yes | 21 | 13 | 73 | 0 | 1.1 |
| *Eubacterium*_sp_WAL_14571 | clade_384 | *Eubacterium* | Eubacteriaceae | Clostridiales | yes | 21 | 7 | 60 | 0 | 1.1 |
| *Anaerosporobacter_mobilis* | clade_396 | *Anaerosporobacter* | Clostridiaceae | Clostridiales | yes | 21 | 7 | 47 | 0 | 1.1 |
| *Coprococcus_eutactus* | clade_543 | *Coprococcus* | Lachnospiraceae | Clostridiales | yes | 21 | 7 | 20 | 0 | 1.1 |
| *Eubacterium*_sp_oral_clone_JH012 | clade_476 | *Eubacterium* | Eubacteriaceae | Clostridiales | yes | 21 | 7 | 13 | 0 | 1.1 |
| *Lachnospira_multipara* | clade_522 | *Lachnospira* | Lachnospiraceae | Clostridiales | yes | 21 | 7 | 13 | 0 | 1.1 |
| *Clostridium_carnis* | clade_253 | *Clostridium* | Clostridiaceae | Clostridiales | yes | 21 | 7 | 0 | 0 | 1.1 |
| *Clostridium_colinum* | clade_576 | *Clostridium* | Clostridiaceae | Clostridiales | yes | 21 | 7 | 0 | 0 | 1.1 |
| *Clostridium_hylemonae* | clade_260 | *Clostridium* | Clostridiaceae | Clostridiales | yes | 21 | 0 | 40 | 0 | 0.7 |
| *Gloeobacter_violaceus* | clade_596 | *Gloeobacter* | unassigned | Gloeobacterales | yes | 21 | 0 | 7 | 0 | 0.7 |
| *Clostridium_algidicarnis* | clade_430 | *Clostridium* | Clostridiaceae | Clostridiales | yes | 14 | 20 | 67 | 0 | 1.1 |
| *Holdemania_filiformis* | clade_485 | *Holdemania* | Erysipelotrichaceae | Erysipelotrichales | yes | 14 | 13 | 73 | 1 | 2.1 |
| *Clostridium_aldenense* | clade_408 | *Clostridium* | Clostridiaceae | Clostridiales | yes | 14 | 13 | 67 | 0 | 1.1 |
| *Sporobacter_termitidis* | clade_572 | *Sporobacter* | Ruminococcaceae | Clostridiales | yes | 14 | 13 | 67 | 1 | 2.1 |
| *Ruminococcus*_sp_ID8 | clade_360 | *Ruminococcus* | Ruminococcaceae | Clostridiales | yes | 14 | 13 | 47 | 0 | 1.1 |
| Lachnospiraceae_*bacterium*_4_1_37FAA | clade_360 | unassigned | Lachnospiraceae | Clostridiales | yes | 14 | 0 | 60 | 0 | 0.7 |
| *Ruminococcus*_sp_18P13 | clade_406 | *Ruminococcus* | Ruminococcaceae | Clostridiales | yes | 14 | 0 | 7 | 0 | 0.7 |
| *Blautia_hydrogenotrophica* | clade_368 | *Blautia* | Lachnospiraceae | Clostridiales | yes | 14 | 0 | 0 | 0 | 0.7 |
| *Anaerotruncus_colihominis* | clade_516 | *Anaerotruncus* | Ruminococcaceae | Clostridiales | yes | 7 | 7 | 93 | 0 | 1.1 |
| *Clostridium_symbiosum* | clade_408 | *Clostridium* | Clostridiaceae | Clostridiales | yes | 7 | 7 | 87 | 0 | 1.1 |
| *Clostridium_lactatifermentans* | clade_576 | *Clostridium* | Clostridiaceae | Clostridiales | yes | 7 | 7 | 80 | 1 | 2.1 |
| *Lactobacillus_rogosae* | clade_522 | *Lactobacillus* | Lactobacillaceae | Lactobacillases | yes | 7 | 7 | 80 | 0 | 1.1 |
| *Clostridium*_sp_HGF2 | clade_351 | *Clostridium* | Clostridiaceae | Clostridiales | yes | 7 | 7 | 47 | 0 | 1.1 |
| *Clostridium*_sp_SY8519 | clade_482 | *Clostridium* | Clostridiaceae | Clostridiales | yes | 7 | 7 | 47 | 0 | 1.1 |
| *Desulfotomaculum_nigrificans* | clade_560 | *Desulfotomaculum* | Peptococcaceae | Clostridiales | yes | 7 | 7 | 27 | 0 | 1.1 |
| *Eubacterium_cylindroides* | clade_385 | unassigned | Erysipelotrichaceae | Erysipelotrichales | yes | 7 | 7 | 7 | 0 | 1.1 |
| *Ruminococcus*_sp_K_1 | clade_309 | *Ruminococcus* | Ruminococcaceae | Clostridiales | yes | 7 | 7 | 0 | 0 | 1.1 |
| *Lachnospiraceae_bacterium*_oral_taxon_F15 | clade_393 | unassigned | Lachnospiraceae | Clostridiales | yes | 7 | 0 | 53 | 0 | 0.7 |
| *Clostridium_nexile* | clade_262 | *Clostridium* | Clostridiaceae | Clostridiales | yes | 7 | 0 | 40 | 1 | 1.7 |
| *Acetanaerobacterium_elongatum* | clade_439 | *Acetanaerobacterium* | Ruminococcaceae | Clostridiales | yes | 7 | 0 | 7 | 0 | 0.7 |
| *Butyricicoccus_pullicaecorum* | clade_572 | *Butyricicoccus* | Clostridiaceae | Clostridiales | yes | 7 | 0 | 0 | 1 | 1.7 |
| *Clostridium_butyricum* | clade_252 | *Clostridium* | Clostridiaceae | Clostridiales | yes | 7 | 0 | 0 | 0 | 0.7 |

TABLE 11-continued

| OTU | Clade | Genus | Family | Order | Spore Former | Percent of Dose Ecologies Occurs | Percent of Engrafted Ecologies Occurs | Percent of Augemented Ecologies Occurs | Keystone OTU | CES |
|---|---|---|---|---|---|---|---|---|---|---|
| *Solobacterium*_*moorei* | clade_388 | *Solobacterium* | Erysipelotrichaceae | Erysipelotrichales | yes | 7 | 0 | 0 | 0 | 0.7 |
| *Bacteroides*_*uniformis* | clade_110 | *Bacteroides* | Bacteroidaceae | Bacteroidales | no | | 87 | 13 | 0 | 4.0 |
| *Alloscardovia*_sp_OB7196 | clade_475 | *Alloscardovia* | Bifidobacteriaceae | Bifidobacteriales | no | | 53 | 33 | 0 | 2.3 |
| *Clostridiales*_*bacterium*_oral_clone_P4PA | clade_558 | unassigned | unassigned | Clostridiales | no | | 47 | 27 | 0 | 2.3 |
| *Enterococcus*_*faecium* | clade_497 | *Enterococcus* | Enterococcaceae | Lactobacillales | no | | 47 | 7 | 0 | 3.0 |
| *Clostridiales*_*bacterium*_oral_taxon_F32 | clade_584 | unassigned | unassigned | Clostridiales | no | | 40 | 0 | 0 | 1.7 |
| *Bifidobacterium*_*breve* | clade_172 | *Bifidobacterium* | Bifidobacteriaceae | Bifidobacteriales | no | | 33 | 7 | 0 | 2.4 |
| *Bifidobacterium*_*longum* | clade_172 | *Bifidobacterium* | Bifidobacteriaceae | Bifidobacteriales | no | | 33 | 0 | 1 | 2.7 |
| *Bacteroides*_*oleiciplenus* | clade_85 | *Bacteroides* | Bacteroidaceae | Bacteroidales | no | | 27 | 47 | 0 | 1.7 |
| *Dialister*_*invisus* | clade_506 | *Dialister* | Veillonellaceae | Selenomonadales | no | | 27 | 7 | 0 | 1.7 |
| *Anaerobaculum*_*hydrogeniformans* | clade_591 | *Anaerobaculum* | Synergistaceae | Synergistales | no | | 20 | 47 | 0 | 1.7 |
| *Streptococcus*_sp_oral_taxon_G63 | clade_98 | *Streptococcus* | Streptococcaceae | Lactobacillales | no | | 20 | 27 | 0 | 1.7 |
| *Streptococcus*_*thermophilus* | clade_98 | *Streptococcus* | Streptococcaceae | Lactobacillales | no | | 20 | 13 | 0 | 2.4 |
| *Dialister*_*micraerophilus* | clade_506 | *Dialister* | Veillonellaceae | Selenomonadales | no | | 20 | 13 | 0 | 1.7 |
| *Bifidobacterium*_*animalis* | clade_172 | *Bifidobacterium* | Bifidobacteriaceae | Bifidobacteriales | no | | 20 | 7 | 0 | 1.7 |
| *Lactobacillus*_*iners* | clade_398 | *Lactobacillus* | Lactobacillaceae | Lactobacillales | no | | 20 | 0 | 0 | 1.7 |
| *Butyrivibrio*_*fibrisolvens* | clade_444 | *Butyrivibrio* | Lachnospiraceae | Clostridiales | no | | 13 | 67 | 0 | 1.1 |
| *Streptococcus*_sp_ACS2 | clade_98 | *Streptococcus* | Streptococcaceae | Lactobacillales | no | | 13 | 33 | 0 | 1.7 |
| *Lactococcus*_*lactis* | clade_401 | *Lactococcus* | Streptococcaceae | Lactobacillales | no | | 13 | 13 | 0 | 1.7 |
| *Lactobacillus*_*delbrueckii* | clade_72 | *Lactobacillus* | Lactobacillaceae | Lactobacillales | no | | 13 | 13 | 0 | 1.7 |
| *Cytophaga*_*xylanolytica* | clade_561 | *Cytophaga* | Cytophagaceae | Cytophagales | no | | 7 | 53 | 0 | 1.1 |
| *Streptococcus*_*gallolyticus* | clade_98 | *Streptococcus* | Streptococcaceae | Lactobacillales | no | | 7 | 33 | 0 | 1.1 |
| *Marvinbryantia*_*formatexigens* | clade_309 | unassigned | Lachnospiraceae | Clostridiales | no | | 7 | 33 | 0 | 1.1 |
| *Akkermansia*_*muciniphila* | clade_583 | *Akkermansia* | Verrucomicrobiaceae | Verrucomicrobiales | no | | 7 | 20 | 1 | 2.7 |
| *Bacteroides*_*dorei* | clade_378 | *Bacteroides* | Bacteroidaceae | Bacteroidales | no | | 7 | 20 | 1 | 2.7 |
| *Megasphaera*_genomosp_type_1_28L | clade_506 | *Megasphaera* | Veillonellaceae | Selenomonadales | no | | 7 | 20 | 0 | 1.1 |
| *Lactobacillus*_*hominis* | clade_398 | *Lactobacillus* | Lactobacillaceae | Lactobacillales | no | | 7 | 13 | 0 | 1.7 |
| *Actinomyces*_*oricola* | clade_54 | *Actinomyces* | Actinomycetaceae | Actinomycetales | no | | 7 | 13 | 0 | 1.1 |
| *Streptobacillus*_*moniliformis* | clade_532 | *Streptobacillus* | Leptotrichiaceae | Fusobacteriales | no | | 7 | 13 | 0 | 1.1 |
| *Streptococcus*_sp_oral_clone_ASCB06 | clade_98 | *Streptococcus* | Streptococcaceae | Lactobacillales | no | | 7 | 7 | 0 | 1.1 |
| *Bacteroides*_sp_D20 | clade_110 | *Bacteroides* | Bacteroidaceae | Bacteroidales | no | | 7 | 7 | 1 | 2.1 |
| *Collinsella*_*intestinalis* | clade_553 | *Collinsella* | Coriobacteriaceae | Coriobacteriales | no | | 7 | 0 | 0 | 1.7 |
| *Methanosphaera*_*stadtmanae* | clade_595 | *Methanosphaera* | Methanobacteriaceae | Methanobacteriales | no | | 7 | 0 | 0 | 1.7 |
| *Streptococcus*_*vestibularis* | clade_98 | *Streptococcus* | Streptococcaceae | Lactobacillales | no | | 7 | 0 | 0 | 1.1 |
| *Clostridiaceae*_*bacterium*_END_2 | clade_368 | unassigned | Clostridiaceae | Clostridiales | no | | 0 | 53 | 0 | 0.7 |
| *Parabacteroides*_*distasonis* | clade_335 | *Parabacteroides* | Porphyromonadaceae | Bacteroidales | no | | 0 | 27 | 0 | 1.3 |
| *Veillonella*_*dispar* | clade_358 | *Veillonella* | Veillonellaceae | Selenomonadales | no | | 0 | 27 | 0 | 0.7 |
| *Bacteroides*_*caccae* | clade_170 | *Bacteroides* | Bacteroidaceae | Bacteroidales | no | | 0 | 20 | 1 | 1.7 |
| *Veillonella*_sp_3_1_44 | clade_358 | *Veillonella* | Veillonellaceae | Selenomonadales | no | | 0 | 20 | 0 | 0.7 |
| *Megasphaera*_*micronuciformis* | clade_493 | *Megasphaera* | Veillonellaceae | Selenomonadales | no | | 0 | 20 | 0 | 0.7 |
| *Oxalobacter*_*formigenes* | clade_357 | *Oxalobacter* | Oxalobacteraceae | Burkholderiales | no | | 0 | 20 | 0 | 0.7 |
| *Streptococcus*_*parasanguinis* | clade_98 | *Streptococcus* | Streptococcaceae | Lactobacillales | no | | 0 | 13 | 1 | 2.3 |
| *Bacteroides*_*fragilis* | clade_65 | *Bacteroides* | Bacteroidaceae | Bacteroidales | no | | 0 | 13 | 0 | 0.7 |
| *Bacteroides*_sp_4_1_36 | clade_110 | *Bacteroides* | Bacteroidaceae | Bacteroidales | no | | 0 | 13 | 0 | 0.7 |
| *Lactobacillus*_sp_BT6 | clade_373 | *Lactobacillus* | Lactobacillaceae | Lactobacillales | no | | 0 | 13 | 0 | 0.7 |
| *Bacteroides*_sp_1_1_14 | clade_65 | *Bacteroides* | Bacteroidaceae | Bacteroidales | no | | 0 | 13 | 0 | 0.7 |
| *Escherichia*_*hermannii* | clade_92 | *Escherichia* | Enterobacteriaceae | Enterobacteriales | no | | 0 | 13 | 0 | 0.7 |
| *Escherichia*_sp_B4 | clade_92 | *Escherichia* | Enterobacteriaceae | Enterobacteriales | no | | 0 | 13 | 0 | 0.7 |

TABLE 11-continued

| OTU | Clade | Genus | Family | Order | Spore Former | Percent of Dose Ecologies Occurs | Percent of Engrafted Ecologies Occurs | Percent of Augemented Ecologies Occurs | Keystone OTU | CES |
|---|---|---|---|---|---|---|---|---|---|---|
| Gemella_moribillorum | clade_450 | Gemella | unassigned | Bacillales | no | | 0 | 13 | 0 | 0.7 |
| Klebsiella_variicola | clade_92 | Klebsiella | Enterobacteriaceae | Enterobacteriales | no | | 0 | 13 | 0 | 0.7 |
| Phascolarctobacterium_succinatutens | clade_556 | Phascolarctobacterium | Acidaminococcaceae | Selenomonadales | no | | 0 | 13 | 0 | 0.7 |
| Streptococcus_sp_CM7 | clade_60 | Streptococcus | Streptococcaceae | Lactobacillales | no | | 0 | 13 | 0 | 0.7 |
| Bilophila_wadsworthia | clade_521 | Bilophila | Desulfovibrionaceae | Desulfovibrionales | no | | 0 | 7 | 1 | 2.3 |
| Streptococcus_sp_oral_clone_GM006 | clade_98 | Streptococcus | Streptococcaceae | Lactobacillales | no | | 0 | 7 | 0 | 1.3 |
| Adlercreutzia_equolifaciens | clade_566 | Adlercreutzia | Coriobacteriaceae | Coriobacteriales | no | | 0 | 7 | 0 | 0.7 |
| Lactobacillus_murinus | clade_449 | Lactobacillus | Lactobacillaceae | Lactobacillales | no | | 0 | 7 | 0 | 0.7 |
| Helicobacter_pullorum | clade_489 | Helicobacter | Helicobacteraceae | Campylobacterales | no | | 0 | 7 | 0 | 0.7 |
| Alistipes_finegoldii | clade_500 | Alistipes | Rikenellaceae | Bacteroidales | no | | 0 | 7 | 0 | 0.7 |
| Averyella_dalhousiensis | clade_92 | Averyella | Enterobacteriaceae | Enterobacteriales | no | | 0 | 7 | 0 | 0.7 |
| Desulfovibrio_desulfuricans | clade_445 | Desulfovibrio | Desulfovibrionaceae | Desulfovibrionales | no | | 0 | 7 | 0 | 0.7 |
| Plesiomonas_shigelloides | clade_92 | Plesiomonas | Enterobacteriaceae | Enterobacteriales | no | | 0 | 7 | 0 | 0.7 |
| Actinomyces_israelii | clade_212 | Actinomyces | Actinomycetaceae | Actinomycetales | no | | 0 | 7 | 0 | 0.7 |
| Bacteroidales_genomosp_P1 | clade_529 | unassigned | unassigned | Bacteroidales | no | | 0 | 7 | 0 | 0.7 |
| Bifidobacterium_bifidum | clade_293 | Bifidobacterium | Bifidobacteriaceae | Bifidobacteriales | no | | 0 | 7 | 0 | 0.7 |
| Cedecea_davisae | clade_92 | Cedecea | Enterobacteriaceae | Enterobacteriales | no | | 0 | 7 | 0 | 0.7 |
| Gardnerella_vaginalis | clade_344 | Gardnerella | Bifidobacteriaceae | Bifidobacteriales | no | | 0 | 7 | 0 | 0.7 |
| Lactobacillus_fermentum | clade_313 | Lactobacillus | Lactobacillaceae | Lactobaciliales | no | | 0 | 7 | 0 | 0.7 |
| Lactobacillus_reuteri | clade_313 | Lactobacillus | Lactobacillaceae | Lactobacillales | no | | 0 | 8 | 0 | 0.7 |
| Lactococcus_raffinolactis | clade_524 | Lactococcus | Streptococcaceae | Lactobacillales | no | | 0 | 7 | 0 | 0.7 |
| Pediococcus_pentosaceus | clade_372 | Pediococcus | Lactobacillaceae | Lactobacillales | no | | 0 | 7 | 0 | 0.7 |
| Prevotella_denticola | clade_83 | Prevotella | Prevotellaceae | Bacteroidales | no | | 0 | 7 | 0 | 0.7 |
| Rothia_mucilaginosa | clade_271 | Rothia | Micrococcaceae | Actinomycetales | no | | 0 | 7 | 0 | 0.7 |
| Sutterella_stercoricanis | clade_432 | Sutterella | Sutterellaceae | Burkholderiales | no | | 0 | 7 | 0 | 0.7 |
| Eggerthella_sp_1_3_56FAA | clade_566 | Eggerthella | Coriobacteriaceae | Coriobacteriales | no | | 0 | 0 | 0 | 1.3 |
| Coriobacteriaceae_bacterium_JC110 | clade_566 | unassigned | Coriobacteriaceae | Coriobacteriales | no | | 0 | 0 | 0 | 1.3 |
| Megamonas_funiformis | clade_542 | Megamonas | Veillonellaceae | Selenomonadales | no | | 0 | 0 | 0 | 1.3 |
| Gordonibacter_pamelaeae | clade_566 | Gordonibacter | Coriobacteriaceae | Coriobacteriales | no | | 0 | 0 | 0 | 1.3 |
| Bifidobacterium_sp_HM2 | clade_172 | Bifidobacterium | Bifidobacteriaceae | Bifidobacteriales | no | | 0 | 0 | 0 | 0.7 |
| Bacteroides_stercoris | clade_85 | Bacteroides | Bacteroidaceae | Bacteroidales | no | | 0 | 0 | 1 | 1.7 |
| Bifidobacterium_angulatum | clade_172 | Bifidobacterium | Bifidobacteriaceae | Bifidobacteriales | no | | 0 | 0 | 0 | 0.7 |
| Parasutterella_excrementihominis | clade_432 | Parasutterella | Sutterellaceae | Burkholderiales | no | | 0 | 0 | 0 | 0.7 |
| Phascolarctobacterium_faecium | clade_556 | Phascolarctobacterium | Acidaminococcaceae | Selenomonadales | no | | 0 | 0 | 0 | 0.7 |
| Cryptobacterium_curtum | clade_566 | Cryptobacterium | Coriobacteriaceae | Coriobacteriales | no | | 0 | 0 | 0 | 0.7 |
| Prevotella_sp_BI_42 | clade_168 | Prevotella | Prevotellaceae | Bacteroidales | no | | 0 | 0 | 0 | 0.7 |
| Slackia_isoflavoniconvertens | clade_566 | Slackia | Coriobacteriaceae | Coriobacteriales | no | | 0 | 0 | 0 | 0.7 |
| Acidaminococcus_sp_D21 | clade_556 | Acidaminococcus | Acidaminococcaceae | Selenomonadales | no | | 0 | 0 | 0 | 0.7 |
| Atopobium_vaginae | clade_539 | Atopobium | Coriobacteriaceae | Coriobacteriales | no | | 0 | 0 | 0 | 0.7 |
| Catabacter_hongkongensis | clade_558 | Catabacter | Catabacteriaceae | Clostridiales | no | | 0 | 0 | 0 | 0.7 |
| Lactobacillus_ruminis | clade_449 | Lactobacillus | Lactobacillaceae | Lactobacillales | no | | 0 | 0 | 0 | 0.7 |
| Lactobacillus_senioris | clade_398 | Lactobacillus | Lactobacillaceae | Lactobacillales | no | | 0 | 0 | 0 | 0.7 |
| Morganella_morganii | clade_89 | Morganella | Enterobacteriaceae | Enterobacteriales | no | | 0 | 0 | 0 | 0.7 |
| Parabacteroides_merdae | clade_286 | Parabacteroides | Porphyromonadaceae | Bacteroidales | no | | 0 | 0 | 1 | 1.7 |
| Peptoniphilus_harei | clade_389 | Peptoniphilus | Clostridiales Family XI | Clostridiales | no | | 0 | 0 | 0 | 0.7 |
| Streptococcus_downei | clade_441 | Streptococcus | Streptococcaceae | Lactobacillales | no | | 0 | 0 | 0 | 0.7 |

TABLE 12

| OTC1 of Composition | OTC2 of Composition | OTC3 of Composition | Clade of OTU1 | Clade of OTU2 | Clade of OTU3 (if applicable) | *C. diff* Inhibition Score | Percent of Dose Ecologies Occurs | Percent of Post-treatment Ecologies |
|---|---|---|---|---|---|---|---|---|
| *Dorea longicatena* | *Eubacterium rectale* | | clade_360 | clade_444 | | ++++ | 92.9 | 100.0 |
| *Ruminococcus torques* | *Ruminococcus torques* | | clade_262 | clade_262 | | ++++ | 92.9 | 93.3 |
| *Coprococcus comes* | *Eubacterium rectale* | | clade_262 | clade_444 | | ++++ | 85.7 | 46.7 |
| *Coprococcus comes* | *Ruminococcus bromii* | | clade_262 | clade_537 | | ++++ | 85.7 | 26.7 |
| *Ruminococcus torques* | *Coprococcus comes* | | clade_262 | clade_262 | | ++++ | 78.6 | 40.0 |
| *Ruminococcus obeum* | *Ruminococcus obeum* | | clade_309 | clade_309 | | ++++ | 64.3 | 33.3 |
| *Ruminococcus obeum* | *Coprococcus comes* | | clade_309 | clade_262 | | ++++ | 64.3 | 20.0 |
| *Ruminococcus obeum* | *Ruminococcus torques* | | clade_309 | clade_262 | | ++++ | 57.1 | 33.3 |
| *Clostridium disporicum* | *Eubacterium rectale* | | clade_253 | clade_444 | | ++++ | 50.0 | 46.7 |
| *Ciostridium mayombei* | *Eubacterium rectale* | *Eubacterium rectale* | clade_354 | clade_444 | clade_444 | ++++ | 50.0 | 20.0 |
| *Ciostridium mayombei* | *Faecalibacterium prausnitzii* | *Eubacterium rectale* | clade_354 | clade_478 | clade_444 | ++++ | 50.0 | 20.0 |
| *Ciostridium mayombei* | *Faecalibacterium prausnitzii* | *Faecalibacterium prausnitzii* | clade_354 | clade_478 | clade_478 | ++++ | 50.0 | 20.0 |
| *Eubacterium rectale* | *Clostridium mayombei* | *Blautia* sp. M25 | clade_444 | clade_354 | clade_309 | ++++ | 50.0 | 20.0 |
| *Eubacterium rectale* | *Clostridium mayombei* | *Clostridium mayombei* | clade_444 | clade_354 | clade_354 | ++++ | 50.0 | 20.0 |
| *Eubacterium rectale* | *Clostridium mayombei* | *Ruminococcus bromii* | clade_444 | clade_354 | clade_537 | ++++ | 50.0 | 20.0 |
| *Faecalibacterium prausnitzii* | *Clostridium mayombei* | *Blautia* sp. M25 | clade_478 | clade_354 | clade_309 | ++++ | 50.0 | 20.0 |
| *Faecalibacterium prausnitzii* | *Clostridium mayombei* | *Clostridium mayombei* | clade_478 | clade_354 | clade_354 | ++++ | 50.0 | 20.0 |
| *Faecalibacterium prausnitzii* | *Clostridium mayombei* | *Ruminococcus bromii* | clade_478 | clade_354 | clade_537 | ++++ | 50.0 | 20.0 |
| *Clostridium mayombei* | *Clostridium mayombei* | | clade_354 | clade_354 | | ++++ | 50.0 | 20.0 |
| *Clostridium mayombei* | *Faecalibacterium prausnitzii* | | clade_354 | clade_478 | | ++++ | 50.0 | 20.0 |
| *Clostridium mayombei* | *Ruminococcus bromii* | | clade_354 | clade_537 | | ++++ | 50.0 | 20.0 |
| *Clostridium mayombei* | *Eubacterium rectale* | | clade_354 | clade_444 | | ++++ | 50.0 | 20.0 |
| *Eubacterium rectale* | *Clostridium disporicum* | *Clostridium mayombei* | clade_444 | clade_253 | clade_354 | ++++ | 42.9 | 13.3 |
| *Faecalibacterium prausnitzii* | *Clostridium disporicum* | *Clostridium mayombei* | clade_478 | clade_253 | clade_354 | ++++ | 42.9 | 13.3 |
| *Clostridium disporicum* | *Clostridium mayombei* | | clade_253 | clade_354 | | ++++ | 42.9 | 13.3 |
| *Clostridium disporicum* | *Coprococcus comes* | | clade_253 | clade_262 | | ++++ | 35.7 | 13.3 |
| *Eubacterium rectale* | *Clostridium orbiscindens* | *Blautia* sp. M25 | clade_444 | clade_494 | clade_309 | ++++ | 28.6 | 80.0 |
| *Faecalibacterium prausnitzii* | *Clostridium orbiscindens* | *Blautia* sp. M25 | clade_478 | clade_494 | clade_309 | ++++ | 28.6 | 73.3 |
| *Clostridium disporicum* | *Clostridium orbiscindens* | | clade_253 | clade_494 | | ++++ | 28.6 | 46.7 |
| *Clostridium hylemonae* | *Eubacterium rectale* | *Eubacterium rectale* | clade_260 | clade_444 | clade_444 | ++++ | 21.4 | 40.0 |
| *Eubacterium rectale* | *Clostridium hylemonae* | *Blautia* sp. M25 | clade_444 | clade_260 | clade_309 | ++++ | 21.4 | 40.0 |
| *Coprococcus comes* | *Clostridium orbiscindens* | *Blautia* sp. M25 | clade_262 | clade_494 | clade_309 | ++++ | 21.4 | 33.3 |
| *Coprococcus comes* | *Clostridium orbiscindens* | | clade_262 | clade_494 | | ++++ | 21.4 | 33.3 |
| *Eubacterium rectale* | *Clostridium mayombei* | *Clostridium orbiscindens* | clade_444 | clade_354 | clade_494 | ++++ | 21.4 | 20.0 |
| *Faecalibacterium prausnitzii* | *Clostridium mayombei* | *Clostridium orbiscindens* | clade_478 | clade_354 | clade_494 | ++++ | 21.4 | 20.0 |
| *Clostridium mayombei* | *Clostridium orbiscindens* | | clade_354 | clade_494 | | ++++ | 21.4 | 20.0 |
| *Clostridium disporicum* | Lachnospiraceae *bacterium* 5_1_57FAA | | clade_253 | clade_260 | | ++++ | 14.3 | 40.0 |
| *Clostridium hylemonae* | Lachnospiraceae *bacterium* 5_1_57FAA | Lachnospiraceae *bacterium* 5_1_57FAA | clade_260 | clade_260 | clade_260 | ++++ | 14.3 | 26.7 |
| *Clostridium hylemonae* | Lachnospiraceae *bacterium* 5_1_57FAA | | clade_260 | clade_260 | | ++++ | 14.3 | 26.7 |
| *Clostridium hylemonae* | Lachnospiraceae *bacterium* 5_1_57FAA | *Eubacterium rectale* | clade_260 | clade_260 | clade_444 | ++++ | 14.3 | 26.7 |
| Lachnospiraceae *bacterium* 5_1_57FAA | *Clostridium hylemonae* | *Blautia* sp. M25 | clade_260 | clade_260 | clade_309 | ++++ | 14.3 | 26.7 |
| *Bacteroides caccae* | *Bacteroides caccae* | | clade_170 | clade_170 | | ++++ | 14.3 | 20.0 |

TABLE 12-continued

| OTC1 of Composition | OTC2 of Composition | OTC3 of Composition | Clade of OTU1 | Clade of OTU2 | Clade of OTU3 (if applicable) | *C. diff* Inhibition Score | Percent of Dose Ecologies Occurs | Percent of Post-treatment Ecologies |
|---|---|---|---|---|---|---|---|---|
| *Clostridium hylemonae* | *Faecalibacterium prausnitzii* | Lachnospiraceae *bacterium* 5_1_57FAA | clade_260 | clade_478 | clade_260 | ++++ | 14.3 | 20.0 |
| *Bacteroides caccae* | *Ruminococcus torques* | | clade_170 | clade_262 | | ++++ | 14.3 | 20.0 |
| *Clostridium mayombei* | *Faecalibacterium prausnitzii* | Lachnospiraceae *bacterium* 5_1_57FAA | clade_354 | clade_478 | clade_260 | ++++ | 14.3 | 13.3 |
| *Clostridium mayombei* | Lachnospiraceae *bacterium* 5_1_57FAA | *Eubacterium rectale* | clade_354 | clade_260 | clade_444 | ++++ | 14.3 | 13.3 |
| *Clostridium mayombei* | Lachnospiraceae *bacterium* 5_1_57FAA | Lachnospiraceae *bacterium* 5_1_57FAA | clade_354 | clade_260 | clade_260 | ++++ | 14.3 | 13.3 |
| Lachnospiraceae *bacterium* 5_1_57FAA | *Clostridium mayombei* | *Blautia* sp. M25 | clade_260 | clade_354 | clade_309 | ++++ | 14.3 | 13.3 |
| Lachnospiraceae *bacterium* 5_1_57FAA | *Clostridium mayombei* | *Clostridium mayombei* | clade_260 | clade_354 | clade_354 | ++++ | 14.3 | 13.3 |
| Lachnospiraceae *bacterium* 5_1_57FAA | *Clostridium mayombei* | *Ruminococcus bromii* | clade_260 | clade_354 | clade_537 | ++++ | 14.3 | 13.3 |
| *Clostridium mayombei* | Lachnospiraceae *bacterium* 5_1_57FAA | | clade_354 | clade_260 | | ++++ | 14.3 | 13.3 |
| *Coprococcus comes* | *Clostridium hylemonae* | *Blautia* sp. M25 | clade_262 | clade_260 | clade_309 | ++++ | 14.3 | 13.3 |
| Lachnospiraceae *bacterium* 5_1_57FAA | *Clostridium disporicum* | *Clostridium mayombei* | clade_260 | clade_253 | clade_354 | ++++ | 14.3 | 6.7 |
| *Dorea longicatena* | *Clostridium symbiosum* | | clade_360 | clade_408 | | ++++ | 7.1 | 93.3 |
| *Clostridium symbiosum* | *Clostridium orbiscindens* | *Clostridium orbiscindens* | clade_408 | clade_494 | clade_494 | ++++ | 7.1 | 80.0 |
| *Clostridium symbiosum* | *Clostridium orbiscindens* | *Blautia* sp. M25 | clade_408 | clade_494 | clade_309 | ++++ | 7.1 | 80.0 |
| *Clostridium orbiscindens* | *Clostridium symbiosum* | Lachnospiraceae *bacterium* 5_1_57FAA | clade_494 | clade_408 | clade_260 | ++++ | 7.1 | 66.7 |
| Lachnospiraceae *bacterium* 5_1_57FAA | *Clostridium orbiscindens* | *Blautia* sp. M25 | clade_260 | clade_494 | clade_309 | ++++ | 7.1 | 66.7 |
| *Clostridium symbiosum* | *Ruminococcus bromii* | | clade_408 | clade_537 | | ++++ | 7.1 | 66.7 |
| *Clostridium disporicum* | *Clostridium symbiosum* | Lachnospiraceae *bacterium* 5_1_57FAA | clade_253 | clade_408 | clade_260 | ++++ | 7.1 | 40.0 |
| *Clostridium hylemonae* | *Clostridium symbiosum* | *Eubacterium rectale* | clade_260 | clade_408 | clade_444 | ++++ | 7.1 | 40.0 |
| *Coprococcus comes* | Lachnospiraceae *bacterium* 5_1_57FAA | | clade_262 | clade_260 | | ++++ | 7.1 | 33.3 |
| *Clostridium symbiosum* | *Clostridium hylemonae* | *Ruminococcus bromii* | clade_408 | clade_260 | clade_537 | ++++ | 7.1 | 33.3 |
| *Clostridium hylemonae* | *Clostridium symbiosum* | Lachnospiraceae *bacterium* 5_1_57FAA | clade_260 | clade_408 | clade_260 | ++++ | 7.1 | 26.7 |
| *Clostridium mayombei* | *Clostridium symbiosum* | *Clostridium symbiosum* | clade_354 | clade_408 | clade_408 | ++++ | 7.1 | 20.0 |
| *Clostridium mayombei* | *Clostridium symbiosum* | *Eubacterium rectale* | clade_354 | clade_408 | clade_444 | ++++ | 7.1 | 20.0 |
| *Clostridium mayombei* | *Clostridium symbiosum* | *Faecalibacterium prausnitzii* | clade_354 | clade_408 | clade_478 | ++++ | 7.1 | 20.0 |
| *Clostridium symbiosum* | *Clostridium mayombei* | *Blautia* sp. M25 | clade_408 | clade_354 | clade_309 | ++++ | 7.1 | 20.0 |
| *Clostridium symbiosum* | *Clostridium mayombei* | *Clostridium mayombei* | clade_408 | clade_354 | clade_354 | ++++ | 7.1 | 20.0 |
| *Clostridium symbiosum* | *Clostridium mayombei* | *Clostridium orbiscindens* | clade_408 | clade_354 | clade_494 | ++++ | 7.1 | 20.0 |
| *Clostridium symbiosum* | *Clostridium mayombei* | *Ruminococcus bromii* | clade_408 | clade_354 | clade_537 | ++++ | 7.1 | 20.0 |
| *Clostridium mayombei* | *Clostridium symbiosum* | | clade_354 | clade_408 | | ++++ | 7.1 | 20.0 |
| *Clostridium mayombei* | *Clostridium symbiosum* | Lachnospiraceae *bacterium* 5_1_57FAA | clade_354 | clade_408 | clade_260 | ++++ | 7.1 | 13.3 |
| *Clostridium symbiosum* | *Clostridium disporicum* | *Clostridium mayombei* | clade_408 | clade_253 | clade_354 | ++++ | 7.1 | 13.3 |
| *Clostridium symbiosum* | *Clostridium mayombei* | *Clostridium hylemonae* | clade_408 | clade_354 | clade_260 | ++++ | 7.1 | 13.3 |
| *Eubacterium rectale* | *Clostridium mayombei* | *Clostridium hylemonae* | clade_444 | clade_354 | clade_260 | ++++ | 7.1 | 13.3 |

TABLE 12-continued

| OTC1 of Composition | OTC2 of Composition | OTC3 of Composition | Clade of OTU1 | Clade of OTU2 | Clade of OTU3 (if applicable) | *C. diff* Inhibition Score | Percent of Dose Ecologies Occurs | Percent of Post-treatment Ecologies |
|---|---|---|---|---|---|---|---|---|
| *Faecalibacterium prausnitzii* | *Clostridium mayombei* | *Clostridium hylemonae* | clade_478 | clade_354 | clade_260 | ++++ | 7.1 | 13.3 |
| Lachnospiraceae bacterium 5_1_57FAA | *Clostridium mayombei* | *Clostridium orbiscindens* | clade_260 | clade_354 | clade_494 | ++++ | 7.1 | 13.3 |
| *Clostridium mayombei* | *Clostridium hylemonae* | | clade_354 | clade_260 | | ++++ | 7.1 | 13.3 |
| *Clostridium hylemonae* | *Coprococcus comes* | Lachnospiraceae *bacterium* 5_1_57FAA | clade_260 | clade_262 | clade_260 | ++++ | 7.1 | 6.7 |
| Lachnospiraceae *bacterium* 5_1_57FAA | *Clostridium mayombei* | *Clostridium hylemonae* | clade_260 | clade_354 | clade_260 | ++++ | 7.1 | 6.7 |

TABLE 13

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 10 | Y | Y | Y | Y | Y | Y | Y | Y | Y | Y |
| 9 | Y | Y | Y | Y | Y | Y | Y | Y | Y | |
| 9 | Y | Y | Y | Y | Y | Y | Y | Y | | Y |
| 9 | Y | Y | Y | Y | Y | Y | Y | | Y | Y |
| 9 | Y | Y | Y | Y | Y | Y | | Y | Y | Y |
| 9 | Y | Y | Y | Y | Y | | Y | Y | Y | Y |
| 9 | Y | Y | Y | Y | | Y | Y | Y | Y | Y |
| 9 | Y | Y | Y | | Y | Y | Y | Y | Y | Y |
| 9 | Y | Y | | Y | Y | Y | Y | Y | Y | Y |
| 9 | Y | | Y | Y | Y | Y | Y | Y | Y | Y |
| 9 | | Y | Y | Y | Y | Y | Y | Y | Y | Y |
| 8 | Y | Y | Y | Y | Y | Y | Y | Y | | |
| 8 | Y | Y | Y | Y | Y | Y | Y | | Y | |
| 8 | Y | Y | Y | Y | Y | Y | Y | | | Y |
| 8 | Y | Y | Y | Y | Y | Y | | Y | Y | |
| 8 | Y | Y | Y | Y | Y | Y | | Y | | Y |
| 8 | Y | Y | Y | Y | Y | Y | | | Y | Y |
| 8 | Y | Y | Y | Y | Y | | Y | Y | Y | |
| 8 | Y | Y | Y | Y | Y | | Y | Y | | Y |
| 8 | Y | Y | Y | Y | Y | | Y | | Y | Y |
| 8 | Y | Y | Y | Y | Y | | | Y | Y | Y |
| 8 | Y | Y | Y | Y | | Y | Y | Y | Y | |
| 8 | Y | Y | Y | Y | | Y | Y | Y | | Y |
| 8 | Y | Y | Y | Y | | Y | Y | | Y | Y |
| 8 | Y | Y | Y | Y | | Y | | Y | Y | Y |
| 8 | Y | Y | Y | Y | | | Y | Y | Y | Y |
| 8 | Y | Y | Y | | Y | Y | Y | Y | Y | |
| 8 | Y | Y | Y | | Y | Y | Y | Y | | Y |
| 8 | Y | Y | Y | | Y | Y | Y | | Y | Y |
| 8 | Y | Y | Y | | Y | Y | | Y | Y | Y |
| 8 | Y | Y | Y | | Y | | Y | Y | Y | Y |
| 8 | Y | Y | Y | | | Y | Y | Y | Y | Y |
| 8 | Y | Y | | Y | Y | Y | Y | Y | Y | |
| 8 | Y | Y | | Y | Y | Y | Y | Y | | Y |
| 8 | Y | Y | | Y | Y | Y | Y | | Y | Y |
| 8 | Y | Y | | Y | Y | Y | | Y | Y | Y |
| 8 | Y | Y | | Y | Y | | Y | Y | Y | Y |
| 8 | Y | Y | | Y | | Y | Y | Y | Y | Y |
| 8 | Y | Y | | | Y | Y | Y | Y | Y | Y |
| 8 | Y | | Y | Y | Y | Y | Y | Y | Y | |
| 8 | Y | | Y | Y | Y | Y | Y | Y | | Y |
| 8 | Y | | Y | Y | Y | Y | Y | | Y | Y |
| 8 | Y | | Y | Y | Y | Y | | Y | Y | Y |
| 8 | Y | | Y | Y | Y | | Y | Y | Y | Y |
| 8 | Y | | Y | Y | | Y | Y | Y | Y | Y |

TABLE 13-continued

| Num. of OTUs | OTU Clade<br>clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
|---|---|---|---|---|---|---|---|---|---|---|
| 8 | Y | | Y | | Y | Y | Y | Y | Y | Y |
| 8 | Y | | | Y | Y | Y | Y | Y | Y | Y |
| 8 | | Y | Y | Y | Y | Y | Y | Y | Y | |
| 8 | | Y | Y | Y | Y | Y | Y | Y | | Y |
| 8 | | Y | Y | Y | Y | Y | Y | | Y | Y |
| 8 | | Y | Y | Y | Y | Y | | Y | Y | Y |
| 8 | | Y | Y | Y | Y | | Y | Y | Y | Y |
| 8 | | Y | Y | Y | | Y | Y | Y | Y | Y |
| 8 | | Y | Y | | Y | Y | Y | Y | Y | Y |
| 8 | | Y | | Y | Y | Y | Y | Y | Y | Y |
| 8 | | | Y | Y | Y | Y | Y | Y | Y | Y |
| 7 | Y | Y | Y | Y | Y | Y | Y | | | |
| 7 | Y | Y | Y | Y | Y | Y | | Y | | |
| 7 | Y | Y | Y | Y | Y | Y | | | Y | |
| 7 | Y | Y | Y | Y | Y | Y | | | | Y |
| 7 | Y | Y | Y | Y | Y | | Y | Y | | |
| 7 | Y | Y | Y | Y | Y | | Y | | Y | |
| 7 | Y | Y | Y | Y | Y | | Y | | | Y |
| 7 | Y | Y | Y | Y | Y | | | Y | Y | |
| 7 | Y | Y | Y | Y | Y | | | Y | | Y |
| 7 | Y | Y | Y | Y | Y | | | | Y | Y |
| 7 | Y | Y | Y | Y | | Y | Y | Y | | |
| 7 | Y | Y | Y | Y | | Y | Y | | Y | |
| 7 | Y | Y | Y | Y | | Y | Y | | | Y |
| 7 | Y | Y | Y | Y | | Y | | Y | Y | |
| 7 | Y | Y | Y | Y | | Y | | Y | | Y |
| 7 | Y | Y | Y | Y | | Y | | | Y | Y |
| 7 | Y | Y | Y | Y | | | Y | Y | Y | |
| 7 | Y | Y | Y | Y | | | Y | Y | | Y |
| 7 | Y | Y | Y | Y | | | Y | | Y | Y |
| 7 | Y | Y | Y | Y | | | | Y | Y | Y |
| 7 | Y | Y | Y | | Y | Y | Y | Y | | |
| 7 | Y | Y | Y | | Y | Y | Y | | Y | |
| 7 | Y | Y | Y | | Y | Y | Y | | | Y |
| 7 | Y | Y | Y | | Y | Y | | Y | Y | |
| 7 | Y | Y | Y | | Y | Y | | Y | | Y |
| 7 | Y | Y | Y | | Y | Y | | | Y | Y |
| 7 | Y | Y | Y | | Y | | Y | Y | Y | |
| 7 | Y | Y | Y | | Y | | Y | Y | | Y |
| 7 | Y | Y | Y | | Y | | Y | | Y | Y |
| 7 | Y | Y | Y | | Y | | | Y | Y | Y |
| 7 | Y | Y | Y | | | Y | Y | Y | Y | |
| 7 | Y | Y | Y | | | Y | Y | Y | | Y |
| 7 | Y | Y | Y | | | Y | Y | | Y | Y |
| 7 | Y | Y | Y | | | Y | | Y | Y | Y |
| 7 | Y | Y | Y | | | | Y | Y | Y | Y |
| 7 | Y | Y | | Y | Y | Y | Y | Y | | |

TABLE 13-continued

| | OTU Clade | | | | | | | | | |
|---|---|---|---|---|---|---|---|---|---|---|
| Num. of OTUs | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 7 | Y | Y | | Y | Y | Y | Y | | Y | |
| 7 | Y | Y | | Y | Y | Y | Y | | | Y |
| 7 | Y | Y | | Y | Y | Y | | Y | Y | |
| 7 | Y | Y | | Y | Y | Y | | Y | | Y |
| 7 | Y | Y | | Y | Y | Y | | | Y | Y |
| 7 | Y | Y | | Y | Y | | Y | Y | Y | |
| 7 | Y | Y | | Y | Y | | Y | Y | | Y |
| 7 | Y | Y | | Y | Y | | Y | | Y | Y |
| 7 | Y | Y | | Y | Y | | | Y | Y | Y |
| 7 | Y | Y | | Y | | Y | Y | Y | Y | |
| 7 | Y | Y | | Y | | Y | Y | Y | | Y |
| 7 | Y | Y | | Y | | Y | Y | | Y | Y |
| 7 | Y | Y | | Y | | Y | | Y | Y | Y |
| 7 | Y | Y | | Y | | | Y | Y | Y | Y |
| 7 | Y | Y | | | Y | Y | Y | Y | Y | |
| 7 | Y | Y | | | Y | Y | Y | Y | | Y |
| 7 | Y | Y | | | Y | Y | Y | | Y | Y |
| 7 | Y | Y | | | Y | Y | | Y | Y | Y |
| 7 | Y | Y | | | Y | | Y | Y | Y | Y |
| 7 | Y | Y | | | | Y | Y | Y | Y | Y |
| 7 | Y | | Y | Y | Y | Y | Y | Y | | |
| 7 | Y | | Y | Y | Y | Y | Y | | Y | |
| 7 | Y | | Y | Y | Y | Y | Y | | | Y |
| 7 | Y | | Y | Y | Y | Y | | Y | Y | |
| 7 | Y | | Y | Y | Y | Y | | Y | | Y |
| 7 | Y | | Y | Y | Y | Y | | | Y | Y |
| 7 | Y | | Y | Y | Y | | Y | Y | Y | |
| 7 | Y | | Y | Y | Y | | Y | Y | | Y |
| 7 | Y | | Y | Y | Y | | Y | | Y | Y |
| 7 | Y | | Y | Y | Y | | | Y | Y | Y |
| 7 | Y | | Y | Y | | Y | Y | Y | Y | |
| 7 | Y | | Y | Y | | Y | Y | Y | | Y |
| 7 | Y | | Y | Y | | Y | Y | | Y | Y |
| 7 | Y | | Y | Y | | Y | | Y | Y | Y |
| 7 | Y | | Y | Y | | | Y | Y | Y | Y |
| 7 | Y | | Y | | Y | Y | Y | Y | Y | |
| 7 | Y | | Y | | Y | Y | Y | Y | | Y |
| 7 | Y | | Y | | Y | Y | Y | | Y | Y |
| 7 | Y | | Y | | Y | Y | | Y | Y | Y |
| 7 | Y | | Y | | Y | | Y | Y | Y | Y |
| 7 | Y | | Y | | | Y | Y | Y | Y | Y |
| 7 | Y | | | Y | Y | Y | Y | Y | Y | |
| 7 | Y | | | Y | Y | Y | Y | Y | | Y |
| 7 | Y | | | Y | Y | Y | Y | | Y | Y |
| 7 | Y | | | Y | Y | Y | | Y | Y | Y |
| 7 | Y | | | Y | Y | | Y | Y | Y | Y |
| 7 | Y | | | Y | | Y | Y | Y | Y | Y |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 7 | Y | | | | Y | Y | Y | Y | Y | Y |
| 7 | | Y | Y | Y | Y | Y | Y | Y | | |
| 7 | | Y | Y | Y | Y | Y | Y | | Y | |
| 7 | | Y | Y | Y | Y | Y | Y | | | Y |
| 7 | | Y | Y | Y | Y | Y | | Y | Y | |
| 7 | | Y | Y | Y | Y | Y | | Y | | Y |
| 7 | | Y | Y | Y | Y | Y | | | Y | Y |
| 7 | | Y | Y | Y | Y | | Y | Y | Y | |
| 7 | | Y | Y | Y | Y | | Y | Y | | Y |
| 7 | | Y | Y | Y | Y | | Y | | Y | Y |
| 7 | | Y | Y | Y | Y | | | Y | Y | Y |
| 7 | | Y | Y | Y | | Y | Y | Y | Y | |
| 7 | | Y | Y | Y | | Y | Y | Y | | Y |
| 7 | | Y | Y | Y | | Y | Y | | Y | Y |
| 7 | | Y | Y | Y | | Y | | Y | Y | Y |
| 7 | | Y | Y | Y | | | Y | Y | Y | Y |
| 7 | | Y | Y | | Y | Y | Y | Y | Y | |
| 7 | | Y | Y | | Y | Y | Y | Y | | Y |
| 7 | | Y | Y | | Y | Y | Y | | Y | Y |
| 7 | | Y | Y | | Y | Y | | Y | Y | Y |
| 7 | | Y | Y | | Y | | Y | Y | Y | Y |
| 7 | | Y | Y | | | Y | Y | Y | Y | Y |
| 7 | | Y | | Y | Y | Y | Y | Y | Y | |
| 7 | | Y | | Y | Y | Y | Y | Y | | Y |
| 7 | | Y | | Y | Y | Y | Y | | Y | Y |
| 7 | | Y | | Y | Y | Y | | Y | Y | Y |
| 7 | | Y | | Y | Y | | Y | Y | Y | Y |
| 7 | | Y | | Y | | Y | Y | Y | Y | Y |
| 7 | | Y | | | Y | Y | Y | Y | Y | Y |
| 7 | | | Y | Y | Y | Y | Y | Y | Y | |
| 7 | | | Y | Y | Y | Y | Y | Y | | Y |
| 7 | | | Y | Y | Y | Y | Y | | Y | Y |
| 7 | | | Y | Y | Y | Y | | Y | Y | Y |
| 7 | | | Y | Y | Y | | Y | Y | Y | Y |
| 7 | | | Y | Y | | Y | Y | Y | Y | Y |
| 7 | | | Y | | Y | Y | Y | Y | Y | Y |
| 7 | | | | Y | Y | Y | Y | Y | Y | Y |
| 6 | Y | Y | Y | Y | Y | Y | | | | |
| 6 | Y | Y | Y | Y | Y | | Y | | | |
| 6 | Y | Y | Y | Y | Y | | | Y | | |
| 6 | Y | Y | Y | Y | Y | | | | Y | |
| 6 | Y | Y | Y | Y | Y | | | | | Y |
| 6 | Y | Y | Y | Y | | Y | Y | | | |
| 6 | Y | Y | Y | Y | | Y | | Y | | |
| 6 | Y | Y | Y | Y | | Y | | | Y | |
| 6 | Y | Y | Y | Y | | Y | | | | Y |
| 6 | Y | Y | Y | Y | | | Y | Y | | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 6 | Y | Y | Y | Y | | | Y | | Y | |
| 6 | Y | Y | Y | Y | | | Y | | | Y |
| 6 | Y | Y | Y | Y | | | | Y | Y | |
| 6 | Y | Y | Y | Y | | | | Y | | Y |
| 6 | Y | Y | Y | Y | | | | | Y | Y |
| 6 | Y | Y | Y | | Y | Y | Y | | | |
| 6 | Y | Y | Y | | Y | Y | | Y | | |
| 6 | Y | Y | Y | | Y | Y | | | Y | |
| 6 | Y | Y | Y | | Y | Y | | | | Y |
| 6 | Y | Y | Y | | Y | | Y | Y | | |
| 6 | Y | Y | Y | | Y | | Y | | Y | |
| 6 | Y | Y | Y | | Y | | Y | | | Y |
| 6 | Y | Y | Y | | Y | | | Y | Y | |
| 6 | Y | Y | Y | | Y | | | Y | | Y |
| 6 | Y | Y | Y | | Y | | | | Y | Y |
| 6 | Y | Y | Y | | | Y | Y | Y | | |
| 6 | Y | Y | Y | | | Y | Y | | Y | |
| 6 | Y | Y | Y | | | Y | Y | | | Y |
| 6 | Y | Y | Y | | | Y | | Y | Y | |
| 6 | Y | Y | Y | | | Y | | Y | | Y |
| 6 | Y | Y | Y | | | Y | | | Y | Y |
| 6 | Y | Y | Y | | | | Y | Y | Y | |
| 6 | Y | Y | Y | | | | Y | Y | | Y |
| 6 | Y | Y | Y | | | | Y | | Y | Y |
| 6 | Y | Y | Y | | | | | Y | Y | Y |
| 6 | Y | Y | | Y | Y | Y | Y | | | |
| 6 | Y | Y | | Y | Y | Y | | Y | | |
| 6 | Y | Y | | Y | Y | Y | | | Y | |
| 6 | Y | Y | | Y | Y | Y | | | | Y |
| 6 | Y | Y | | Y | Y | | Y | Y | | |
| 6 | Y | Y | | Y | Y | | Y | | Y | |
| 6 | Y | Y | | Y | Y | | Y | | | Y |
| 6 | Y | Y | | Y | Y | | | Y | Y | |
| 6 | Y | Y | | Y | Y | | | Y | | Y |
| 6 | Y | Y | | Y | Y | | | | Y | Y |
| 6 | Y | Y | | Y | | Y | Y | Y | | |
| 6 | Y | Y | | Y | | Y | Y | | Y | |
| 6 | Y | Y | | Y | | Y | Y | | | Y |
| 6 | Y | Y | | Y | | Y | | Y | Y | |
| 6 | Y | Y | | Y | | Y | | Y | | Y |
| 6 | Y | Y | | Y | | Y | | | Y | Y |
| 6 | Y | Y | | Y | | | Y | Y | Y | |
| 6 | Y | Y | | Y | | | Y | Y | | Y |
| 6 | Y | Y | | Y | | | Y | | Y | Y |
| 6 | Y | Y | | Y | | | | Y | Y | Y |
| 6 | Y | Y | | | Y | Y | Y | Y | | |
| 6 | Y | Y | | | Y | Y | Y | | Y | |

TABLE 13-continued

| | OTU Clade | | | | | | | | | |
|---|---|---|---|---|---|---|---|---|---|---|
| Num. of OTUs | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 6 | Y | Y | | | Y | Y | Y | | | Y |
| 6 | Y | Y | | | Y | Y | | Y | Y | |
| 6 | Y | Y | | | Y | Y | | Y | | Y |
| 6 | Y | Y | | | Y | Y | | | Y | Y |
| 6 | Y | Y | | | Y | | Y | Y | Y | |
| 6 | Y | Y | | | Y | | Y | Y | | Y |
| 6 | Y | Y | | | Y | | Y | | Y | Y |
| 6 | Y | Y | | | Y | | | Y | Y | Y |
| 6 | Y | Y | | | | Y | Y | Y | Y | |
| 6 | Y | Y | | | | Y | Y | Y | | Y |
| 6 | Y | Y | | | | Y | Y | | Y | Y |
| 6 | Y | Y | | | | Y | | Y | Y | Y |
| 6 | Y | Y | | | | | Y | Y | Y | Y |
| 6 | Y | | Y | Y | Y | Y | Y | | | |
| 6 | Y | | Y | Y | Y | Y | | Y | | |
| 6 | Y | | Y | Y | Y | Y | | | Y | |
| 6 | Y | | Y | Y | Y | Y | | | | Y |
| 6 | Y | | Y | Y | Y | | Y | Y | | |
| 6 | Y | | Y | Y | Y | | Y | | Y | |
| 6 | Y | | Y | Y | Y | | Y | | | Y |
| 6 | Y | | Y | Y | Y | | | Y | Y | |
| 6 | Y | | Y | Y | Y | | | Y | | Y |
| 6 | Y | | Y | Y | Y | | | | Y | Y |
| 6 | Y | | Y | Y | | Y | Y | Y | | |
| 6 | Y | | Y | Y | | Y | Y | | Y | |
| 6 | Y | | Y | Y | | Y | Y | | | Y |
| 6 | Y | | Y | Y | | Y | | Y | Y | |
| 6 | Y | | Y | Y | | Y | | Y | | Y |
| 6 | Y | | Y | Y | | Y | | | Y | Y |
| 6 | Y | | Y | Y | | | Y | Y | Y | |
| 6 | Y | | Y | Y | | | Y | Y | | Y |
| 6 | Y | | Y | Y | | | Y | | Y | Y |
| 6 | Y | | Y | Y | | | | Y | Y | Y |
| 6 | Y | | Y | | Y | Y | Y | Y | | |
| 6 | Y | | Y | | Y | Y | Y | | Y | |
| 6 | Y | | Y | | Y | Y | Y | | | Y |
| 6 | Y | | Y | | Y | Y | | Y | Y | |
| 6 | Y | | Y | | Y | Y | | Y | | Y |
| 6 | Y | | Y | | Y | Y | | | Y | Y |
| 6 | Y | | Y | | Y | | Y | Y | Y | |
| 6 | Y | | Y | | Y | | Y | Y | | Y |
| 6 | Y | | Y | | Y | | Y | | Y | Y |
| 6 | Y | | Y | | Y | | | Y | Y | Y |
| 6 | Y | | Y | | | Y | Y | Y | Y | |
| 6 | Y | | Y | | | Y | Y | Y | | Y |
| 6 | Y | | Y | | | Y | Y | | Y | Y |
| 6 | Y | | Y | | | Y | | Y | Y | Y |

TABLE 13-continued

| Num. of OTUs | OTU Clade clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
|---|---|---|---|---|---|---|---|---|---|---|
| 6 | Y | | Y | | | | Y | Y | Y | Y |
| 6 | Y | | | Y | Y | Y | Y | Y | | |
| 6 | Y | | | Y | Y | Y | Y | | Y | |
| 6 | Y | | | Y | Y | Y | Y | | | Y |
| 6 | Y | | | Y | Y | Y | | Y | Y | |
| 6 | Y | | | Y | Y | Y | | Y | | Y |
| 6 | Y | | | Y | Y | Y | | | Y | Y |
| 6 | Y | | | Y | Y | | Y | Y | Y | |
| 6 | Y | | | Y | Y | | Y | Y | | Y |
| 6 | Y | | | Y | Y | | Y | | Y | Y |
| 6 | Y | | | Y | Y | | | Y | Y | Y |
| 6 | Y | | | Y | | Y | Y | Y | Y | |
| 6 | Y | | | Y | | Y | Y | Y | | Y |
| 6 | Y | | | Y | | Y | Y | | Y | Y |
| 6 | Y | | | Y | | Y | | Y | Y | Y |
| 6 | Y | | | Y | | | Y | Y | Y | Y |
| 6 | Y | | | | Y | Y | Y | Y | Y | |
| 6 | Y | | | | Y | Y | Y | Y | | Y |
| 6 | Y | | | | Y | Y | Y | | Y | Y |
| 6 | Y | | | | Y | Y | | Y | Y | Y |
| 6 | Y | | | | Y | | Y | Y | Y | Y |
| 6 | Y | | | | | Y | Y | Y | Y | Y |
| 6 | | Y | Y | Y | Y | Y | Y | | | |
| 6 | | Y | Y | Y | Y | Y | | Y | | |
| 6 | | Y | Y | Y | Y | Y | | | Y | |
| 6 | | Y | Y | Y | Y | Y | | | | Y |
| 6 | | Y | Y | Y | Y | | Y | Y | | |
| 6 | | Y | Y | Y | Y | | Y | | Y | |
| 6 | | Y | Y | Y | Y | | Y | | | Y |
| 6 | | Y | Y | Y | Y | | | Y | Y | |
| 6 | | Y | Y | Y | Y | | | Y | | Y |
| 6 | | Y | Y | Y | Y | | | | Y | Y |
| 6 | | Y | Y | Y | | Y | Y | Y | | |
| 6 | | Y | Y | Y | | Y | Y | | Y | |
| 6 | | Y | Y | Y | | Y | Y | | | Y |
| 6 | | Y | Y | Y | | Y | | Y | Y | |
| 6 | | Y | Y | Y | | Y | | Y | | Y |
| 6 | | Y | Y | Y | | Y | | | Y | Y |
| 6 | | Y | Y | Y | | | Y | Y | Y | |
| 6 | | Y | Y | Y | | | Y | Y | | Y |
| 6 | | Y | Y | Y | | | Y | | Y | Y |
| 6 | | Y | Y | Y | | | | Y | Y | Y |
| 6 | | Y | Y | | Y | Y | Y | Y | | |
| 6 | | Y | Y | | Y | Y | Y | | Y | |
| 6 | | Y | Y | | Y | Y | Y | | | Y |
| 6 | | Y | Y | | Y | Y | | Y | Y | |
| 6 | | Y | Y | | Y | Y | | Y | | Y |

TABLE 13-continued

| Num. of OTUs | OTU Clade: clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
|---|---|---|---|---|---|---|---|---|---|---|
| 6 | | Y | Y | | Y | Y | | | Y | Y |
| 6 | | Y | Y | | Y | | Y | Y | Y | |
| 6 | | Y | Y | | Y | | Y | Y | | Y |
| 6 | | Y | Y | | Y | | Y | | Y | Y |
| 6 | | Y | Y | | Y | | | Y | Y | Y |
| 6 | | Y | Y | | | Y | Y | Y | Y | |
| 6 | | Y | Y | | | Y | Y | Y | | Y |
| 6 | | Y | Y | | | Y | Y | | Y | Y |
| 6 | | Y | Y | | | Y | | Y | Y | Y |
| 6 | | Y | Y | | | | Y | Y | Y | Y |
| 6 | | Y | | Y | Y | Y | Y | Y | | |
| 6 | | Y | | Y | Y | Y | Y | | Y | |
| 6 | | Y | | Y | Y | Y | Y | | | Y |
| 6 | | Y | | Y | Y | Y | | Y | Y | |
| 6 | | Y | | Y | Y | Y | | Y | | Y |
| 6 | | Y | | Y | Y | Y | | | Y | Y |
| 6 | | Y | | Y | Y | | Y | Y | Y | |
| 6 | | Y | | Y | Y | | Y | Y | | Y |
| 6 | | Y | | Y | Y | | Y | | Y | Y |
| 6 | | Y | | Y | Y | | | Y | Y | Y |
| 6 | | Y | | Y | | Y | Y | Y | Y | |
| 6 | | Y | | Y | | Y | Y | Y | | Y |
| 6 | | Y | | Y | | Y | Y | | Y | Y |
| 6 | | Y | | Y | | Y | | Y | Y | Y |
| 6 | | Y | | Y | | | Y | Y | Y | Y |
| 6 | | Y | | | Y | Y | Y | Y | Y | |
| 6 | | Y | | | Y | Y | Y | Y | | Y |
| 6 | | Y | | | Y | Y | Y | | Y | Y |
| 6 | | Y | | | Y | Y | | Y | Y | Y |
| 6 | | Y | | | Y | | Y | Y | Y | Y |
| 6 | | Y | | | | Y | Y | Y | Y | Y |
| 6 | | | Y | Y | Y | Y | Y | Y | | |
| 6 | | | Y | Y | Y | Y | Y | | Y | |
| 6 | | | Y | Y | Y | Y | Y | | | Y |
| 6 | | | Y | Y | Y | Y | | Y | Y | |
| 6 | | | Y | Y | Y | Y | | Y | | Y |
| 6 | | | Y | Y | Y | Y | | | Y | Y |
| 6 | | | Y | Y | Y | | Y | Y | Y | |
| 6 | | | Y | Y | Y | | Y | Y | | Y |
| 6 | | | Y | Y | Y | | Y | | Y | Y |
| 6 | | | Y | Y | Y | | | Y | Y | Y |
| 6 | | | Y | Y | | Y | Y | Y | Y | |
| 6 | | | Y | Y | | Y | Y | Y | | Y |
| 6 | | | Y | Y | | Y | Y | | Y | Y |
| 6 | | | Y | Y | | Y | | Y | Y | Y |
| 6 | | | Y | Y | | | Y | Y | Y | Y |
| 6 | | | Y | | Y | Y | Y | Y | Y | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 6 | | | Y | | Y | Y | Y | Y | | Y |
| 6 | | | Y | | Y | Y | Y | | Y | Y |
| 6 | | | Y | | Y | Y | | Y | Y | Y |
| 6 | | | Y | | Y | | Y | Y | Y | Y |
| 6 | | | Y | | | Y | Y | Y | Y | Y |
| 6 | | | | Y | Y | Y | Y | Y | Y | |
| 6 | | | | Y | Y | Y | Y | Y | | Y |
| 6 | | | | Y | Y | Y | Y | | Y | Y |
| 6 | | | | Y | Y | Y | | Y | Y | Y |
| 6 | | | | Y | Y | | Y | Y | Y | Y |
| 6 | | | | Y | | Y | Y | Y | Y | Y |
| 6 | | | | | Y | Y | Y | Y | Y | Y |
| 5 | Y | Y | Y | Y | Y | | | | | |
| 5 | Y | Y | Y | Y | | Y | | | | |
| 5 | Y | Y | Y | Y | | | Y | | | |
| 5 | Y | Y | Y | Y | | | | Y | | |
| 5 | Y | Y | Y | Y | | | | | Y | |
| 5 | Y | Y | Y | Y | | | | | | Y |
| 5 | Y | Y | Y | | Y | Y | | | | |
| 5 | Y | Y | Y | | Y | | Y | | | |
| 5 | Y | Y | Y | | Y | | | Y | | |
| 5 | Y | Y | Y | | Y | | | | Y | |
| 5 | Y | Y | Y | | Y | | | | | Y |
| 5 | Y | Y | Y | | | Y | Y | | | |
| 5 | Y | Y | Y | | | Y | | Y | | |
| 5 | Y | Y | Y | | | Y | | | Y | |
| 5 | Y | Y | Y | | | Y | | | | Y |
| 5 | Y | Y | Y | | | | Y | Y | | |
| 5 | Y | Y | Y | | | | Y | | Y | |
| 5 | Y | Y | Y | | | | Y | | | Y |
| 5 | Y | Y | Y | | | | | Y | Y | |
| 5 | Y | Y | Y | | | | | Y | | Y |
| 5 | Y | Y | Y | | | | | | Y | Y |
| 5 | Y | Y | | Y | Y | Y | | | | |
| 5 | Y | Y | | Y | Y | | Y | | | |
| 5 | Y | Y | | Y | Y | | | Y | | |
| 5 | Y | Y | | Y | Y | | | | Y | |
| 5 | Y | Y | | Y | Y | | | | | Y |
| 5 | Y | Y | | Y | | Y | Y | | | |
| 5 | Y | Y | | Y | | Y | | Y | | |
| 5 | Y | Y | | Y | | Y | | | Y | |
| 5 | Y | Y | | Y | | Y | | | | Y |
| 5 | Y | Y | | Y | | | Y | Y | | |
| 5 | Y | Y | | Y | | | Y | | Y | |
| 5 | Y | Y | | Y | | | Y | | | Y |
| 5 | Y | Y | | Y | | | | Y | Y | |
| 5 | Y | Y | | Y | | | | Y | | Y |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 5 | Y | Y | | Y | | | | | Y | Y |
| 5 | Y | Y | | | Y | Y | Y | | | |
| 5 | Y | Y | | | Y | Y | | Y | | |
| 5 | Y | Y | | | Y | Y | | | Y | |
| 5 | Y | Y | | | Y | Y | | | | Y |
| 5 | Y | Y | | | Y | | Y | Y | | |
| 5 | Y | Y | | | Y | | Y | | Y | |
| 5 | Y | Y | | | Y | | Y | | | Y |
| 5 | Y | Y | | | Y | | | Y | Y | |
| 5 | Y | Y | | | Y | | | Y | | Y |
| 5 | Y | Y | | | Y | | | | Y | Y |
| 5 | Y | Y | | | | Y | Y | Y | | |
| 5 | Y | Y | | | | Y | Y | | Y | |
| 5 | Y | Y | | | | Y | Y | | | Y |
| 5 | Y | Y | | | | Y | | Y | Y | |
| 5 | Y | Y | | | | Y | | Y | | Y |
| 5 | Y | Y | | | | Y | | | Y | Y |
| 5 | Y | Y | | | | | Y | Y | Y | |
| 5 | Y | Y | | | | | Y | Y | | Y |
| 5 | Y | Y | | | | | Y | | Y | Y |
| 5 | Y | Y | | | | | | Y | Y | Y |
| 5 | Y | | Y | Y | Y | Y | | | | |
| 5 | Y | | Y | Y | Y | | Y | | | |
| 5 | Y | | Y | Y | Y | | | Y | | |
| 5 | Y | | Y | Y | Y | | | | Y | |
| 5 | Y | | Y | Y | Y | | | | | Y |
| 5 | Y | | Y | Y | | Y | Y | | | |
| 5 | Y | | Y | Y | | Y | | Y | | |
| 5 | Y | | Y | Y | | Y | | | Y | |
| 5 | Y | | Y | Y | | Y | | | | Y |
| 5 | Y | | Y | Y | | | Y | Y | | |
| 5 | Y | | Y | Y | | | Y | | Y | |
| 5 | Y | | Y | Y | | | Y | | | Y |
| 5 | Y | | Y | Y | | | | Y | Y | |
| 5 | Y | | Y | Y | | | | Y | | Y |
| 5 | Y | | Y | Y | | | | | Y | Y |
| 5 | Y | | Y | | Y | Y | Y | | | |
| 5 | Y | | Y | | Y | Y | | Y | | |
| 5 | Y | | Y | | Y | Y | | | Y | |
| 5 | Y | | Y | | Y | Y | | | | Y |
| 5 | Y | | Y | | Y | | Y | Y | | |
| 5 | Y | | Y | | Y | | Y | | Y | |
| 5 | Y | | Y | | Y | | Y | | | Y |
| 5 | Y | | Y | | Y | | | Y | Y | |
| 5 | Y | | Y | | Y | | | Y | | Y |
| 5 | Y | | Y | | Y | | | | Y | Y |
| 5 | Y | | Y | | | Y | Y | Y | | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 5 | Y | | Y | | | Y | Y | | Y | |
| 5 | Y | | Y | | | Y | Y | | | Y |
| 5 | Y | | Y | | | Y | | Y | Y | |
| 5 | Y | | Y | | | Y | | Y | | Y |
| 5 | Y | | Y | | | Y | | | Y | Y |
| 5 | Y | | Y | | | | Y | Y | Y | |
| 5 | Y | | Y | | | | Y | Y | | Y |
| 5 | Y | | Y | | | | Y | | Y | Y |
| 5 | Y | | Y | | | | | Y | Y | Y |
| 5 | Y | | | Y | Y | Y | Y | | | |
| 5 | Y | | | Y | Y | Y | | Y | | |
| 5 | Y | | | Y | Y | Y | | | Y | |
| 5 | Y | | | Y | Y | Y | | | | Y |
| 5 | Y | | | Y | Y | | Y | Y | | |
| 5 | Y | | | Y | Y | | Y | | Y | |
| 5 | Y | | | Y | Y | | Y | | | Y |
| 5 | Y | | | Y | Y | | | Y | Y | |
| 5 | Y | | | Y | Y | | | Y | | Y |
| 5 | Y | | | Y | Y | | | | Y | Y |
| 5 | Y | | | Y | | Y | Y | Y | | |
| 5 | Y | | | Y | | Y | Y | | Y | |
| 5 | Y | | | Y | | Y | Y | | | Y |
| 5 | Y | | | Y | | Y | | Y | Y | |
| 5 | Y | | | Y | | Y | | Y | | Y |
| 5 | Y | | | Y | | Y | | | Y | Y |
| 5 | Y | | | Y | | | Y | Y | Y | |
| 5 | Y | | | Y | | | Y | Y | | Y |
| 5 | Y | | | Y | | | Y | | Y | Y |
| 5 | Y | | | Y | | | | Y | Y | Y |
| 5 | Y | | | | Y | Y | Y | Y | | |
| 5 | Y | | | | Y | Y | Y | | Y | |
| 5 | Y | | | | Y | Y | Y | | | Y |
| 5 | Y | | | | Y | Y | | Y | Y | |
| 5 | Y | | | | Y | Y | | Y | | Y |
| 5 | Y | | | | Y | Y | | | Y | Y |
| 5 | Y | | | | Y | | Y | Y | Y | |
| 5 | Y | | | | Y | | Y | Y | | Y |
| 5 | Y | | | | Y | | Y | | Y | Y |
| 5 | Y | | | | Y | | | Y | Y | Y |
| 5 | Y | | | | | Y | Y | Y | Y | |
| 5 | Y | | | | | Y | Y | Y | | Y |
| 5 | Y | | | | | Y | Y | | Y | Y |
| 5 | Y | | | | | Y | | Y | Y | Y |
| 5 | Y | | | | | | Y | Y | Y | Y |
| 5 | | Y | Y | Y | Y | Y | | | | |
| 5 | | Y | Y | Y | Y | | Y | | | |
| 5 | | Y | Y | Y | Y | | | Y | | |

TABLE 13-continued

| Num. of OTUs | OTU Clade clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
|---|---|---|---|---|---|---|---|---|---|---|
| 5 | | Y | Y | Y | Y | | | | Y | |
| 5 | | Y | Y | Y | Y | | | | | Y |
| 5 | | Y | Y | Y | | Y | Y | | | |
| 5 | | Y | Y | Y | | Y | | Y | | |
| 5 | | Y | Y | Y | | Y | | | Y | |
| 5 | | Y | Y | Y | | Y | | | | Y |
| 5 | | Y | Y | Y | | | Y | Y | | |
| 5 | | Y | Y | Y | | | Y | | Y | |
| 5 | | Y | Y | Y | | | Y | | | Y |
| 5 | | Y | Y | Y | | | | Y | Y | |
| 5 | | Y | Y | Y | | | | Y | | Y |
| 5 | | Y | Y | Y | | | | | Y | Y |
| 5 | | Y | Y | | Y | Y | Y | | | |
| 5 | | Y | Y | | Y | Y | | Y | | |
| 5 | | Y | Y | | Y | Y | | | Y | |
| 5 | | Y | Y | | Y | Y | | | | Y |
| 5 | | Y | Y | | Y | | Y | Y | | |
| 5 | | Y | Y | | Y | | Y | | Y | |
| 5 | | Y | Y | | Y | | Y | | | Y |
| 5 | | Y | Y | | Y | | | Y | Y | |
| 5 | | Y | Y | | Y | | | Y | | Y |
| 5 | | Y | Y | | Y | | | | Y | Y |
| 5 | | Y | Y | | | Y | Y | Y | | |
| 5 | | Y | Y | | | Y | Y | | Y | |
| 5 | | Y | Y | | | Y | Y | | | Y |
| 5 | | Y | Y | | | Y | | Y | Y | |
| 5 | | Y | Y | | | Y | | Y | | Y |
| 5 | | Y | Y | | | Y | | | Y | Y |
| 5 | | Y | Y | | | | Y | Y | Y | |
| 5 | | Y | Y | | | | Y | Y | | Y |
| 5 | | Y | Y | | | | Y | | Y | Y |
| 5 | | Y | Y | | | | | Y | Y | Y |
| 5 | | Y | | Y | Y | Y | Y | | | |
| 5 | | Y | | Y | Y | Y | | Y | | |
| 5 | | Y | | Y | Y | Y | | | Y | |
| 5 | | Y | | Y | Y | Y | | | | Y |
| 5 | | Y | | Y | Y | | Y | Y | | |
| 5 | | Y | | Y | Y | | Y | | Y | |
| 5 | | Y | | Y | Y | | Y | | | Y |
| 5 | | Y | | Y | Y | | | Y | Y | |
| 5 | | Y | | Y | Y | | | Y | | Y |
| 5 | | Y | | Y | Y | | | | Y | Y |
| 5 | | Y | | Y | | Y | Y | Y | | |
| 5 | | Y | | Y | | Y | Y | | Y | |
| 5 | | Y | | Y | | Y | Y | | | Y |
| 5 | | Y | | Y | | Y | | Y | Y | |
| 5 | | Y | | Y | | Y | | Y | | Y |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 5 | | Y | | Y | | Y | | | Y | Y |
| 5 | | Y | | Y | | | Y | Y | Y | |
| 5 | | Y | | Y | | | Y | Y | | Y |
| 5 | | Y | | Y | | | Y | | Y | Y |
| 5 | | Y | | Y | | | | Y | Y | Y |
| 5 | | Y | | | Y | Y | Y | Y | | |
| 5 | | Y | | | Y | Y | Y | | Y | |
| 5 | | Y | | | Y | Y | Y | | | Y |
| 5 | | Y | | | Y | Y | | Y | Y | |
| 5 | | Y | | | Y | Y | | Y | | Y |
| 5 | | Y | | | Y | Y | | | Y | Y |
| 5 | | Y | | | Y | | Y | Y | Y | |
| 5 | | Y | | | Y | | Y | Y | | Y |
| 5 | | Y | | | Y | | Y | | Y | Y |
| 5 | | Y | | | Y | | | Y | Y | Y |
| 5 | | Y | | | | Y | Y | Y | Y | |
| 5 | | Y | | | | Y | Y | Y | | Y |
| 5 | | Y | | | | Y | Y | | Y | Y |
| 5 | | Y | | | | Y | | Y | Y | Y |
| 5 | | Y | | | | | Y | Y | Y | Y |
| 5 | | | Y | Y | Y | Y | Y | | | |
| 5 | | | Y | Y | Y | Y | | Y | | |
| 5 | | | Y | Y | Y | Y | | | Y | |
| 5 | | | Y | Y | Y | Y | | | | Y |
| 5 | | | Y | Y | Y | | Y | Y | | |
| 5 | | | Y | Y | Y | | Y | | Y | |
| 5 | | | Y | Y | Y | | Y | | | Y |
| 5 | | | Y | Y | Y | | | Y | Y | |
| 5 | | | Y | Y | Y | | | Y | | Y |
| 5 | | | Y | Y | Y | | | | Y | Y |
| 5 | | | Y | Y | | Y | Y | Y | | |
| 5 | | | Y | Y | | Y | Y | | Y | |
| 5 | | | Y | Y | | Y | Y | | | Y |
| 5 | | | Y | Y | | Y | | Y | Y | |
| 5 | | | Y | Y | | Y | | Y | | Y |
| 5 | | | Y | Y | | Y | | | Y | Y |
| 5 | | | Y | Y | | | Y | Y | Y | |
| 5 | | | Y | Y | | | Y | Y | | Y |
| 5 | | | Y | Y | | | Y | | Y | Y |
| 5 | | | Y | Y | | | | Y | Y | Y |
| 5 | | | Y | | Y | Y | Y | Y | | |
| 5 | | | Y | | Y | Y | Y | | Y | |
| 5 | | | Y | | Y | Y | Y | | | Y |
| 5 | | | Y | | Y | Y | | Y | Y | |
| 5 | | | Y | | Y | Y | | Y | | Y |
| 5 | | | Y | | Y | Y | | | Y | Y |
| 5 | | | Y | | Y | | Y | Y | Y | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 5 | | | Y | | Y | | Y | Y | | Y |
| 5 | | | Y | | Y | | Y | | Y | Y |
| 5 | | | Y | | Y | | | Y | Y | Y |
| 5 | | | Y | | | Y | Y | Y | Y | |
| 5 | | | Y | | | Y | Y | Y | | Y |
| 5 | | | Y | | | Y | Y | | Y | Y |
| 5 | | | Y | | | Y | | Y | Y | Y |
| 5 | | | Y | | | | Y | Y | Y | Y |
| 5 | | | | Y | Y | Y | Y | Y | | |
| 5 | | | | Y | Y | Y | Y | | Y | |
| 5 | | | | Y | Y | Y | Y | | | Y |
| 5 | | | | Y | Y | Y | | Y | Y | |
| 5 | | | | Y | Y | Y | | Y | | Y |
| 5 | | | | Y | Y | Y | | | Y | Y |
| 5 | | | | Y | Y | | Y | Y | Y | |
| 5 | | | | Y | Y | | Y | Y | | Y |
| 5 | | | | Y | Y | | Y | | Y | Y |
| 5 | | | | Y | Y | | | Y | Y | Y |
| 5 | | | | Y | | Y | Y | Y | Y | |
| 5 | | | | Y | | Y | Y | Y | | Y |
| 5 | | | | Y | | Y | Y | | Y | Y |
| 5 | | | | Y | | Y | | Y | Y | Y |
| 5 | | | | Y | | | Y | Y | Y | Y |
| 5 | | | | | Y | Y | Y | Y | Y | |
| 5 | | | | | Y | Y | Y | Y | | Y |
| 5 | | | | | Y | Y | Y | | Y | Y |
| 5 | | | | | Y | Y | | Y | Y | Y |
| 5 | | | | | Y | | Y | Y | Y | Y |
| 5 | | | | | | Y | Y | Y | Y | Y |
| 4 | Y | Y | Y | Y | | | | | | |
| 4 | Y | Y | Y | | Y | | | | | |
| 4 | Y | Y | Y | | | Y | | | | |
| 4 | Y | Y | Y | | | | Y | | | |
| 4 | Y | Y | Y | | | | | Y | | |
| 4 | Y | Y | Y | | | | | | Y | |
| 4 | Y | Y | Y | | | | | | | Y |
| 4 | Y | Y | | Y | Y | | | | | |
| 4 | Y | Y | | Y | | Y | | | | |
| 4 | Y | Y | | Y | | | Y | | | |
| 4 | Y | Y | | Y | | | | Y | | |
| 4 | Y | Y | | Y | | | | | Y | |
| 4 | Y | Y | | Y | | | | | | Y |
| 4 | Y | Y | | | Y | Y | | | | |
| 4 | Y | Y | | | Y | | Y | | | |
| 4 | Y | Y | | | Y | | | Y | | |
| 4 | Y | Y | | | Y | | | | Y | |
| 4 | Y | Y | | | Y | | | | | Y |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 4 | Y | Y | | | | Y | Y | | | |
| 4 | Y | Y | | | | Y | | Y | | |
| 4 | Y | Y | | | | Y | | | Y | |
| 4 | Y | Y | | | | Y | | | | Y |
| 4 | Y | Y | | | | | Y | Y | | |
| 4 | Y | Y | | | | | Y | | Y | |
| 4 | Y | Y | | | | | Y | | | Y |
| 4 | Y | Y | | | | | | Y | Y | |
| 4 | Y | Y | | | | | | Y | | Y |
| 4 | Y | Y | | | | | | | Y | Y |
| 4 | Y | | Y | Y | Y | | | | | |
| 4 | Y | | Y | Y | | Y | | | | |
| 4 | Y | | Y | Y | | | Y | | | |
| 4 | Y | | Y | Y | | | | Y | | |
| 4 | Y | | Y | Y | | | | | Y | |
| 4 | Y | | Y | Y | | | | | | Y |
| 4 | Y | | Y | | Y | Y | | | | |
| 4 | Y | | Y | | Y | | Y | | | |
| 4 | Y | | Y | | Y | | | Y | | |
| 4 | Y | | Y | | Y | | | | Y | |
| 4 | Y | | Y | | Y | | | | | Y |
| 4 | Y | | Y | | | Y | Y | | | |
| 4 | Y | | Y | | | Y | | Y | | |
| 4 | Y | | Y | | | Y | | | Y | |
| 4 | Y | | Y | | | Y | | | | Y |
| 4 | Y | | Y | | | | Y | Y | | |
| 4 | Y | | Y | | | | Y | | Y | |
| 4 | Y | | Y | | | | Y | | | Y |
| 4 | Y | | Y | | | | | Y | Y | |
| 4 | Y | | Y | | | | | Y | | Y |
| 4 | Y | | Y | | | | | | Y | Y |
| 4 | Y | | | Y | Y | Y | | | | |
| 4 | Y | | | Y | Y | | Y | | | |
| 4 | Y | | | Y | Y | | | Y | | |
| 4 | Y | | | Y | Y | | | | Y | |
| 4 | Y | | | Y | Y | | | | | Y |
| 4 | Y | | | Y | | Y | Y | | | |
| 4 | Y | | | Y | | Y | | Y | | |
| 4 | Y | | | Y | | Y | | | Y | |
| 4 | Y | | | Y | | Y | | | | Y |
| 4 | Y | | | Y | | | Y | Y | | |
| 4 | Y | | | Y | | | Y | | Y | |
| 4 | Y | | | Y | | | Y | | | Y |
| 4 | Y | | | Y | | | | Y | Y | |
| 4 | Y | | | Y | | | | Y | | Y |
| 4 | Y | | | Y | | | | | Y | Y |
| 4 | Y | | | | Y | Y | Y | | | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 4 | Y | | | | Y | Y | | Y | | |
| 4 | Y | | | | Y | Y | | | Y | |
| 4 | Y | | | | Y | Y | | | | Y |
| 4 | Y | | | | Y | | Y | Y | | |
| 4 | Y | | | | Y | | Y | | Y | |
| 4 | Y | | | | Y | | Y | | | Y |
| 4 | Y | | | | Y | | | Y | Y | |
| 4 | Y | | | | Y | | | Y | | Y |
| 4 | Y | | | | Y | | | | Y | Y |
| 4 | Y | | | | | Y | Y | Y | | |
| 4 | Y | | | | | Y | Y | | Y | |
| 4 | Y | | | | | Y | Y | | | Y |
| 4 | Y | | | | | Y | | Y | Y | |
| 4 | Y | | | | | Y | | Y | | Y |
| 4 | Y | | | | | Y | | | Y | Y |
| 4 | Y | | | | | | Y | Y | Y | |
| 4 | Y | | | | | | Y | Y | | Y |
| 4 | Y | | | | | | Y | | Y | Y |
| 4 | Y | | | | | | | Y | Y | Y |
| 4 | | Y | Y | Y | Y | | | | | |
| 4 | | Y | Y | Y | | Y | | | | |
| 4 | | Y | Y | Y | | | Y | | | |
| 4 | | Y | Y | Y | | | | Y | | |
| 4 | | Y | Y | Y | | | | | Y | |
| 4 | | Y | Y | Y | | | | | | Y |
| 4 | | Y | Y | | Y | Y | | | | |
| 4 | | Y | Y | | Y | | Y | | | |
| 4 | | Y | Y | | Y | | | Y | | |
| 4 | | Y | Y | | Y | | | | Y | |
| 4 | | Y | Y | | Y | | | | | Y |
| 4 | | Y | Y | | | Y | Y | | | |
| 4 | | Y | Y | | | Y | | Y | | |
| 4 | | Y | Y | | | Y | | | Y | |
| 4 | | Y | Y | | | Y | | | | Y |
| 4 | | Y | Y | | | | Y | Y | | |
| 4 | | Y | Y | | | | Y | | Y | |
| 4 | | Y | Y | | | | Y | | | Y |
| 4 | | Y | Y | | | | | Y | Y | |
| 4 | | Y | Y | | | | | Y | | Y |
| 4 | | Y | Y | | | | | | Y | Y |
| 4 | | Y | | Y | Y | Y | | | | |
| 4 | | Y | | Y | Y | | Y | | | |
| 4 | | Y | | Y | Y | | | Y | | |
| 4 | | Y | | Y | Y | | | | Y | |
| 4 | | Y | | Y | Y | | | | | Y |
| 4 | | Y | | Y | | Y | Y | | | |
| 4 | | Y | | Y | | Y | | Y | | |

TABLE 13-continued

| Num. of OTUs | OTU Clade | | | | | | | | |
|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 4 | | Y | | Y | | Y | | | Y | |
| 4 | | Y | | Y | | Y | | | | Y |
| 4 | | Y | | Y | | | Y | Y | | |
| 4 | | Y | | Y | | | Y | | Y | |
| 4 | | Y | | Y | | | Y | | | Y |
| 4 | | Y | | Y | | | | Y | Y | |
| 4 | | Y | | Y | | | | Y | | Y |
| 4 | | Y | | Y | | | | | Y | Y |
| 4 | | Y | | | Y | Y | Y | | | |
| 4 | | Y | | | Y | Y | | Y | | |
| 4 | | Y | | | Y | Y | | | Y | |
| 4 | | Y | | | Y | Y | | | | Y |
| 4 | | Y | | | Y | | Y | Y | | |
| 4 | | Y | | | Y | | Y | | Y | |
| 4 | | Y | | | Y | | Y | | | Y |
| 4 | | Y | | | Y | | | Y | Y | |
| 4 | | Y | | | Y | | | Y | | Y |
| 4 | | Y | | | Y | | | | Y | Y |
| 4 | | Y | | | | Y | Y | Y | | |
| 4 | | Y | | | | Y | Y | | Y | |
| 4 | | Y | | | | Y | Y | | | Y |
| 4 | | Y | | | | Y | | Y | Y | |
| 4 | | Y | | | | Y | | Y | | Y |
| 4 | | Y | | | | Y | | | Y | Y |
| 4 | | Y | | | | | Y | Y | Y | |
| 4 | | Y | | | | | Y | Y | | Y |
| 4 | | Y | | | | | Y | | Y | Y |
| 4 | | Y | | | | | | Y | Y | Y |
| 4 | | | Y | Y | Y | Y | | | | |
| 4 | | | Y | Y | Y | | Y | | | |
| 4 | | | Y | Y | Y | | | Y | | |
| 4 | | | Y | Y | Y | | | | Y | |
| 4 | | | Y | Y | Y | | | | | Y |
| 4 | | | Y | Y | | Y | Y | | | |
| 4 | | | Y | Y | | Y | | Y | | |
| 4 | | | Y | Y | | Y | | | Y | |
| 4 | | | Y | Y | | Y | | | | Y |
| 4 | | | Y | Y | | | Y | Y | | |
| 4 | | | Y | Y | | | Y | | Y | |
| 4 | | | Y | Y | | | Y | | | Y |
| 4 | | | Y | Y | | | | Y | Y | |
| 4 | | | Y | Y | | | | Y | | Y |
| 4 | | | Y | Y | | | | | Y | Y |
| 4 | | | Y | | Y | Y | Y | | | |
| 4 | | | Y | | Y | Y | | Y | | |
| 4 | | | Y | | Y | Y | | | Y | |
| 4 | | | Y | | Y | Y | | | | Y |

TABLE 13-continued

| | OTU Clade | | | | | | | | | |
|---|---|---|---|---|---|---|---|---|---|---|
| Num. of OTUs | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 4 | | | Y | | Y | | Y | Y | | |
| 4 | | | Y | | Y | | Y | | Y | |
| 4 | | | Y | | Y | | Y | | | Y |
| 4 | | | Y | | Y | | | Y | Y | |
| 4 | | | Y | | Y | | | Y | | Y |
| 4 | | | Y | | Y | | | | Y | Y |
| 4 | | | Y | | | Y | Y | Y | | |
| 4 | | | Y | | | Y | Y | | Y | |
| 4 | | | Y | | | Y | Y | | | Y |
| 4 | | | Y | | | Y | | Y | Y | |
| 4 | | | Y | | | Y | | Y | | Y |
| 4 | | | Y | | | Y | | | Y | Y |
| 4 | | | Y | | | | Y | Y | Y | |
| 4 | | | Y | | | | Y | Y | | Y |
| 4 | | | Y | | | | Y | | Y | Y |
| 4 | | | Y | | | | | Y | Y | Y |
| 4 | | | | Y | Y | Y | Y | | | |
| 4 | | | | Y | Y | Y | | Y | | |
| 4 | | | | Y | Y | Y | | | Y | |
| 4 | | | | Y | Y | Y | | | | Y |
| 4 | | | | Y | Y | | Y | Y | | |
| 4 | | | | Y | Y | | Y | | Y | |
| 4 | | | | Y | Y | | Y | | | Y |
| 4 | | | | Y | Y | | | Y | Y | |
| 4 | | | | Y | Y | | | Y | | Y |
| 4 | | | | Y | Y | | | | Y | Y |
| 4 | | | | Y | | Y | Y | Y | | |
| 4 | | | | Y | | Y | Y | | Y | |
| 4 | | | | Y | | Y | Y | | | Y |
| 4 | | | | Y | | Y | | Y | Y | |
| 4 | | | | Y | | Y | | Y | | Y |
| 4 | | | | Y | | Y | | | Y | Y |
| 4 | | | | Y | | | Y | Y | Y | |
| 4 | | | | Y | | | Y | Y | | Y |
| 4 | | | | Y | | | Y | | Y | Y |
| 4 | | | | Y | | | | Y | Y | Y |
| 4 | | | | | Y | Y | Y | Y | | |
| 4 | | | | | Y | Y | Y | | Y | |
| 4 | | | | | Y | Y | Y | | | Y |
| 4 | | | | | Y | Y | | Y | Y | |
| 4 | | | | | Y | Y | | Y | | Y |
| 4 | | | | | Y | Y | | | Y | Y |
| 4 | | | | | Y | | Y | Y | Y | |
| 4 | | | | | Y | | Y | Y | | Y |
| 4 | | | | | Y | | Y | | Y | Y |
| 4 | | | | | Y | | | Y | Y | Y |
| 4 | | | | | | Y | Y | Y | Y | |

TABLE 13-continued

| Num. of OTUs | OTU Clade | | | | | | | | | |
|---|---|---|---|---|---|---|---|---|---|---|
| | clade_309 *Blautia luti* | clade_309 *Blautia schinkii* | clade_309 *Blautia* sp. M25 | clade_408 *Clostridium citroniae* | clade_537 *Clostridium leptum* | clade_444 *Eubacterium rectale* | clade_478 *Faecalibacterium prausnitzii* | clade_360 Lachnospiraceae *bacterium* 2_1_58FAA | clade_537 *Ruminococcus bromii* | clade_478 *Subdoligranulum variabile* |
| 4 | | | | | | Y | Y | Y | | Y |
| 4 | | | | | | Y | Y | | Y | Y |
| 4 | | | | | | Y | | Y | Y | Y |
| 4 | | | | | | | Y | Y | Y | Y |

TABLE 14

Post-Treatment Ecologies

| OTU 1 | OTU 2 | OTU 3 | Percent of doses in which the ternary is present | Percent of post-treatment patients in which the ternary is present |
|---|---|---|---|---|
| *Blautia* sp. M25 | *Faecalibacterium prausnitzii* | *Ruminococcus bromii* | 100 | 75 |
| *Blautia* sp. M25 | *Faecalibacterium prausnitzii* | *Ruminococcus obeum* | 100 | 89 |
| *Blautia* sp. M25 | *Faecalibacterium prausnitzii* | *Ruminococcus* sp. 5_1_39BFAA | 100 | 89 |
| *Blautia* sp. M25 | *Faecalibacterium prausnitzii* | *Ruminococcus torques* | 100 | 93 |
| *Blautia* sp. M25 | *Ruminococcus bromii* | *Ruminococcus obeum* | 100 | 71 |
| *Blautia* sp. M25 | *Ruminococcus bromii* | *Ruminococcus* sp. 5_1_39BFAA | 100 | 71 |
| *Blautia* sp. M25 | *Ruminococcus bromii* | *Ruminococcus torques* | 100 | 75 |
| *Blautia* sp. M25 | *Ruminococcus obeum* | *Ruminococcus* sp. 5_1_39BFAA | 100 | 86 |
| *Blautia* sp. M25 | *Ruminococcus obeum* | *Ruminococcus torques* | 100 | 89 |
| *Blautia* sp. M25 | *Ruminococcus* sp. 5_1_39BFAA | *Ruminococcus torques* | 100 | 89 |
| *Clostridium hathewayi* | *Clostridium orbiscindens* | *Escherichia coli* | 0 | 100 |
| *Clostridium hathewayi* | *Clostridium orbiscindens* | Lachnospiraceae bacterium 3_1_57FAA_CT1 | 0 | 100 |
| *Clostridium hathewayi* | *Clostridium orbiscindens* | *Ruminococcus torques* | 0 | 100 |
| *Clostridium hathewayi* | *Escherichia coli* | Lachnospiraceae bacterium 3_1_57FAA_CT1 | 0 | 100 |
| *Clostridium hathewayi* | *Escherichia coli* | *Ruminococcus torques* | 0 | 100 |
| *Clostridium orbiscindens* | *Escherichia coli* | Lachnospiraceae bacterium 3_1_57FAA_CT1 | 0 | 100 |
| *Clostridium orbiscindeas* | *Escherichia coli* | *Ruminococcus torques* | 0 | 100 |
| *Clostridium orbiscindens* | *Ruminococcus torques* | *Streptococcus salivarius* | 0 | 100 |
| *Faecalibacterium prausnitzii* | *Ruminococcus bromii* | *Ruminococcus obeum* | 100 | 75 |
| *Faecalibacterium prausnitzii* | *Ruminococcus bromii* | *Ruminococcus* sp. 5_1_39BFAA | 100 | 71 |
| *Faecalibacterium prausnitzii* | *Ruminococcus bromii* | *Ruminococcus torques* | 100 | 75 |
| *Faecalibacterium prausnitzii* | *Ruminococcus obeum* | *Ruminococcus* sp. 5_1_39BFAA | 100 | 86 |
| *Faecalibacterium prausnitzii* | *Ruminococcus obeum* | *Ruminococcus torques* | 100 | 93 |
| *Faecalibacterium prausnitzii* | *Ruminococcus* sp. 5_1_39BFAA | *Ruminococcus torques* | 100 | 89 |
| *Ruminococcus bromii* | *Ruminococcus obeum* | *Ruminococcus* sp. 5_1_9BFAA | 100 | 68 |
| *Ruminococcus bromii* | *Ruminococcus obeum* | *Ruminococcus torques* | 100 | 79 |
| *Ruminococcus bromii* | *Ruminococcus* sp. 5_1_39BFAA | *Ruminococcus torques* | 100 | 71 |
| *Ruminococcus obeum* | *Ruminococcus* sp. 5_1_39BFAA | *Ruminococcus torques* | 100 | 89 |

TABLE 15

Engrafting OTUs

| OTU 1 | OTU 2 | OTU 3 |
|---|---|---|
| *Blautia* sp. M25 | *Clostridiales* sp. SSC/2 | *Coprococcus catus* |
| *Blautia* sp. M25 | *Clostridiales* sp. SSC/2 | *Faecalibacterium prausnitzii* |
| *Blautia* sp. M25 | *Clostridiales* sp. SSC/2 | *Ruminococcus bromii* |
| *Blautia* sp. M25 | *Clostridiales* sp. SSC/2 | *Ruminococcus obeum* |
| *Blautia* sp. M25 | *Clostridiales* sp. SSC/2 | *Ruminococcus* sp. 5_1_39BFAA |
| *Blautia* sp. M25 | *Clostridiales* sp. SSC/2 | *Ruminococcus torques* |
| *Blautia* sp. M25 | *Coproeoceus catus* | *Faecalibacterium prausnitzii* |
| *Blautia* sp. M25 | *Coprococcus catus* | *Ruminococcus bromii* |
| *Blautia* sp. M25 | *Coproeoceus catus* | *Ruminococcus obeum* |
| *Blautia* sp. M25 | *Coprococcus catus* | *Ruminococcus* sp. 5_1_39BFAA |

TABLE 15-continued

| Engrafting OTUs | | |
|---|---|---|
| OTU 1 | OTU 2 | OTU 3 |
| *Blautia* sp. M25 | *Coprococcus catus* | *Ruminococcus torques* |
| *Blautia* sp. M25 | *Eubacterium hallii* | *Faecalibacterium prausnitzii* |
| *Blautia* sp. M25 | *Eubacterium hallii* | *Ruminococcus bromii* |
| *Blautia* sp. M25 | *Eubacterium hallii* | *Ruminococcus obeum* |
| *Blautia* sp. M25 | *Eubacterium hallii* | *Ruminococcus* sp. 5_1_39BFAA |
| *Blautia* sp. M25 | *Eubacterium hallii* | *Ruminococcus torques* |
| *Blautia* sp. M25 | *Faecalibacterium prausnitzii* | *Gemmiger formicilis* |
| *Blautia* sp. M25 | *Gemmiger formicilis* | *Ruminococcus bromii* |
| *Blautia* sp. M25 | *Gemmiger formicilis* | *Ruminococcus obeum* |
| *Blautia* sp. M25 | *Gemmiger formicilis* | *Ruminococcus* sp. 5_1_39BFAA |
| *Blautia* sp. M25 | *Gemmiger formicilis* | *Ruminococcus torques* |
| *Clostridiales* sp. SSC/2 | *Coprococcus catus* | *Faecalibacterium prausnitzii* |
| *Clostridiales* sp. SSC/2 | *Coprococcus catus* | *Ruminococcus bromii* |
| *Clostridiales* sp. SSC/2 | *Coprococcus catus* | *Ruminococcus obeum* |
| *Clostridiales* sp. SSC/2 | *Coprococcus catus* | *Ruminococcus* sp. 5_1_39BFAA |
| *Clostridiales* sp. SSC/2 | *Coprococcus catus* | *Ruminococcus torques* |
| *Clostridiales* sp. SSC/2 | *Faecalibacterium prausnitzii* | *Ruminococcus bromii* |
| *Clostridiales* sp. SSC/2 | *Faecalibacterium prausnitzii* | *Ruminococcus obeum* |
| *Clostridiales* sp. SSC/2 | *Faecalibacterium prausnitzii* | *Ruminococcus* sp. 5_1_39BFAA |
| *Clostridiales* sp. SSC/2 | *Faecalibacterium prausnitzii* | *Ruminococcus torques* |
| *Clostridiales* sp. SSC/2 | *Ruminococcus bromii* | *Ruminococcus obeum* |
| *Clostridiales* sp. SSC/2 | *Ruminococcus bromii* | *Ruminococcus* sp. 5_1_39BFAA |
| *Clostridiales* sp. SSC/2 | *Ruminococcus bromii* | *Ruminococcus torques* |
| *Clostridiales* sp. SSC/2 | *Ruminococcus obeum* | *Ruminococcus* sp. 5_1_39BFAA |
| *Clostridiales* sp. SSC/2 | *Ruminococcus obeum* | *Ruminococcus torques* |
| *Clostridiales* sp. SSC/2 | *Ruminococcus* sp. 5_1_39BFAA | *Ruminococcus torques* |
| *Coprococcus catus* | *Faecalibacterium prausnitzii* | *Ruminococcus bromii* |
| *Coprococcus catus* | *Faecalibacterium prausnitzii* | *Ruminococcus obeum* |
| *Coprococcus catus* | *Faecalibacterium prausnitzii* | *Ruminococcus* sp. 5_1_39BFAA |
| *Coprococcus catus* | *Faecalibacterium prausnitzii* | *Ruminococcus torques* |
| *Coprococcus catus* | *Ruminococcus bromii* | *Ruminococcus obeum* |
| *Coprococcus catus* | *Ruminococcus bromii* | *Ruminococcus* sp. 5_1_39BFAA |
| *Coprococcus catus* | *Ruminococcus bromii* | *Ruminococcus torques* |
| *Coprococcus catus* | *Ruminococcus obeum* | *Ruminococcus* sp. 5_1_39BFAA |
| *Coprococcus catus* | *Ruminococcus obeum* | *Ruminococcus torques* |
| *Coprococcus catus* | *Ruminococcus* sp. 5_1_39BFAA | *Ruminococcus torques* |
| *Eubacterium hallii* | *Faecalibacterium prausnitzii* | *Ruminococcus bromii* |
| *Eubacterium hallii* | *Faecalibacterium prausnitzii* | *Ruminococcus obeum* |
| *Eubacterium hallii* | *Faecalibacterium prausnitzii* | *Ruminococcus* sp. 5_1_39BFAA |
| *Eubacterium hallii* | *Faecalibacterium prausnitzii* | *Ruminococcus torques* |
| *Eubacterium hallii* | *Ruminococcus bromii* | *Ruminococcus obeum* |
| *Eubacterium hallii* | *Ruminococcus bromii* | *Ruminococcus* sp. 5_1_39BFAA |
| *Eubacterium hallii* | *Ruminococcus bromii* | *Ruminococcus torques* |
| *Eubacterium hallii* | *Ruminococcus obeum* | *Ruminococcus* sp. 5_1_39BFAA |
| *Eubacterium hallii* | *Ruminococcus obeum* | *Ruminococcus torques* |
| *Eubacterium hallii* | *Ruminococcus* sp. 5_1_39BFAA | *Ruminococcus torques* |
| *Faecalibacterium prausnitzii* | *Gemmiger formicilis* | *Ruminococcus bromii* |
| *Faecalibacterium prausnitzii* | *Gemmiger formicilis* | *Ruminococcus obeum* |
| *Faecalibacterium prausnitzii* | *Gemmiger formicilis* | *Ruminococcus* sp. 5_1_39BFAA |
| *Faecalibacterium prausnitzii* | *Gemmiger formicilis* | *Ruminococcus torques* |
| *Gemmiger formicilis* | *Ruminococcus bromii* | *Ruminococcus obeum* |
| *Gemmiger formicilis* | *Ruminococcus bromii* | *Ruminococcus* sp. 5_1_39BFAA |
| *Gemmiger formicilis* | *Ruminococcus bromii* | *Ruminococcus torques* |
| *Gemmiger formicilis* | *Ruminococcus obeum* | *Ruminococcus* sp. 5_1_39BFAA |
| *Gemmiger formicilis* | *Ruminococcus obeum* | *Ruminococcus torques* |

TABLE 15-continued

| Engrafting OTUs | | |
|---|---|---|
| OTU 1 | OTU 2 | OTU 3 |
| *Gemmiger formicilis* | *Ruminococcus* sp. 5_1_39BFAA | *Ruminococcus torques* |

TABLE 16

| Augmenting OTUs | | | |
|---|---|---|---|
| OTU 1 | OTU 2 | OTU 3 | Percent of post-treatment patients in which the ternary is present |
| *Anaerotruncus colihominis* | *Clostridium orbiscindens* | *Escherichia coli* | 75 |
| *Clostridium lactatifermentans* | *Clostridium orbiscindens* | *Escherichia coli* | 79 |
| *Clostridium lactatifermentans* | *Clostridium orbiscindens* | *Streptococcus salivarius* | 79 |
| *Clostridium lactatifermentans* | *Escherichia coli* | *Streptococcus salivarius* | 75 |
| *Clostridium orbiscindens* | *Clostridium* sp. NML 04A032 | *Escherichia coli* | 89 |
| *Clostridium orbiscindens* | *Clostridium* sp. NML 04A032 | *Oscillibacter* sp. G2 | 89 |
| *Clostridium orbiscindens* | *Clostridium* sp. NML 04A032 | *Streptococcus salivarius* | 93 |

TABLE 16-continued

| Augmenting OTUs | | | |
|---|---|---|---|
| OTU 1 | OTU 2 | OTU 3 | Percent of post-treatment patients in which the ternary is present |
| *Clostridium orbiscindens* | *Escherichia coli* | *Klebsiella* sp. SRC_DSD2 | 75 |
| *Clostridium orbiscindens* | *Escherichia coli* | *Oscillibacter* sp. G2 | 89 |
| *Clostridium orbiscindens* | *Escherichia coli* | *Streptococcus salivarius* | 96 |
| *Clostridium orbiscindens* | *Oscillibacter* sp. G2 | *Streptococcus salivarius* | 89 |
| *Clostridium* sp. NML 04A032 | *Escherichia coli* | *Oscillibacter* sp. G2 | 82 |
| *Clostridium* sp. NML 04A032 | *Escherichia coli* | *Streptococcus salivarius* | 86 |
| *Clostridium* sp. NML 04A032 | *Oscillibacter* sp. G2 | *Streptococcus salivarius* | 86 |
| *Escherichia coli* | *Oscillibacter* sp. G2 | *Streptococcus salivarius* | 82 |

TABLE 17

| Ternary OTU combinations in administered spore ecology doses resulting in augmentation or engraftment of the OTU *Clostridiales* sp. SM4/1 | | | |
|---|---|---|---|
| OTU 1 | OTU 2 | OTU 3 | Percent of doses in which the ternary is present |
| *Clostridium saccharogumia* | *Eubacterium rectale* | *Faecalibacterium prausnitzii* | 85 |
| *Clostridium saccharogumia* | *Eubacterium rectale* | *Ruminococcus torques* | 85 |
| *Clostridium saccharogumia* | *Faecalibacterium prausnitzii* | *Ruminococcus torques* | 85 |
| *Blautia* sp. M25 | *Clostridium saccharogumia* | *Eubacterium rectale* | 85 |
| *Blautia* sp. M25 | *Clostridium saccharogumia* | *Faecalibacterium prausnitzii* | 85 |
| *Blautia* sp. M25 | *Clostridium saccharogumia* | *Ruminococcus torques* | 85 |
| *Clostridium saccharogumia* | *Eubacterium rectale* | *Ruminococcus obeum* | 85 |
| *Clostridium saccharogumia* | *Eubacterium rectale* | *Ruminococcus* sp. 5_1_39BFAA | 85 |
| *Clostridium saccharogumia* | *Faecalibacterium prausnitzii* | *Ruminococcus obeum* | 85 |
| *Clostridium saccharogumia* | *Faecalibacterium prausnitzii* | *Ruminococcus* sp. 5_1_39BFAA | 85 |
| *Clostridium saccharogumia* | *Ruminococcus obeum* | *Ruminococcus torques* | 85 |
| *Clostridium saccharogumia* | *Ruminococcus* sp. 5_1_39BFAA | *Ruminococcus torques* | 85 |
| *Blautia* sp. M25 | *Clostridium saccharogumia* | *Ruminococcus* sp. 5_1_39BFAA | 85 |
| *Blautia* sp. M25 | *Clostridium saccharogumia* | *Ruminococcus obeum* | 85 |
| *Clostridium saccharogumia* | *Ruminococcus obeum* | *Ruminococcus* sp. 5_1_39BFAA | 85 |

TABLE 17-continued

Ternary OTU combinations in administered spore ecology doses resulting in augmentation or engraftment of the OTU *Clostridiales* sp. SM4/1

| OTU 1 | OTU 2 | OTU 3 | Percent of doses in which the ternary is present |
|---|---|---|---|
| *Clostridium saccharogumia* | *Faecalibacterium prausnitzii* | *Ruminococcus bromii* | 85 |
| *Blautia* sp. M25 | *Clostridium saccharogumia* | *Ruminococcus bromii* | 85 |
| *Clostridium saccharogumia* | *Eubacterium rectale* | *Ruminococcus bromii* | 85 |
| *Clostridium saccharogumia* | *Ruminococcus bromii* | *Ruminococcus obeum* | 85 |
| *Clostridium saccharogumia* | *Ruminococcus bromii* | *Ruminococcus* sp. 5_1_39BFAA | 85 |
| *Clostridium saccharogumia* | *Ruminococcus bromii* | *Ruminococcus torques* | 85 |
| *Clostridiales* sp. SSC/2 | *Clostridium saccharogumia* | *Eubacterium rectale* | 80 |
| *Clostridiales* sp. SSC/2 | *Clostridium saccharogumia* | *Faecalibacterium prausnitzii* | 80 |
| *Clostridiales* sp. SSC/2 | *Clostridium saccharogumia* | *Ruminococcus torques* | 80 |
| *Blautia* sp. M25 | *Clostridiales* sp. *SSC/2* | *Clostridium saccharogumia* | 80 |
| *Blautia* sp. M25 | *Clostridium saccharogumia* | *Ruminococcus lactaris* | 80 |
| *Clostridiales* sp. *SSC/2* | *Clostridium saccharogumia* | *Ruminococcus obeum* | 80 |
| *Clostridiales* sp. SSC/2 | *Clostridium saccharogumia* | *Ruminococcus* sp. 5_1_39BFAA | 80 |
| *Clostridium lavalense* | *Clostridium saccharogumia* | *Eubacterium rectale* | 80 |
| *Clostridium lavalense* | *Clostridium saccharogumia* | *Faecalibacterium prausnitzii* | 80 |
| *Clostridium lavalense* | *Clostridium saccharogumia* | *Ruminococcus torques* | 80 |
| *Clostridium saccharogumia* | *Eubacterium rectale* | *Ruminococcus lactaris* | 80 |
| *Clostridium saccharogumia* | *Ruminococcus lactaris* | *Ruminococcus* sp. 5_1_39BFAA | 80 |
| *Clostridium saccharogumia* | *Ruminococcus lactaris* | *Ruminococcus torques* | 80 |
| *Blautia* sp. M25 | *Clostridium lavalense* | *Clostridium saccharogumia* | 80 |
| *Clostridium asparagiforme* | *Clostridium saccharogumia* | *Eubacterium rectale* | 80 |
| *Clostridium asparagiforme* | *Clostridium saccharogumia* | *Faecalibacterium prausnitzii* | 80 |
| *Clostridium asparagiforme* | *Clostridium saccharogumia* | *Ruminococcus torques* | 80 |
| *Clostridium lavalense* | *Clostridium saccharogumia* | *Ruminococcus obeum* | 80 |
| *Clostridium lavalense* | *Clostridium saccharogumia* | *Ruminococcus* sp. 5_1_39BFAA | 80 |
| *Clostridium saccharogumia* | *Eubacterium rectale* | *Gemmiger formicilis* | 80 |
| *Clostridium saccharogumia* | *Faecalibacterium prausnitzii* | *Ruminococcus lactaris* | 80 |
| *Clostridium saccharogumia* | *Gemmiger formicilis* | *Ruminococcus torques* | 80 |
| *Clostridium saccharogumia* | *Ruminococcus lactaris* | *Ruminococcus obeum* | 80 |
| *Clostridium saccharogumia* | *Faecalibacterium prausnitzii* | *Gemmiger formicilis* | 80 |
| *Blautia* sp. M25 | *Clostridium asparagiforme* | *Clostridium saccharogumia* | 80 |
| *Blautia* sp. M25 | *Clostridium saccharogumia* | *Gemmiger formicilis* | 80 |
| *Clostridium asparagiforme* | *Clostridium saccharogumia* | *Ruminococcus obeum* | 80 |
| *Clostridium asparagiforme* | *Clostridium saccharogumia* | *Ruminococcus* sp. 5_1_39BFAA | 80 |
| *Clostridium saccharogumia* | *Coprococcus comes* | *Eubacterium rectale* | 80 |

TABLE 17-continued

Ternary OTU combinations in administered spore ecology doses resulting in augmentation or engraftment of the OTU *Clostridiales* sp. SM4/1

| OTU 1 | OTU 2 | OTU 3 | Percent of doses in which the ternary is present |
|---|---|---|---|
| *Clostridium saccharogumia* | *Coprococcus comes* | *Faecalibacterium prausnitzii* | 80 |
| *Clostridium saccharogumia* | *Coprococcus comes* | *Ruminococcus obeum* | 80 |
| *Clostridium saccharogumia* | *Coprococcus comes* | *Ruminococcus torques* | 80 |
| *Clostridium saccharogumia* | *Dorea formicigenerans* | *Eubacterium rectale* | 80 |
| *Clostridium saccharogumia* | *Dorea formicigenerans* | *Faecalibacterium prausnitzii* | 80 |
| *Clostridium saccharogumia* | *Dorea formicigenerans* | *Ruminococcus obeum* | 80 |
| *Clostridium saccharogumia* | *Dorea formicigenerans* | *Ruminococcus torques* | 80 |
| *Clostridium saccharogumia* | *Gemmiger formicilis* | *Ruminococcus obeum* | 80 |
| *Clostridium saccharogumia* | *Gemmiger formicilis* | *Ruminococcus* sp. 5_1_39BFAA | 80 |
| *Clostridium asparagiforme* | *Clostridium lavalense* | *Clostridium saccharogumia* | 80 |
| *Blautia* sp. M25 | *Clostridium saccharogumia* | *Coprococcus comes* | 80 |
| *Blautia* sp. M25 | *Clostridium saccharogumia* | *Dorea formicigenerans* | 80 |
| *Blautia* sp. M25 | *Clostridium saccharogumia* | *Eubacterium hallii* | 80 |
| *Clostridiales* sp. SSC/2 | *Clostridium saccharogumia* | *Ruminococcus bromii* | 80 |
| *Clostridium asparagiforme* | *Clostridium saccharogumia* | *Ruminococcus bromii* | 80 |
| *Clostridium asparagiforme* | *Clostridium saccharogumia* | *Ruminococcus lactaris* | 80 |
| *Clostridium lavalense* | *Clostridium saccharogumia* | *Dorea formicigenerans* | 80 |
| *Clostridium lavalense* | *Clostridium saccharogumia* | *Ruminococcus bromii* | 80 |
| *Clostridium lavalense* | *Clostridium saccharogumia* | *Ruminococcus lactaris* | 80 |
| *Clostridium saccharogumia* | *Coprococcus comes* | *Ruminococcus* sp. 5_1_39BFAA | 80 |
| *Clostridium saccharogumia* | *Dorea formicigenerans* | *Ruminococcus lactaris* | 80 |
| *Clostridium saccharogumia* | *Dorea formicigenerans* | *Ruminococcus* sp. 5_1_39BFAA | 80 |
| *Clostridium saccharogumia* | *Eubacterium hallii* | *Eubacterium rectale* | 80 |
| *Clostridium saccharogumia* | *Eubacterium hallii* | *Faecalibacterium prausnitzii* | 80 |
| *Clostridium saccharogumia* | *Eubacterium hallii* | *Ruminococcus lactaris* | 80 |
| *Clostridium saccharogumia* | *Eubacterium hallii* | *Ruminococcus obeum* | 80 |
| *Clostridium saccharogumia* | *Eubacterium hallii* | *Ruminococcus* sp. 5_1_39BFAA | 80 |
| *Clostridium saccharogumia* | *Eubacterium hallii* | *Ruminococcus torques* | 80 |
| *Clostridium saccharogumia* | *Ruminococcus bromii* | *Ruminococcus lactaris* | 80 |
| *Clostridium asparagiforme* | *Clostridium saccharogumia* | *Coprococcus comes* | 80 |
| *Clostridium asparagiforme* | *Clostridium saccharogumia* | *Eubacterium hallii* | 80 |
| *Clostridium lavalense* | *Clostridium saccharogumia* | *Coprococcus comes* | 80 |
| *Clostridium saccharogumia* | *Coprococcus comes* | *Ruminococcus bromii* | 80 |
| *Clostridium saccharogumia* | *Coprococcus comes* | *Ruminococcus lactaris* | 80 |
| *Clostridium saccharogumia* | *Gemmiger formicilis* | *Ruminococcus bromii* | 80 |

TABLE 17-continued

Ternary OTU combinations in administered spore ecology doses resulting in augmentation or engraftment of the OTU *Clostridiales* sp. SM4/1

| OTU 1 | OTU 2 | OTU 3 | Percent of doses in which the ternary is present |
|---|---|---|---|
| *Blautia* sp. M25 | *Clostridium saccharogumia* | *Coprococcus catus* | 80 |
| *Blautia* sp. M25 | *Clostridium saccharogumia* | *Dorea longicatena* | 80 |
| *Clostridium asparagiforme* | *Clostridium saccharogumia* | *Dorea formicigenerans* | 80 |
| *Clostridium asparagiforme* | *Clostridium saccharogumia* | *Dorea longicatena* | 80 |
| *Clostridium lavalense* | *Clostridium saccharogumia* | *Dorea longicatena* | 80 |
| *Clostridium lavalense* | *Clostridium saccharogumia* | *Eubacterium hallii* | 80 |
| *Clostridium saccharogumia* | *Coprococcus catus* | *Eubacterium rectale* | 80 |
| *Clostridium saccharogumia* | *Coprococcus catus* | *Faecalibacterium prausnitzii* | 80 |
| *Clostridium saccharogumia* | *Coprococcus catus* | *Ruminococcus* sp. 5_1_39BFAA | 80 |
| *Clostridium saccharogumia* | *Coprococcus catus* | *Ruminococcus torques* | 80 |
| *Clostridium saccharogumia* | *Coprococcus comes* | *Dorea formicigenerans* | 80 |
| *Clostridium saccharogumia* | *Coprococcus comes* | *Eubacterium hallii* | 80 |
| *Clostridium saccharogumia* | *Dorea formicigenerans* | *Eubacterium hallii* | 80 |
| *Clostridium saccharogumia* | *Dorea formicigenerans* | *Ruminococcus bromii* | 80 |
| *Clostridium saccharogumia* | *Dorea longicatena* | *Eubacterium rectale* | 80 |
| *Clostridium saccharogumia* | *Dorea longicatena* | *Faecalibacterium prausnitzii* | 80 |
| *Clostridium saccharogumia* | *Dorea longicatena* | *Ruminococcus obeum* | 80 |
| *Clostridium saccharogumia* | *Dorea longicatena* | *Ruminococcus* sp. 5_1_39BFAA | 80 |
| *Clostridium saccharogumia* | *Dorea longicatena* | *Ruminococcus torques* | 80 |
| *Clostridium saccharogumia* | *Eubacterium hallii* | *Ruminococcus bromii* | 80 |
| *Clostridiales* sp. SSC/2 | *Clostridium saccharogumia* | *Coprococcus catus* | 80 |
| *Clostridium saccharogumia* | *Coprococcus catus* | *Ruminococcus obeum* | 80 |
| *Clostridium saccharogumia* | *Dorea longicatena* | *Eubacterium hallii* | 80 |
| *Clostridium saccharogumia* | *Dorea longicatena* | *Ruminococcus bromii* | 80 |
| *Clostridium saccharogumia* | *Dorea longicatena* | *Ruminococcus lactaris* | 80 |
| *Clostridium saccharogumia* | *Dorea formicigenerans* | *Dorea longicatena* | 80 |
| *Clostridium saccharogumia* | *Coprococcus catus* | *Ruminococcus bromii* | 80 |
| *Clostridium saccharogumia* | *Coprococcus comes* | *Dorea longicatena* | 80 |
| *Blautia* sp. M25 | *Clostridium algidixylanolyticum* | *Faecalibacterium prausnitzii* | 75 |
| *Clostridium algidixylanolyticum* | *Faecalibacterium prausnitzii* | *Ruminococcus obeum* | 75 |
| *Clostridium algidixylanolyticum* | *Faecalibacterium prausnitzii* | *Ruminococcus torques* | 75 |
| *Blautia* sp. M25 | *Clostridium algidixylanolyticum* | *Ruminococcus obeum* | 75 |
| *Blautia* sp. M25 | *Clostridium algidixylanolyticum* | *Ruminococcus torques* | 75 |
| *Clostridium algidixylanolyticum* | *Faecalibacterium prausnitzii* | *Ruminococcus* sp. 5_1_39BFAA | 75 |
| *Clostridium algidixylanolyticum* | *Ruminococcus obeum* | *Ruminococcus torques* | 75 |

TABLE 17-continued

Ternary OTU combinations in administered spore ecology doses resulting in augmentation or engraftment of the OTU *Clostridiales* sp. SM4/1

| OTU 1 | OTU 2 | OTU 3 | Percent of doses in which the ternary is present |
|---|---|---|---|
| *Blautia* sp. M25 | *Clostridium algidixylanolyticum* | *Ruminococcus* sp. 5_1_39BFAA | 75 |
| *Clostridium algidixylanolyticum* | *Ruminococcus* sp. 5_1_39BFAA | *Ruminococcus torques* | 75 |
| *Clostridium algidixylanolyticum* | *Ruminococcus obeum* | *Ruminococcus* sp. 5_1_39BFAA | 75 |
| *Clostridiales* sp. SSC/2 | *Clostridium algidixylanolyticum* | *Ruminococcus torques* | 75 |
| *Clostridiales* sp. SSC/2 | *Clostridium algidixylanolyticum* | *Faecalibacterium prausnitzii* | 75 |
| *Clostridiales* sp. SSC/2 | *Clostridium algidixylanolyticum* | *Ruminococcus obeum* | 75 |
| *Clostridiales* sp. SSC/2 | *Clostridium algidixylanolyticum* | *Ruminococcus* sp. 5_1_39BFAA | 75 |
| *Clostridium algidixylanolyticum* | *Ruminococcus bromii* | *Ruminococcus torques* | 75 |
| *Blautia* sp. M25 | *Clostridiales* sp. SSC/2 | *Clostridium algidixylanolyticum* | 75 |
| *Blautia* sp. M25 | *Clostridium algidixylanolyticum* | *Ruminococcus bromii* | 75 |
| *Clostridium algidixylanolyticum* | *Faecalibacterium prausnitzii* | *Ruminococcus bromii* | 75 |
| *Clostridium algidixylanolyticum* | *Ruminococcus bromii* | *Ruminococcus obeum* | 75 |
| *Clostridium algidixylanolyticum* | *Ruminococcus bromii* | *Ruminococcus* sp. 5_1_39BFAA | 75 |
| *Clostridiales* sp. SSC/2 | *Clostridium algidixylanolyticum* | *Ruminococcus bromii* | 75 |
| *Clostridium algidixylanolyticum* | *Coprococcus catus* | *Faecalibacterium prausnitzii* | 75 |
| *Clostridium algidixylanolyticum* | *Coprococcus catus* | *Ruminococcus* sp. 5_1_39BFAA | 75 |
| *Blautia* sp. M25 | *Clostridium algidixylanolyticum* | *Coprococcus catus* | 75 |
| *Clostridium algidixylanolyticum* | *Coprococcus catus* | *Ruminococcus obeum* | 75 |
| *Clostridium algidixylanolyticum* | *Coprococcus catus* | *Ruminococcus torques* | 75 |
| *Clostridiales* sp. SSC/2 | *Clostridium saccharogumia* | *Ruminococcus lactaris* | 75 |
| *Clostridiales* sp. SSC/2 | *Clostridium algidixylanolyticum* | *Coprococcus catus* | 75 |
| *Clostridiales* sp. SSC/2 | *Clostridium saccharogumia* | *Gemmiger formicilis* | 75 |
| *Clostridiales* sp. SSC/2 | *Clostridium lavalense* | *Clostridium saccharogumia* | 75 |
| *Clostridiales* sp. SSC/2 | *Clostridium saccharogumia* | *Dorea formicigenerans* | 75 |
| *Clostridium algidixylanolyticum* | *Coprococcus catus* | *Ruminococcus bromii* | 75 |
| *Clostridium lavalense* | *Clostridium saccharogumia* | *Gemmiger formicilis* | 75 |
| *Clostridium saccharogumia* | *Gemmiger formicilis* | *Ruminococcus lactaris* | 75 |
| *Clostridiales* sp. SSC/2 | *Clostridium asparagiforme* | *Clostridium saccharogumia* | 75 |
| *Clostridiales* sp. SSC/2 | *Clostridium saccharogumia* | *Coprococcus comes* | 75 |
| *Clostridiales* sp. SSC/2 | *Clostridium saccharogumia* | *Eubacterium hallii* | 75 |
| *Clostridium saccharogumia* | *Dorea formicigenerans* | *Gemmiger formicilis* | 75 |
| *Clostridium asparagiforme* | *Clostridium saccharogumia* | *Gemmiger formicilis* | 75 |
| *Clostridium saccharogumia* | *Coprococcus comes* | *Gemmiger formicilis* | 75 |
| *Clostridium asparagiforme* | *Clostridium saccharogumia* | *Coprococcus catus* | 75 |
| *Clostridium lavalense* | *Clostridium saccharogumia* | *Coprococcus catus* | 75 |

TABLE 17-continued

Ternary OTU combinations in administered spore ecology doses resulting in augmentation or engraftment of the OTU *Clostridiales* sp. SM4/1

| OTU 1 | OTU 2 | OTU 3 | Percent of doses in which the ternary is present |
|---|---|---|---|
| *Clostridium saccharogumia* | *Eubacterium hallii* | *Gemmiger formicilis* | 75 |
| *Blautia* sp. M25 | *Clostridium saccharogumia* | *Eubacterium ramulus* | 75 |
| *Clostridiales* sp. SSC/2 | *Clostridium saccharogumia* | *Dorea longicatena* | 75 |
| *Clostridiales* sp. SSC/2 | *Clostridium saccharogumia* | *Eubacterium ramulus* | 75 |
| *Clostridium saccharogumia* | *Coprococcus catus* | *Ruminococcus lactaris* | 75 |
| *Clostridium saccharogumia* | *Eubacterium ramulus* | *Eubacterium rectale* | 75 |
| *Clostridium saccharogumia* | *Eubacterium ramulus* | *Faecalibacterium prausnitzii* | 75 |
| *Clostridium saccharogumia* | *Eubacterium ramulus* | *Ruminococcus obeum* | 75 |
| *Clostridium saccharogumia* | *Eubacterium ramulus* | *Ruminococcus* sp. 5_1_39BFAA | 75 |
| *Clostridium saccharogumia* | *Eubacterium ramulus* | *Ruminococcus torques* | 75 |
| *Clostridium asparagiforme* | *Clostridium saccharogumia* | *Eubacterium ramulus* | 75 |
| *Clostridium saccharogumia* | *Coprococcus catus* | *Dorea longicatena* | 75 |
| *Clostridium saccharogumia* | *Coprococcus catus* | *Eubacterium hallii* | 75 |
| *Clostridium saccharogumia* | *Coprococcus catus* | *Gemmiger formicilis* | 75 |
| *Clostridium saccharogumia* | *Coprococcus comes* | *Eubacterium ramulus* | 75 |
| *Clostridium saccharogumia* | *Dorea longicatena* | *Gemmiger formicilis* | 75 |
| *Clostridium saccharogumia* | *Eubacterium hallii* | *Eubacterium ramulus* | 75 |
| *Clostridium saccharogumia* | *Eubacterium ramulus* | *Ruminococcus lactaris* | 75 |
| *Clostridium lavalense* | *Clostridium saccharogumia* | *Eubacterium ramulus* | 75 |
| *Clostridium saccharogumia* | *Coprococcus catus* | *Coprococcus comes* | 75 |
| *Clostridium saccharogumia* | *Coprococcus catus* | *Dorea formicigenerans* | 75 |
| *Clostridium saccharogumia* | *Dorea formicigenerans* | *Eubacterium ramulus* | 75 |
| *Clostridium saccharogumia* | *Eubacterium ramulus* | *Ruminococcus bromii* | 75 |
| *Clostridium saccharogumia* | *Coprococcus catus* | *Eubacterium ramulus* | 75 |
| *Clostridium saccharogumia* | *Dorea longicatena* | *Eubacterium ramulus* | 75 |

TABLE 18

Ternary OTU combinations in administered spore ecology doses that result in augmentation or engraftment of the OTU *Clostridiales* sp. SSC/2.

| OTU 1 | OTU 2 | OTU 3 | Percent of doses in which the ternary is present |
|---|---|---|---|
| *Faecalibacterium prausnitzii* | *Ruminococcus obeum* | *Turicibacter sanguinis* | 85 |
| *Faecalibacterium prausnitzii* | *Ruminococcus torques* | *Turicibacter sanguinis* | 85 |

TABLE 18-continued

Ternary OTU combinations in administered spore ecology doses that result in augmentation or engraftment of the OTU *Clostridiales* sp. SSC/2.

| OTU 1 | OTU 2 | OTU 3 | Percent of doses in which the ternary is present |
|---|---|---|---|
| *Blautia* sp. M25 | *Faecalibacterium prausnitzii* | *Turicibacter sanguinis* | 85 |
| *Blautia* sp. M25 | *Ruminococcus torques* | *Turicibacter sanguinis* | 85 |

TABLE 18-continued

Ternary OTU combinations in administered spore ecology doses that result in augmentation or engraftment of the OTU *Clostridiales* sp. SSC/2.

| OTU 1 | OTU 2 | OTU 3 | Percent of doses in which the ternary is present |
|---|---|---|---|
| *Faecalibacterium prausnitzii* | *Ruminococcus* sp. 5_1_39BFAA | *Turicibacter sanguinis* | 85 |
| *Ruminococcus obeum* | *Ruminococcus torques* | *Turicibacter sanguinis* | 85 |
| *Ruminococcus obeum* | *Ruminococcus* sp. 5_1_39BFAA | *Turicibacter sanguinis* | 85 |
| *Ruminococcus* sp. 5_1_39BFAA | *Ruminococcus torques* | *Turicibacter sanguinis* | 85 |
| *Blautia* sp. M25 | *Ruminococcus obeum* | *Turicibacter sanguinis* | 85 |
| *Faecalibacterium prausnitzii* | *Ruminococcus bromii* | *Turicibacter sanguinis* | 85 |
| *Ruminococcus bromii* | *Ruminococcus obeum* | *Turicibacter sanguinis* | 85 |
| *Ruminococcus bromii* | *Ruminococcus torques* | *Turicibacter sanguinis* | 85 |
| *Blautia* sp. M25 | *Ruminococcus* sp. 5_1_39BFAA | *Turicibacter sanguinis* | 85 |
| *Ruminococcus bromii* | *Ruminococcus* sp. 5_1_39BFAA | *Turicibacter sanguinis* | 85 |
| *Blautia* sp. M25 | *Ruminococcus bromii* | *Turicibacter sanguinis* | 85 |
| *Clostridiales* sp. SSC/2 | *Faecalibacterium prausnitzii* | *Turicibacter sanguinis* | 80 |
| *Clostridiales* sp. SSC/2 | *Ruminococcus obeum* | *Turicibacter sanguinis* | 80 |
| *Clostridiales* sp. SSC/2 | *Ruminococcus* sp. 5_1_39BFAA | *Turicibacter sanguinis* | 80 |
| *Clostridiales* sp. SSC/2 | *Ruminococcus torques* | *Turicibacter sanguinis* | 80 |
| *Blautia* sp. M25 | *Clostridiales* sp. SSC/2 | *Turicibacter sanguinis* | 80 |
| *Blautia* sp. M25 | *Gemmiger formicilis* | *Turicibacter sanguinis* | 80 |
| *Gemmiger formicilis* | *Ruminococcus obeum* | *Turicibacter sanguinis* | 80 |
| *Gemmiger formicilis* | *Ruminococcus* sp. 5_1_39BFAA | *Turicibacter sanguinis* | 80 |
| *Gemmiger formicilis* | *Ruminococcus torques* | *Turicibacter sanguinis* | 80 |
| *Faecalibacterium prausnitzii* | *Gemmiger formicilis* | *Turicibacter sanguinis* | 80 |
| *Clostridiales* sp. SSC/2 | *Ruminococcus bromii* | *Turicibacter sanguinis* | 80 |
| *Eubacterium hallii* | *Faecalibacterium prausnitzii* | *Turicibacter sanguinis* | 80 |
| *Eubacterium hallii* | *Ruminococcus obeum* | *Turicibacter sanguinis* | 80 |
| *Eubacterium hallii* | *Ruminococcus* sp. 5_1_39BFAA | *Turicibacter sanguinis* | 80 |
| *Eubacterium hallii* | *Ruminococcus torques* | *Turicibacter sanguinis* | 80 |
| *Gemmiger formicilis* | *Ruminococcus bromii* | *Turicibacter sanguinis* | 80 |
| *Blautia* sp. M25 | *Eubacterium hallii* | *Turicibacter sanguinis* | 80 |
| *Eubacterium hallii* | *Ruminococcus bromii* | *Turicibacter sanguinis* | 80 |
| *Blautia* sp. M25 | *Coprococcus catus* | *Turicibacter sanguinis* | 80 |
| *Coprococcus catus* | *Faecalibacterium prausnitzii* | *Turicibacter sanguinis* | 80 |
| *Coprococcus catus* | *Ruminococcus obeum* | *Turicibacter sanguinis* | 80 |
| *Coprococcus catus* | *Ruminococcus* sp. 5_1_39BFAA | *Turicibacter sanguinis* | 80 |
| *Coprococcus catus* | *Ruminococcus torques* | *Turicibacter sanguinis* | 80 |
| *Clostridiales* sp. SSC/2 | *Coprococcus catus* | *Turicibacter sanguinis* | 80 |

TABLE 18-continued

Ternary OTU combinations in administered spore ecology doses that result in augmentation or engraftment of the OTU *Clostridiales* sp. SSC/2.

| OTU 1 | OTU 2 | OTU 3 | Percent of doses in which the ternary is present |
|---|---|---|---|
| *Coprococcus catus* | *Ruminococcus bromii* | *Turicibacter sanguinis* | 80 |
| *Clostridium bartlettii* | *Faecalibacterium prausnitzii* | *Ruminococcus obeum* | 75 |
| *Clostridium bartlettii* | *Faecalibacterium prausnitzii* | *Ruminococcus torques* | 75 |
| *Blautia* sp. M25 | *Clostridium bartlettii* | *Faecalibacterium prausnitzii* | 75 |
| *Clostridium bartlettii* | *Ruminococcus obeum* | *Ruminococcus torques* | 75 |
| *Clostridium bartlettii* | *Ruminococcus* sp. 5_1_39BFAA | *Ruminococcus torques* | 75 |
| *Blautia* sp. M25 | *Clostridium bartlettii* | *Ruminococcus torques* | 75 |
| *Clostridium bartlettii* | *Faecalibacterium prausnitzii* | *Ruminococcus* sp. 5_1_39BFAA | 75 |
| *Blautia* sp. M25 | *Clostridium bartlettii* | *Ruminococcus obeum* | 75 |
| *Clostridium bartlettii* | *Ruminococcus obeum* | *Ruminococcus* sp. 5_1_39BFAA | 75 |
| *Blautia* sp. M25 | *Clostridium bartlettii* | *Ruminococcus* sp. 5_1_39BFAA | 75 |
| *Clostridium bartlettii* | *Ruminococcus bromii* | *Ruminococcus torques* | 75 |
| *Clostridium bartlettii* | *Faecalibacterium prausnitzii* | *Ruminococcus bromii* | 75 |
| *Clostridium bartlettii* | *Ruminococcus bromii* | *Ruminococcus obeum* | 75 |
| *Blautia* sp. M25 | *Clostridium bartlettii* | *Ruminococcus bromii* | 75 |
| *Clostridium bartlettii* | *Ruminococcus bromii* | *Ruminococcus* sp. 5_1_39BFAA | 75 |
| *Eubacterium rectale* | *Faecalibacterium prausnitzii* | *Turicibacter sanguinis* | 75 |
| *Eubacterium rectale* | *Ruminococcus obeum* | *Turicibacter sanguinis* | 75 |
| *Eubacterium rectale* | *Ruminococcus* sp. 5_1_39BFAA | *Turicibacter sanguinis* | 75 |
| *Eubacterium rectale* | *Ruminococcus torques* | *Turicibacter sanguinis* | 75 |
| *Blautia* sp. M25 | *Eubacterium rectale* | *Turicibacter sanguinis* | 75 |
| *Clostridium asparagiforme* | *Faecalibacterium prausnitzii* | *Turicibacter sanguinis* | 75 |
| *Clostridium asparagiforme* | *Ruminococcus obeum* | *Turicibacter sanguinis* | 75 |
| *Clostridium asparagiforme* | *Ruminococcus* sp. 5_1_39BFAA | *Turicibacter sanguinis* | 75 |
| *Eubacterium rectale* | *Ruminococcus bromii* | *Turicibacter sanguinis* | 75 |
| *Clostridium asparagiforme* | *Ruminococcus torques* | *Turicibacter sanguinis* | 75 |
| *Blautia* sp. M25 | *Clostridium asparagiforme* | *Turicibacter sanguinis* | 75 |
| *Clostridiales* sp. SSC/2 | *Eubacterium hallii* | *Turicibacter sanguinis* | 75 |
| *Clostridiales* sp. SSC/2 | *Gemmiger formicilis* | *Turicibacter sanguinis* | 75 |
| *Clostridium asparagiforme* | *Ruminococcus bromii* | *Turicibacter sanguinis* | 75 |
| *Clostridium* sp. SS2/1 | *Ruminococcus torques* | *Turicibacter sanguinis* | 75 |
| *Clostridium asparagiforme* | *Eubacterium hallii* | *Turicibacter sanguinis* | 75 |
| *Clostridium* sp. SS2/1 | *Faecalibacterium prausnitzii* | *Turicibacter sanguinis* | 75 |
| *Clostridium* sp. SS2/1 | *Ruminococcus obeum* | *Turicibacter sanguinis* | 75 |
| *Clostridium* sp. SS2/1 | *Ruminococcus* sp. 5_1_39BFAA | *Turicibacter sanguinis* | 75 |

TABLE 18-continued

Ternary OTU combinations in administered spore ecology doses that result in augmentation or engraftment of the OTU *Clostridiales* sp. SSC/2.

| OTU 1 | OTU 2 | OTU 3 | Percent of doses in which the ternary is present |
|---|---|---|---|
| *Eubacterium hallii* | *Gemmiger formicilis* | *Turicibacter sanguinis* | 75 |
| *Clostridiales* sp. SSC/2 | *Clostridium* sp. SS2/1 | *Turicibacter sanguinis* | 75 |
| *Blautia* sp. M25 | *Clostridium* sp. SS2/1 | *Turicibacter sanguinis* | 75 |
| *Clostridium* sp. SS2/1 | *Ruminococcus bromii* | *Turicibacter sanguinis* | 75 |
| *Clostridium* sp. SS2/1 | *Coprococcus catus* | *Turicibacter sanguinis* | 75 |
| *Collinsella aerofaciens* | *Faecalibacterium prausnitzii* | *Turicibacter sanguinis* | 75 |
| *Collinsella aerofaciens* | *Ruminococcus bromii* | *Turicibacter sanguinis* | 75 |
| *Collinsella aerofaciens* | *Ruminococcus obeum* | *Turicibacter sanguinis* | 75 |
| *Collinsella aerofaciens* | *Ruminococcus torques* | *Turicibacter sanguinis* | 75 |
| *Coprococcus catus* | *Eubacterium hallii* | *Turicibacter sanguinis* | 75 |
| *Coprococcus catus* | *Gemmiger formicilis* | *Turicibacter sanguinis* | 75 |
| *Blautia* sp. M25 | *Collinsella aerofaciens* | *Turicibacter sanguinis* | 75 |
| *Collinsella aerofaciens* | *Eubacterium hallii* | *Turicibacter sanguinis* | 75 |
| *Collinsella aerofaciens* | *Ruminococcus* sp. 5_1_39BFAA | *Turicibacter sanguinis* | 75 |

TABLE 19

Ternary OTU combinations in administered spore ecology doses that result in augmentation or engraftment of the OTU *Clostridium* sp. NML 04A032.

| OTU 1 | OTU 2 | OTU 3 | Percent of doses in which the ternary is present |
|---|---|---|---|
| *Clostridium asparagiforme* | *Faecalibacterium prausnitzii* | *Ruminococcus champanellensis* | 80 |
| *Clostridium asparagiforme* | *Ruminococcus champanellensis* | *Ruminococcus torques* | 80 |
| *Clostridium asparagiforme* | *Ruminococcus champanellensis* | *Ruminococcus obeum* | 80 |
| *Blautia* sp. M25 | *Clostridium asparagiforme* | *Ruminococcus champanellensis* | 80 |
| *Clostridium asparagiforme* | *Ruminococcus champanellensis* | *Ruminococcus* sp. 5_1_39BFAA | 80 |
| *Clostridium asparagiforme* | *Ruminococcus bromii* | *Ruminococcus champanellensis* | 80 |
| *Clostridium asparagiforme* | *Eubacterium hallii* | *Ruminococcus champanellensis* | 80 |
| *Clostridiales bacterium* 1_7_47FAA | *Eubacterium rectale* | *Faecalibacterium prausnitzii* | 75 |
| *Clostridiales bacterium* 1_7_47FAA | *Eubacterium rectale* | *Ruminococcus obeum* | 75 |
| *Clostridiales bacterium* 1_7_47FAA | *Eubacterium rectale* | *Ruminococcus torques* | 75 |
| *Blautia* sp. M25 | *Clostridiales bacterium* 1_7_47FAA | *Eubacterium rectale* | 75 |

TABLE 19-continued

Ternary OTU combinations in administered spore ecology doses that result in augmentation or engraftment of the OTU *Clostridium* sp. NML 04A032.

| OTU 1 | OTU 2 | OTU 3 | Percent of doses in which the ternary is present |
|---|---|---|---|
| *Clostridiales bacterium* 1_7_47FAA | *Eubacterium rectale* | *Ruminococcus* sp. 5_1_39BFAA | 75 |
| *Eubacterium rectale* | *Faecalibacterium prausnitzii* | *Ruminococcus champanellensis* | 75 |
| *Faecalibacterium prausnitzii* | *Ruminococcus champanellensis* | *Ruminococcus lactaris* | 75 |
| *Clostridiales bacterium* 1_7_47FAA | *Clostridium asparagiforme* | *Faecalibacterium prausnitzii* | 75 |
| *Clostridiales bacterium* 1_7_47FAA | *Clostridium asparagiforme* | *Ruminococcus torques* | 75 |
| *Blautia* sp. M25 | *Ruminococcus champanellensis* | *Ruminococcus lactaris* | 75 |
| *Eubacterium rectale* | *Ruminococcus champanellensis* | *Ruminococcus obeum* | 75 |
| *Eubacterium rectale* | *Ruminococcus champanellensis* | *Ruminococcus torques* | 75 |
| *Ruminococcus champanellensis* | *Ruminococcus lactaris* | *Ruminococcus obeum* | 75 |
| *Clostridiales bacterium* 1_7_47FAA | *Clostridium asparagiforme* | *Ruminococcus obeum* | 75 |
| *Ruminococcus champanellensis* | *Ruminococcus lactaris* | *Ruminococcus torques* | 75 |
| *Blautia* sp. M25 | *Eubacterium rectale* | *Ruminococcus champanellensis* | 75 |
| *Clostridium lavalense* | *Faecalibacterium prausnitzii* | *Ruminococcus champanellensis* | 75 |
| *Eubacterium rectale* | *Ruminococcus champanellensis* | *Ruminococcus lactaris* | 75 |
| *Clostridiales bacterium* 1_7_47FAA | *Clostridium asparagiforme* | *Ruminococcus* sp. 5_1_39BFAA | 75 |
| *Clostridiales bacterium* 1_7_47FAA | *Eubacterium rectale* | *Ruminococcus bromii* | 75 |
| *Clostridium lavalense* | *Ruminococcus champanellensis* | *Ruminococcus obeum* | 75 |
| *Clostridium lavalense* | *Ruminococcus champanellensis* | *Ruminococcus torques* | 75 |
| *Eubacterium rectale* | *Ruminococcus champanellensis* | *Ruminococcus* sp. 5_1_39BFAA | 75 |
| *Ruminococcus bromii* | *Ruminococcus champanellensis* | *Ruminococcus lactaris* | 75 |
| *Ruminococcus champanellensis* | *Ruminococcus lactaris* | *Ruminococcus* sp. 5_1_39BFAA | 75 |
| *Blautia* sp. M25 | *Clostridiales bacterium* 1_7_47FAA | *Clostridium asparagiforme* | 75 |
| *Clostridium lavalense* | *Eubacterium rectale* | *Ruminococcus champanellensis* | 75 |
| *Clostridium lavalense* | *Ruminococcus champanellensis* | *Ruminococcus lactaris* | 75 |
| *Clostridium lavalense* | *Ruminococcus champanellensis* | *Ruminococcus* sp. 5_1_39BFAA | 75 |
| *Blautia* sp. M25 | *Clostridium lavalense* | *Ruminococcus champanellensis* | 75 |
| *Clostridium asparagiforme* | *Eubacterium rectale* | *Ruminococcus champanellensis* | 75 |
| *Clostridium lavalense* | *Ruminococcus bromii* | *Ruminococcus champanellensis* | 75 |
| *Eubacterium rectale* | *Ruminococcus bromii* | *Ruminococcus champanellensis* | 75 |
| *Clostridiales bacterium* 1_7_47FAA | *Clostridium asparagiforme* | *Ruminococcus bromii* | 75 |
| *Clostridium asparagiforme* | *Ruminococcus champanellensis* | *Ruminococcus lactaris* | 75 |

TABLE 19-continued

Ternary OTU combinations in administered spore ecology doses that result in augmentation or engraftment of the OTU *Clostridium* sp. NML 04A032.

| OTU 1 | OTU 2 | OTU 3 | Percent of doses in which the ternary is present |
|---|---|---|---|
| *Clostridiales bacterium* 1_7_47FAA | *Clostridium asparagiforme* | *Eubacterium hallii* | 75 |
| *Clostridium asparagiforme* | *Clostridium lavalense* | *Ruminococcus champanellensis* | 75 |
| *Coprococcus comes* | *Eubacterium rectale* | *Ruminococcus champanellensis* | 75 |
| *Coprococcus comes* | *Faecalibacterium prausnitzii* | *Ruminococcus champanellensis* | 75 |
| *Coprococcus comes* | *Ruminococcus champanellensis* | *Ruminococcus obeum* | 75 |
| *Coprococcus comes* | *Ruminococcus champanellensis* | *Ruminococcus torques* | 75 |
| *Dorea formicigenerans* | *Eubacterium rectale* | *Ruminococcus champanellensis* | 75 |
| *Dorea formicigenerans* | *Faecalibacterium prausnitzii* | *Ruminococcus champanellensis* | 75 |
| *Dorea formicigenerans* | *Ruminococcus champanellensis* | *Ruminococcus obeum* | 75 |
| *Dorea formicigenerans* | *Ruminococcus champanellensis* | *Ruminococcus torques* | 75 |
| *Dorea longicatena* | *Ruminococcus champanellensis* | *Ruminococcus obeum* | 75 |
| *Blautia* sp. M25 | *Coprococcus comes* | *Ruminococcus champanellensis* | 75 |
| *Blautia* sp. M25 | *Dorea longicatena* | *Ruminococcus champanellensis* | 75 |
| *Dorea formicigenerans* | *Ruminococcus champanellensis* | *Ruminococcus lactaris* | 75 |
| *Dorea longicatena* | *Faecalibacterium prausnitzii* | *Ruminococcus champanellensis* | 75 |
| *Dorea longicatena* | *Ruminococcus champanellensis* | *Ruminococcus torques* | 75 |
| *Eubacterium hallii* | *Eubacterium rectale* | *Ruminococcus champanellensis* | 75 |
| *Eubacterium hallii* | *Ruminococcus champanellensis* | *Ruminococcus lactaris* | 75 |
| *Blautia* sp. M25 | *Dorea formicigenerans* | *Ruminococcus champanellensis* | 75 |
| *Clostridium asparagiforme* | *Dorea longicatena* | *Ruminococcus champanellensis* | 75 |
| *Clostridium asparagiforme* | *Gemmiger formicilis* | *Ruminococcus champanellensis* | 75 |
| *Clostridium lavalense* | *Dorea formicigenerans* | *Ruminococcus champanellensis* | 75 |
| *Dorea formicigenerans* | *Ruminococcus champanellensis* | *Ruminococcus* sp. 5_1_39BFAA | 75 |
| *Dorea longicatena* | *Eubacterium rectale* | *Ruminococcus champanellensis* | 75 |
| *Dorea longicatena* | *Ruminococcus champanellensis* | *Ruminococcus lactaris* | 75 |
| *Clostridiales* sp. SSC/2 | *Clostridium asparagiforme* | *Ruminococcus champanellensis* | 75 |
| *Clostridium asparagiforme* | *Coprococcus comes* | *Ruminococcus champanellensis* | 75 |
| *Clostridium asparagiforme* | *Dorea formicigenerans* | *Ruminococcus champanellensis* | 75 |
| *Clostridium lavalense* | *Dorea longicatena* | *Ruminococcus champanellensis* | 75 |
| *Coprococcus comes* | *Ruminococcus bromii* | *Ruminococcus champanellensis* | 75 |
| *Coprococcus comes* | *Ruminococcus champanellensis* | *Ruminococcus lactaris* | 75 |
| *Coprococcus comes* | *Ruminococcus champanellensis* | *Ruminococcus* sp. 5_1_39BFAA | 75 |
| *Dorea longicatena* | *Ruminococcus bromii* | *Ruminococcus champanellensis* | 75 |
| *Dorea longicatena* | *Ruminococcus champanellensis* | *Ruminococcus* sp. 5_1_39BFAA | 75 |
| *Clostridium asparagiforme* | *Coprococcus catus* | *Ruminococcus champanellensis* | 75 |
| *Clostridium lavalense* | *Eubacterium hallii* | *Ruminococcus champanellensis* | 75 |
| *Dorea formicigenerans* | *Eubacterium hallii* | *Ruminococcus champanellensis* | 75 |
| *Dorea formicigenerans* | *Dorea longicatena* | *Ruminococcus champanellensis* | 75 |
| *Clostridium lavalense* | *Coprococcus comes* | *Ruminococcus champanellensis* | 75 |
| *Coprococcus comes* | *Dorea formicigenerans* | *Ruminococcus champanellensis* | 75 |
| *Coprococcus comes* | *Eubacterium hallii* | *Ruminococcus champanellensis* | 75 |
| *Dorea formicigenerans* | *Ruminococcus bromii* | *Ruminococcus champanellensis* | 75 |
| *Coprococcus comes* | *Dorea longicatena* | *Ruminococcus champanellensis* | 75 |
| *Dorea longicatena* | *Eubacterium hallii* | *Ruminococcus champanellensis* | 75 |
| *Clostridium asparagiforme* | *Collinsella aerofaciens* | *Ruminococcus champanellensis* | 75 |

TABLE 20

Ternary OTU combinations in administered spore ecology doses that result in augmentation or engraftment of the OTUs *Clostridium* sp. NML 04A032, *Ruminococcus lactaris*, and *Ruminococcus* torques.

| OTU 1 | OTU 2 | OTU 3 | Percent of doses in which the ternary is present |
|---|---|---|---|
| *Clostridiales* sp. SM4/1 | *Faecalibacterium prausnitzii* | *Ruminococcus obeum* | 75 |
| *Clostridiales* sp. SM4/1 | *Faecalibacterium prausnitzii* | *Ruminococcus torques* | 75 |
| *Clostridiales* sp. SM4/1 | *Ruminococcus obeum* | *Ruminococcus torques* | 75 |
| *Blautia* sp. M25 | *Clostridiales* sp. SM4/1 | *Faecalibacterium prausnitzii* | 75 |
| *Clostridiales* sp. SM4/1 | *Ruminococcus* sp. 5_1_39BFAA | *Ruminococcus torques* | 75 |
| *Blautia* sp. M25 | *Clostridiales* sp. SM4/1 | *Ruminococcus torques* | 75 |
| *Clostridiales* sp. SM4/1 | *Faecalibacterium prausnitzii* | *Ruminococcus* sp. 5_1_39BFAA | 75 |
| *Blautia* sp. M25 | *Clostridiales* sp. SM4/1 | *Ruminococcus obeum* | 75 |
| *Blautia* sp. M25 | *Clostridiales* sp. SM4/1 | *Ruminococcus* sp. 5_1_39BFAA | 75 |
| *Clostridiales* sp. SM4/1 | *Ruminococcus obeum* | *Ruminococcus* sp. 5_1_39BFAA | 75 |
| *Clostridiales* sp. SM4/1 | *Clostridium asparagiforme* | *Faecalibacterium prausnitzii* | 75 |
| *Clostridiales* sp. SM4/1 | *Clostridium asparagiforme* | *Ruminococcus torques* | 75 |
| *Clostridiales* sp. SM4/1 | *Clostridium asparagiforme* | *Ruminococcus obeum* | 75 |
| *Blautia* sp. M25 | *Clostridiales* sp. SM4/1 | *Ruminococcus bromii* | 75 |
| *Clostridiales* sp. SM4/1 | *Faecalibacterium prausnitzii* | *Ruminococcus bromii* | 75 |
| *Clostridiales* sp. SM4/1 | *Ruminococcus bromii* | *Ruminococcus obeum* | 75 |

TABLE 20-continued

Ternary OTU combinations in administered spore ecology doses that result in augmentation or engraftment of the OTUs *Clostridium* sp. NML 04A032, *Ruminococcus lactaris*, and *Ruminococcus* torques.

| OTU 1 | OTU 2 | OTU 3 | Percent of doses in which the ternary is present |
|---|---|---|---|
| *Clostridiales* sp. SM4/1 | *Ruminococcus bromii* | *Ruminococcus* sp. 5_1_39BFAA | 75 |
| *Clostridiales* sp. SM4/1 | *Ruminococcus bromii* | *Ruminococcus torques* | 75 |
| *Blautia* sp. M25 | *Clostridiales* sp. SM4/1 | *Clostridium asparagiforme* | 75 |
| *Clostridiales* sp. SM4/1 | *Clostridium asparagiforme* | *Ruminococcus* sp. 5_1_39BFAA | 75 |
| *Clostridiales* sp. SM4/1 | *Eubacterium hallii* | *Faecalibacterium prausnitzii* | 75 |
| *Clostridiales* sp. SM4/1 | *Eubacterium hallii* | *Ruminococcus obeum* | 75 |
| *Clostridiales* sp. SM4/1 | *Eubacterium hallii* | *Ruminococcus torques* | 75 |
| *Blautia* sp. M25 | *Clostridiales* sp. SM4/1 | *Eubacterium hallii* | 75 |
| *Clostridiales* sp. SM4/1 | *Eubacterium hallii* | *Ruminococcus* sp. 5_1_39BFAA | 75 |
| *Clostridiales* sp. SM4/1 | *Clostridium asparagiforme* | *Ruminococcus bromii* | 75 |
| *Clostridiales* sp. SM4/1 | *Clostridium asparagiforme* | *Eubacterium hallii* | 75 |
| *Clostridiales* sp. SM4/1 | *Eubacterium hallii* | *Ruminococcus bromii* | 75 |

TABLE 21

Ternary OTU combinations in administered spore ecology doses that result in augmentation or engraftment of the OTUs *Eubacterium* rectale, *Faecalibacterium prausnitzii*, *Oscillibacter* sp. G2, *Ruminococcus lactaris*, and *Ruminococcus* torques.

| OTU 1 | OTU 2 | OTU 3 | Percent of doses in which the ternary is present |
|---|---|---|---|
| *Clostridium bifermentans* | *Faecalibacterium prausnitzii* | *Ruminococcus obeum* | 75 |
| *Clostridium bifermentans* | *Ruminococcus obeum* | *Ruminococcus torques* | 75 |
| *Clostridium bifermentans* | *Ruminococcus obeum* | *Ruminococcus* sp. 5_1_39BFAA | 75 |
| *Blautia* sp. M25 | *Clostridium bifermentans* | *Faecalibacterium prausnitzii* | 75 |
| *Blautia* sp. M25 | *Clostridium bifermentans* | *Ruminococcus torques* | 75 |
| *Clostridium bifermentans* | *Faecalibacterium prausnitzii* | *Ruminococcus* sp. 5_1_39BFAA | 75 |
| *Clostridium bifermentans* | *Faecalibacterium prausnitzii* | *Ruminococcus torques* | 75 |
| *Clostridium bifermentans* | *Ruminococcus* sp. 5_1_39BFAA | *Ruminococcus torques* | 75 |
| *Blautia* sp. M25 | *Clostridium bifermentans* | *Ruminococcus obeum* | 75 |
| *Blautia* sp. M25 | *Clostridium bifermentans* | *Ruminococcus* sp. 5_1_39BFAA | 75 |
| *Clostridium bifermentans* | *Ruminococcus bromii* | *Ruminococcus obeum* | 75 |
| *Blautia* sp. M25 | *Clostridium bifermentans* | *Gemmiger formicilis* | 75 |
| *Clostridium bifermentans* | *Faecalibacterium prausnitzii* | *Ruminococcus bromii* | 75 |
| *Clostridium bifermentans* | *Gemmiger formicilis* | *Ruminococcus obeum* | 75 |

TABLE 21-continued

Ternary OTU combinations in administered spore ecology doses that result in augmentation or engraftment of the OTUs *Eubacterium* rectale, *Faecalibacterium prausnitzii*, *Oscillibacter* sp. G2, *Ruminococcus lactaris*, and *Ruminococcus* torques.

| OTU 1 | OTU 2 | OTU 3 | Percent of doses in which the ternary is present |
|---|---|---|---|
| *Clostridium bifermentans* | *Gemmiger formicilis* | *Ruminococcus* sp. 5_1_39BFAA | 75 |
| *Clostridium bifermentans* | *Ruminococcus bromii* | *Ruminococcus torques* | 75 |
| *Clostridium bifermentans* | *Faecalibacterium prausnitzii* | *Gemmiger formicilis* | 75 |
| *Blautia* sp. M25 | *Clostridium bifermentans* | *Ruminococcus bromii* | 75 |
| *Clostridium bifermentans* | *Gemmiger formicilis* | *Ruminococcus torques* | 75 |
| *Clostridium bifermentans* | *Ruminococcus bromii* | *Ruminococcus* sp. 5_1_39BFAA | 75 |
| *Clostridium bifermentans* | *Gemmiger formicilis* | *Ruminococcus bromii* | 75 |

TABLE 22

Selected OTUs that may be present in the tables, specification, or in the art with their alternate names, e.g., the current name used per NCBI. Reference 1 is Kaur et al., "*Hungatella effluvii* gen. nov., sp. nov., an obligately anaerobic bacterium isolated from an effluent treatment plant, and reclassification of *Clostridium hathewayi* as *Hungatella hathewayi* gen. nov., comb. nov.", Int J Sys Evol Microbiol, March 2014, vol. 64, pp. 710-718. Reference 2 is Gerritsen et al., "Characterization of *Romboutsia ilealis* gen. nov., sp. nov., isolated from the gastro-intestinal tract of a rat, and proposal for the reclassification of five closely related members of the genus *Clostridium* into the genera *Romboutsia* gen. nov., *Intestinibacter* gen, nov., *Terrisporobacter* gen. nov. and *Asaccharospora* gen. nov.", Int J Sys Evol Microbiol, May 2014, vol. 64, pp. 1600-1616.

| OTU name | Alternate OTU name | Reference |
|---|---|---|
| *Clostridium hathewayi* | *Hungatella hathewayi* | 1 |
| *Clostridium lituseburense* | *Romboutsia lituseburense* | 2 |
| *Clostridium bartlettii* | *Intestinibacter bartlettii* | 2 |
| *Clostridium glycolicum* | *Terrisporobacter glycolicus* | 2 |
| *Clostridium mayombei* | *Terrisporobacter mayombei* | 2 |
| *Clostridium irregulare* | *Asaccharospora irregularis* | 2 |

SEQUENCE LISTING

The patent contains a lengthy sequence listing. A copy of the sequence listing is available in electronic form from the USPTO web site (https://seqdata.uspto.gov/?pageRequest=docDetail&DocID=US11918612B2). An electronic copy of the sequence listing will also be available from the USPTO upon request and payment of the fee set forth in 37 CFR 1.19(b)(3).

What is claimed is:

1. A composition comprising: (a) a first species of an isolated *bacterium* capable of forming a spore, (b) a second species of isolated *bacterium* capable of forming a spore, (c) a third species of isolated *bacterium* capable of forming a spore, and (d) a capsule;

wherein the capsule encapsulates the first species, the second species, and the third species;

wherein the first species, the second species, and the third species of bacteria are not identical;

wherein the first species is *Clostridium orbiscindens*, the second species is *Clostridium bolteae*, and the third species is Lachnospiraceae *bacterium* 5_1_57FAA, wherein the *Clostridium orbiscindens* comprises a 16S rDNA sequence that is at least 97% identical to the sequence set forth in SEQ ID NO: 609;

and wherein a combination of the first species, the second species, and the third species is capable of decreasing and/or inhibiting the growth and/or colonization of at least one type of pathogenic bacteria.

2. The composition of claim 1, wherein the at least one type of pathogenic bacteria is selected from the group consisting of *Yersinia, Vibrio, Treponema, Streptococcus, Staphylococcus, Shigella, Salmonella, Rickettsia, Orientia, Pseudomonas, Providencia, Proteus, Propionibacterium, Neisseria, Mycoplasma, Mycobacterium, Morganella, Listeria, Leptospira, Legionella, Klebsiella, Helicobacter, Haemophilus, Fusobacterium, Francisella, Escherichia, Ehrlichia, Enterococcus, Coxiella, Corynebacterium, Clostridium Chlamydia, Chlamydophila, Campylobacter, Burkholderia, Brucella, Borrelia, Bordetella, Bifidobacterium, Bacillus*, multi-drug resistant bacteria, carbapenem-resistant Enterobacteriaceae (CRE), extended spectrum beta-lactam resistant Enterococci (ESBL), and vancomycin-resistant Enterococci (VRE).

3. The composition of claim 1, wherein the combination of the first species, the second species, and the third species is capable of synergistically inhibiting the growth and/or colonization of the at least one type of pathogenic bacteria.

4. A single dose unit comprising the composition of claim 1.

5. The composition of claim 2, wherein the at least one type of pathogenic bacteria is *Clostridium difficile.*

6. The composition of claim 1, wherein one or more of the first species, the second species, and the third species are in the form of spores.

7. The composition of claim 1, wherein the capsule is enterically coated.

8. The composition of claim 1, which further comprises glycerol.

9. The composition of claim 1, wherein the *Clostridium orbiscindens* comprises a 16S rDNA sequence that is at least 98% identical to the sequence set forth in SEQ ID NO: 609.

10. The composition of claim 1, wherein the *Clostridium orbiscindens* comprises a 16S rDNA sequence that is at least 99% identical to the sequence set forth in SEQ ID NO: 609.

11. The composition of claim 1, wherein the *Clostridium orbiscindens* comprises the 16S rDNA sequence set forth in SEQ ID NO: 609.

12. The composition of claim 1, wherein the *Clostridium bolteae* comprises a 16S rDNA sequence that is at least 97% identical to the sequence set forth in SEQ ID NO: 559.

13. The composition of claim 1, wherein the *Clostridium bolteae* comprises a 16S rDNA sequence that is at least 98% identical to the sequence set forth in SEQ ID NO: 559.

14. The composition of claim 1, wherein the *Clostridium bolteae* comprises a 16S rDNA sequence that is at least 99% identical to the sequence set forth in SEQ ID NO: 559.

15. The composition of claim 1, wherein the *Clostridium bolteae* comprises the 16S rDNA sequence set forth in SEQ ID NO: 559.

16. The composition of claim 1, wherein the Lachnospiraceae *bacterium* 5_1_57FAA comprises a 16S rDNA sequence that is at least 97% identical to the sequence set forth in SEQ ID NO: 1054.

17. The composition of claim 1, wherein the Lachnospiraceae *bacterium* 5_1_57FAA comprises a 16S rDNA sequence that is at least 98% identical to the sequence set forth in SEQ ID NO: 1054.

18. The composition of claim 1, wherein the Lachnospiraceae *bacterium* 5_1_57FAA comprises a 16S rDNA sequence that is at least 99% identical to the sequence set forth in SEQ ID NO: 1054.

19. The composition of claim 1, wherein the Lachnospiraceae *bacterium* 5_1_57FAA comprises the 16S rDNA sequence set forth in SEQ ID NO: 1054.

* * * * *